United States Patent
Jung et al.

(10) Patent No.: US 12,167,689 B2
(45) Date of Patent: *Dec. 10, 2024

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Tae Yoon Park, Daejeon (KR); Seong Mi Cho, Daejeon (KR); Jeong Wook Mun, Daejeon (KR); Jung Ha Lee, Daejeon (KR); Mi Young Chae, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/842,520

(22) Filed: Jun. 16, 2022

(65) Prior Publication Data

US 2022/0336757 A1 Oct. 20, 2022

Related U.S. Application Data

(63) Continuation of application No. 15/771,066, filed as application No. PCT/KR2017/006274 on Jun. 15, 2017, now Pat. No. 11,903,311.

(30) Foreign Application Priority Data

Jul. 20, 2016 (KR) .......................... 10-2016-0092202
Jun. 14, 2017 (KR) .......................... 10-2017-0075029

(51) Int. Cl.
*H10K 85/60* (2023.01)
*C07D 405/04* (2006.01)
(Continued)

(52) U.S. Cl.
CPC ....... *H10K 85/6576* (2023.02); *C07D 405/04* (2013.01); *C07D 405/10* (2013.01);
(Continued)

(58) Field of Classification Search
CPC ............ H01L 51/0074; H01L 51/0052; H01L 51/0054; H01L 51/0058; H01L 51/0067; H01L 51/0072; H01L 51/0073; H01L 51/0094; H01L 51/5024; H01L 51/5092; H01L 51/5206; H01L 51/5221; H01L 51/0085; H01L 51/5016; H01L 51/5056; H01L 51/5072; H01L 2251/5384;
(Continued)

(56) References Cited

U.S. PATENT DOCUMENTS 7,274,141 B2  9/2007 Leo et al.
8,367,850 B2  2/2013 Ma et al.
(Continued)

FOREIGN PATENT DOCUMENTS

| EP | 2991128 A1 | 3/2016 |
|---|---|---|
| JP | 5831654 | 12/2015 |
| JP | 2016-051901 | 4/2016 |
| JP | 6007467 | 10/2016 |
| JP | 2017-107992 | 6/2017 |
| JP | 2018-536024 | 12/2018 |
| JP | 2019-513833 | 5/2019 |
| JP | 2019-524741 | 9/2019 |
| KR | 10-2000-0051826 | 8/2000 |
| KR | 10-1431644 | 8/2014 |

(Continued)

*Primary Examiner* — Dylan C Kershner
(74) *Attorney, Agent, or Firm* — Bryan Cave Leighton Paisner LLP

(57) ABSTRACT

Provided is a heterocyclic compound of Chemical Formula 1:

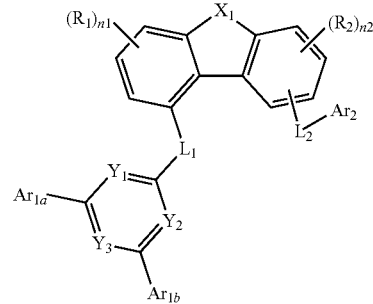

wherein:

$X_1$ is O or S;

$L_1$ is a single bond or an unsubstituted phenylene;

$L_2$ is a single bond, or a substituted or unsubstituted: phenylene, naphthylene, or biphenylenyl;

$Y_1$ to $Y_3$ are each independently N or $CR_3$, where at least one is N;

$Ar_{1a}$ and $Ar_{1b}$ are each independently a substituted or unsubstituted: $C_{6-60}$ aryl or $C_{1-60}$ heteroaryl containing 1 to 3 heteroatoms selected from N, O and S;

$R_1$ and $R_2$ are each independently hydrogen, deuterium, cyano, or a substituted or unsubstituted $C_{1-10}$ alkyl;

each $R_3$ is independently hydrogen, deuterium, halogen, cyano, nitro, amino, or a substituted or unsubstituted: $C_{1-60}$ alkyl, $C_{1-60}$ haloalkyl, $C_{1-60}$ alkoxy, a $C_{1-60}$ haloalkoxy, $C_{3-60}$ cycloalkyl, $C_{2-60}$ alkenyl, $C_{6-60}$ aryl, $C_{6-60}$ aryloxy, or a $C_{1-60}$ heteroaryl containing at least one heteroatom selected from N, O and S;

and an organic light emitting device comprising the same.

9 Claims, 1 Drawing Sheet

(51) Int. Cl.
*C07D 405/10* (2006.01)
*C07D 405/14* (2006.01)
*C07D 409/04* (2006.01)
*C07D 409/10* (2006.01)
*C07D 409/14* (2006.01)
*C07F 7/08* (2006.01)
*C09K 11/06* (2006.01)
*H05B 33/20* (2006.01)
*H10K 50/11* (2023.01)
*H10K 50/12* (2023.01)
*H10K 50/15* (2023.01)
*H10K 50/16* (2023.01)
*H10K 50/17* (2023.01)
*H10K 50/81* (2023.01)
*H10K 50/82* (2023.01)
*H10K 85/30* (2023.01)
*H10K 85/40* (2023.01)
*H10K 101/10* (2023.01)
*H10K 101/00* (2023.01)

(52) U.S. Cl.
CPC ......... *C07D 405/14* (2013.01); *C07D 409/04* (2013.01); *C07D 409/10* (2013.01); *C07D 409/14* (2013.01); *C07F 7/0812* (2013.01); *C09K 11/06* (2013.01); *H05B 33/20* (2013.01); *H10K 50/11* (2023.02); *H10K 85/40* (2023.02); *H10K 85/615* (2023.02); *H10K 85/622* (2023.02); *H10K 85/626* (2023.02); *H10K 85/654* (2023.02); *H10K 85/6572* (2023.02); *H10K 85/6574* (2023.02); *H10K 50/12* (2023.02); *H10K 50/15* (2023.02); *H10K 50/16* (2023.02); *H10K 50/171* (2023.02); *H10K 50/81* (2023.02); *H10K 50/82* (2023.02); *H10K 85/342* (2023.02); *H10K 2101/10* (2023.02); *H10K 2101/90* (2023.02)

(58) Field of Classification Search
CPC ................ C07D 409/10; C07D 409/14; H10K 85/6576; H10K 85/615; H10K 85/622; H10K 85/626; H10K 85/654; H10K 85/6572; H10K 85/6574; H10K 85/40; H10K 50/12; H10K 50/171; H10K 50/15; H10K 50/16; H10K 50/11; H10K 2101/10
See application file for complete search history.

(56) References Cited

U.S. PATENT DOCUMENTS

| | | | |
|---|---|---|---|
| 9,190,620 B2 | 11/2015 | Zeng et al. | |
| 9,334,260 B2 | 5/2016 | Parham et al. | |
| 9,406,892 B2 | 8/2016 | Zeng et al. | |
| 10,622,565 B2 | 4/2020 | Parham et al. | |
| 11,251,377 B2* | 2/2022 | Cha | C09K 11/06 |
| 11,594,685 B2* | 2/2023 | Huh | H10K 99/00 |
| 11,685,859 B2* | 6/2023 | Ha | H10K 85/6576 |
| | | | 257/40 |
| 11,800,730 B2* | 10/2023 | Cho | H10K 50/171 |
| 2006/0088728 A1 | 4/2006 | Kwong et al. | |
| 2012/0235123 A1 | 9/2012 | Lee et al. | |
| 2015/0171340 A1* | 6/2015 | Lee | H10K 85/6574 |
| | | | 544/333 |
| 2015/0228908 A1 | 8/2015 | Lee et al. | |
| 2015/0349268 A1 | 12/2015 | Zeng et al. | |
| 2016/0028021 A1 | 1/2016 | Zeng et al. | |
| 2016/0093808 A1* | 3/2016 | Adamovich | H10K 85/657 |
| | | | 252/301.16 |
| 2016/0329506 A1 | 11/2016 | Lee et al. | |
| 2017/0054087 A1 | 2/2017 | Zeng et al. | |
| 2017/0133602 A1 | 5/2017 | Lee et al. | |
| 2017/0186965 A1 | 6/2017 | Parham et al. | |
| 2017/0207399 A1 | 7/2017 | Parham et al. | |
| 2017/0237017 A1 | 8/2017 | Parham et al. | |
| 2018/0037546 A1 | 2/2018 | Sugino et al. | |
| 2018/0337348 A1* | 11/2018 | Jung | H10K 85/622 |
| 2019/0013490 A1 | 1/2019 | Cho et al. | |
| 2019/0084967 A1 | 3/2019 | Parham et al. | |
| 2019/0165282 A1 | 5/2019 | Parham et al. | |
| 2019/0214573 A1 | 7/2019 | Ryu et al. | |

FOREIGN PATENT DOCUMENTS

| | | |
|---|---|---|
| KR | 10-2015-0031396 | 3/2015 |
| KR | 10-2015-0074603 | 7/2015 |
| KR | 10-2015-0136027 | 12/2015 |
| KR | 10-2016-0006633 | 1/2016 |
| KR | 10-2016-0028524 | 3/2016 |
| KR | 10-1600453 | 3/2016 |
| KR | 10-2016-0080090 | 7/2016 |
| KR | 10-2016-0085206 | 7/2016 |
| TW | 201609675 | 3/2016 |
| TW | 201623303 | 7/2016 |
| WO | 2003-012890 A2 | 2/2003 |
| WO | 2015-105251 | 7/2015 |
| WO | 2015-169412 | 11/2015 |
| WO | 2016-015810 | 2/2016 |
| WO | 2016-023608 | 2/2016 |
| WO | 2016-108596 A2 | 7/2016 |
| WO | 2017-076485 | 5/2017 |
| WO | 2017-178311 | 10/2017 |

* cited by examiner

HETEROCYCLIC COMPOUND AND ORGANIC LIGHT EMITTING DEVICE COMPRISING THE SAME

CROSS-REFERENCE TO RELATED APPLICATIONS

This application is a continuation of co-pending U.S. patent application Ser. No. 15/771,066, which is the U.S. National Stage Application of International Application No. PCT/KR2017/006274, filed Jun. 15, 2017, which claims the benefit of Korean Patent Application No. 10-2016-0092202 filed on Jul. 20, 2016, and Korean Patent Application No. 10-2017-0075029 filed on Jun. 14, 2017, the disclosures of each of which are incorporated herein by reference in their entirety for all purposes as if fully set forth below.

TECHNICAL FIELD

The present invention relates to a novel heterocyclic compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode to the organic material layer, and when the injected holes and the electrons meet each other, an exciton is formed, and light is emitted when the exciton falls to a ground state again.

There is a continuing demand for developing a new material for organic materials used in such organic light emitting devices.

PRIOR ART LITERATURE

Patent Literature (Patent Literature 1) Korean Patent Laid-open Publication No. 10-2000-0051826

BRIEF DESCRIPTION

Technical Problem

It is one object of the present invention to provide a novel heterocyclic compound and an organic light emitting device comprising the same.

Technical Solution

The present invention provides a compound represented by the following Chemical Formula 1:

[Chemical Formula 1]

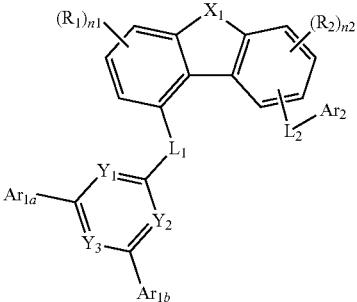

In Chemical Formula 1,
$X_1$ is O or S,
$L_1$ and $L_2$ are each independently a single bond; a substituted or unsubstituted $C_{6-60}$ arylene; or a substituted or unsubstituted $C_{1-60}$ heteroarylene containing one or more heteroatoms selected from the group consisting of O, N, Si and S,
$Y_1$ to $Y_3$ are each independently N or $CR_3$, provided that at least one of $Y_1$ to $Y_3$ is N,
$Ar_{1a}$ and $Ar_{1b}$ are each independently a substituted or unsubstituted $C_{6-60}$ aryl; or a substituted or unsubstituted $C_{1-60}$ heteroaryl containing 1 to 3 heteroatoms selected from the group consisting of N, O and S,
$Ar_2$ is a substituted or unsubstituted $C_{6-60}$ aryl,
$R_1$ to $R_3$ are each independently hydrogen; deuterium; halogen; cyano; nitro; amino; a substituted or unsubstituted $C_{1-60}$ alkyl; a substituted or unsubstituted $C_{1-60}$ haloalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; a substituted or unsubstituted $C_{2-60}$ alkenyl; a substituted or unsubstituted $C_{6-60}$ aryl; a substituted or unsubstituted CF-so aryloxy; or a substituted or unsubstituted $C_{1-60}$ heteroaryl containing at least one heteroatom selected from the group consisting of N, O and S, and
$n_1$ and $n_2$ are each independently an integer of 0 to 3.

In addition, the present invention provides an organic light emitting device comprising a first electrode; a second electrode provided to face the first electrode; and one or more organic material layers provided between the first electrode and the second electrode, wherein one or more of the organic layers comprises a compound represented by Chemical Formula 1.

Advantageous Effects

The compound represented by Chemical Formula 1 can be used as a material of an organic material layer of an organic light emitting device and can exhibit improved efficiency, a low driving voltage and/or improved lifetime characteristics of the organic light emitting device. In particular, the compound represented by Chemical Formula 1 can be used as a host material of the light emitting layer.

DETAILED DESCRIPTION

Figure 1:
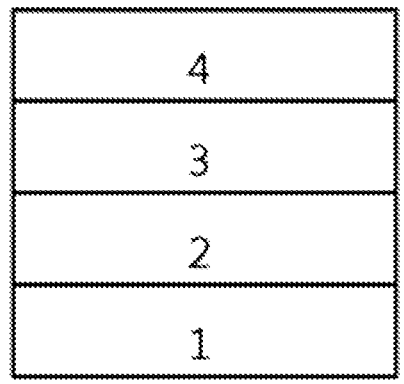
FIG. 1 shows an example of an organic light emitting device comprising a substrate 1, an anode 2, a light emitting layer 3, and a cathode 4.

Hereinafter, the present invention will be described in more detail to help understanding of the present invention.

In the present specification,

means a bond connected to another substituent group, and a single bond means when a separate atom does not exist in a portion denoted by $L_1$ and $L_2$.

As used herein, the term "substituted or unsubstituted" means that substitution is performed by one or more substituent groups selected from the group consisting of deuterium; a halogen group; a cyano group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl groups; an aralkenyl group; an alkylaryl group; an alkylamine group; an aralkylamine group; a heteroarylamine group; an arylamine group; an arylphosphine group; or heteroaryl containing at least one of N, O, and S atoms, or there is no substituent group, or substitution is performed by a substituent group where two or more substituent groups of the exemplified substituent groups are connected or there is no substituent group. For example, the term "substituent group where two or more substituent groups are connected" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be compounds having the following structures, but is not limited thereto:

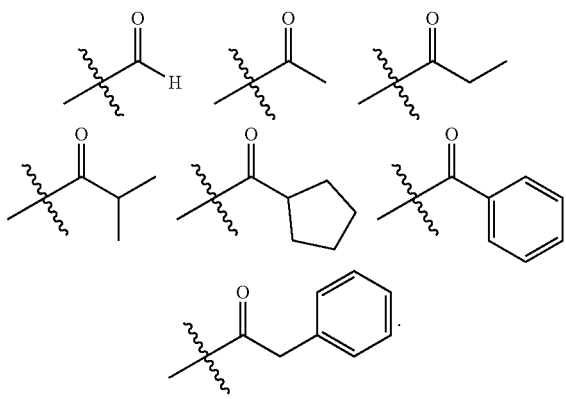

In the present specification, oxygen of an ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto:

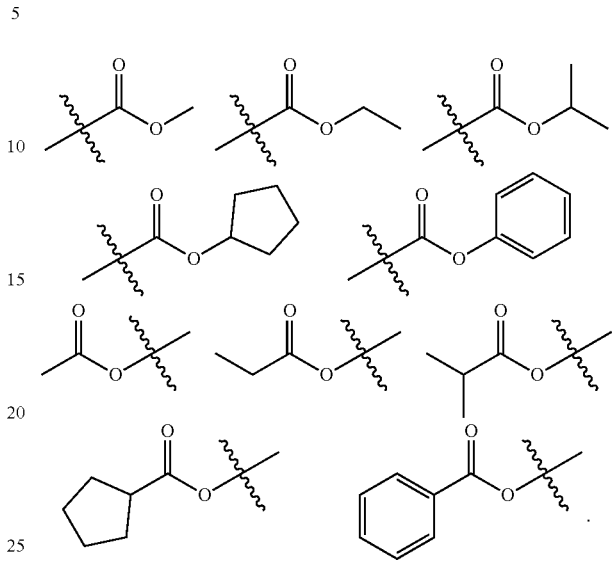

In the present specification, the number of carbon atoms in an imide group is not particularly limited but is preferably 1 to 25. Specifically, the imide group may be compounds having the following structures, but is not limited thereto:

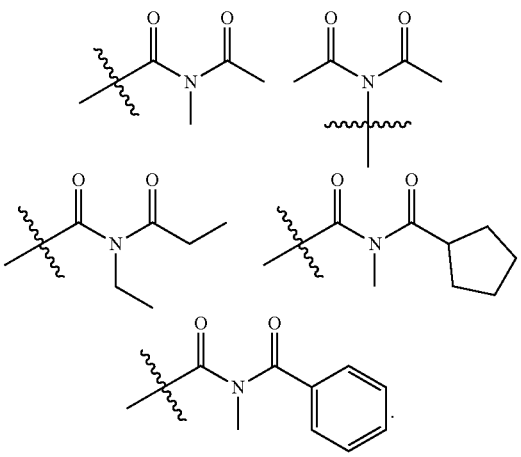

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be bonded to each other to form a spiro structure. In the case where the fluorenyl group is substituted,

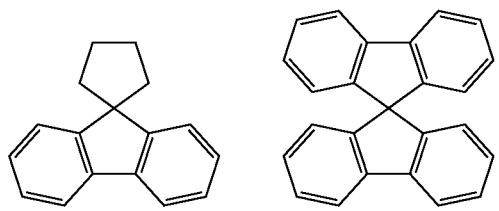

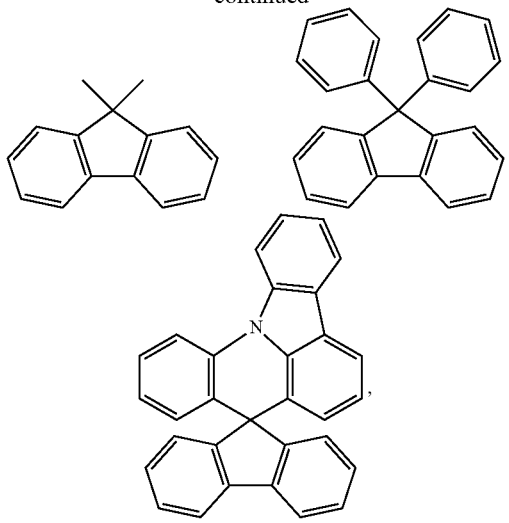

and the like can be formed. However, the structure is not limited thereto.

In the present specification, the heterocyclic group is a heterocyclic group containing one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Meanwhile, the present invention also provides a compound represented by Chemical Formula 1.

Specifically, the compound represented by Chemical Formula 1 can be represented by the following Chemical Formulas 1-1 to 1-4:

[Chemical Formula 1-1]

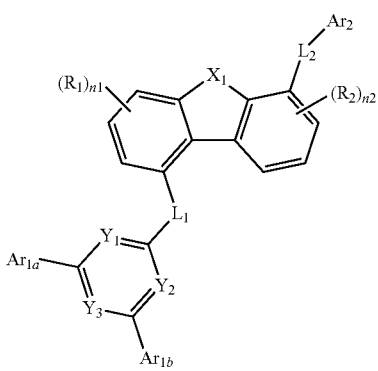

[Chemical Formula 1-2]

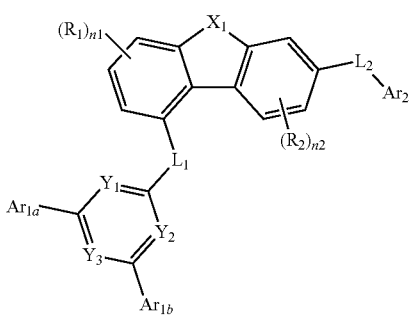

[Chemical Formula 1-3]

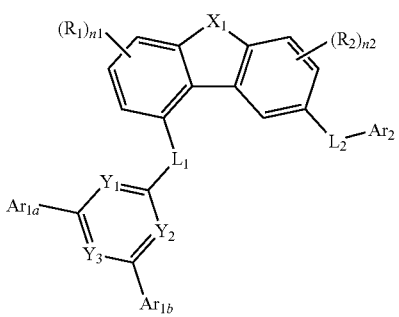

[Chemical Formula 1-4]

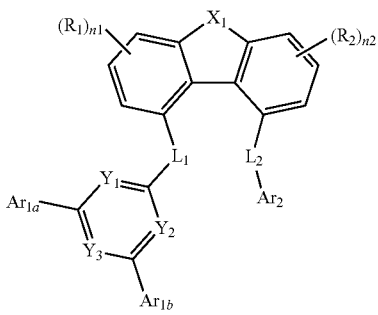

In the above chemical formulas 1-1 to 1-4, $L_1$, $L_2$, $Y_1$ to $Y_3$, $Ar_{1a}$, $Ar_{1b}$, $Ar_2$, $R_1$, $R_2$, n1 and n2 are as defined in Chemical Formula 1.

Preferably, in Chemical Formula 1, $L_1$ and $L_2$ are each independently a single bond; or a substituted or unsubstituted $C_{6-20}$ arylenyl.

For example, $L_1$ and $L_2$ are each independently a single bond; a substituted or unsubstituted phenylene; a substituted or unsubstituted naphthylene; or a substituted or unsubstituted biphenylenyl.

Specifically, for example, $L_1$ and $L_2$ may each independently be a single bond, or any one selected from the group consisting of:

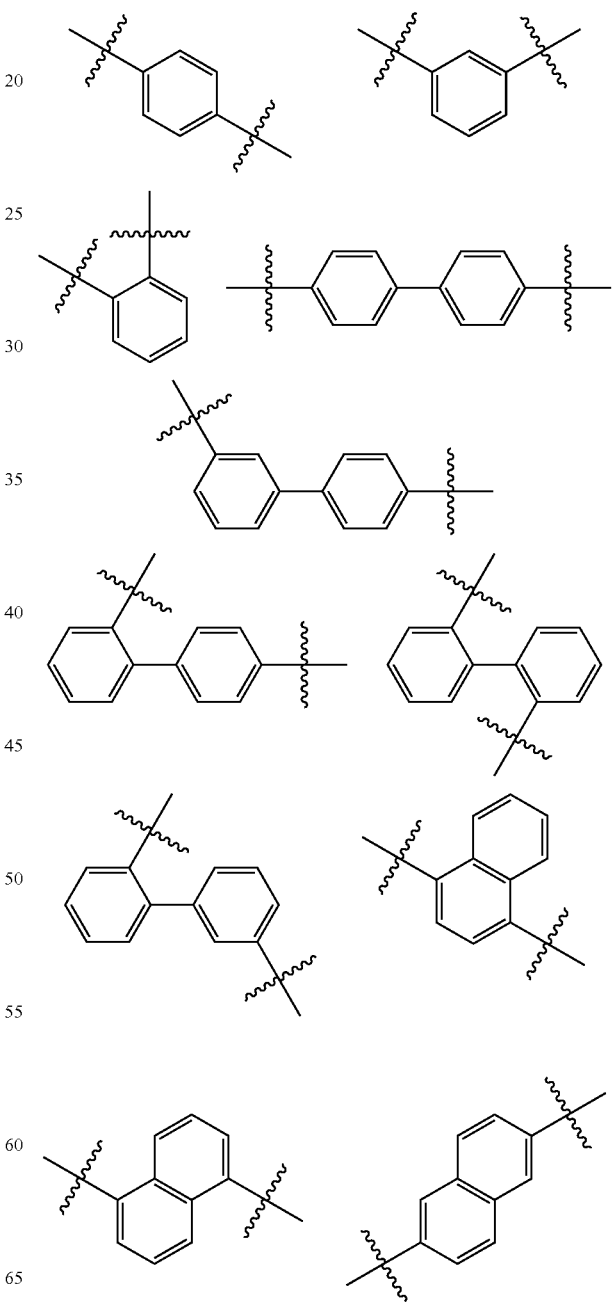

-continued

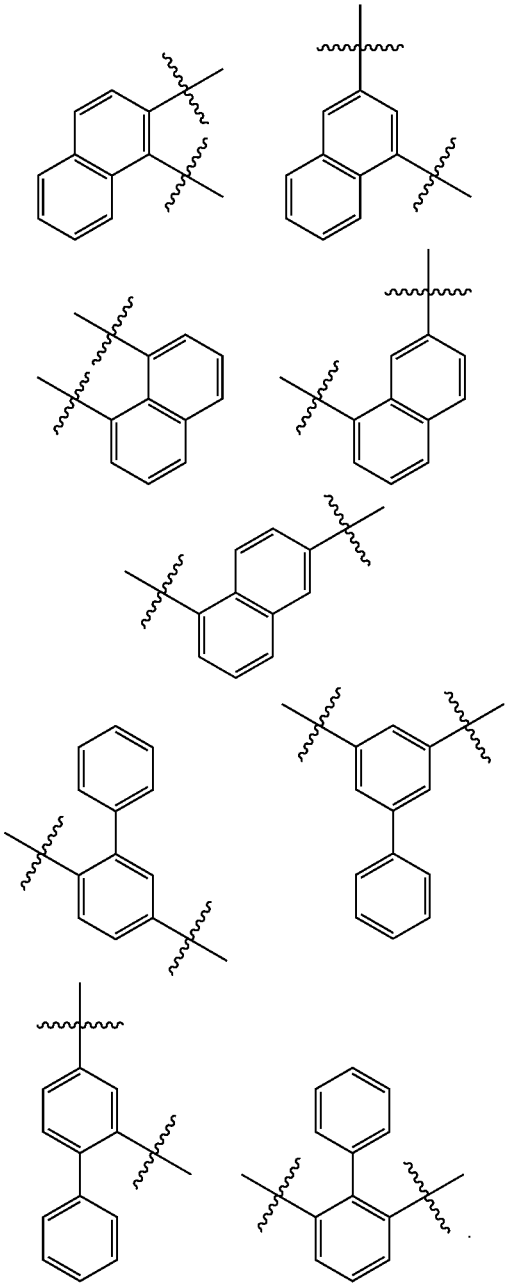

Preferably, in Chemical Formula 1,
$Y_1$ is N, $Y_2$ is N, and $Y_3$ is N; or
$Y_1$ is N, $Y_2$ is N, and $Y_3$ is $CR_3$; or
$Y_1$ is N, $Y_2$ is $CR_3$, and $Y_3$ is N; or
$Y_1$ is N, $Y_2$ is $CR_3$, and $Y_3$ or $CR_3$; or
$Y_1$ is $CR_3$, $Y_2$ is $CR_3$, and $Y_3$ is N.

Preferably, in Chemical Formula 1,
$Y_1$ is N, $Y_2$ is N, and $Y_3$ is N; or
$Y_1$ is N, $Y_2$ is N, and $Y_3$ is CH; or
$Y_1$ is N, $Y_2$ is CH, and $Y_3$ is N; or
$Y_1$ is N, $Y_2$ is CH, and $Y_3$ is CH; or
$Y_1$ is CH, $Y_2$ is CH, and $Y_3$ is N.

Preferably, in Chemical Formula 1, $Ar_{1a}$ and $Ar_{1b}$ are each independently a substituted or unsubstituted $C_{6-20}$ aryl; or a substituted or unsubstituted $C_{1-20}$ heteroaryl containing one heteroatom selected from the group consisting of N, O, and S.

For example, $Ar_1$ and $Ar_{1b}$ may be each independently any one selected from the group consisting of:

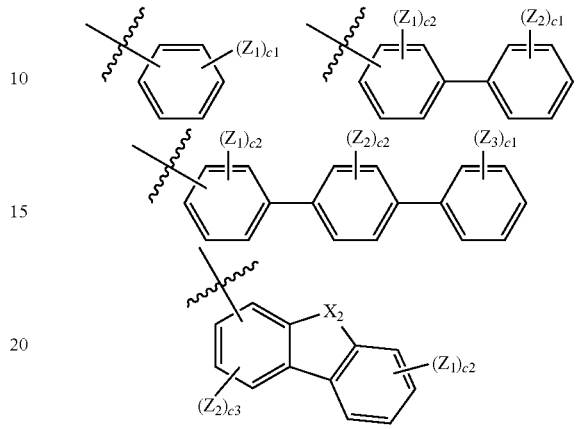

wherein,
$X_2$ is O, S, $NZ_4$, or $CZ_5Z_6$,
$Z_1$ to $Z_6$ are each independently hydrogen; deuterium; halogen; cyano; nitro; amino; a substituted or unsubstituted $C_{1-20}$ alkyl, a substituted or unsubstituted $C_{1-20}$ haloalkyl, a substituted or unsubstituted $C_{1-20}$ aryl, or a substituted or unsubstituted $C_{1-20}$ heteroaryl containing one or more heteroatoms selected from the group consisting of N, O and S,
c1 is an integer of 0 to 5,
c2 is an integer of 0 to 4, and
c3 is an integer of 0 to 3.

In this case, c1 represents the number of $Z_1$, and when c1 is 2 or more, two or more $Z_1$ may be the same as or different from each other. The description of c2 and c3 can be understood with reference to the description of c1 and the structure of the above chemical formula.

Specifically, for example, $Ar_{1a}$ and $Ar_{1b}$ may be each independently any one selected from the group consisting of:

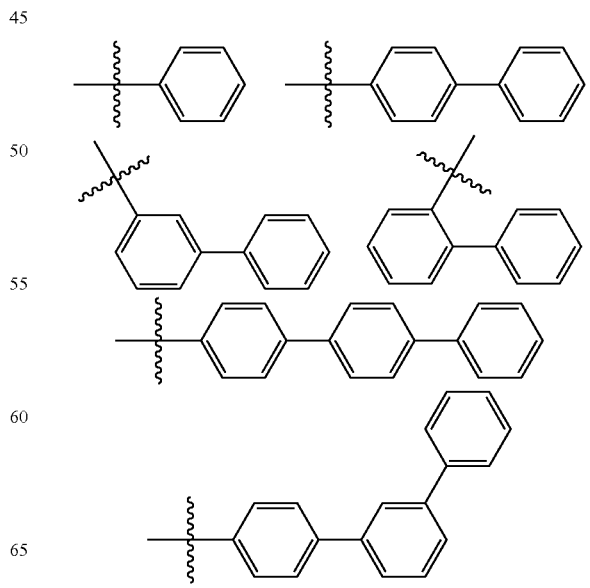

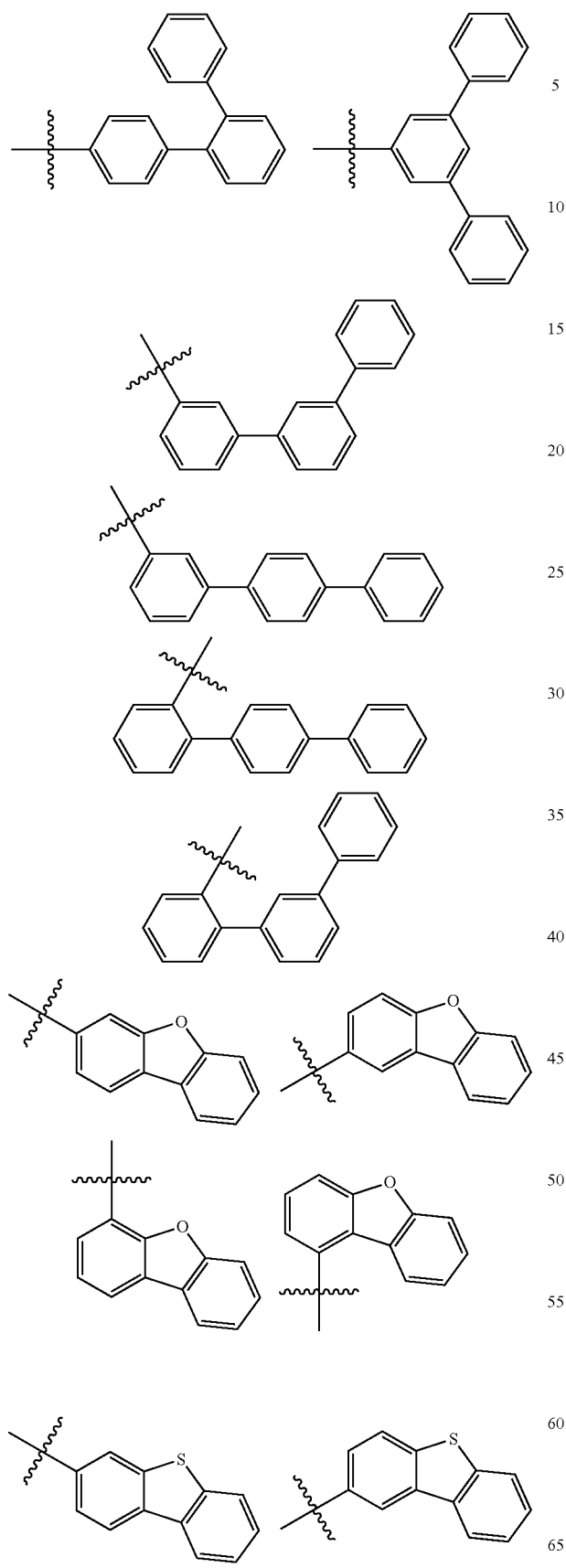
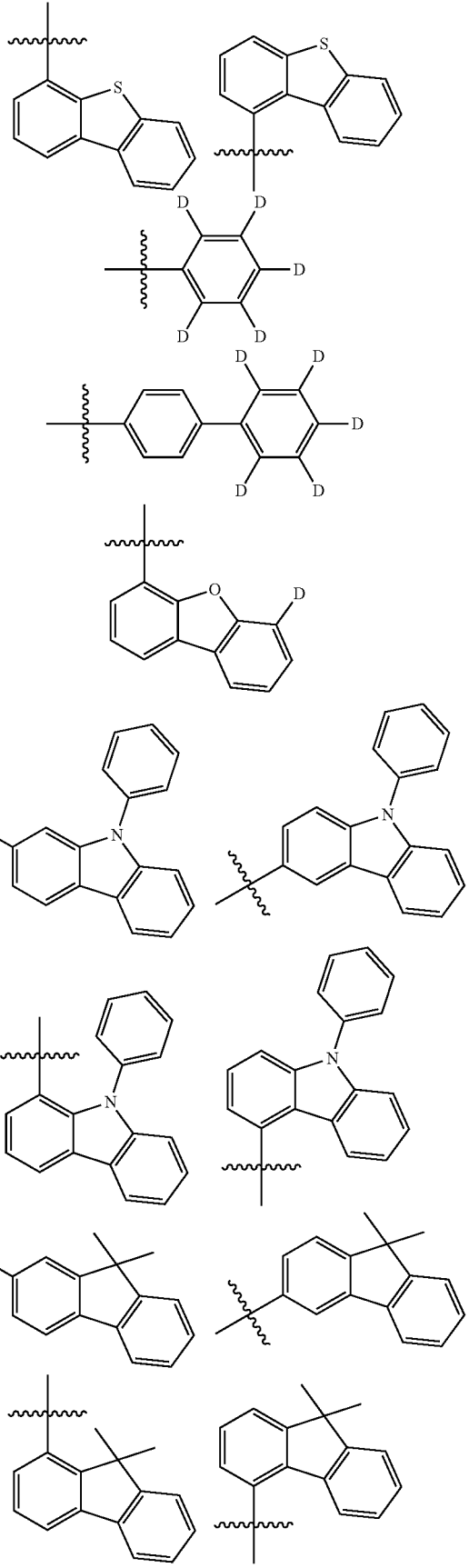

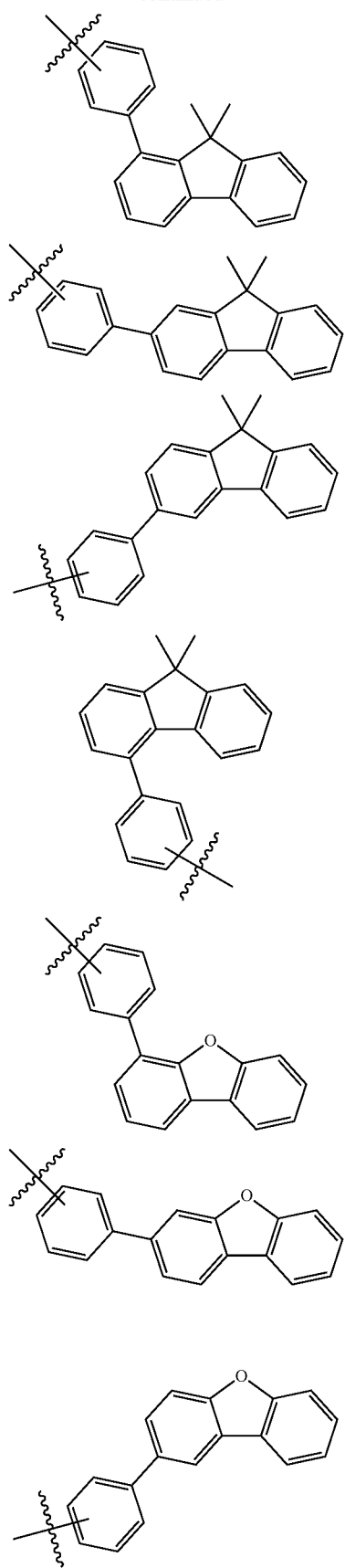
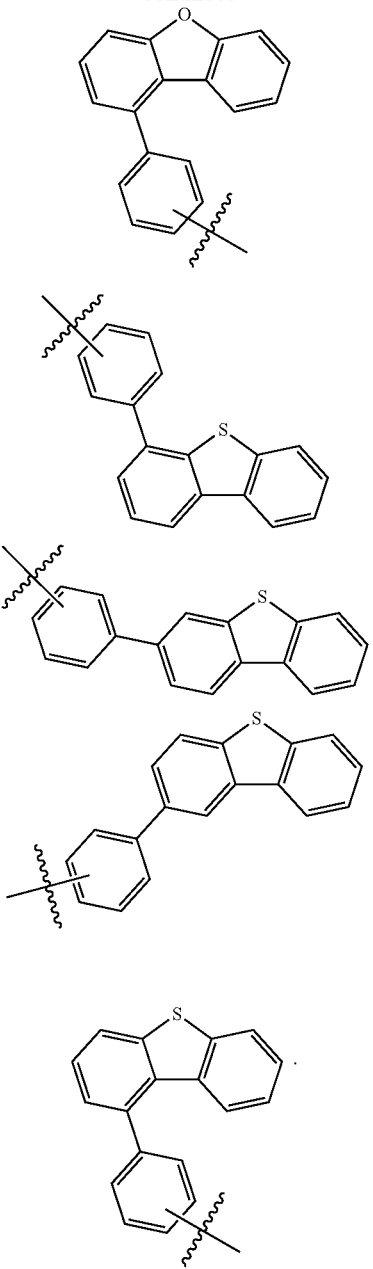

Further, in Chemical Formula 1, $Ar_2$ is substituted or unsubstituted $C_{6-60}$ aryl. Here, aryl does not include non-aromatic condensed rings. Specifically, a substituted or unsubstituted fluorenyl group is excluded from $Ar_2$ of the present invention.

Preferably, $Ar_2$ is a $C_{6-60}$ aryl which unsubstituted or substituted by a substituent independently selected from the group consisting of: deuterium; halogen; cyano; nitro; amino; a substituted or unsubstituted $C_{1-60}$ alkyl; a substituted or unsubstituted $C_{1-60}$ haloalkyl; $Si(Q_1)(Q_2)(Q_3)$; $C(Q_4)(Q_5)(Q_6)$ and $C_{6-60}$ aryl, wherein $Q_1$ to $Q_6$ are each independently hydrogen; deuterium; halogen; cyano; nitro; amino; a substituted or unsubstituted $C_{1-20}$ alkyl; or a substituted or unsubstituted $C_{6-20}$ aryl.

For example, Ar$_2$ may be any one selected from the group consisting of:
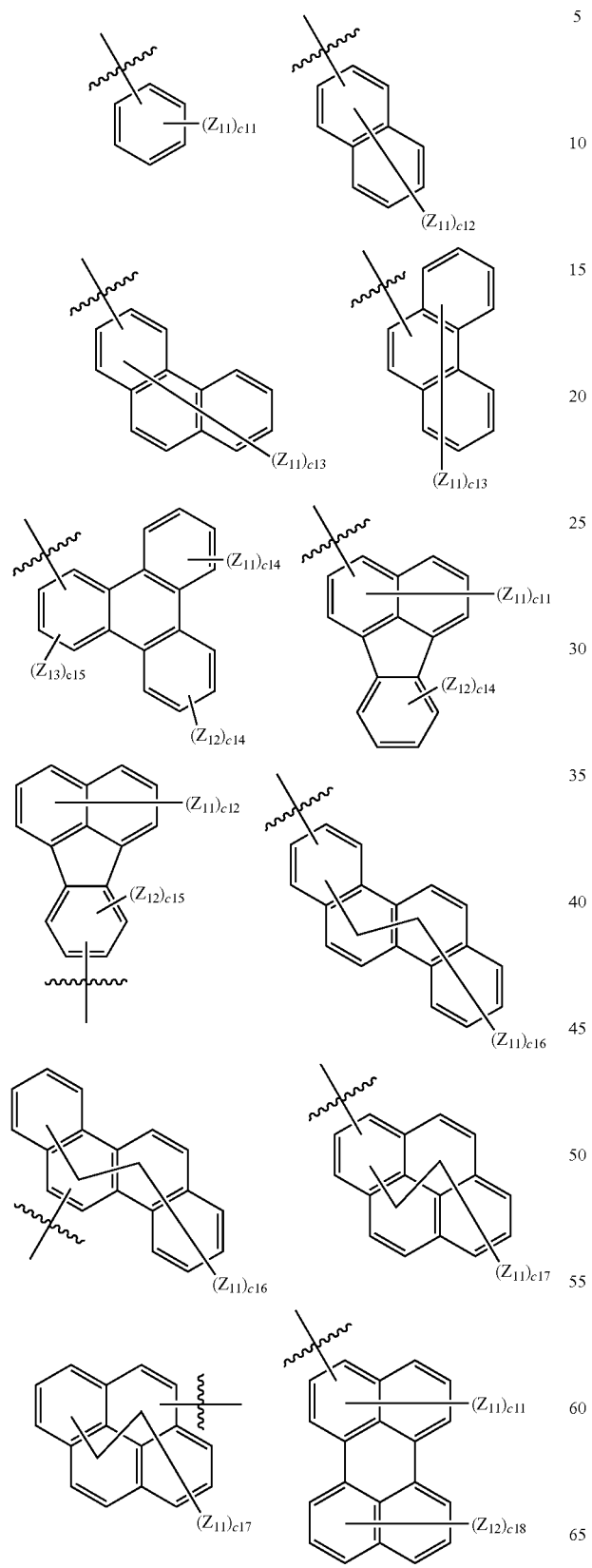
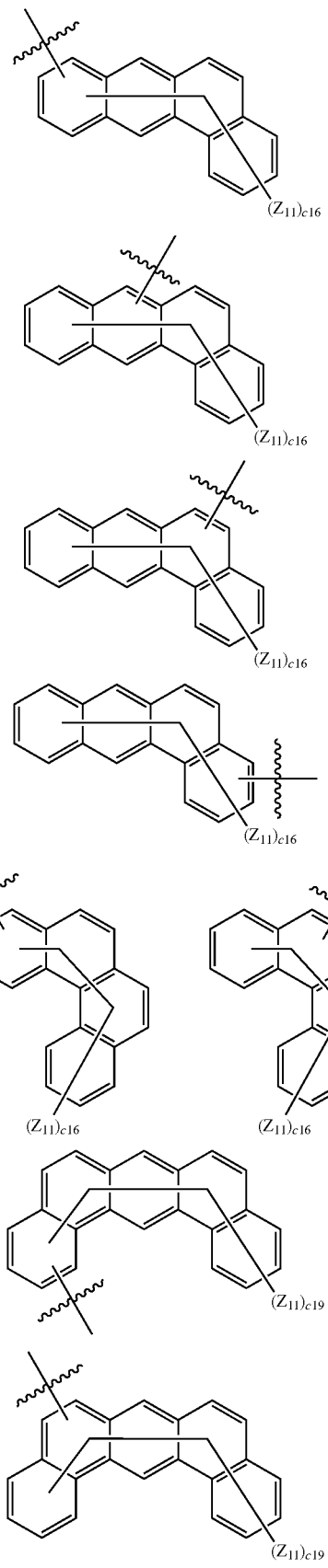

-continued

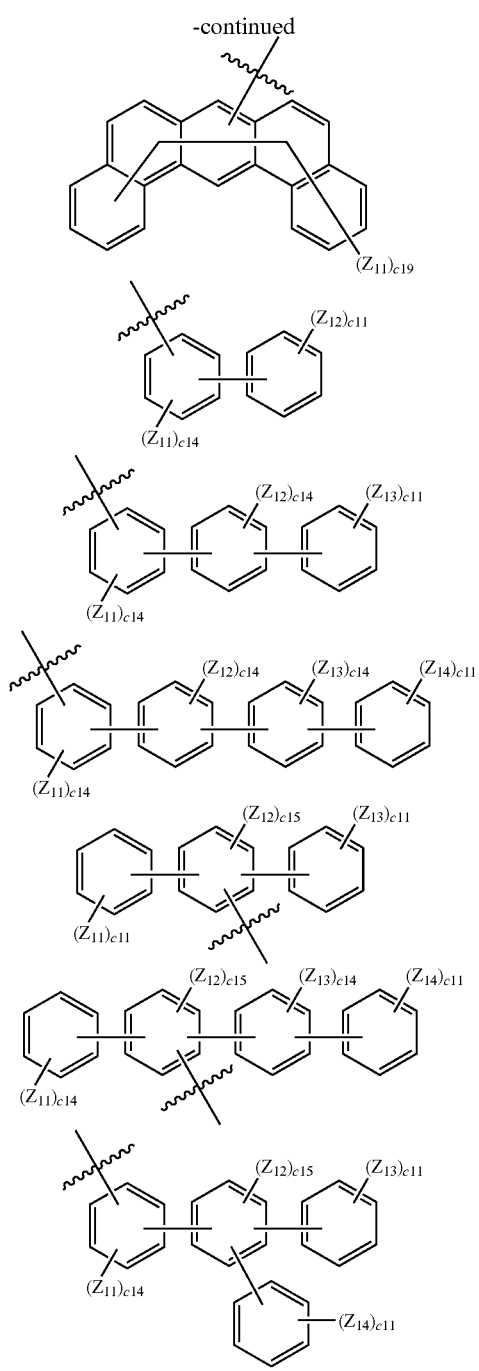

wherein
$Z_{11}$ to $Z_{14}$ are each independently hydrogen; deuterium; halogen; cyano; nitro; amino; a substituted or unsubstituted $C_{1-60}$ alkyl; a substituted or unsubstituted $C_{1-60}$ haloalkyl; $Si(Q_1)(Q_2)(Q_3)$; $C(Q_4)(Q_5)(Q_6)$ and $C_{6-60}$ aryl,
  wherein $Q_1$ to $Q_6$ are each independently hydrogen; deuterium; halogen; cyano; nitro; amino; a substituted or unsubstituted $C_{1-20}$ alkyl; or a substituted or unsubstituted $C_{6-20}$ aryl,
c11 is an integer of 0 to 5,
c12 is an integer of 0 to 7,
c13 is an integer of 0 to 9,
c14 is an integer of 0 to 4,
c15 is an integer of 0 to 3,
c16 is an integer of 0 to 11,
c17 is an integer of 0 to 9,
c18 is an integer of 0 to 6, and
c19 is an integer of 0 to 12.

Here, c11 represents the number of $Z_{11}$, and when c11 is 2 or more, two or more $Z_{11}$ may be the same as or different from each other. The description of c12 to c19 can be understood with reference to the description of c11 and the structure of the above chemical formula.

Preferably, $Q_1$ to $Q_6$ are hydrogen; deuterium; halogen; cyano; nitro; amino; methyl; or phenyl.

Specifically, for example, $Ar_2$ may be any one selected from the group consisting of:

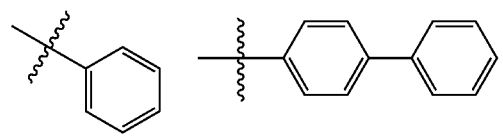

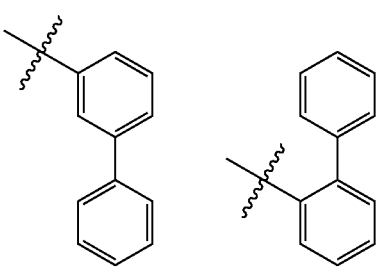

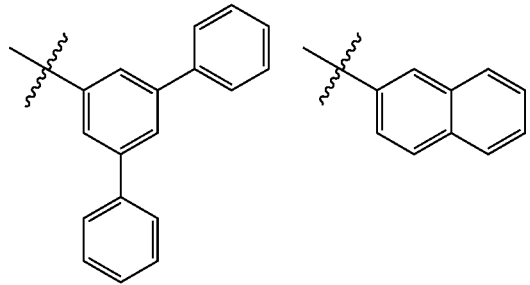

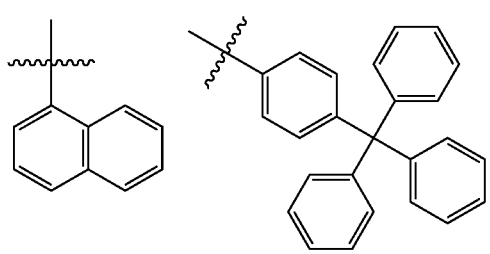

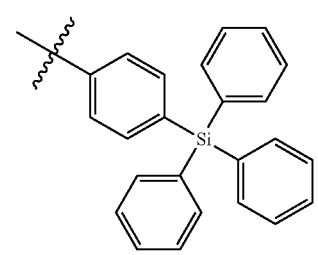

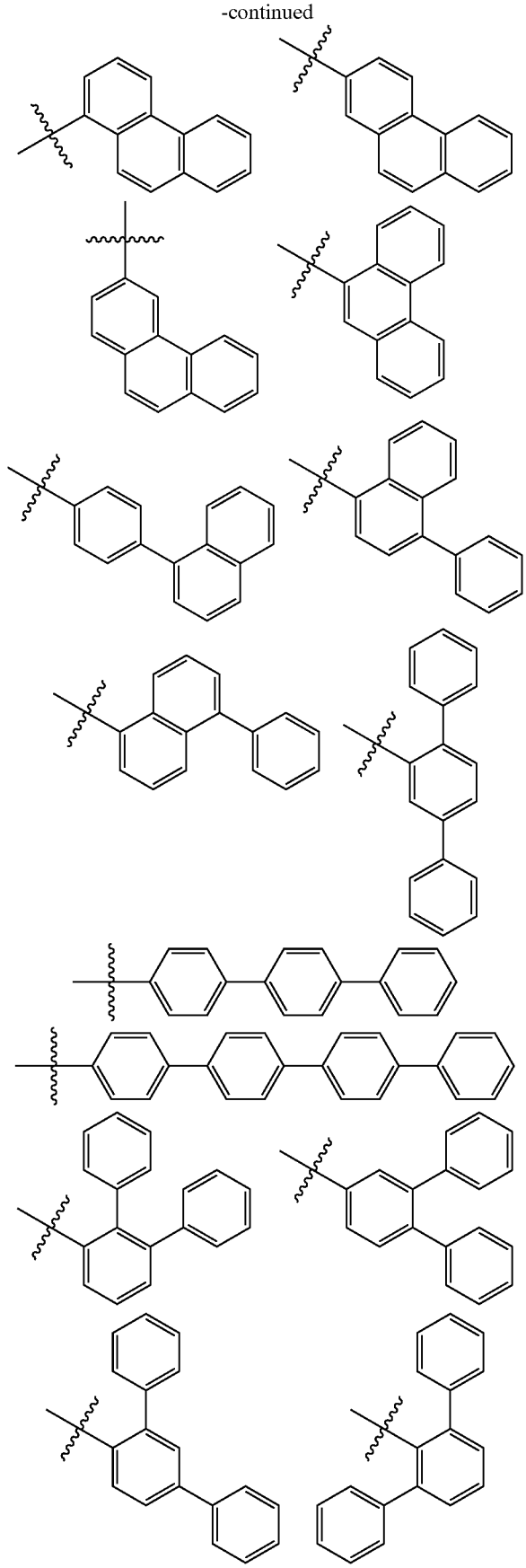
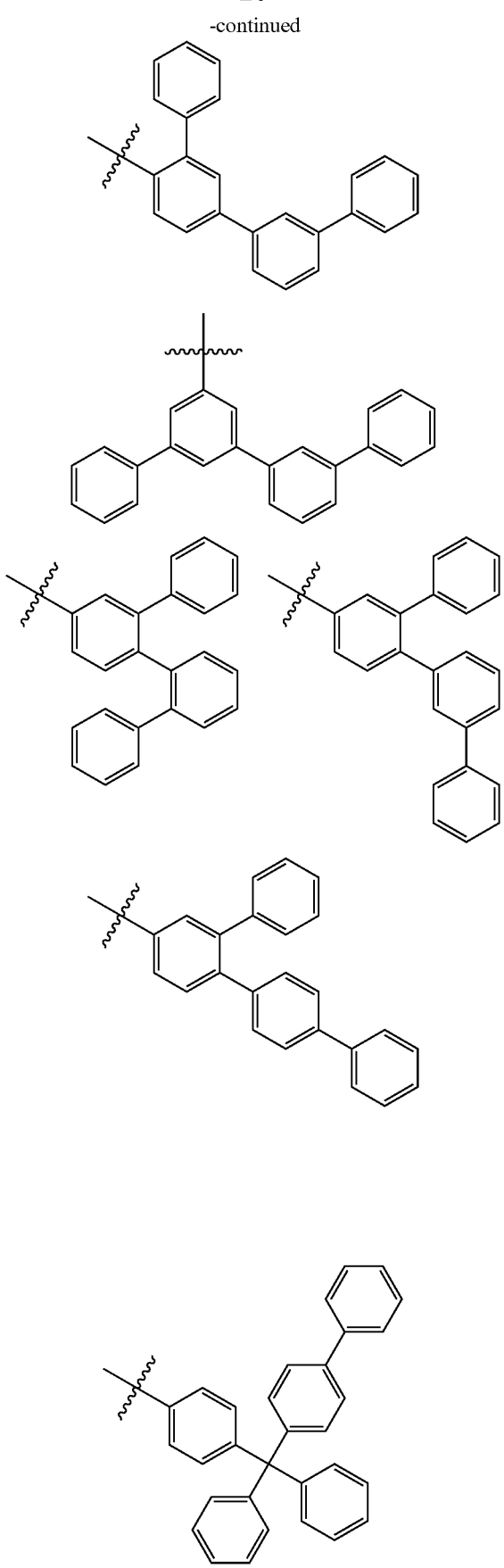

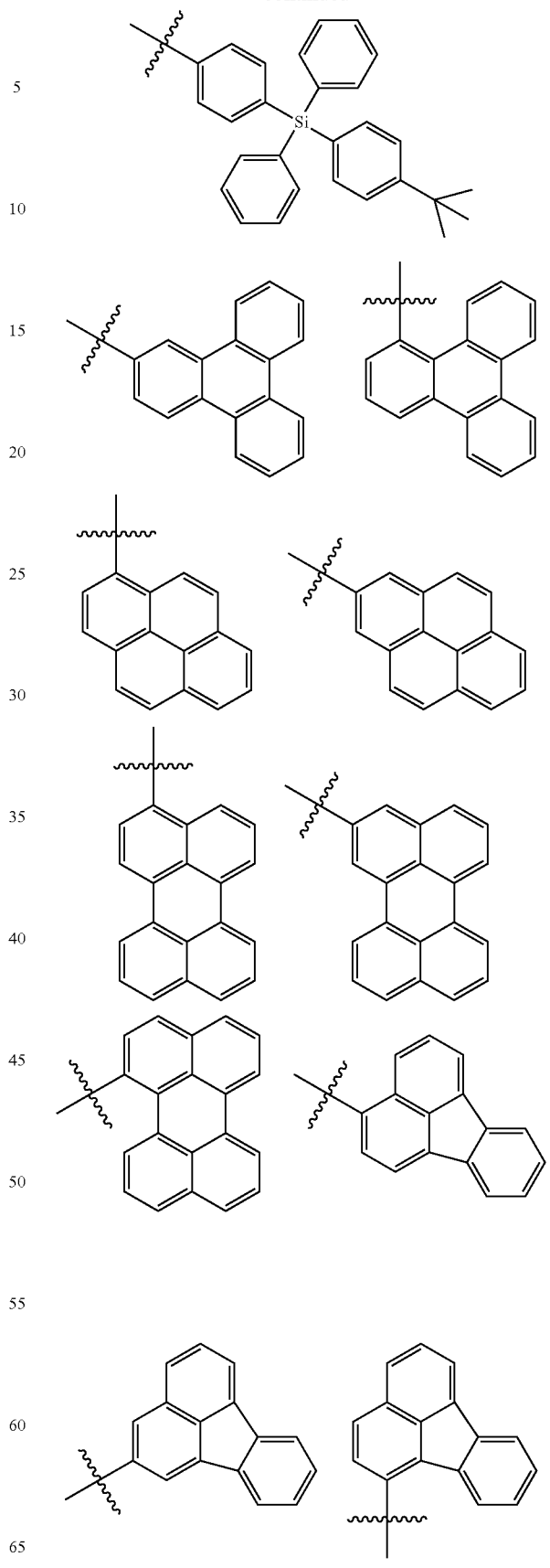

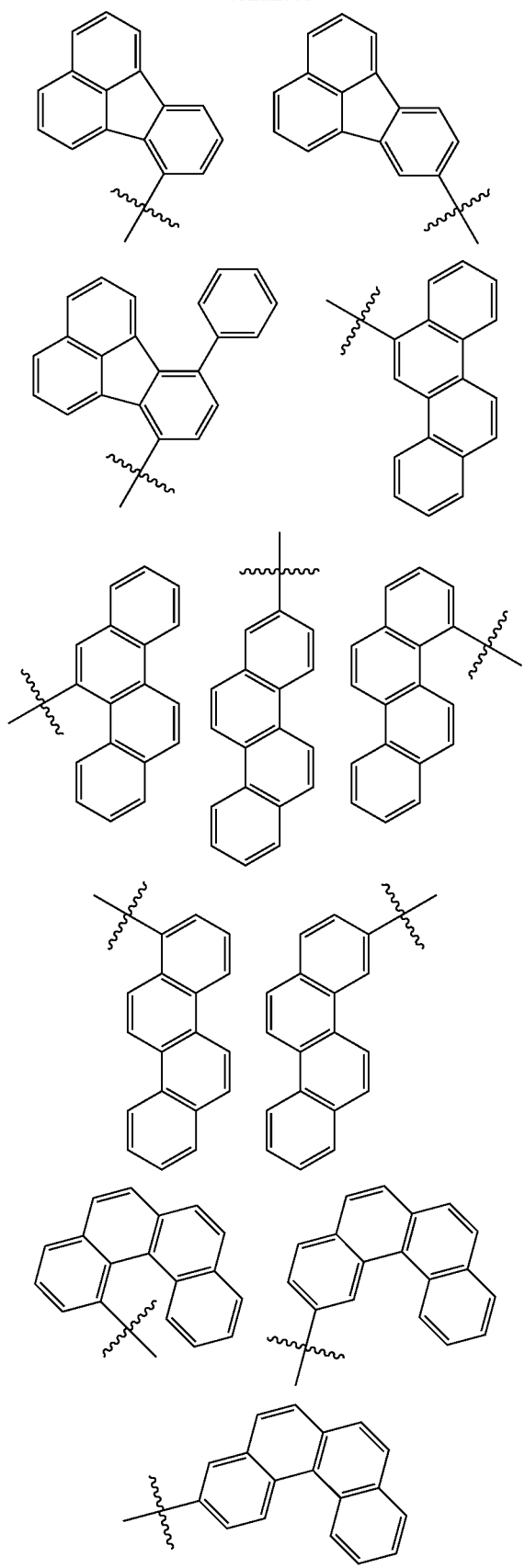
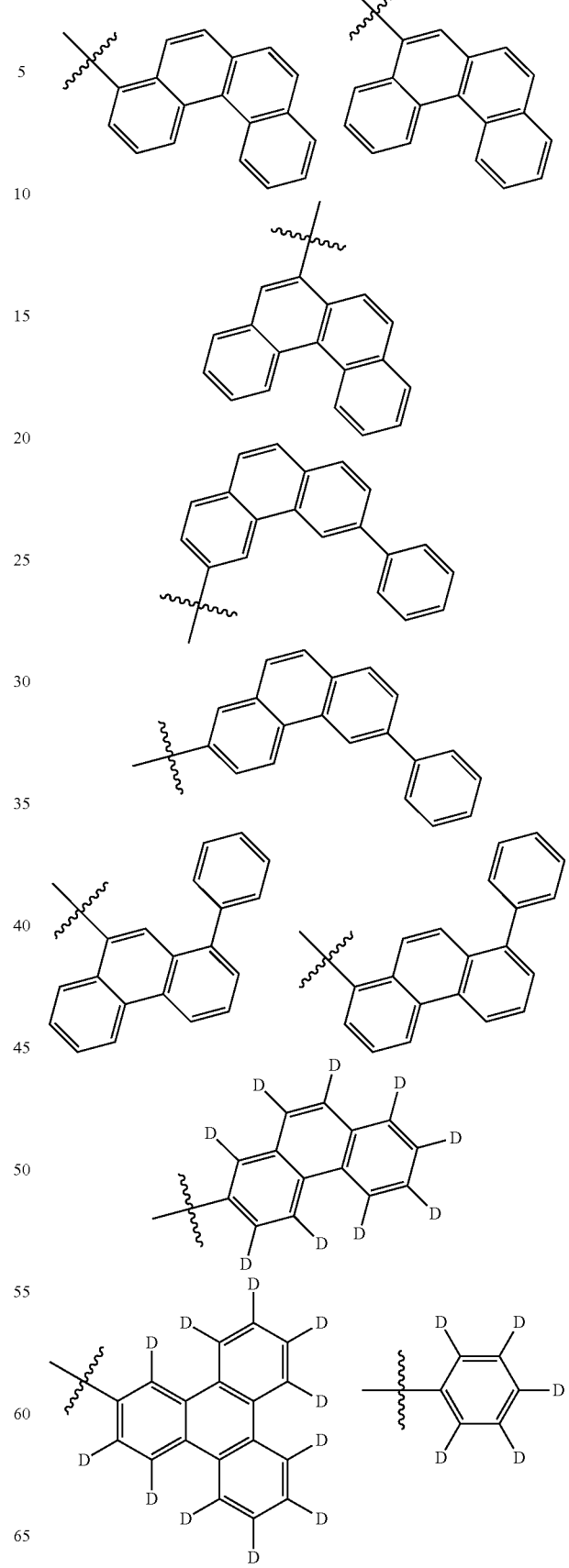

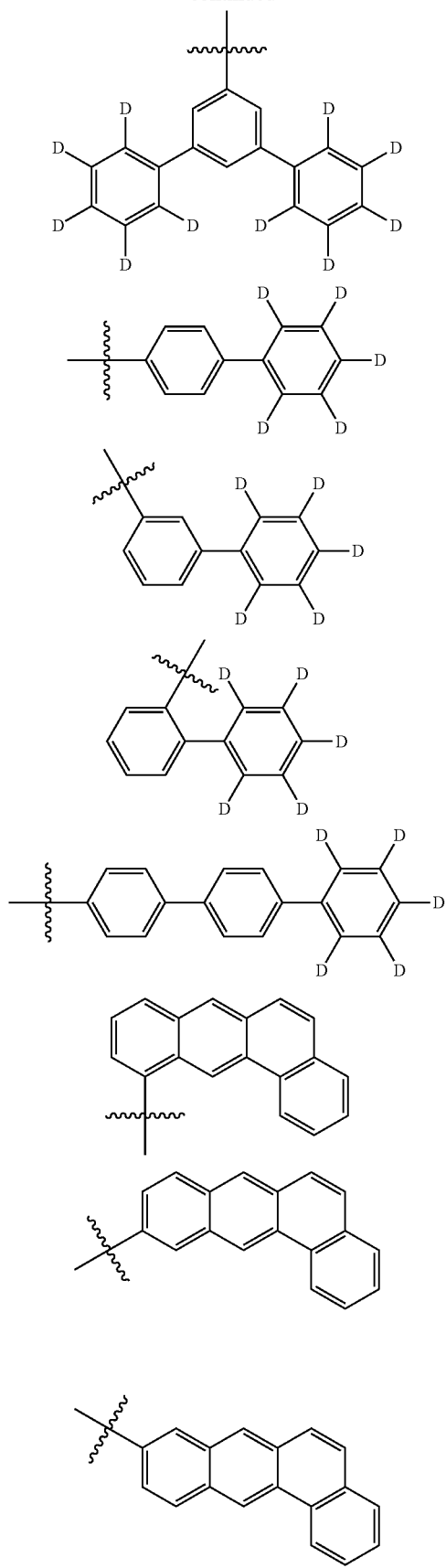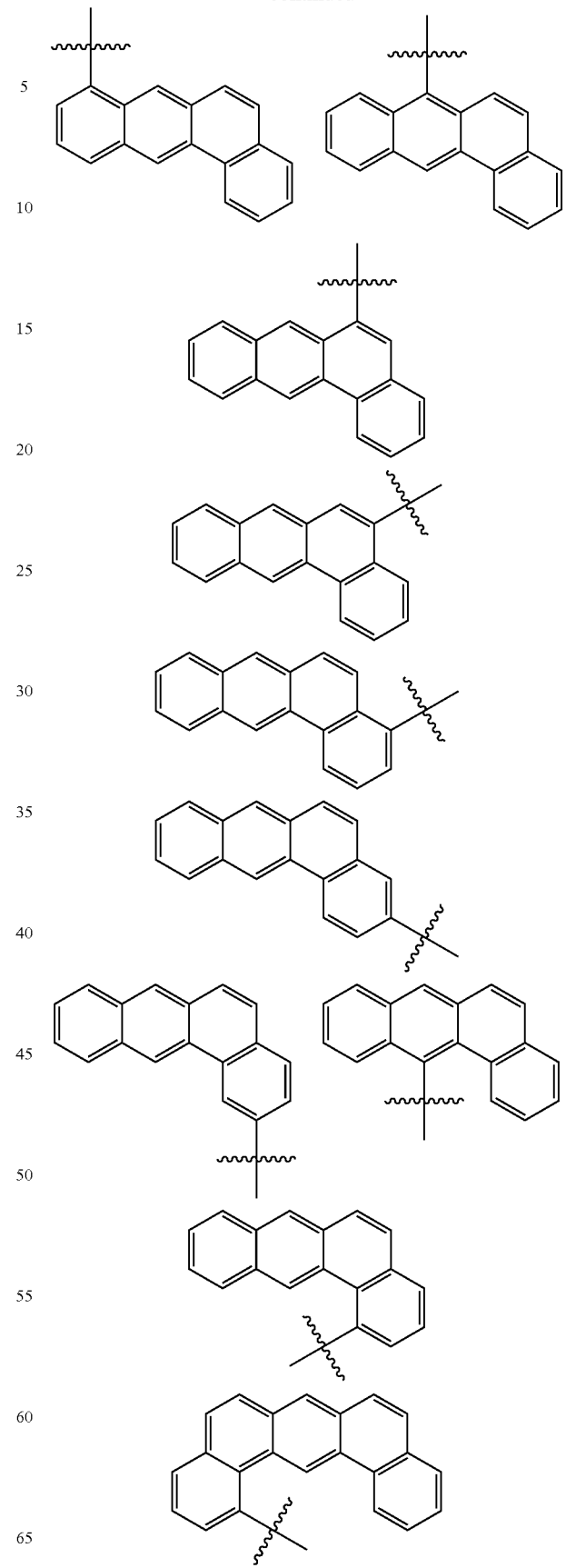

-continued

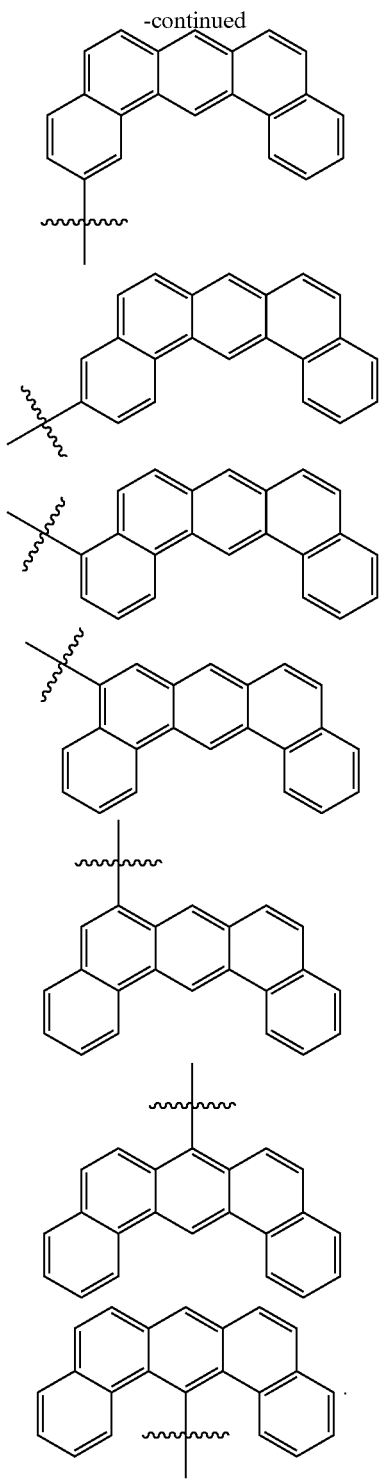

Further, in Chemical Formula 1, $R_1$ to $R_3$ are each independently hydrogen; deuterium; cyano; or a substituted or unsubstituted $C_{1-10}$ alkyl.

For example, $R_1$ and $R_2$ may be each independently hydrogen, deuterium, cyano, methyl, or deuterium-substituted methyl, and $R_3$ may be hydrogen.

In Chemical Formula 1, n1 represents the number of $R_1$, and when n1 is 2 or more, two or more $R_1$ may be the same as or different from each other. The description of n2 can be understood with reference to the description of n1 and the structure of Chemical Formula 1.

For example, the compound may be selected from the group consisting of the following compounds:

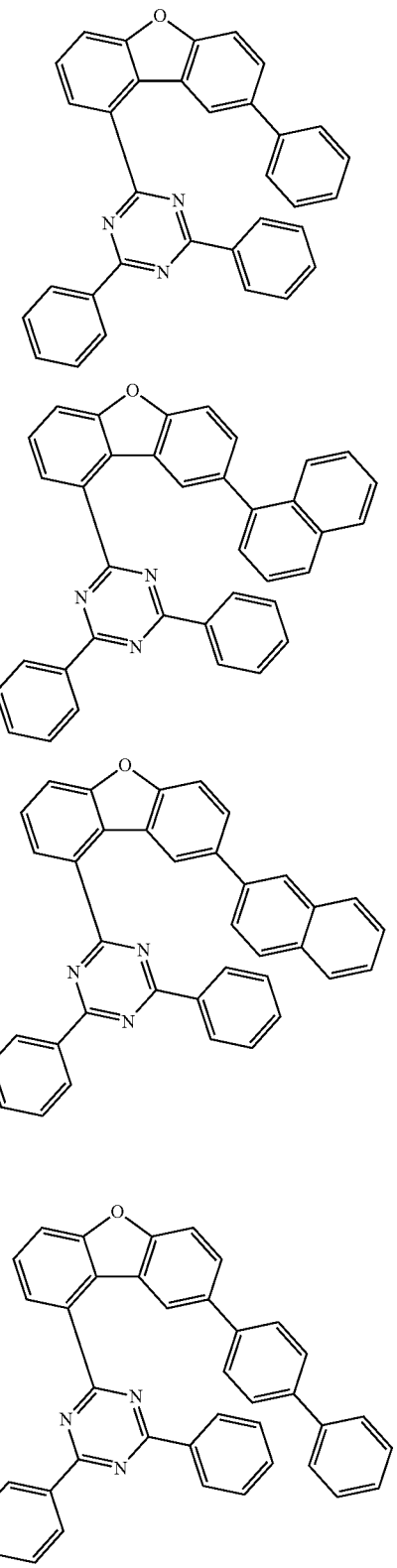

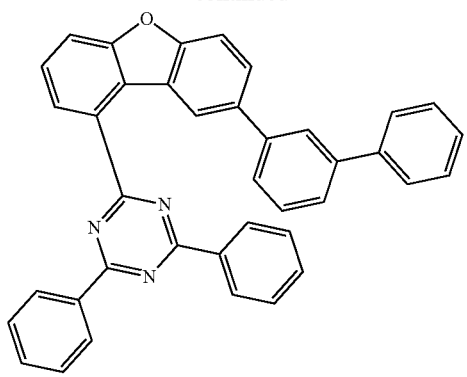
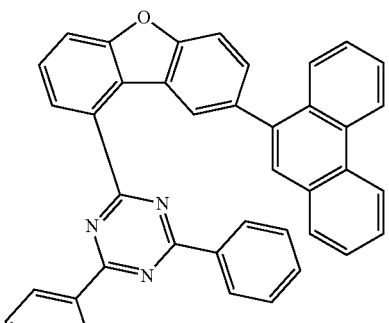
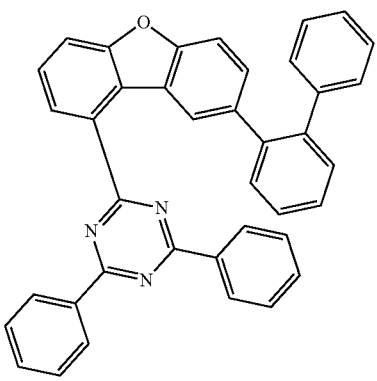
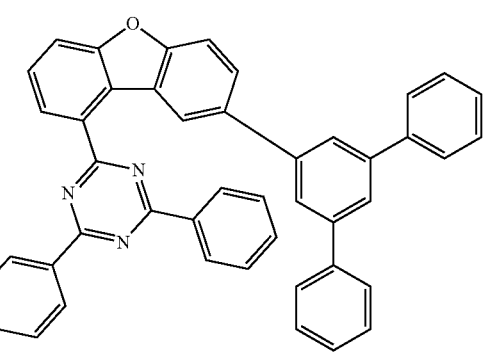
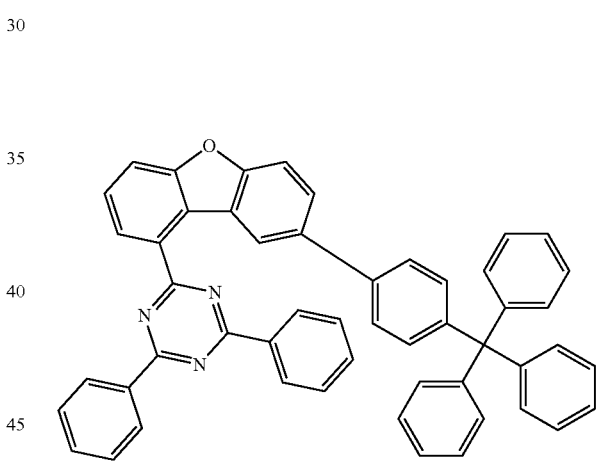
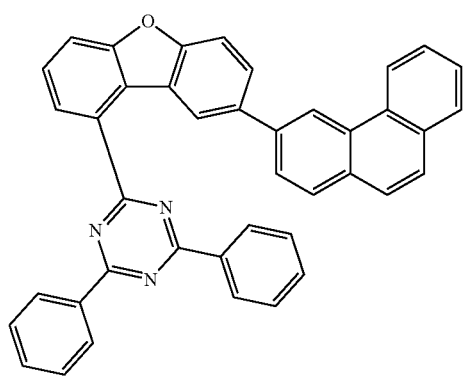
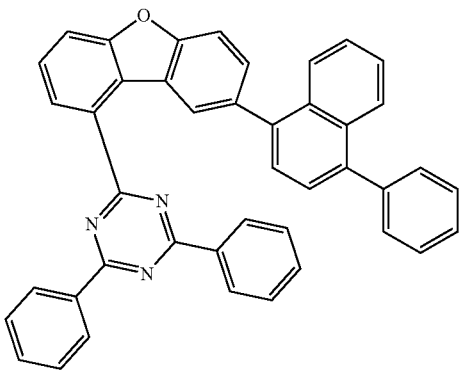

-continued
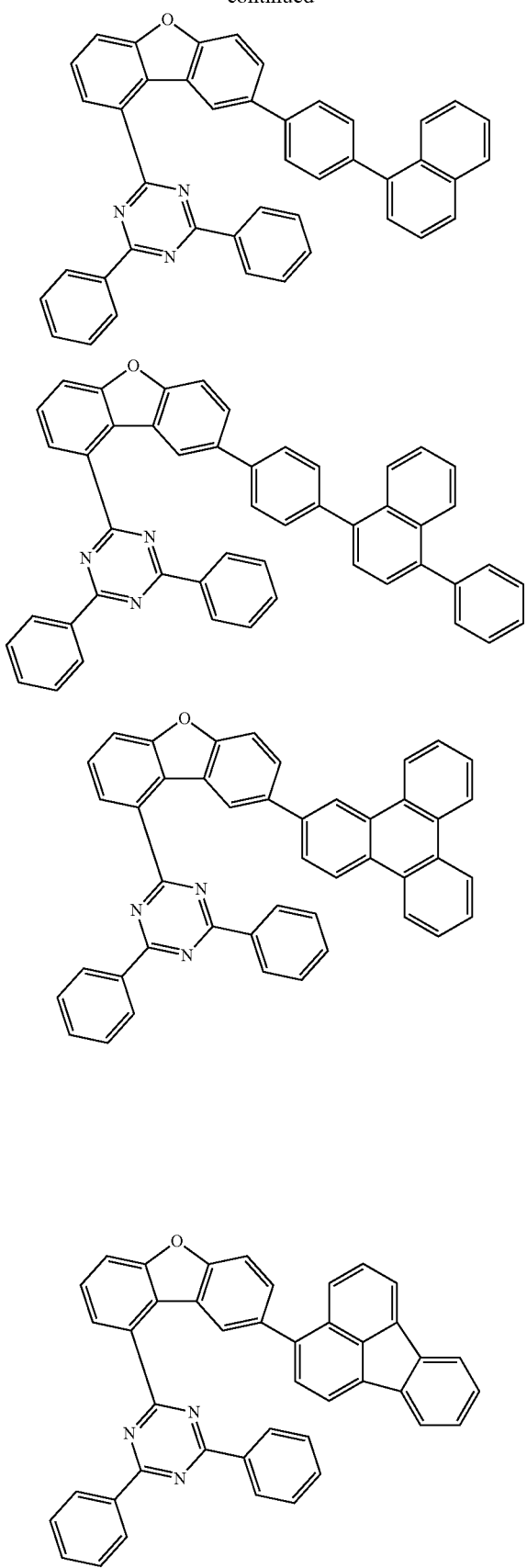
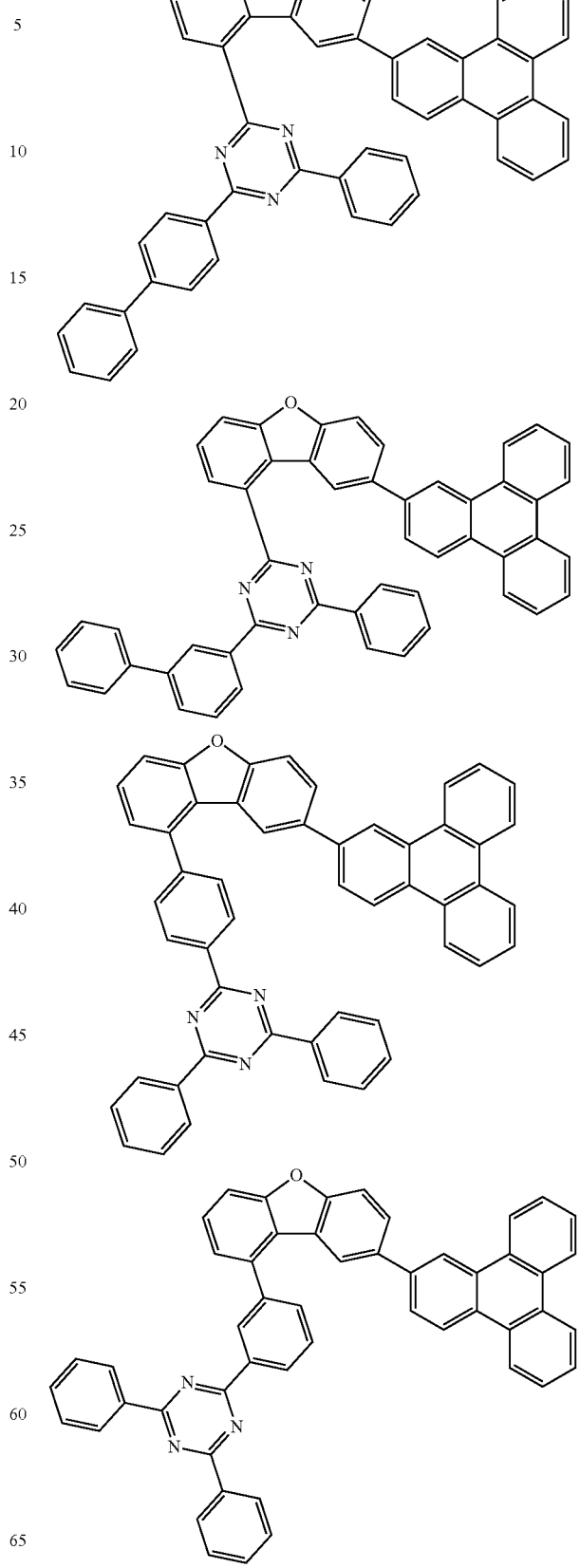

33
-continued
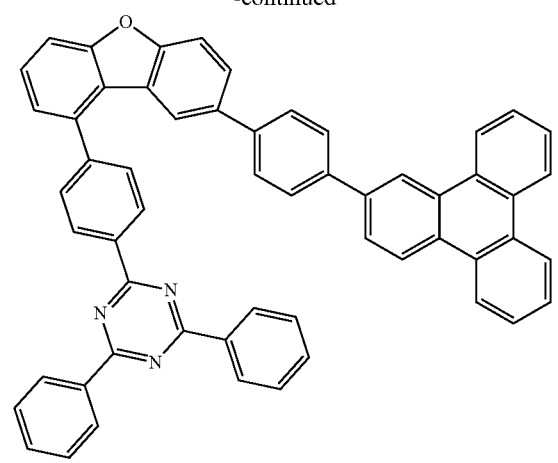
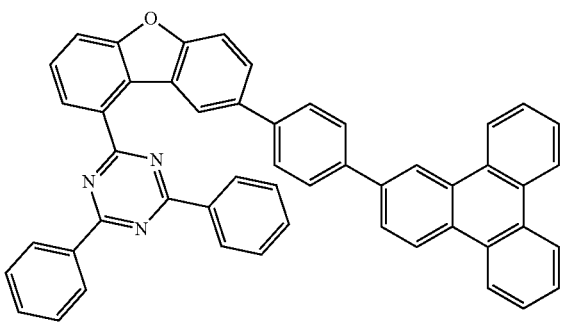
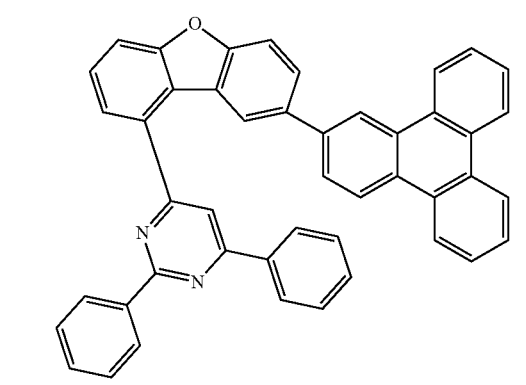
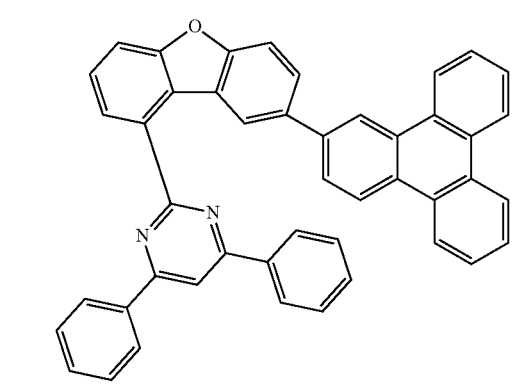
34
-continued
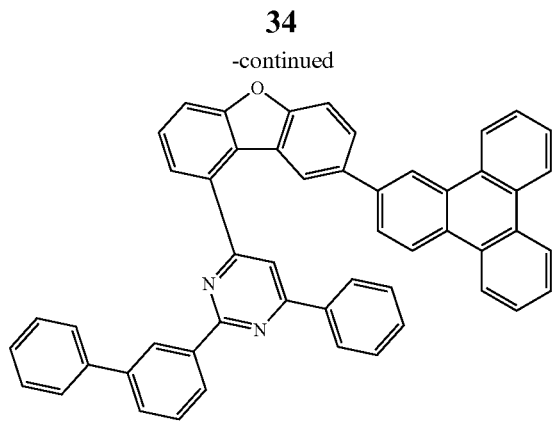
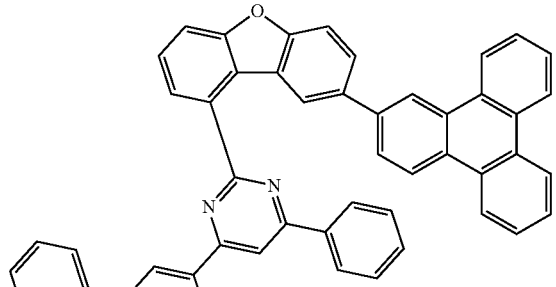
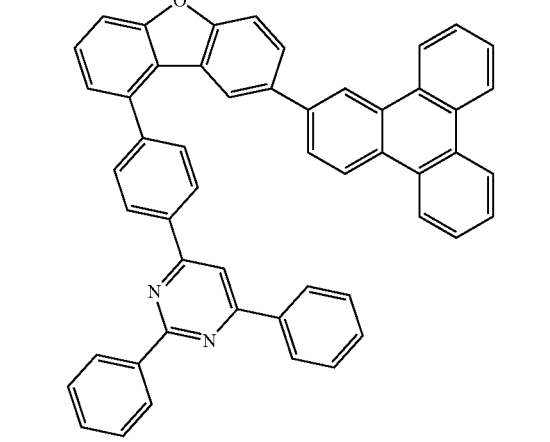
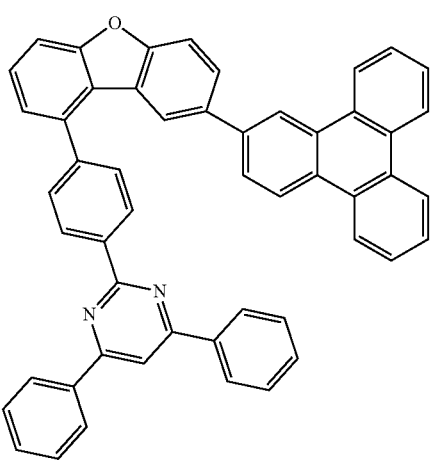

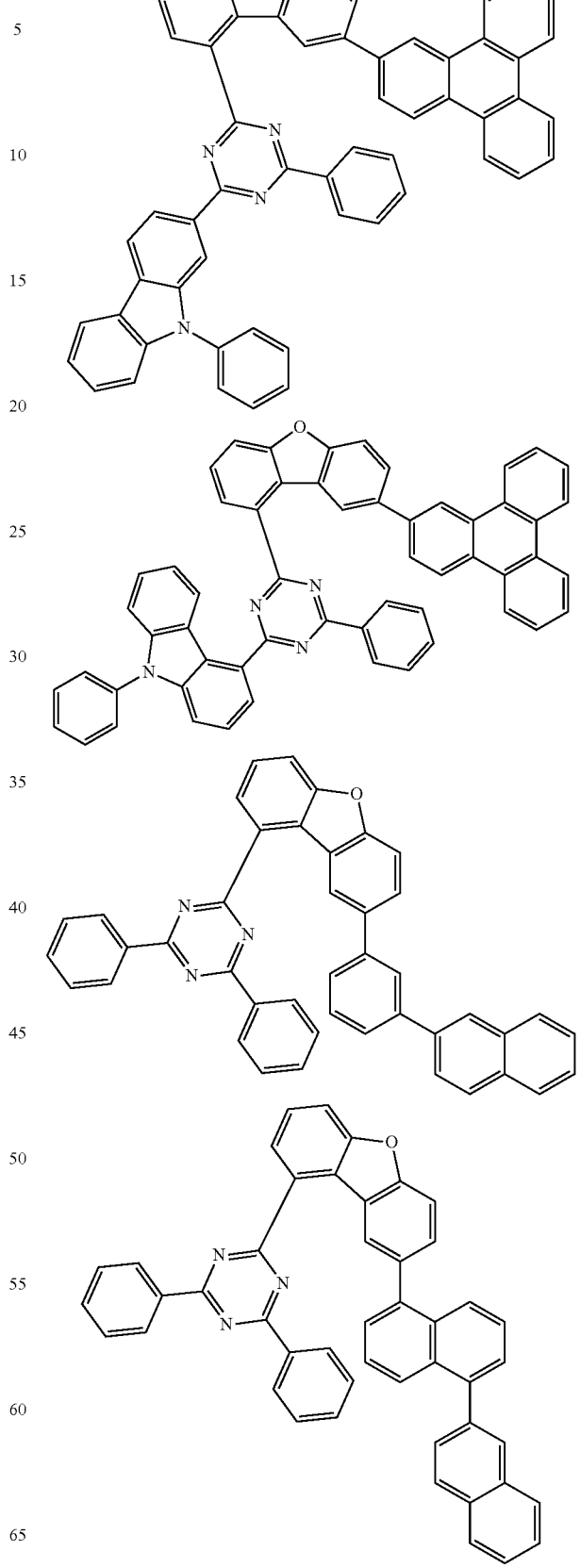

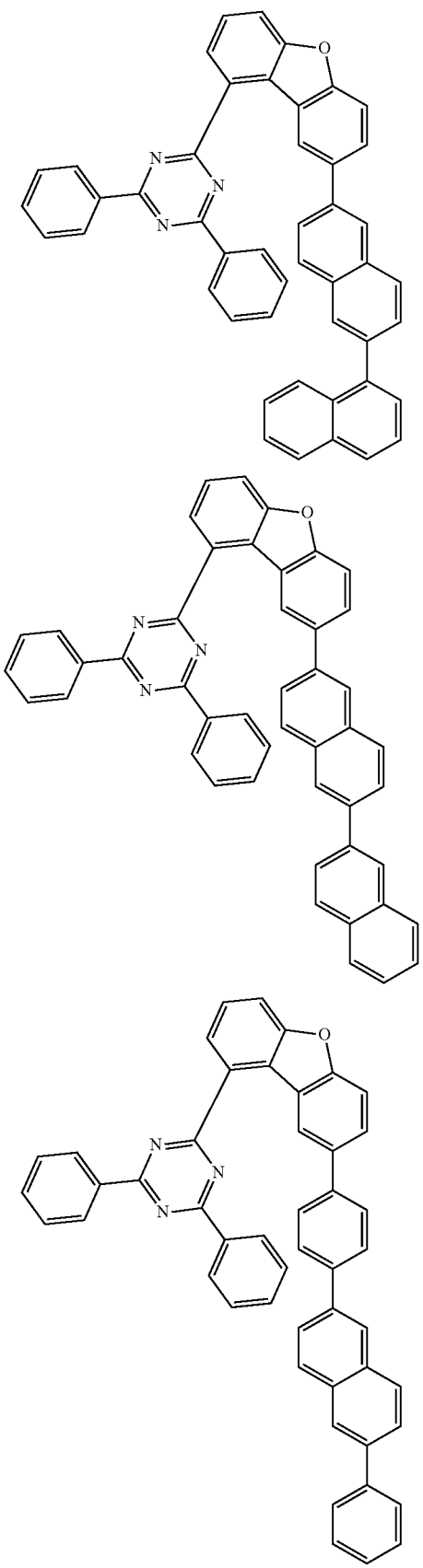
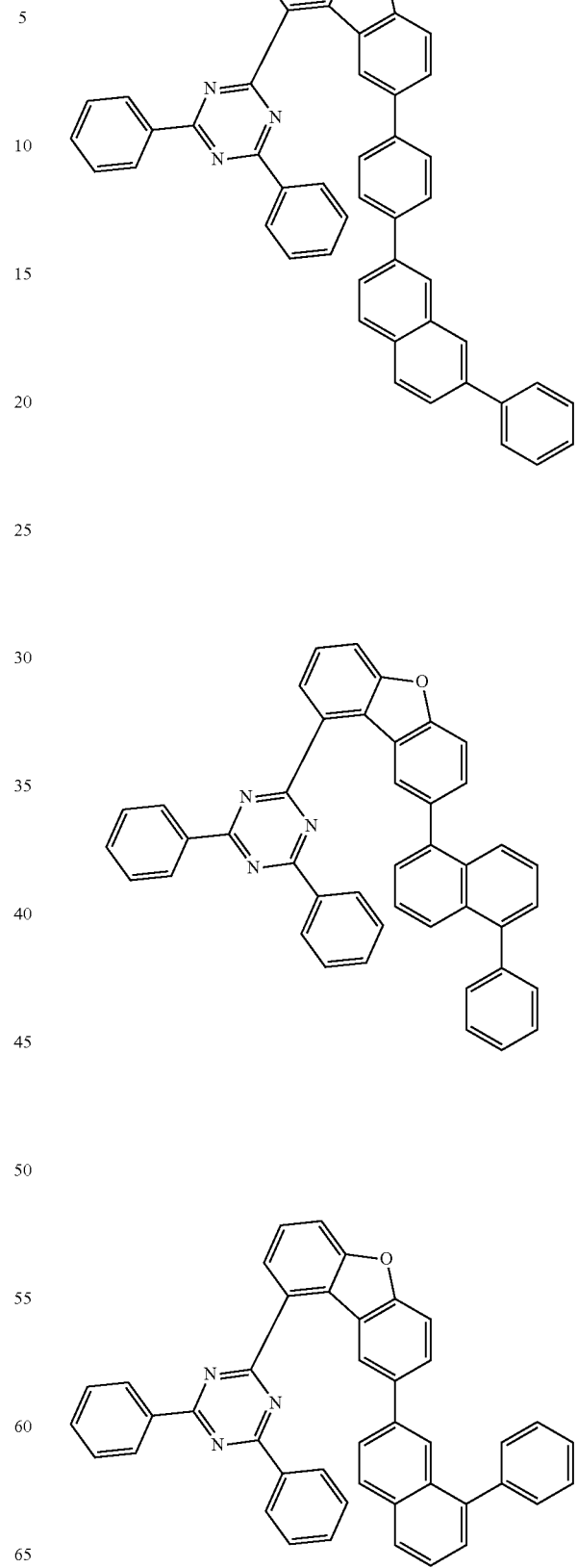

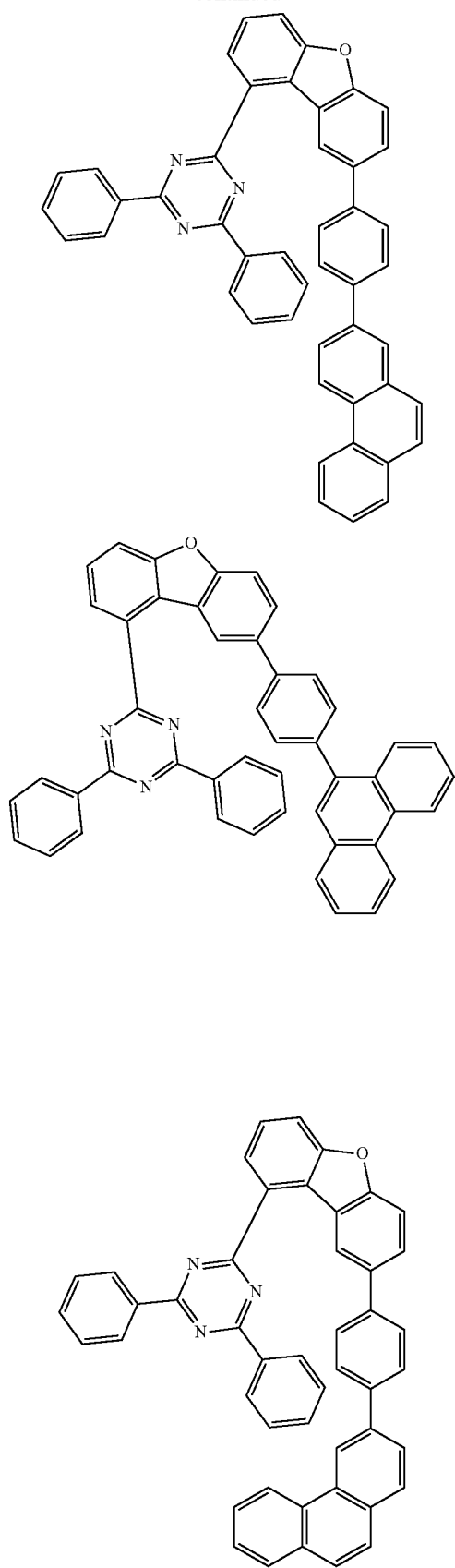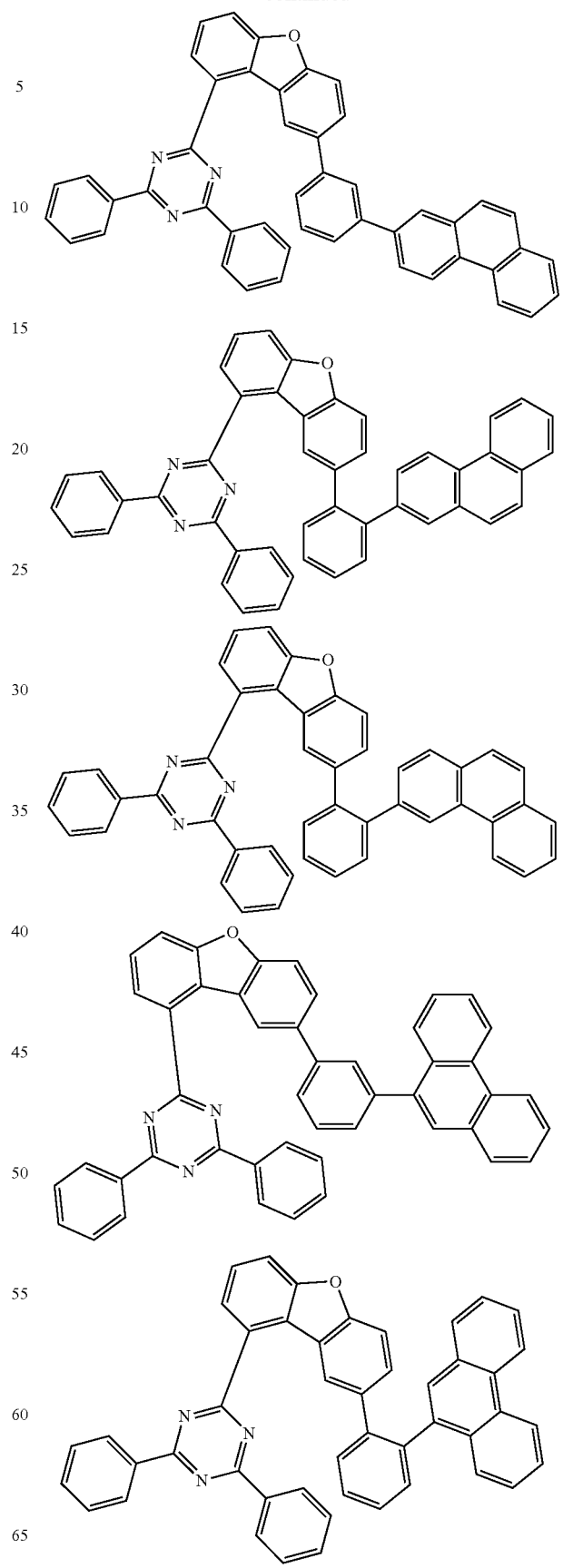

41
-continued
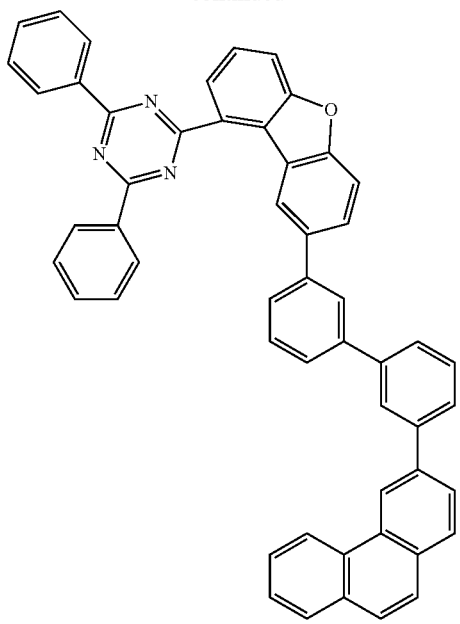
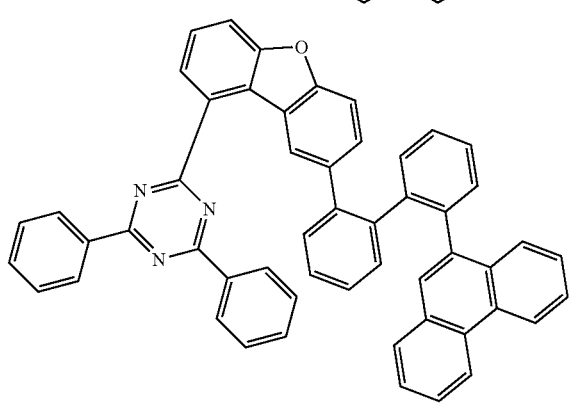
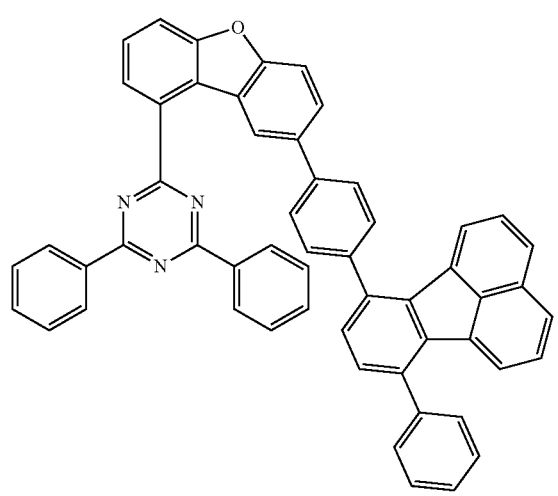
42
-continued
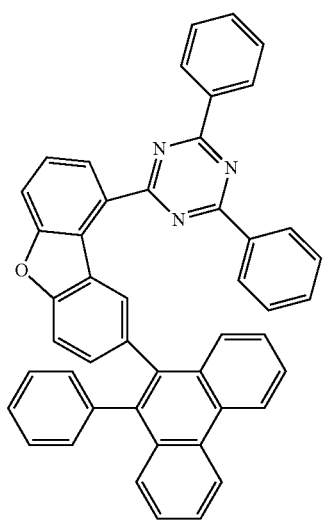
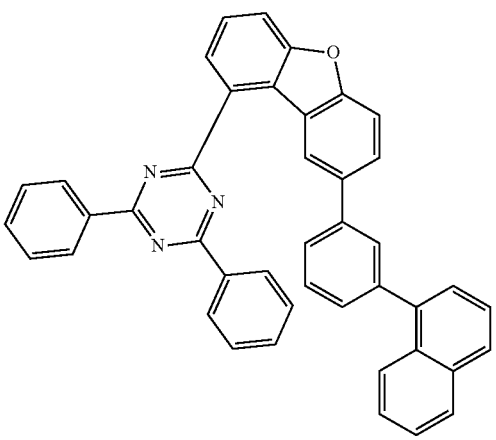
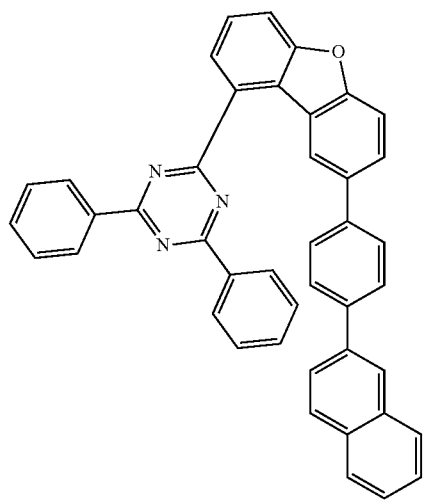

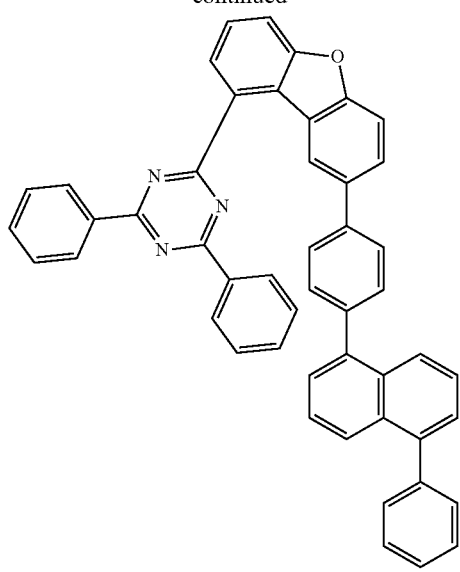
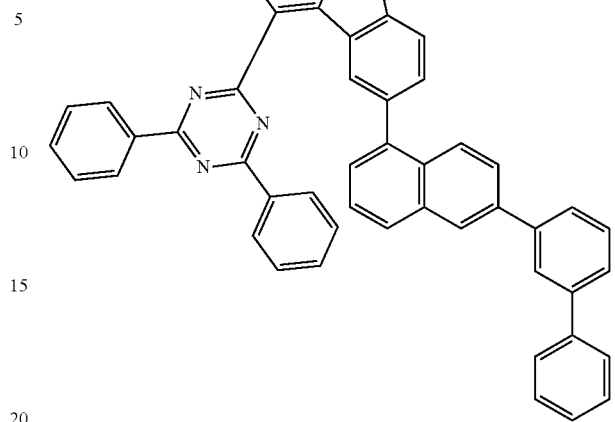
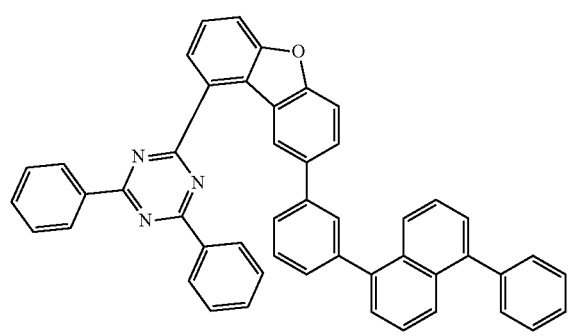
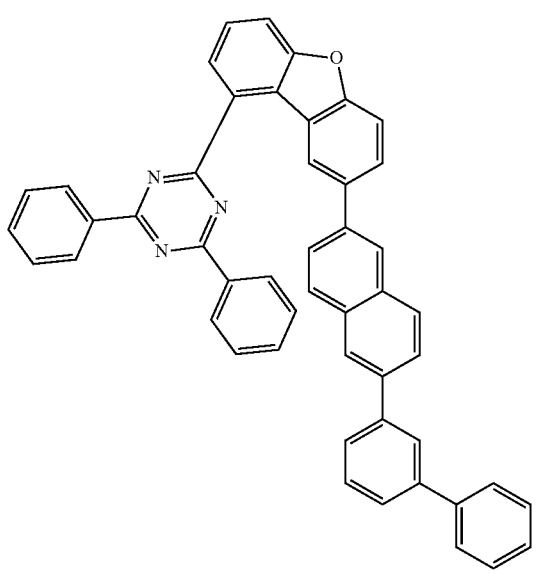
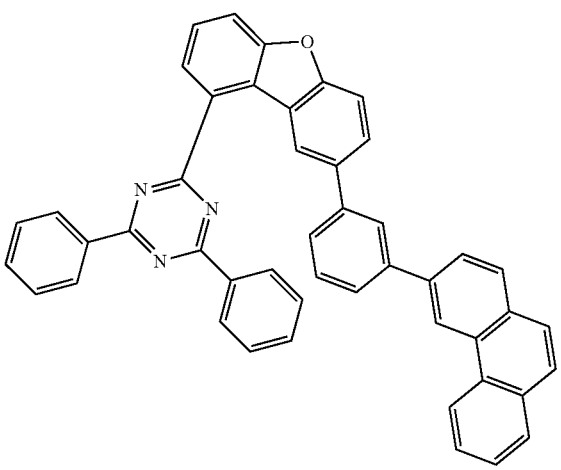

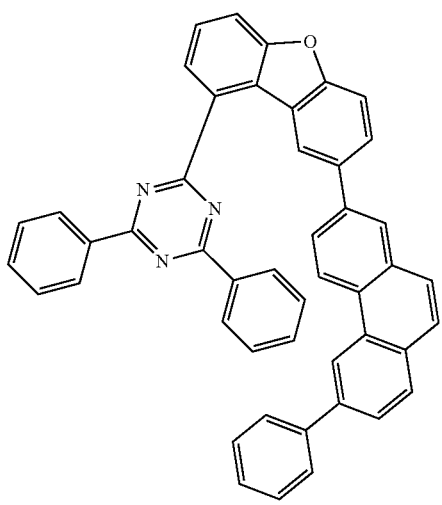
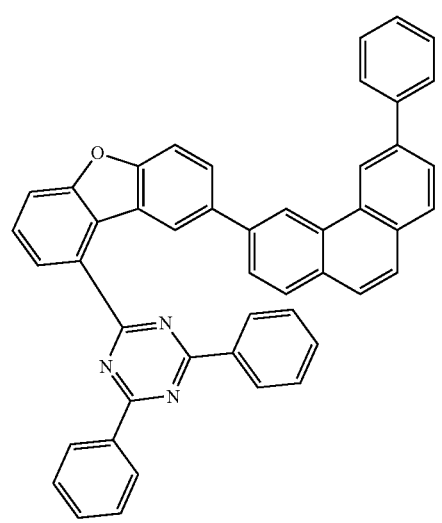
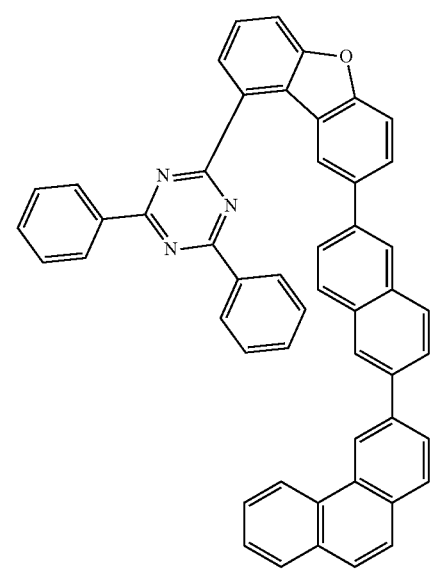
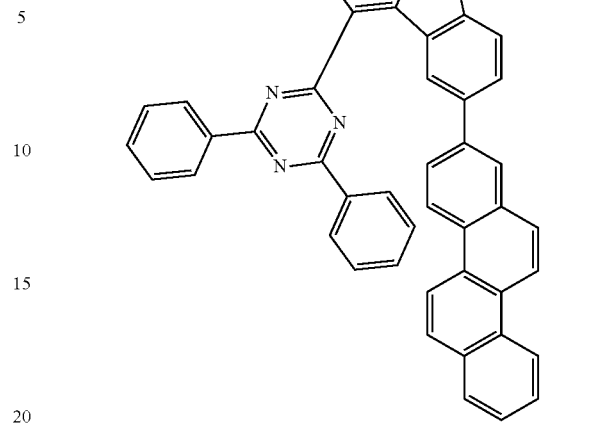
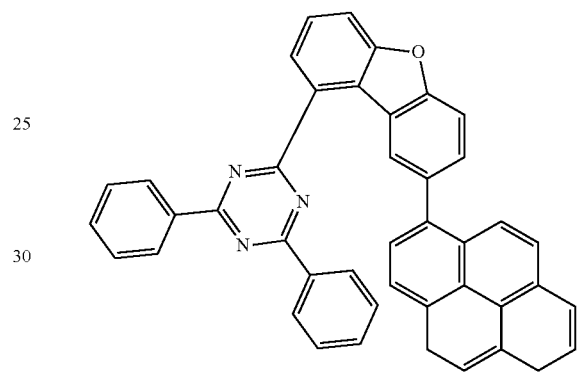
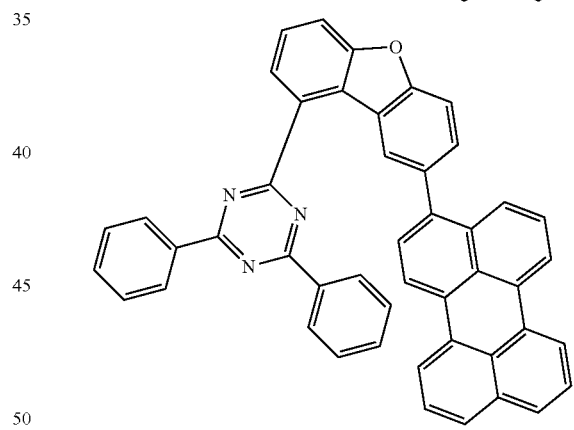
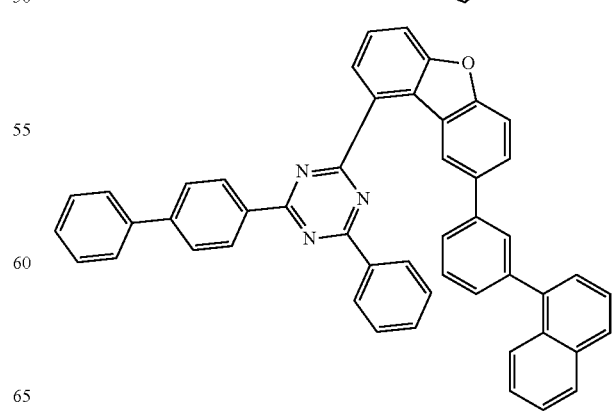

47
-continued
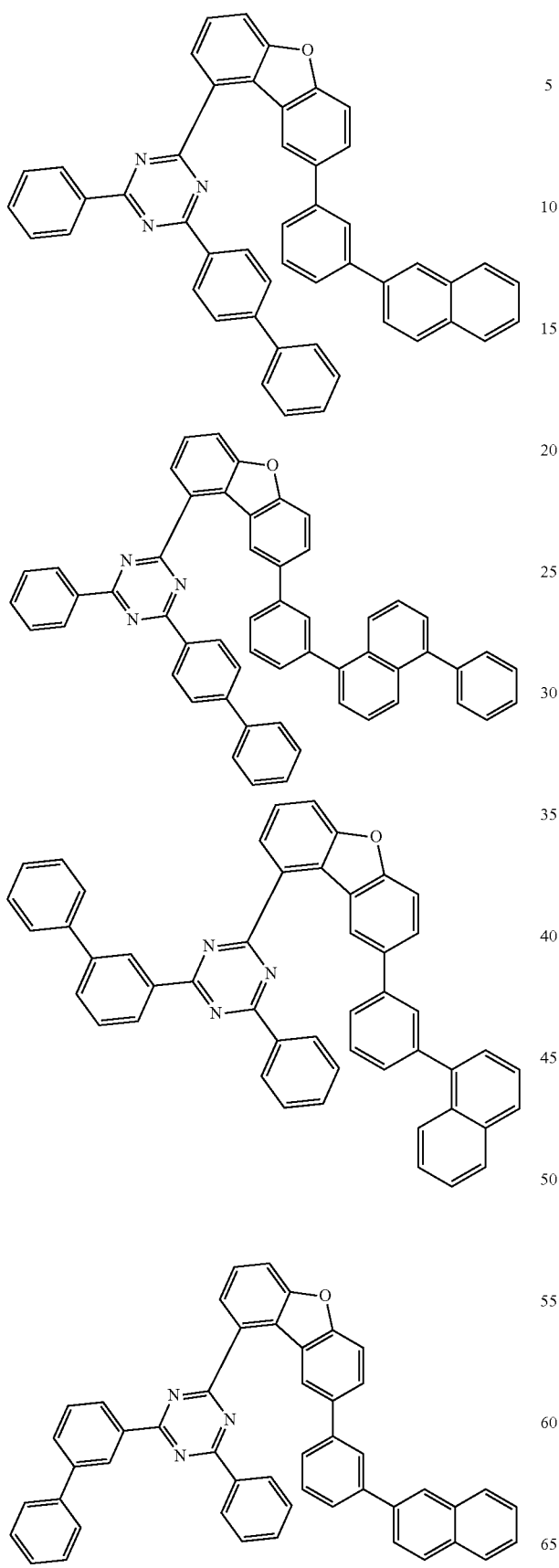
48
-continued
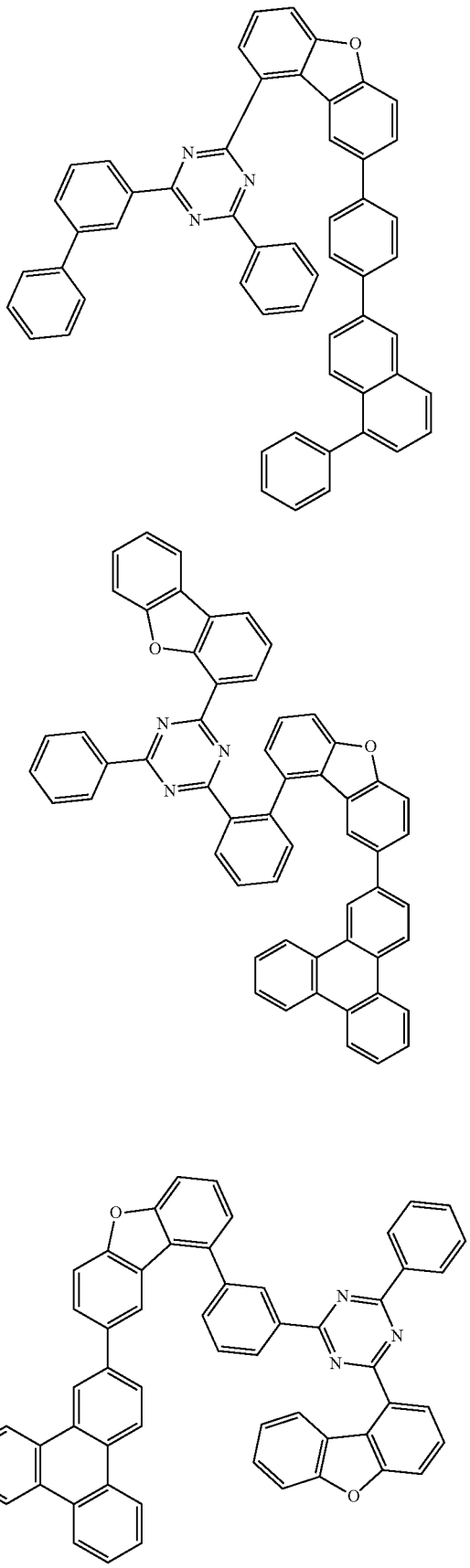

49
-continued
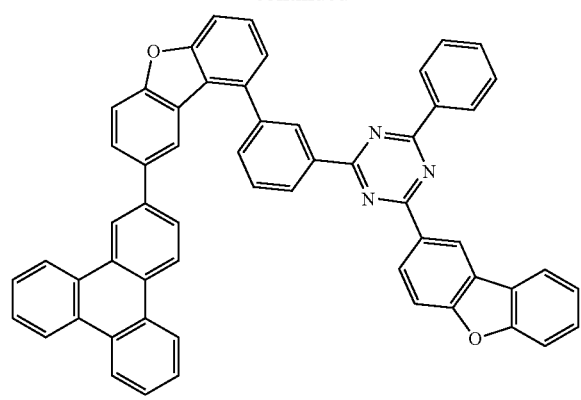
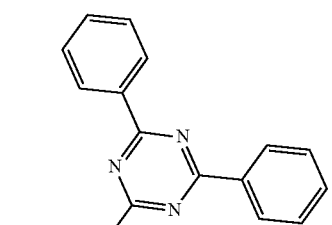
50
-continued
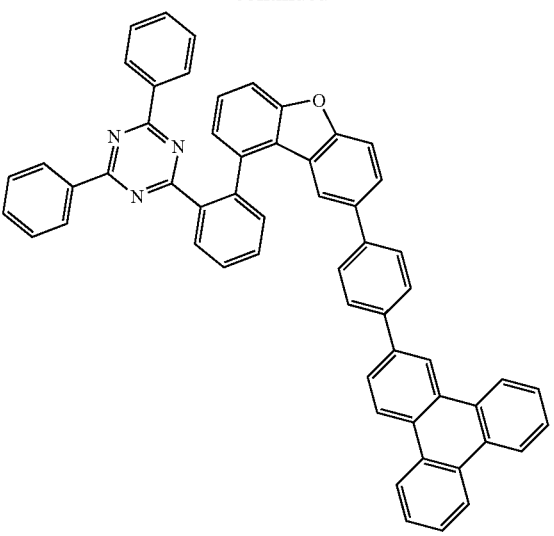
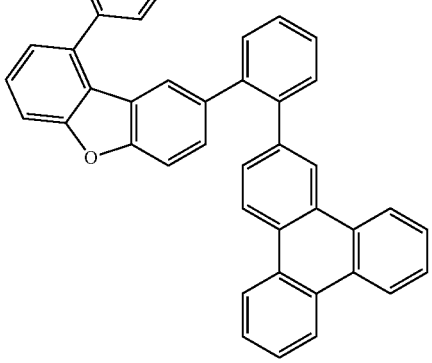
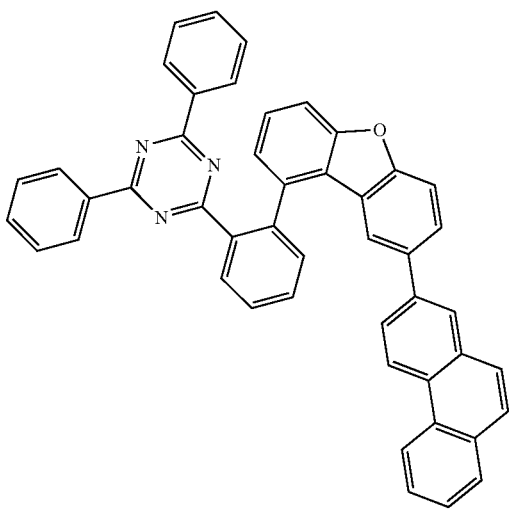

-continued
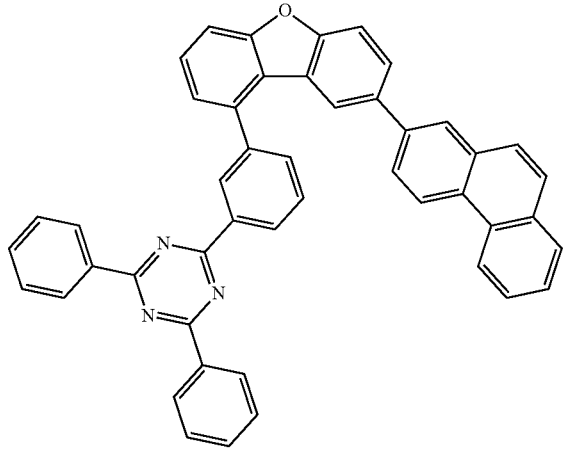
-continued
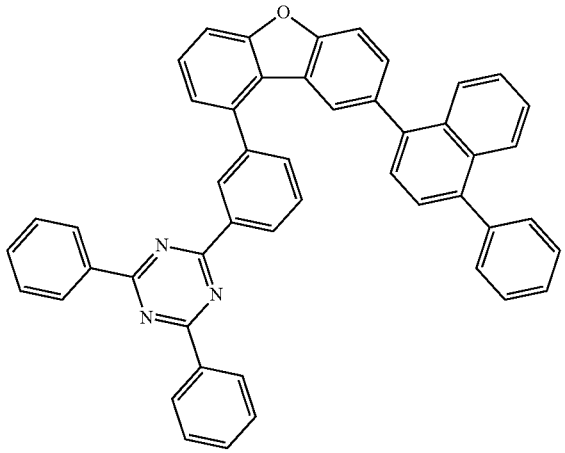
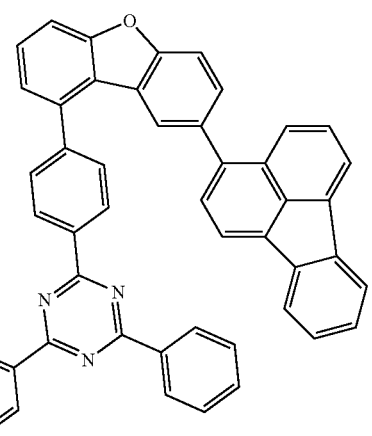
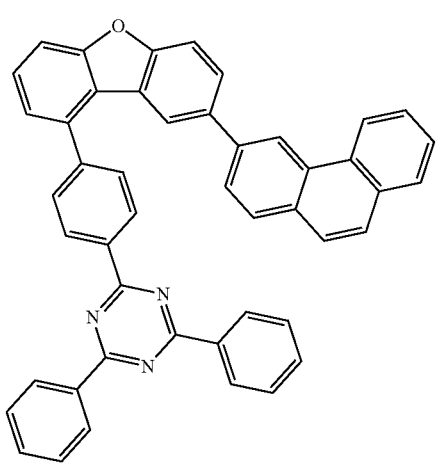
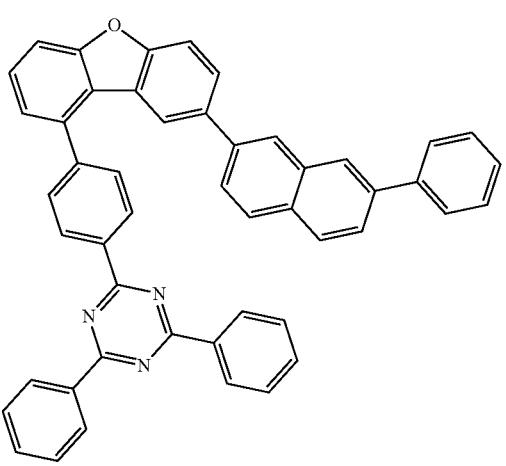

53
-continued
54
-continued
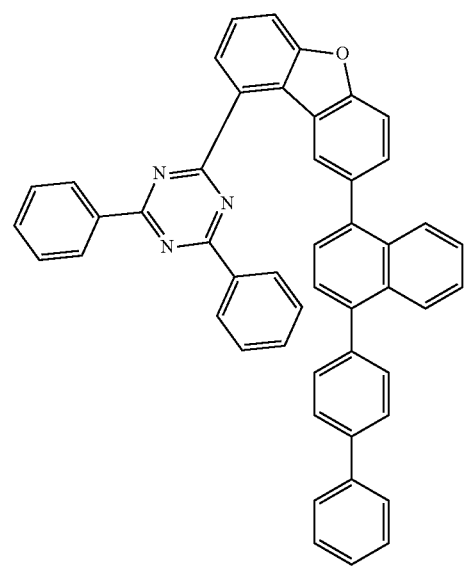
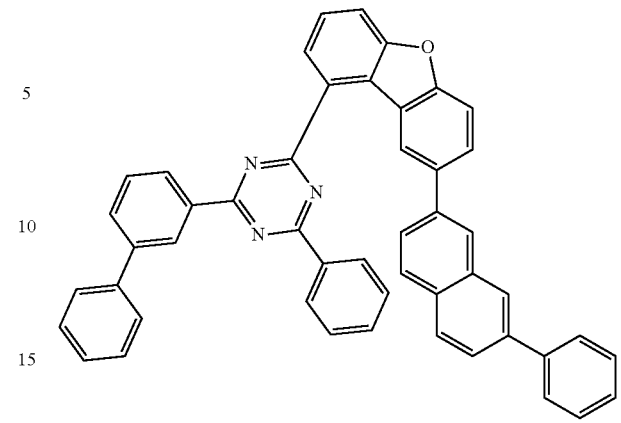
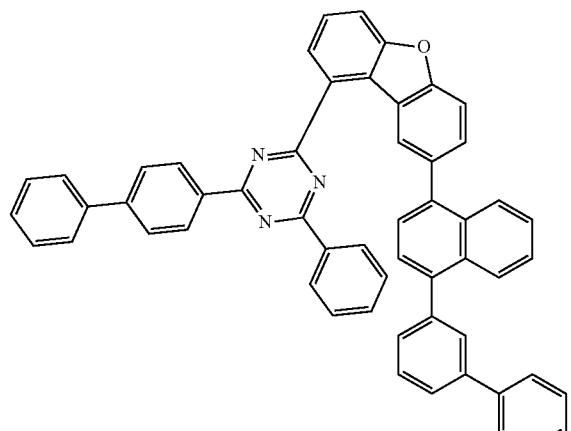
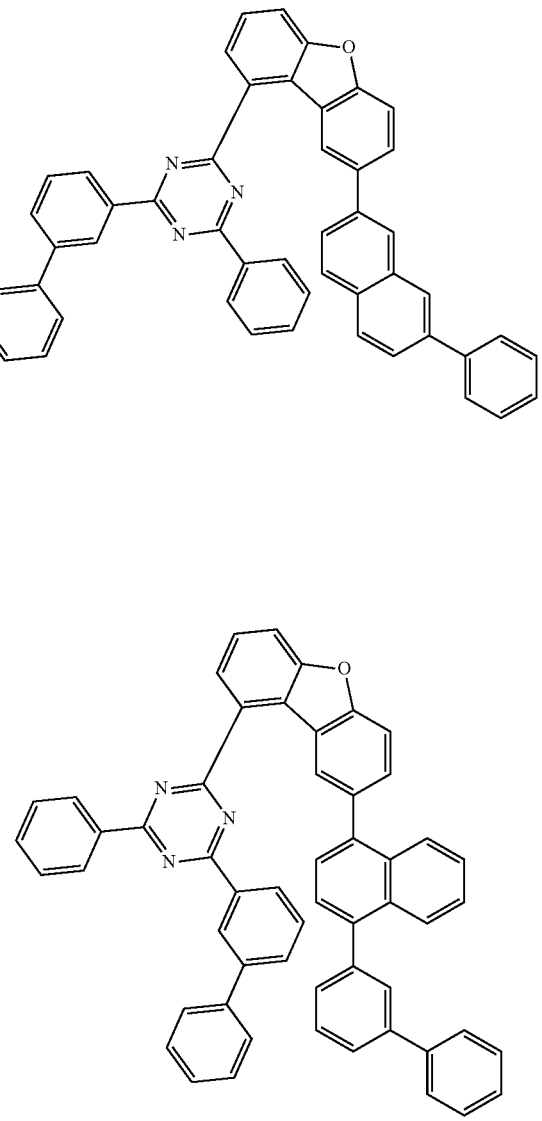
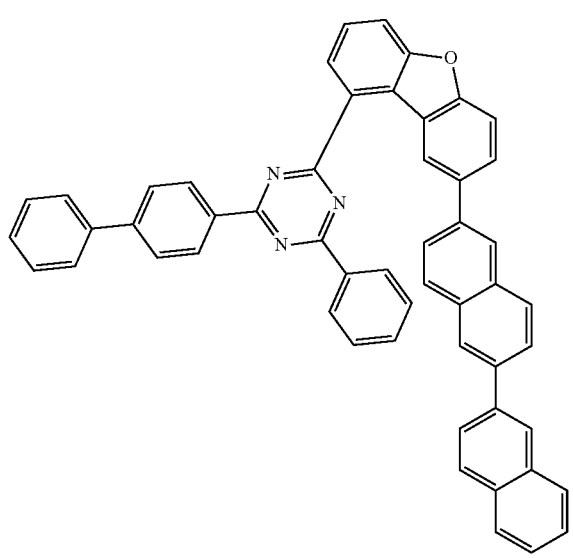

55
-continued
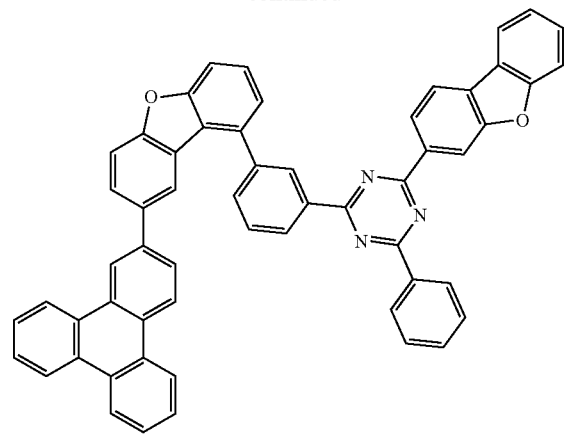
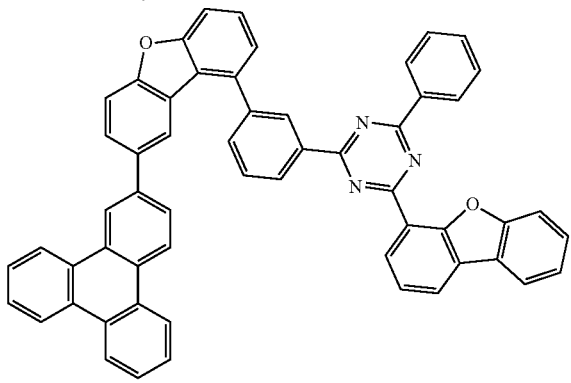
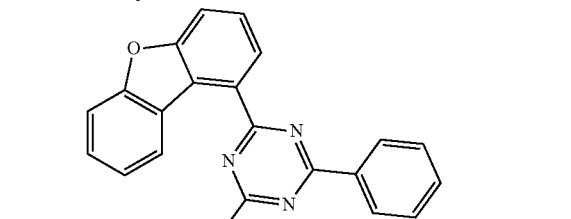
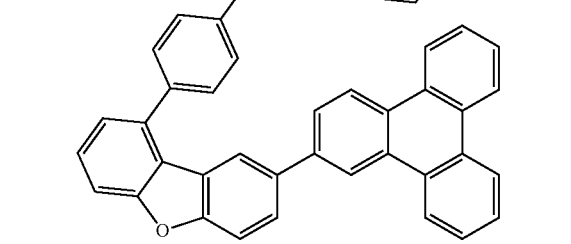
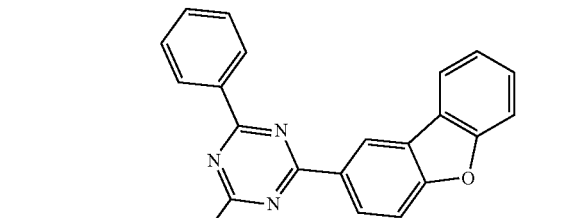
56
-continued
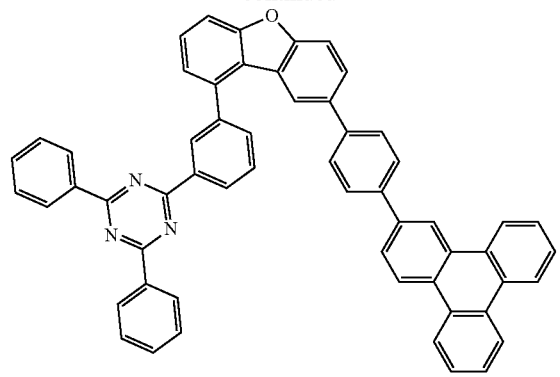
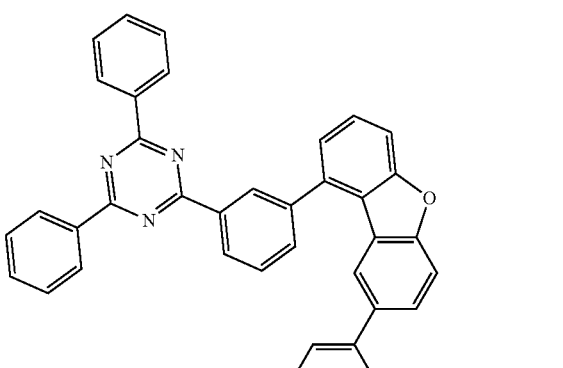
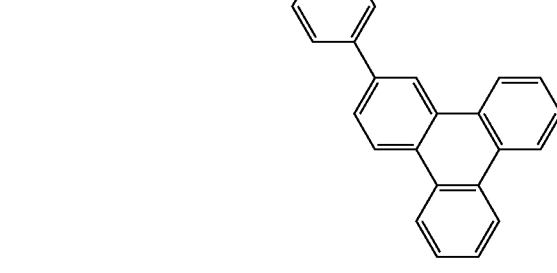
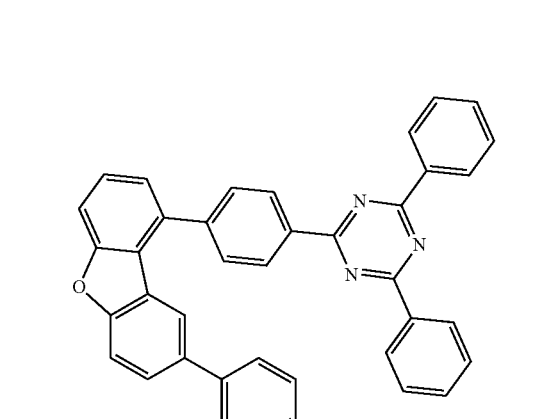
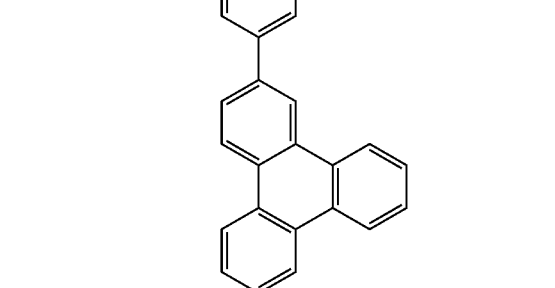

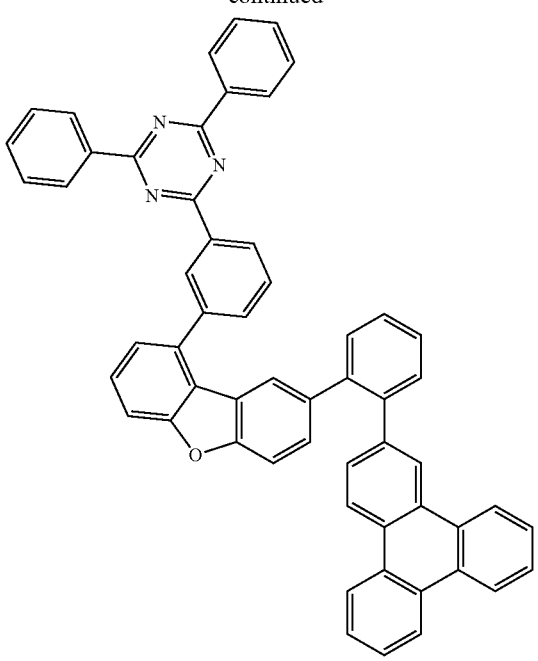
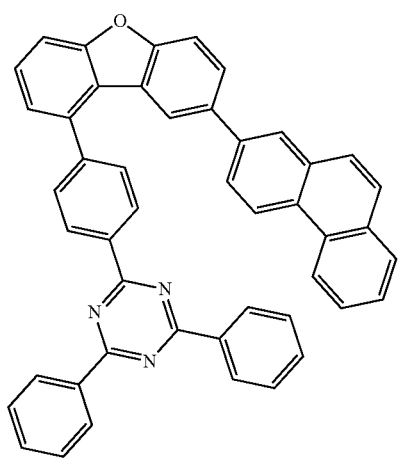
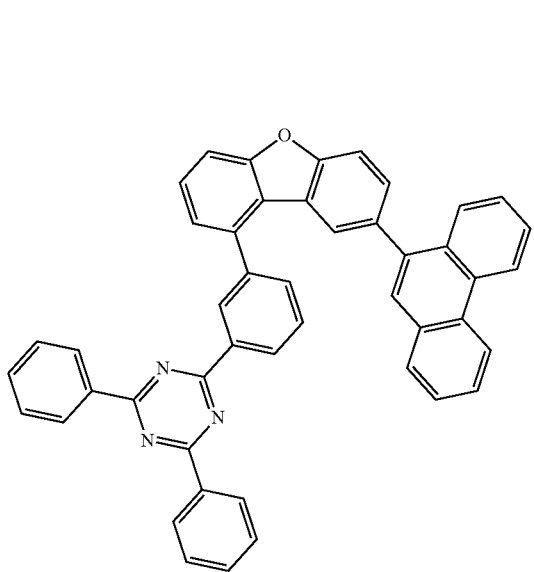
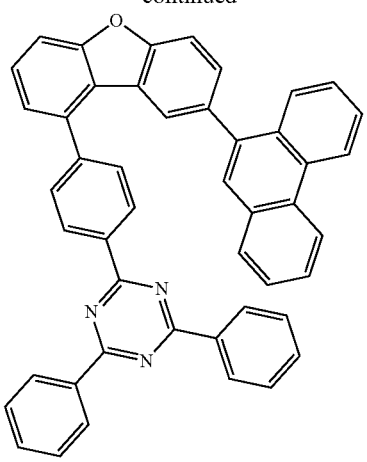
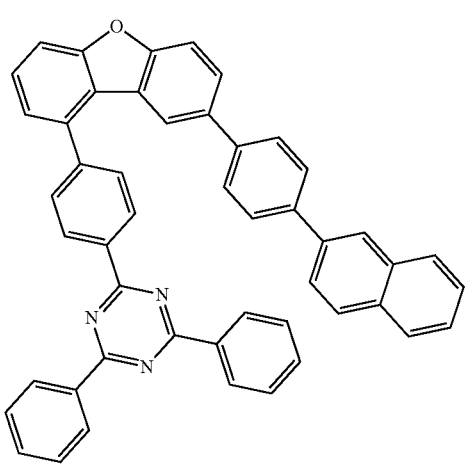
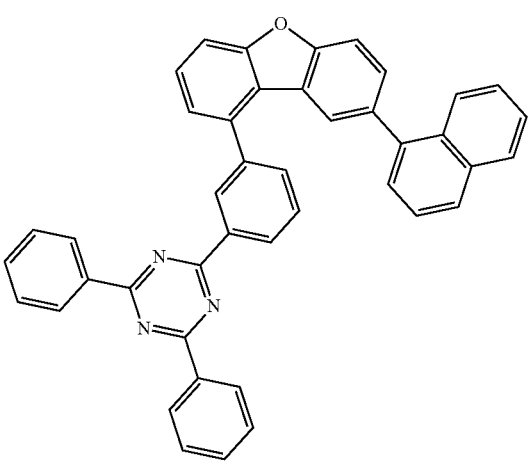

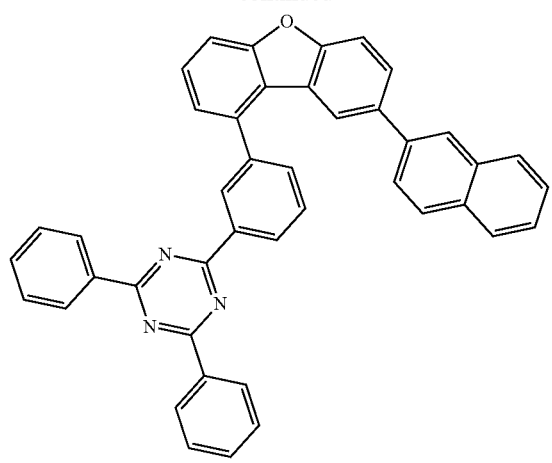
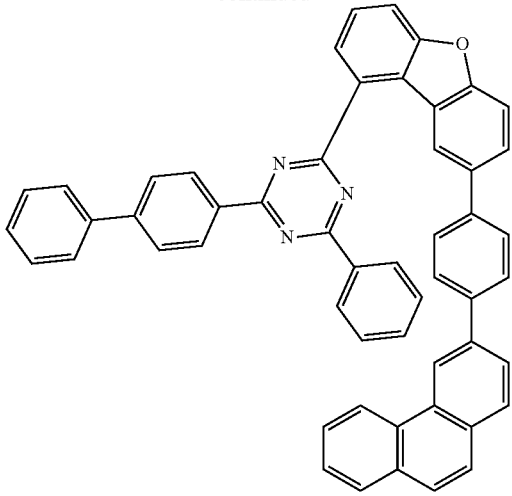
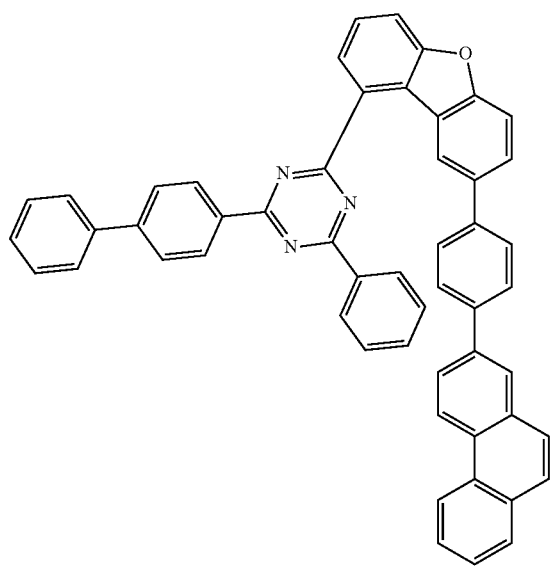
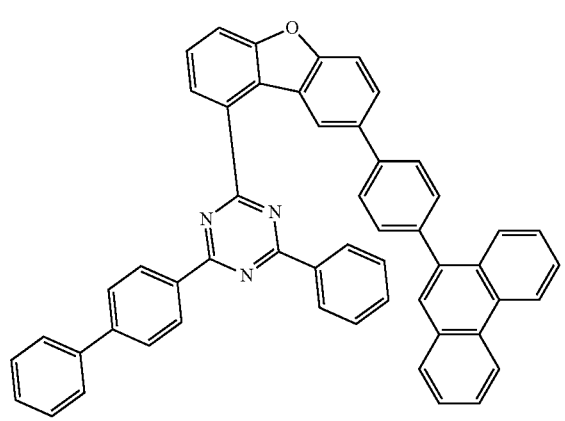
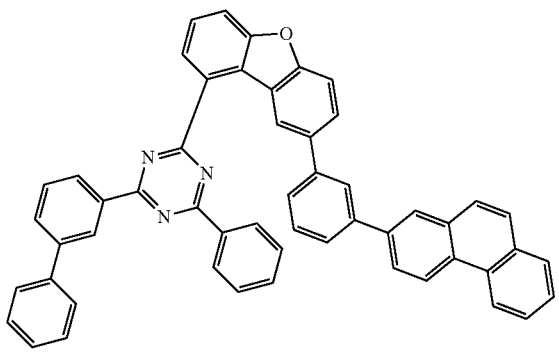

-continued
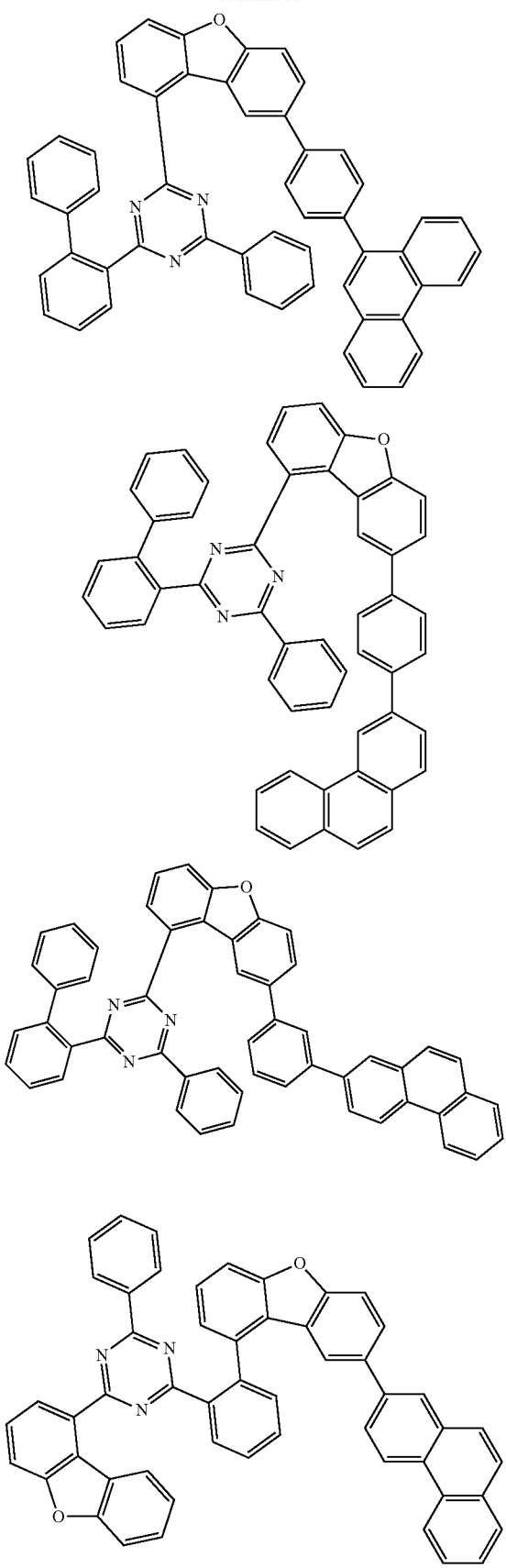
-continued
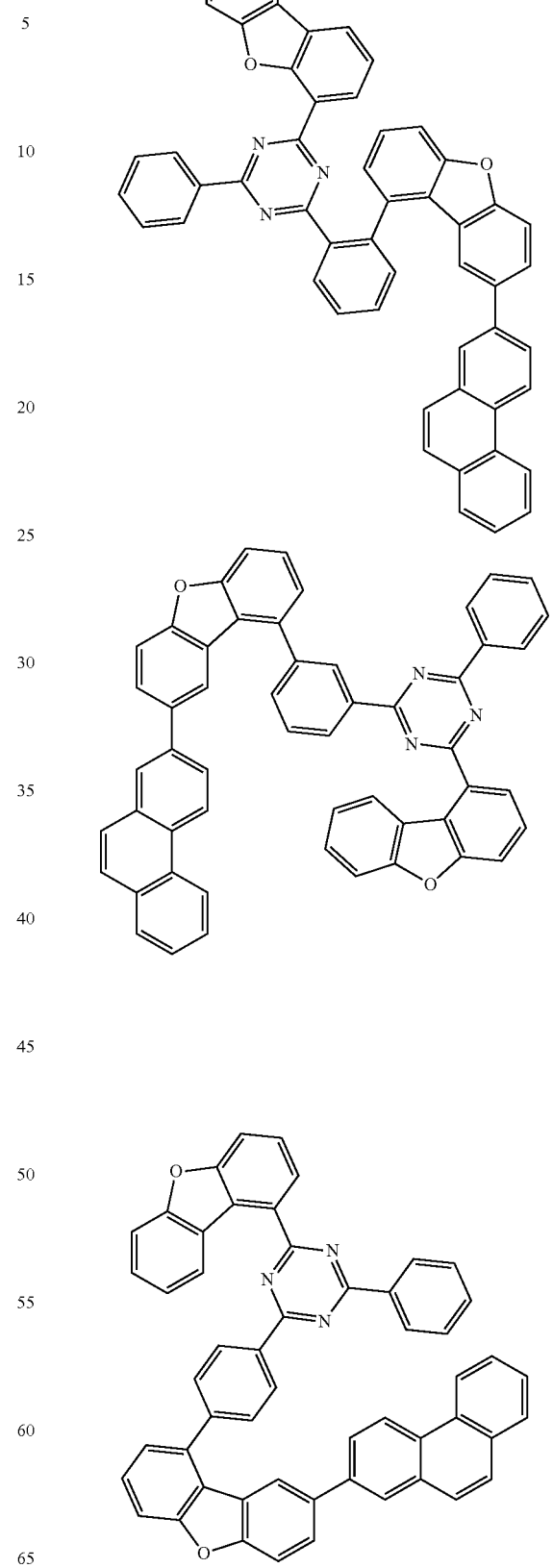

63
-continued
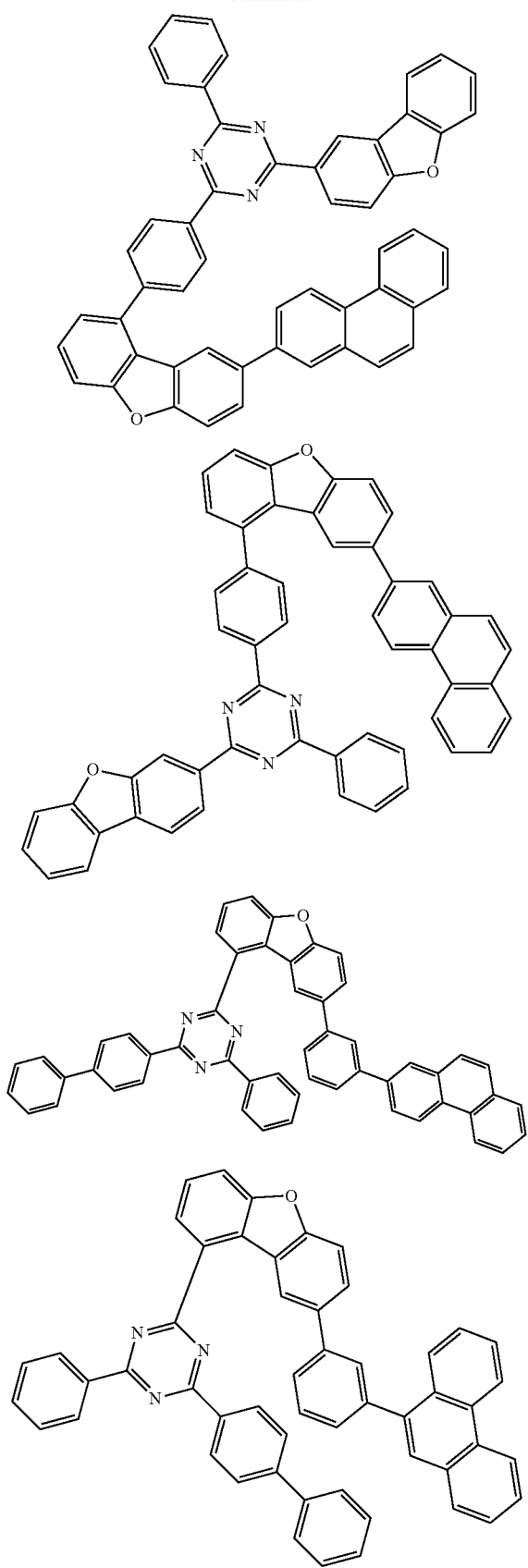
64
-continued
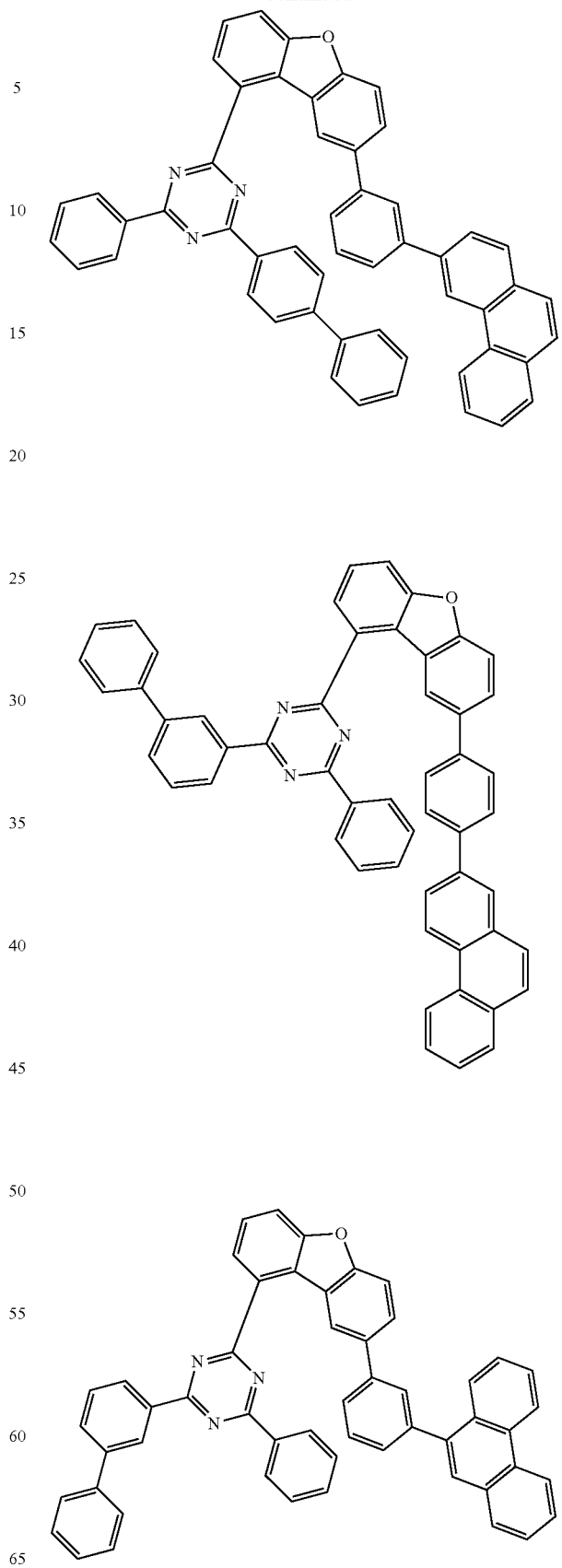

65
-continued
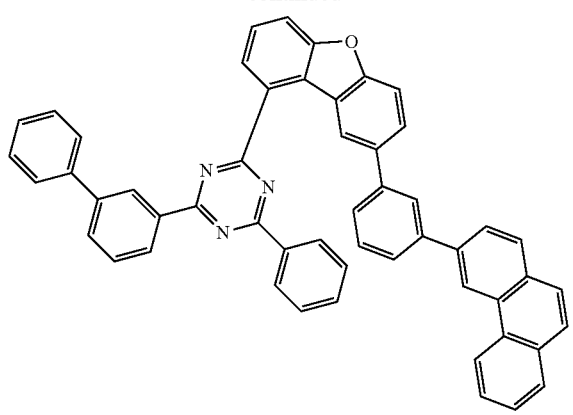
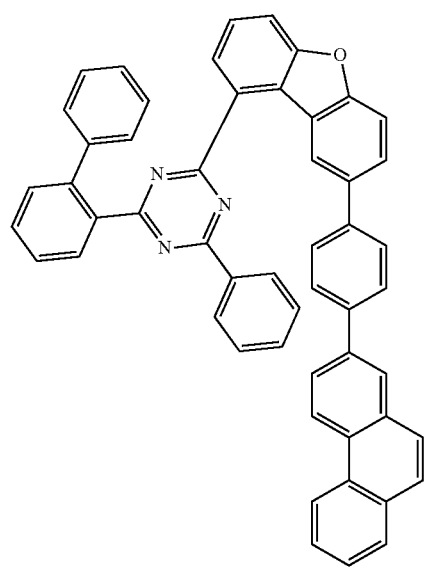
66
-continued
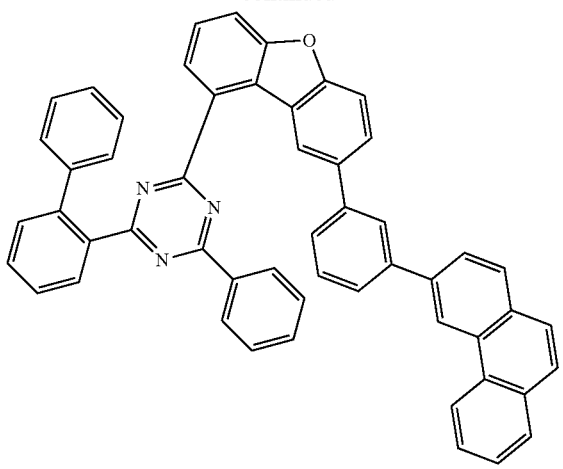
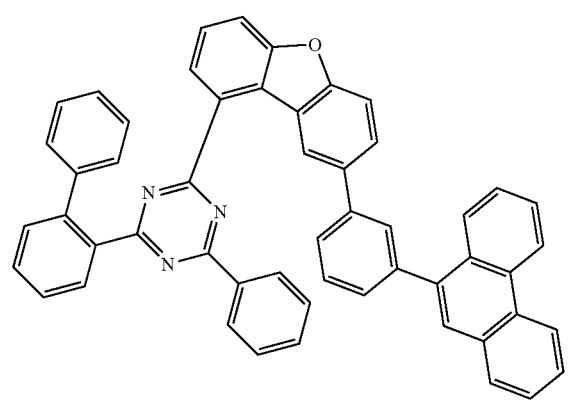
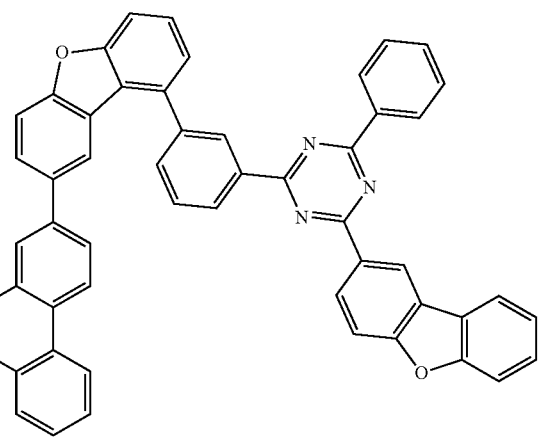

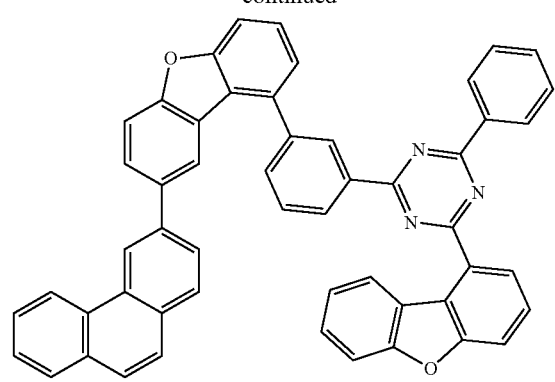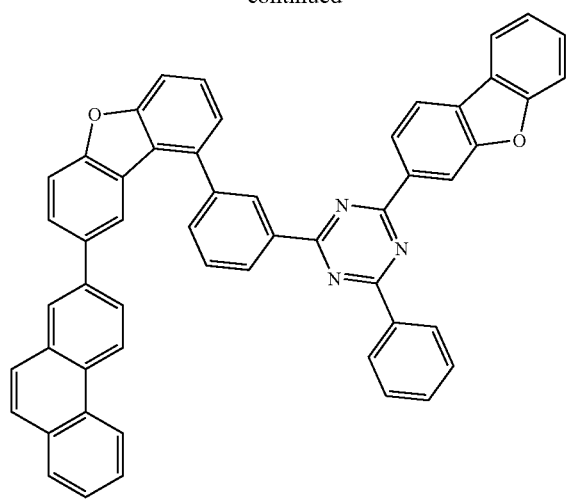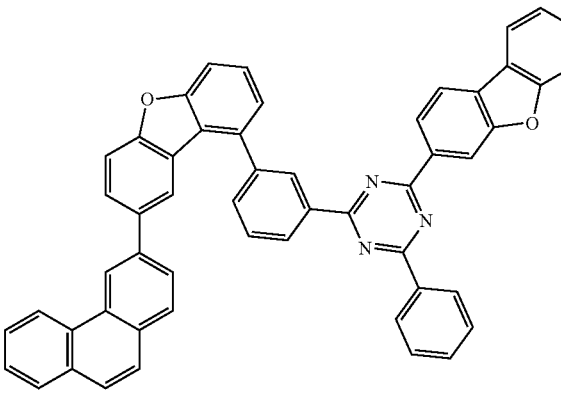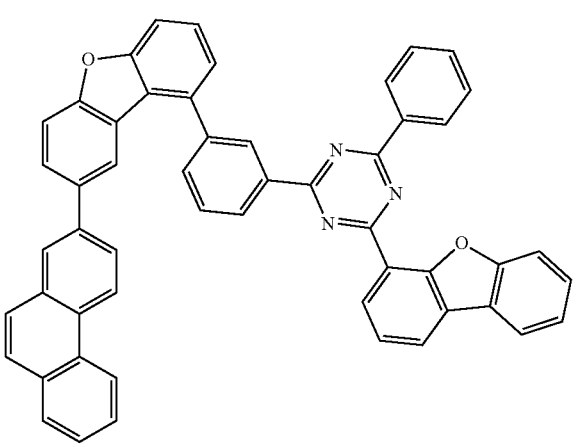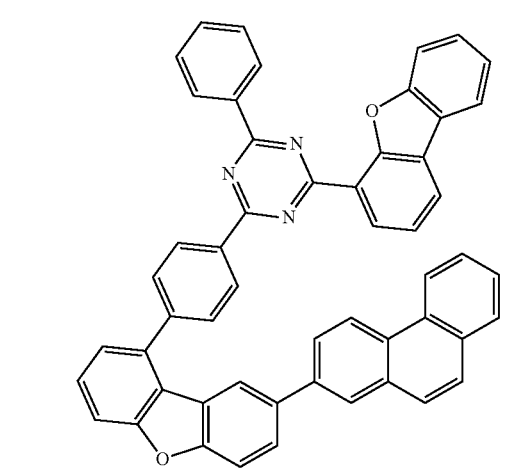

-continued
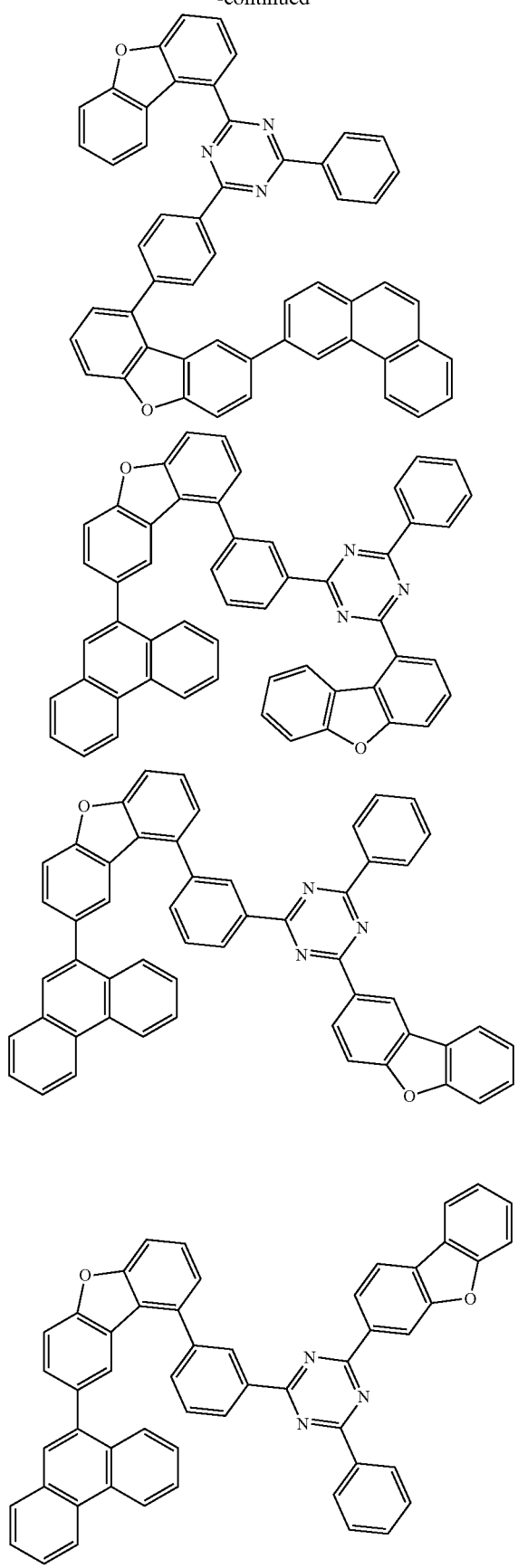
-continued
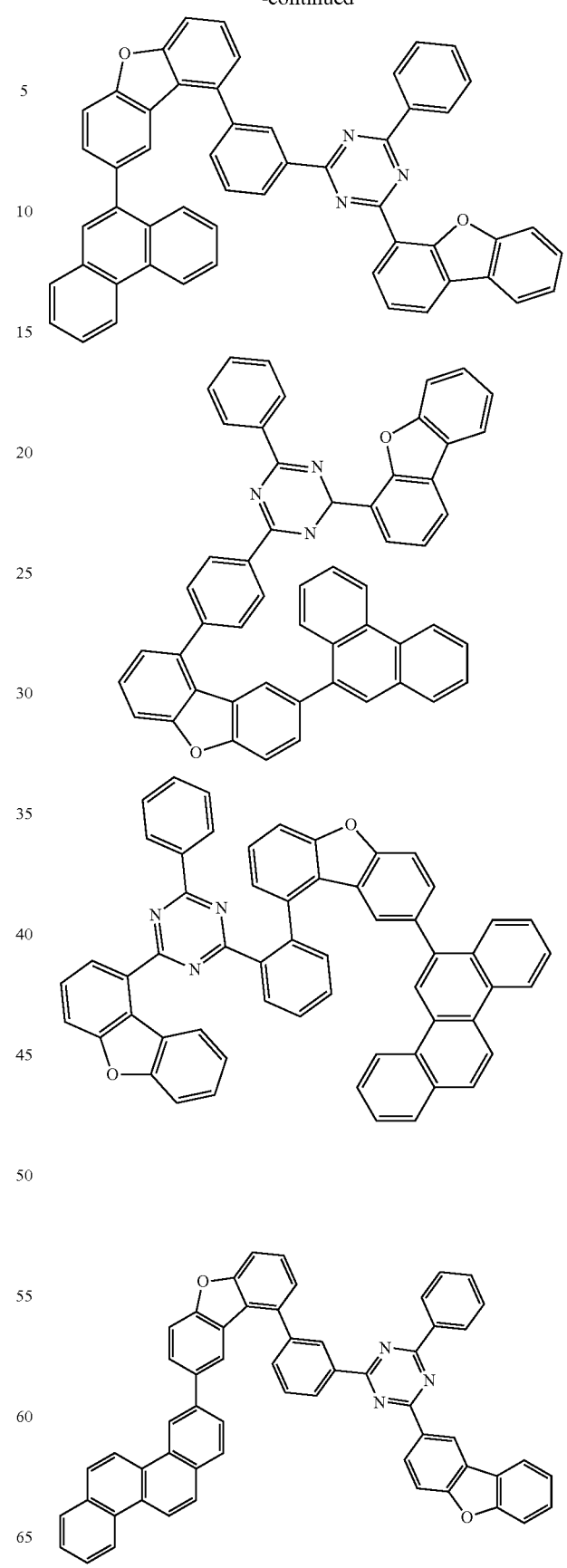

71
-continued
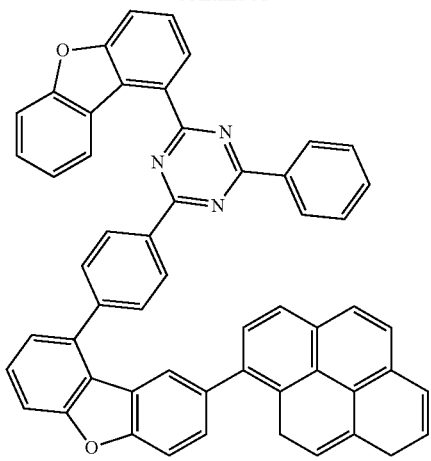
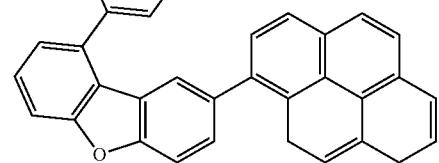
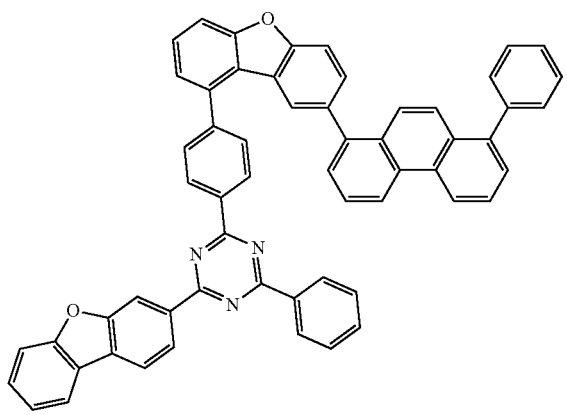
72
-continued
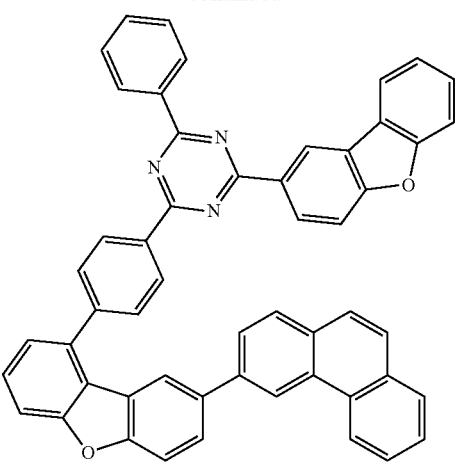
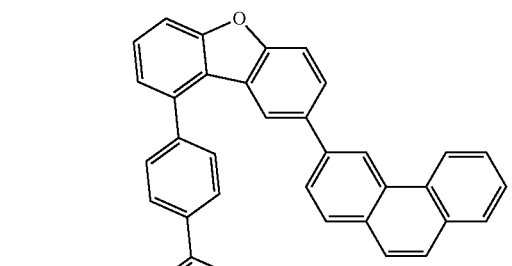
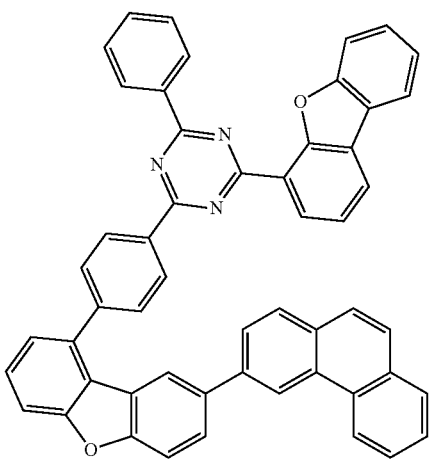

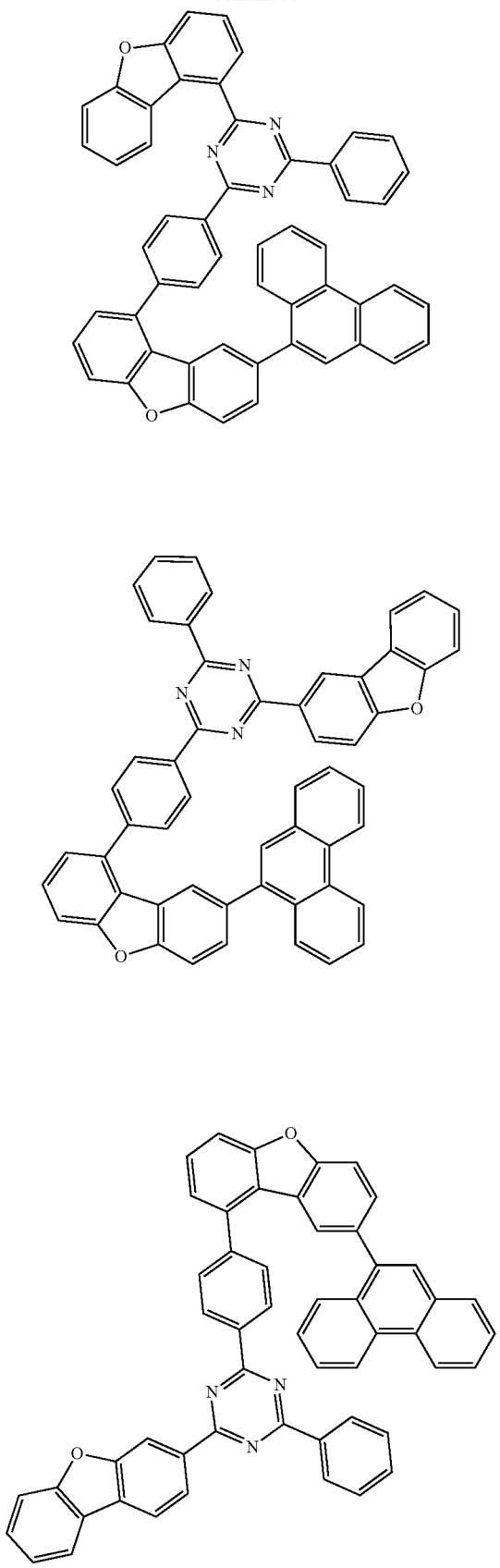

75
-continued
76
-continued
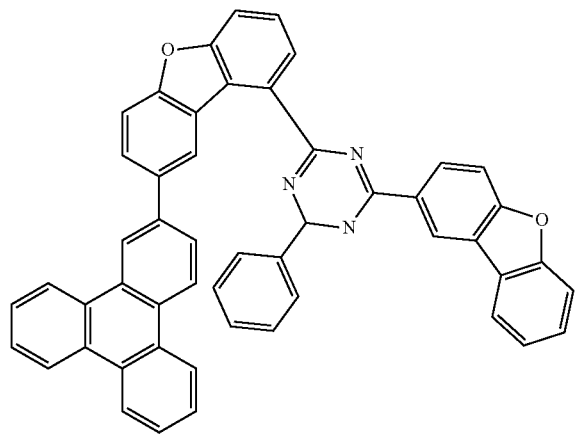
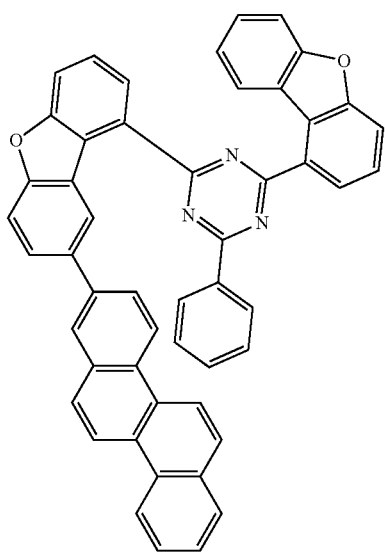
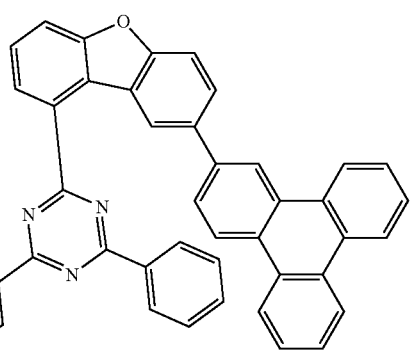
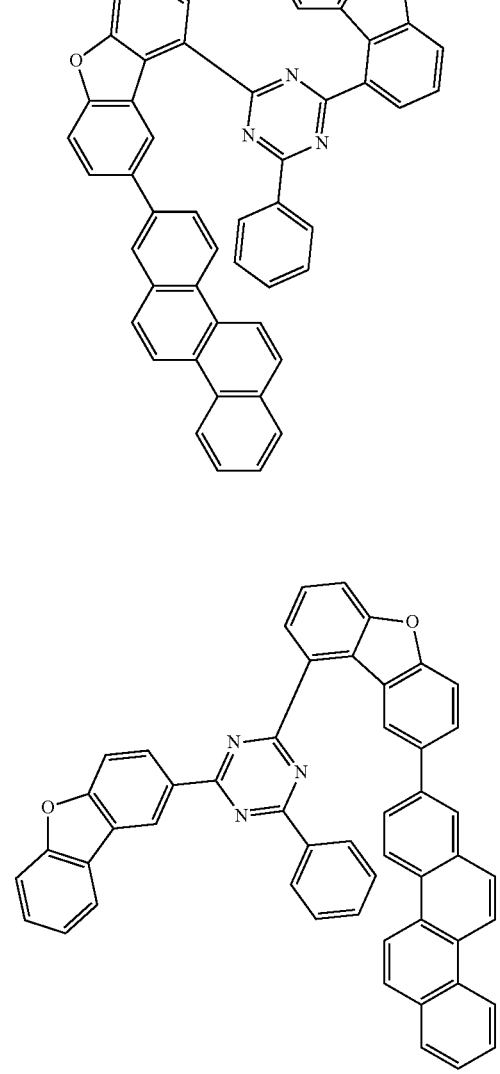
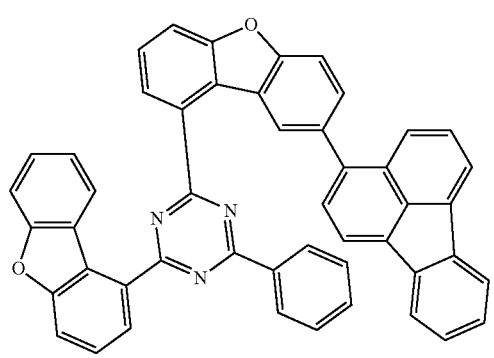
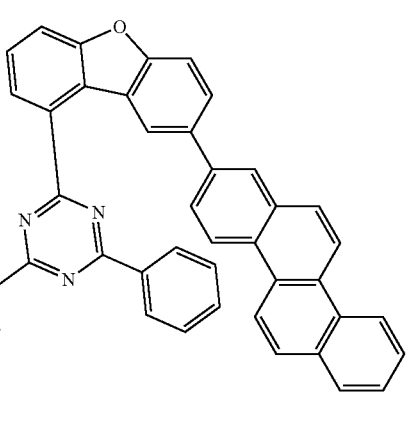

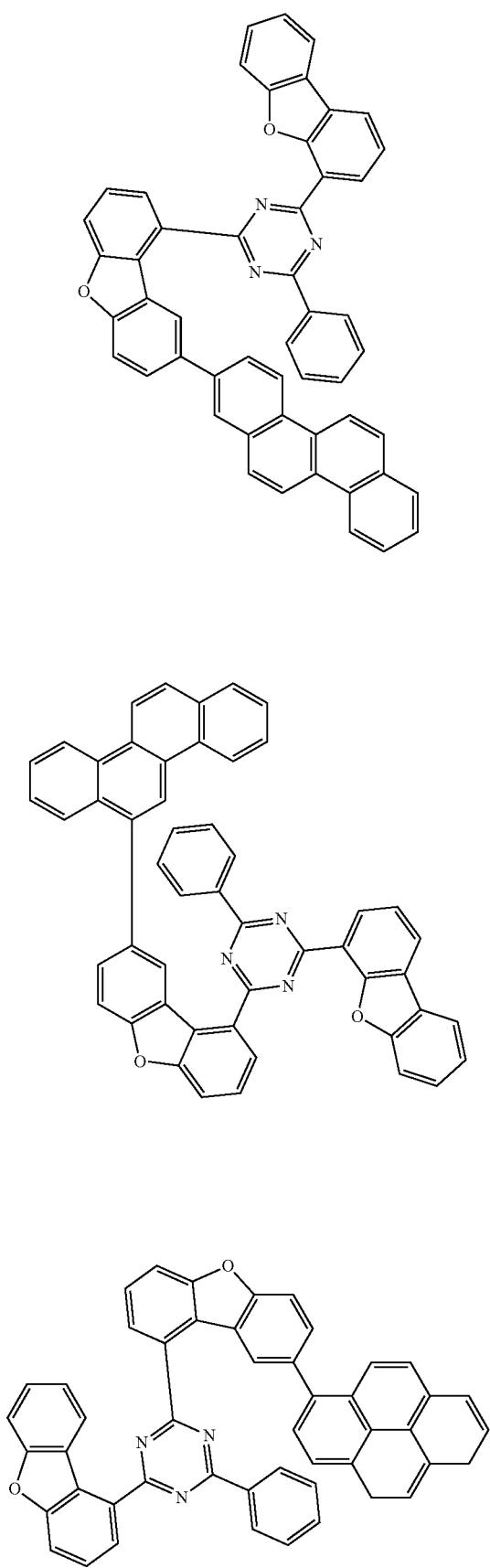
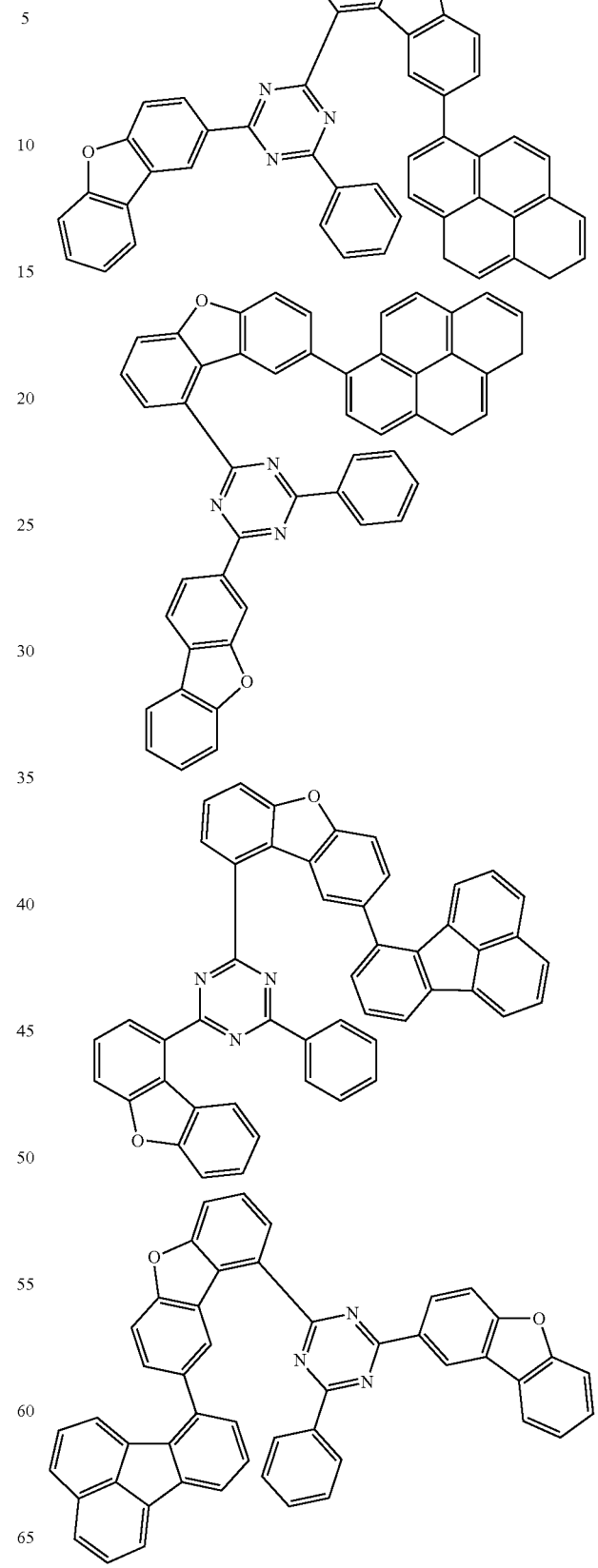

79
-continued
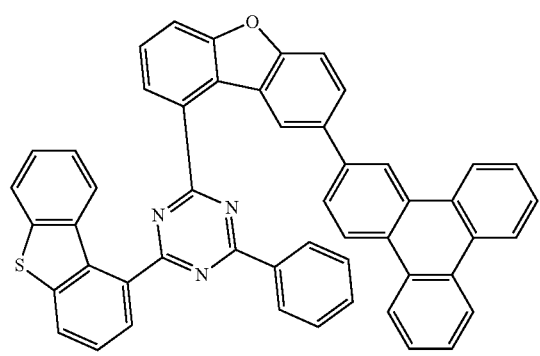
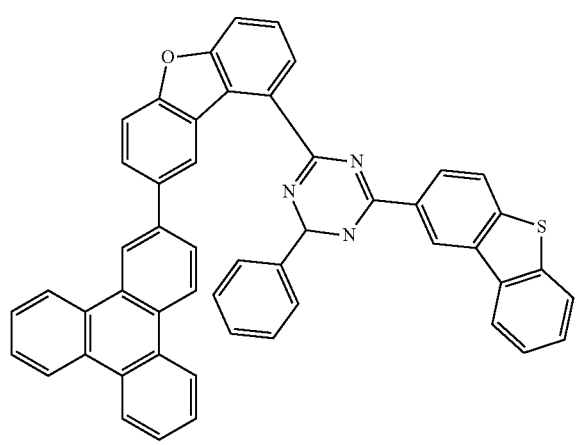
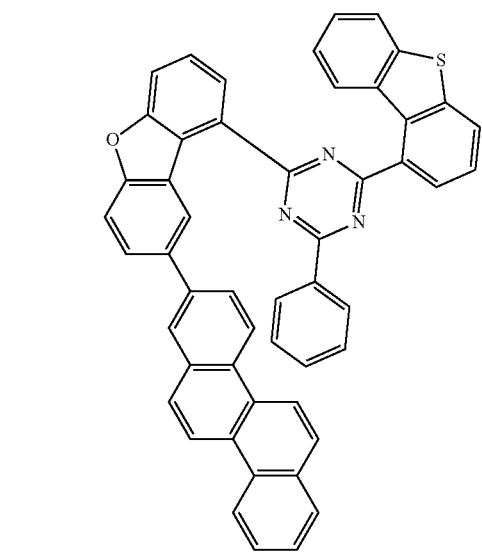
80
-continued
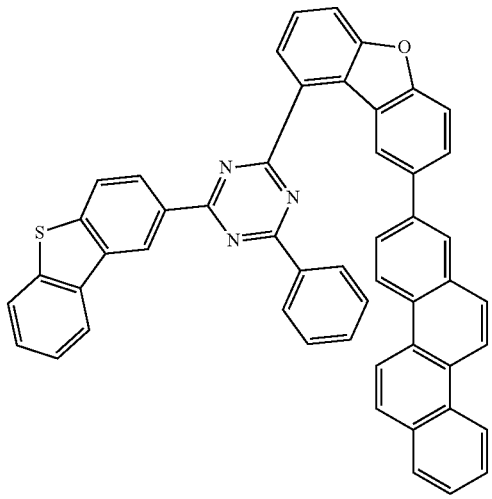
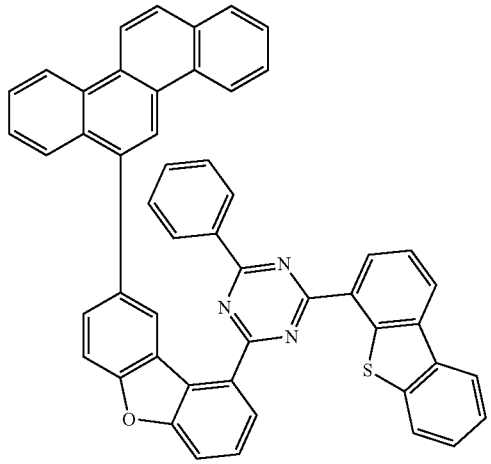
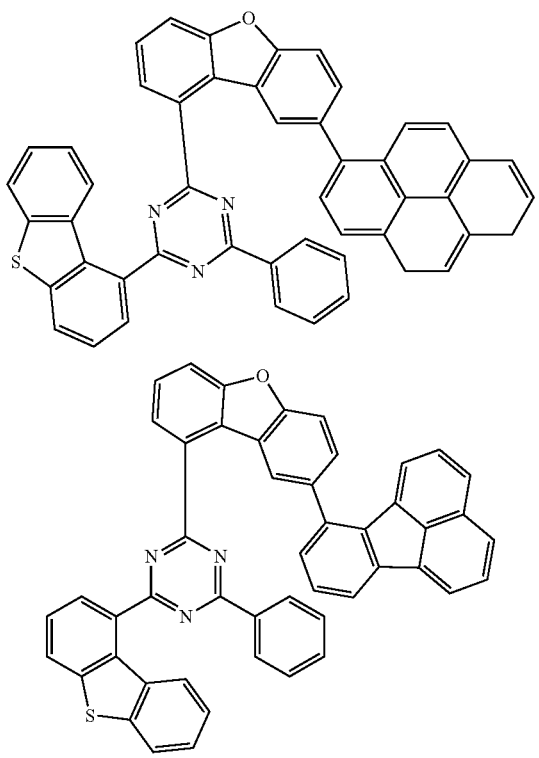

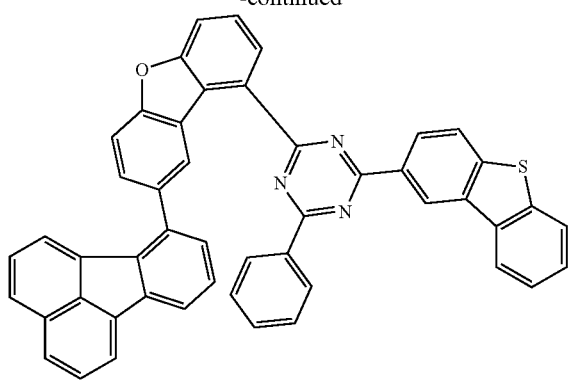
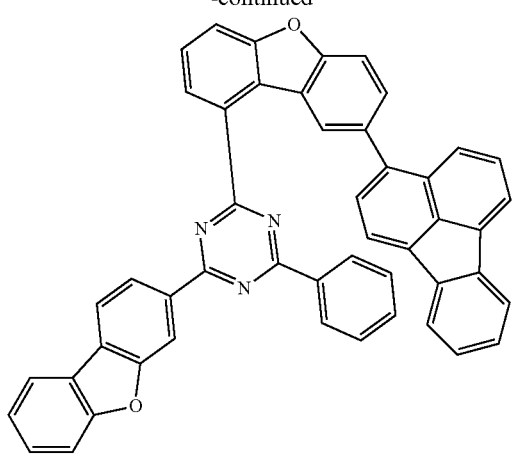
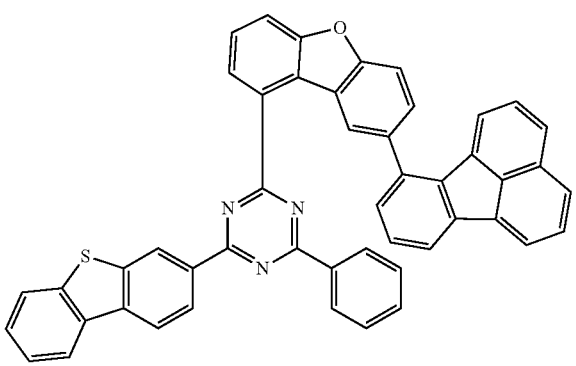
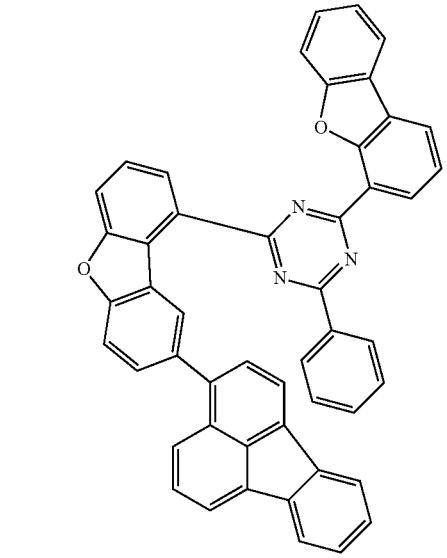
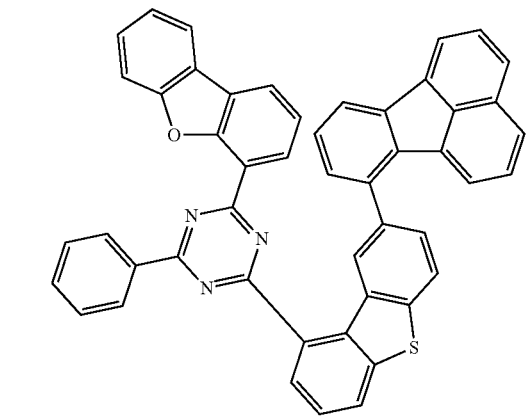
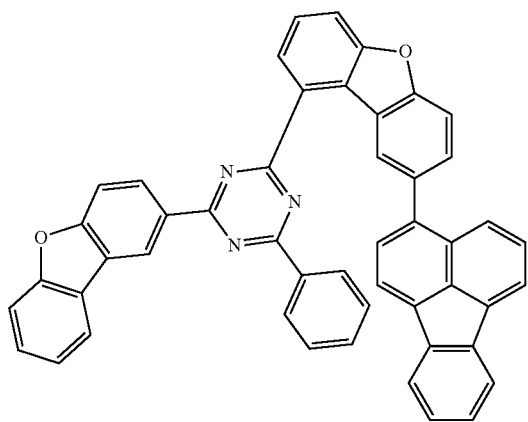
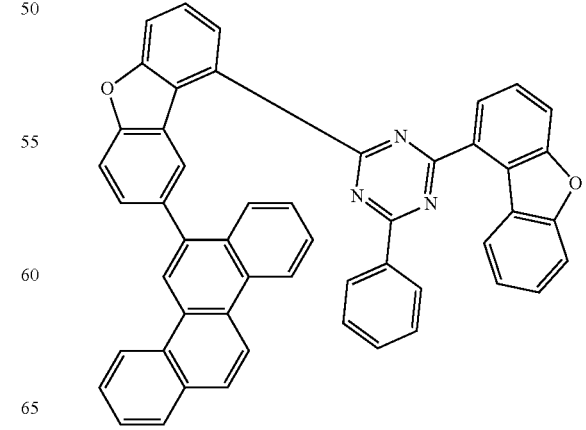

83
-continued
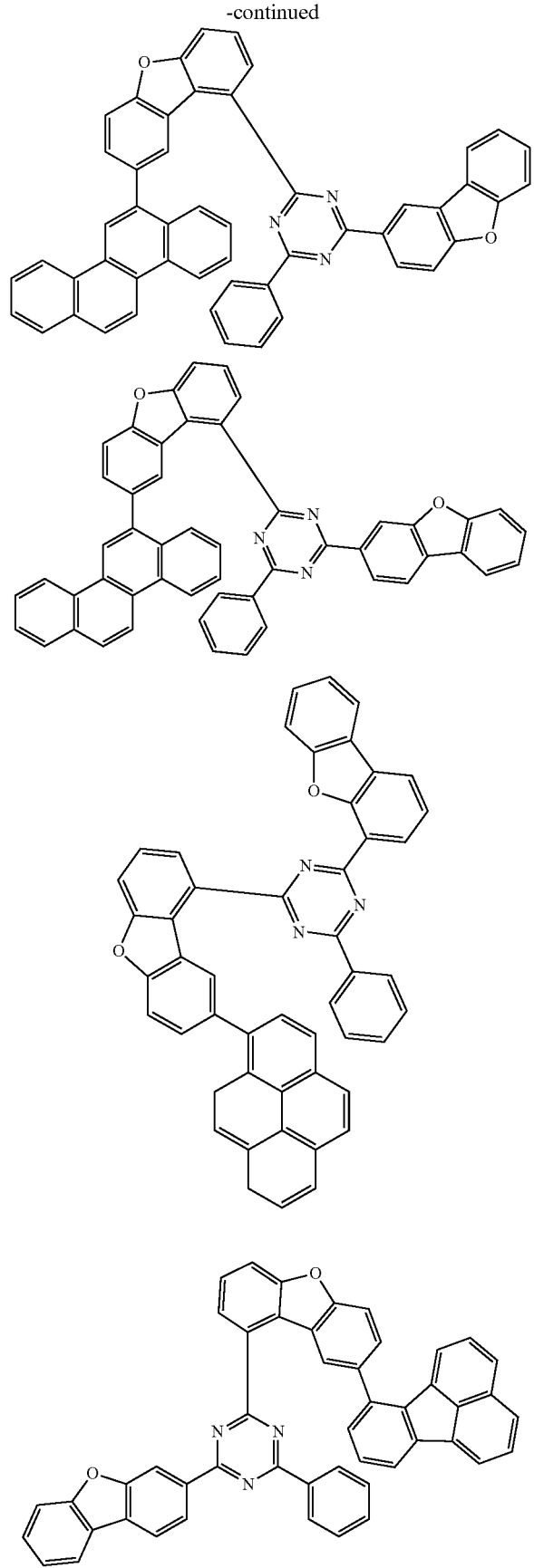
84
-continued
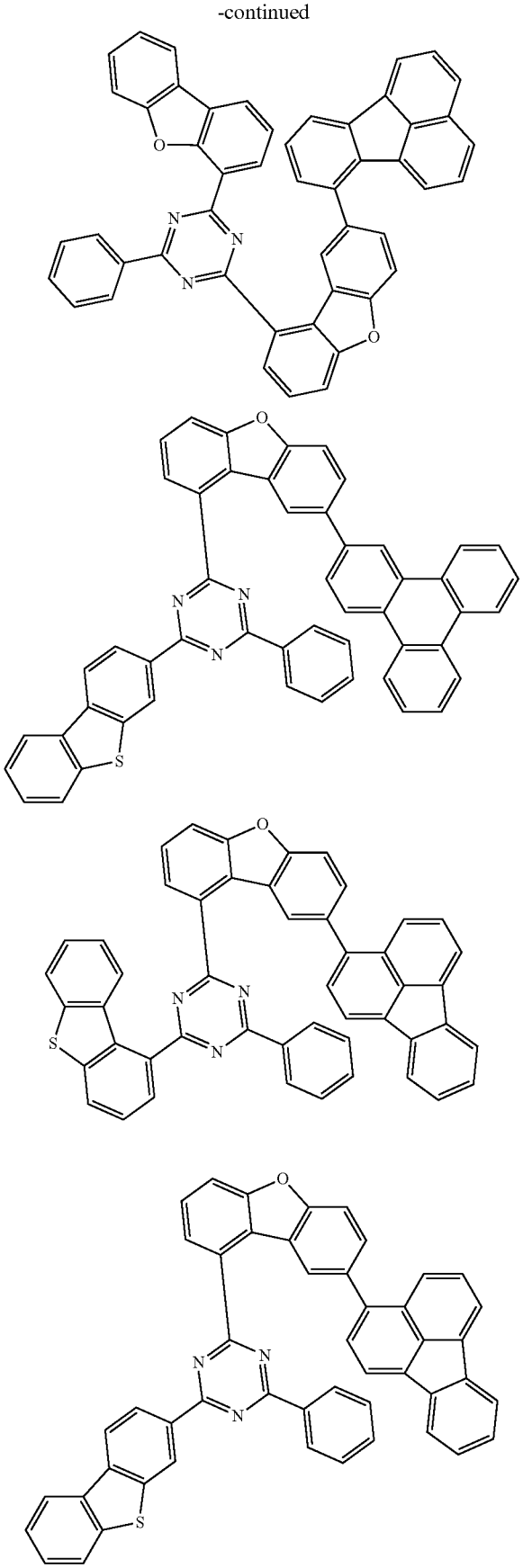

85
-continued
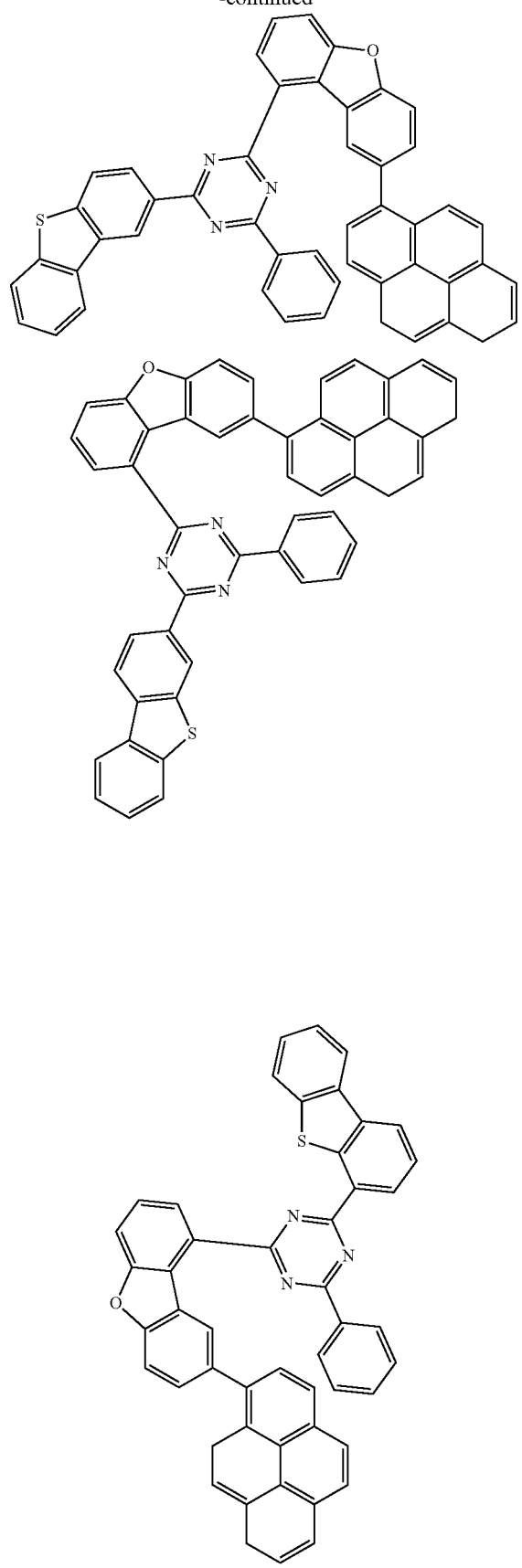
86
-continued
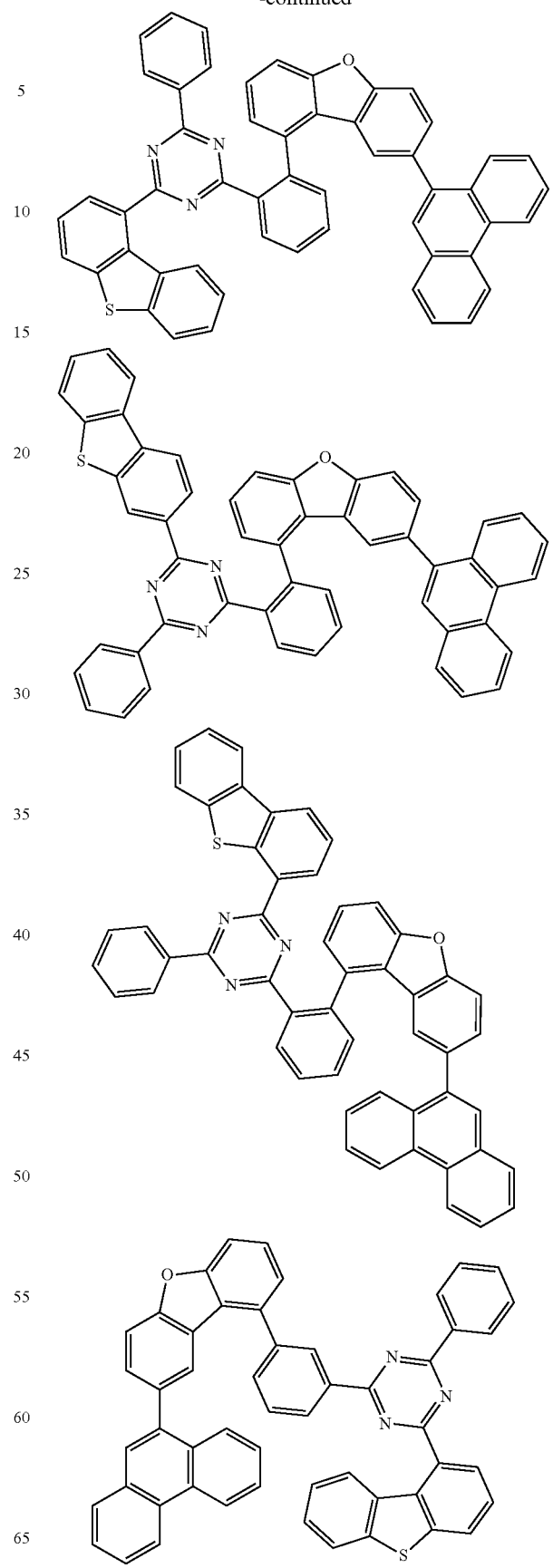

87
-continued
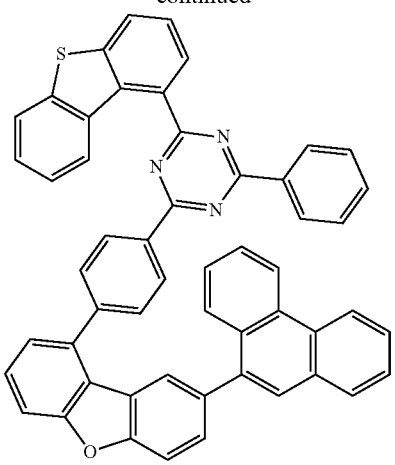
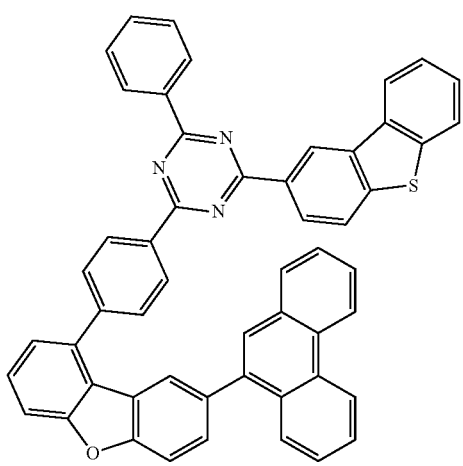
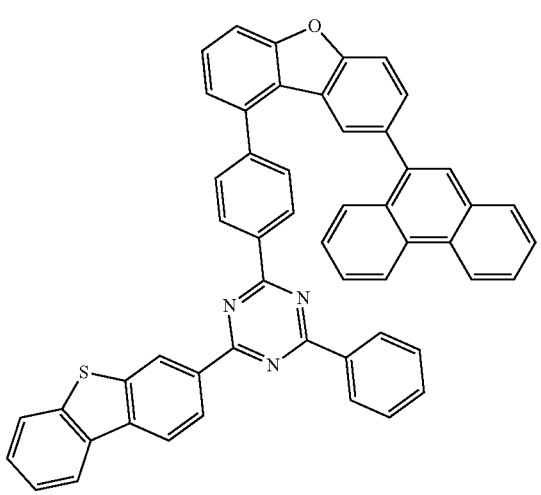
88
-continued
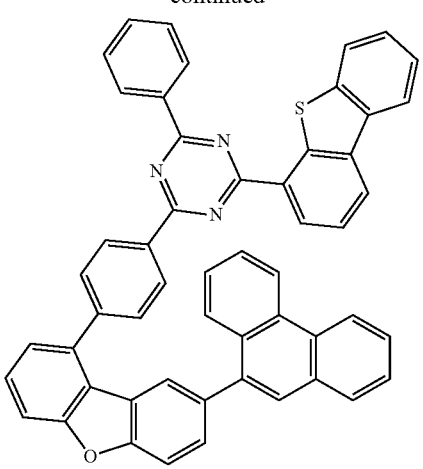
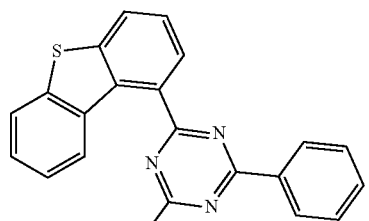
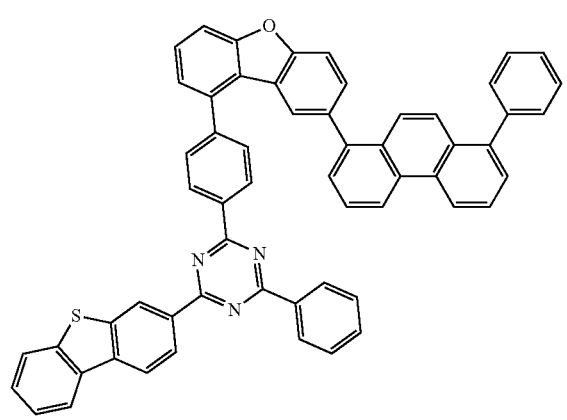

89
-continued
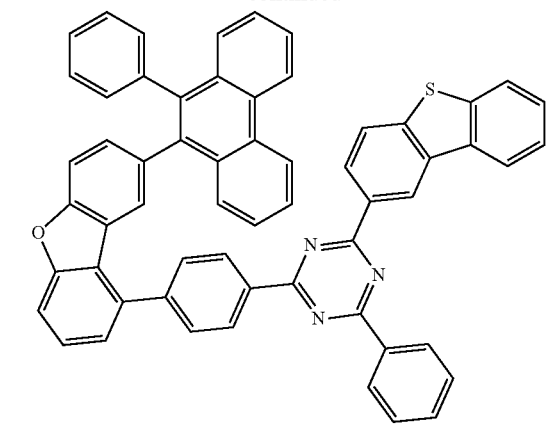
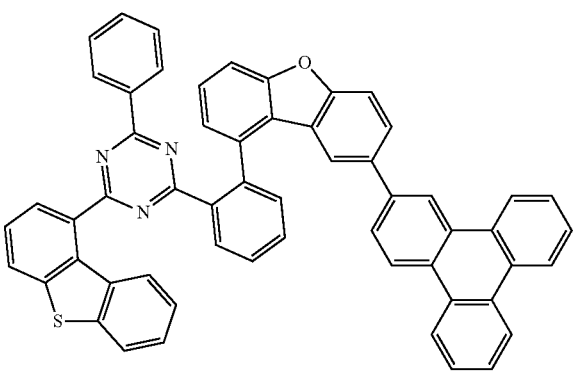
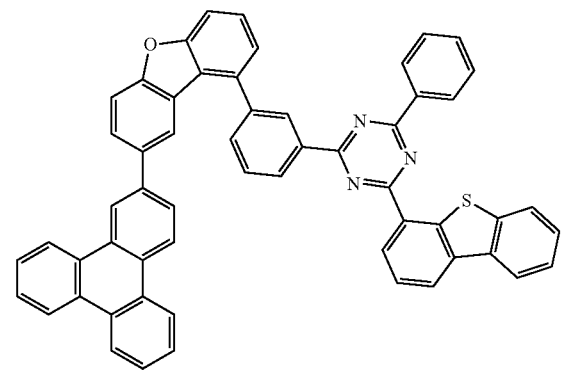
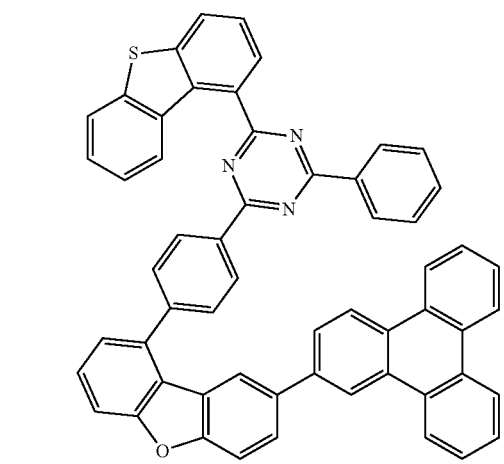
90
-continued
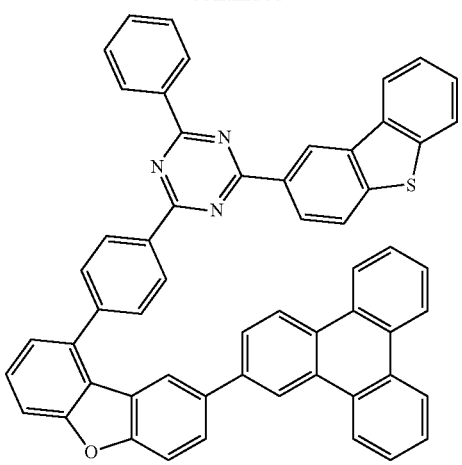
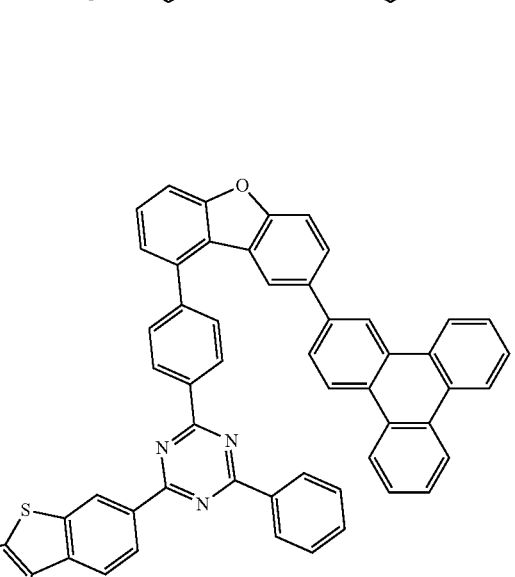
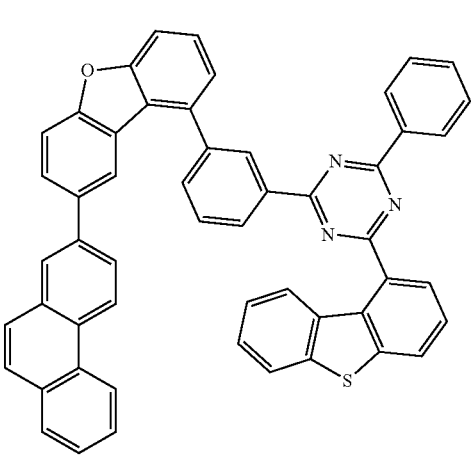

91
-continued
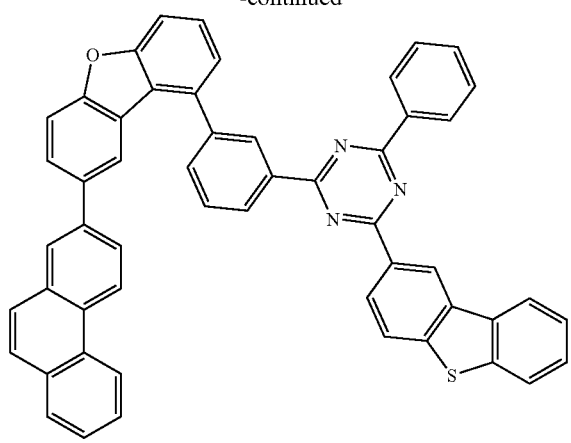
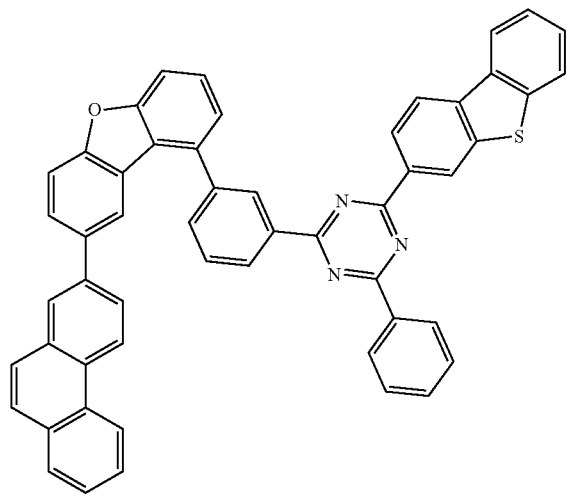
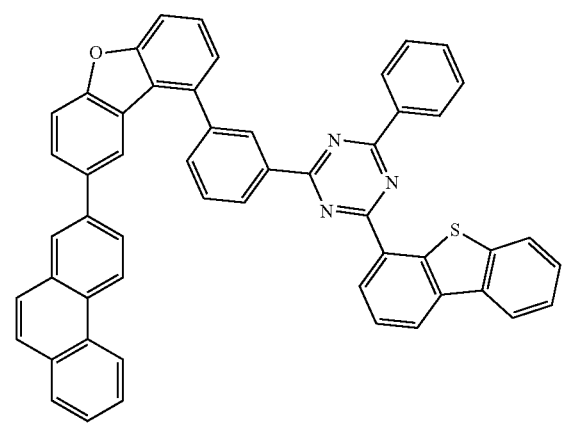
92
-continued
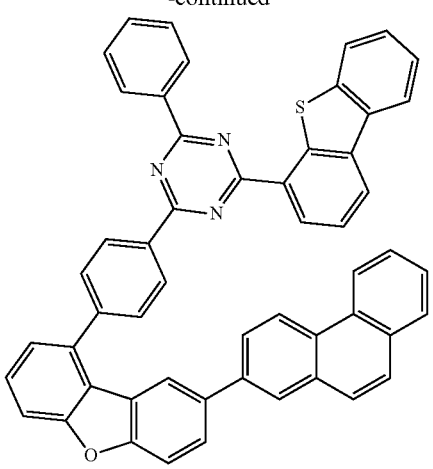
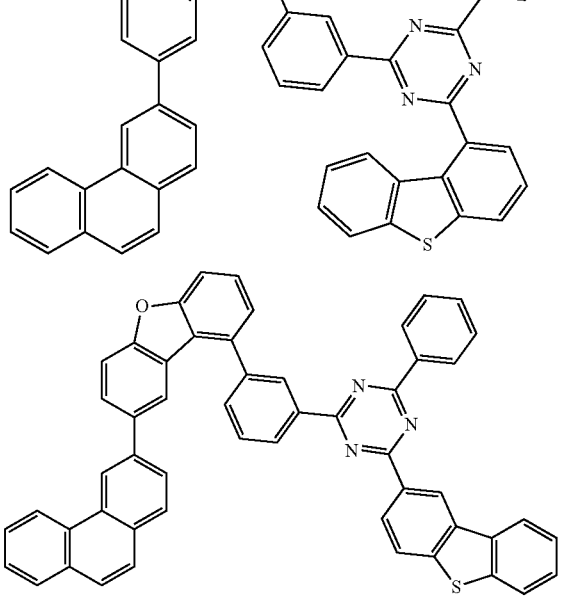
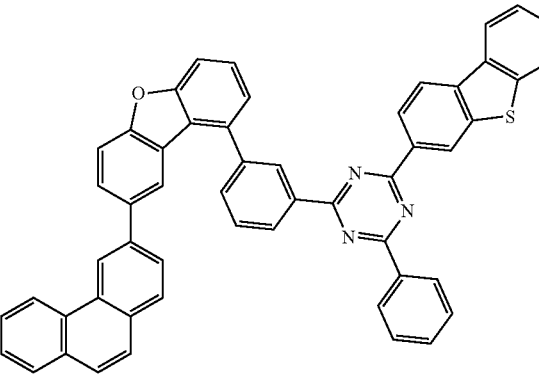

-continued
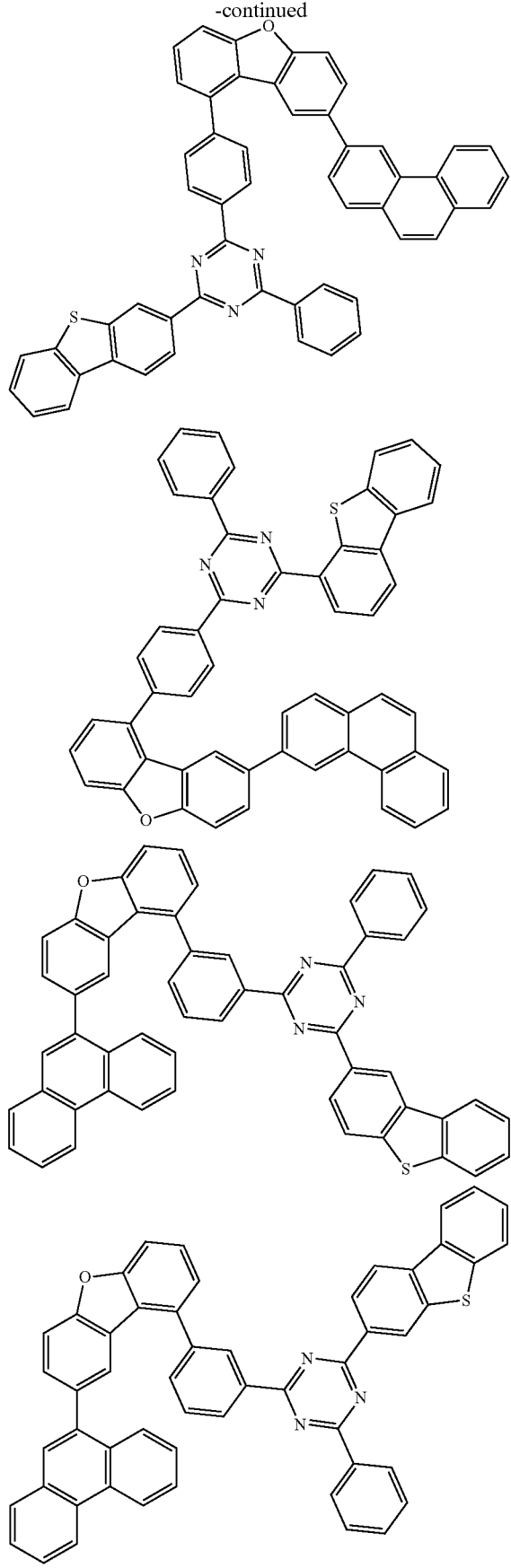
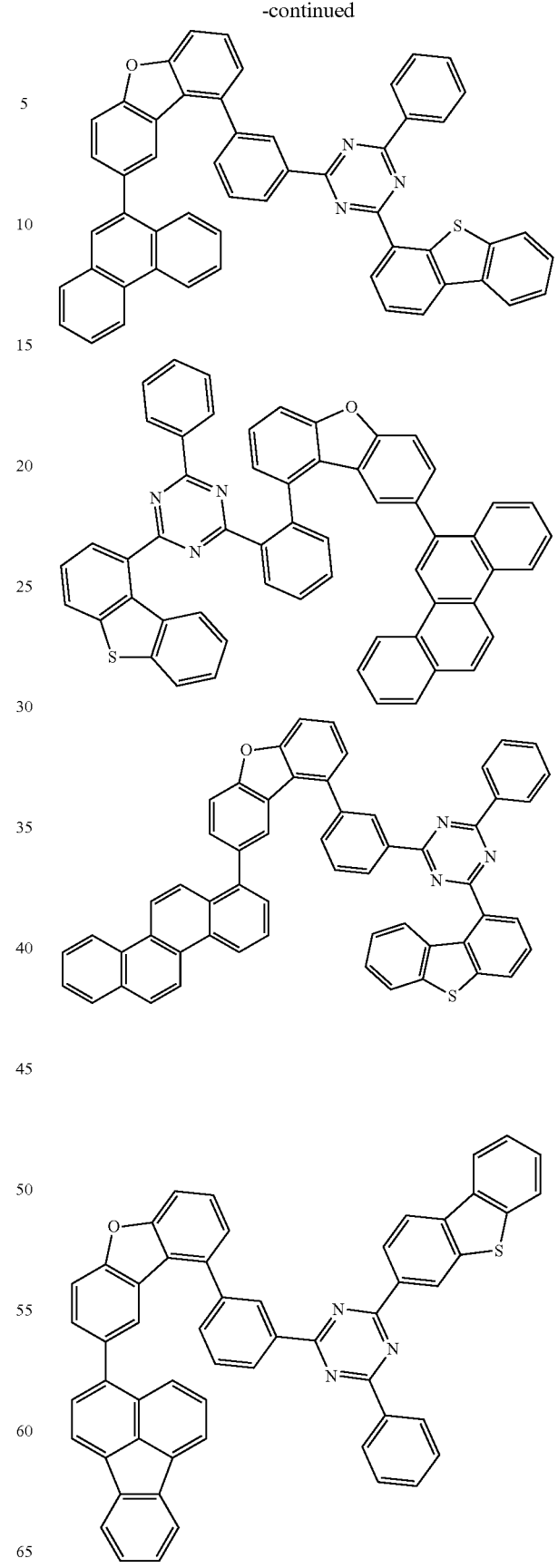

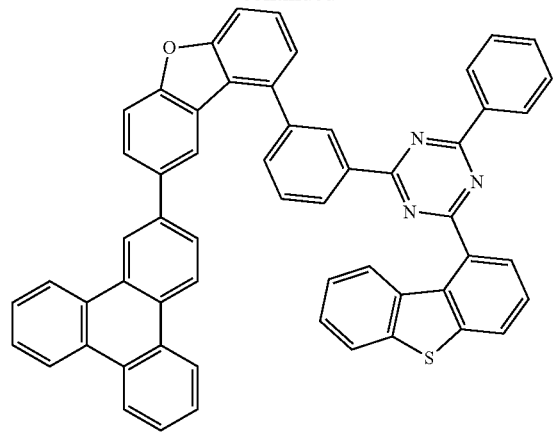
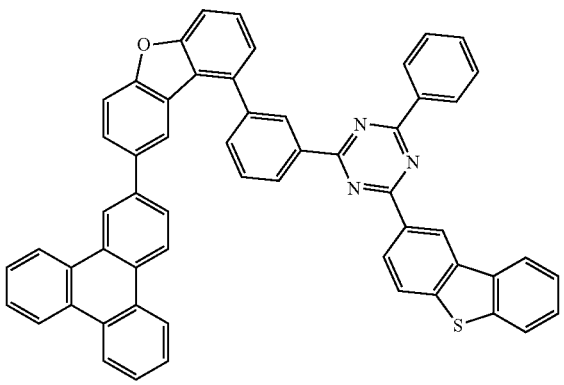
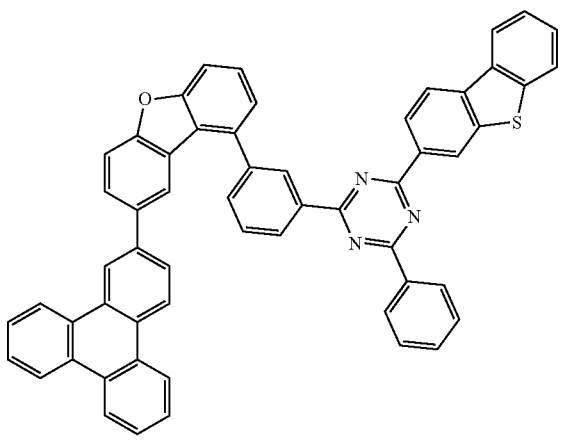
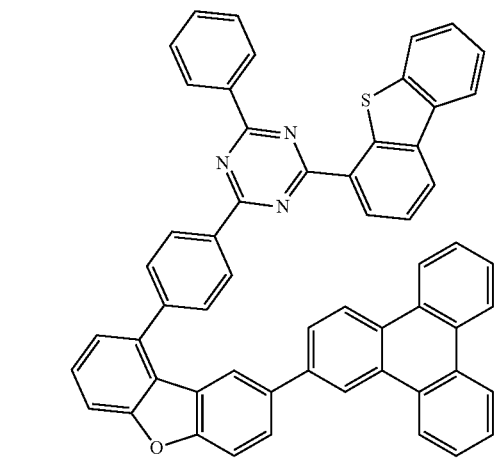
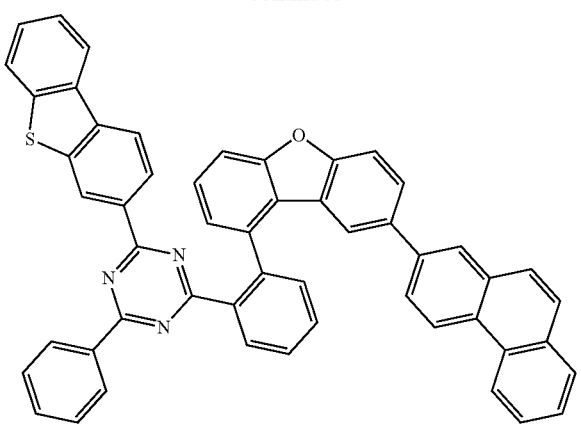
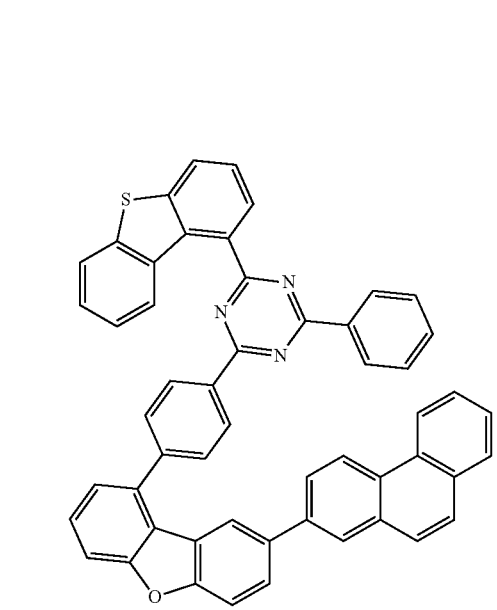
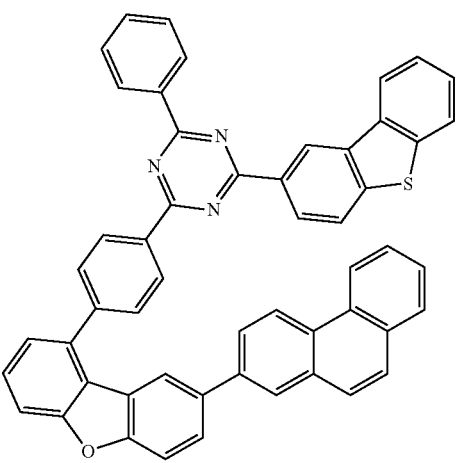

97
-continued
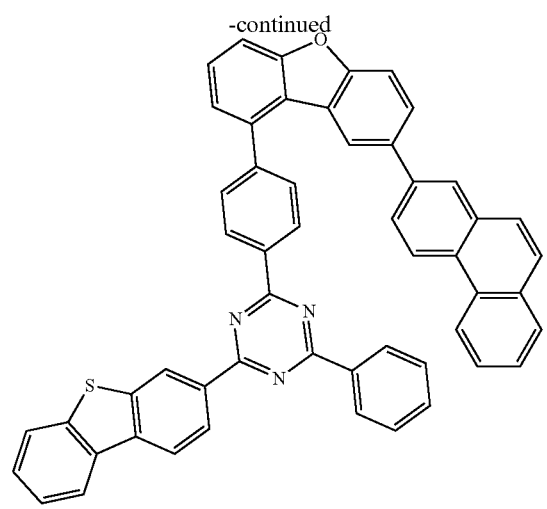
98
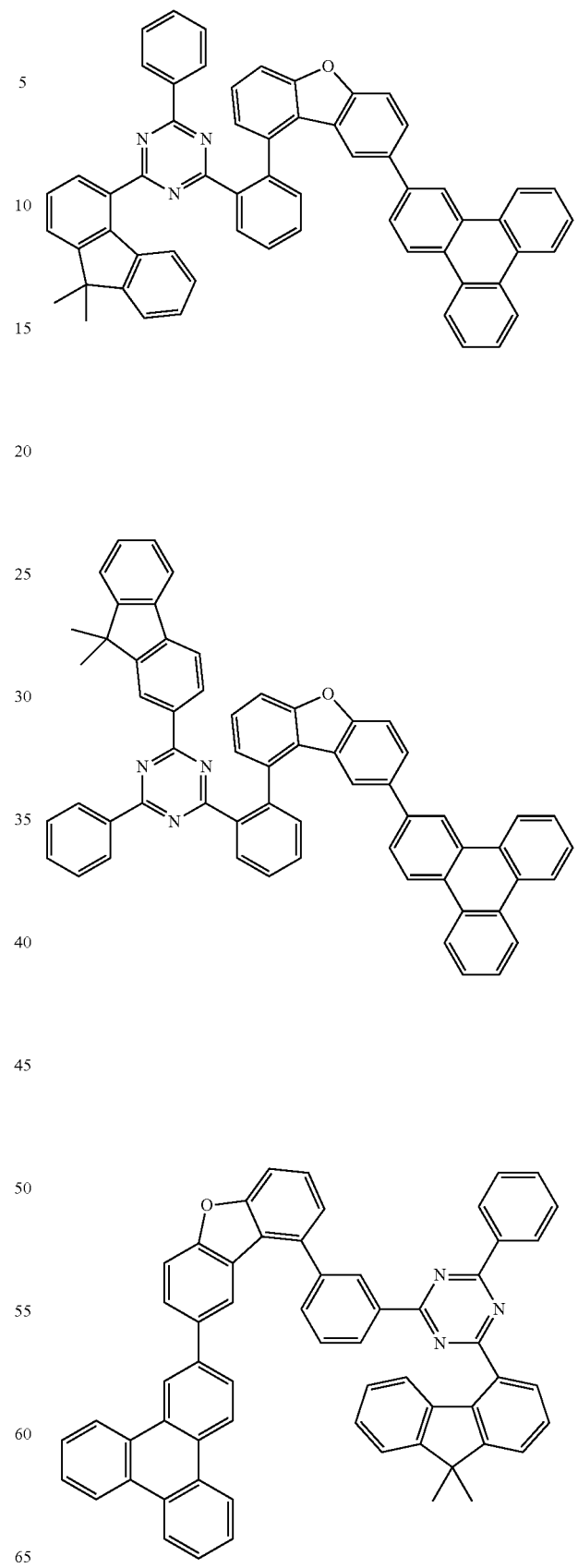

99
-continued
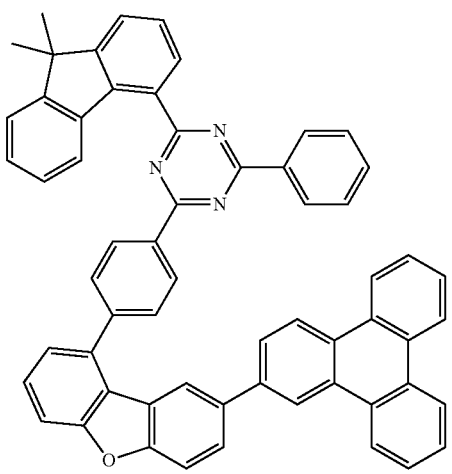
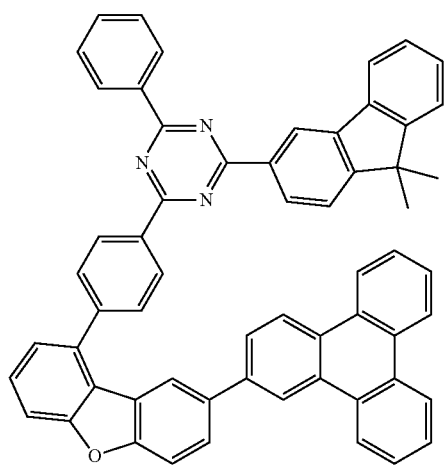
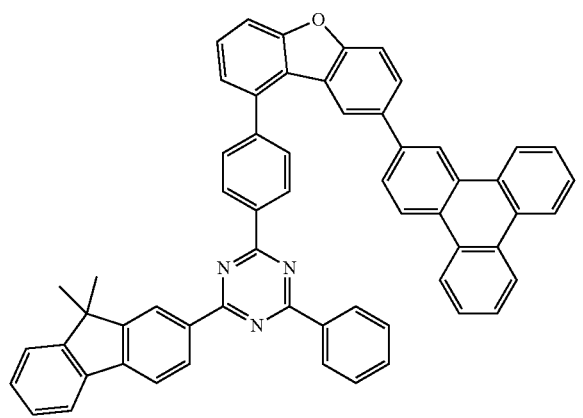
100
-continued
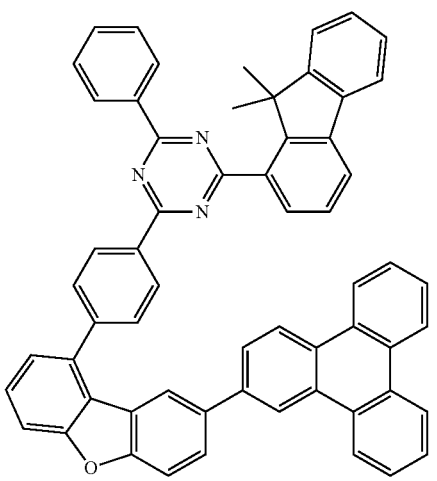
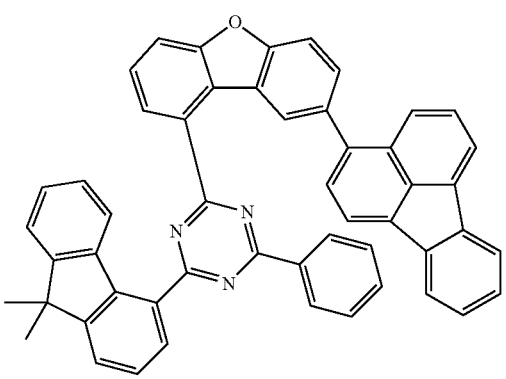
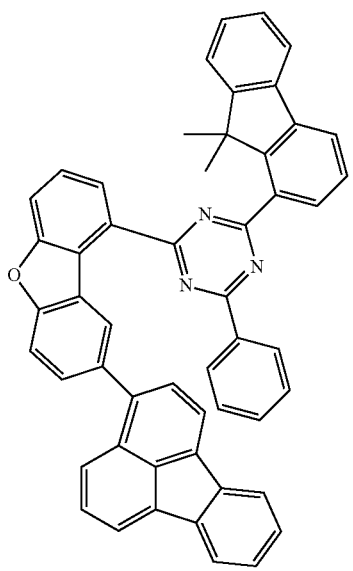

101
-continued
102
-continued
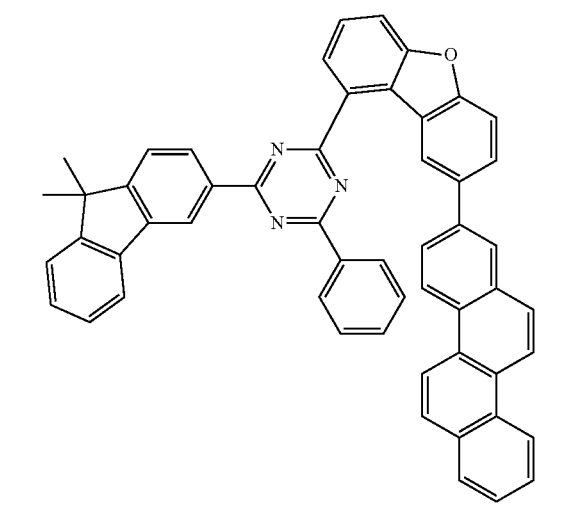
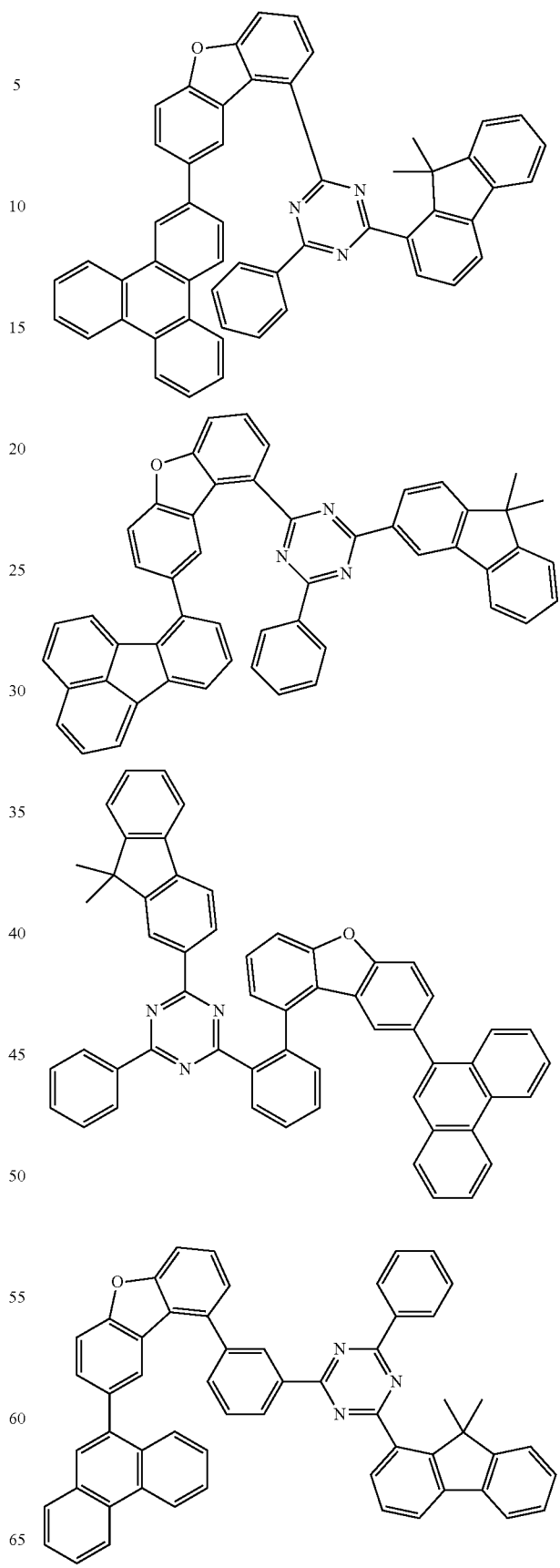

103
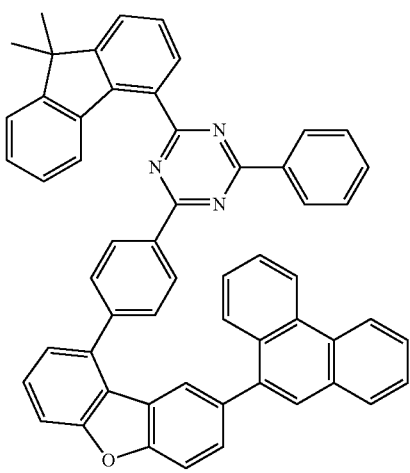
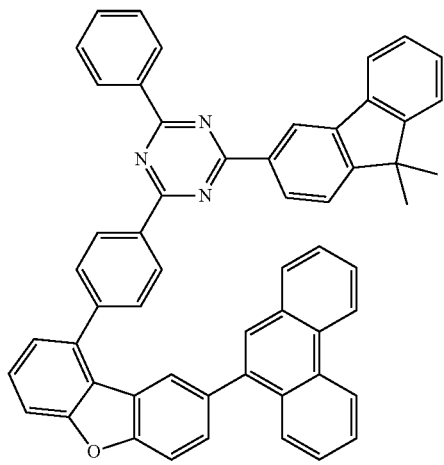
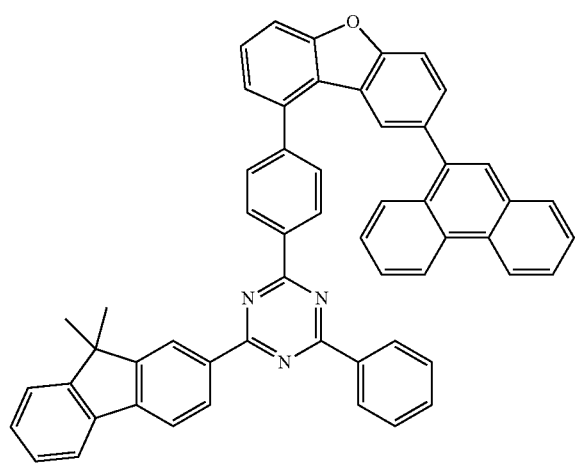
104
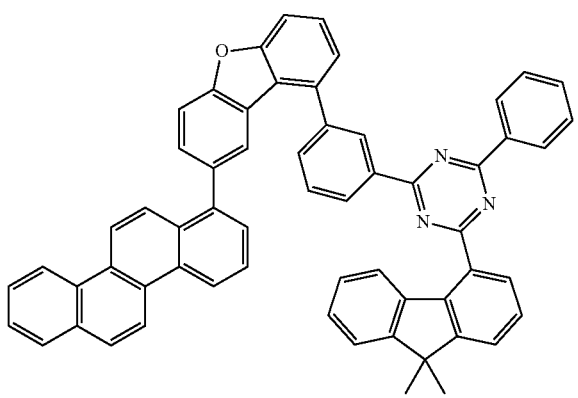
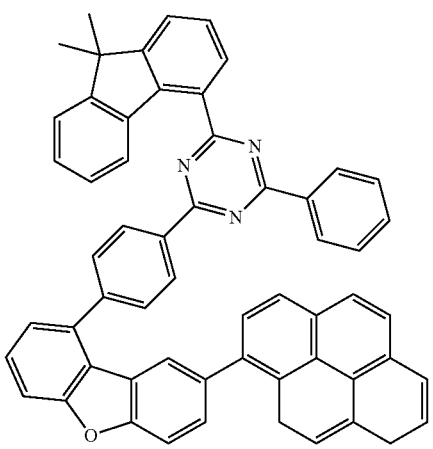

105
-continued
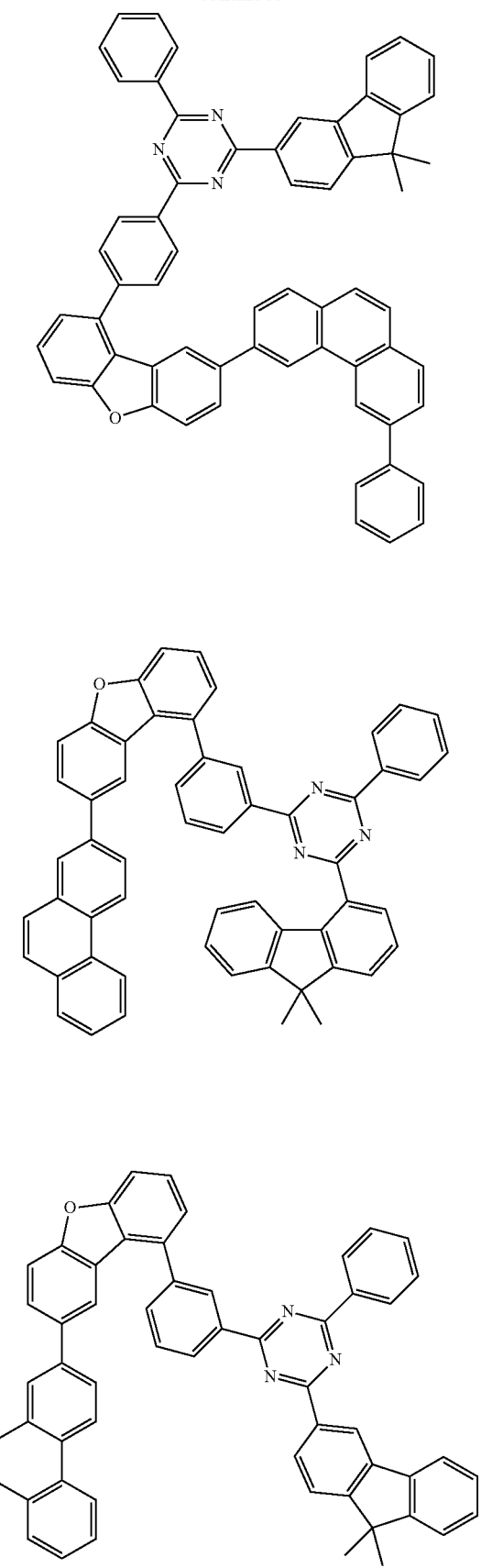
106
-continued
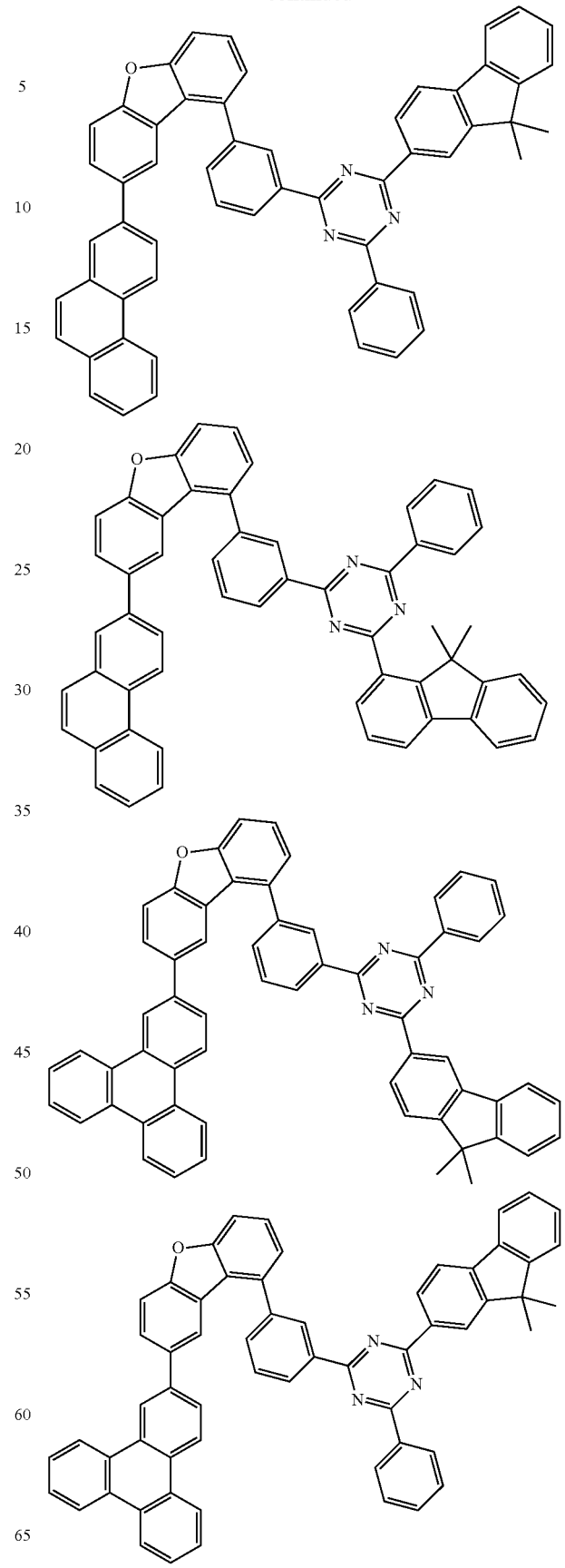

107
-continued
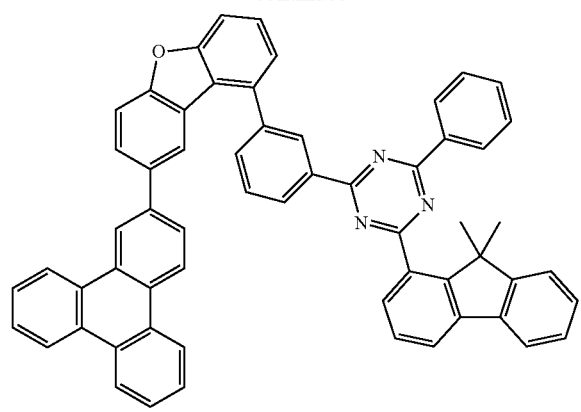
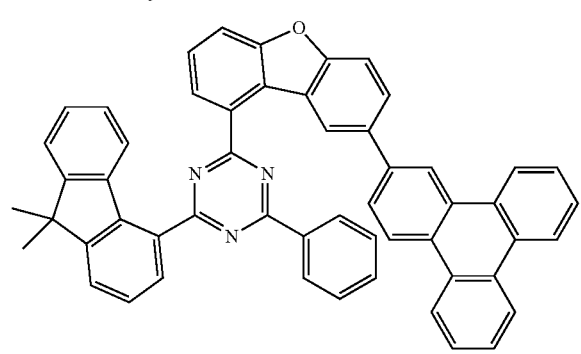
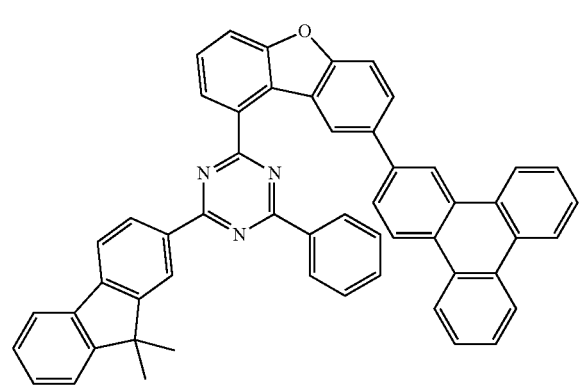
108
-continued
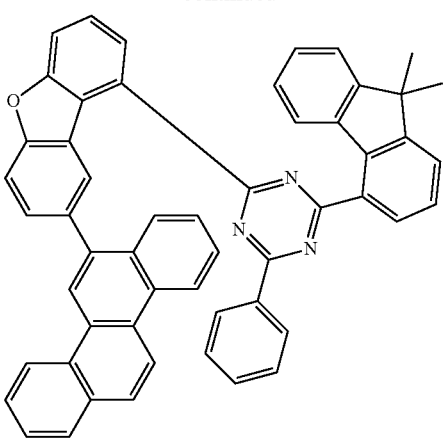
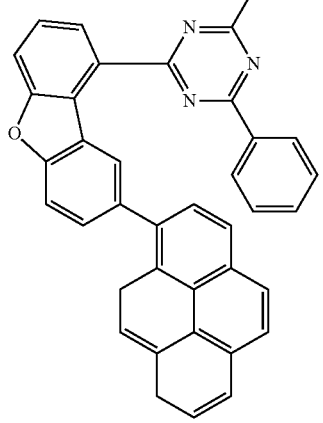
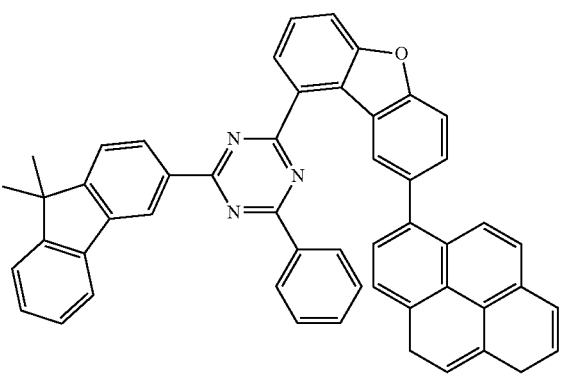

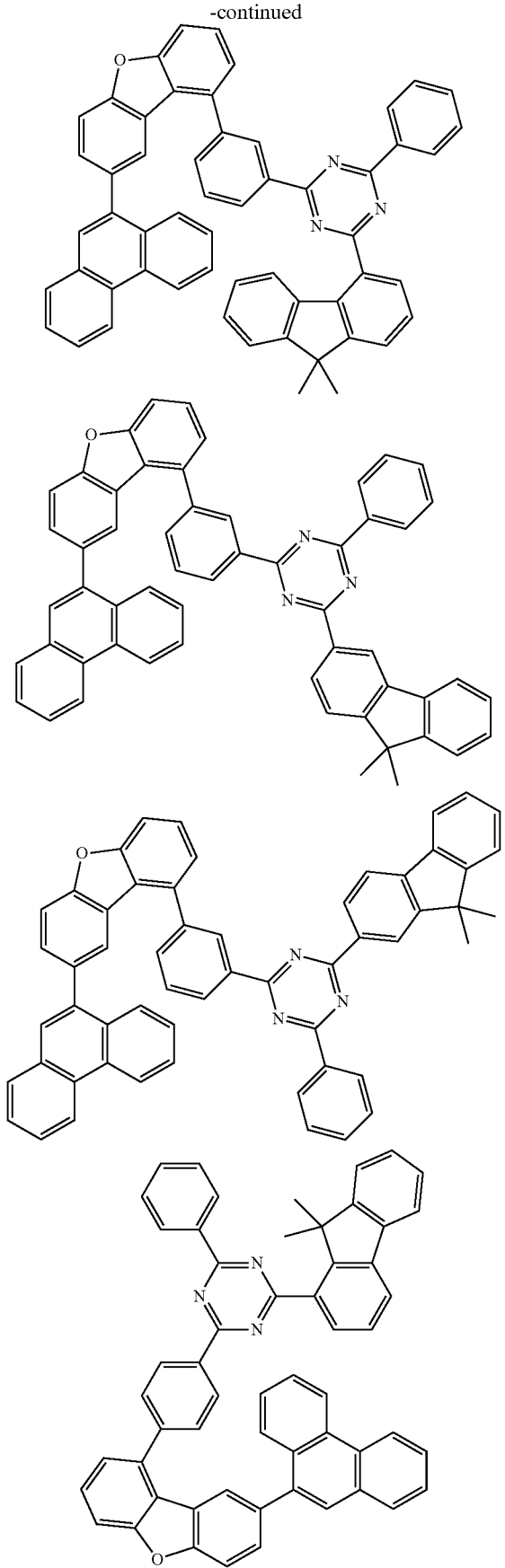

111
-continued
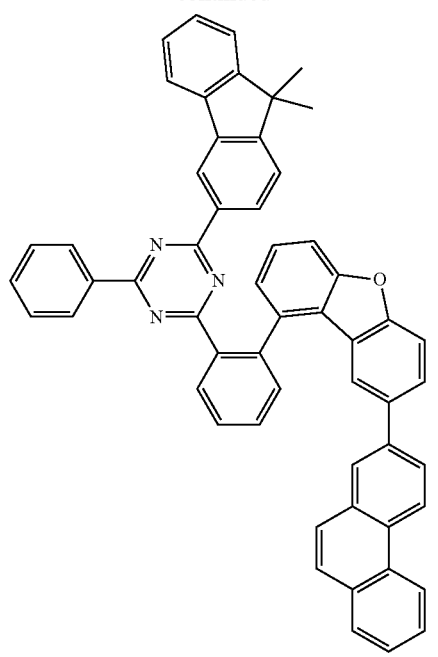
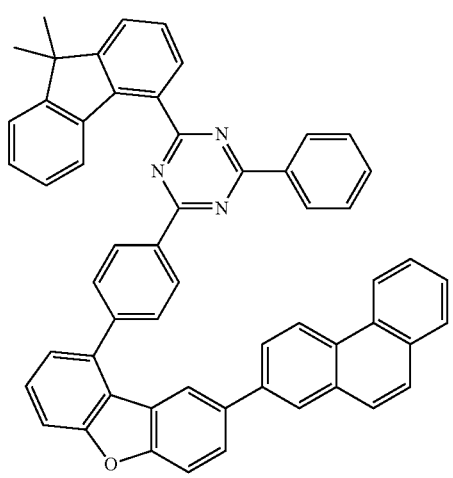
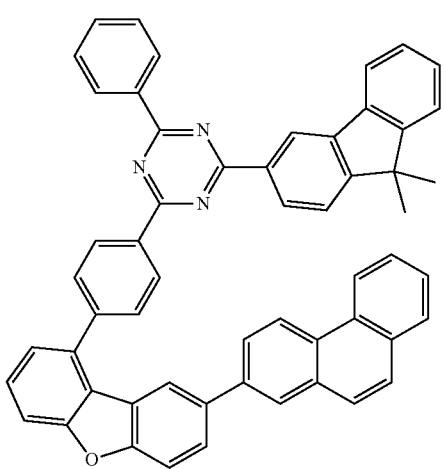
112
-continued
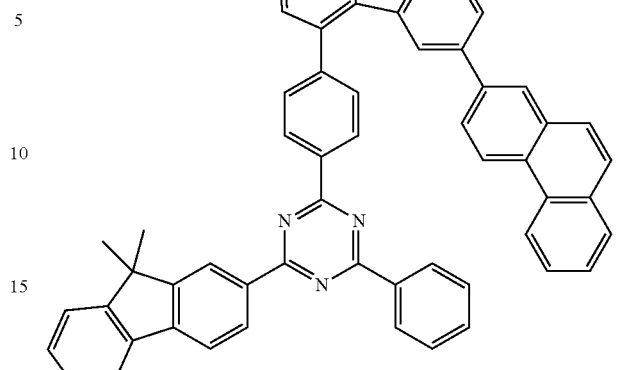
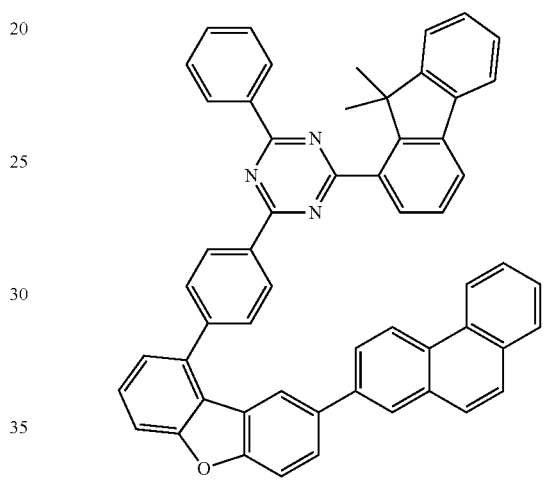
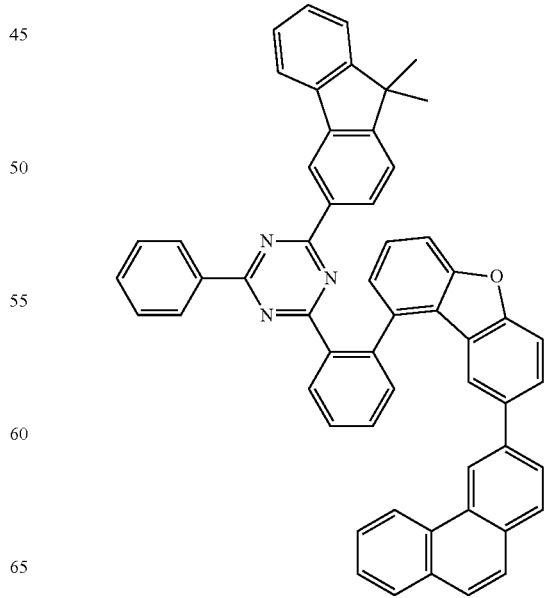

113
-continued
114
-continued
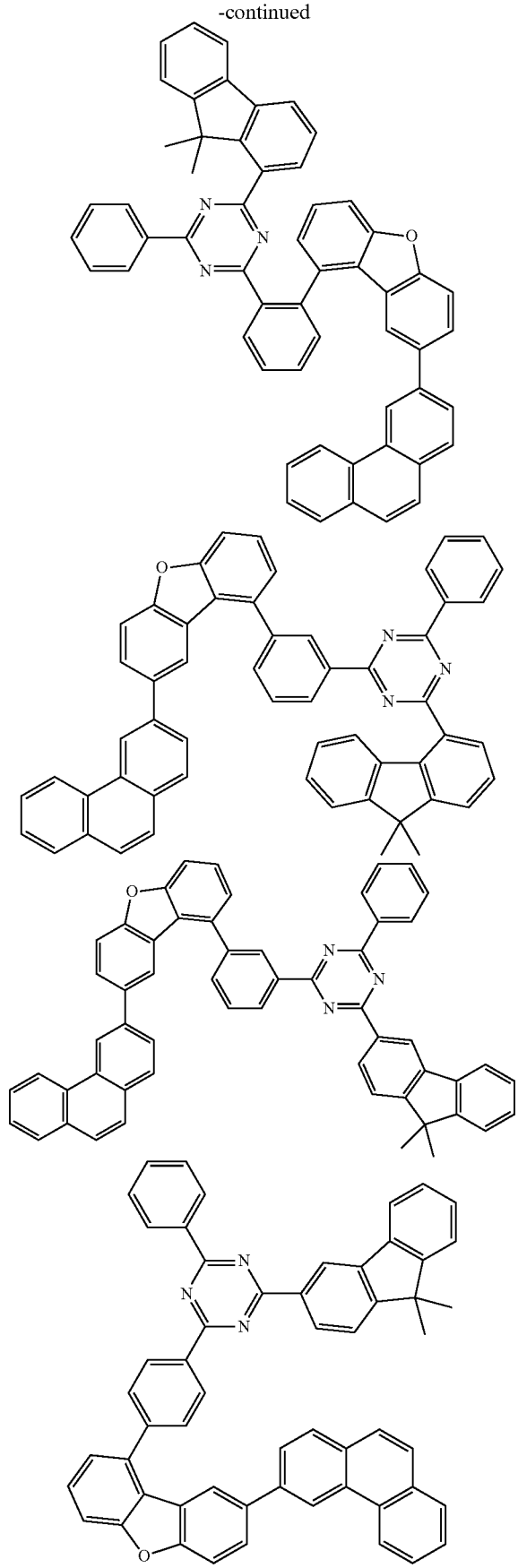
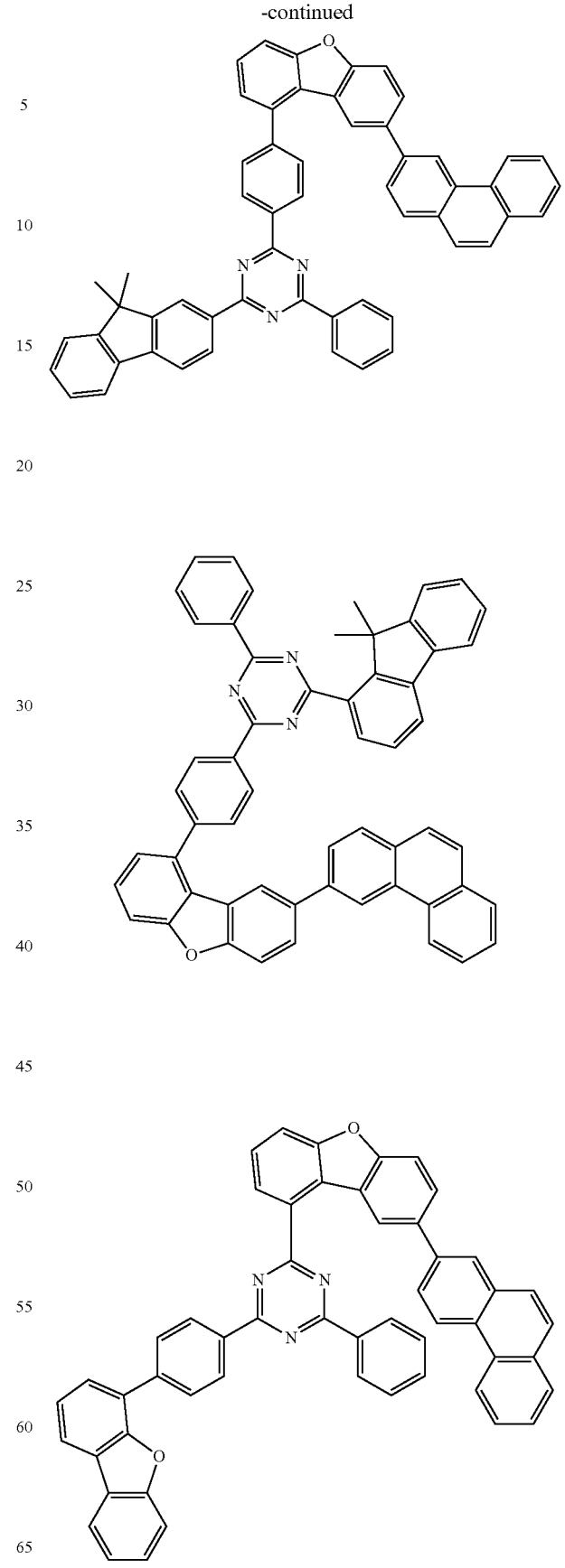

115
-continued
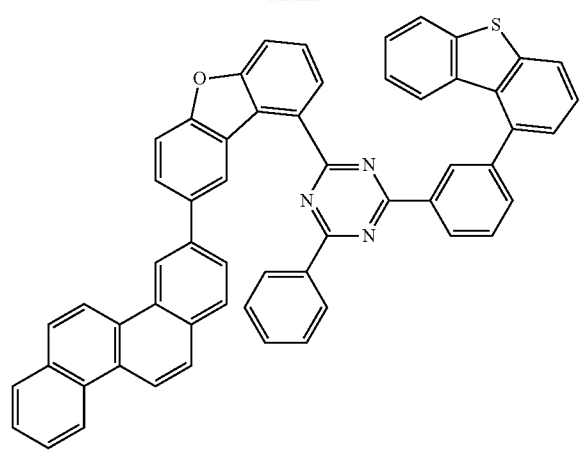
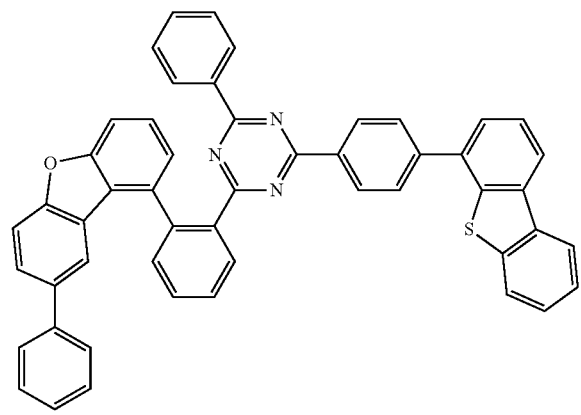
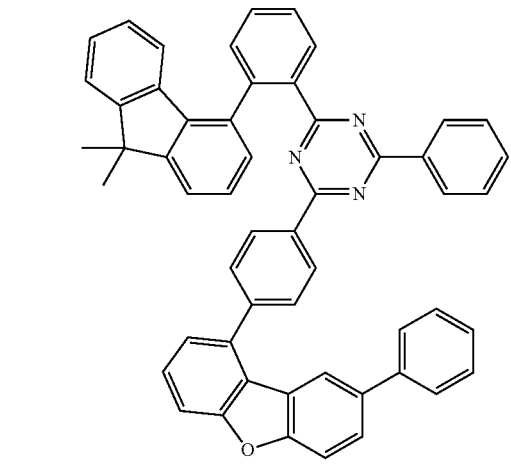
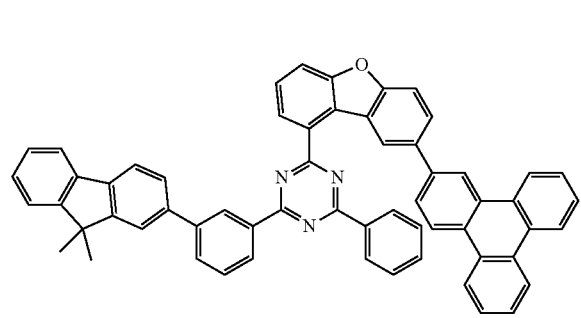
116
-continued
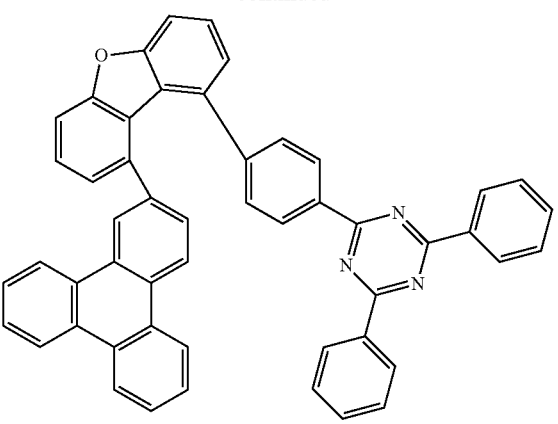
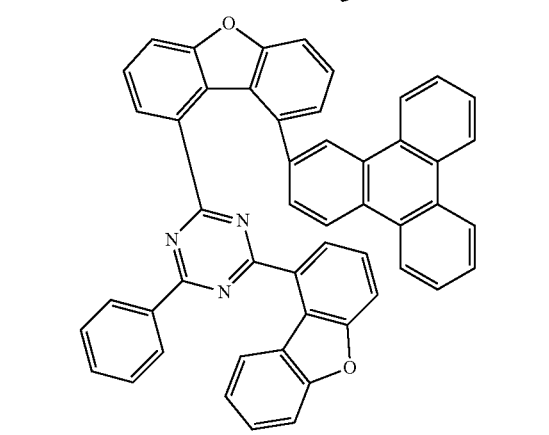
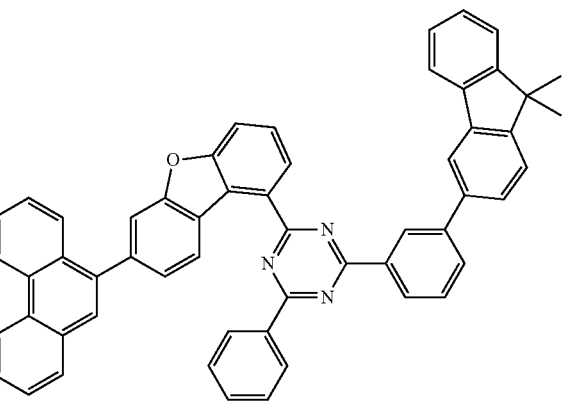
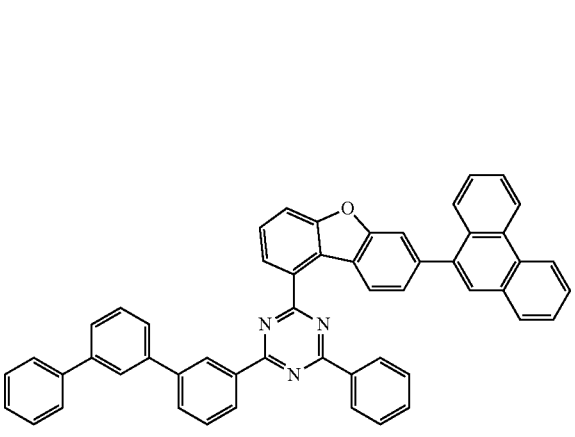

117
-continued
118
-continued
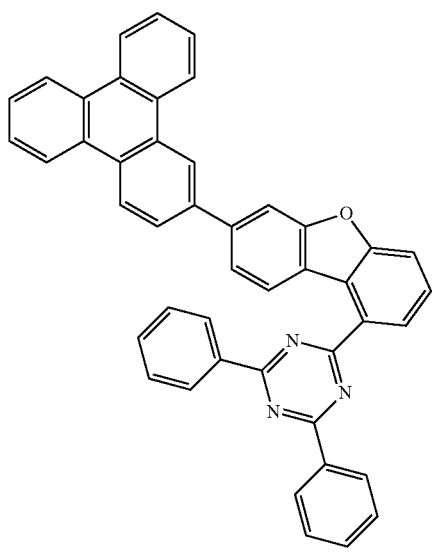
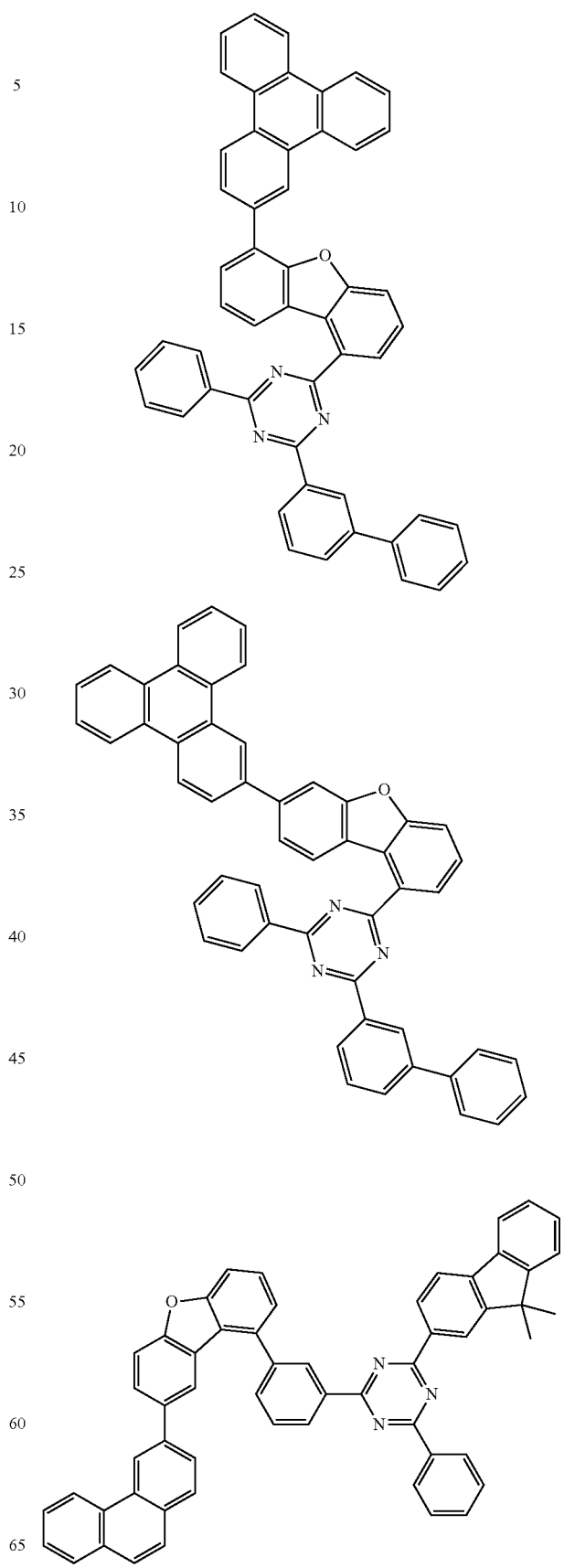

119
-continued
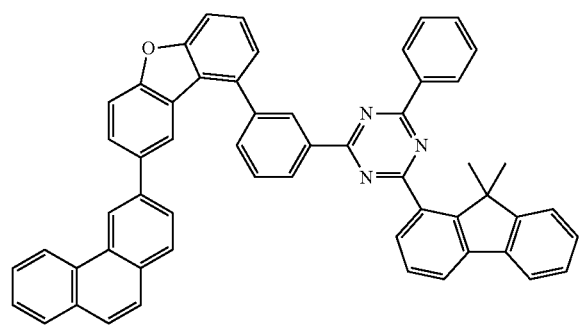
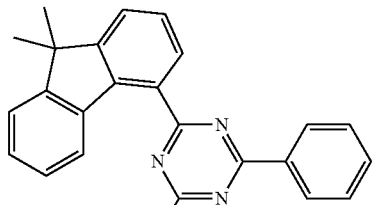
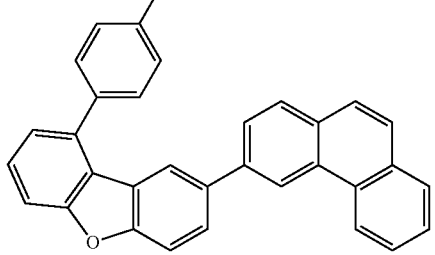
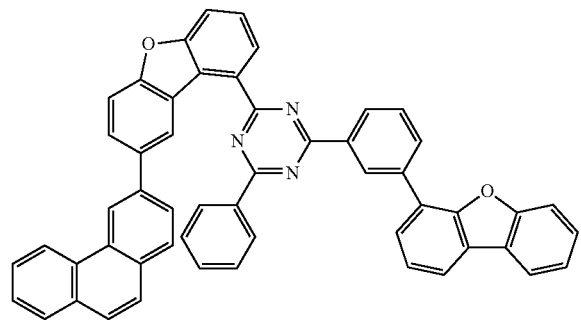
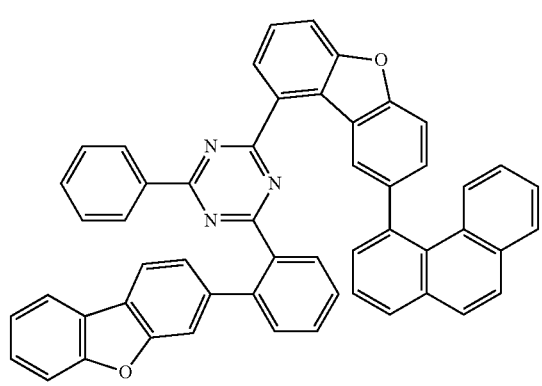
120
-continued
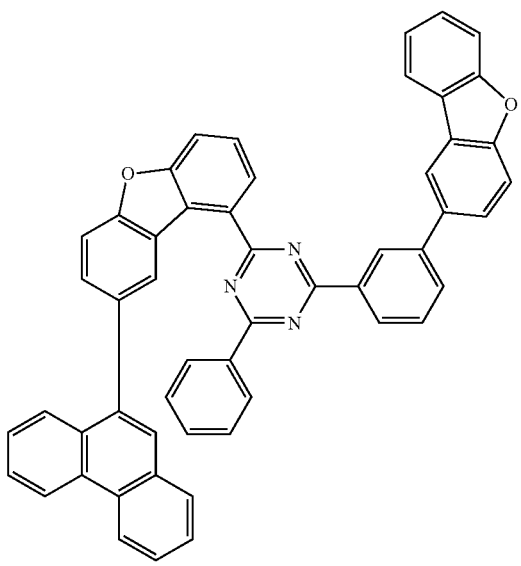
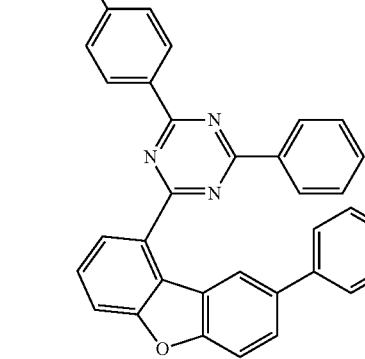
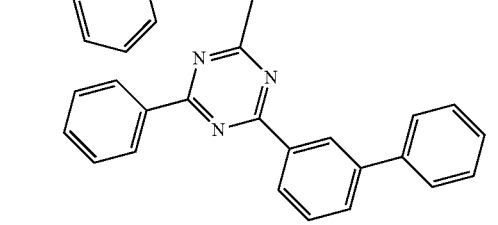

121
-continued
122
-continued
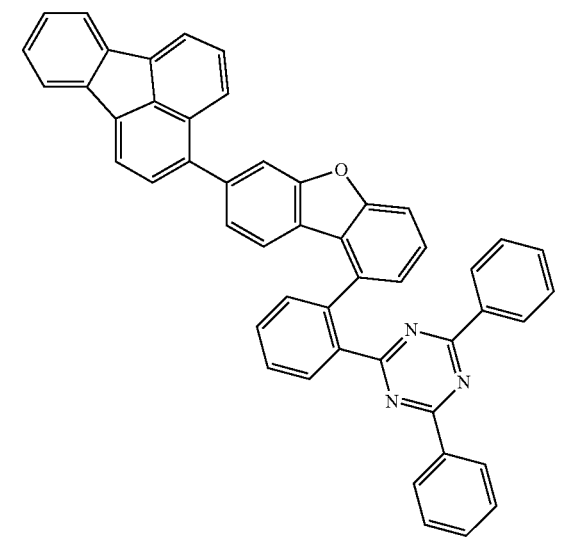
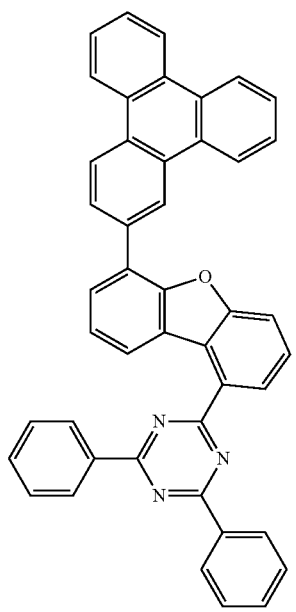
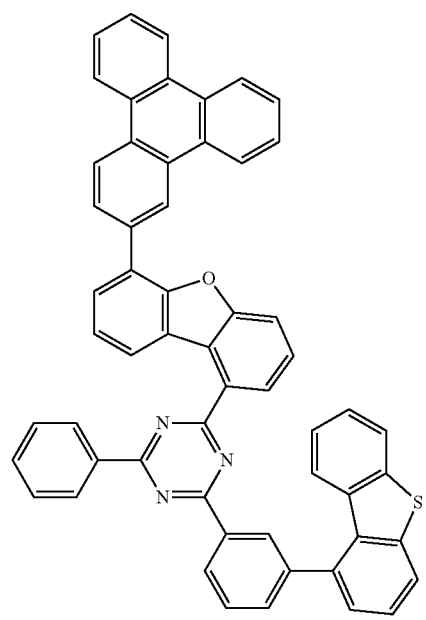
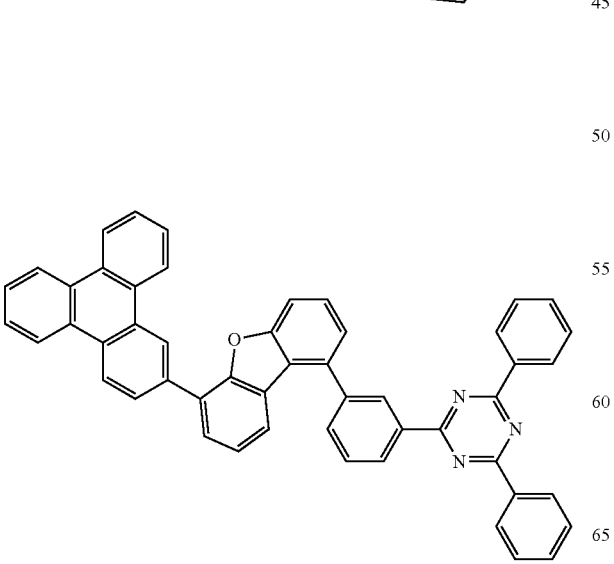
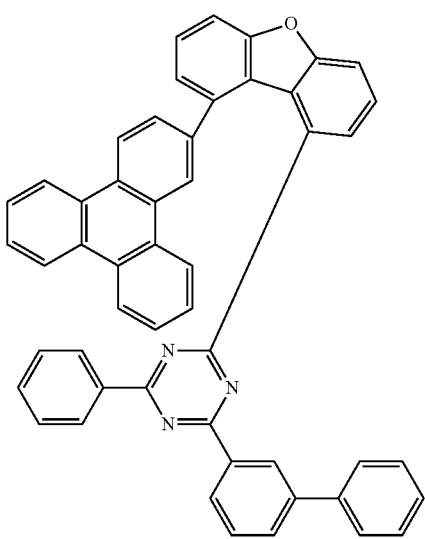

123
-continued
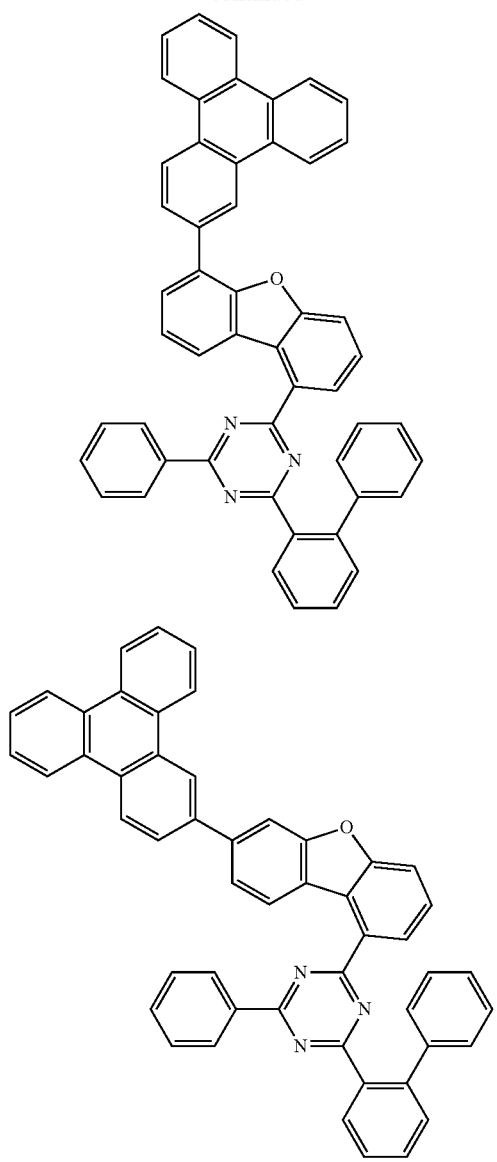
124
-continued
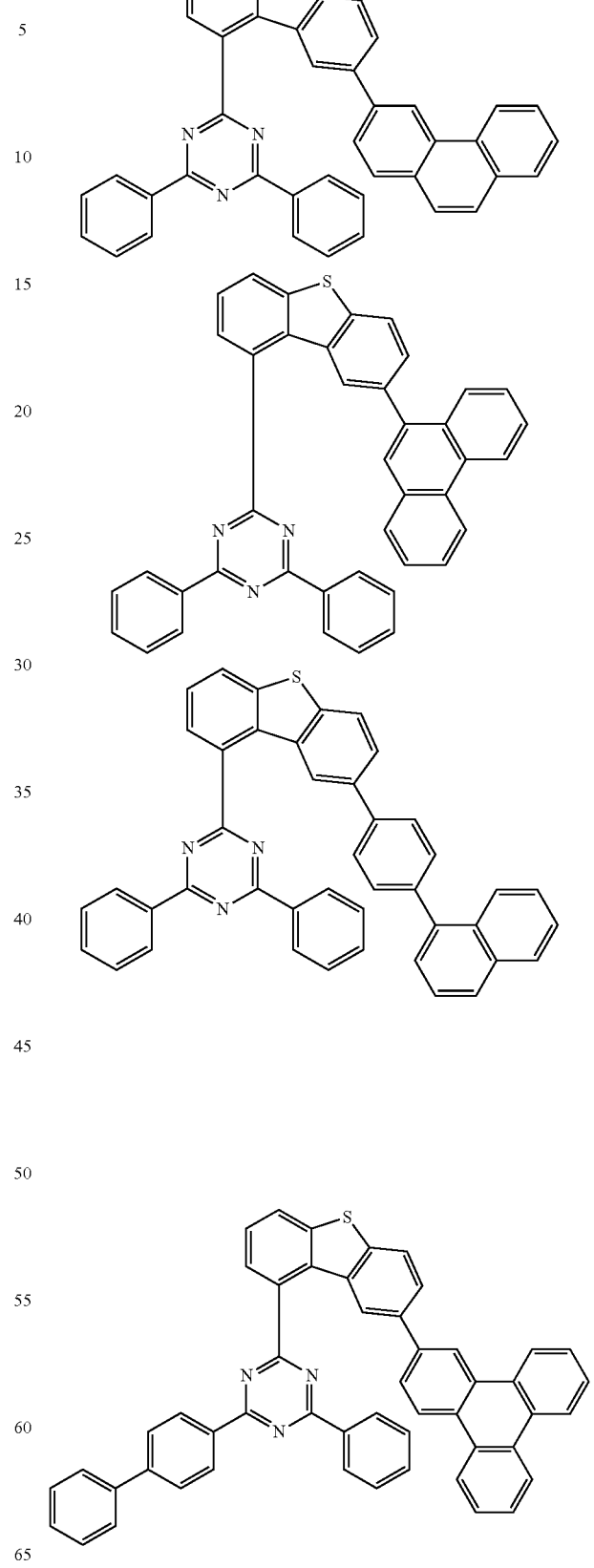

125
-continued
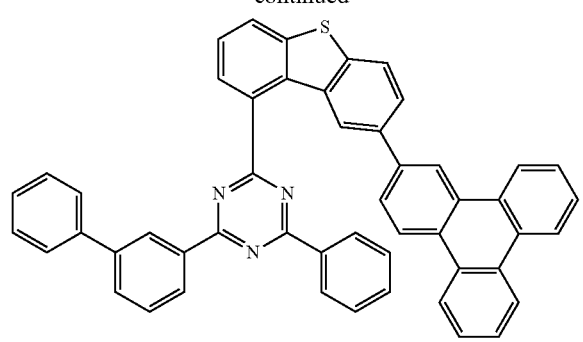
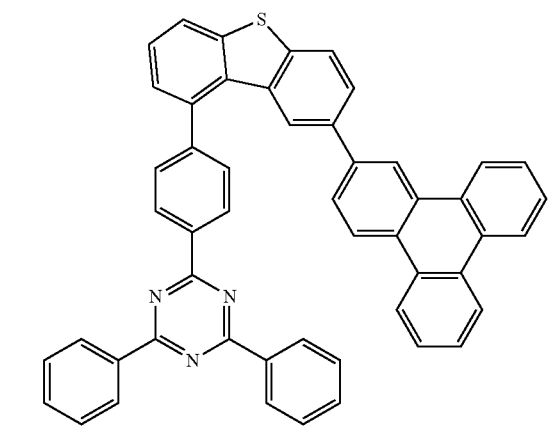
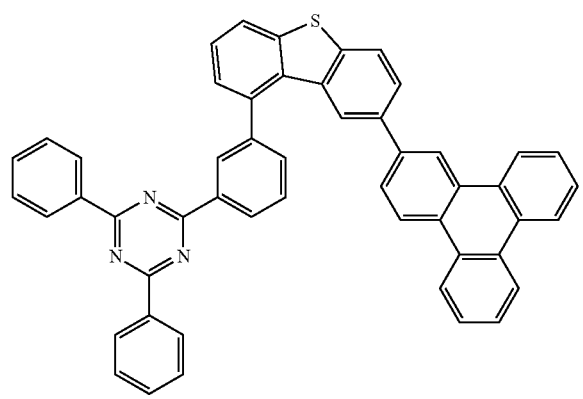
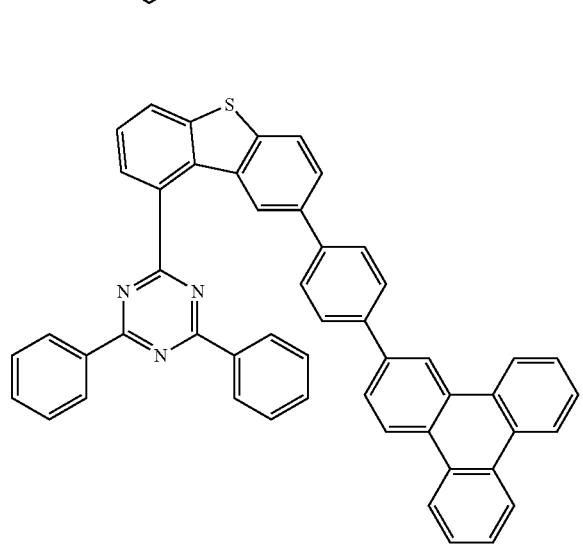
126
-continued
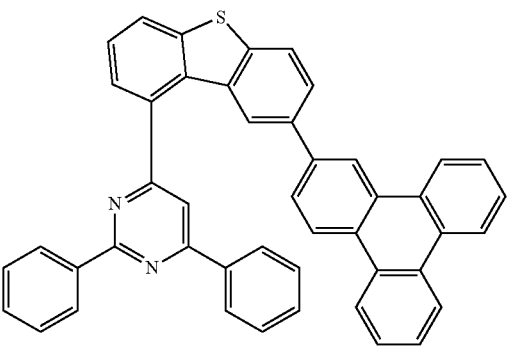
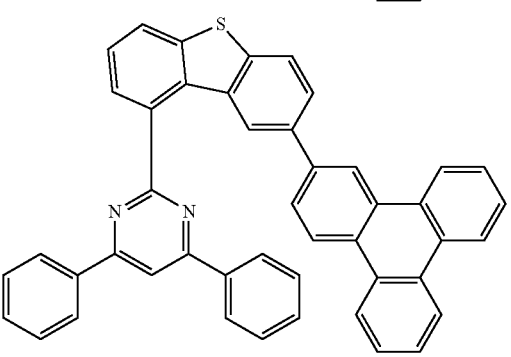
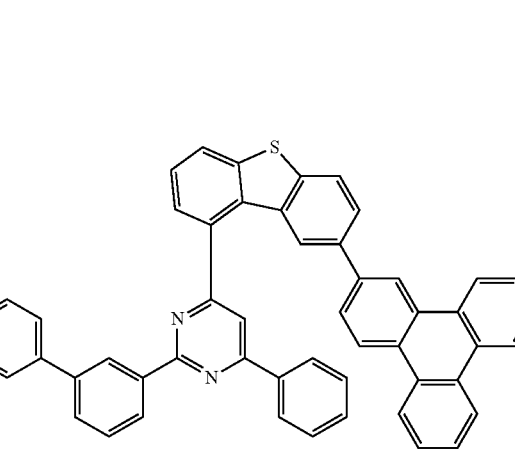
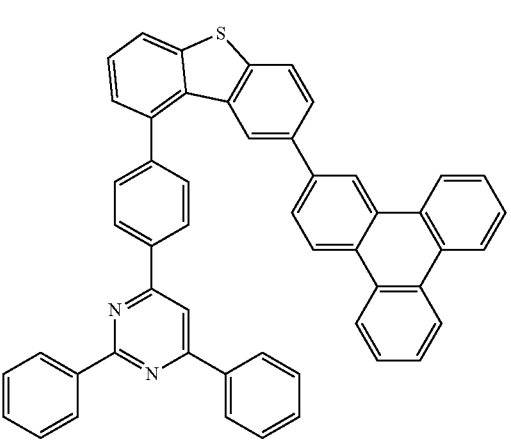

127
-continued
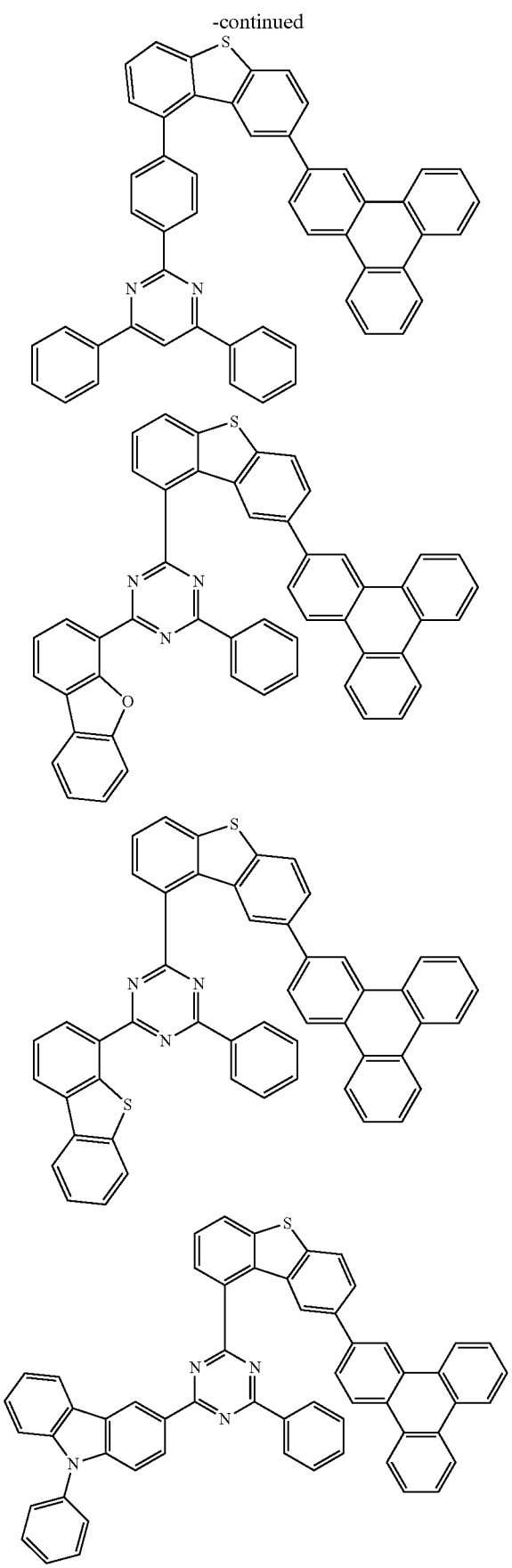
128
-continued
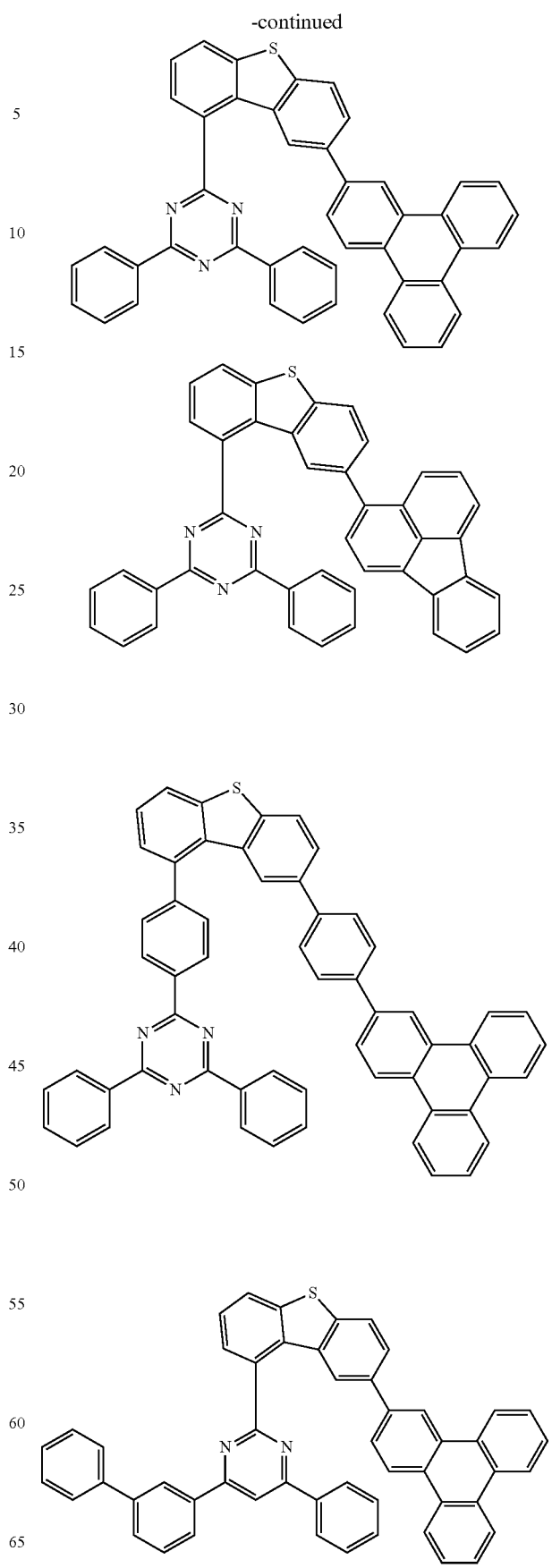

129
-continued
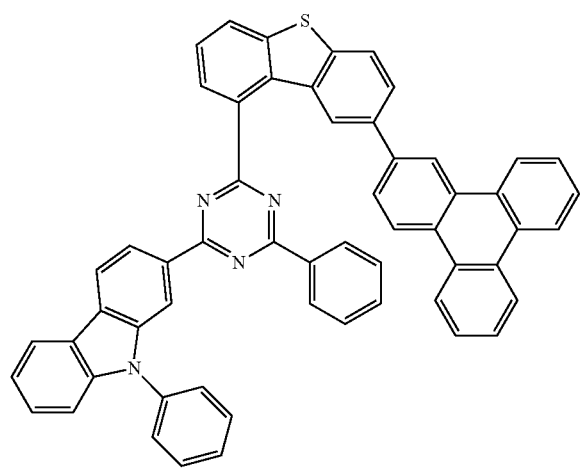
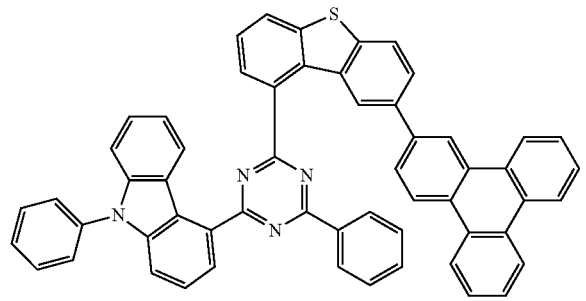
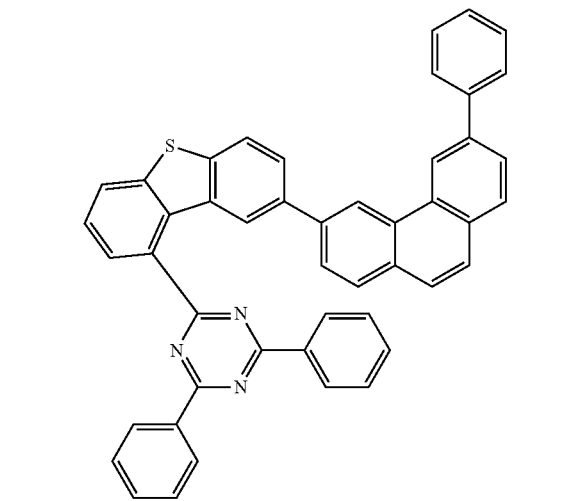
130
-continued
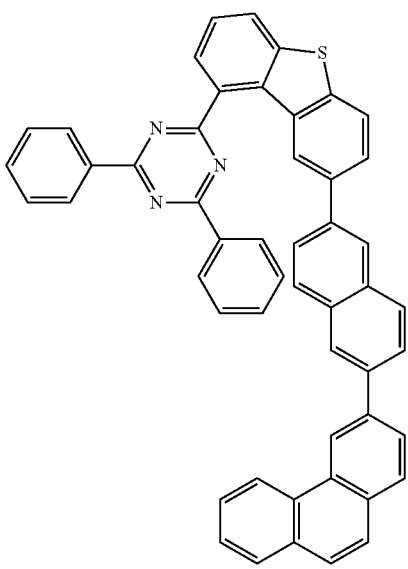
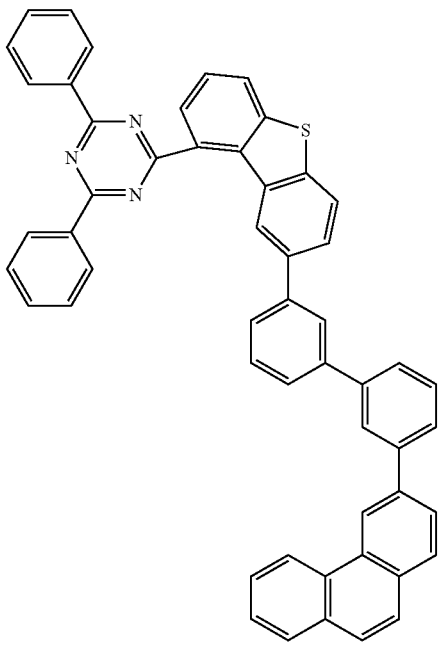
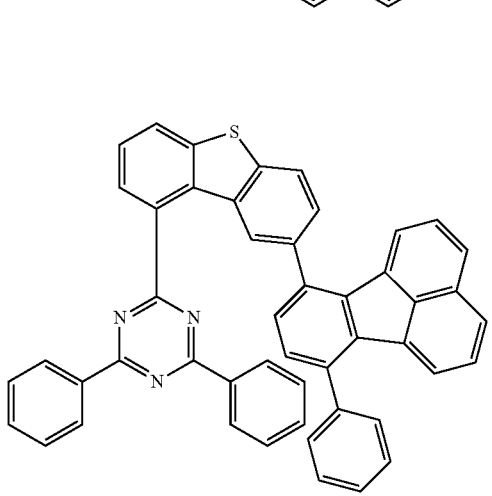

131
-continued
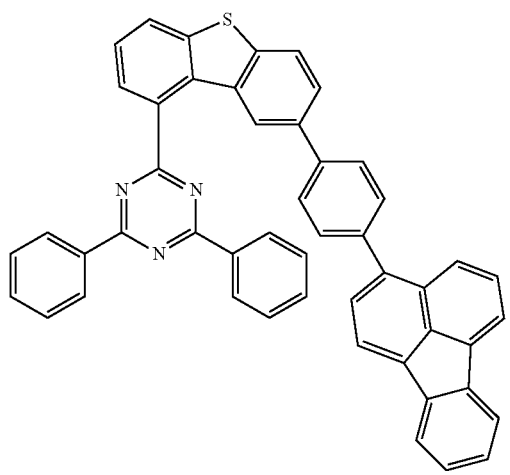
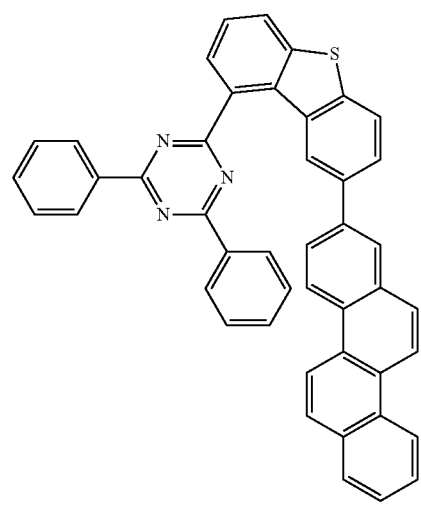
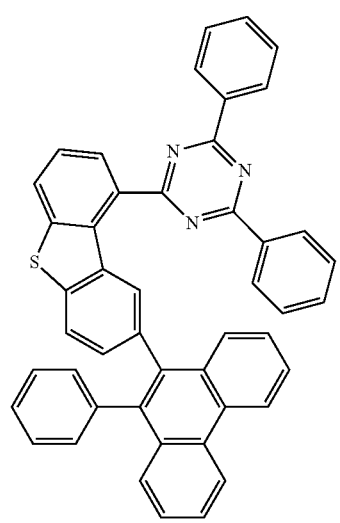
132
-continued
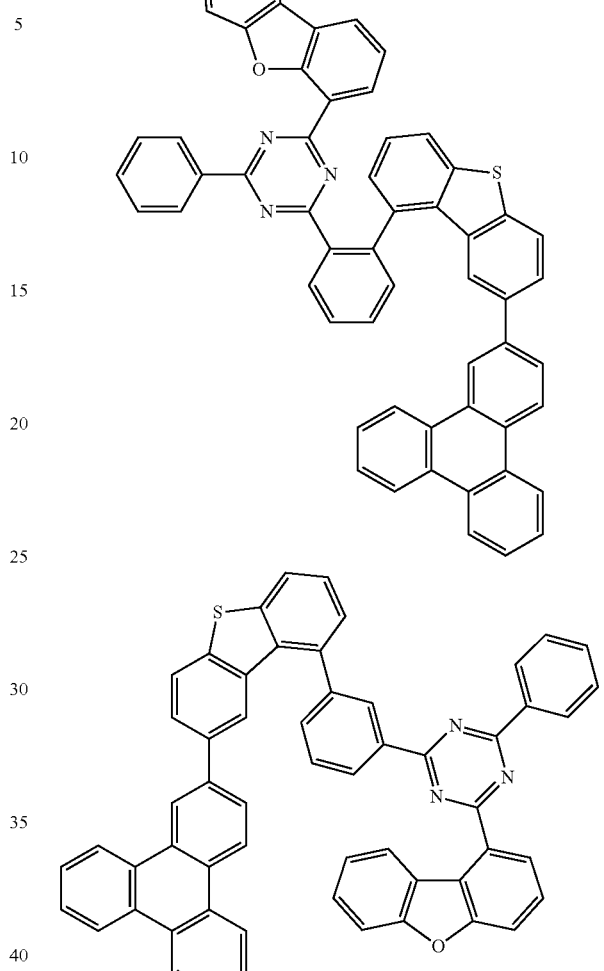
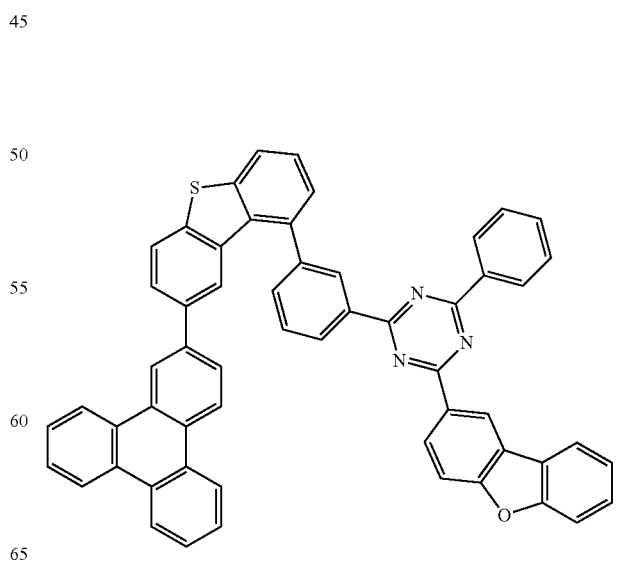

133
-continued
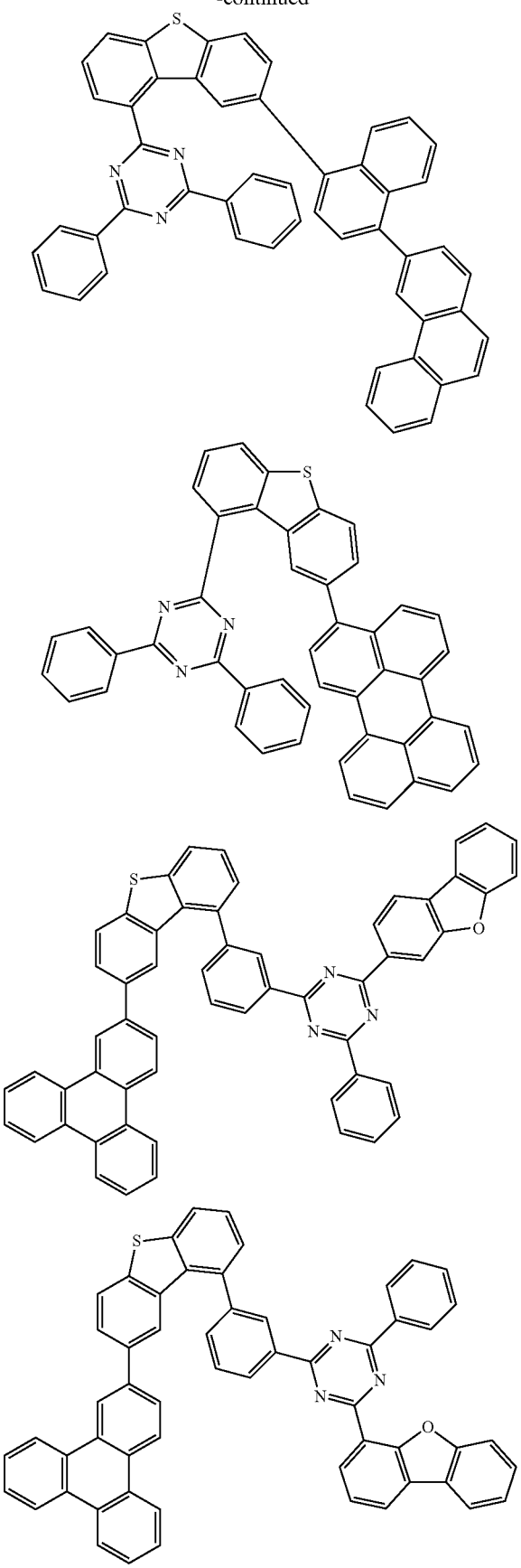
134
-continued
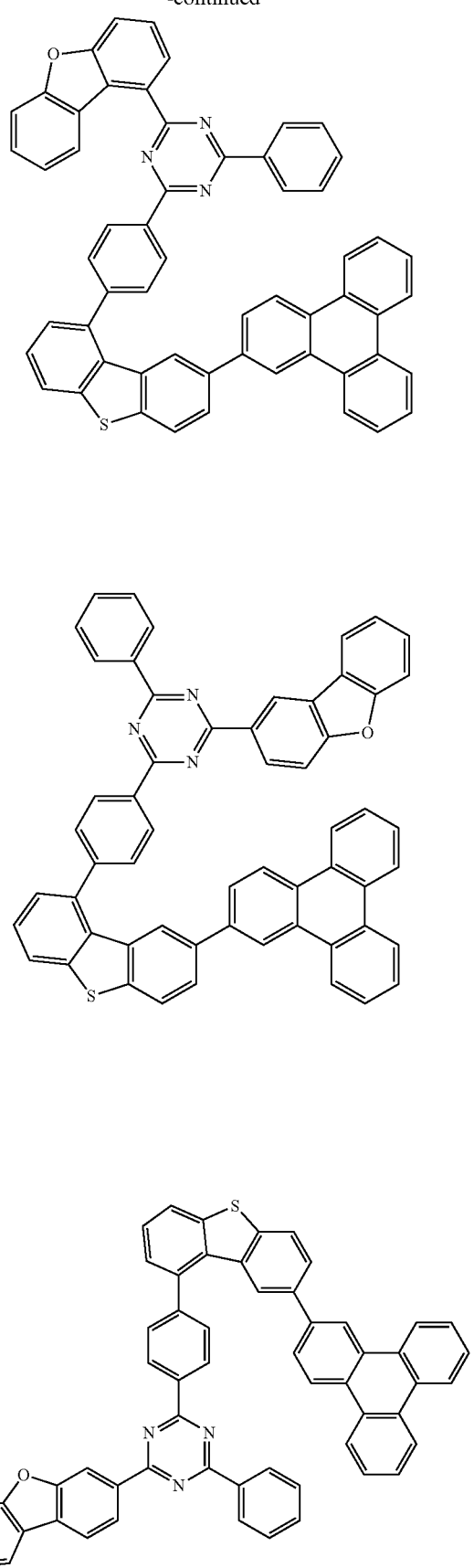

135
-continued
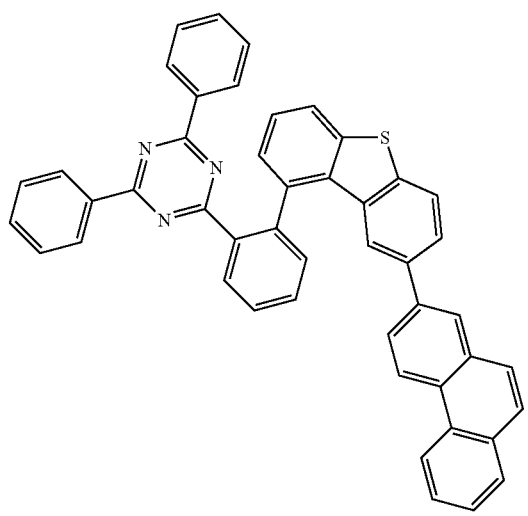
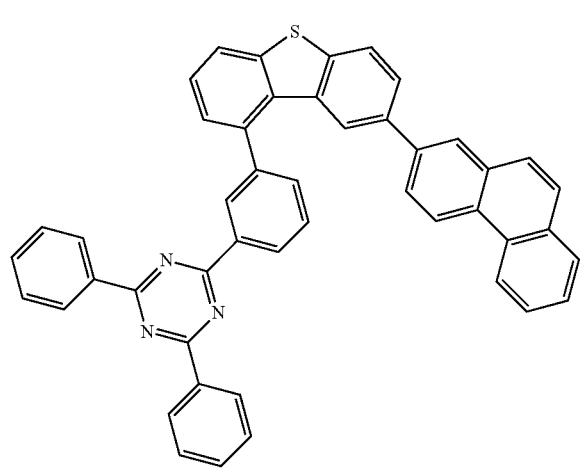
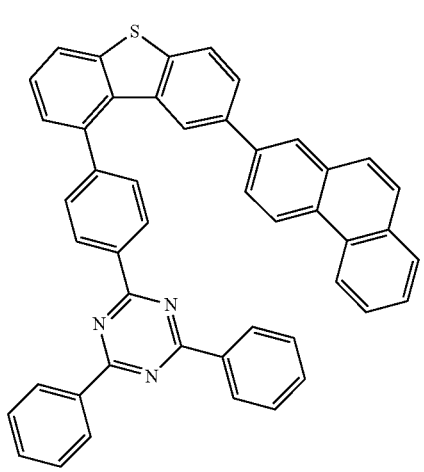
136
-continued
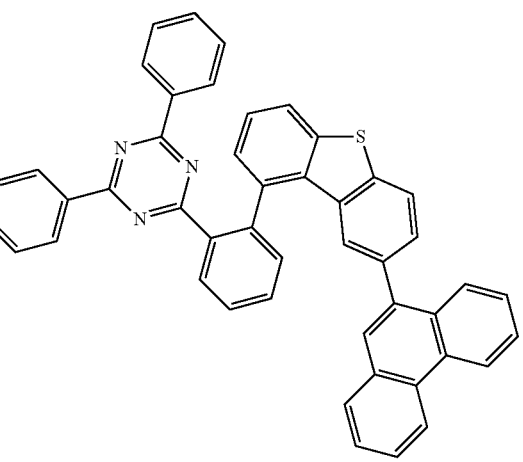
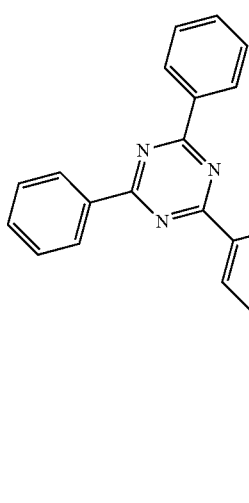
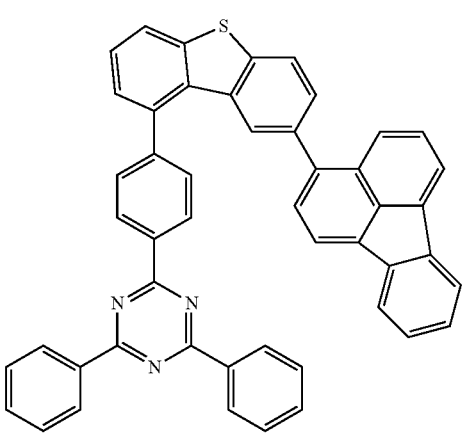

137
-continued
138
-continued
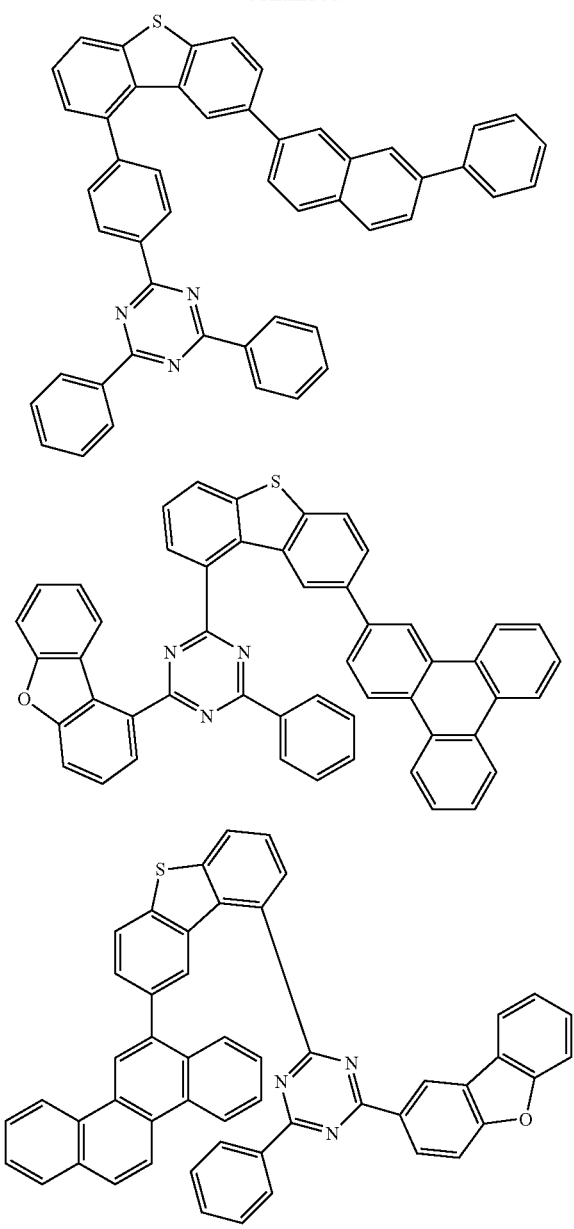
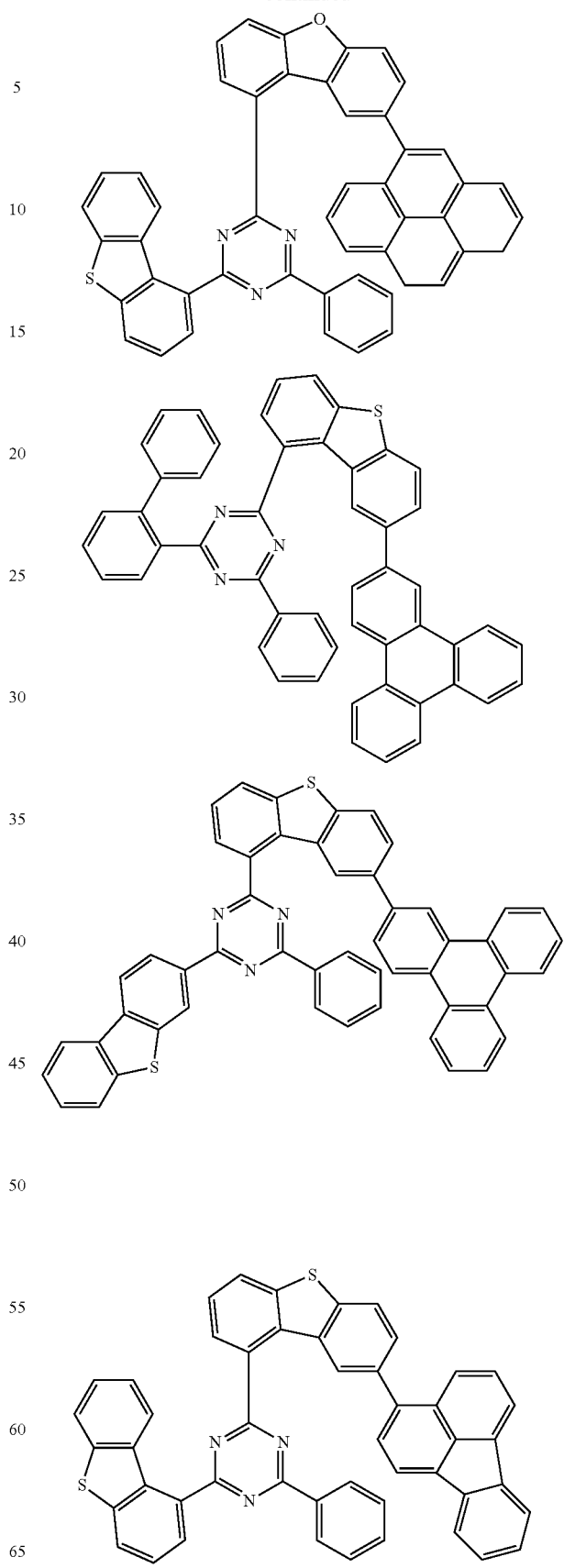

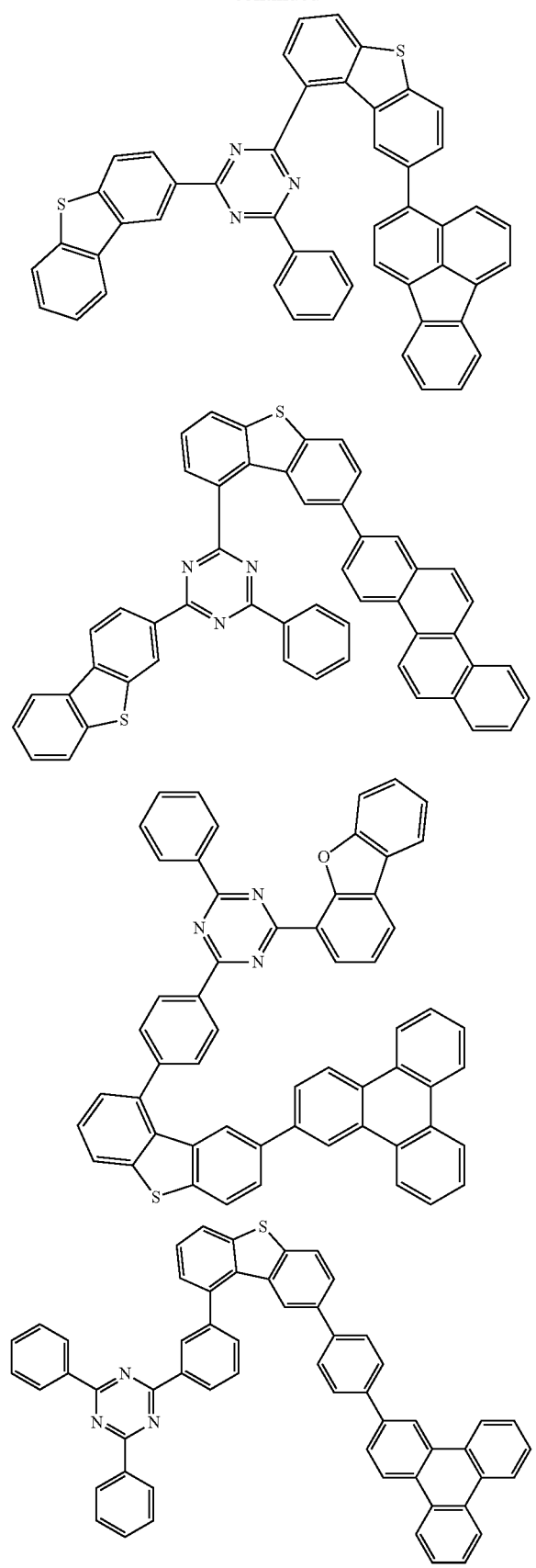
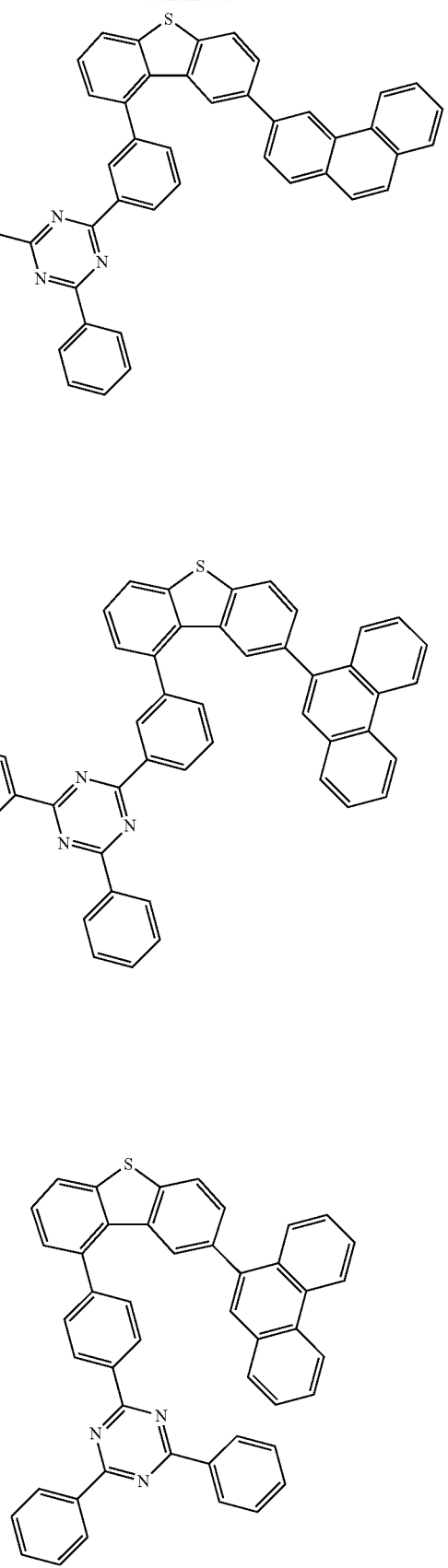

141
-continued
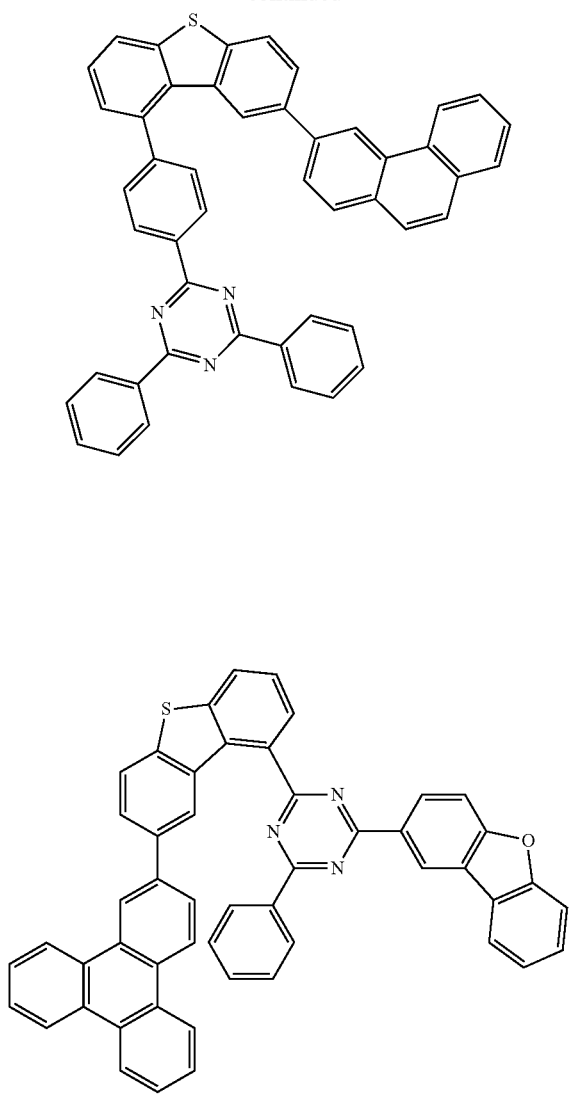
142
-continued
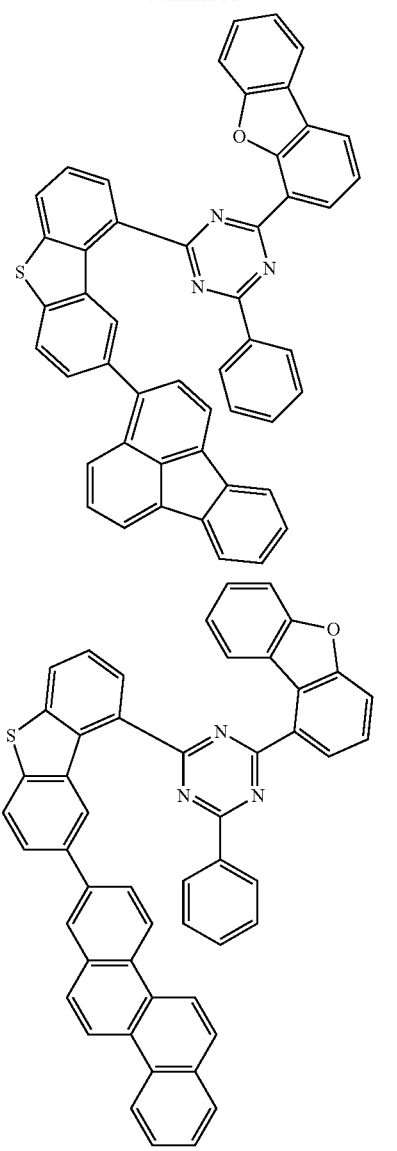
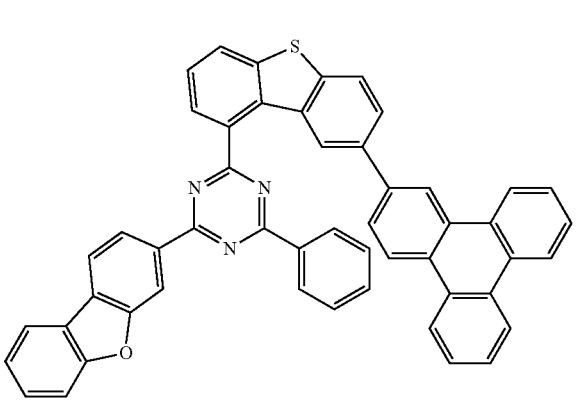
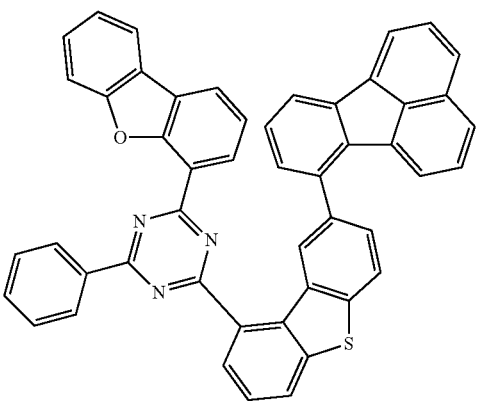

-continued
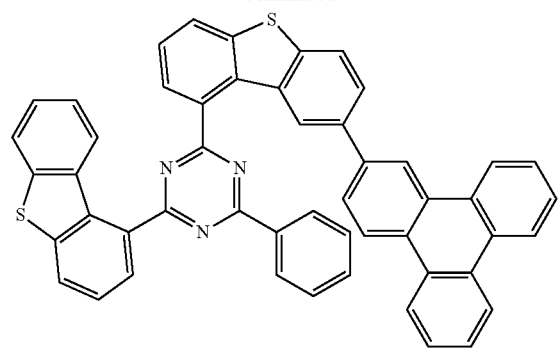
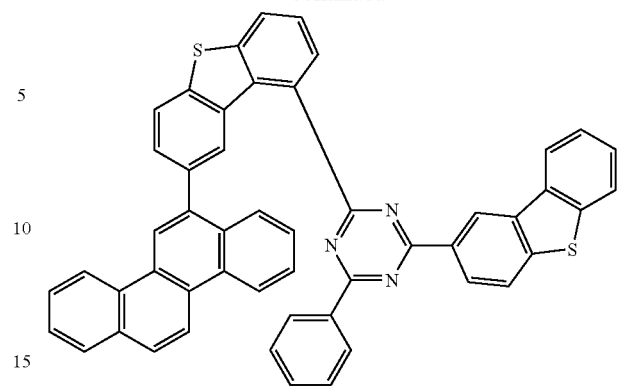
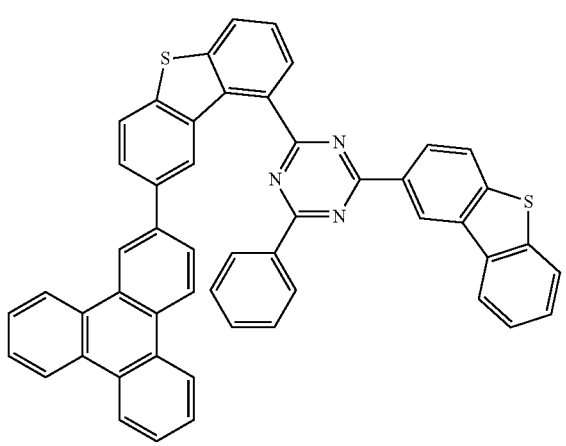
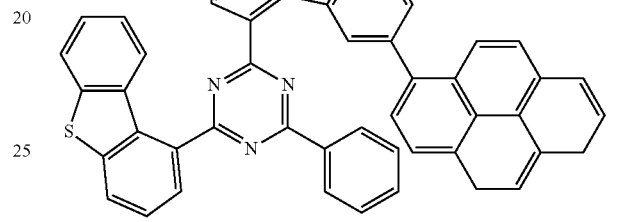
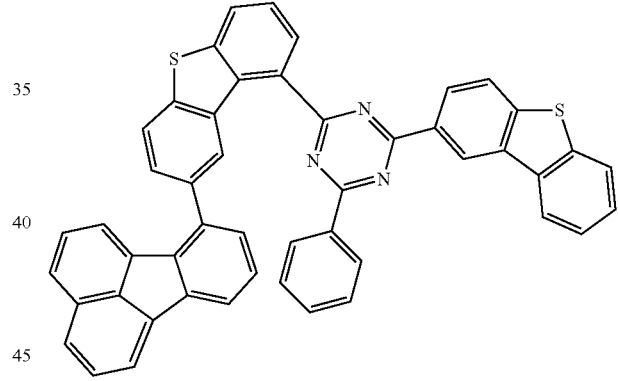
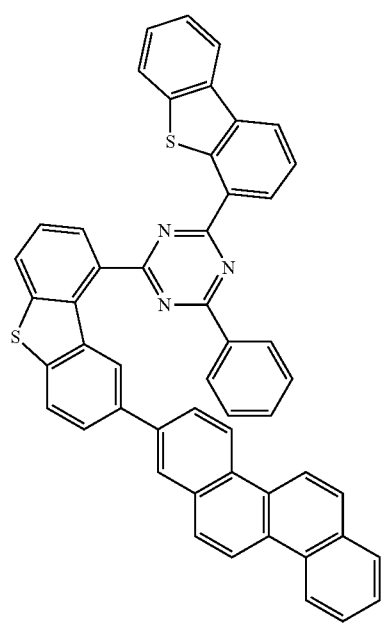
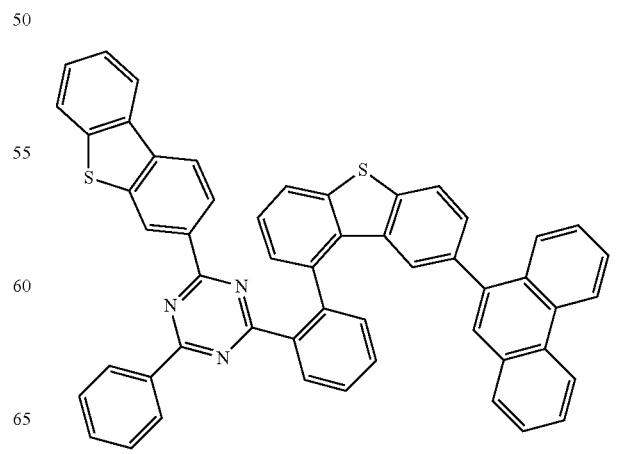

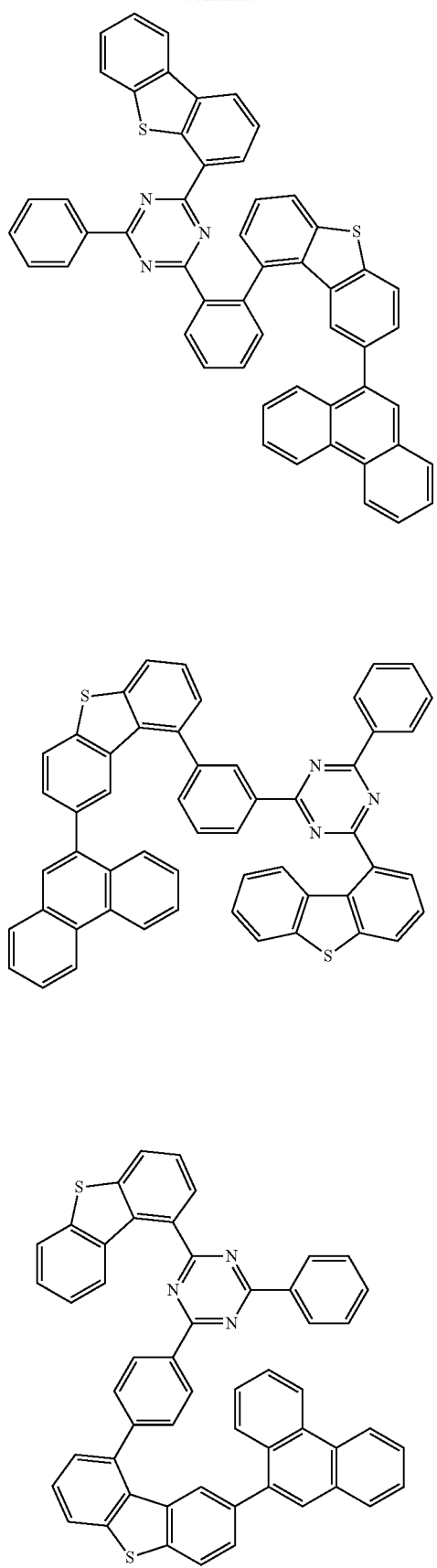
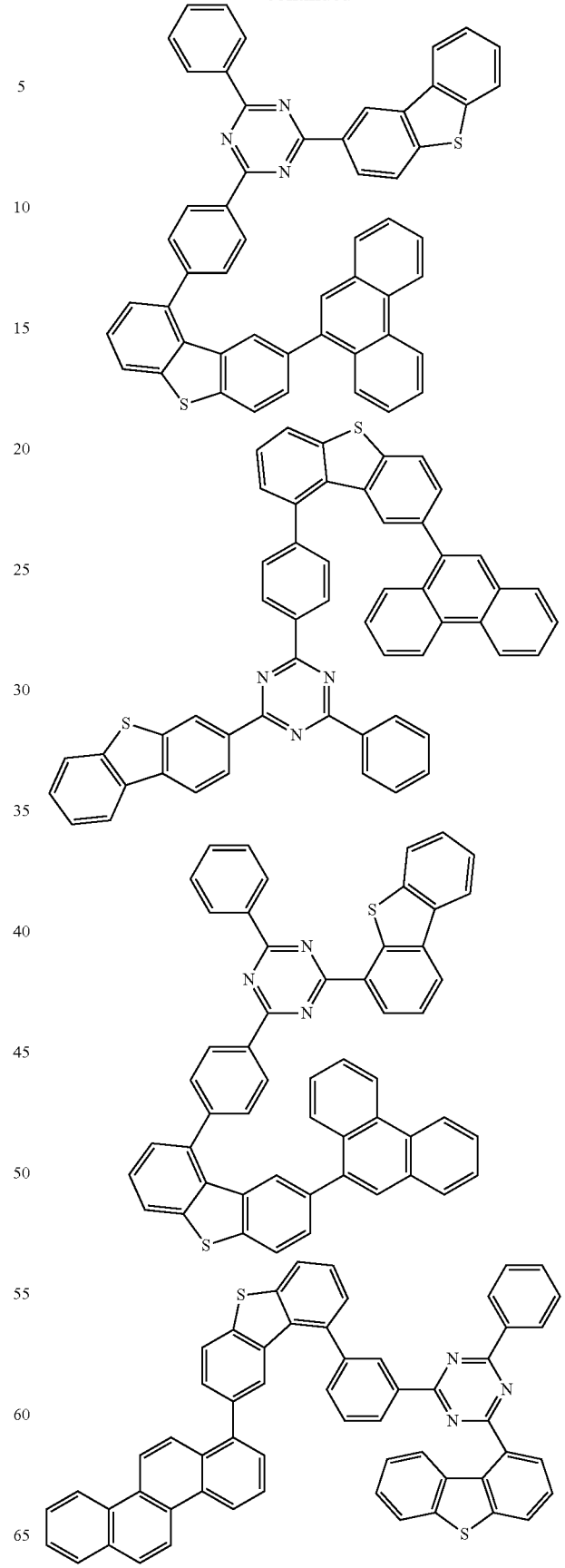

147
-continued
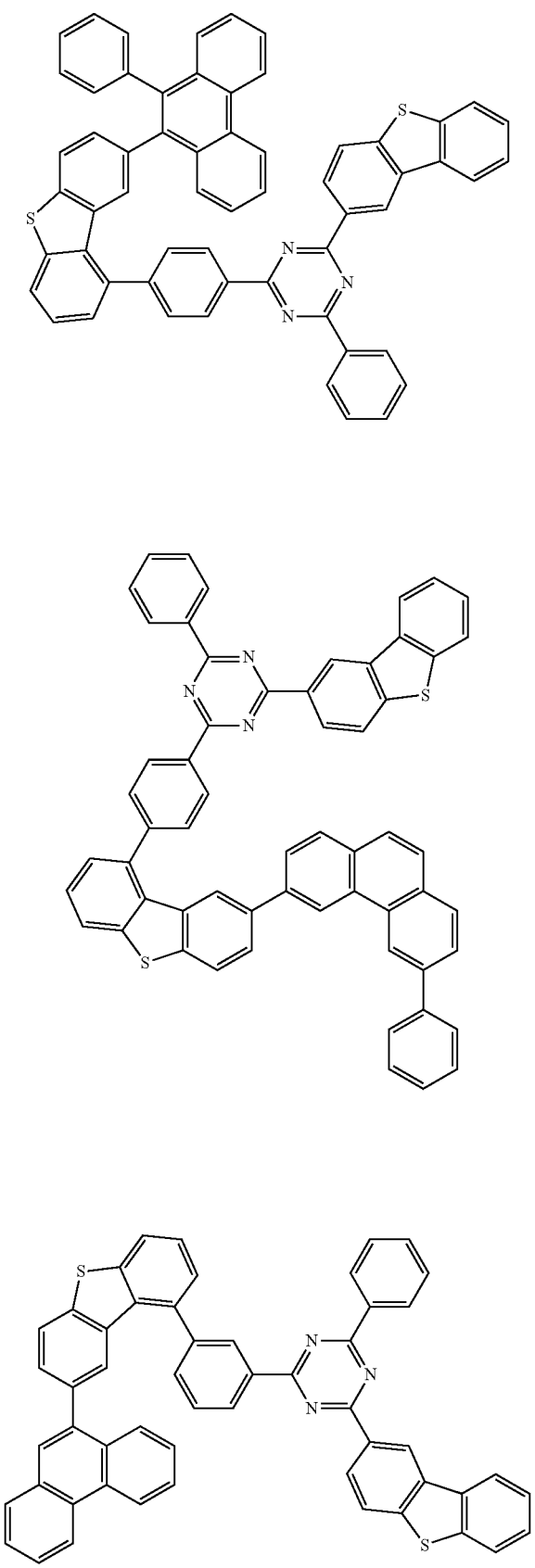
148
-continued
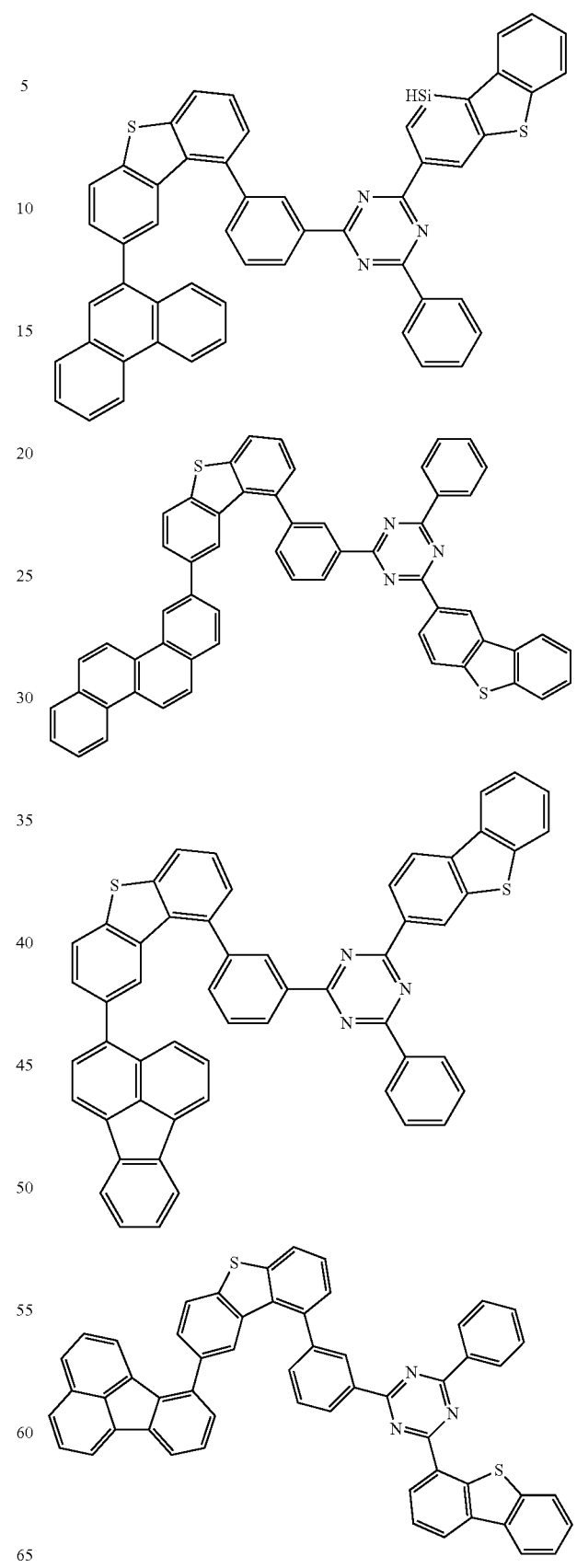

149
-continued
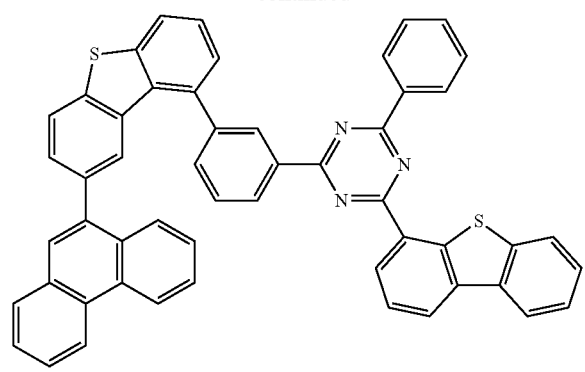
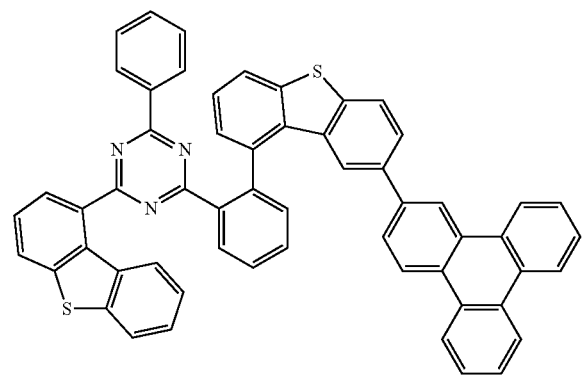
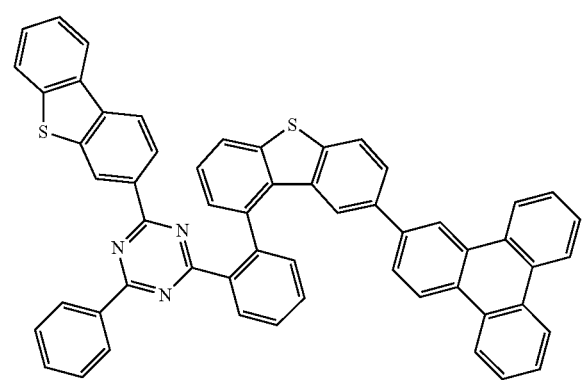
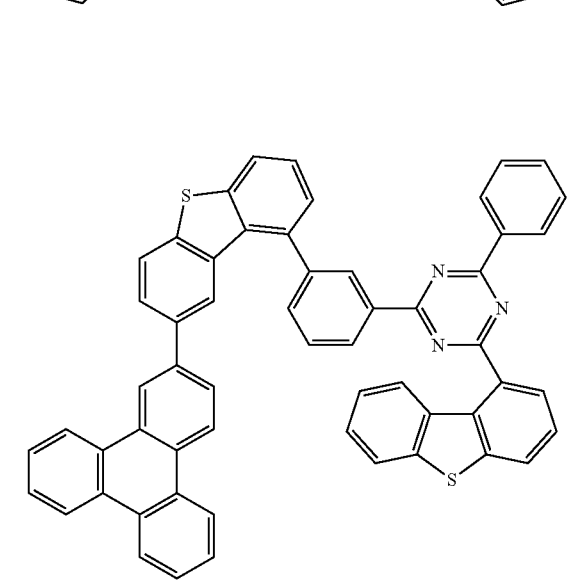
150
-continued
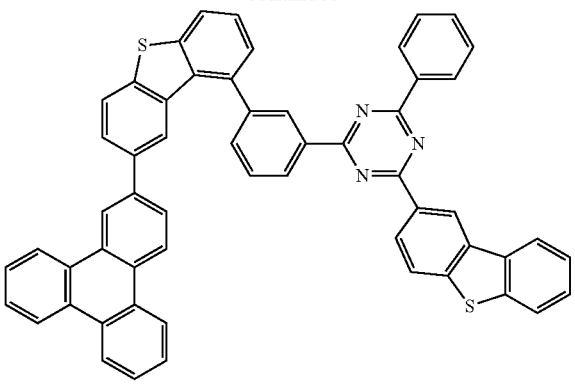
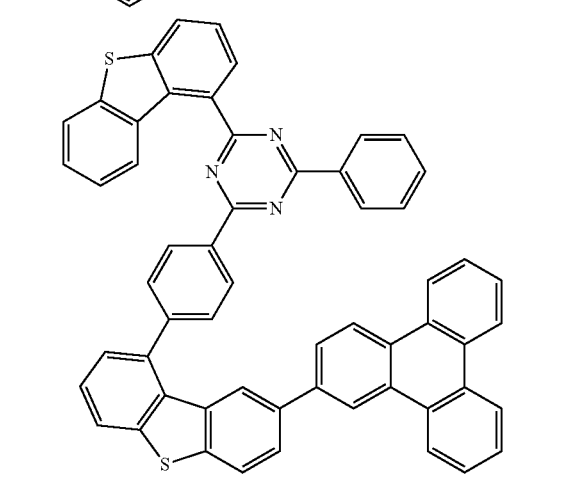
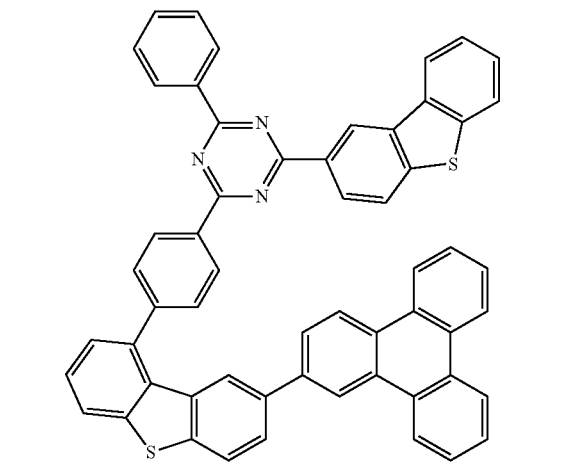
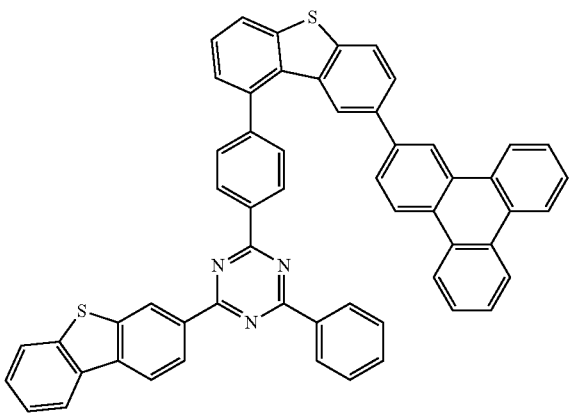

151
-continued
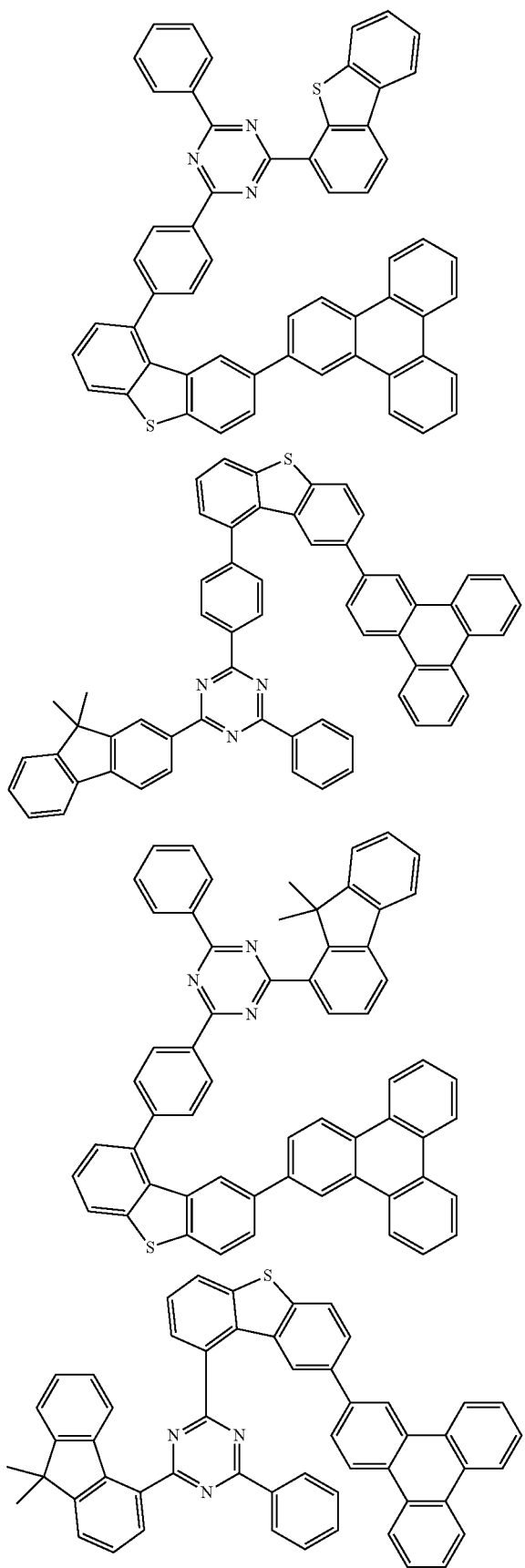
152
-continued
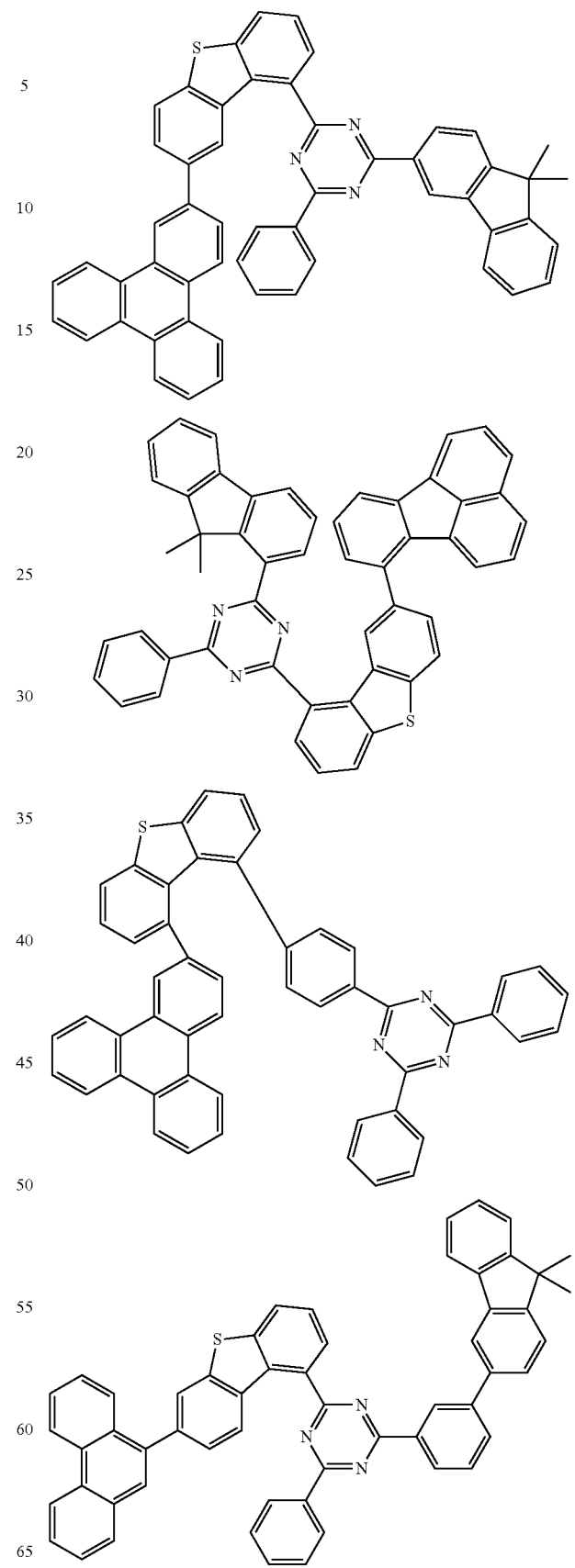

153
-continued
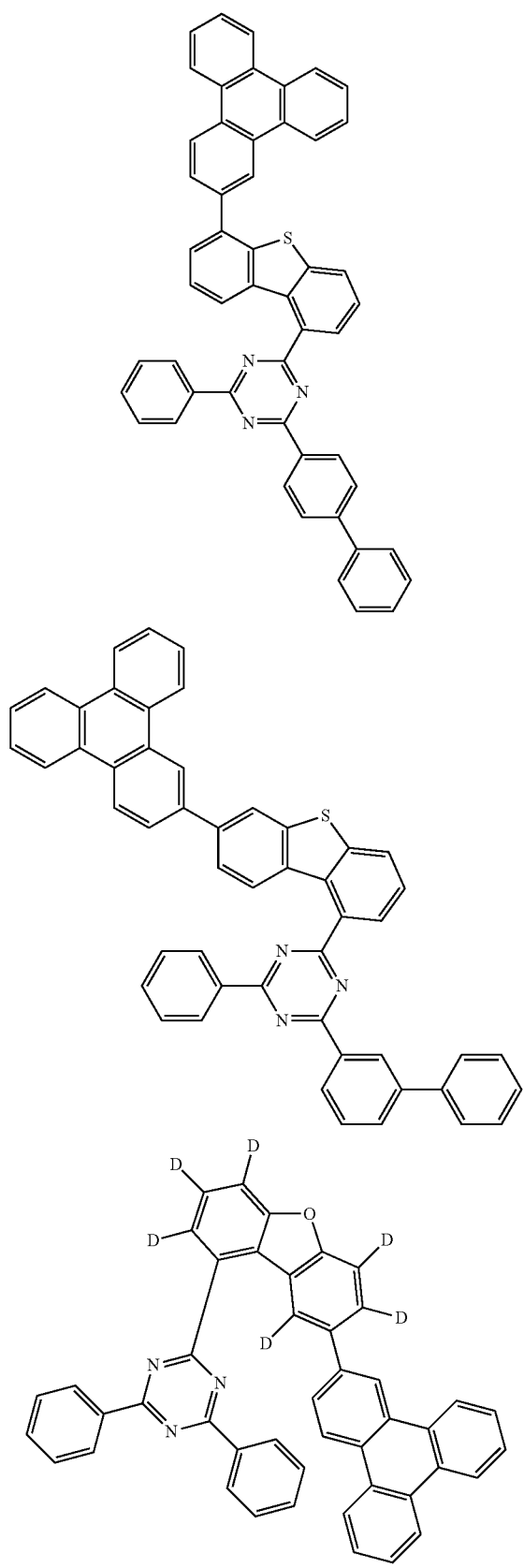
154
-continued
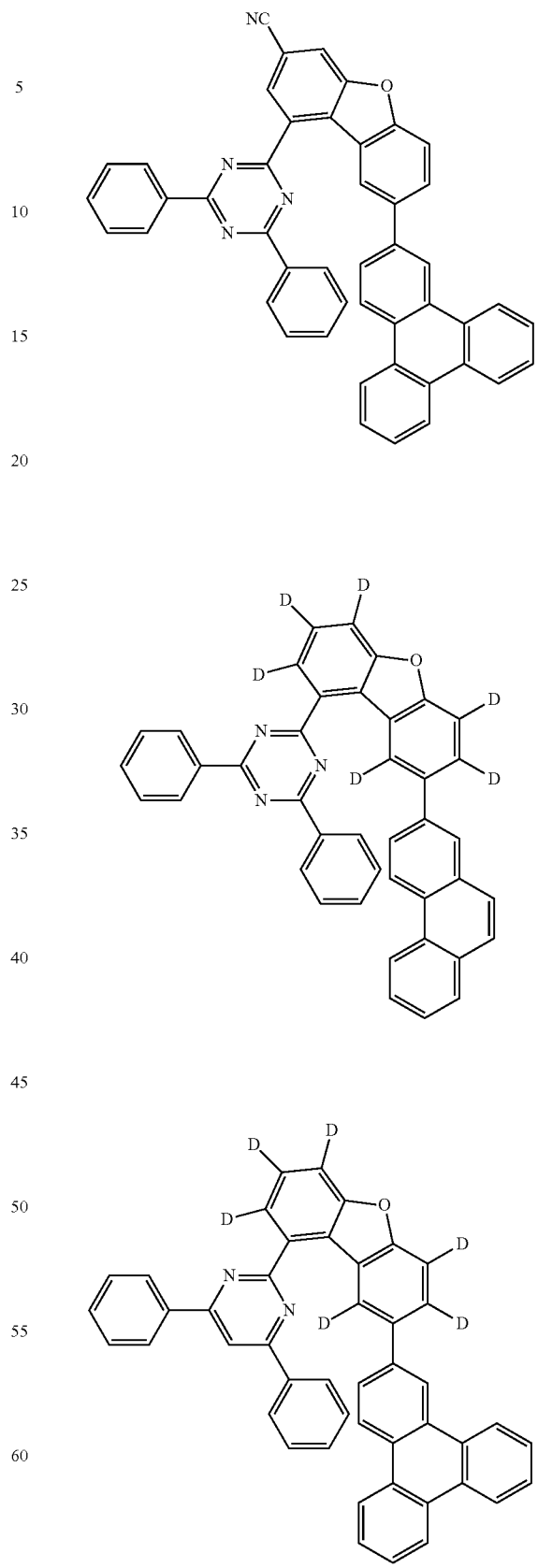

155
-continued
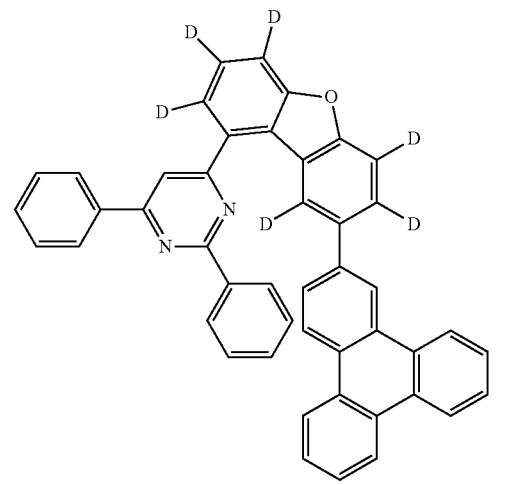
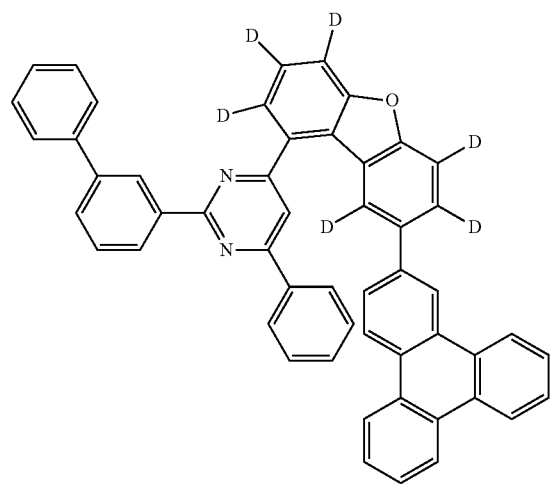
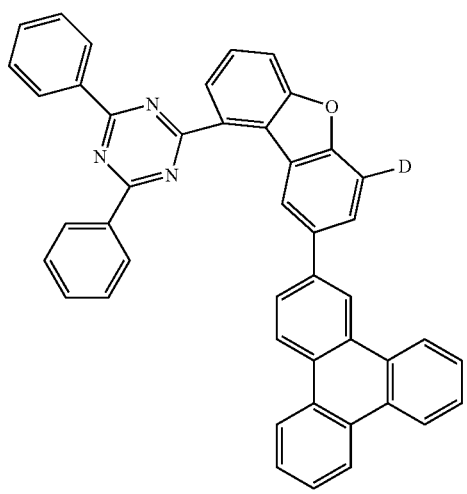
156
-continued
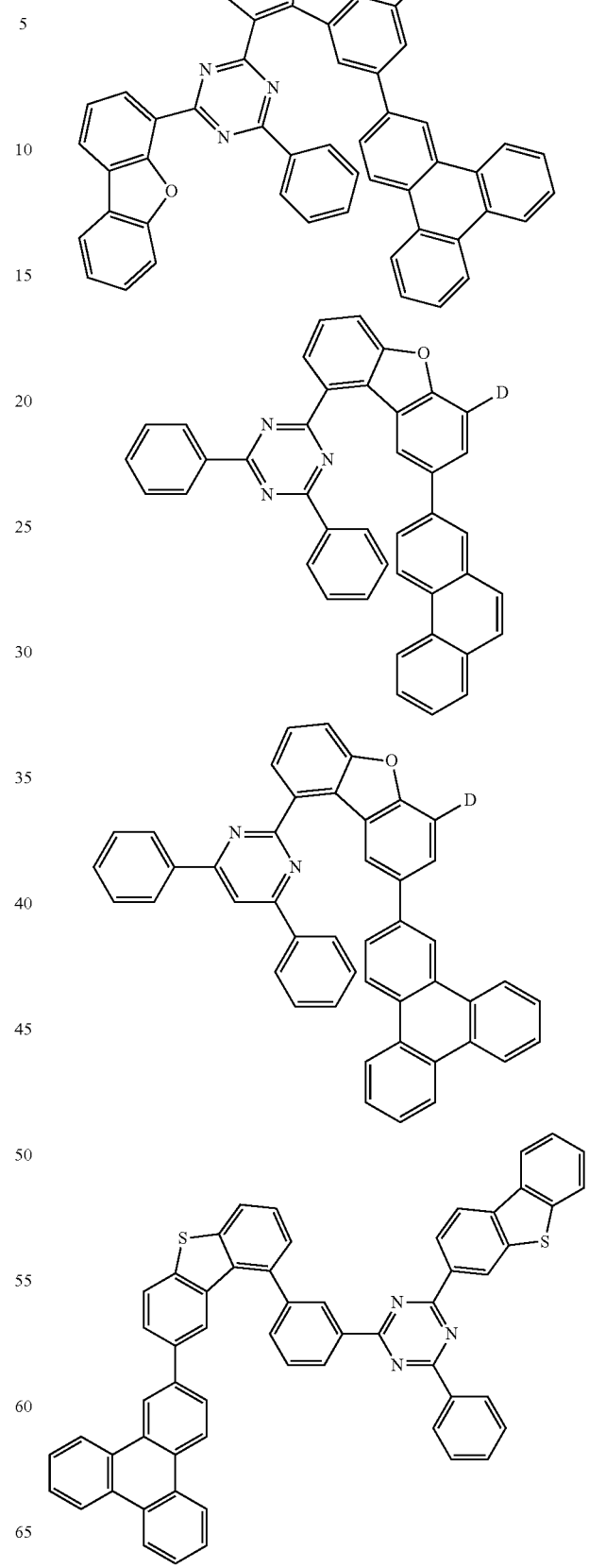

157
-continued
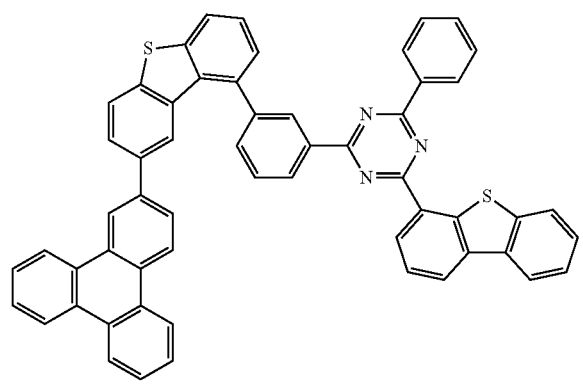
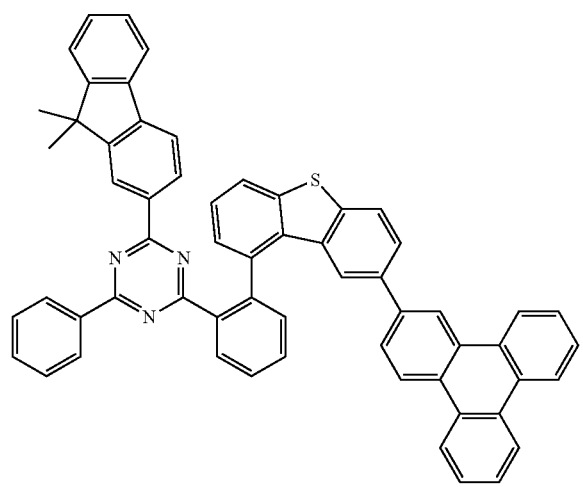
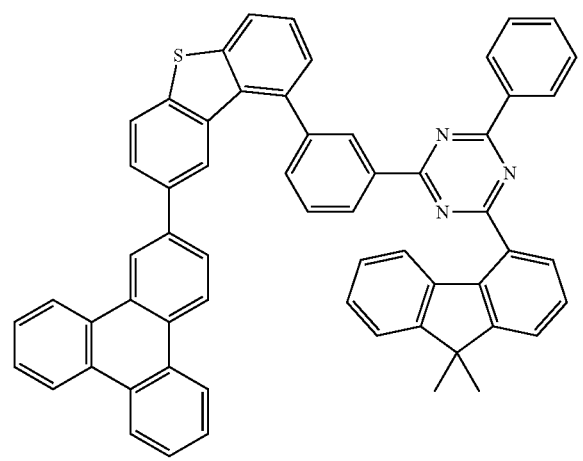
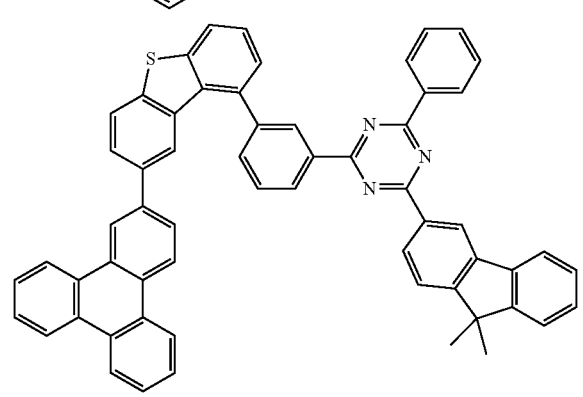
158
-continued
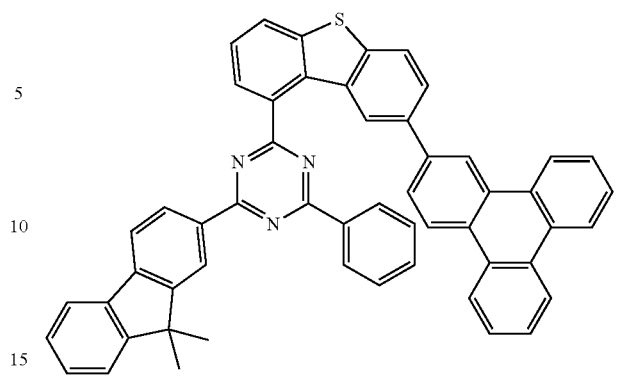
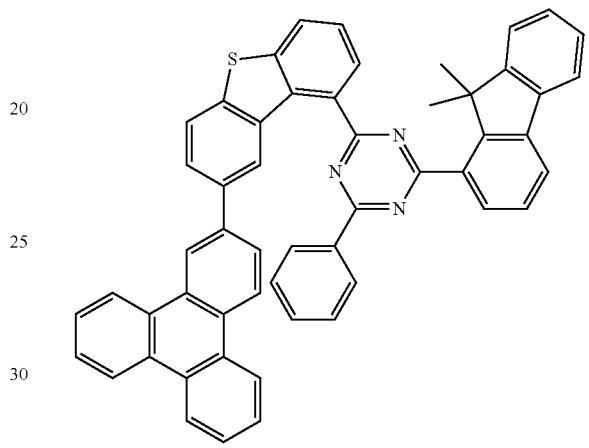
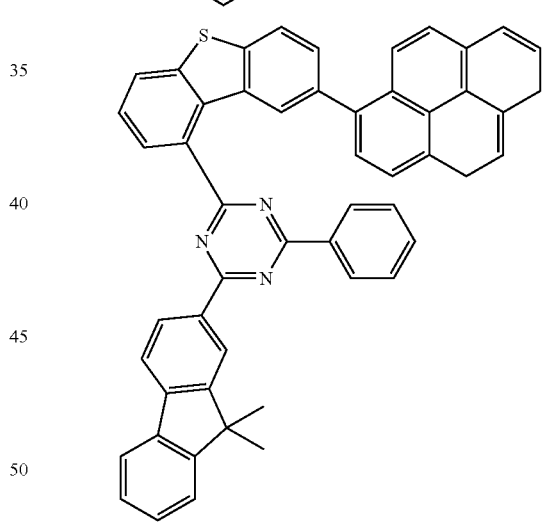
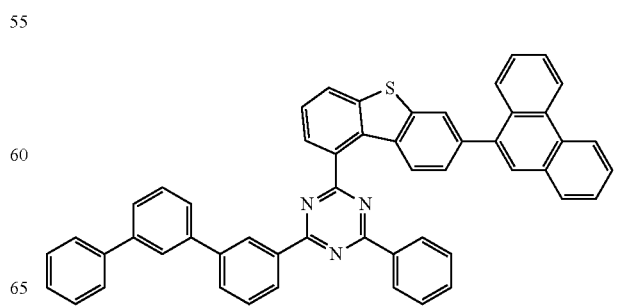

159
-continued
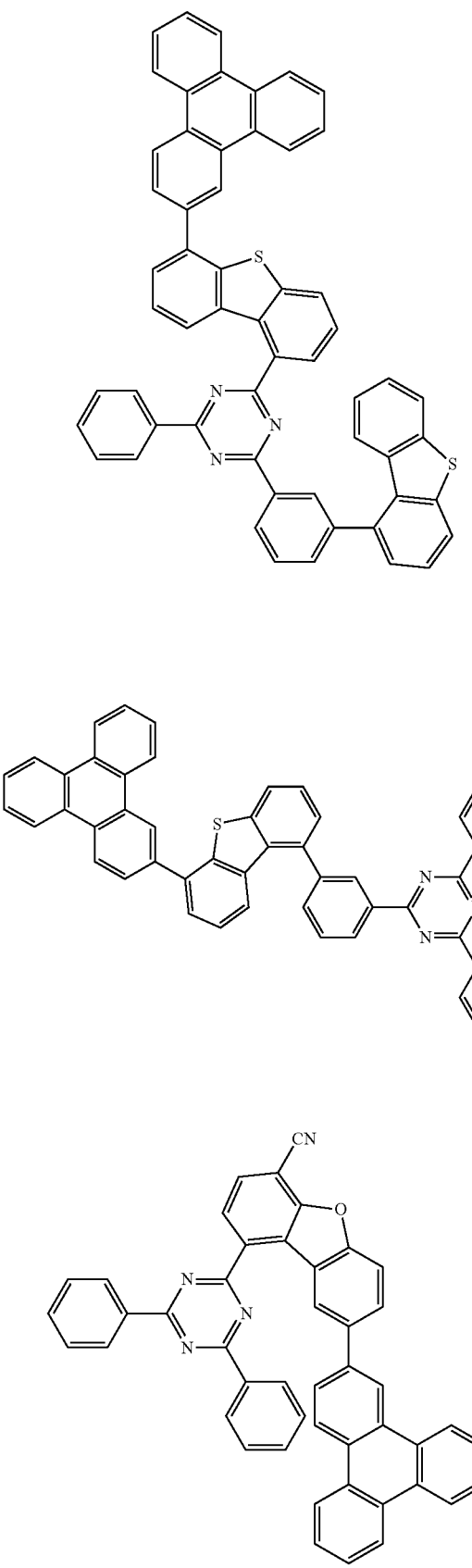
160
-continued
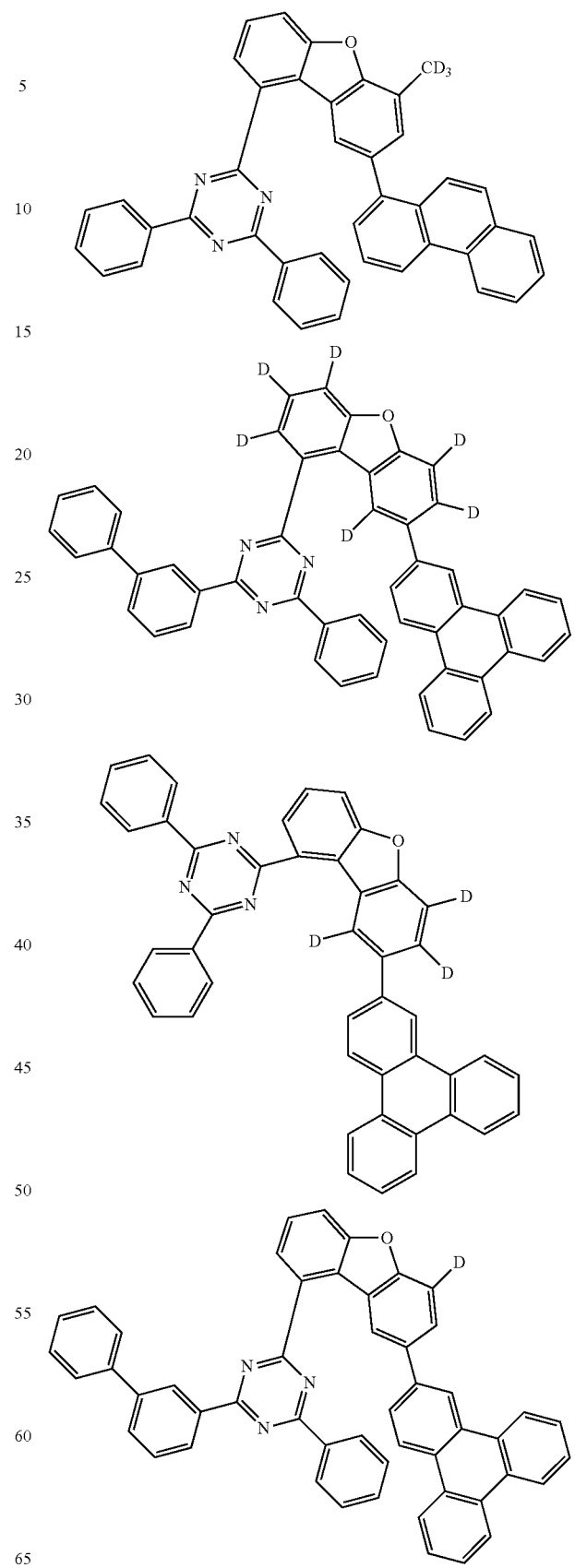

161
-continued
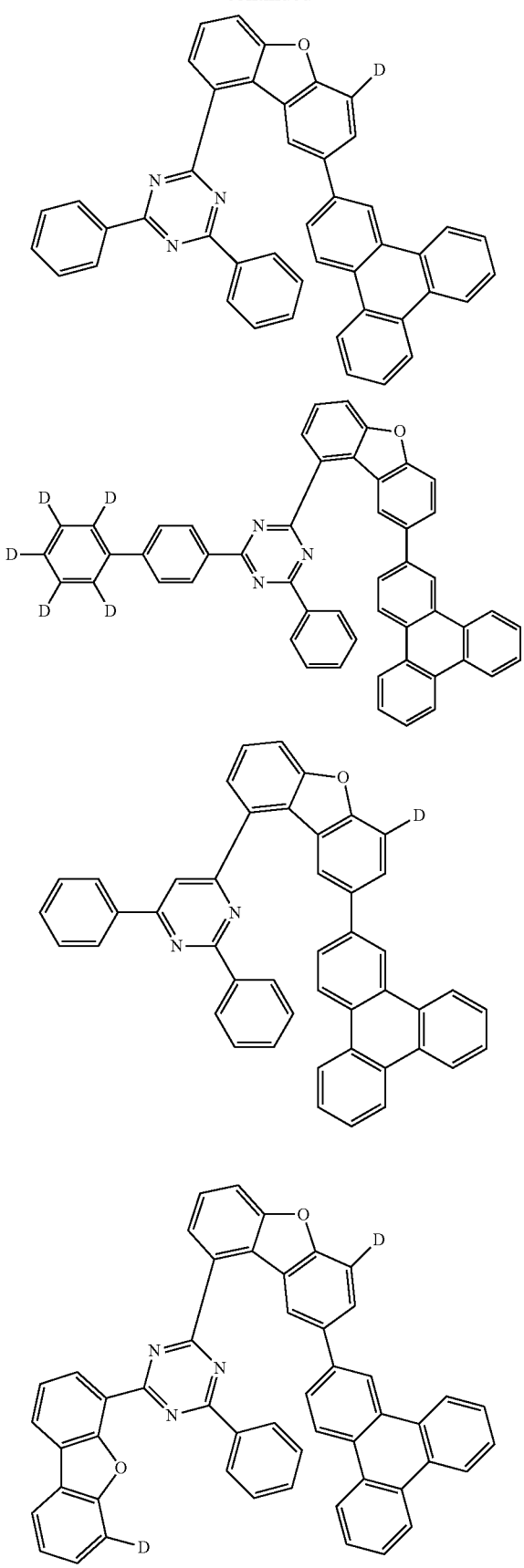
162
-continued
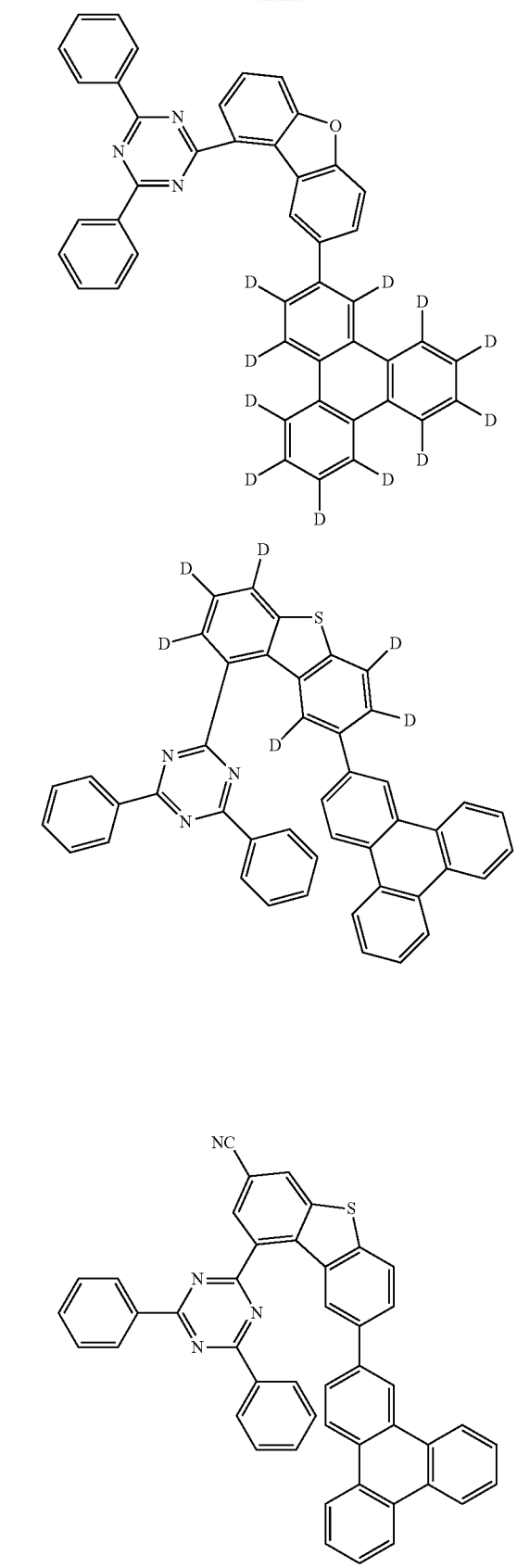

163
-continued
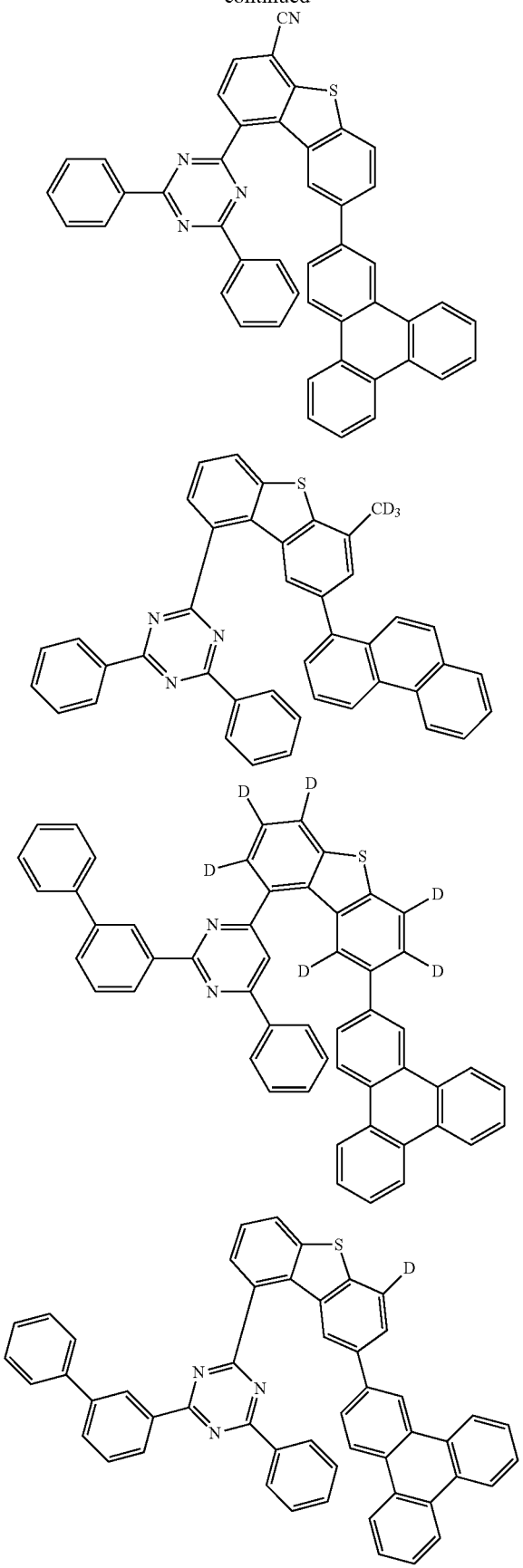
164
-continued
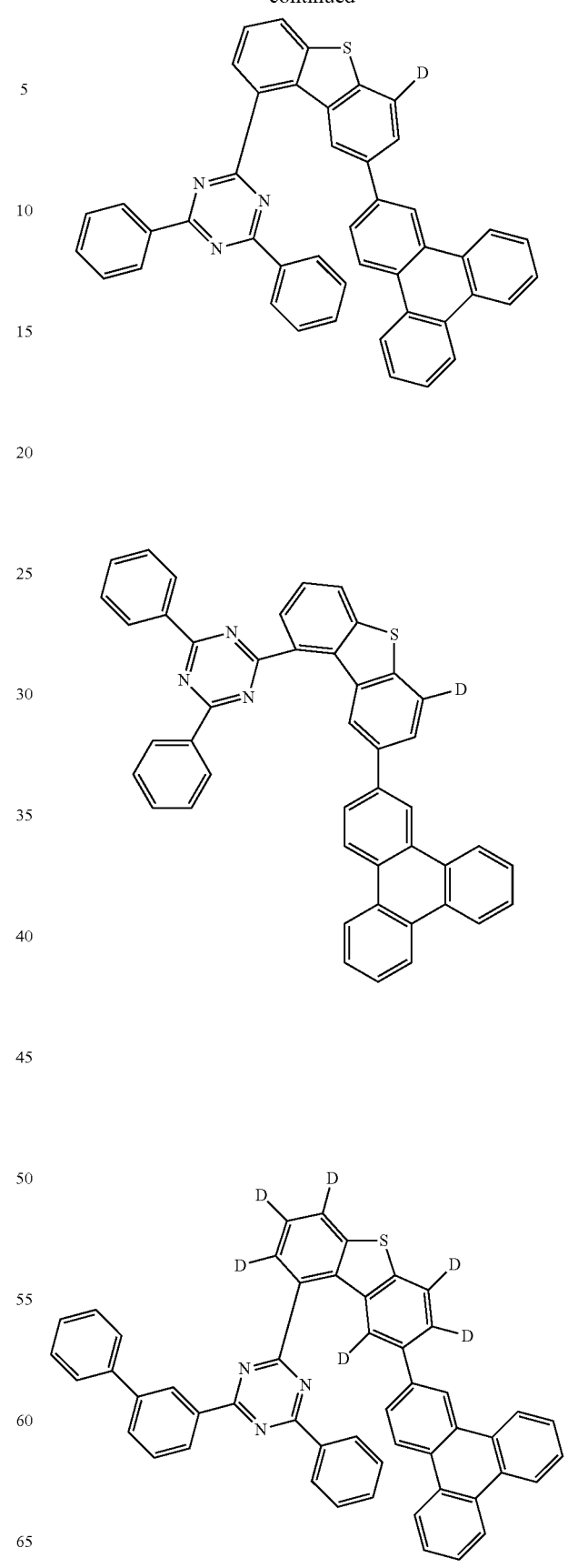

165
-continued
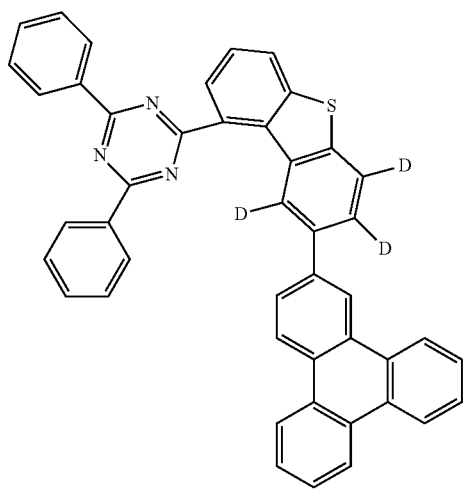
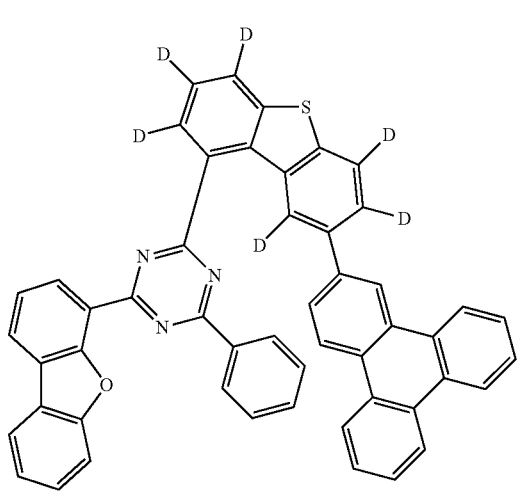
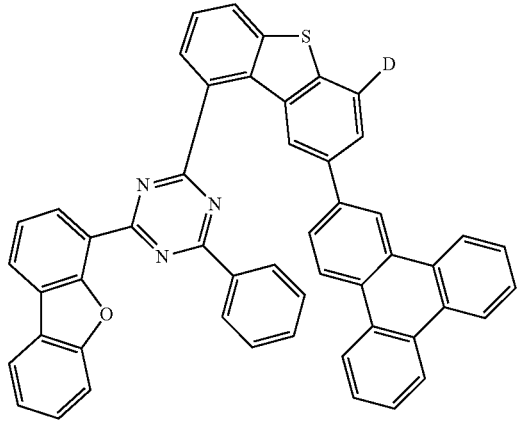
166
-continued
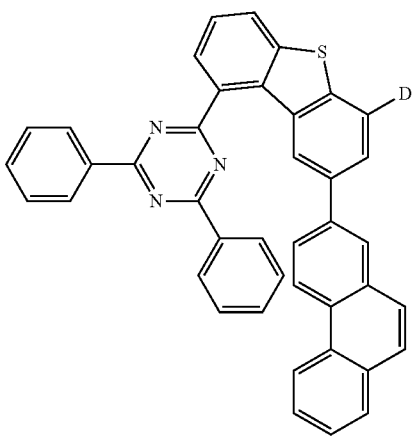
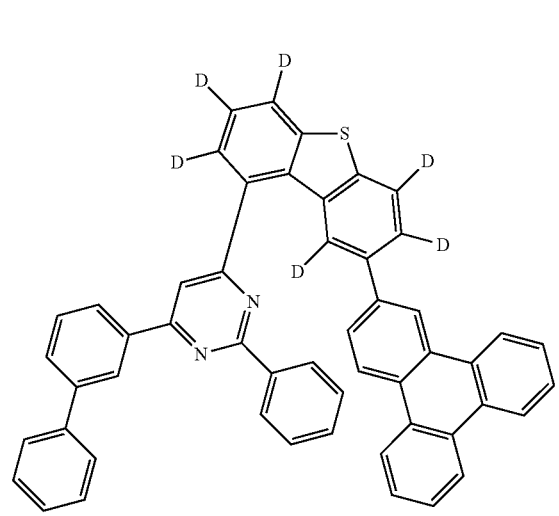
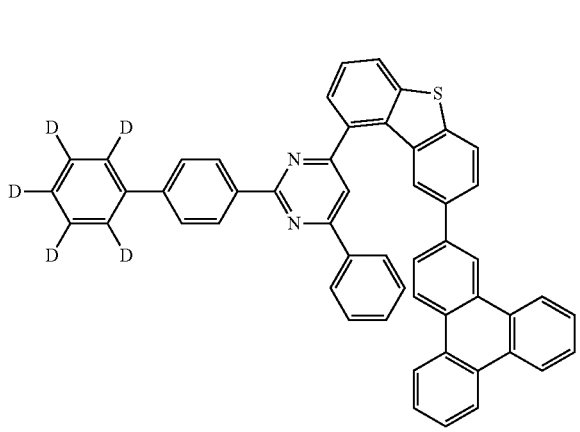

167
-continued
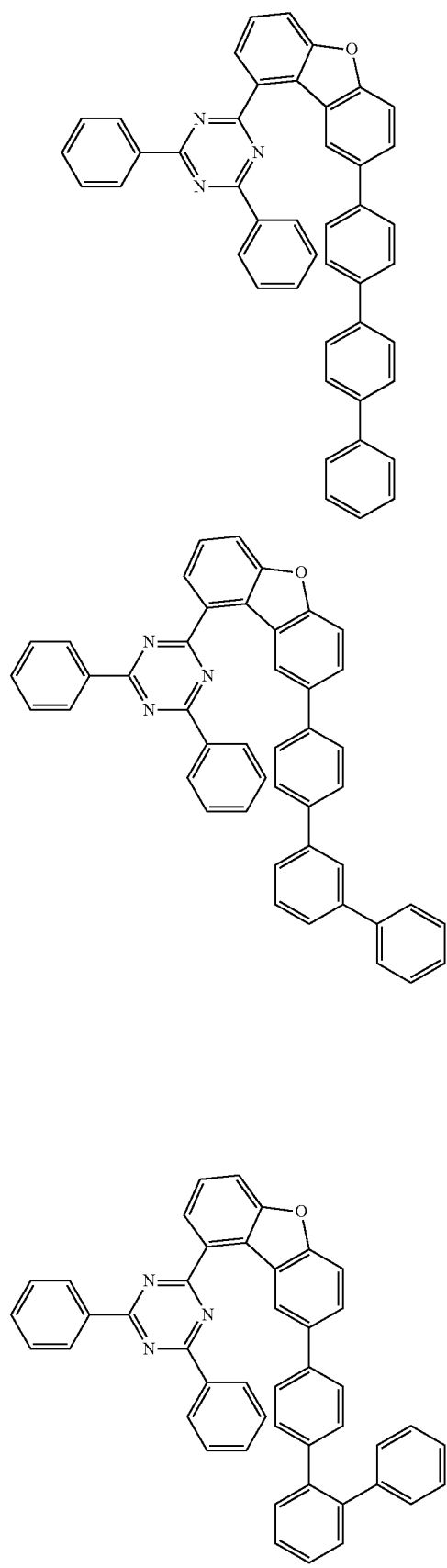
168
-continued
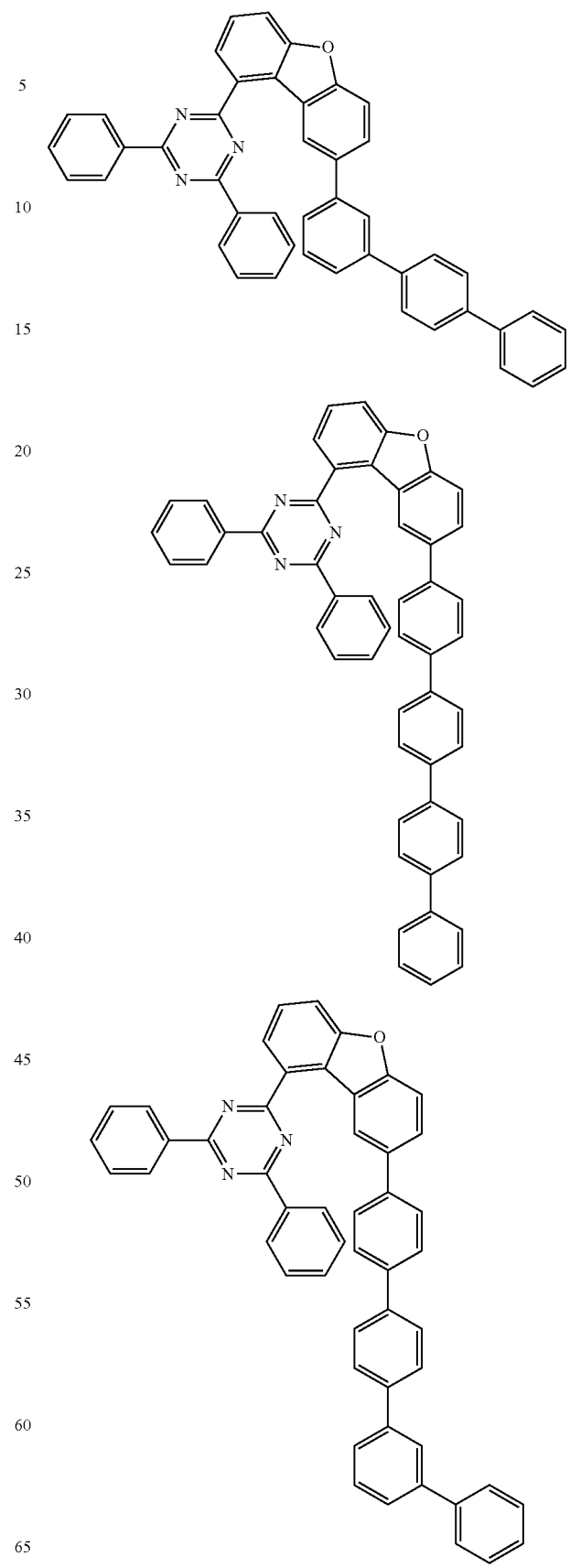

169
-continued
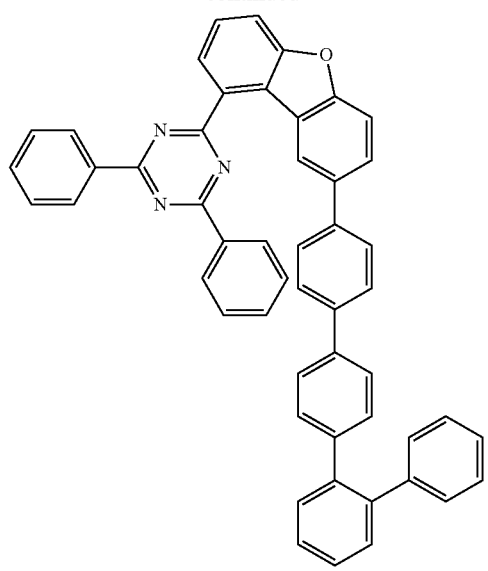 [SMILES: c1ccc(-c2nc(-c3ccccc3)nc(-c3cccc4oc5ccc(-c6ccc(-c7ccc(-c8ccccc8-c8ccccc8)cc7)cc6)cc5c34)n2)cc1]
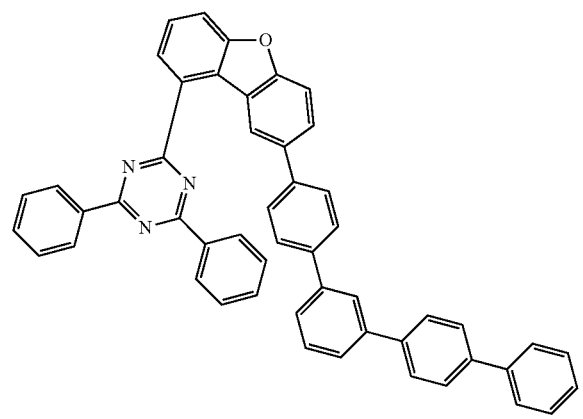
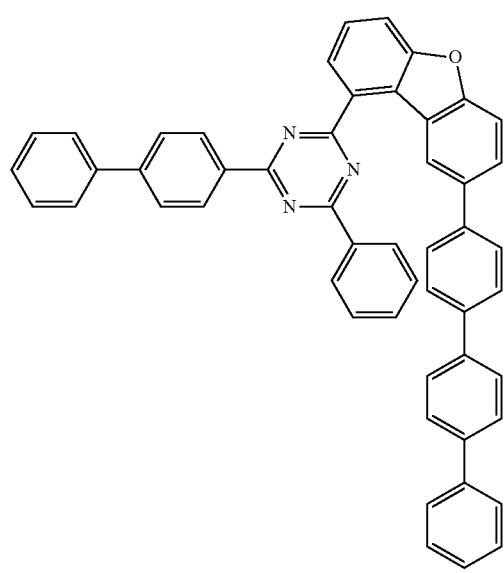
170
-continued
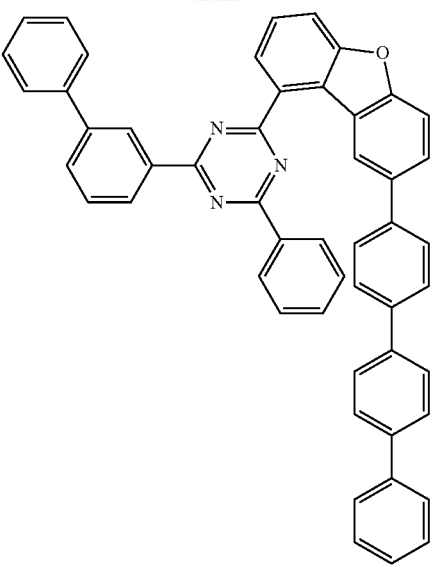
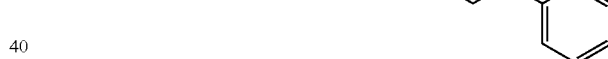
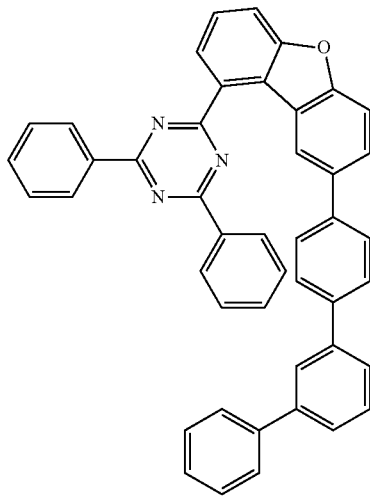

171
-continued
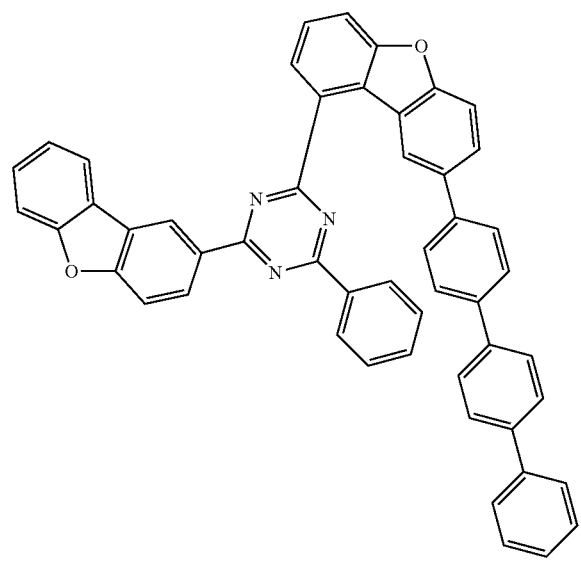
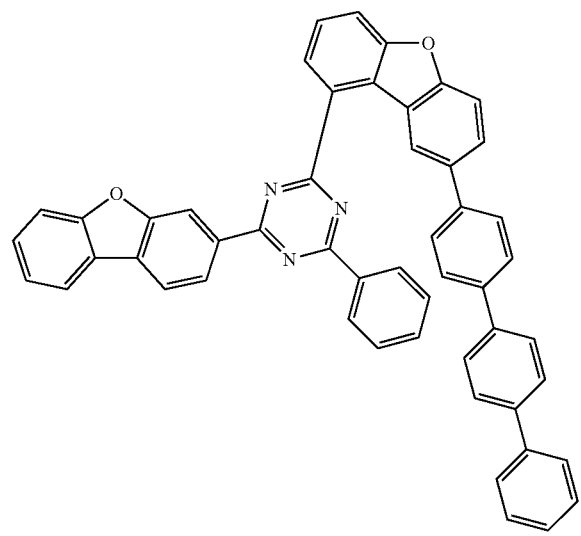
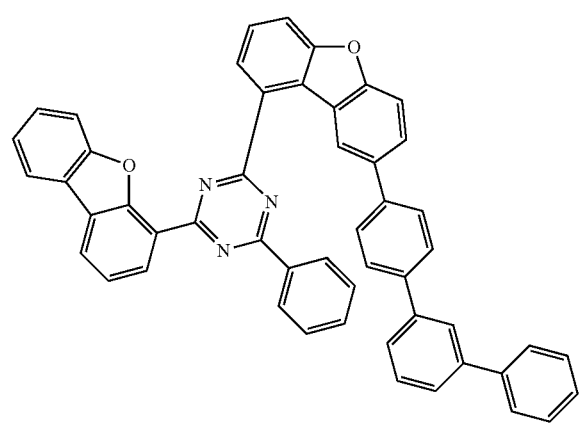
172
-continued
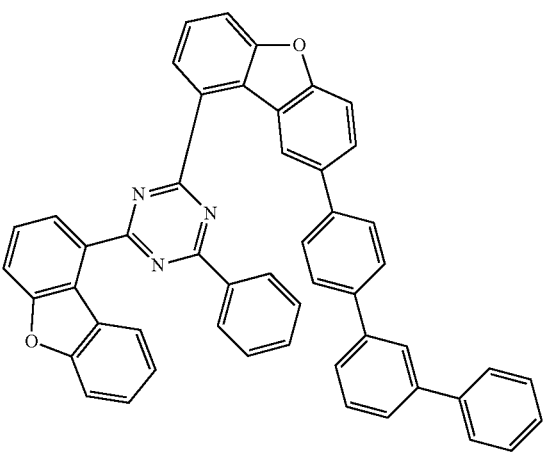
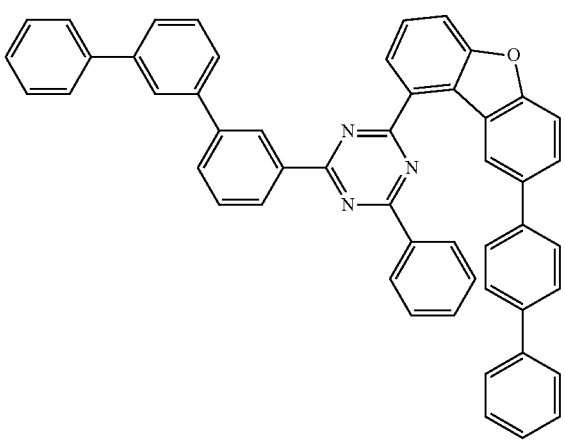
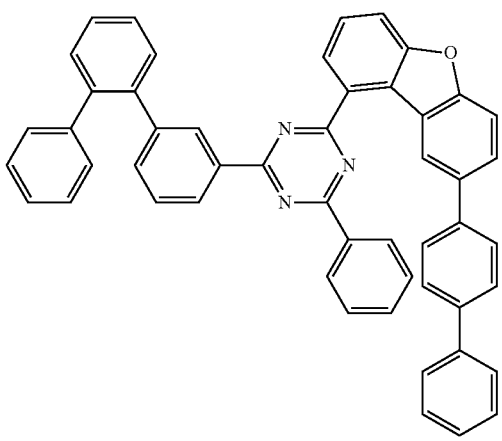

173
-continued
174
-continued
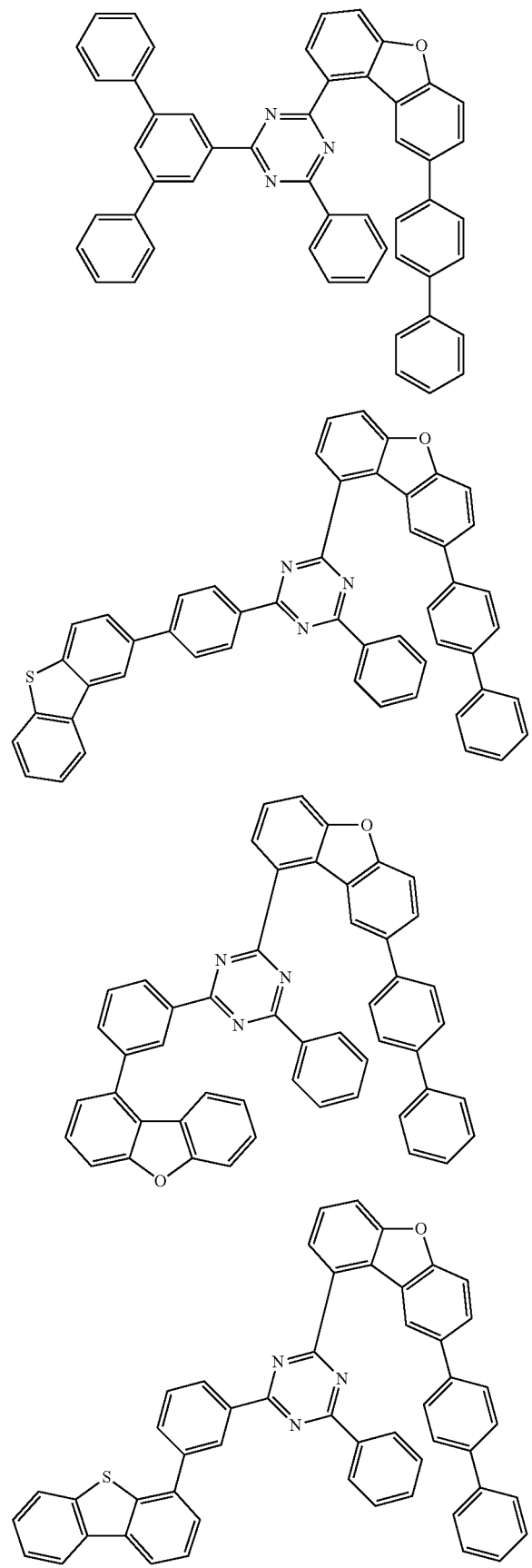
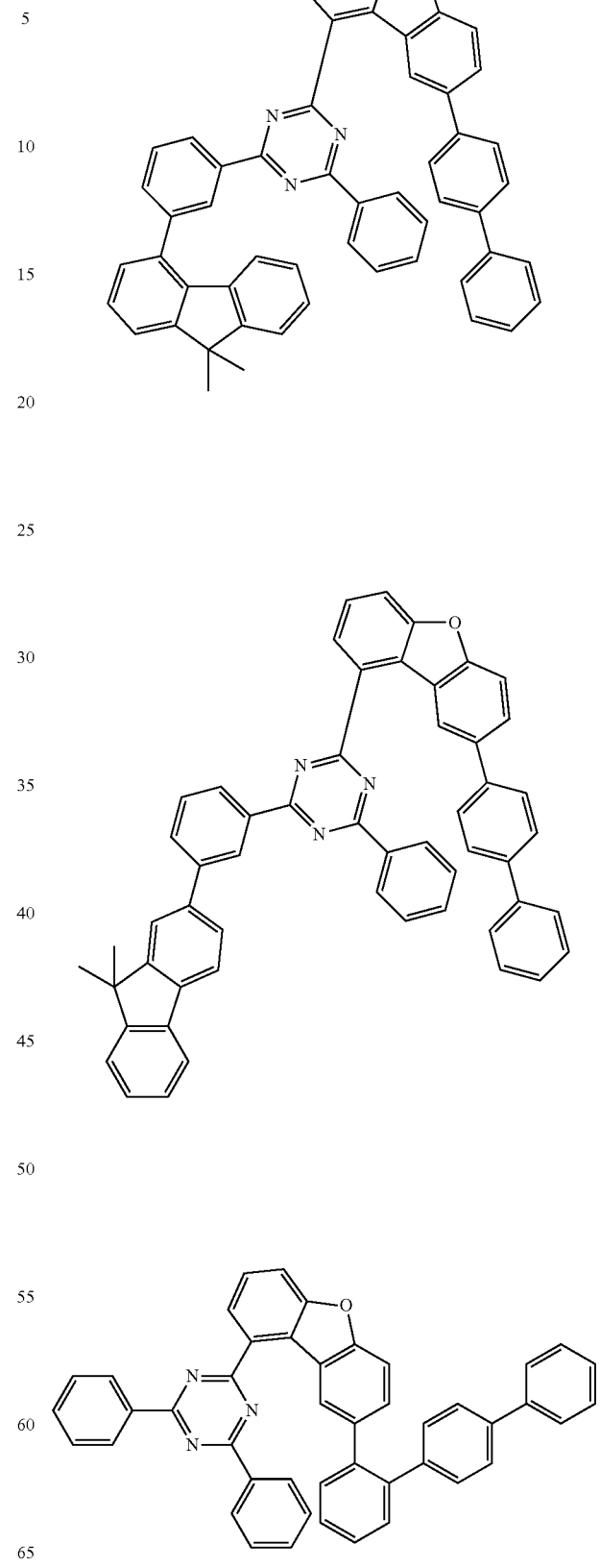

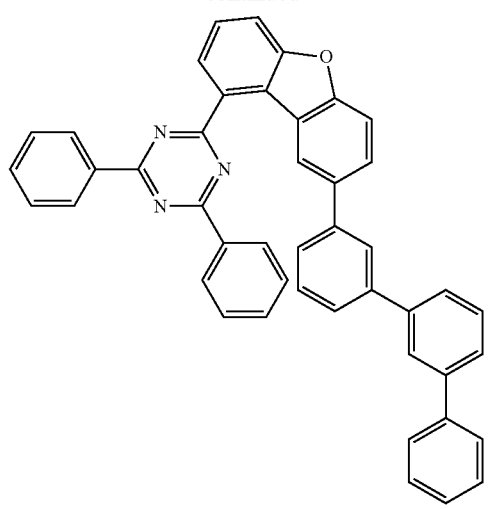
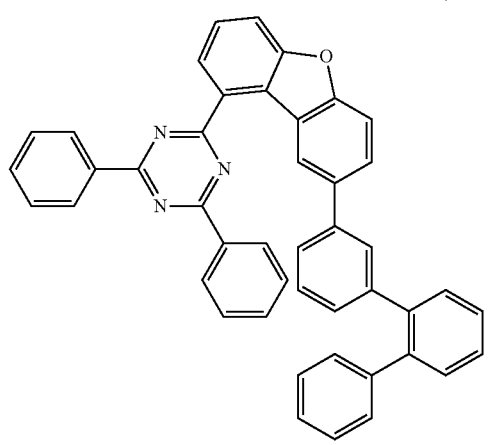
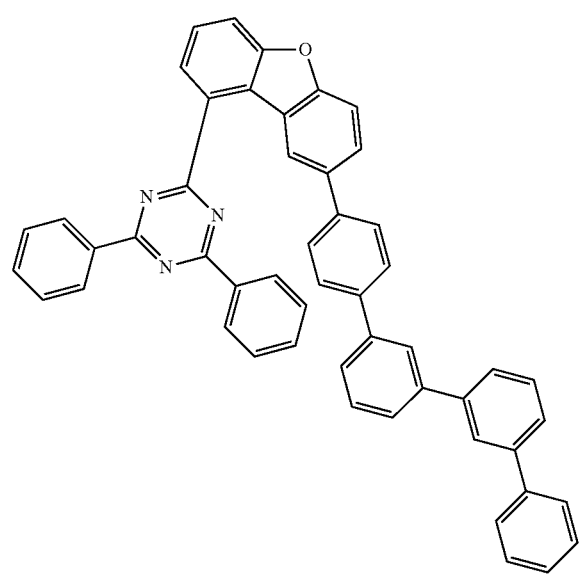
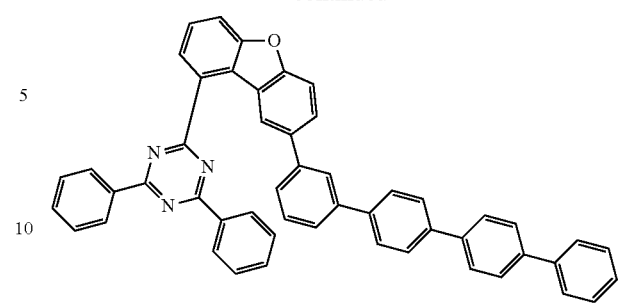
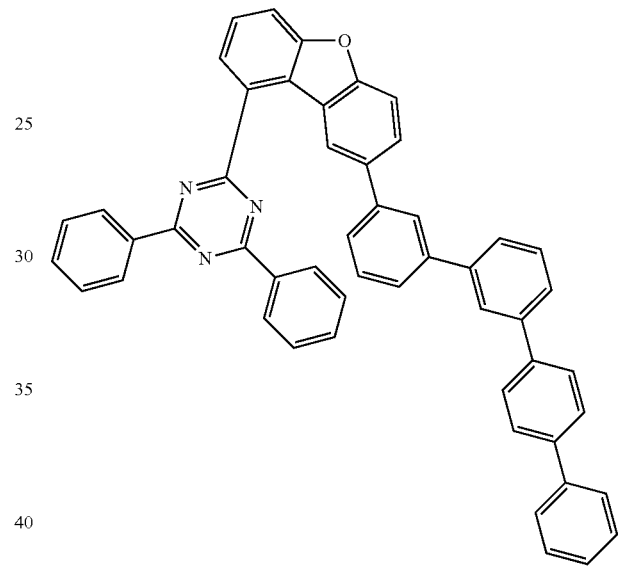
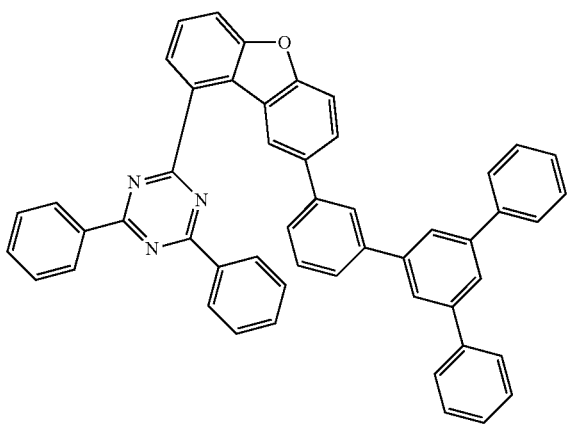

177
-continued
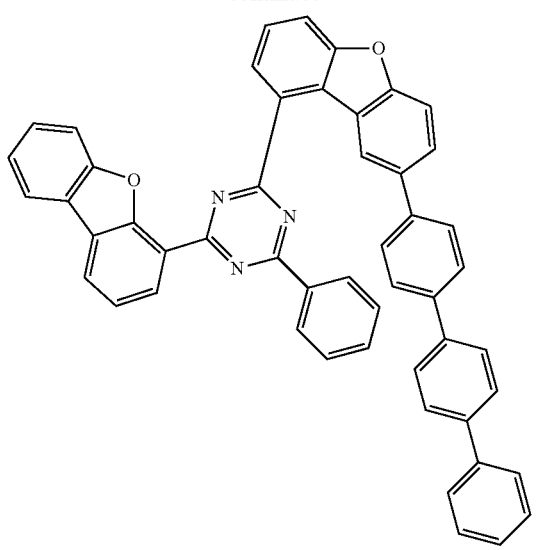
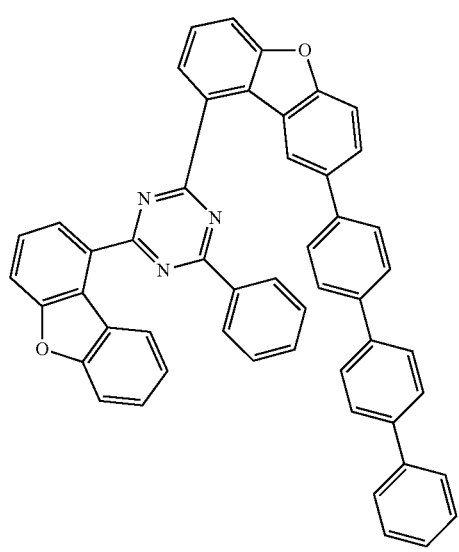
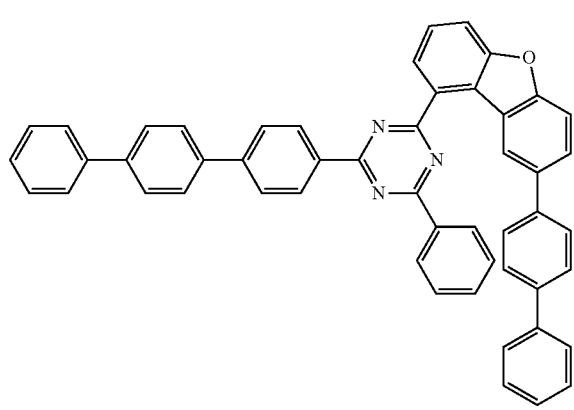
178
-continued
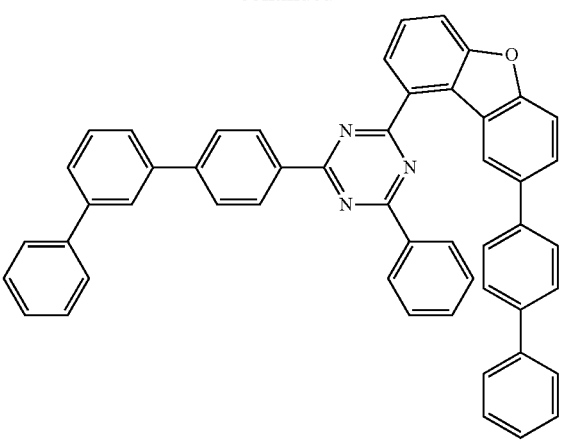
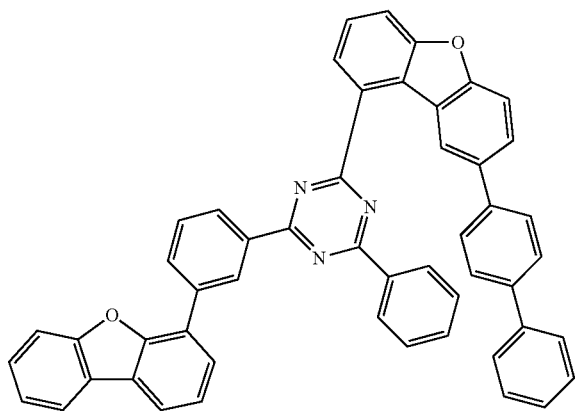

179
-continued
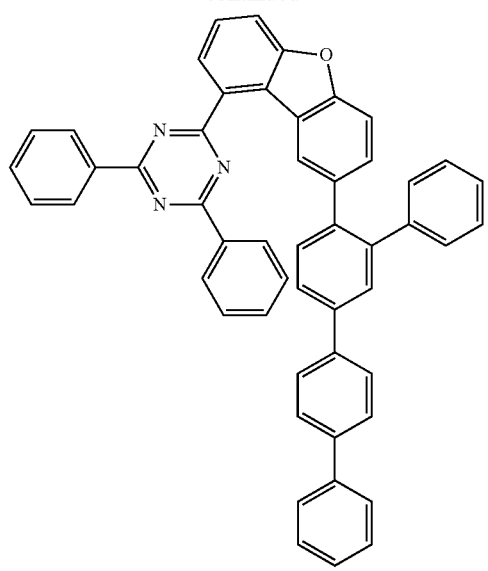
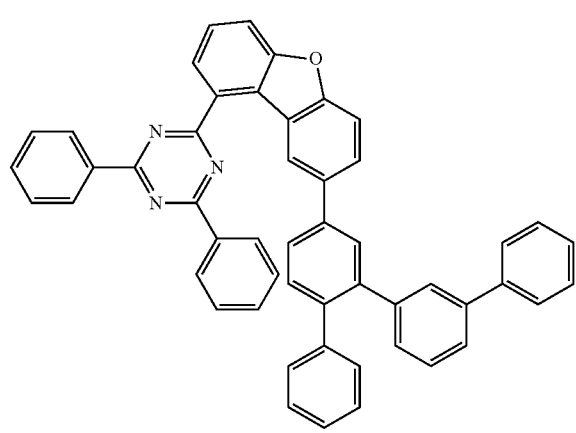
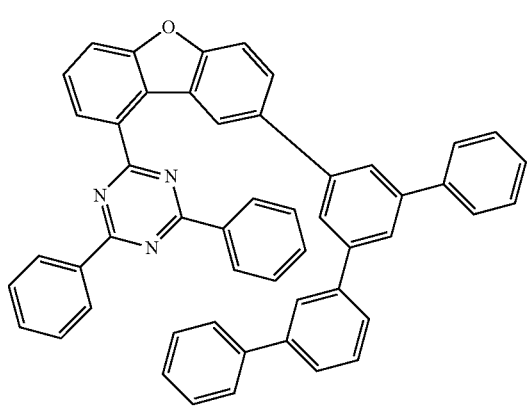
180
-continued
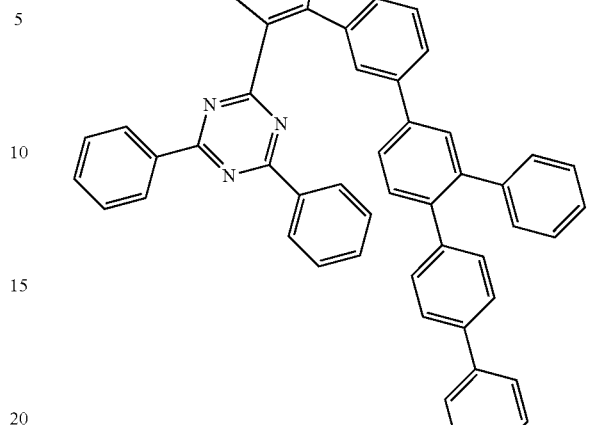
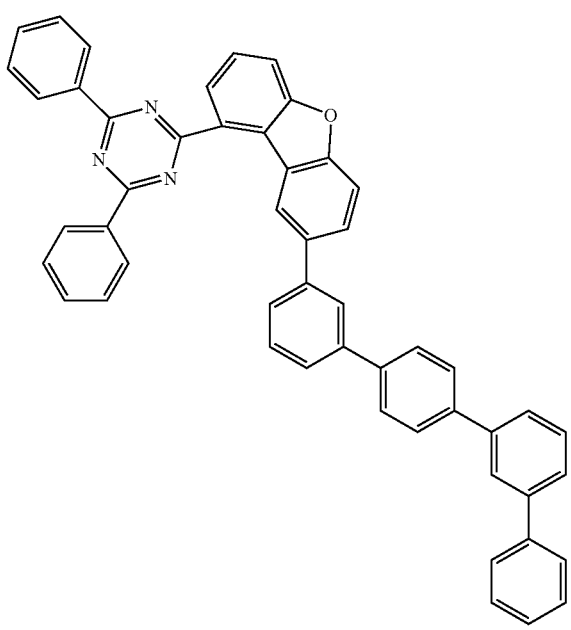
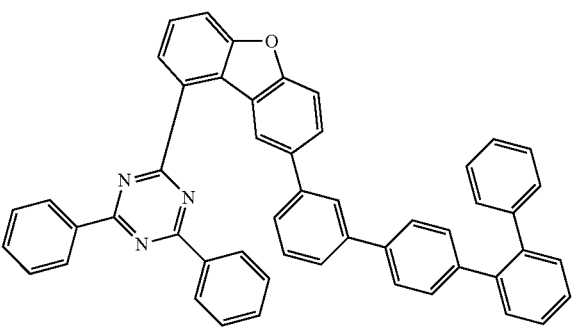

181
-continued
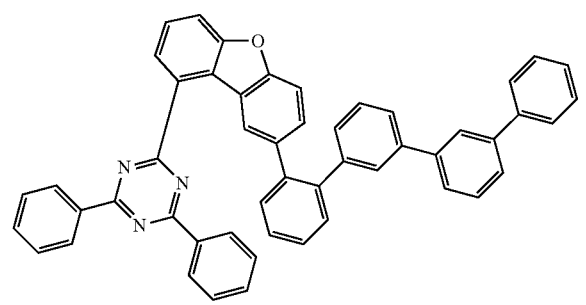
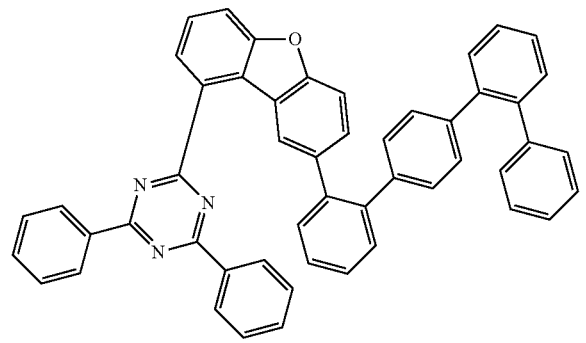
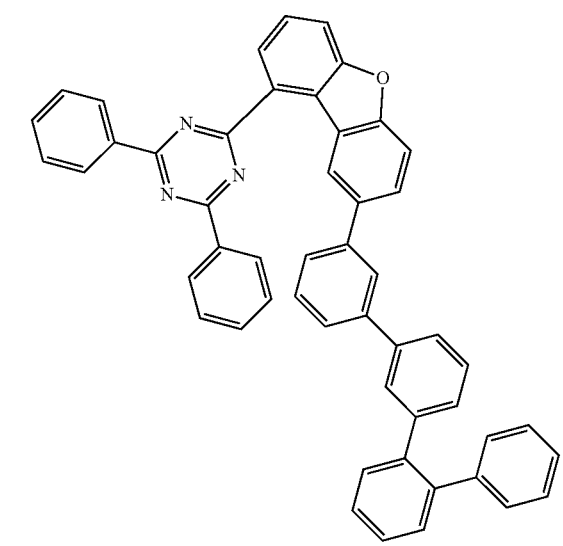
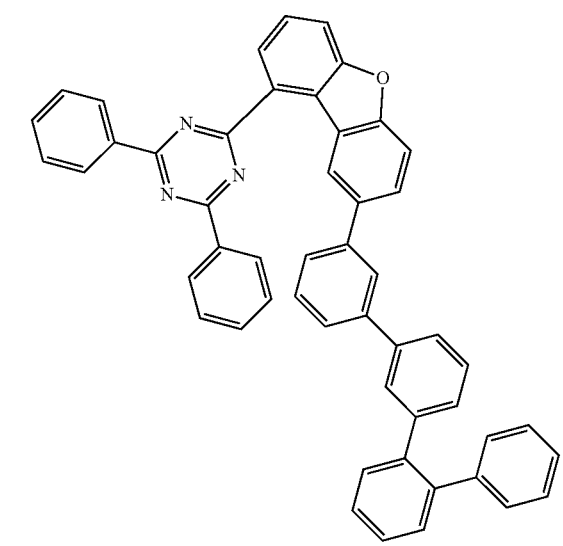
182
-continued
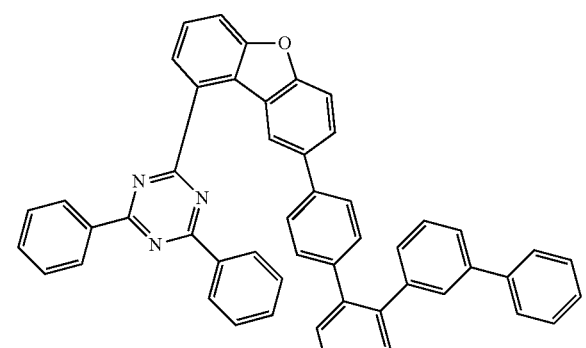

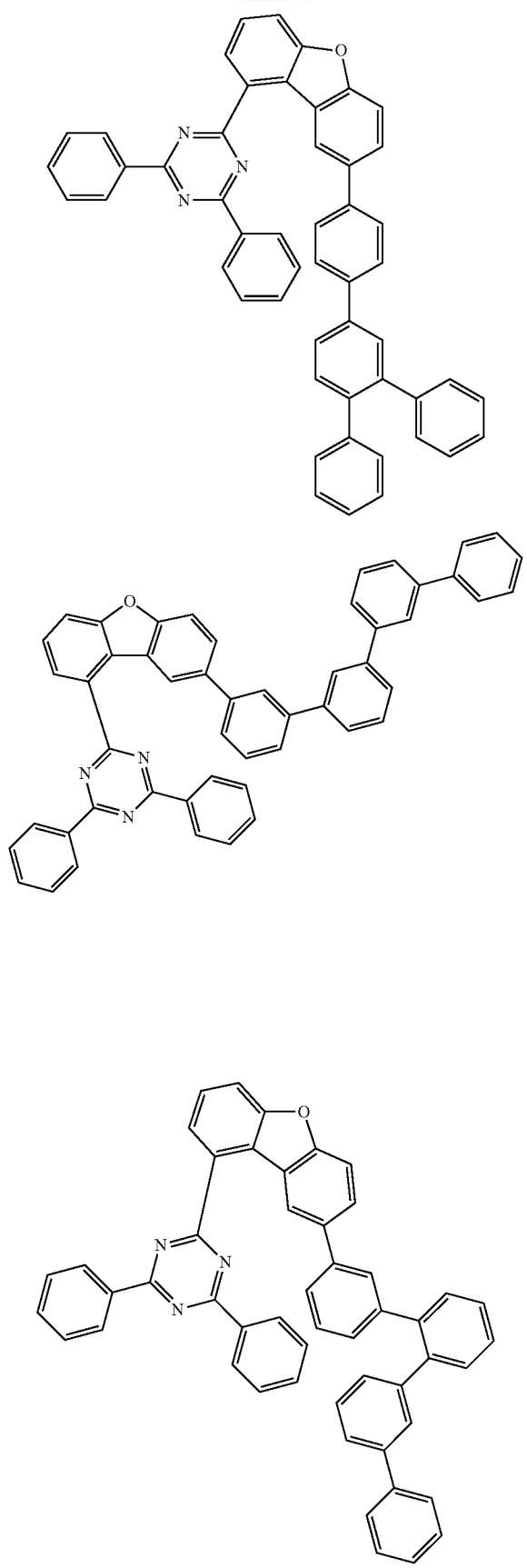
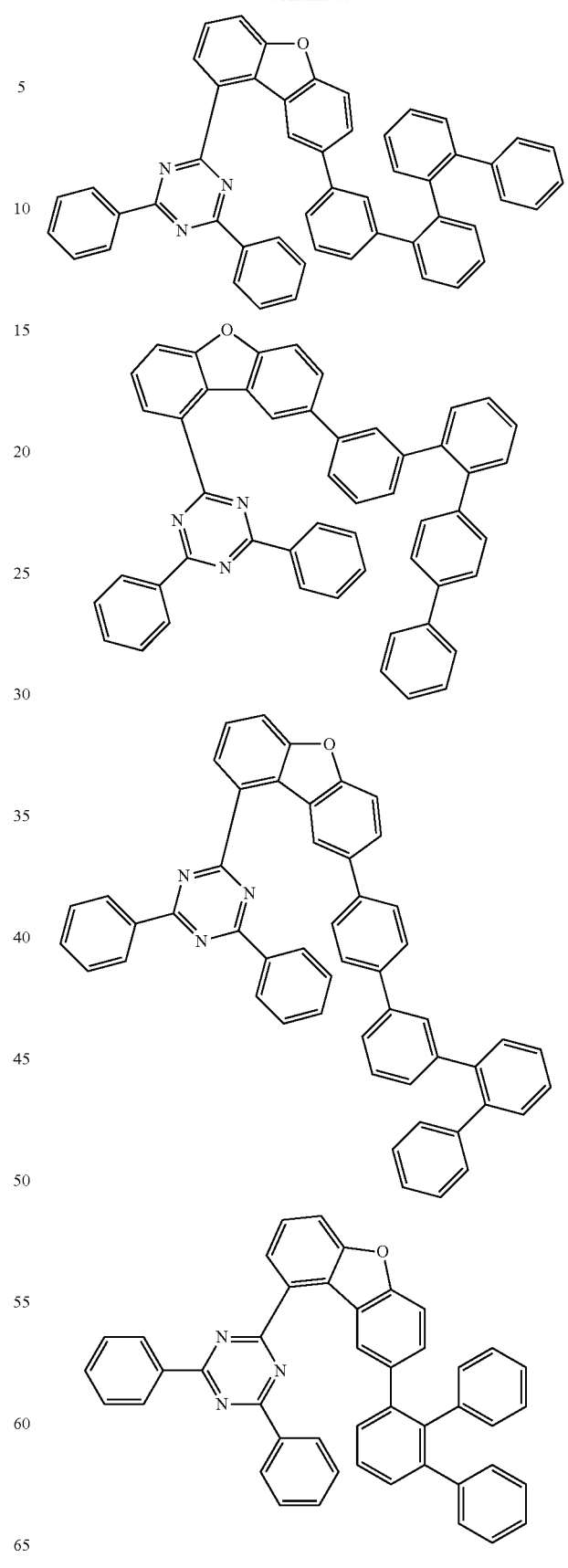

185
-continued
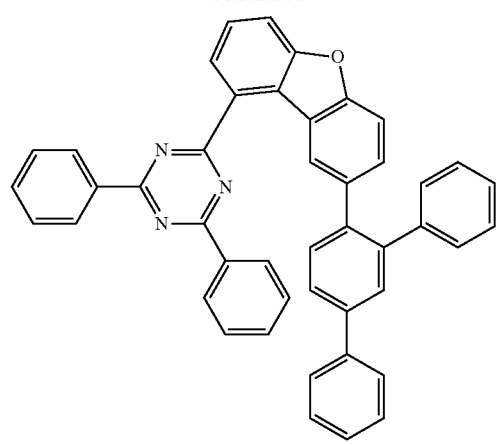
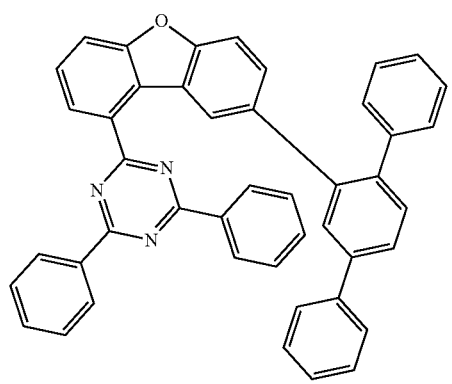
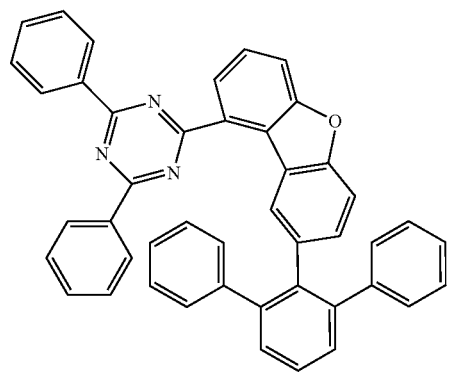
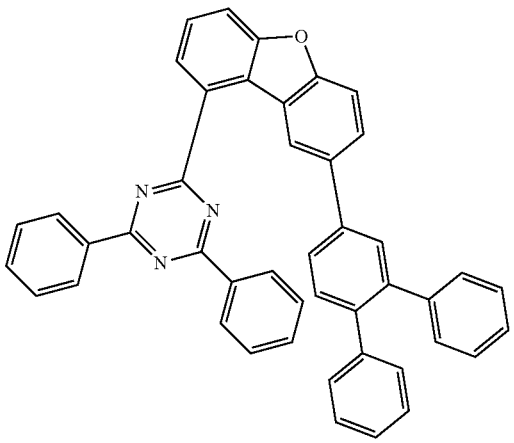
186
-continued
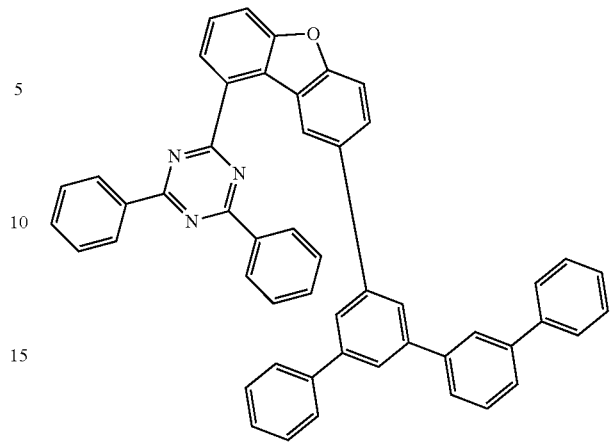
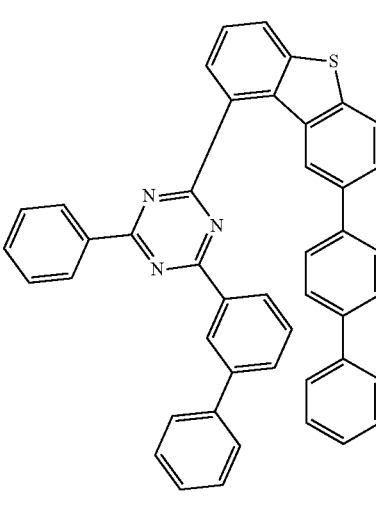
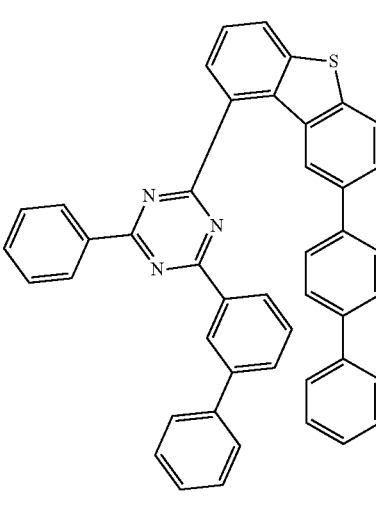
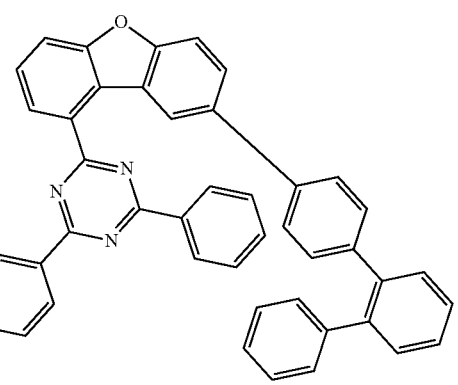

187
-continued
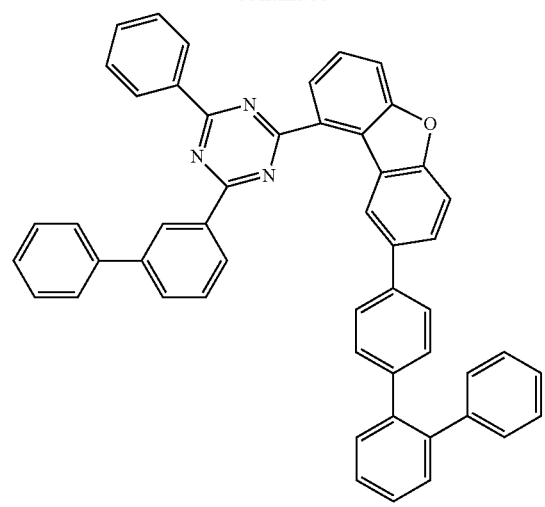
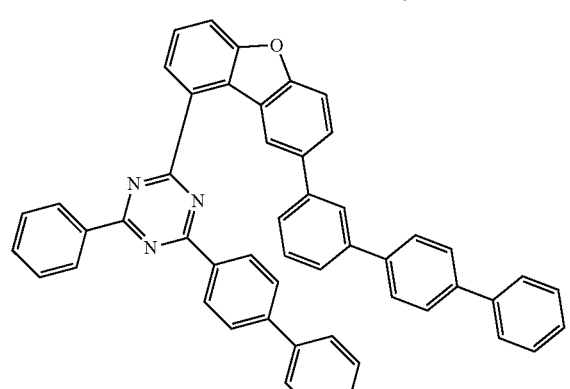
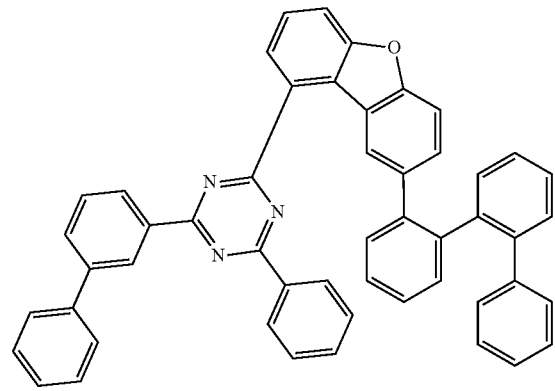
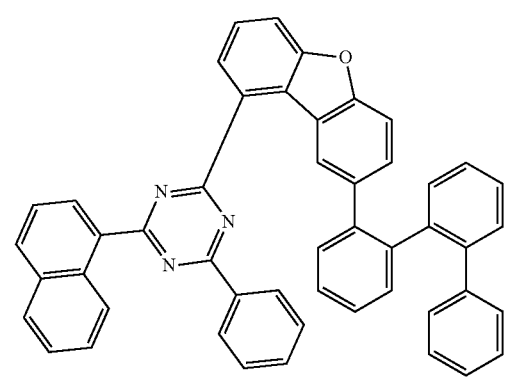
188
-continued
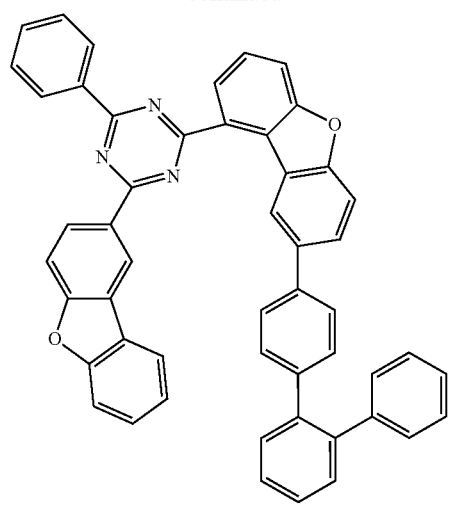
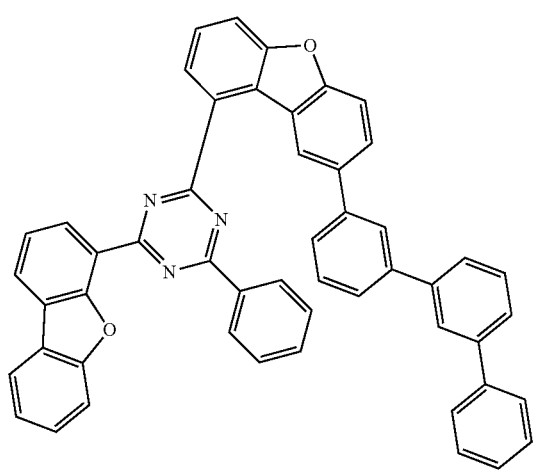
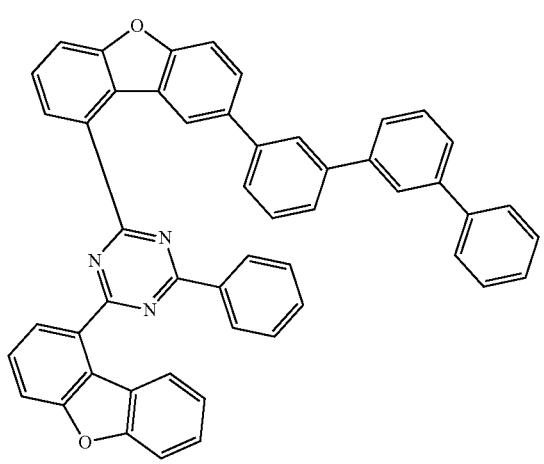

189
-continued
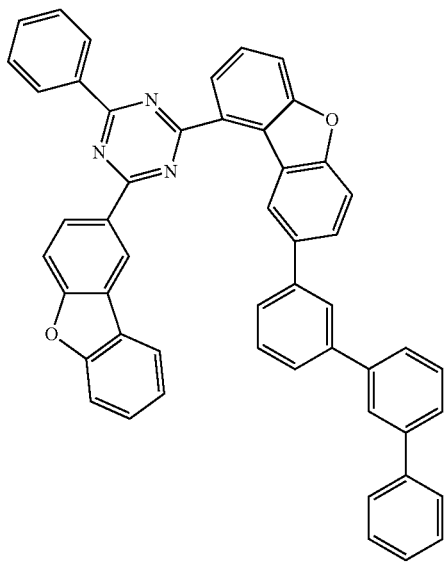
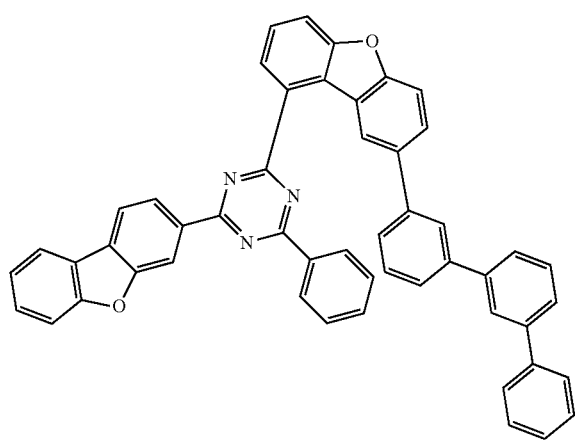
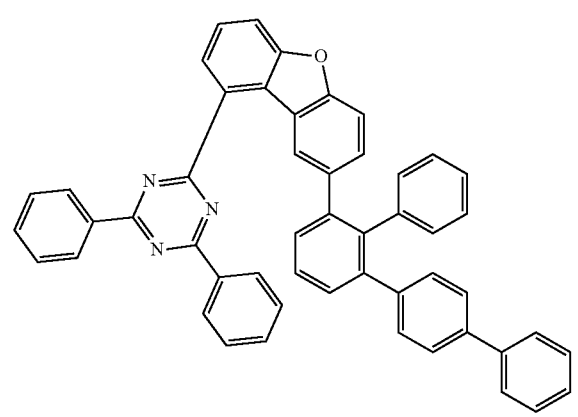
190
-continued
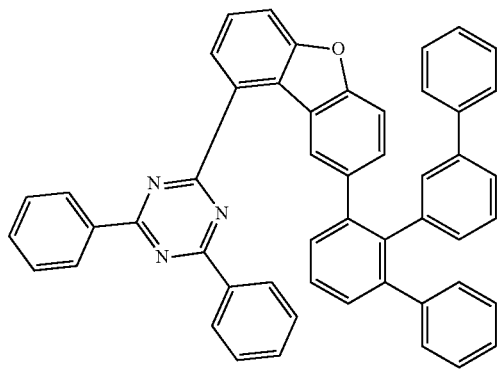
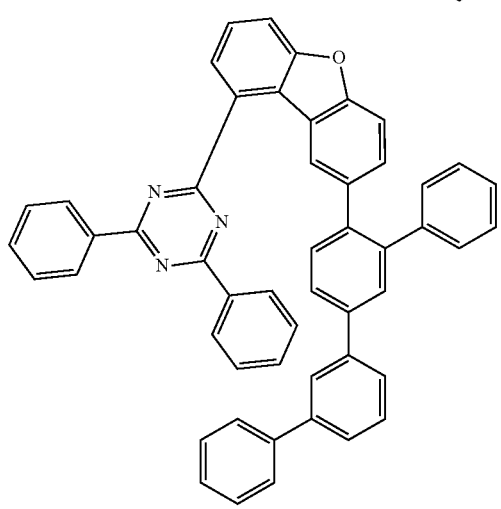
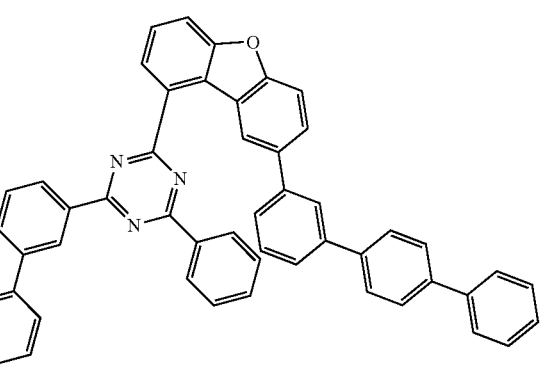
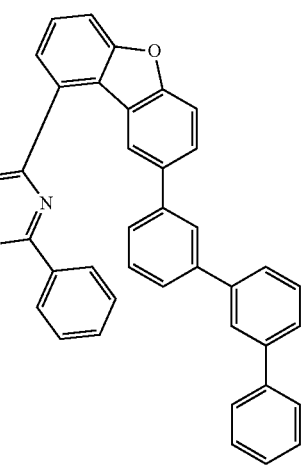

191
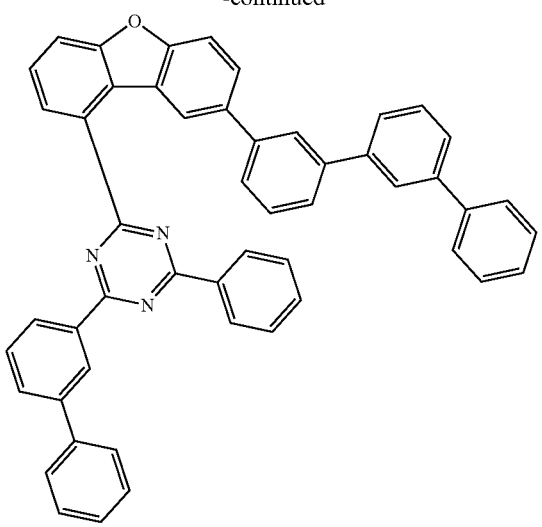
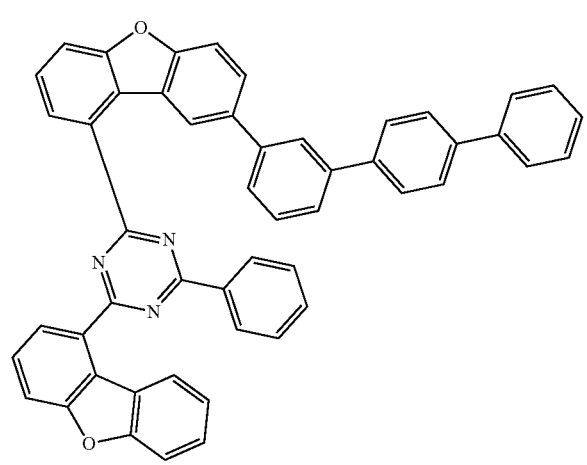
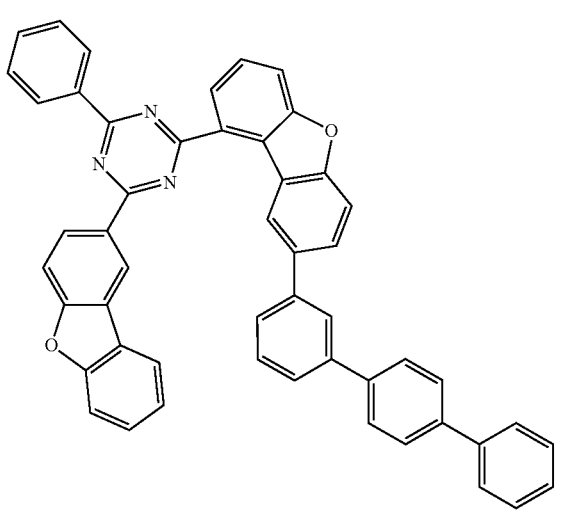
192
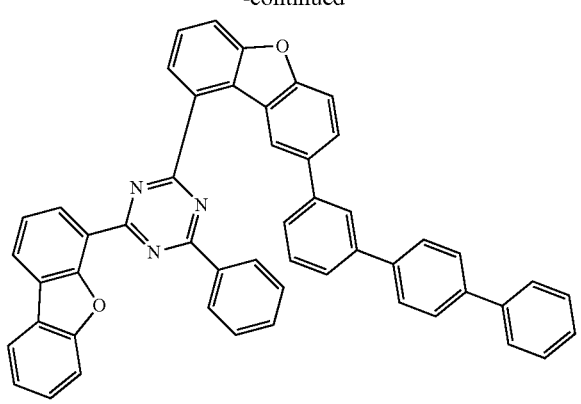
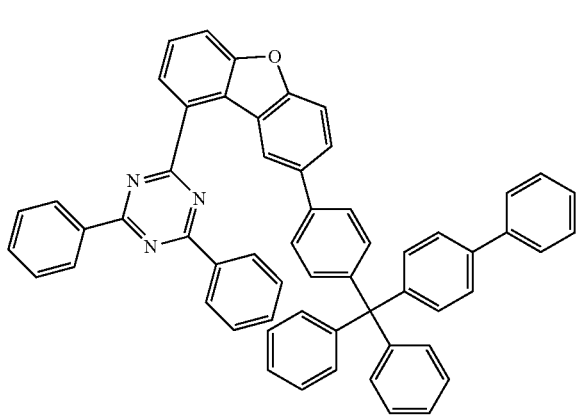
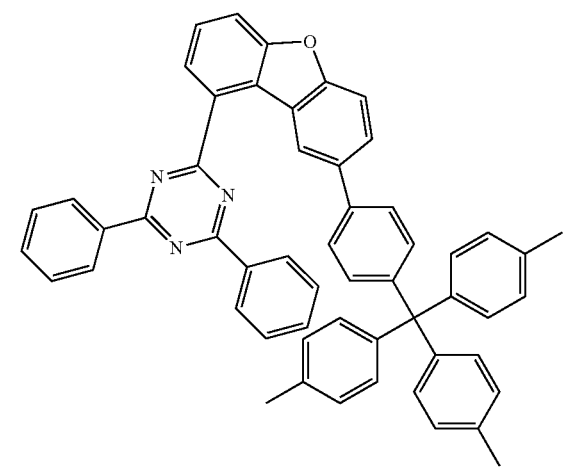

193
-continued
194
-continued
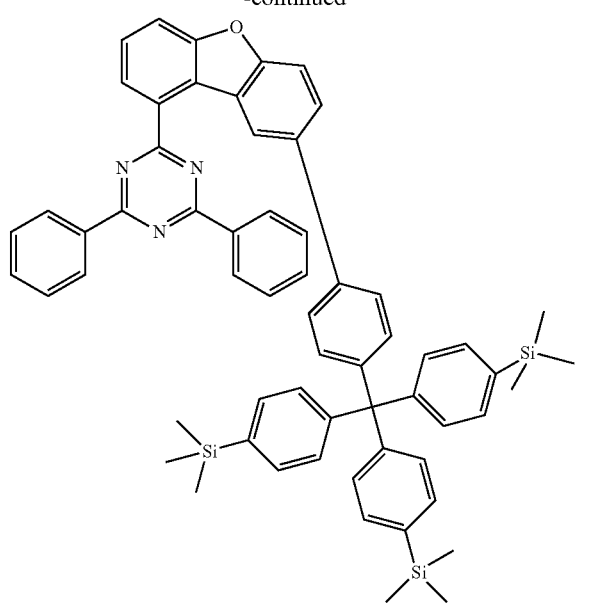
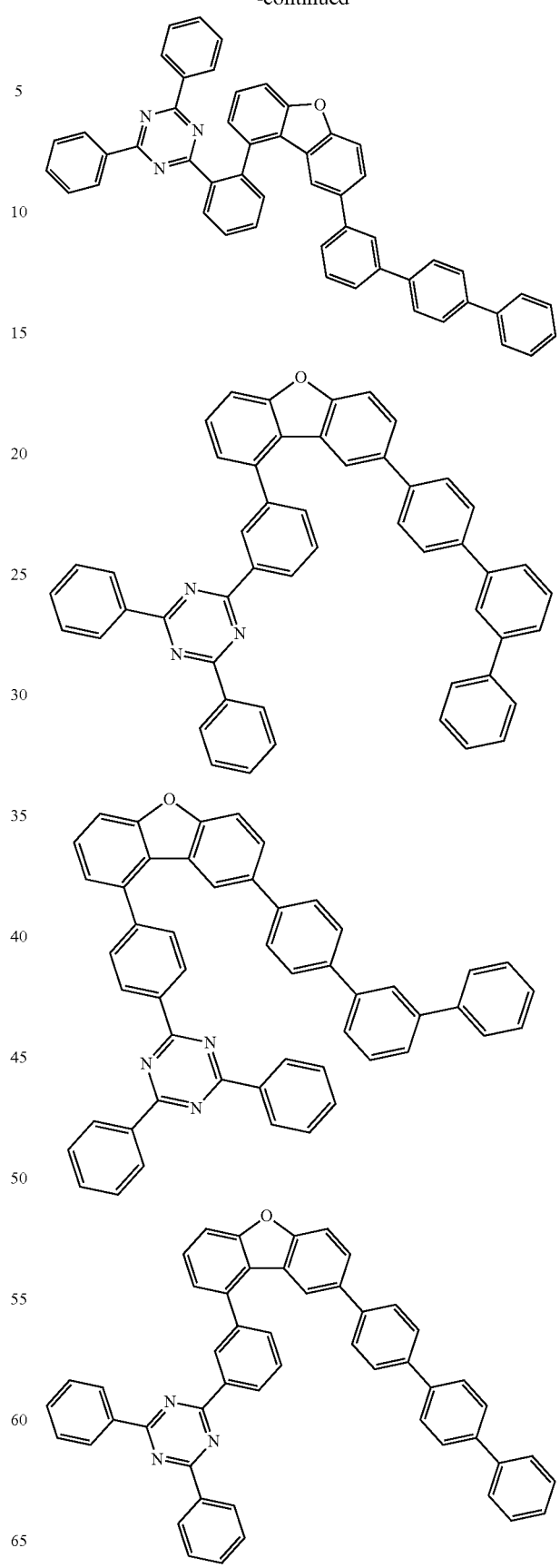

195
-continued
196
-continued
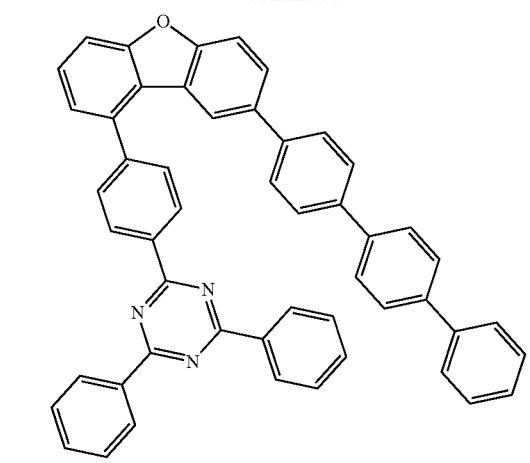
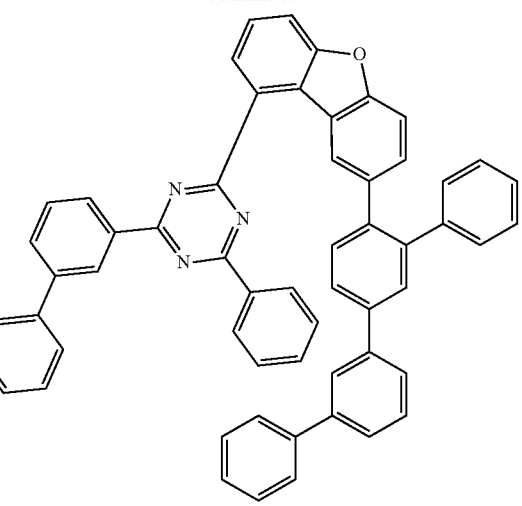
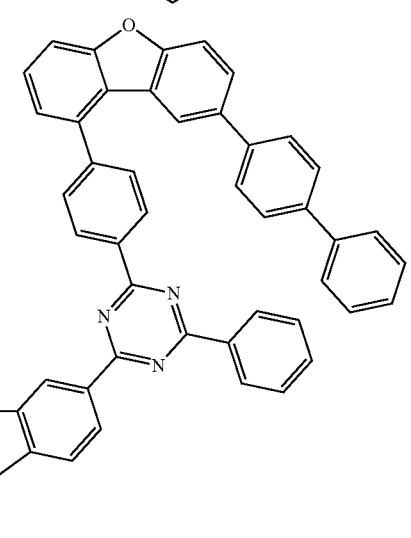
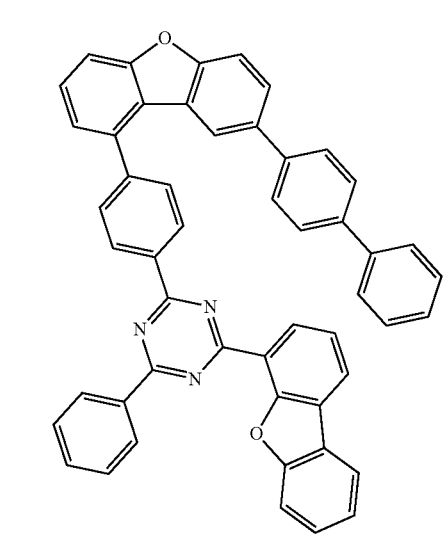

197
-continued
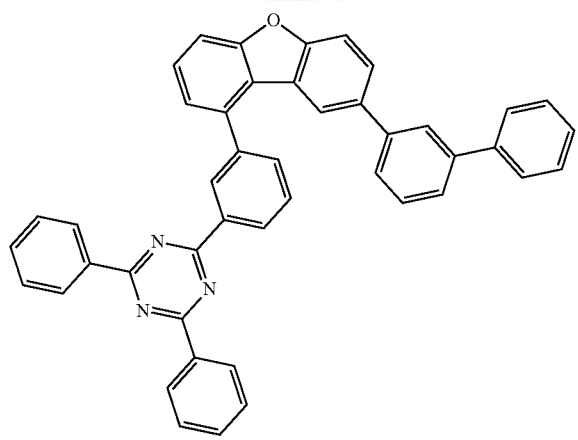
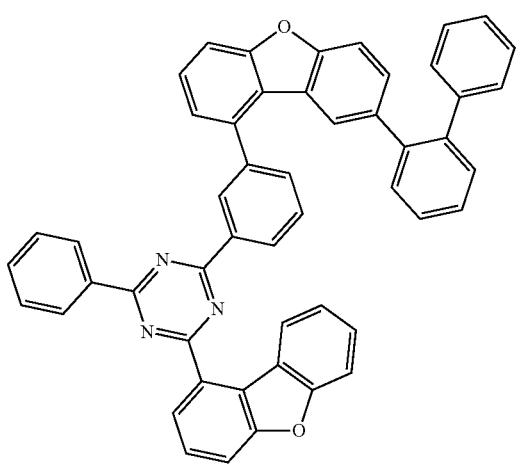
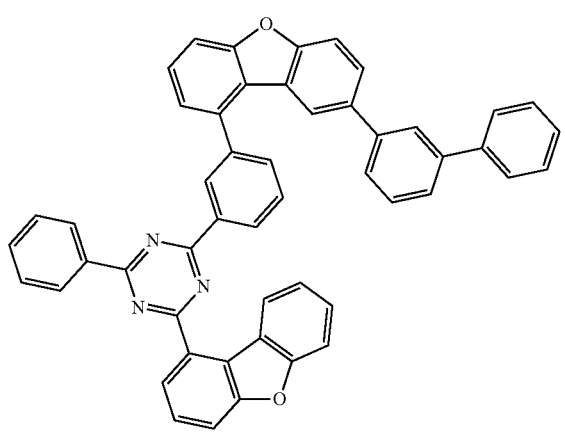
198
-continued
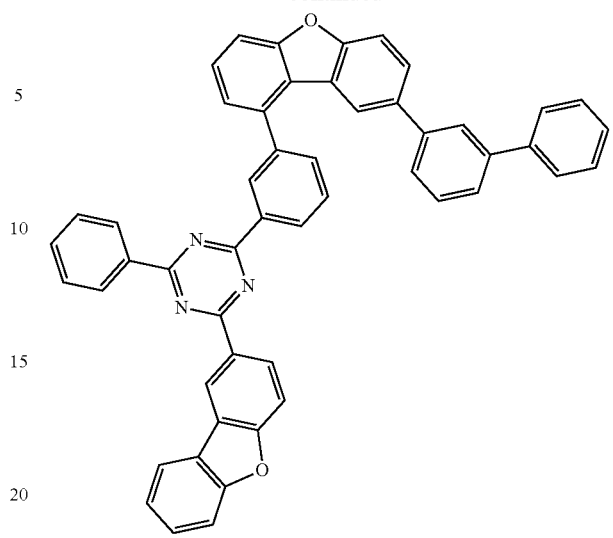
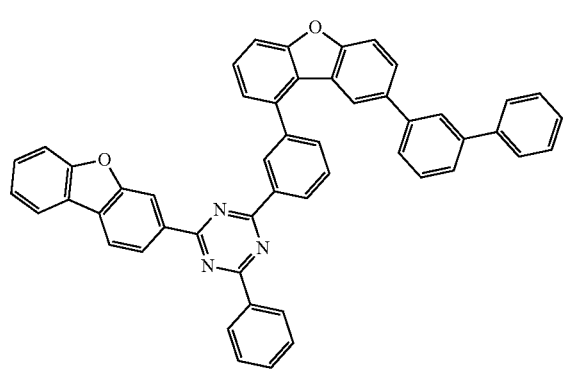
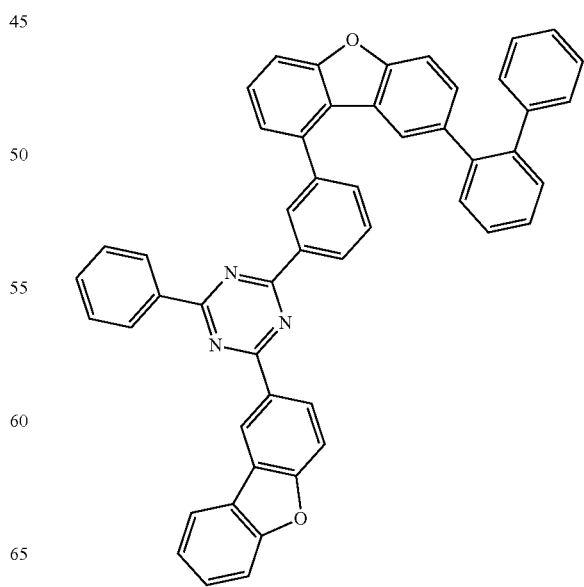

199
-continued
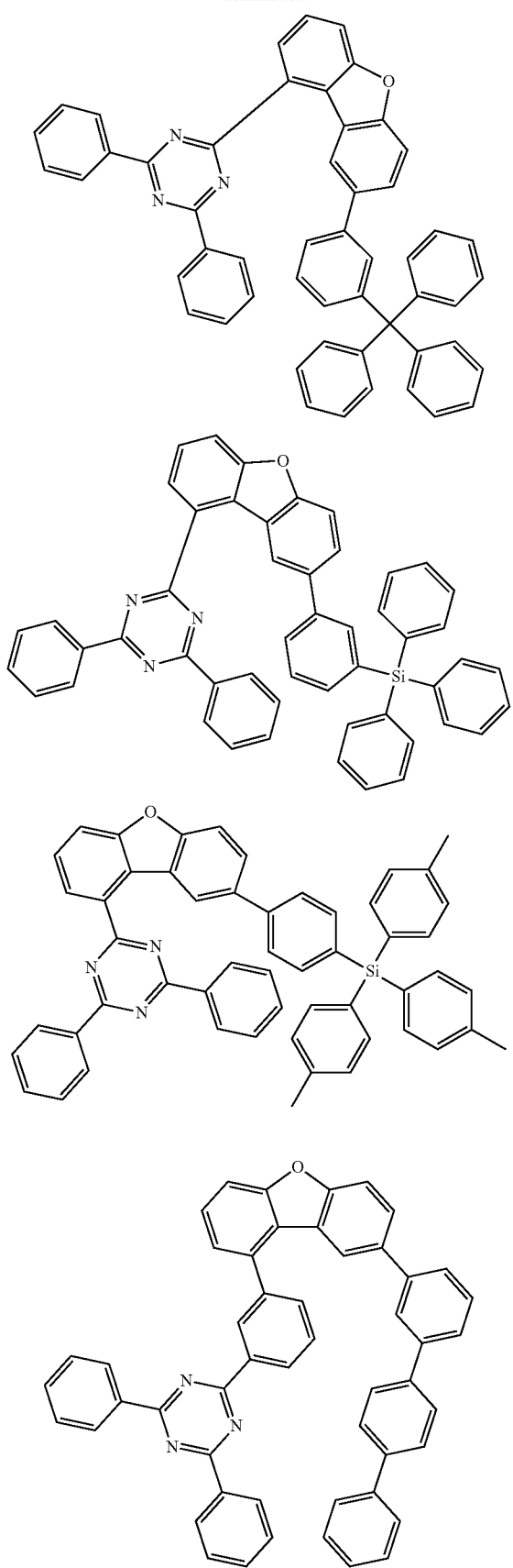
200
-continued
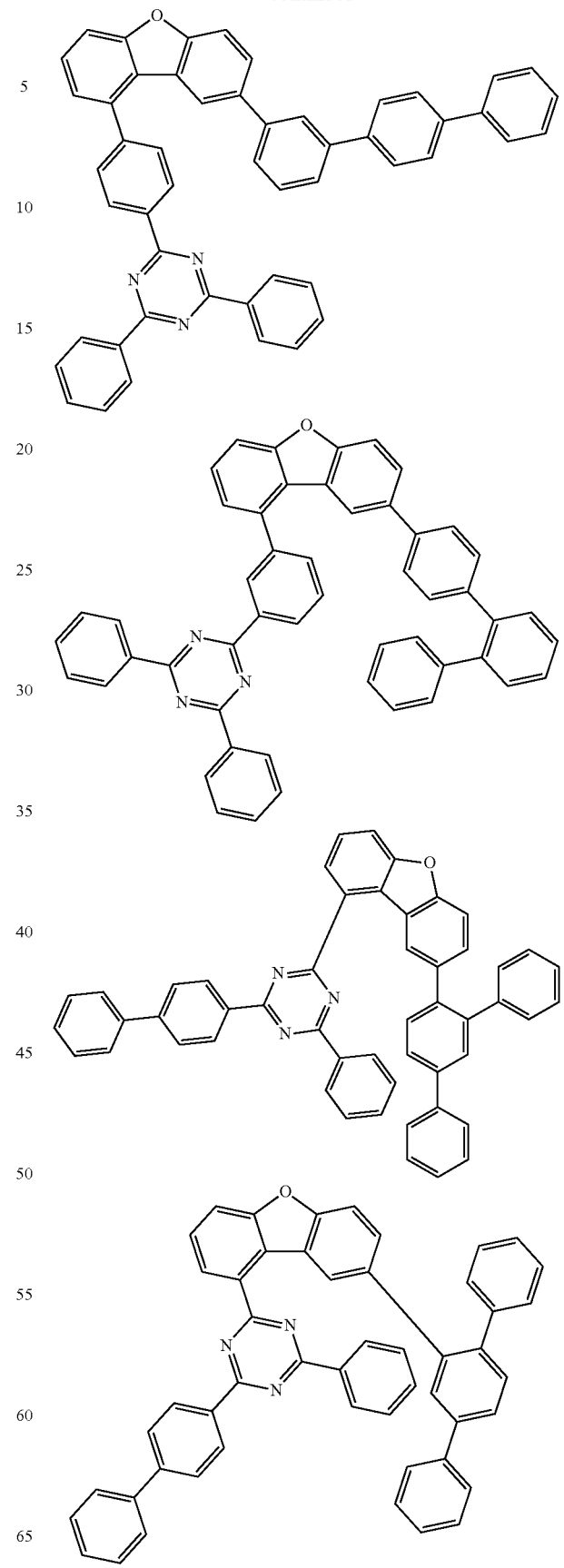

201
-continued
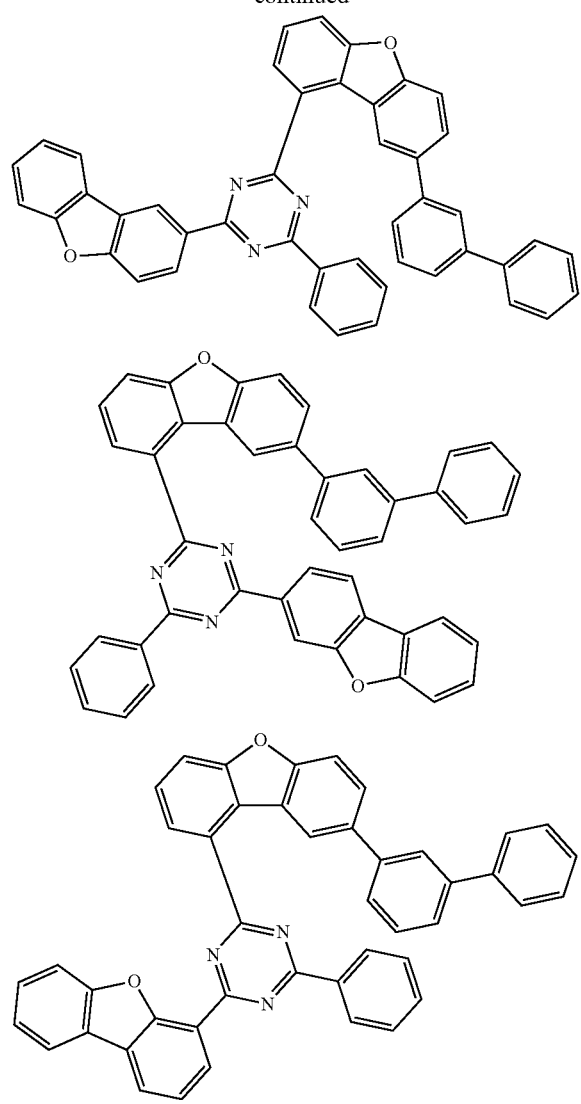
202
-continued
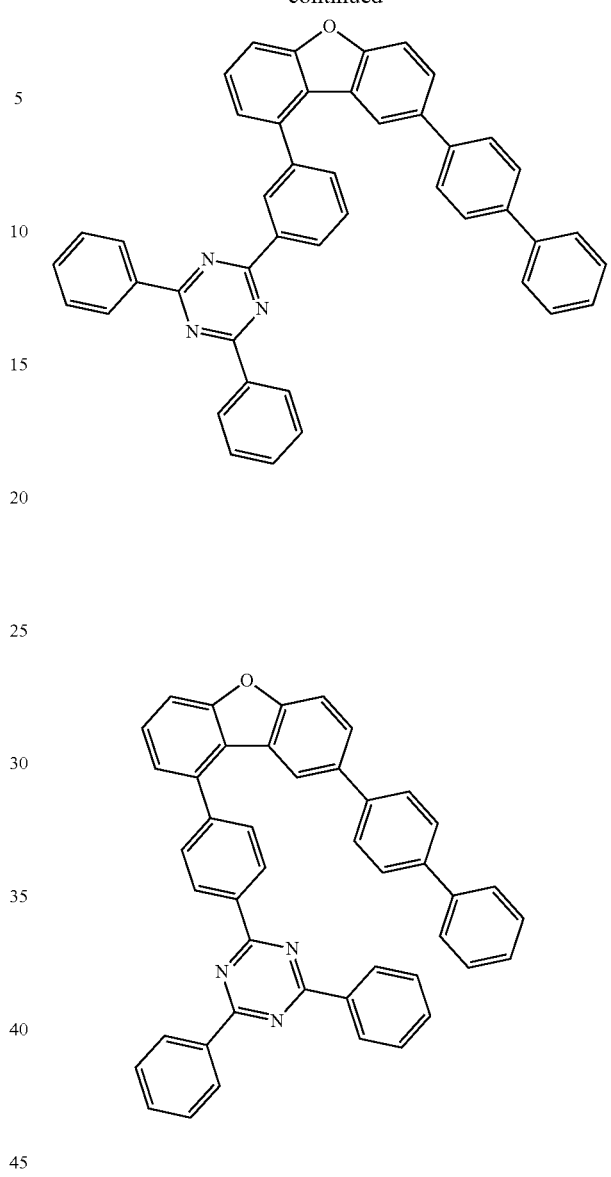
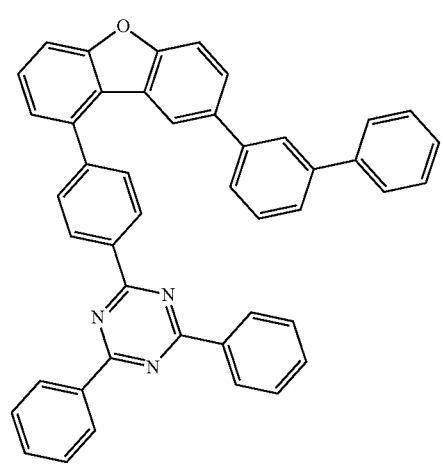

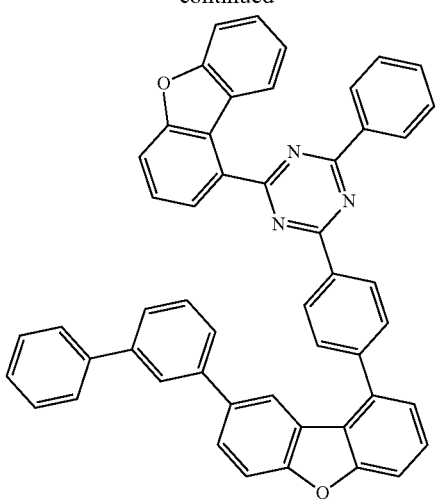
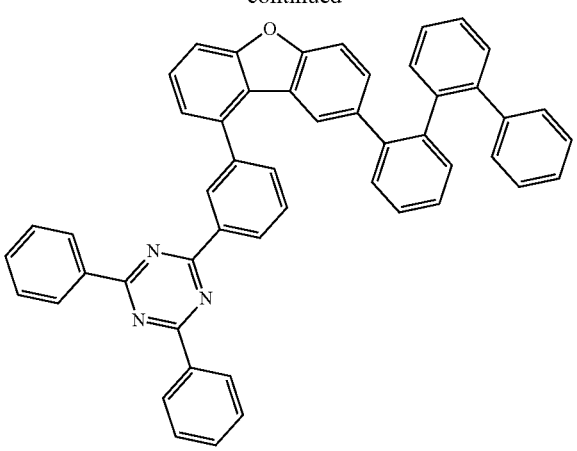
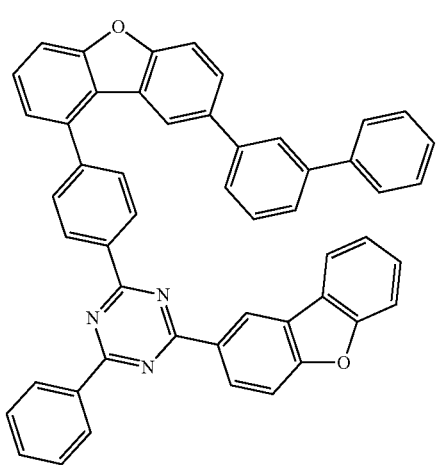
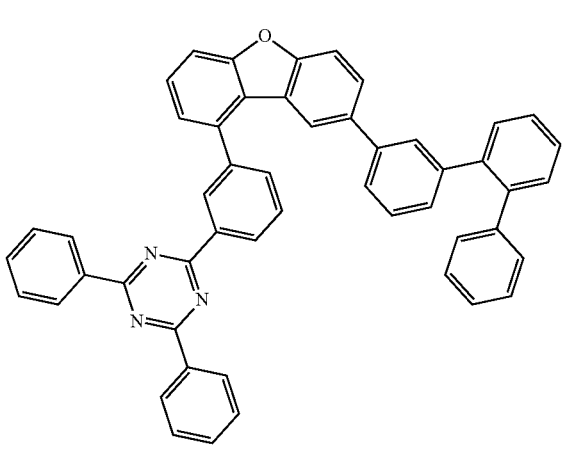
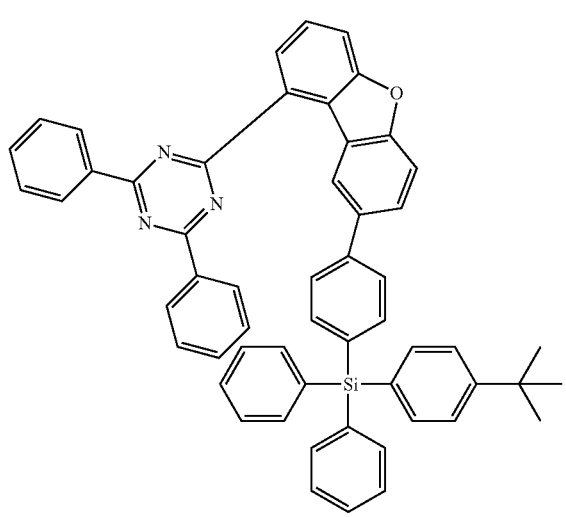
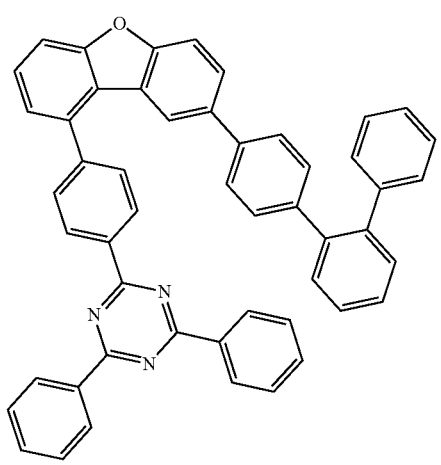

205
-continued
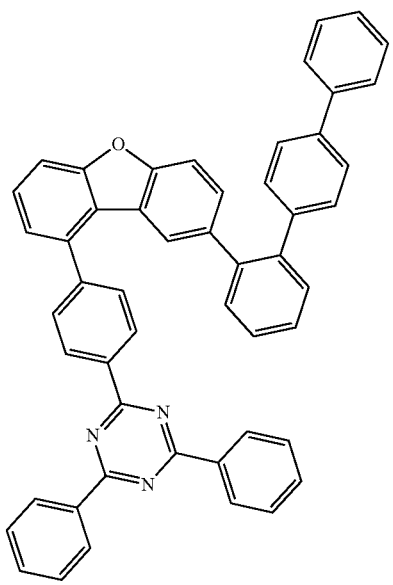
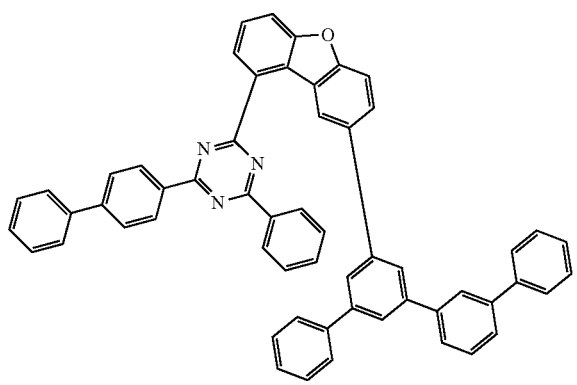
206
-continued
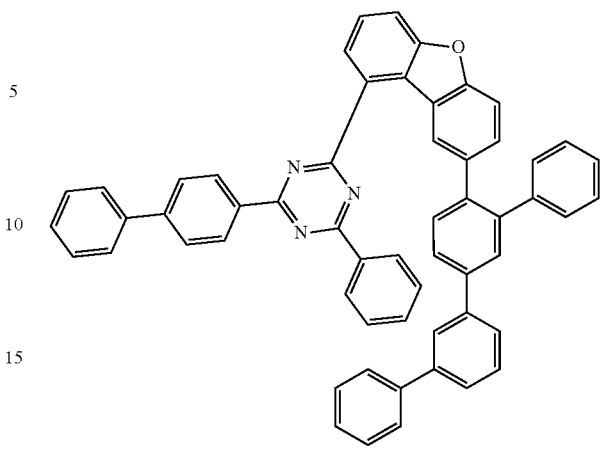
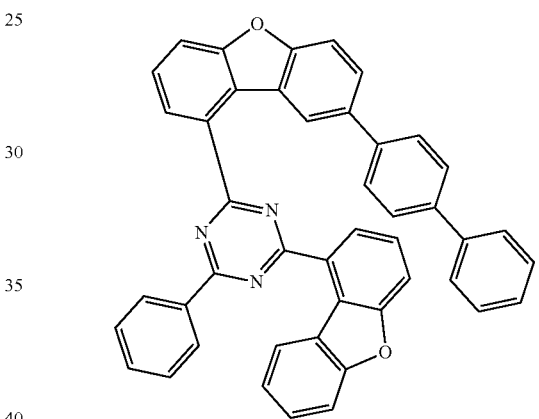
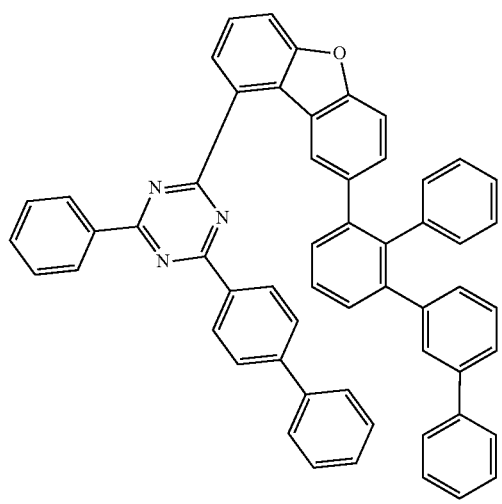
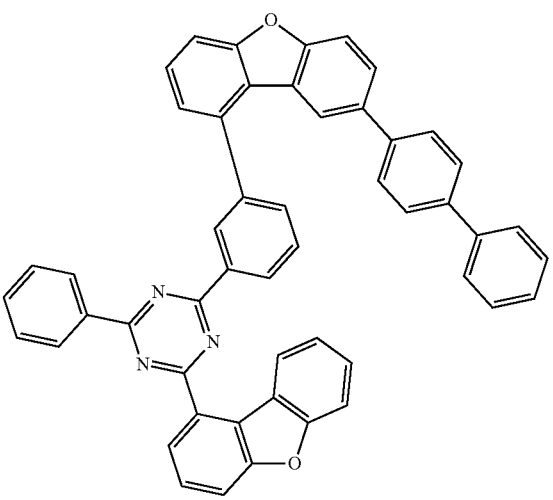

207
-continued
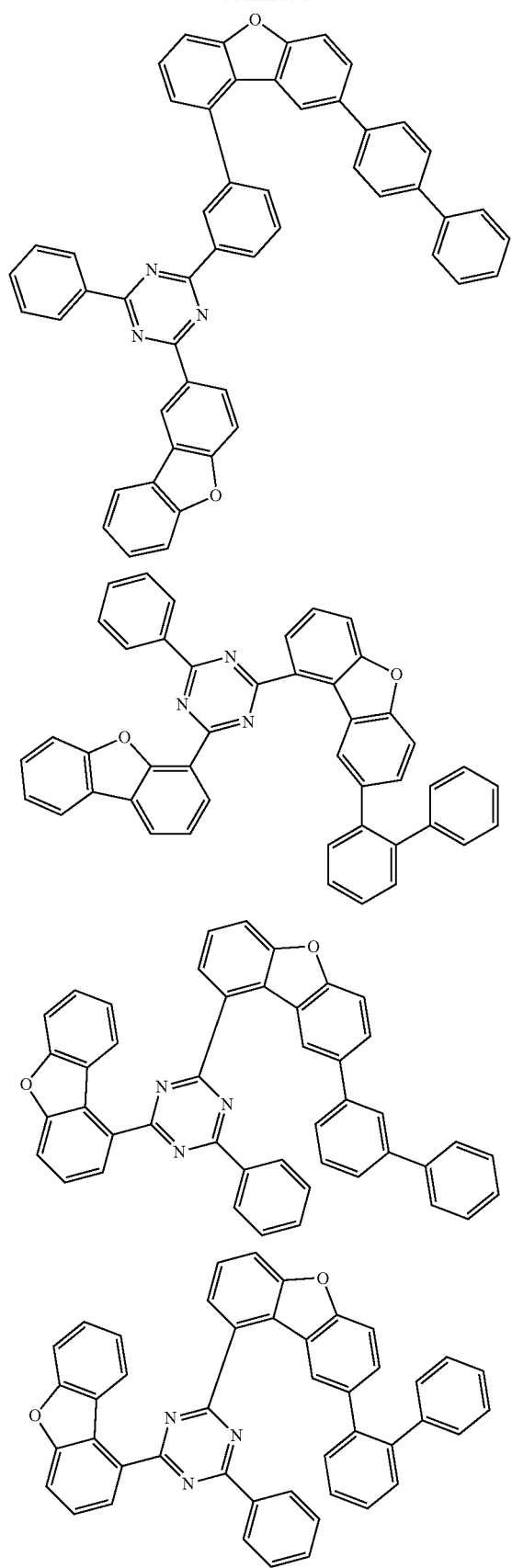
208
-continued
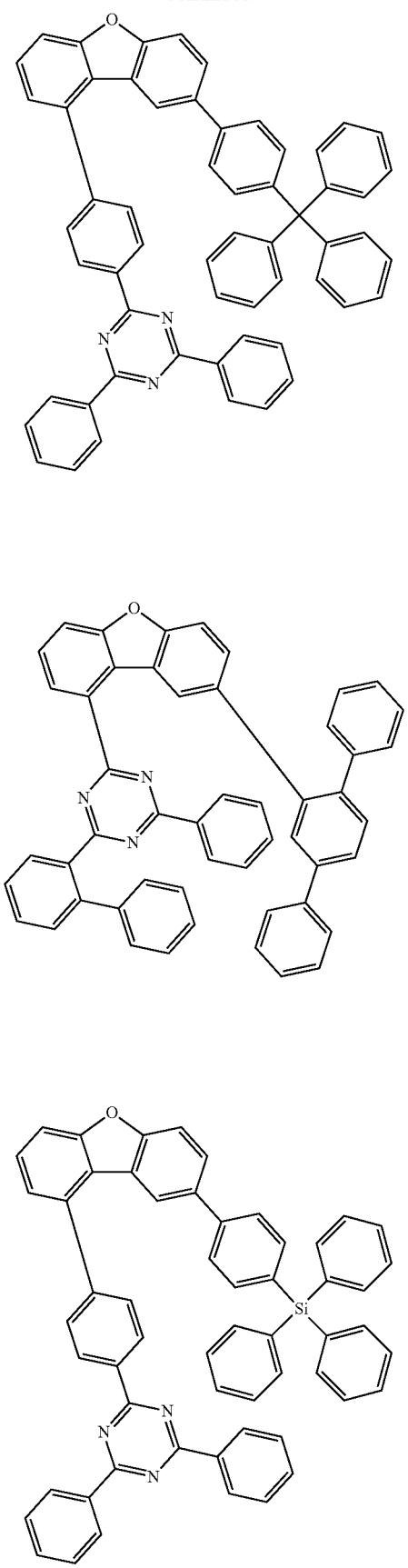

209
-continued
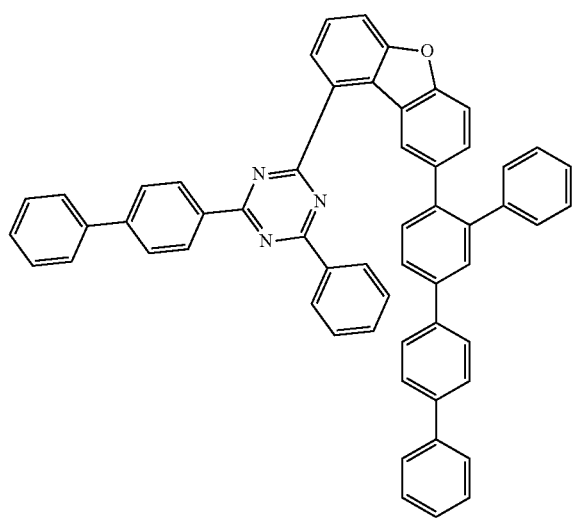
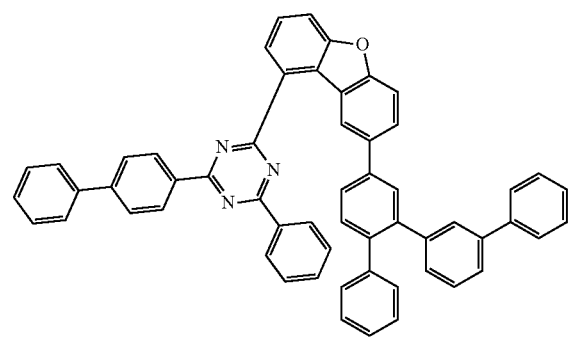
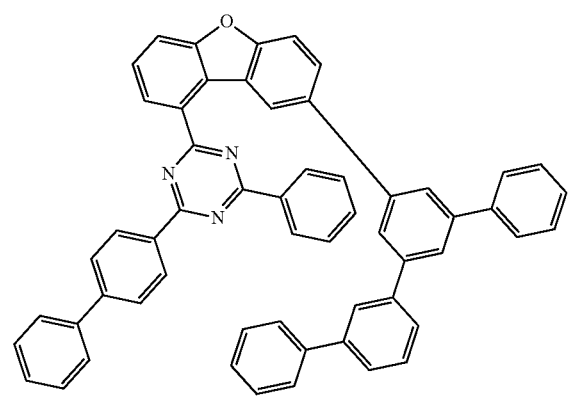
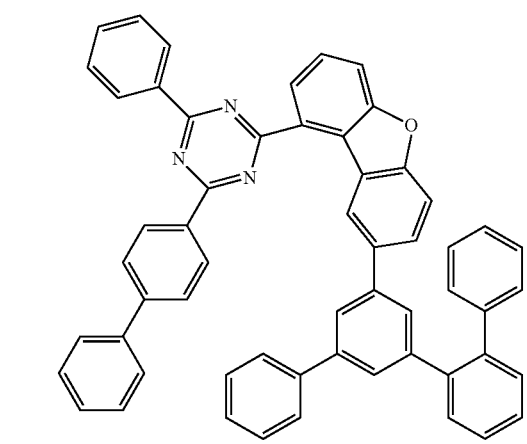
210
-continued
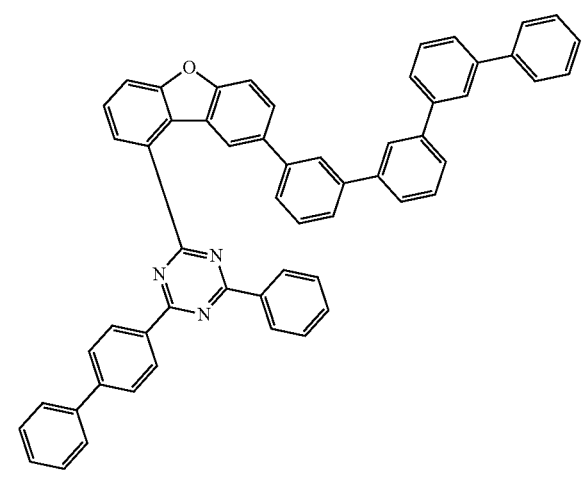
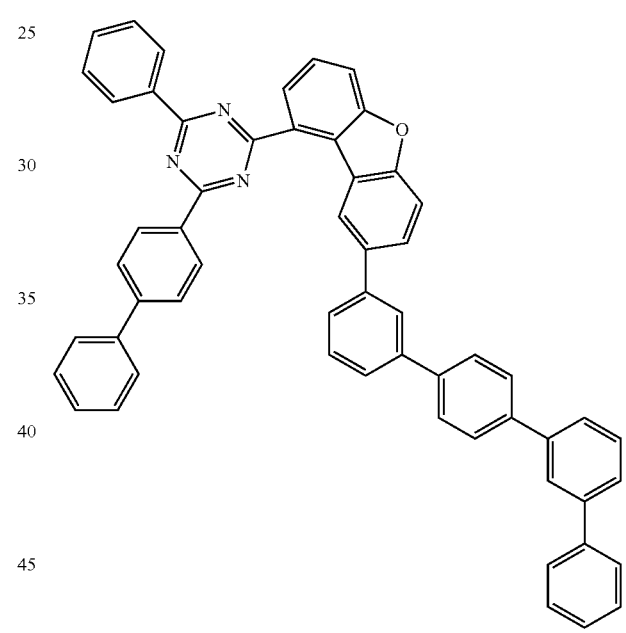
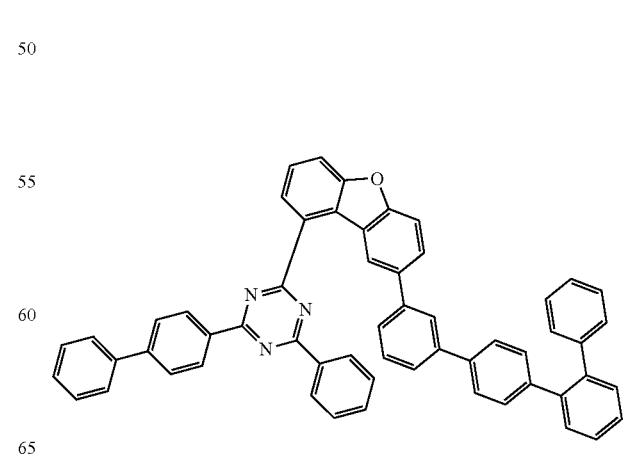

211
-continued
212
-continued
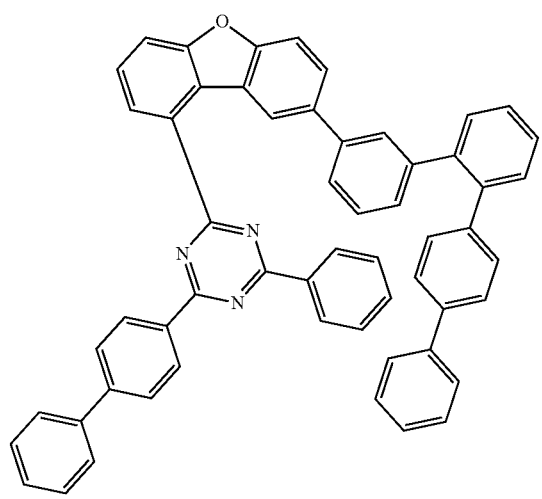
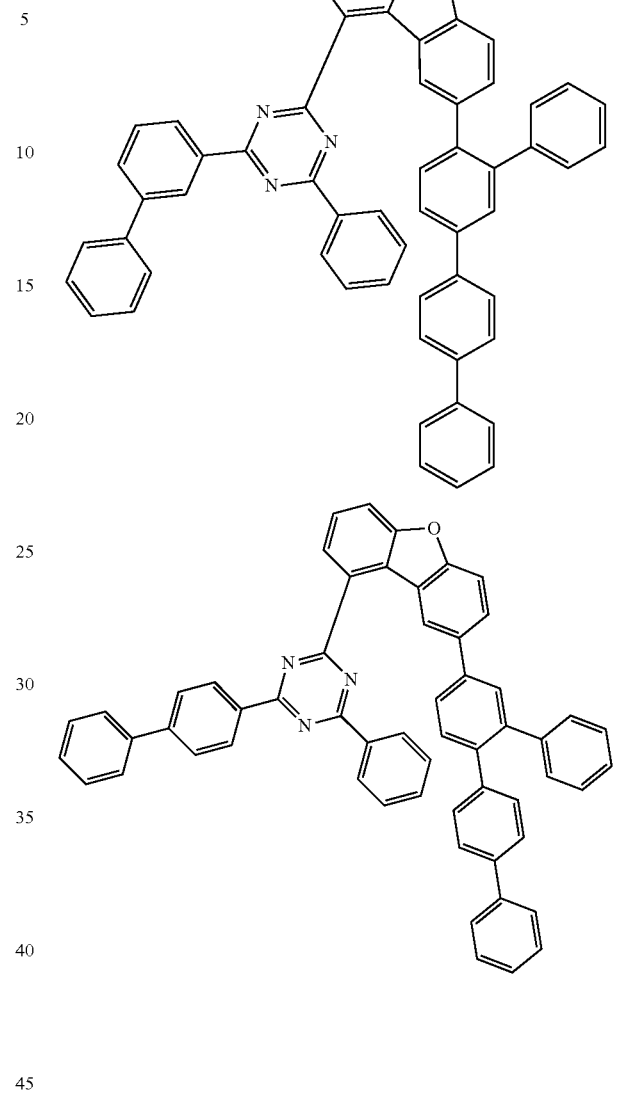
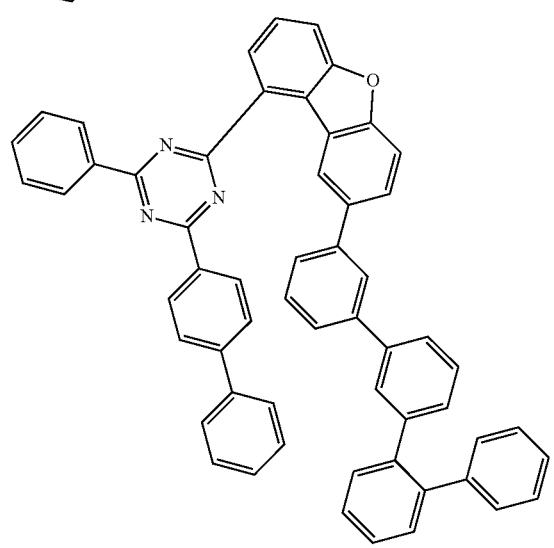
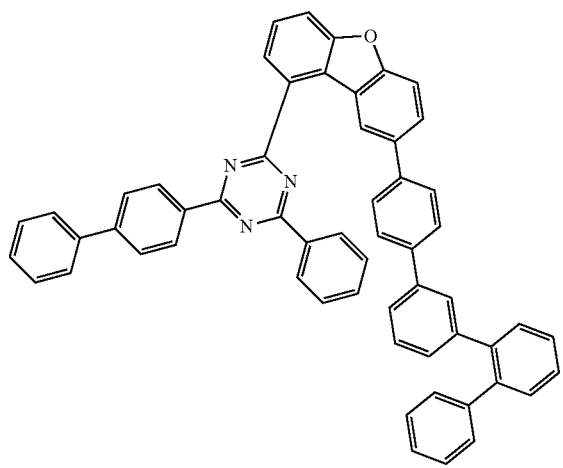

213
-continued
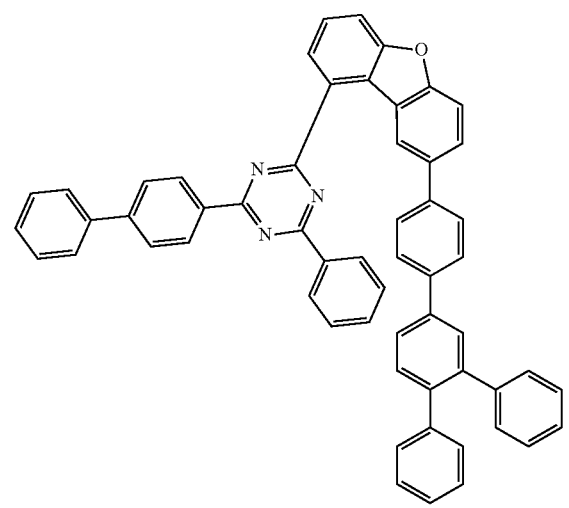
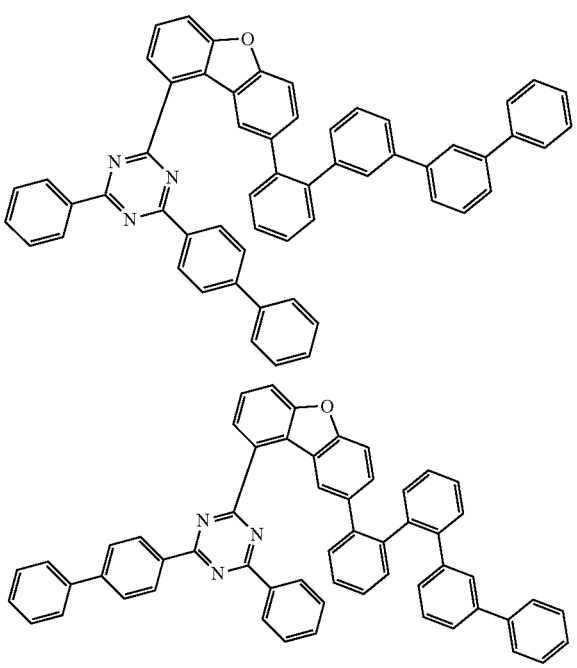
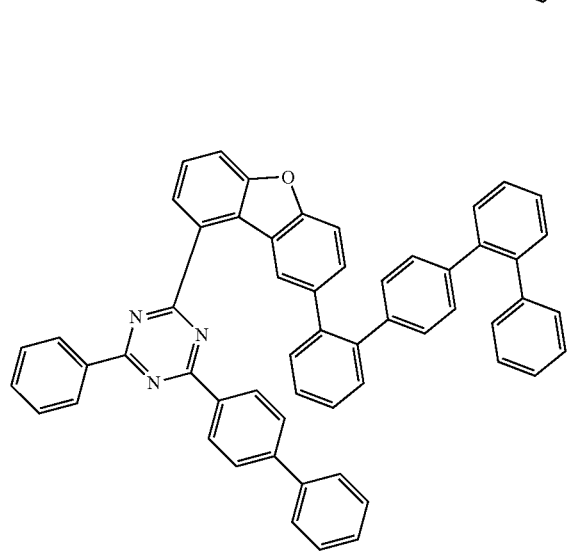
214
-continued
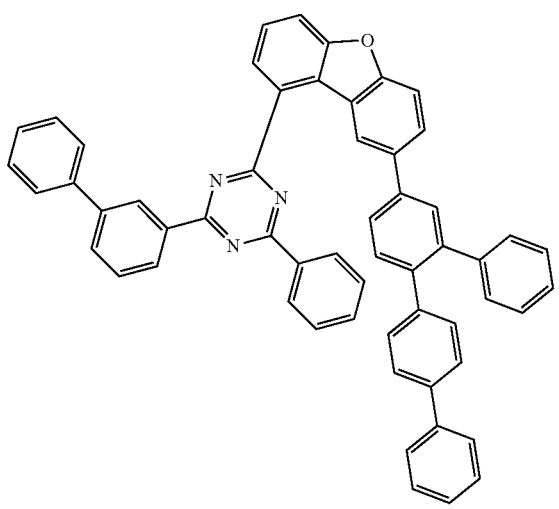

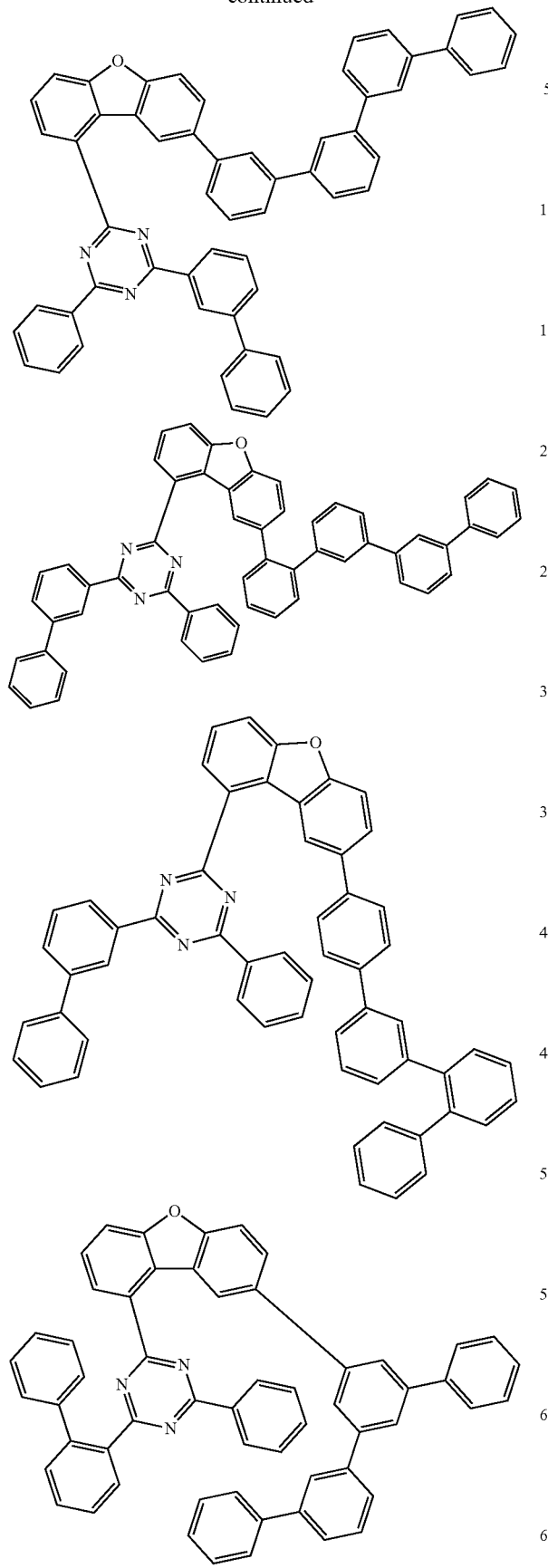
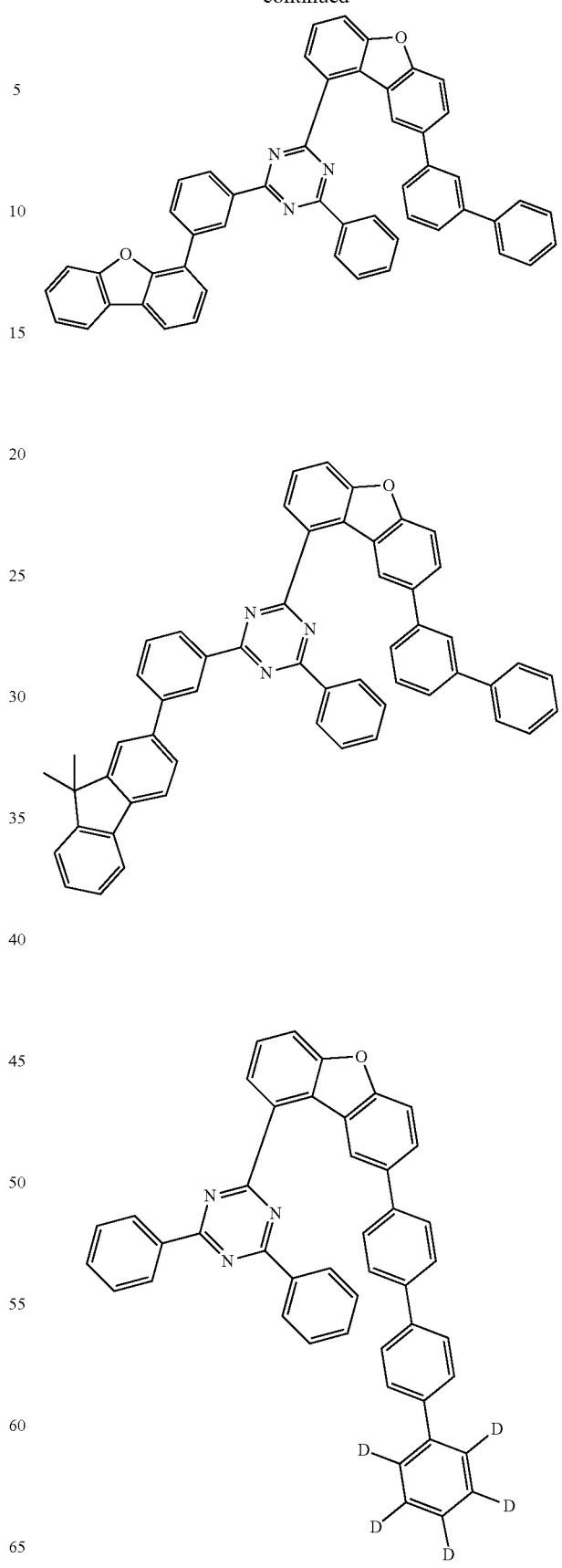

217
-continued
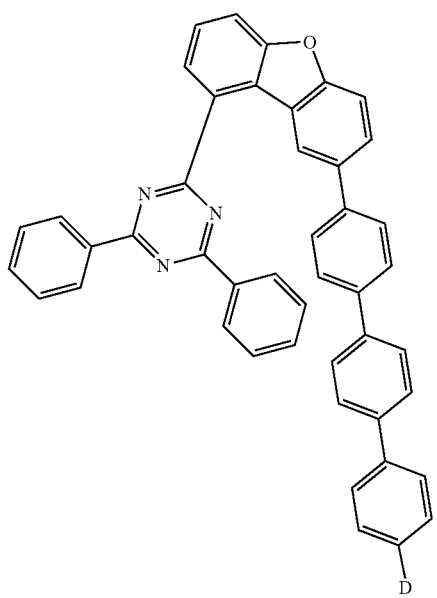
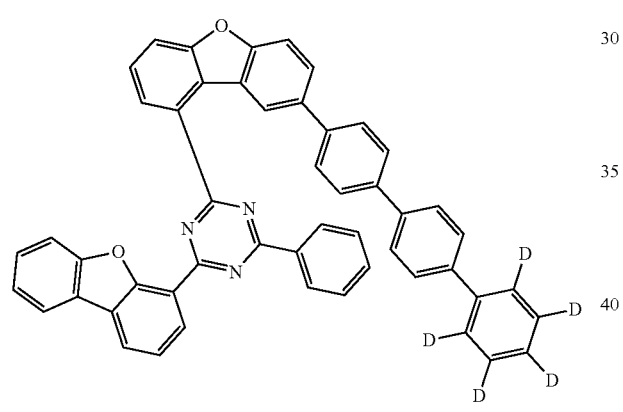
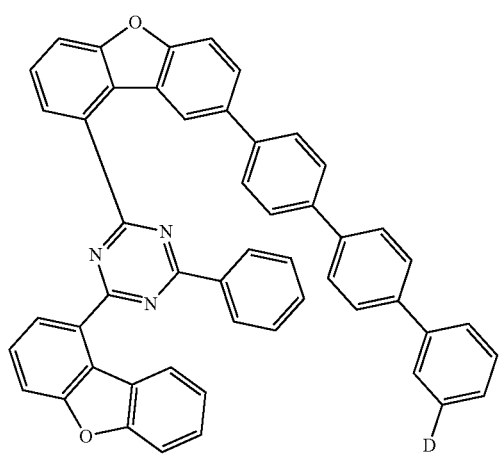
218
-continued
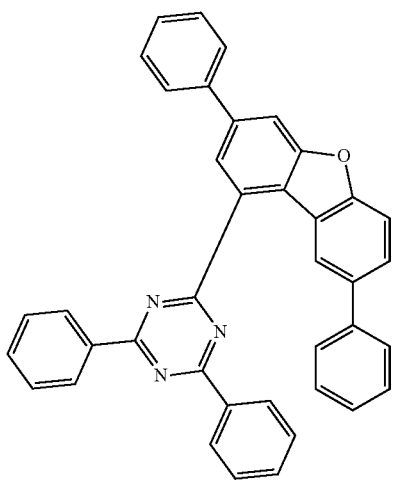
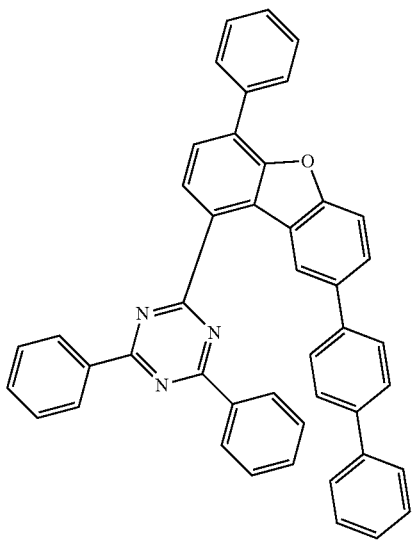
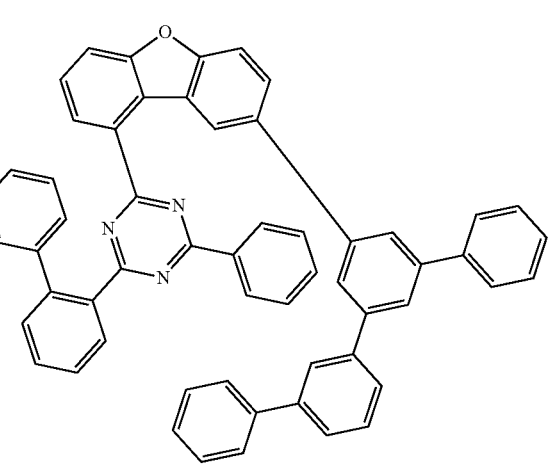

219
-continued
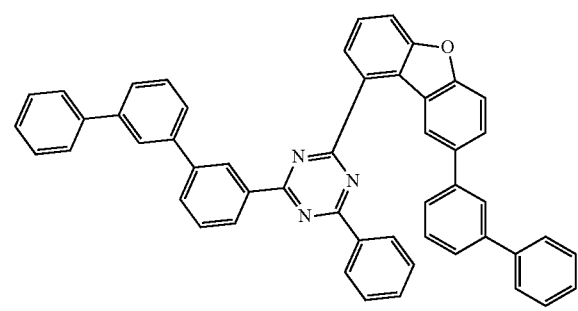
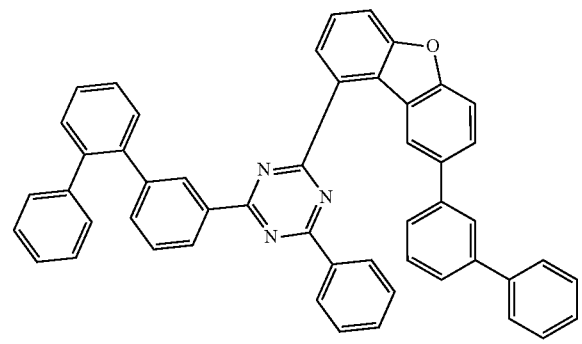
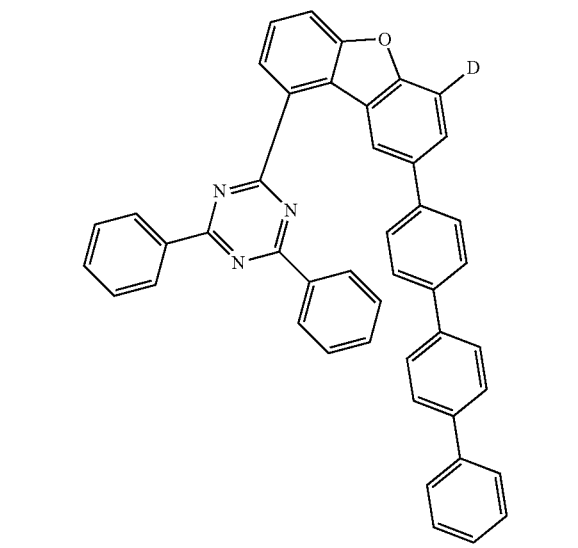
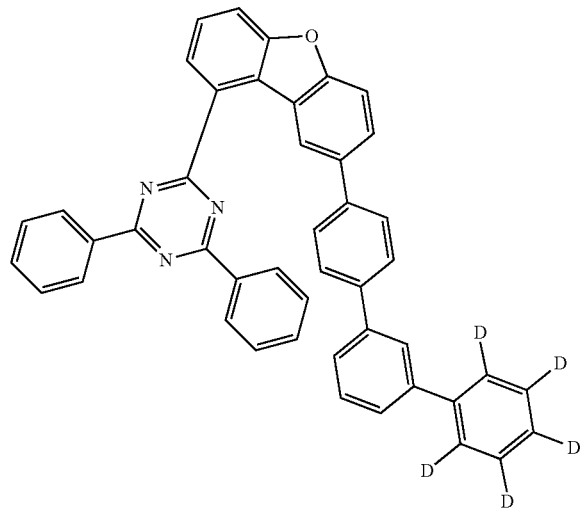
220
-continued
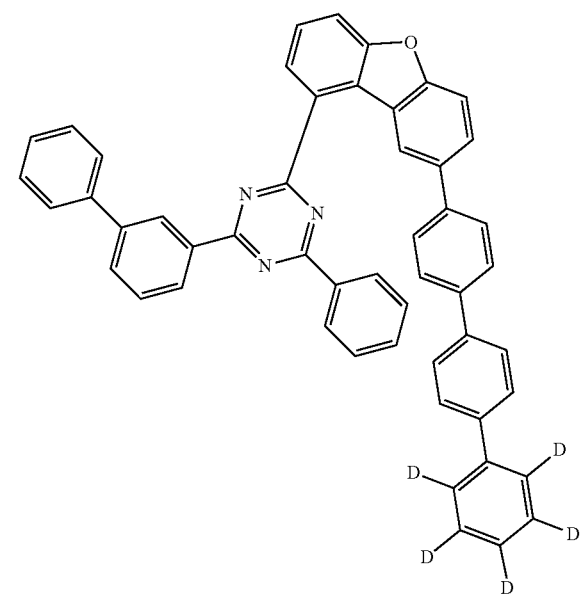
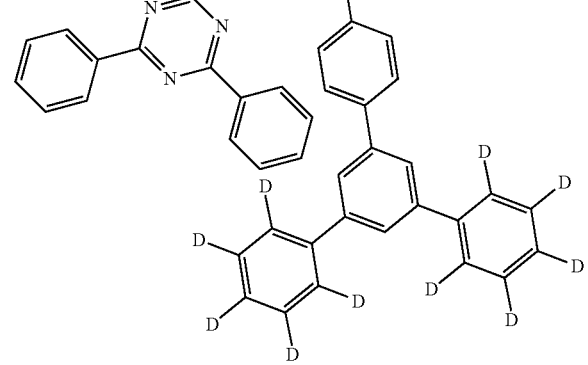
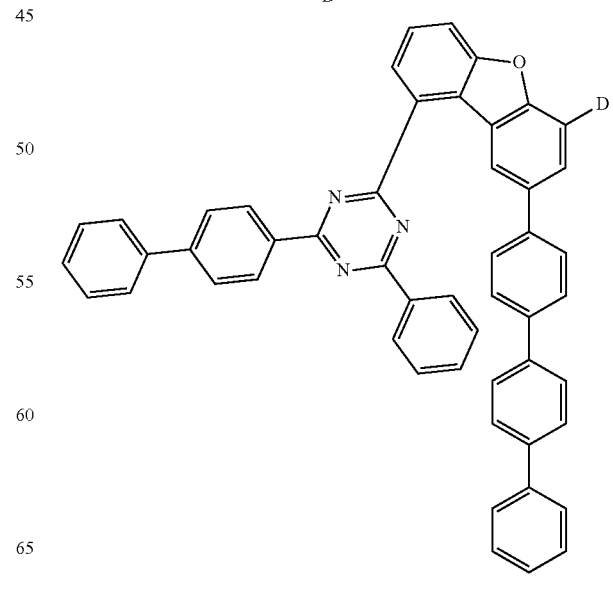

221 -continued
222 -continued
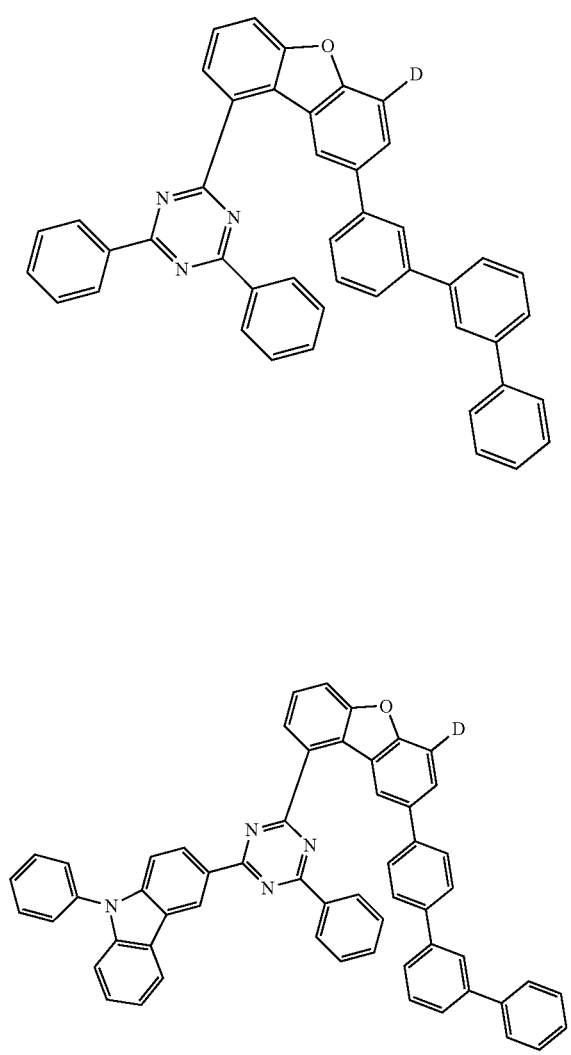
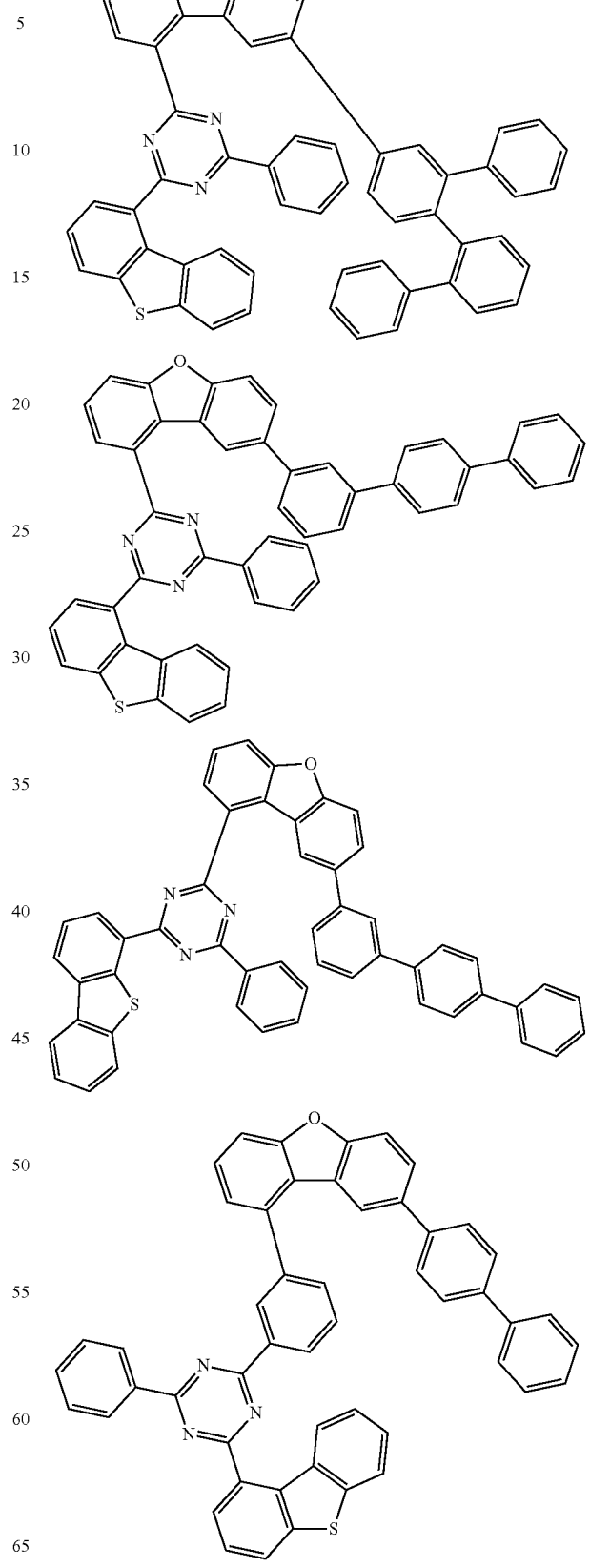

223
-continued
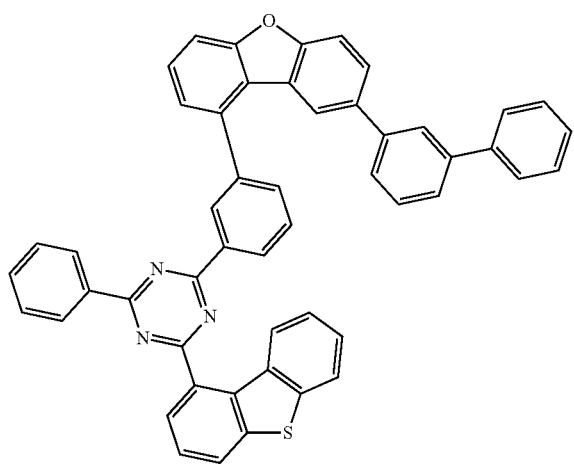
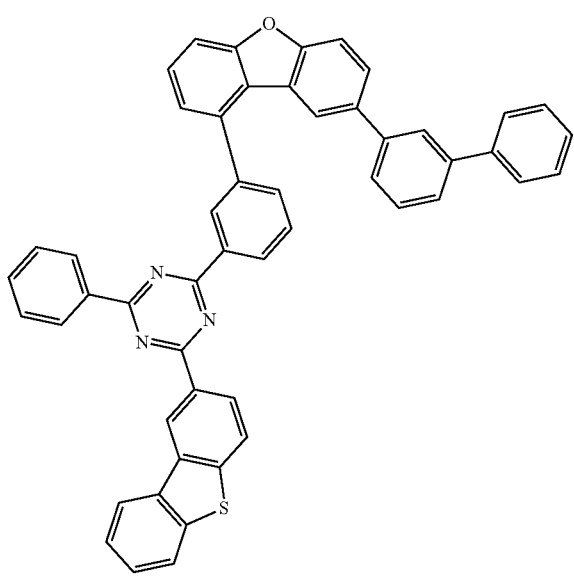
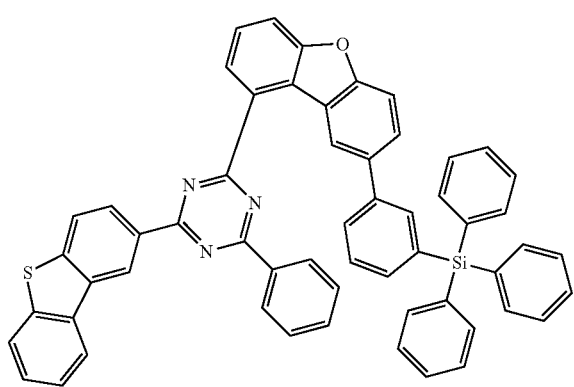
224
-continued
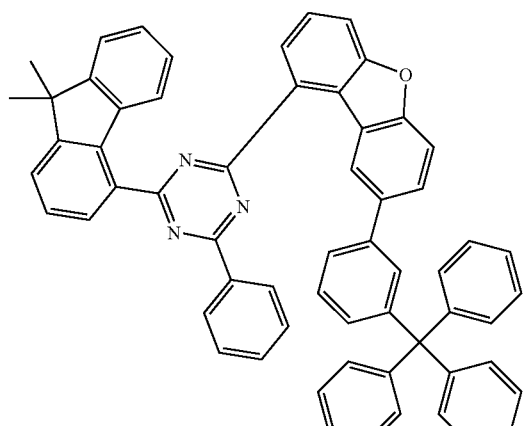
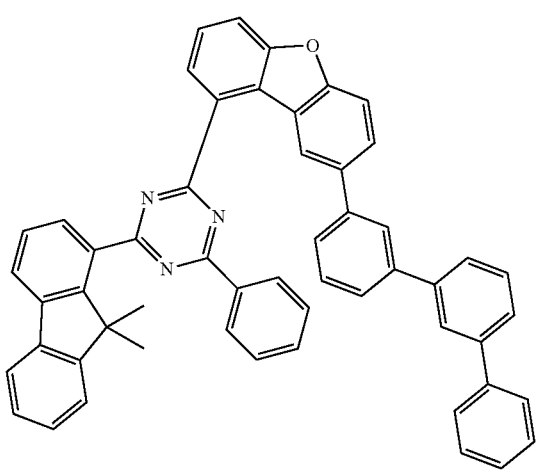
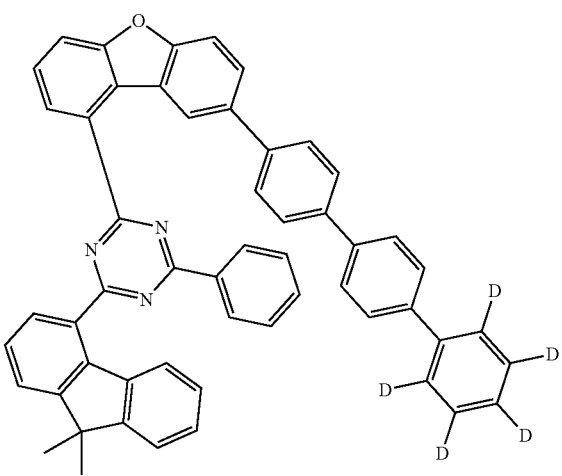

225
-continued
226
-continued
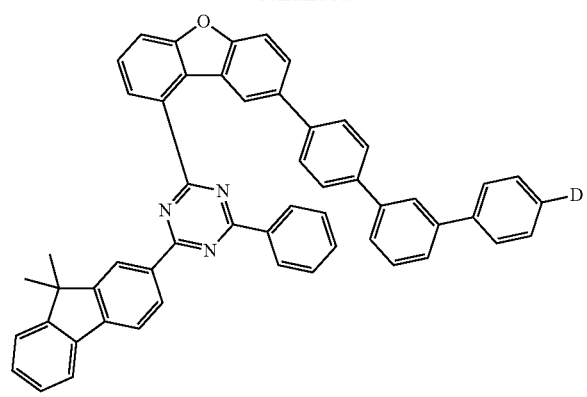
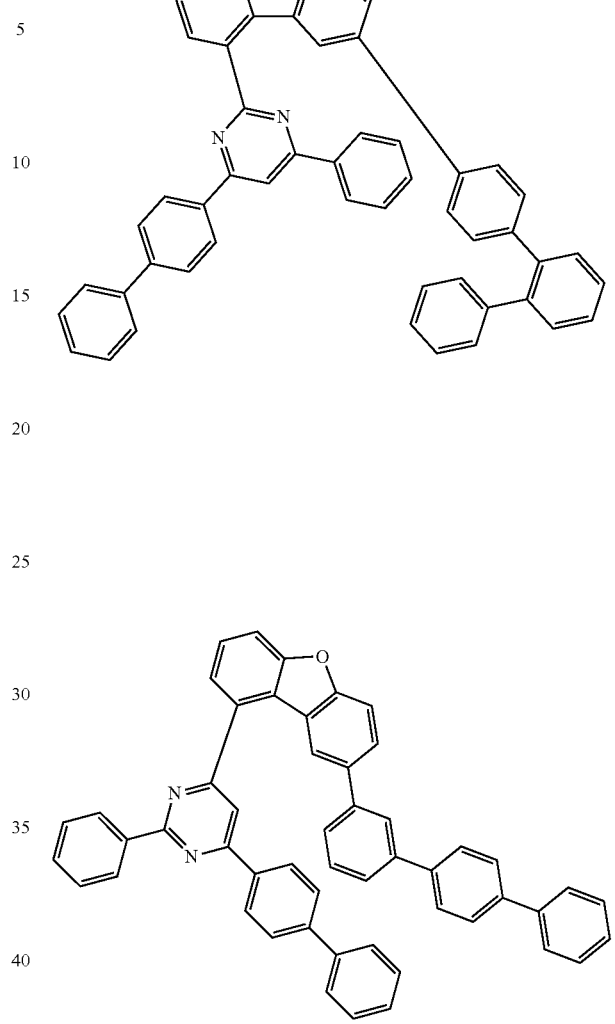
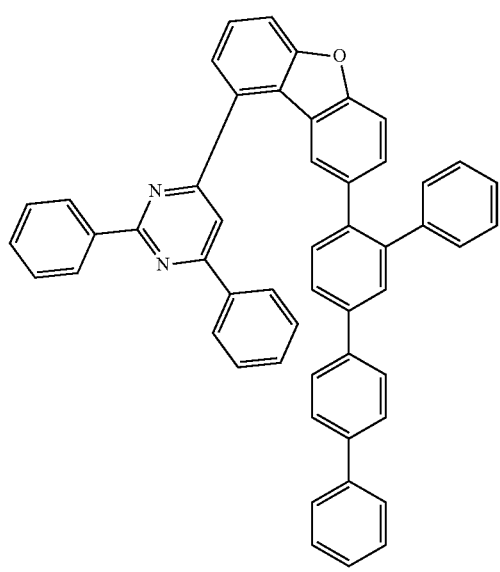
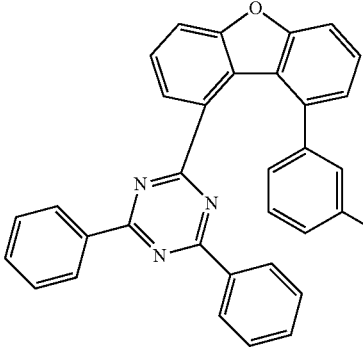

227
-continued
228
-continued
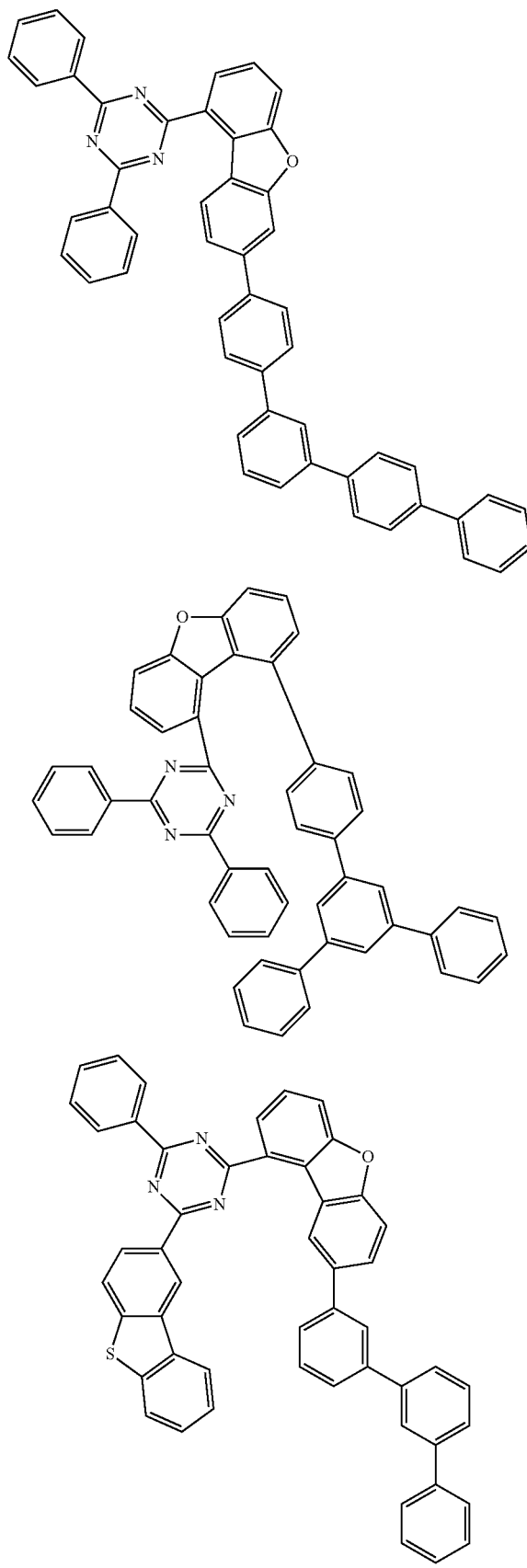
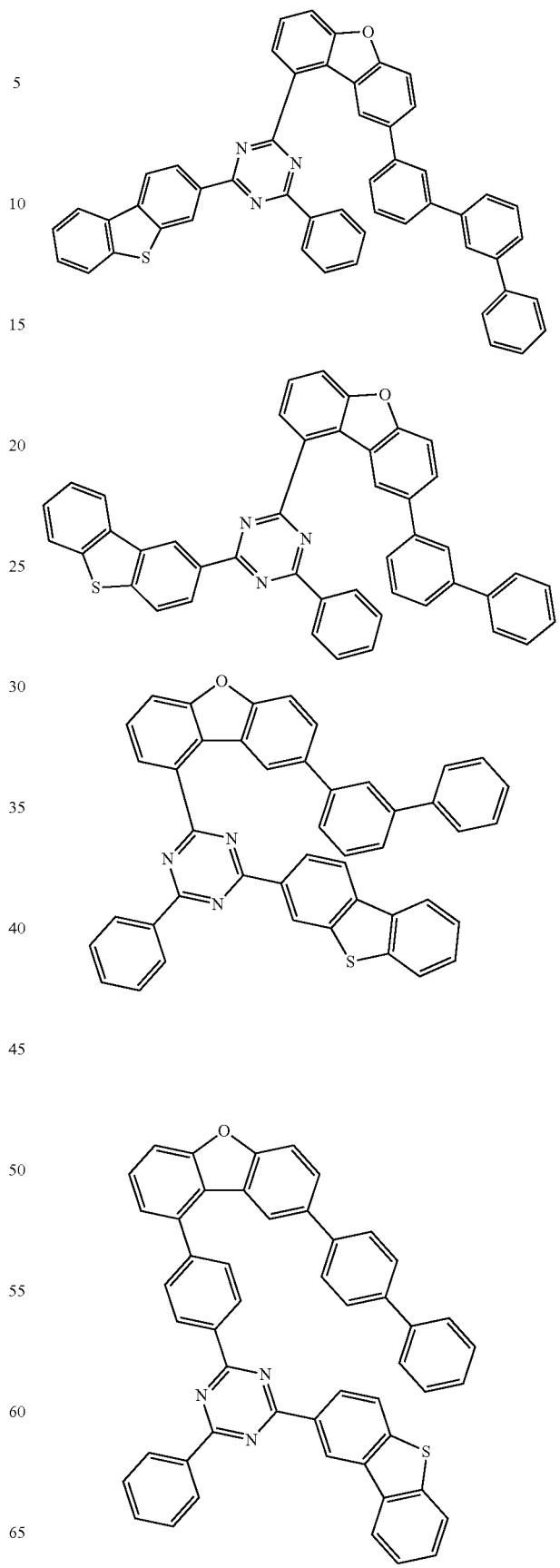

229
-continued
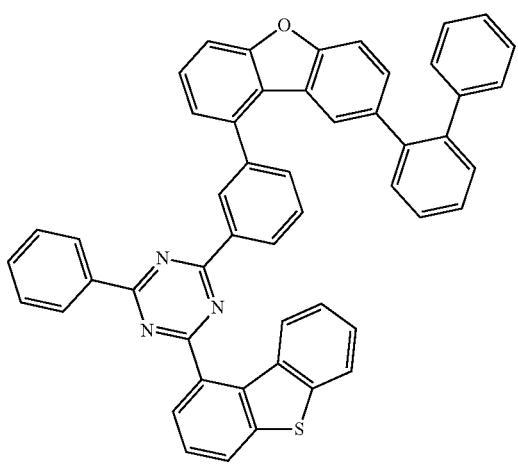
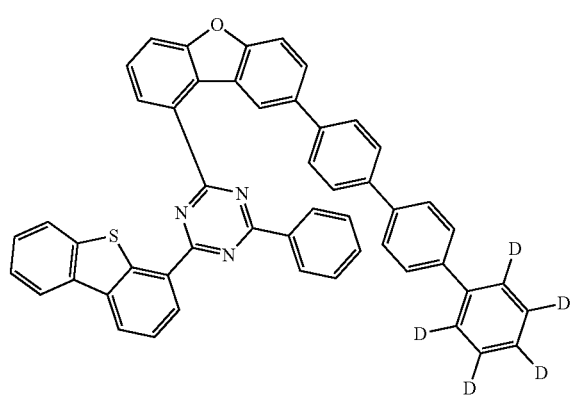
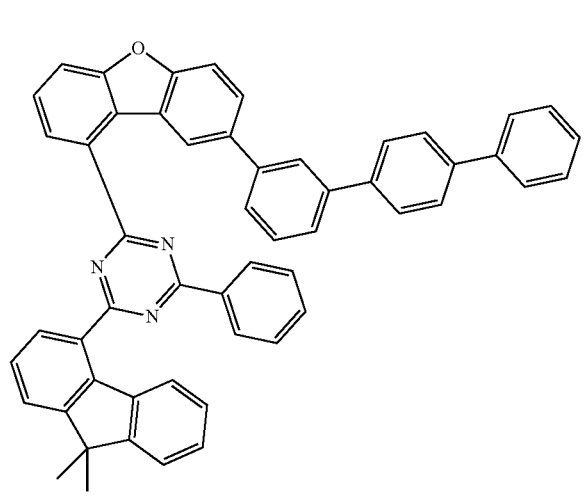
230
-continued
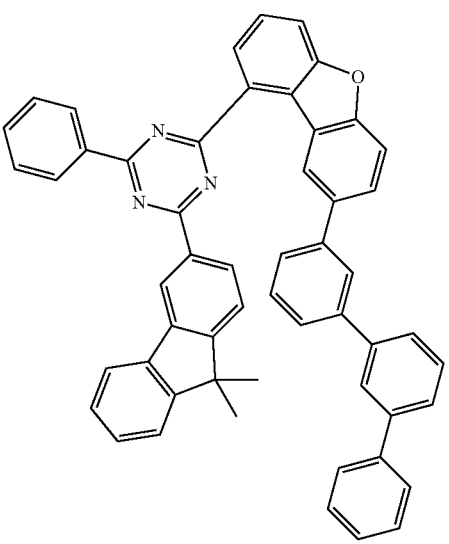
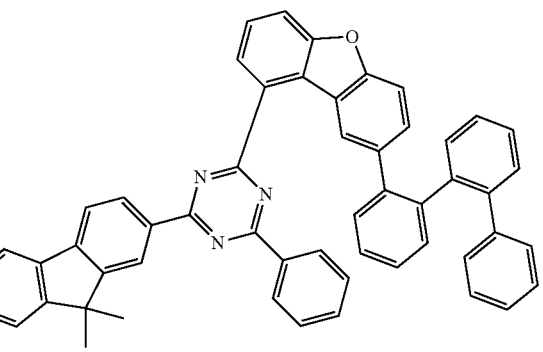
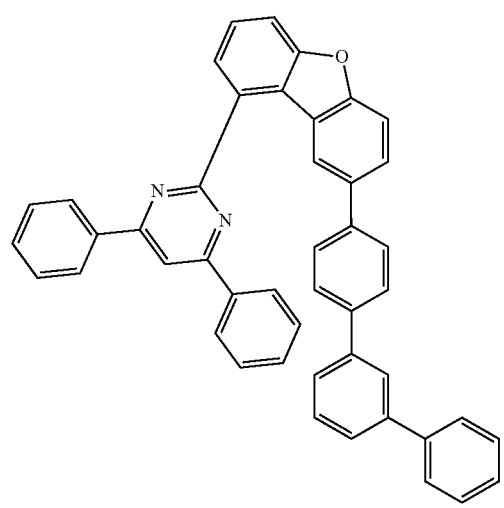

231
-continued
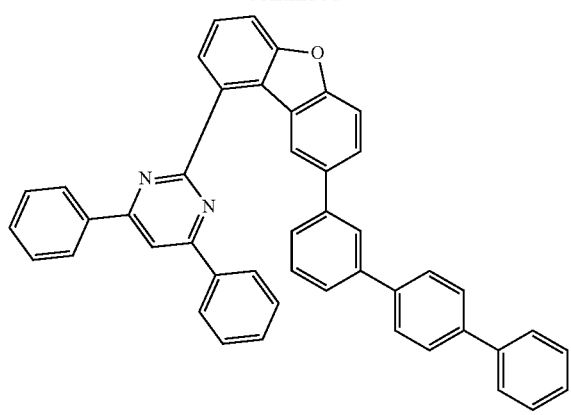
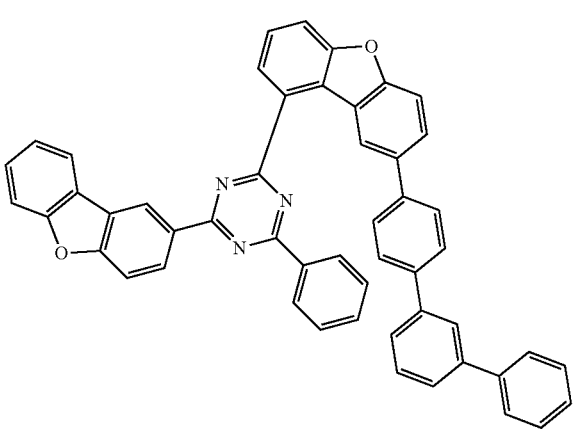
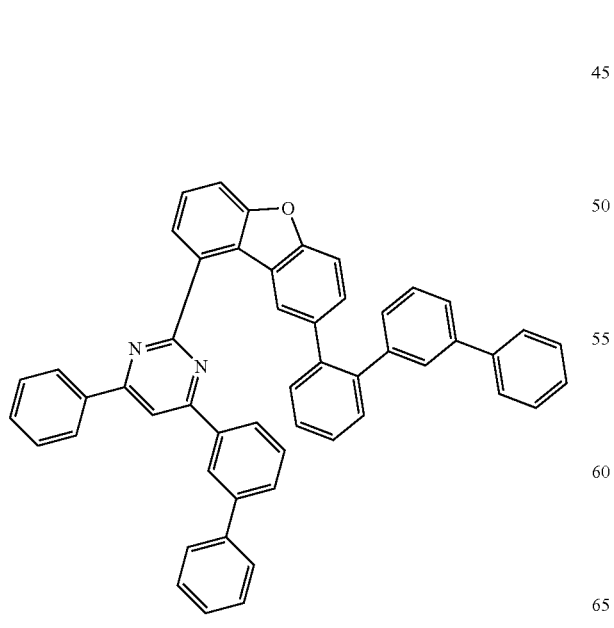
232
-continued
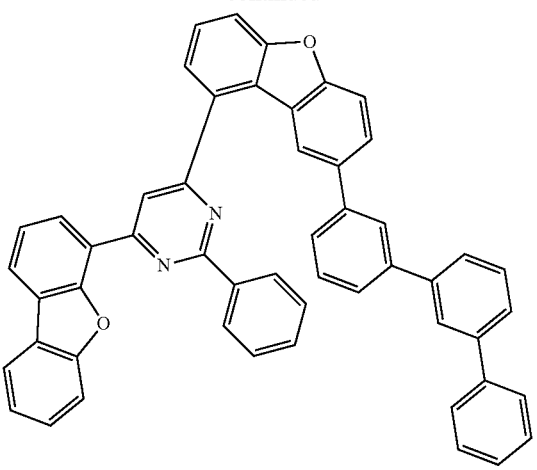
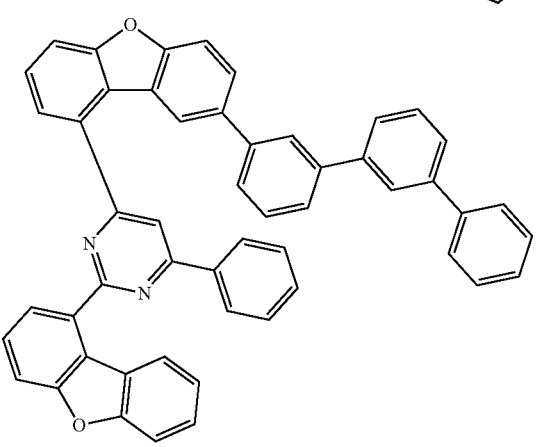
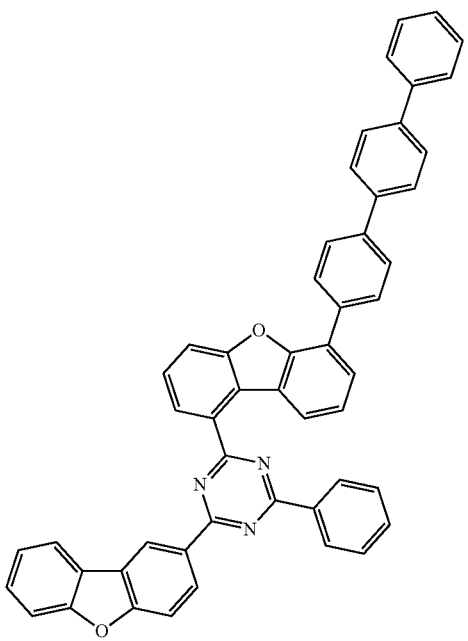

233
-continued
234
-continued
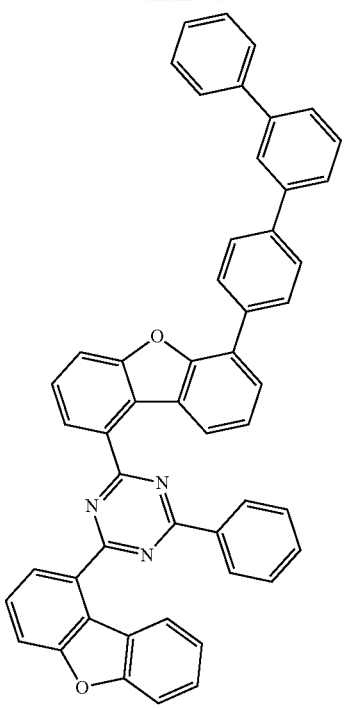
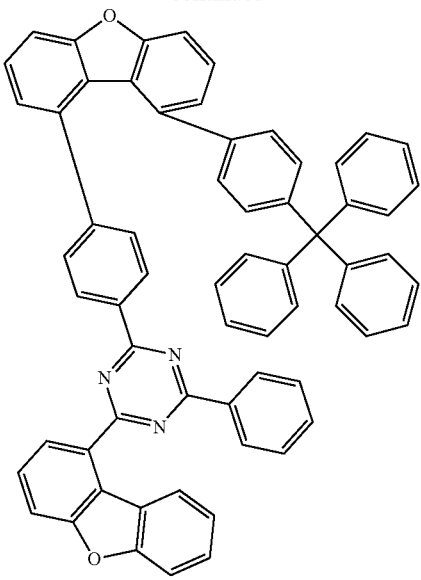
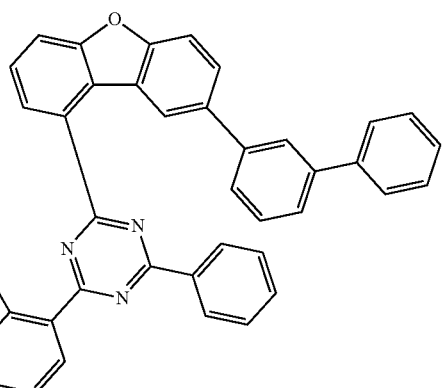
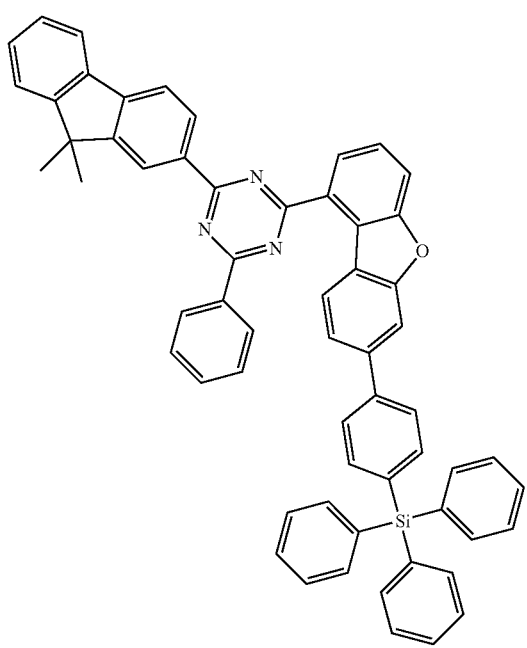
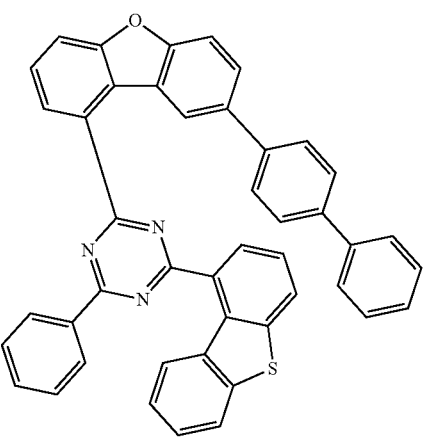

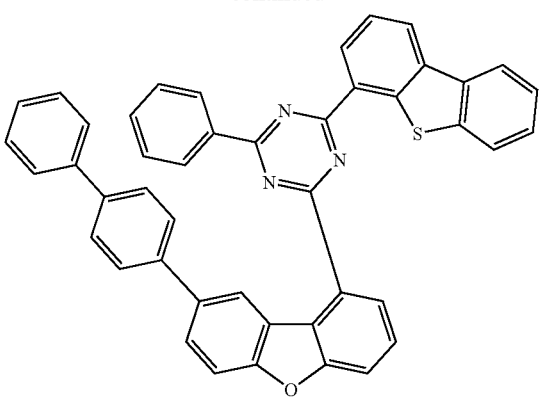
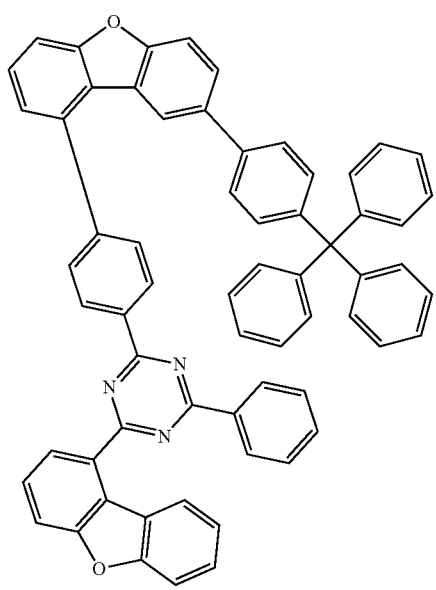
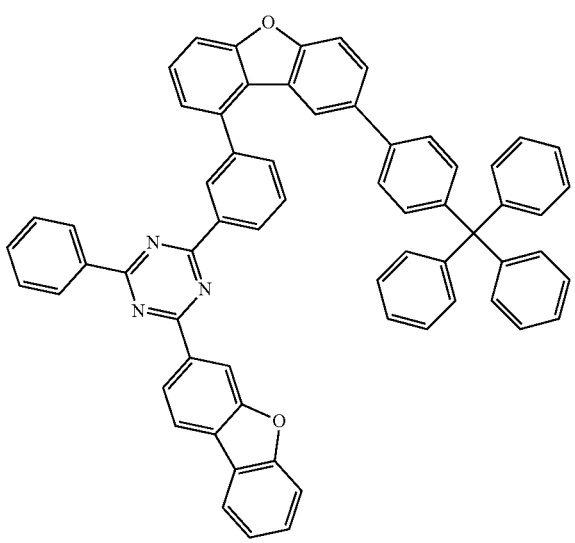
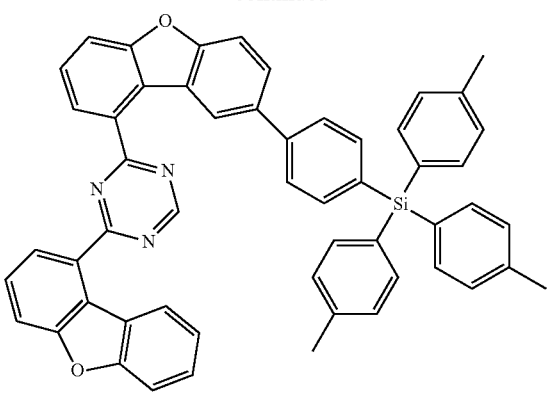
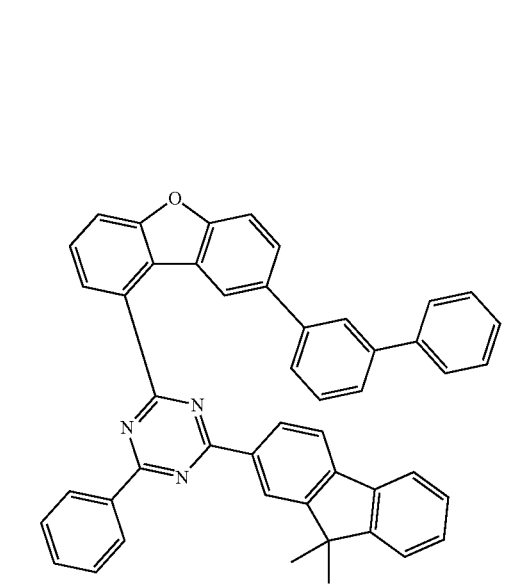
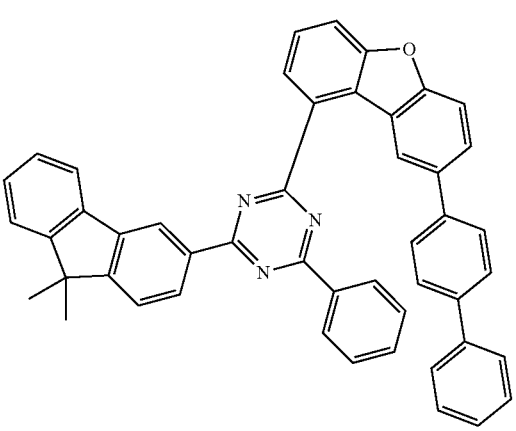

237
-continued
238
-continued
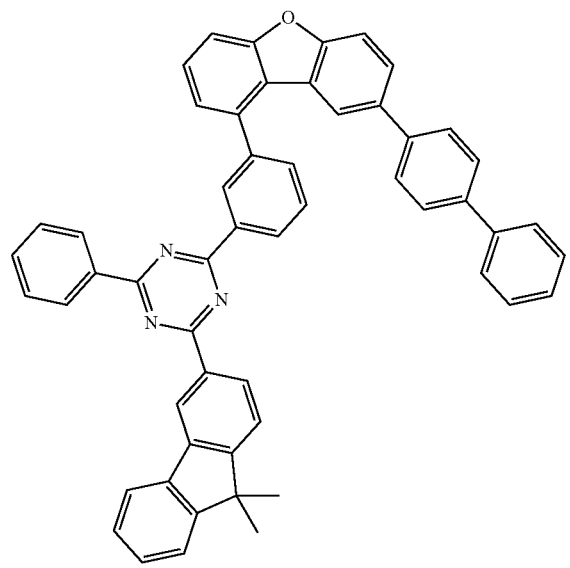
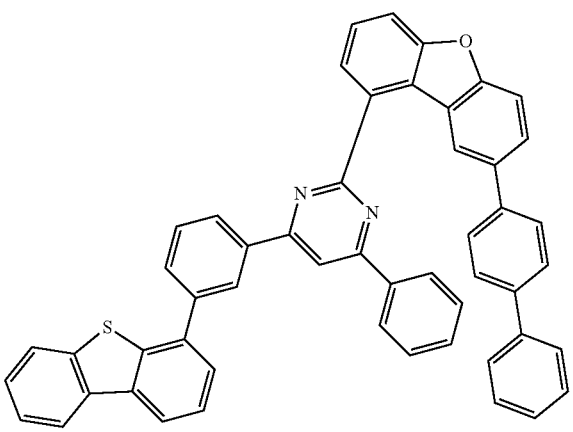
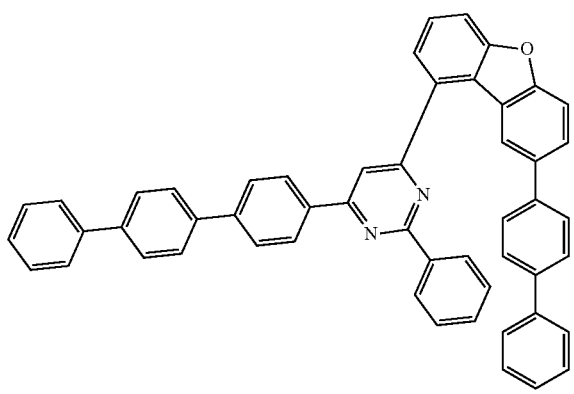
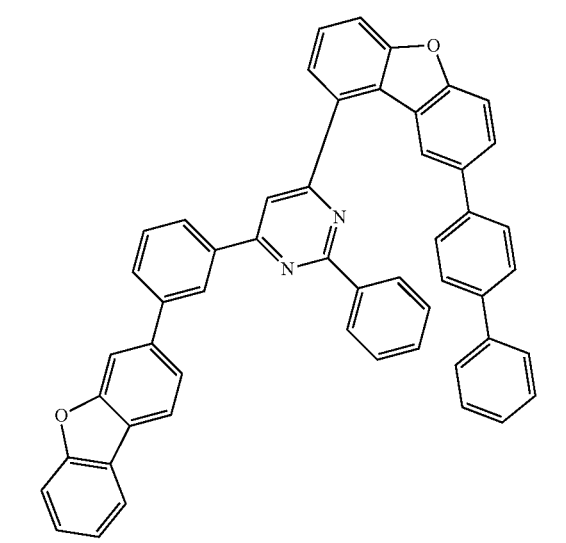
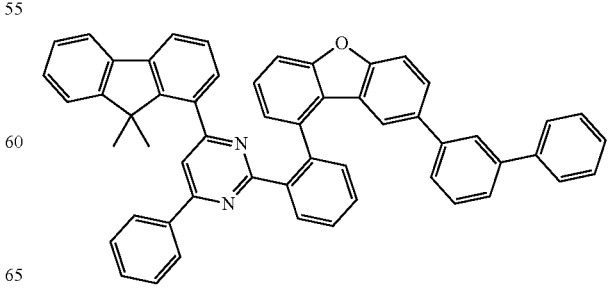

-continued
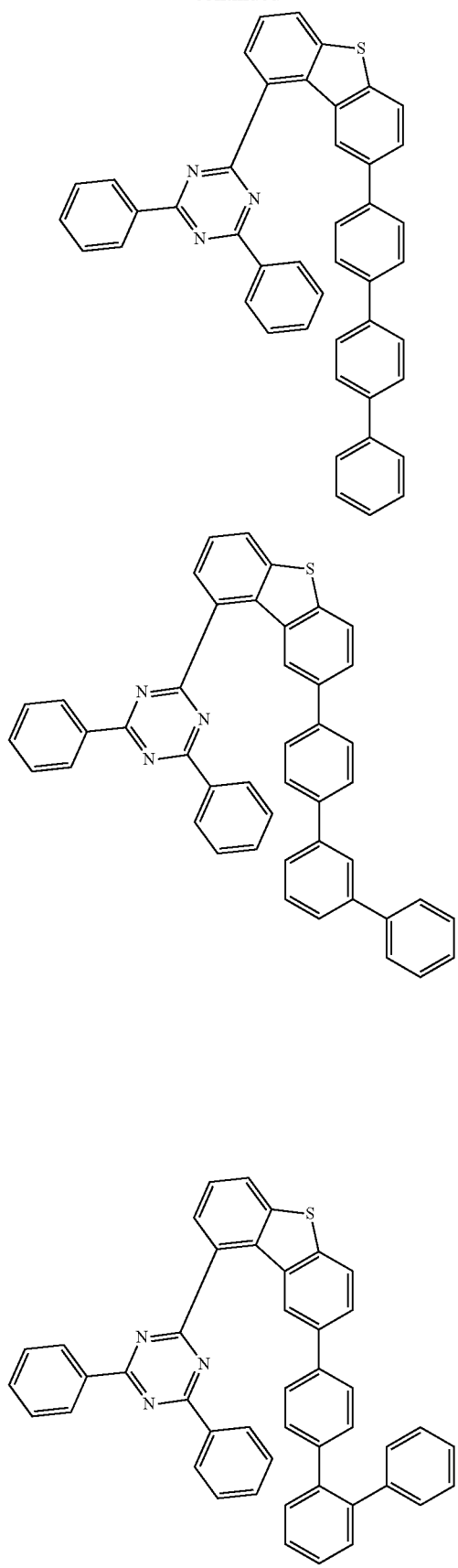
-continued
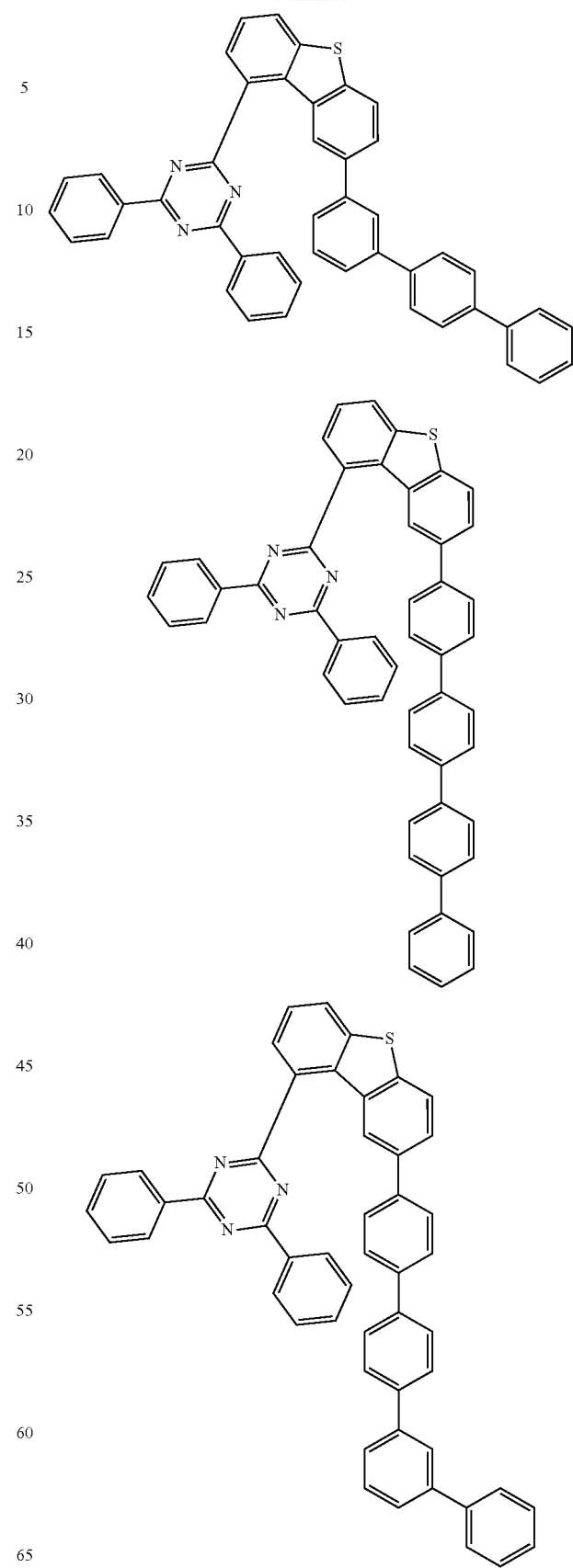

241
-continued
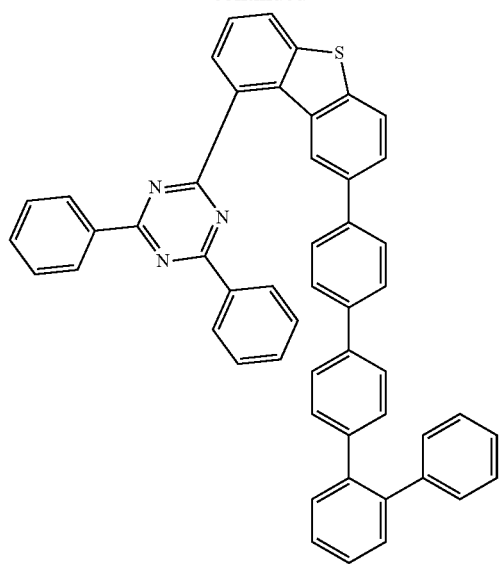
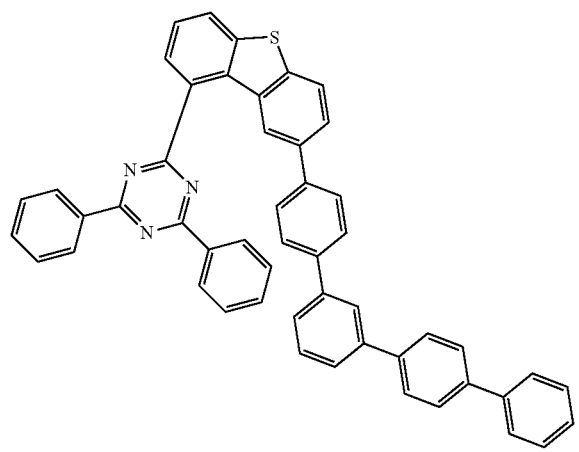
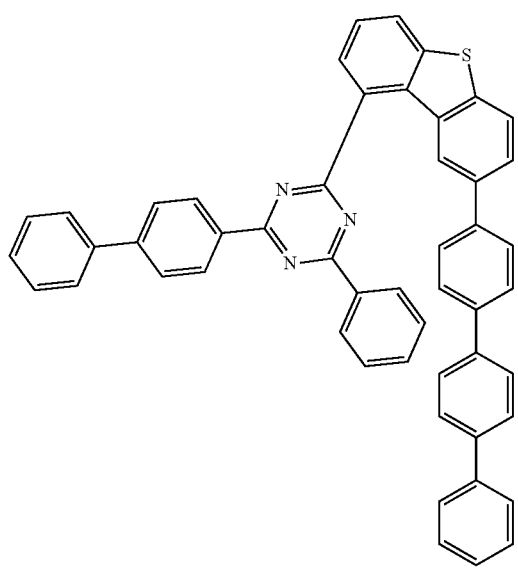
242
-continued
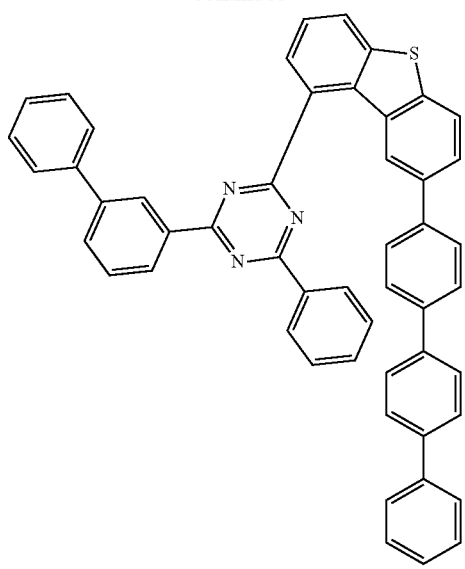
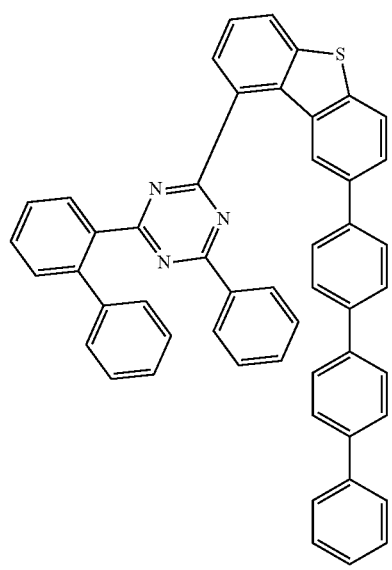
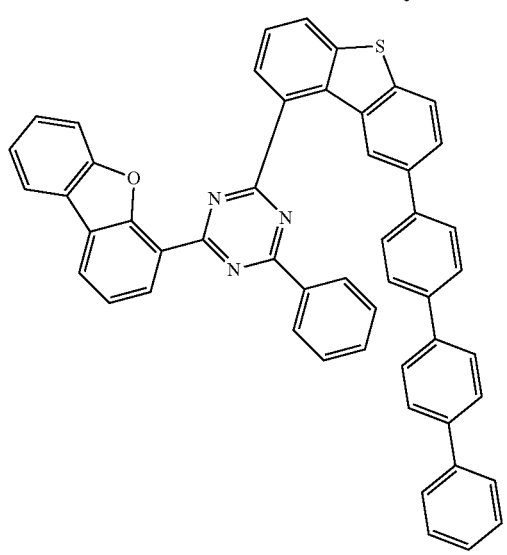

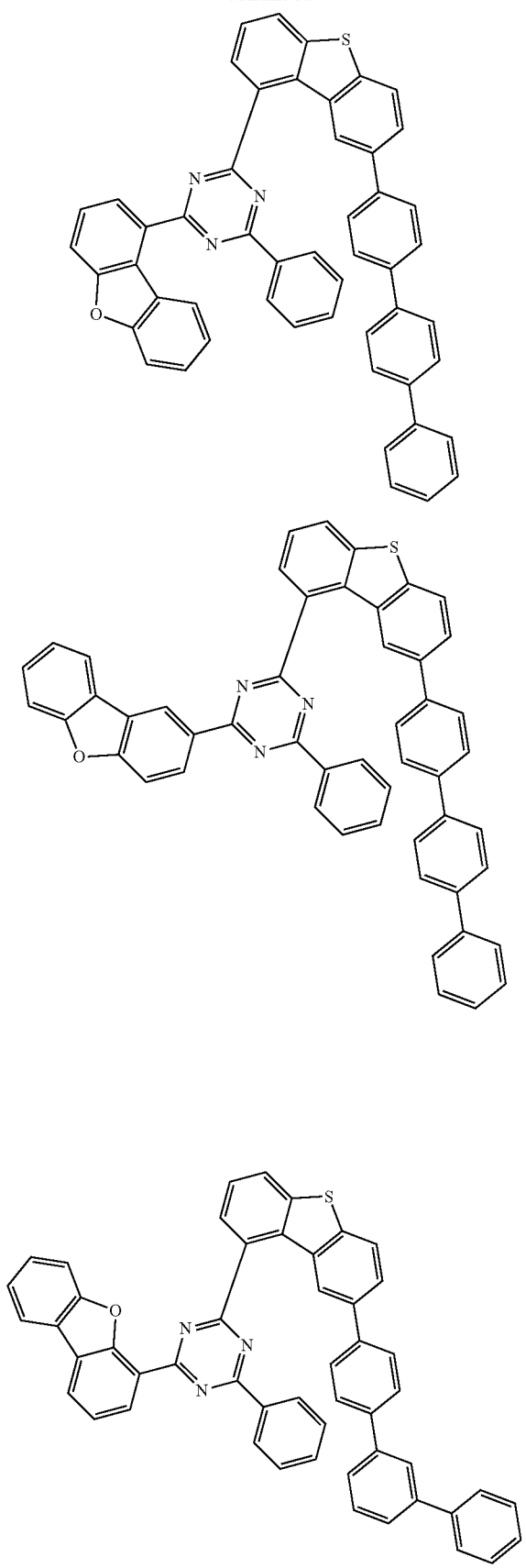
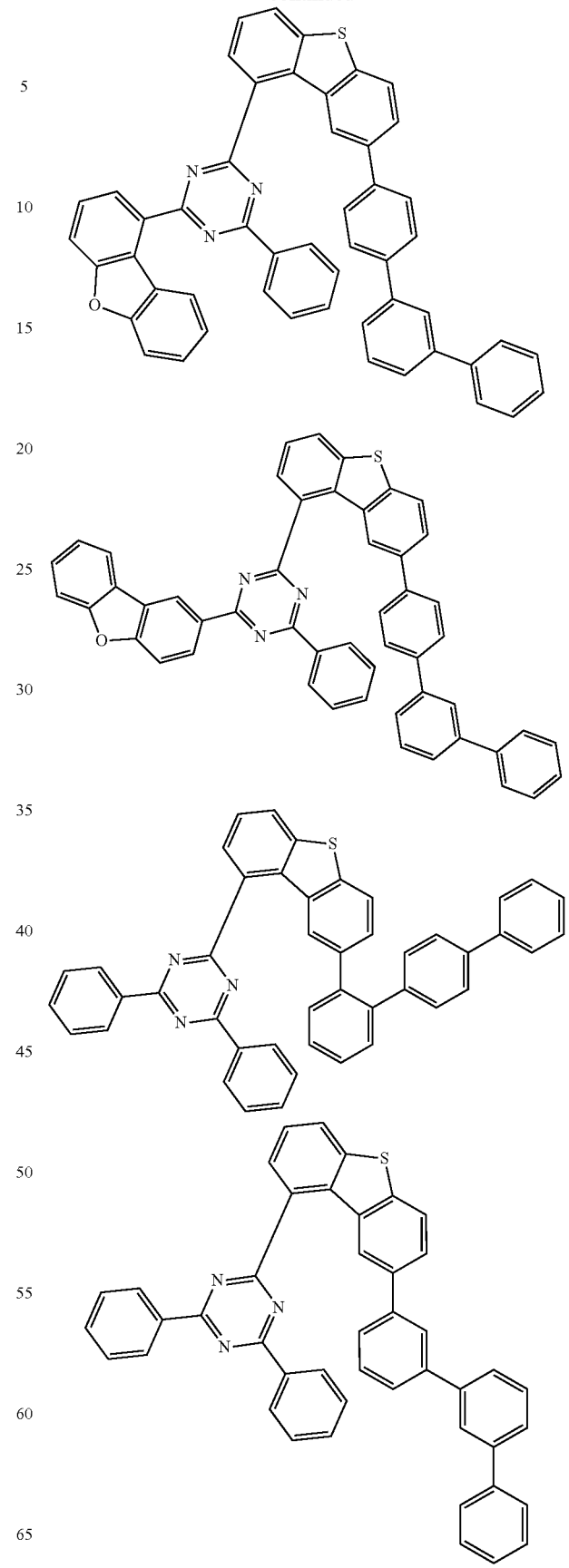

245
-continued
246
-continued
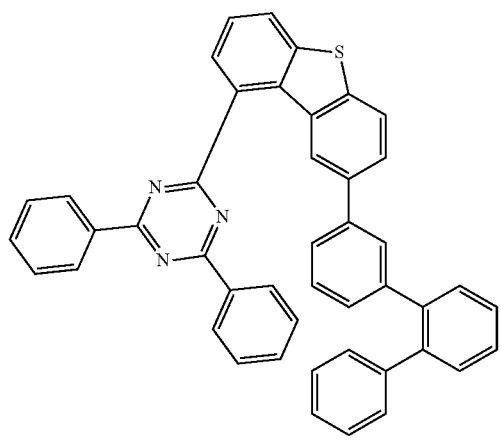
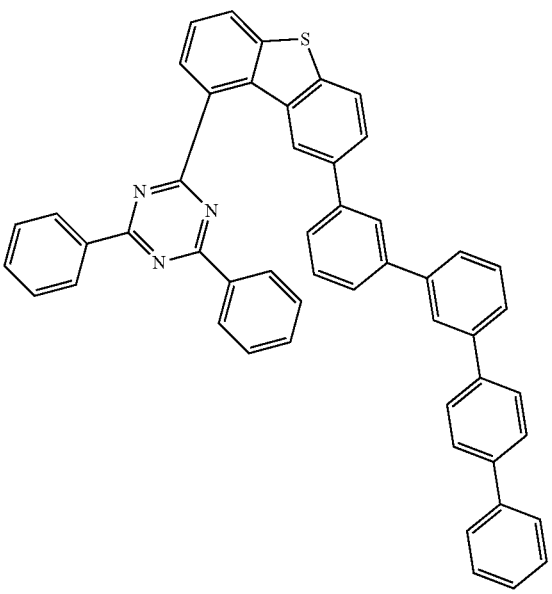
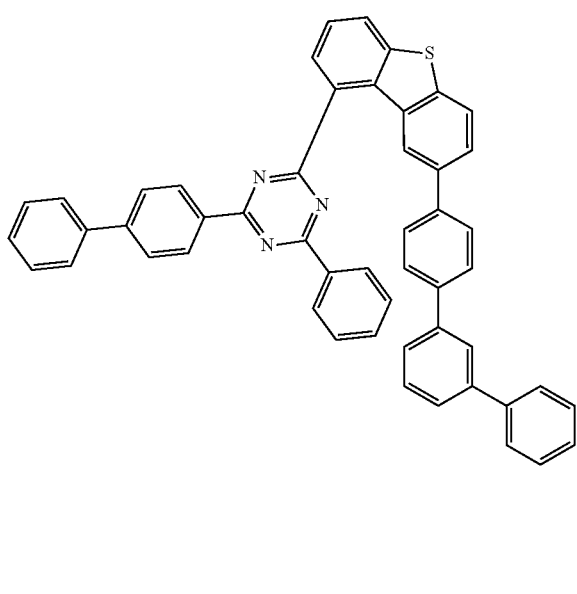
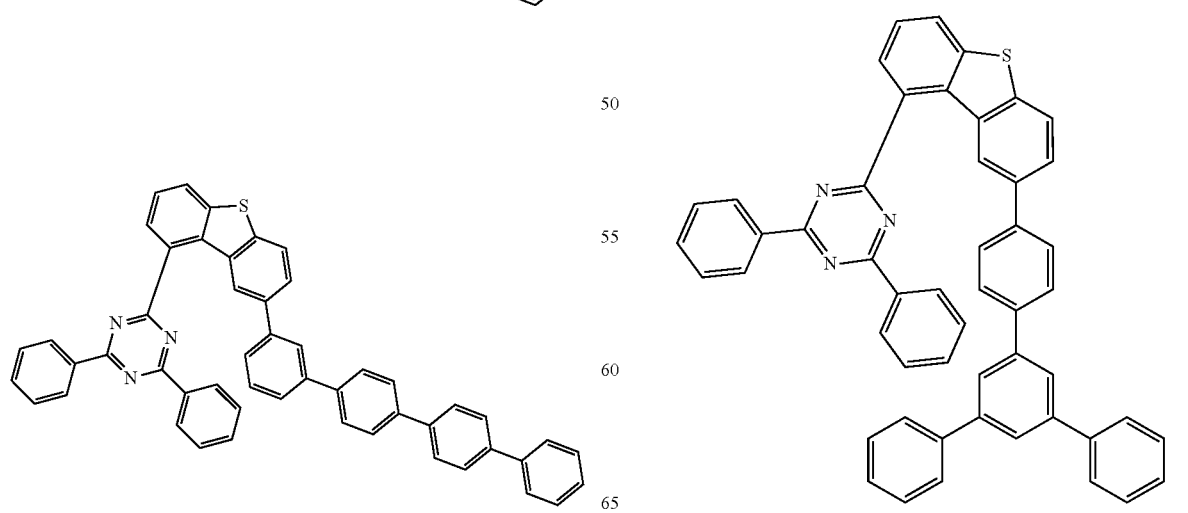

247
-continued
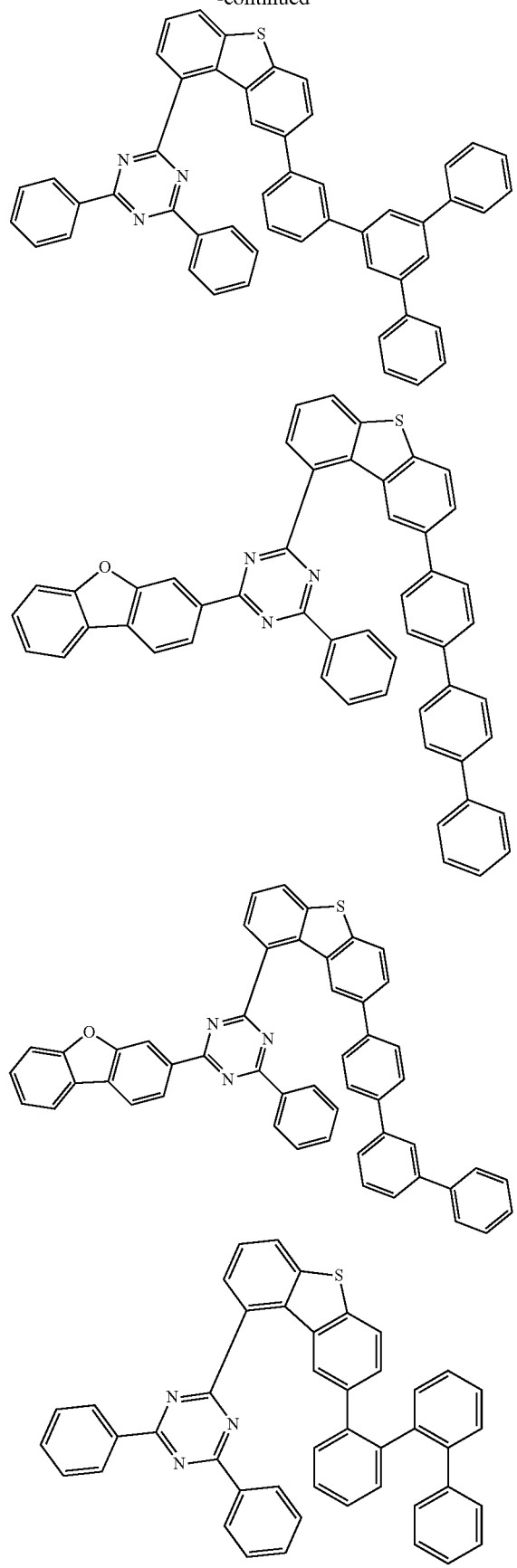
248
-continued
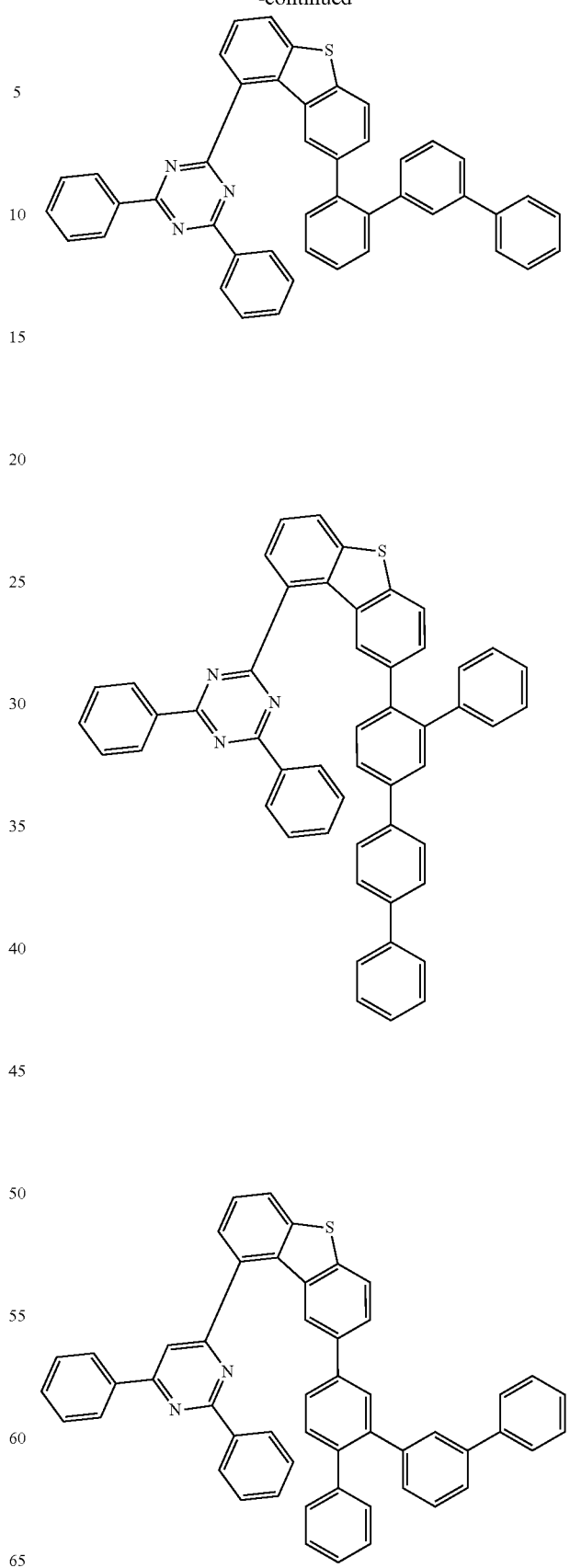

249
-continued
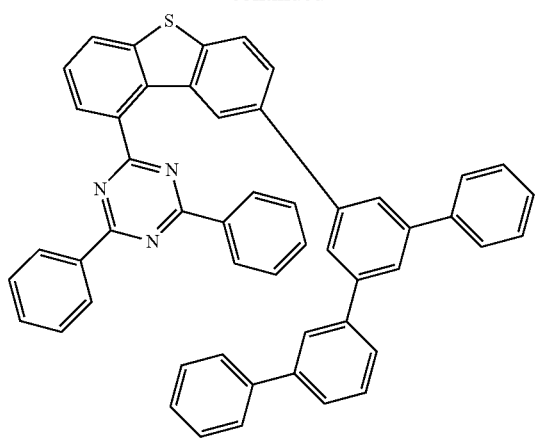
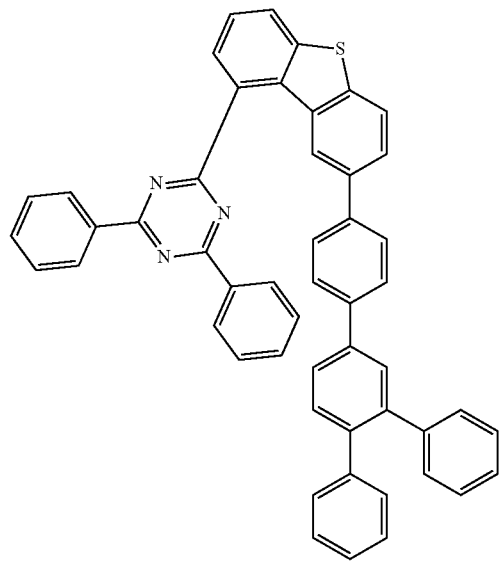
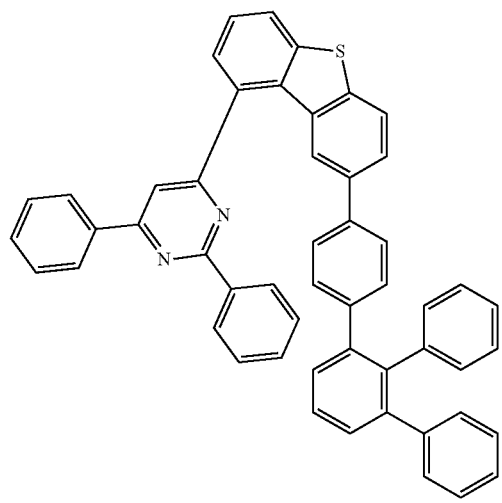
250
-continued
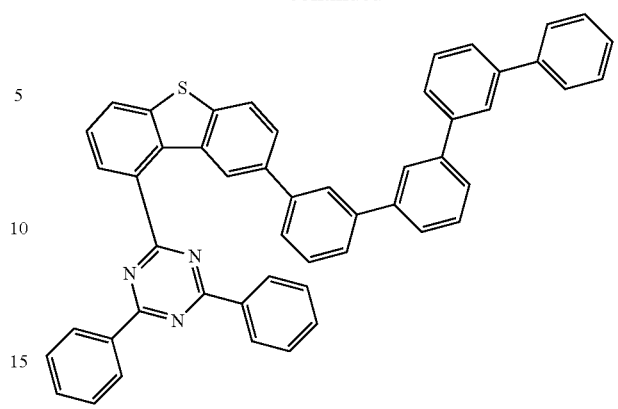
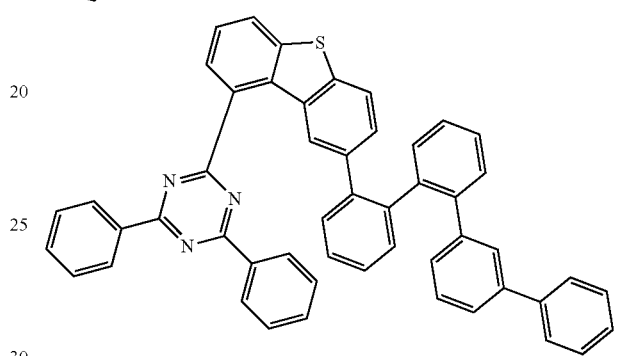
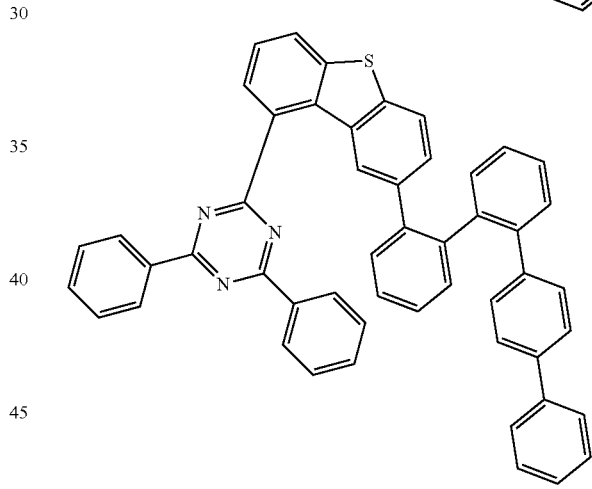
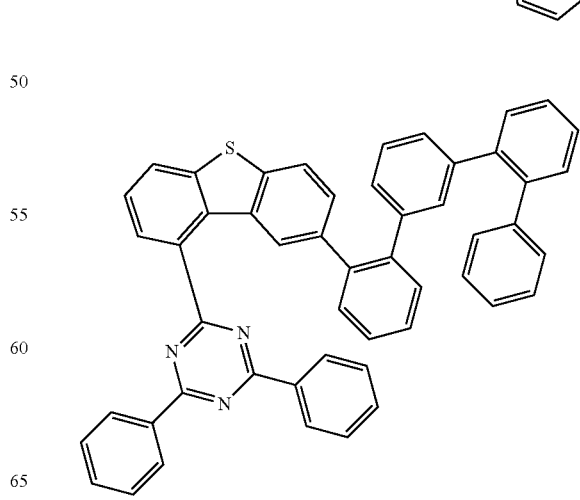

251
-continued
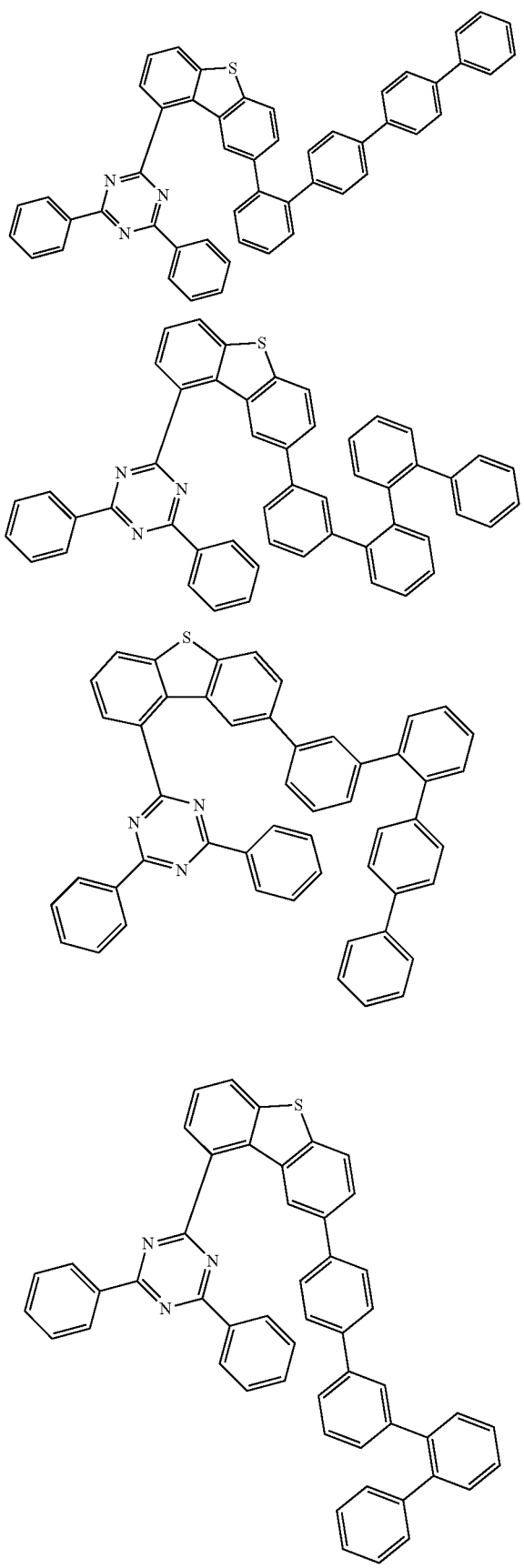
252
-continued
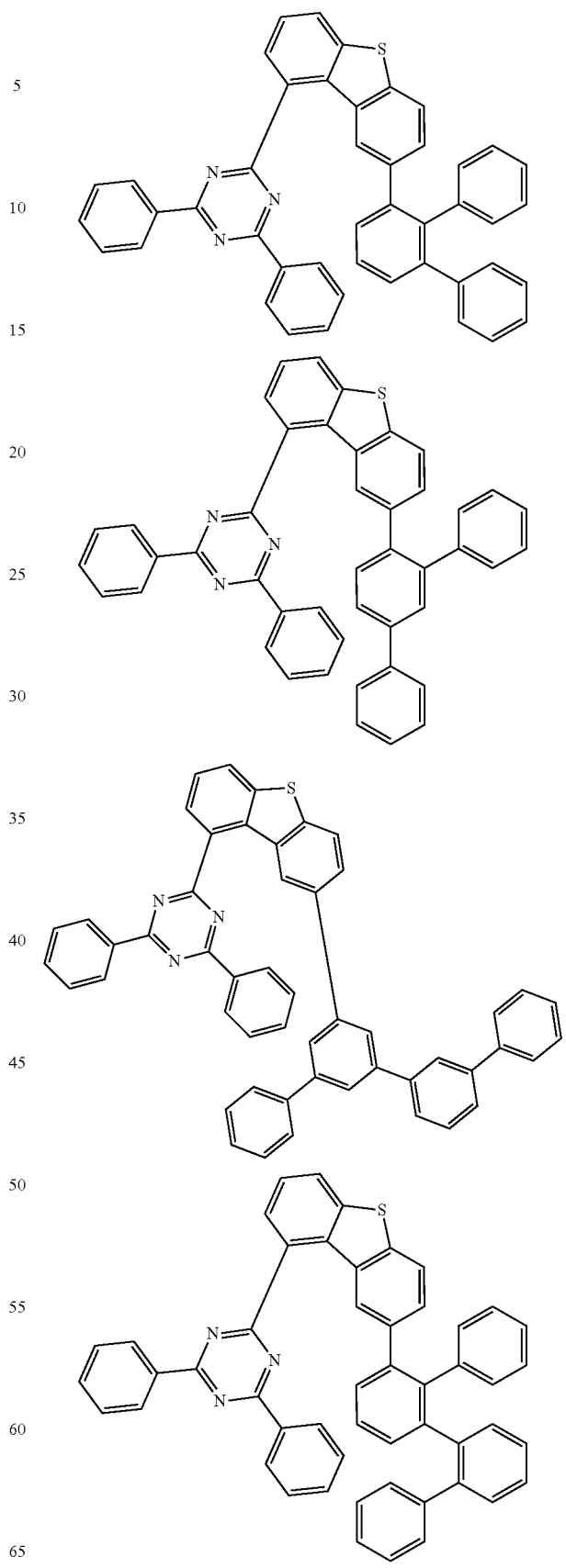

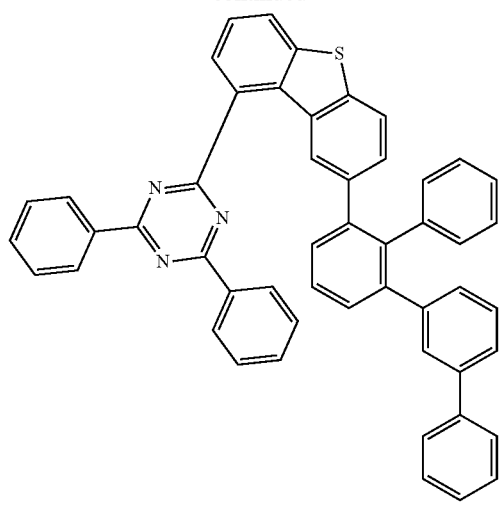
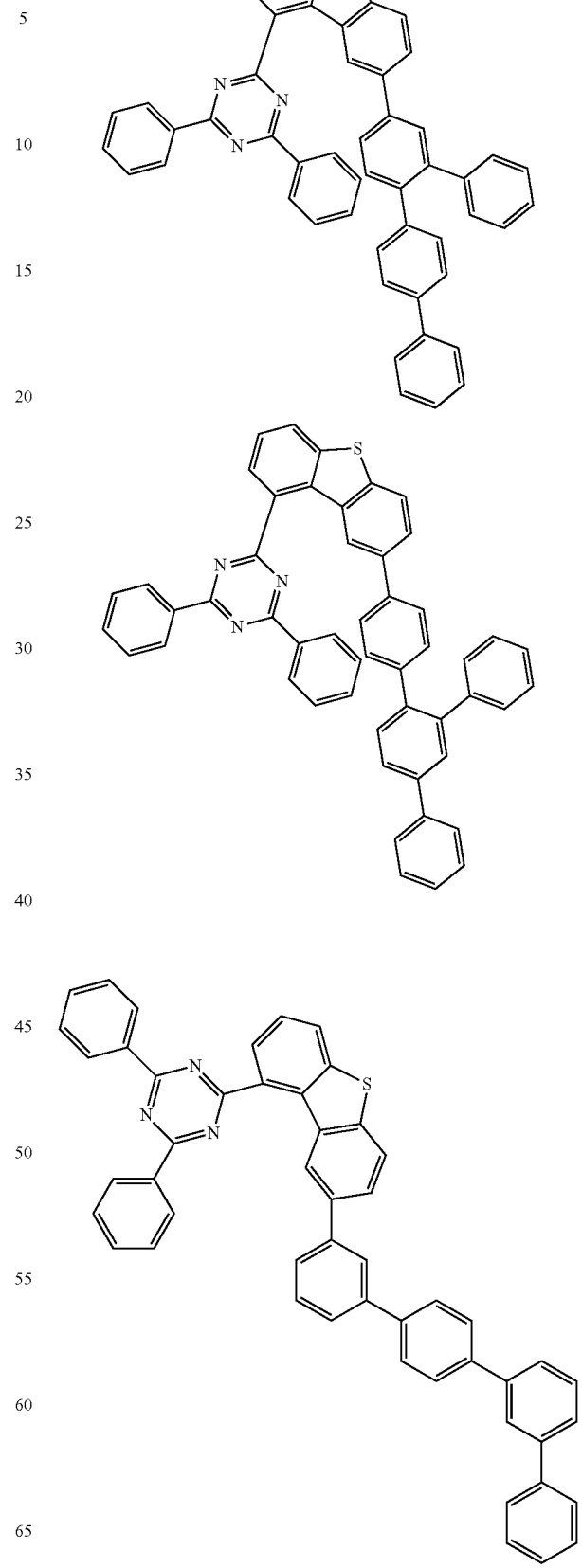

255
-continued
256
-continued
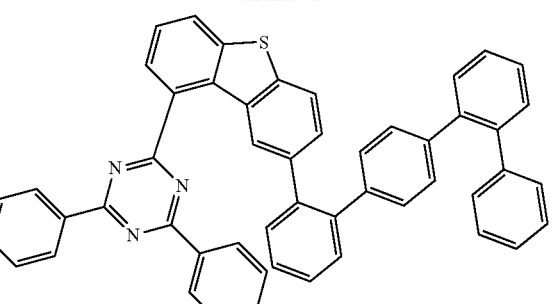
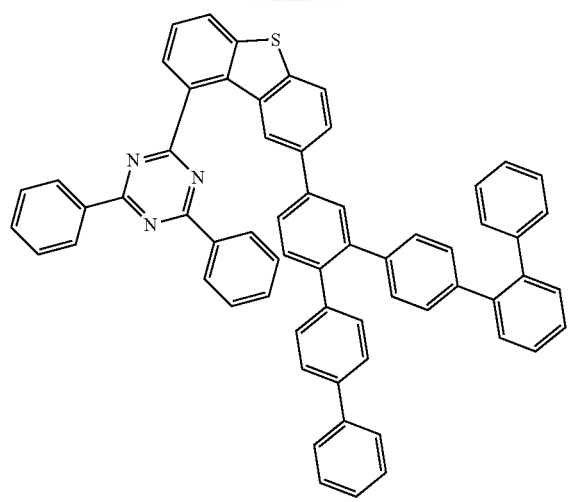
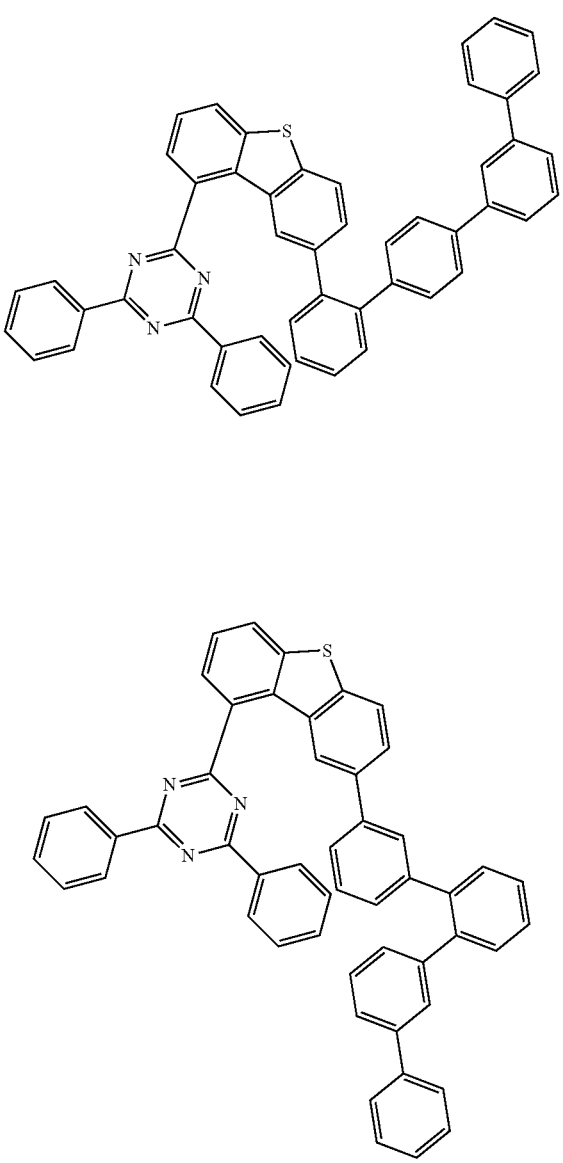
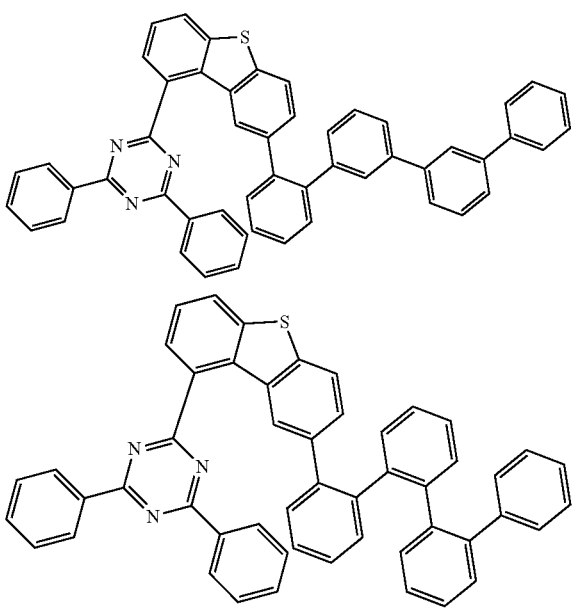
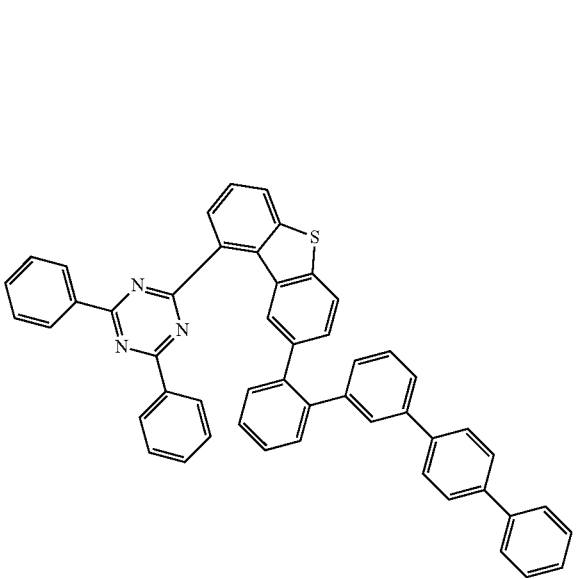

257
-continued
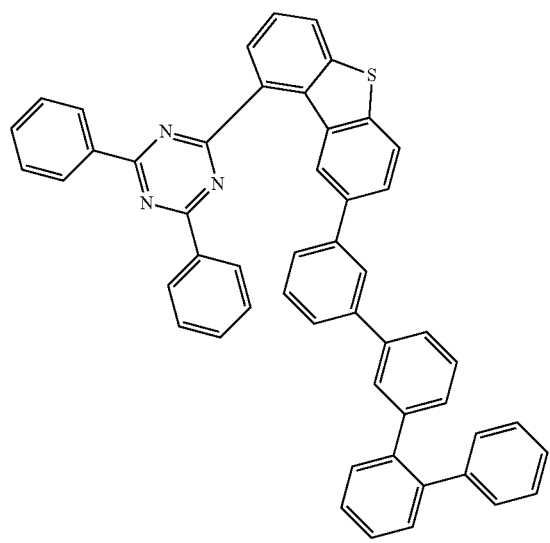
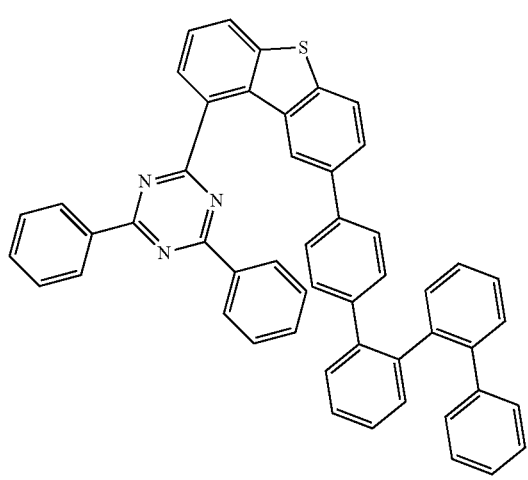
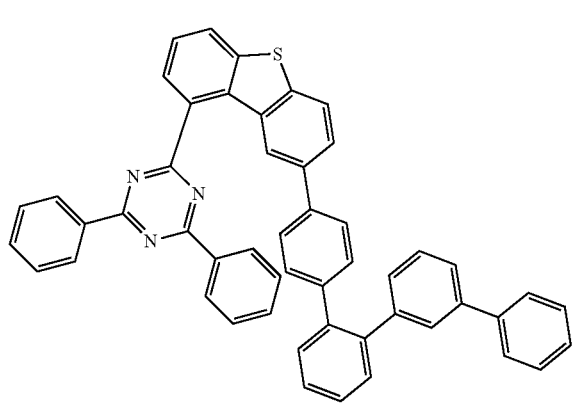
258
-continued
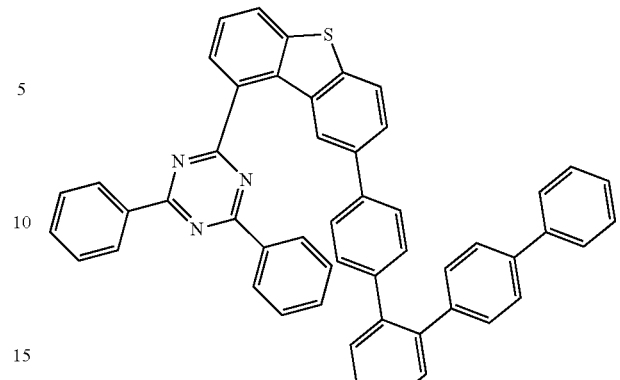
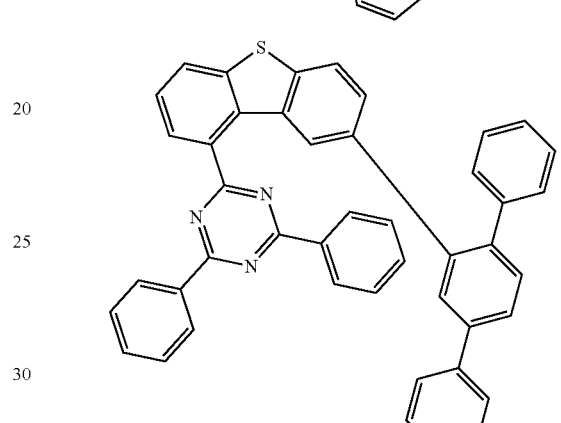
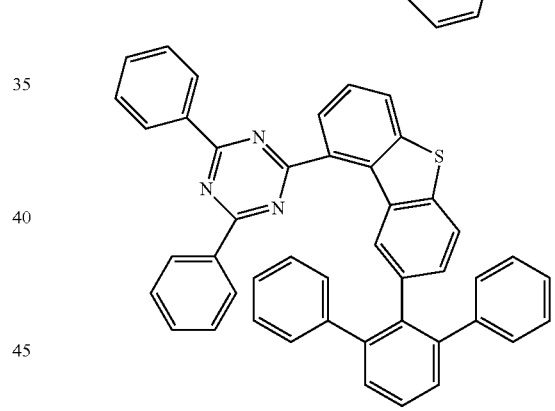
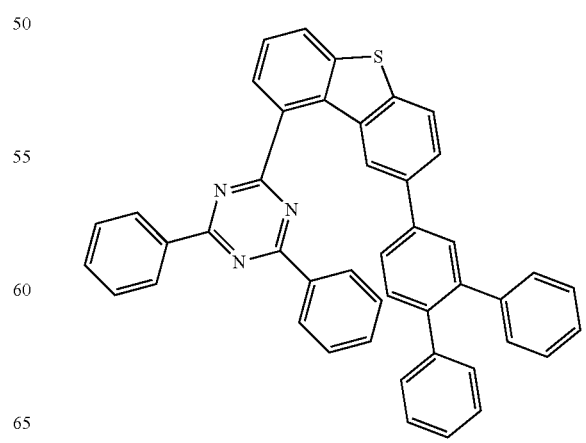

259
-continued
260
-continued
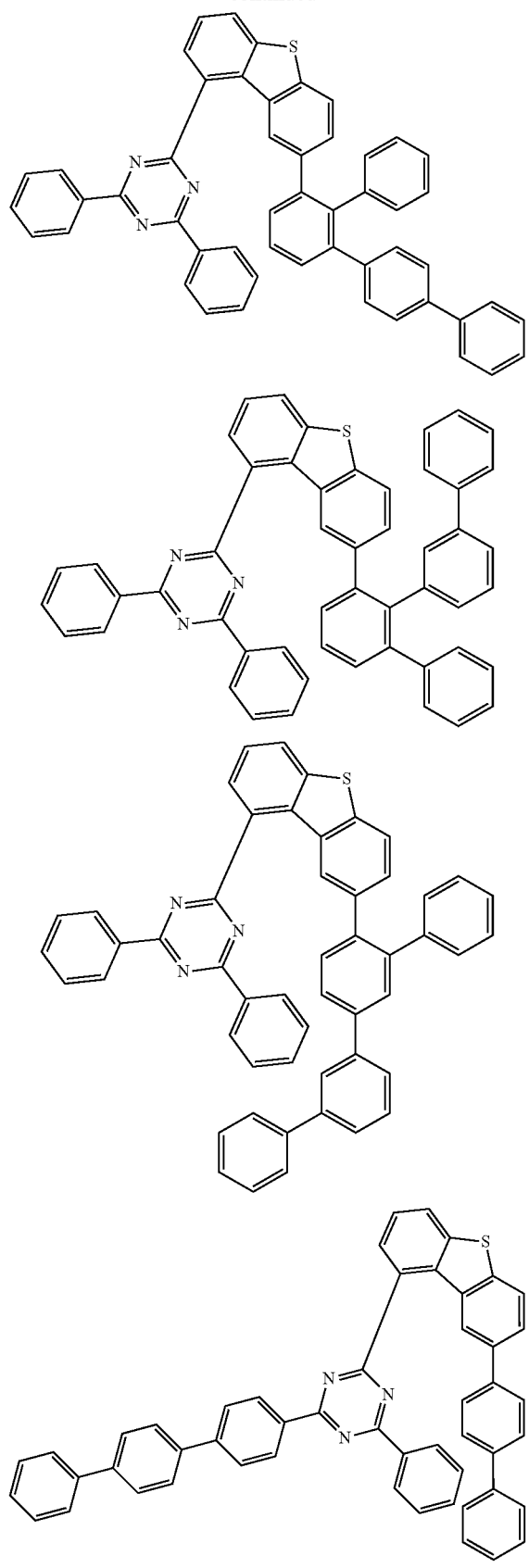
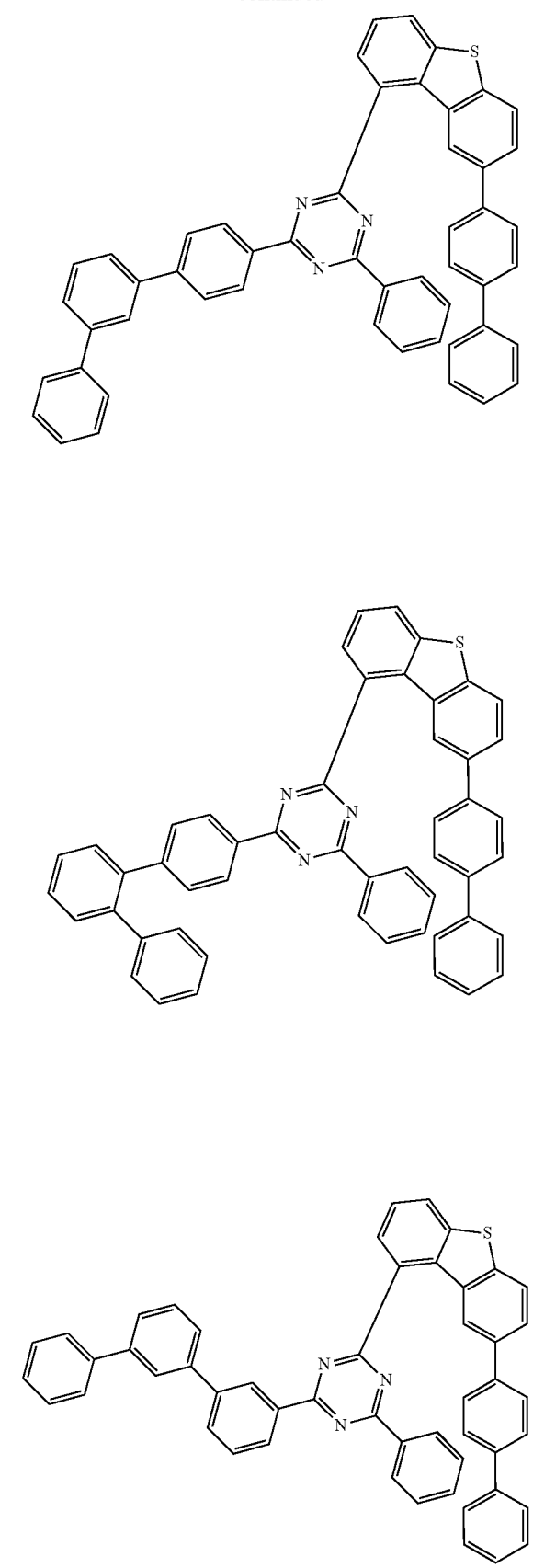

261
-continued
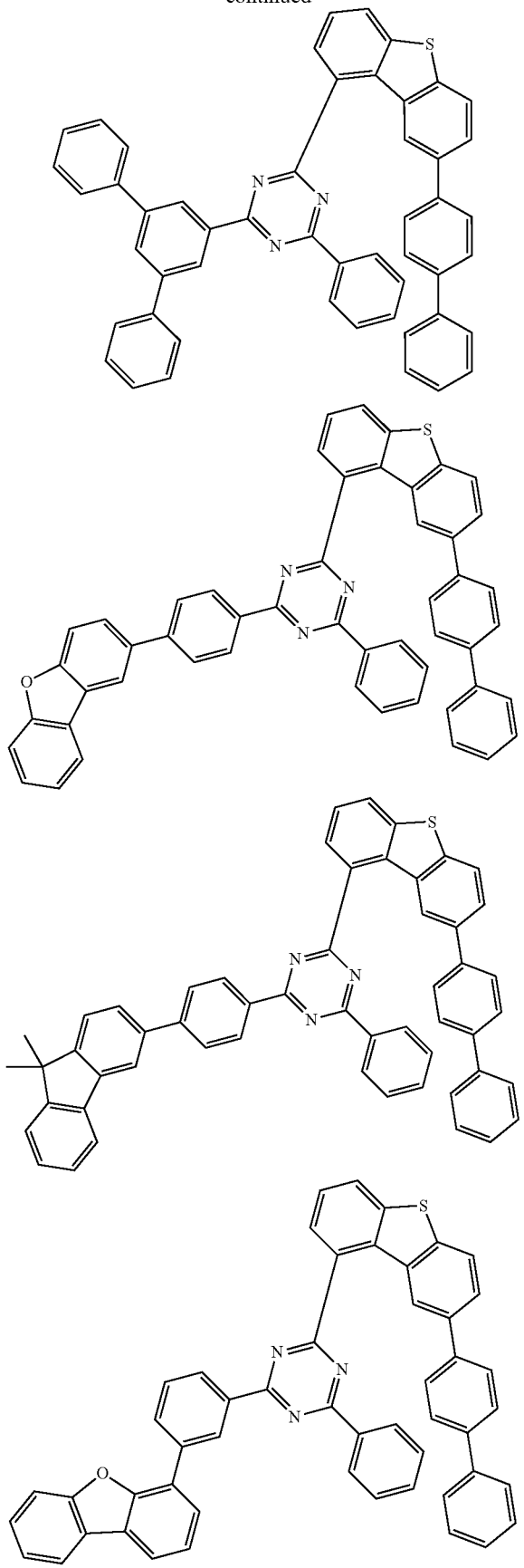
262
-continued
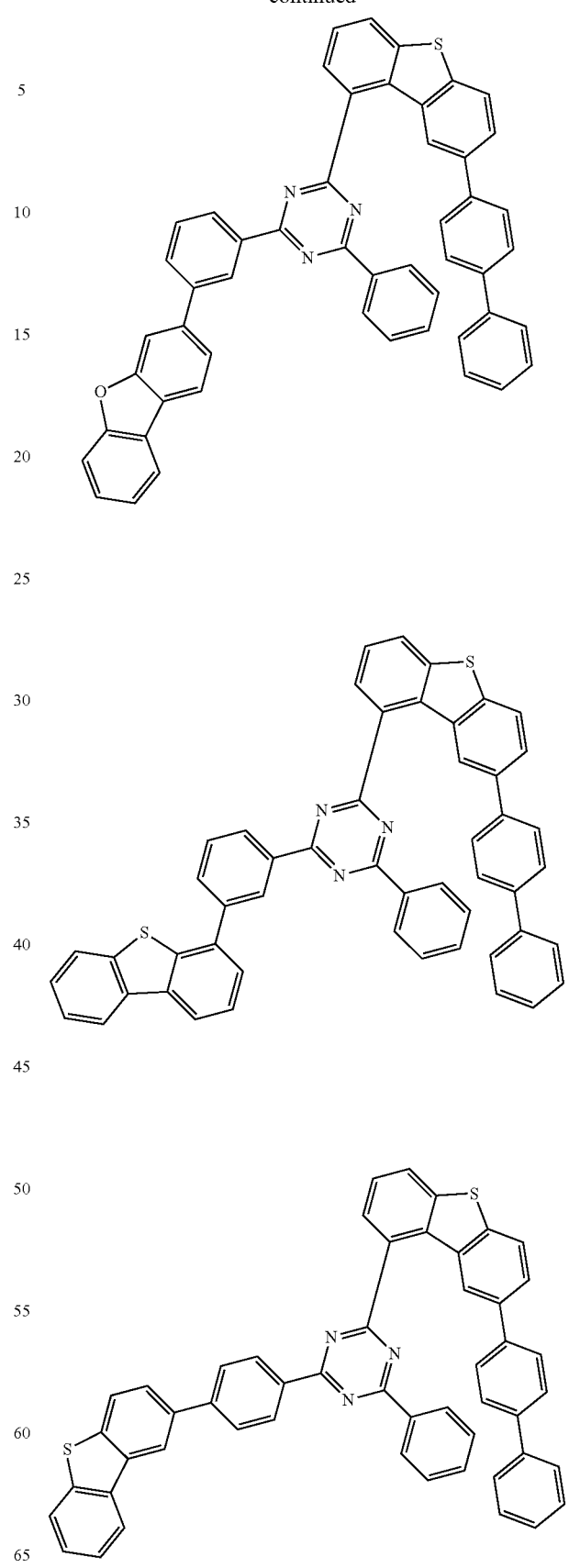

263
-continued
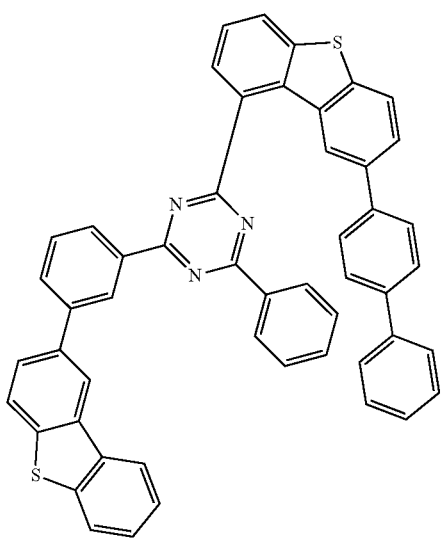
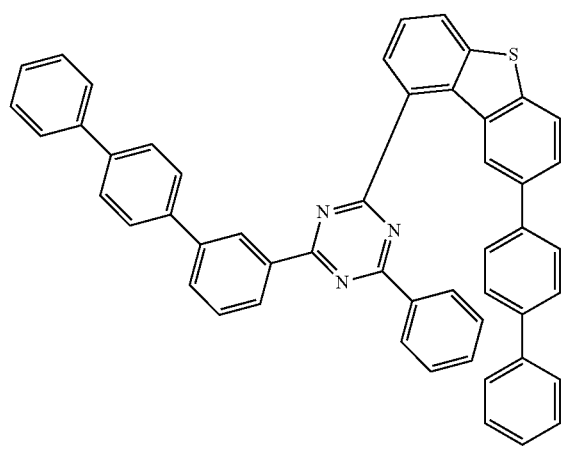
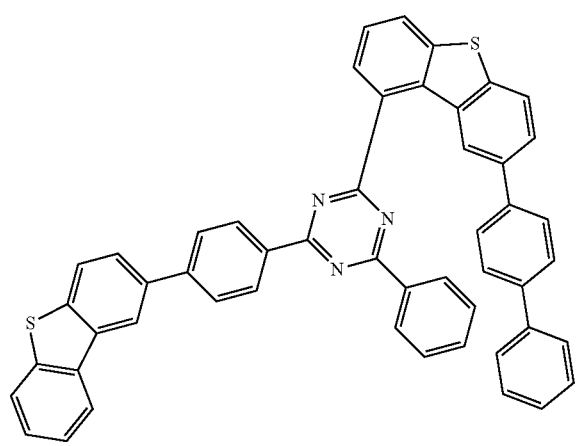
264
-continued
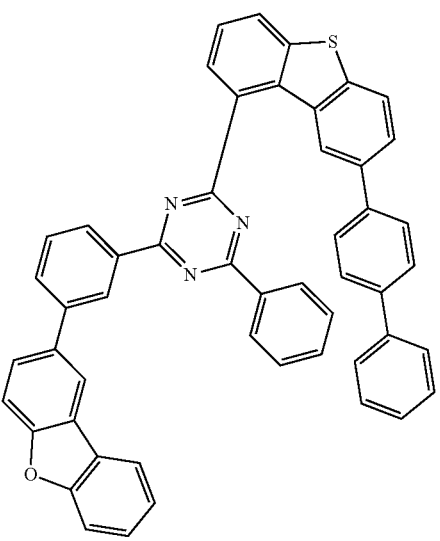
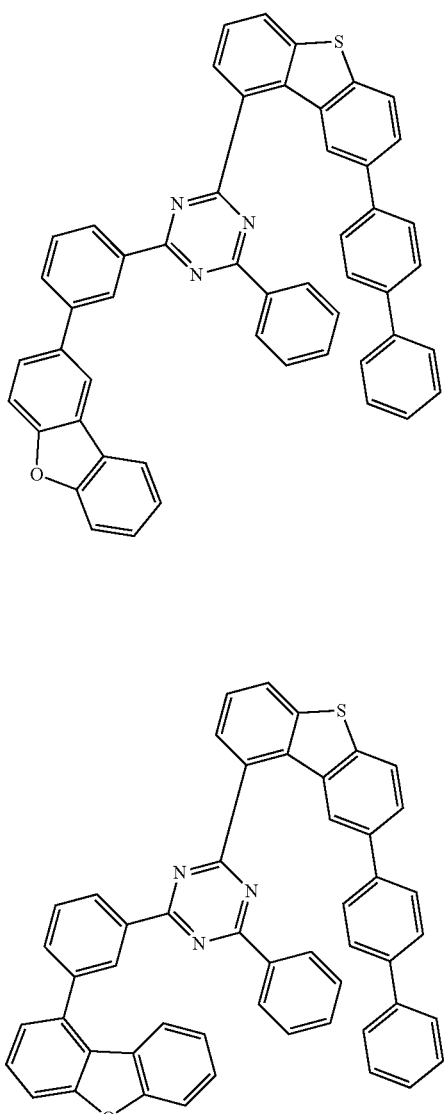
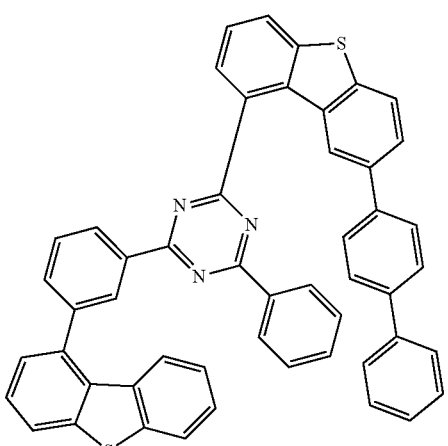

265
-continued
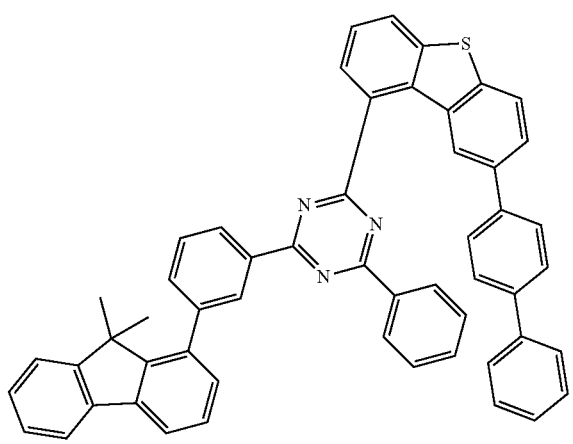 [SMILES: CC1(C)c2ccccc2-c2cccc(-c3cccc(-c4nc(-c5ccccc5)nc(-c5cccc6sc7ccc(-c8ccc(-c9ccccc9)cc8)cc7c56)n4)c3)c21]
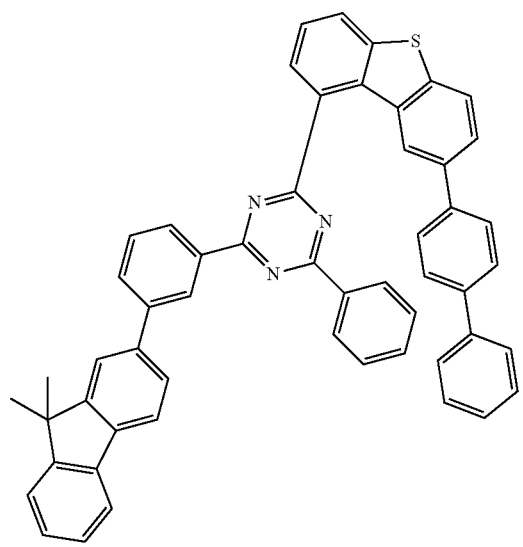
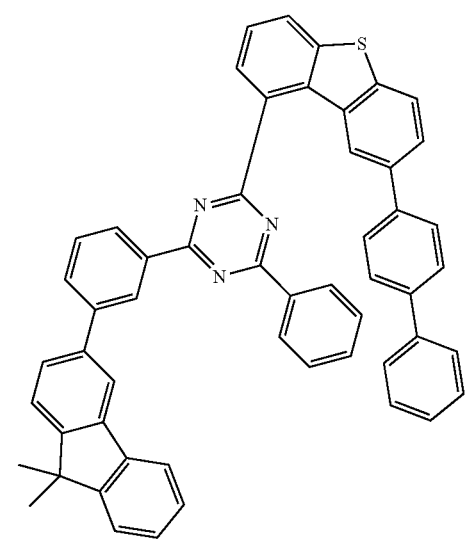
266
-continued
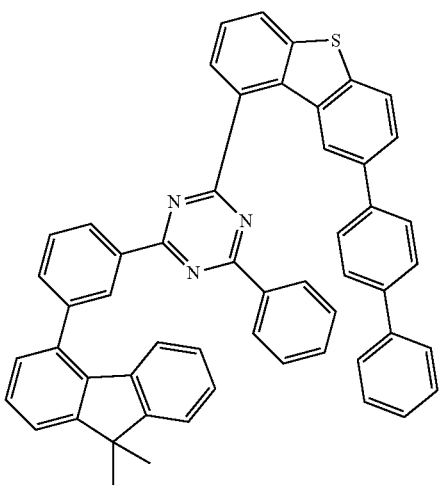
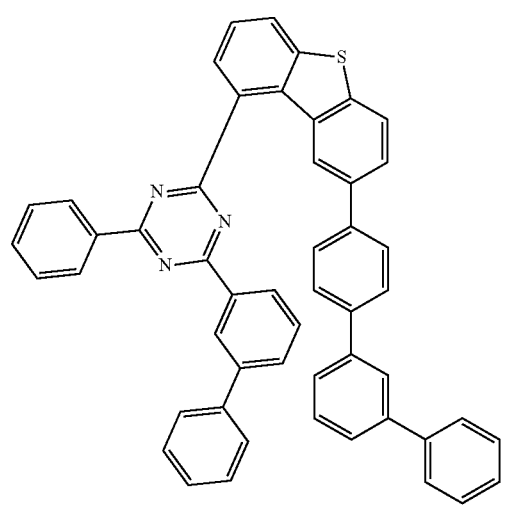
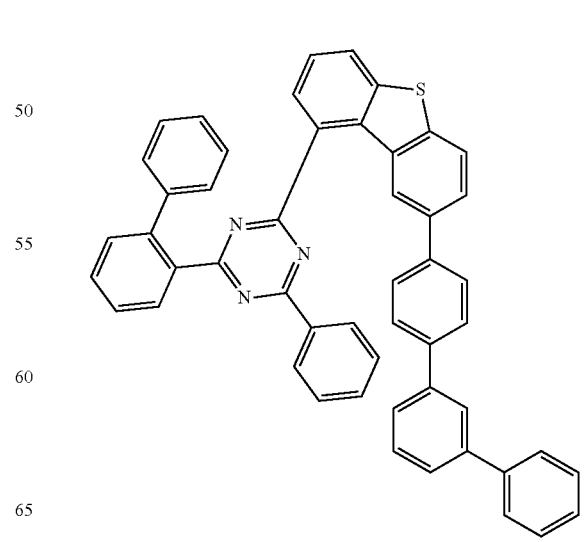

267
-continued
268
-continued
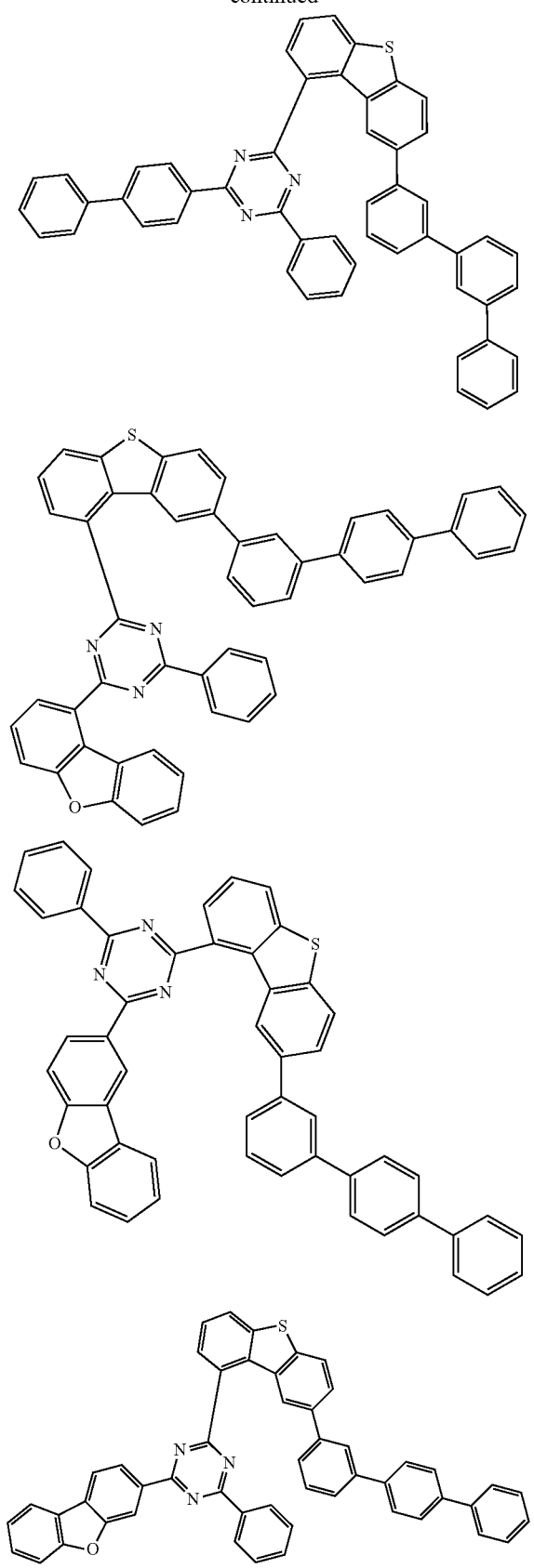
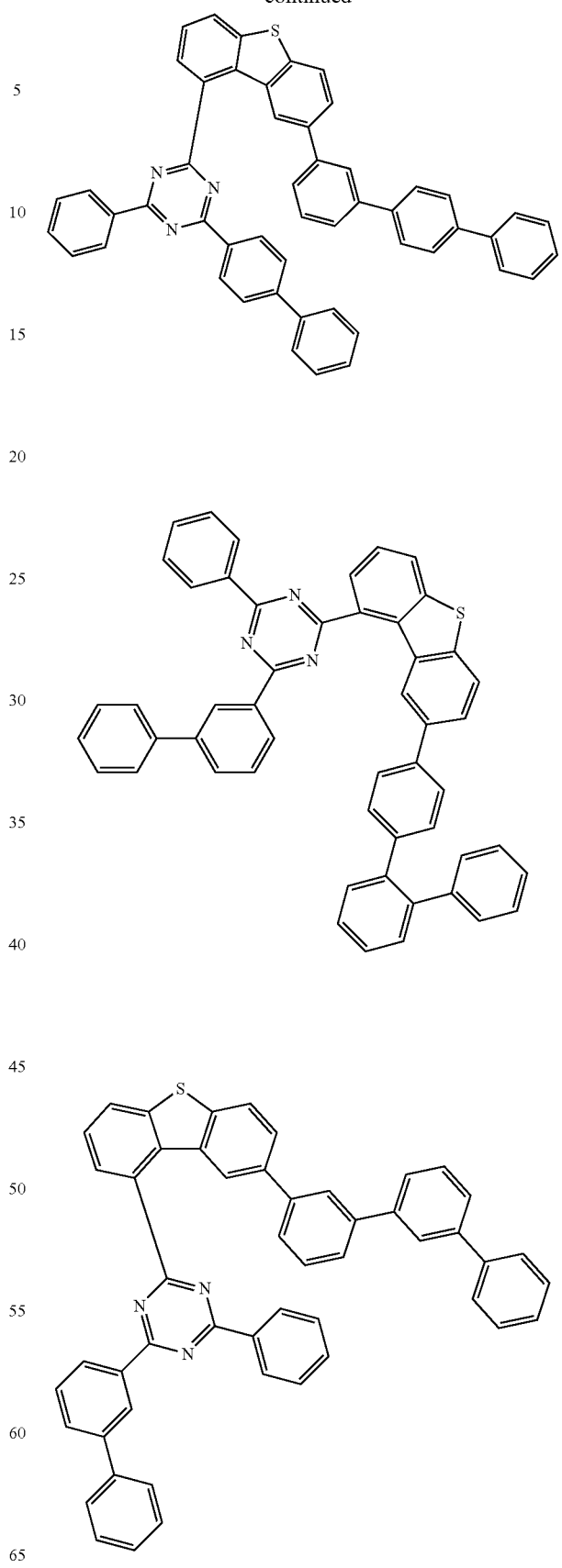

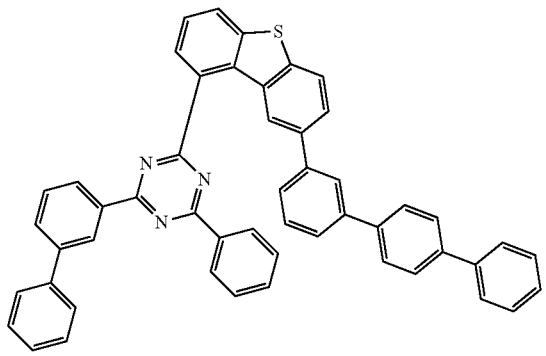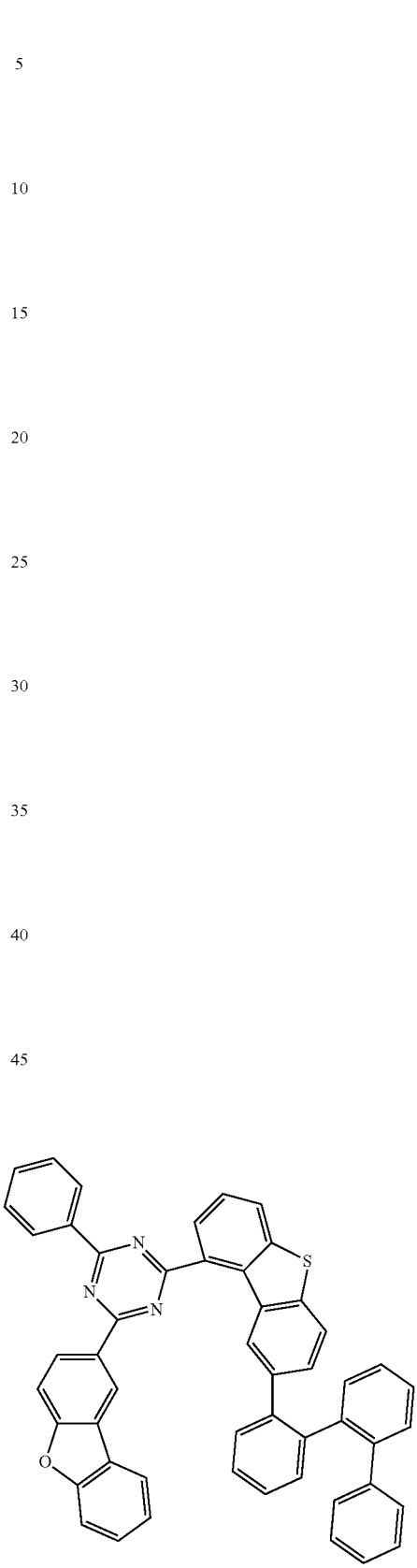

-continued
271 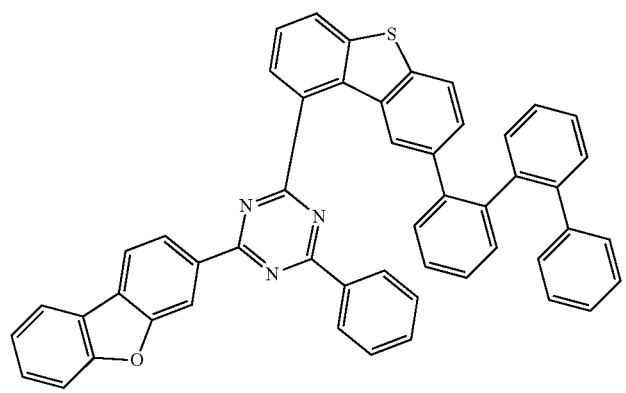
272 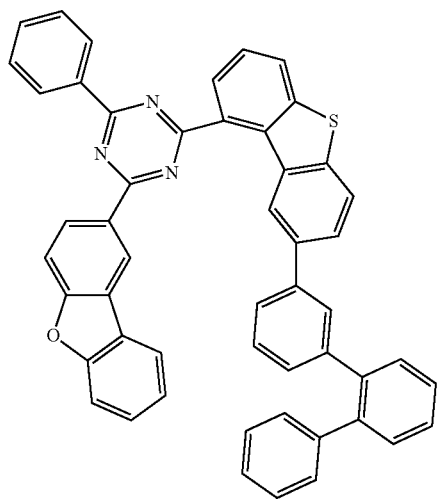
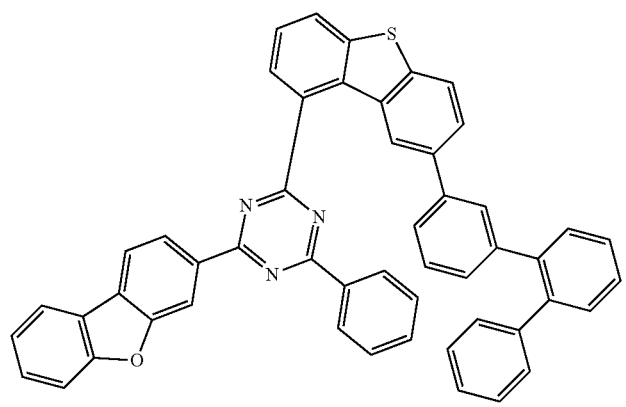
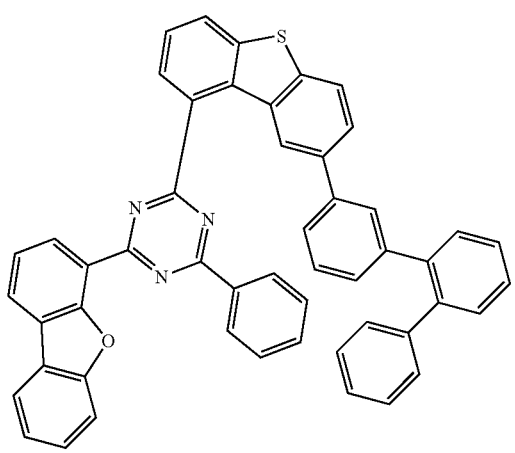
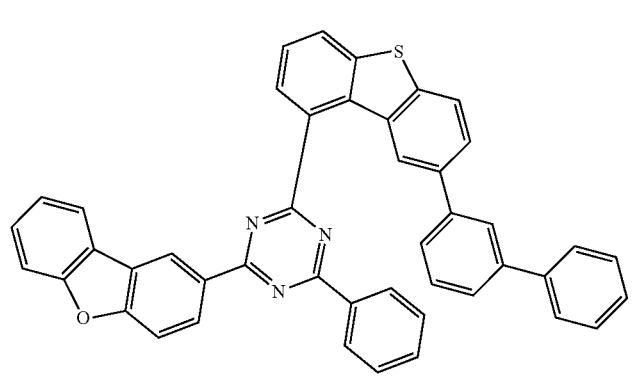
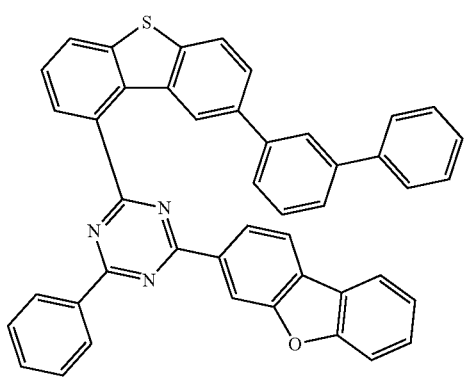

-continued
273
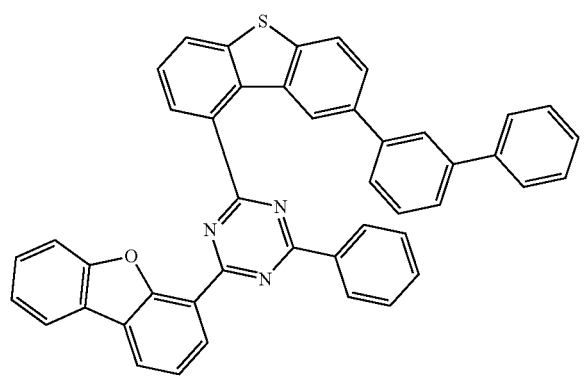
274
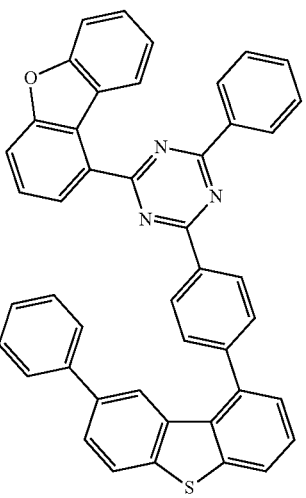
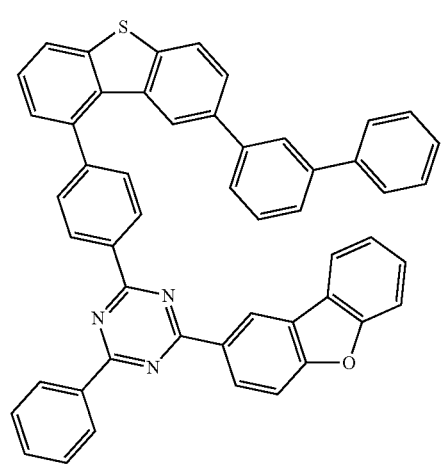
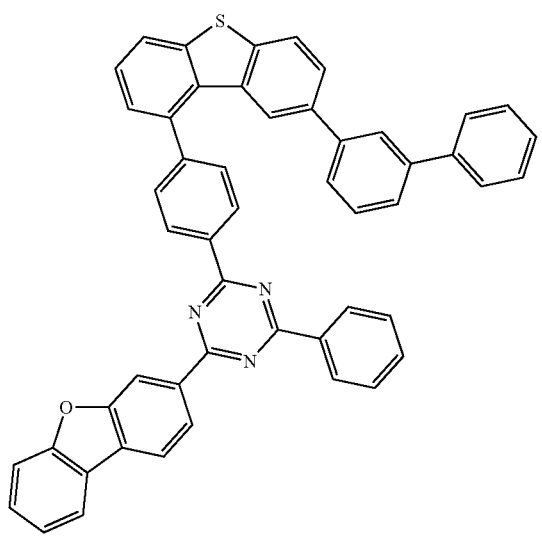
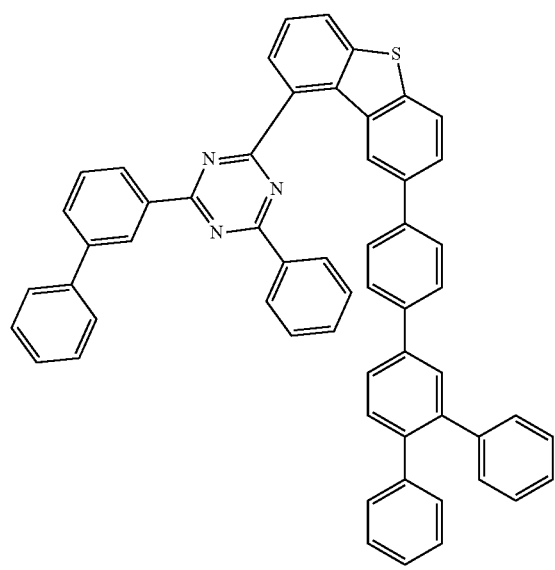
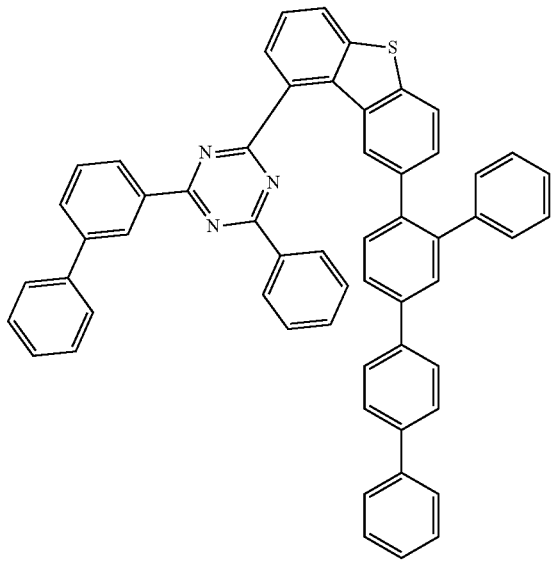

-continued
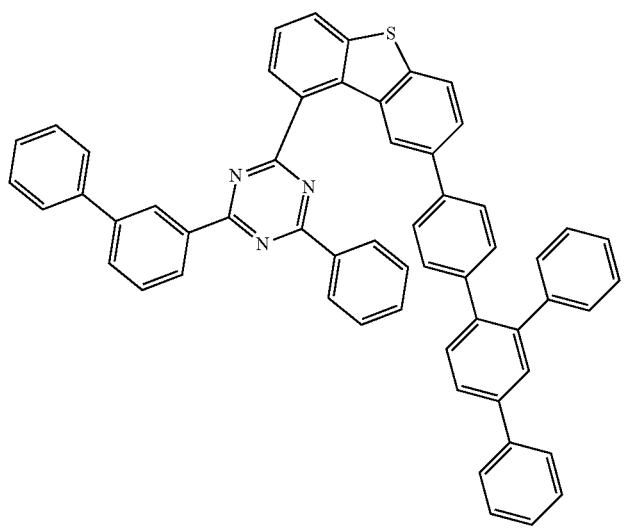
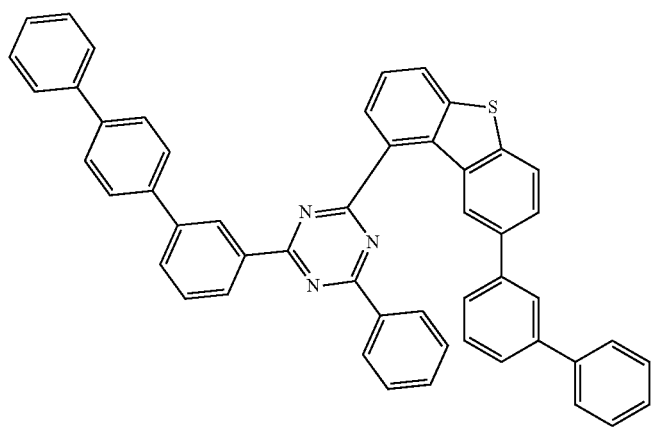
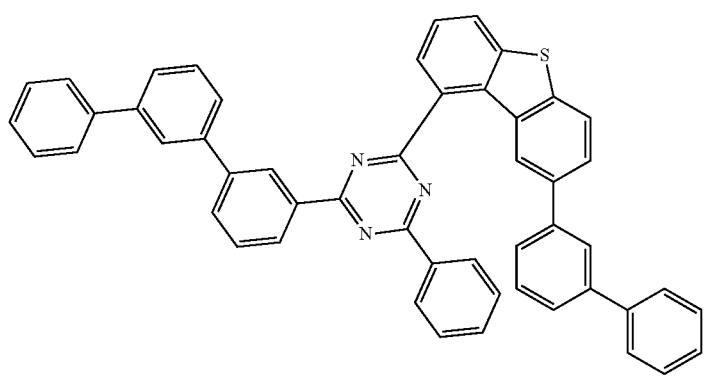

277 278
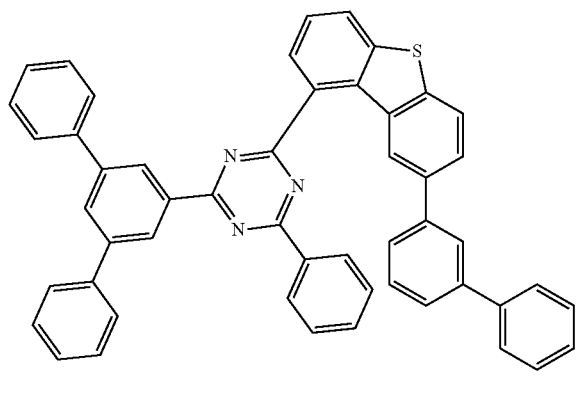
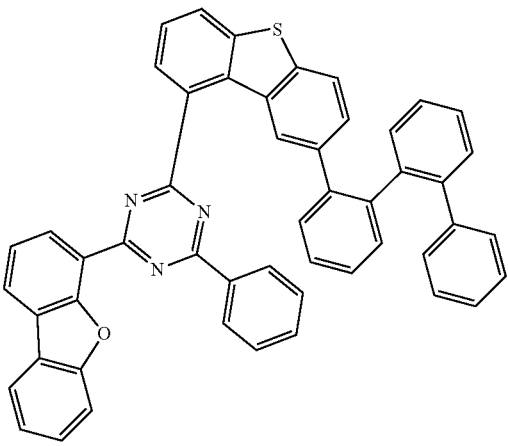
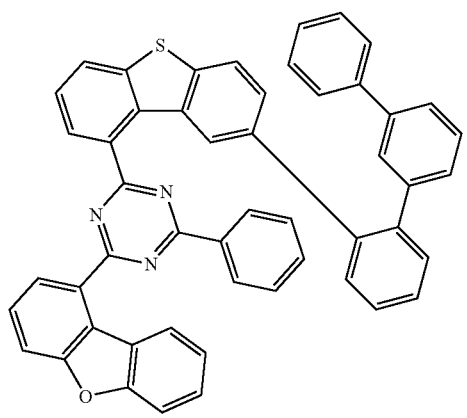
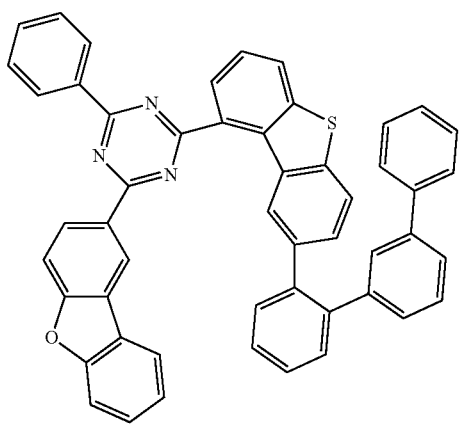
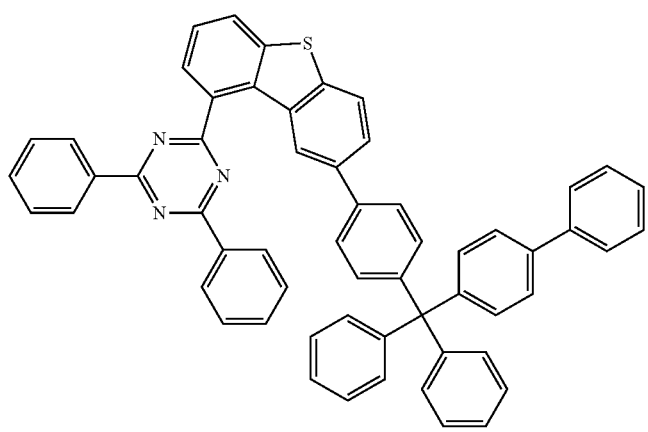

-continued
279
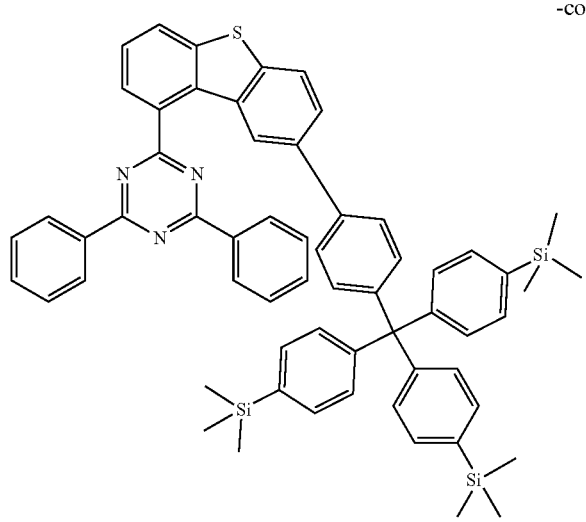
280
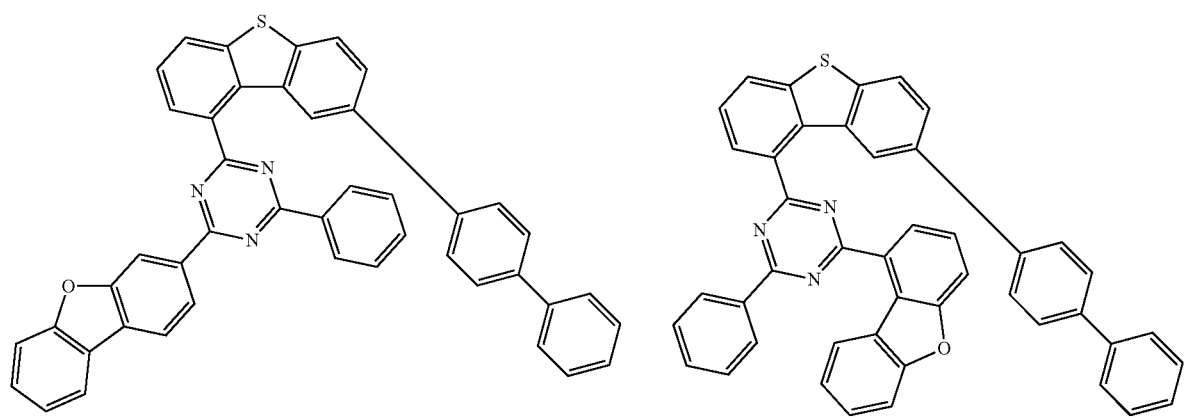
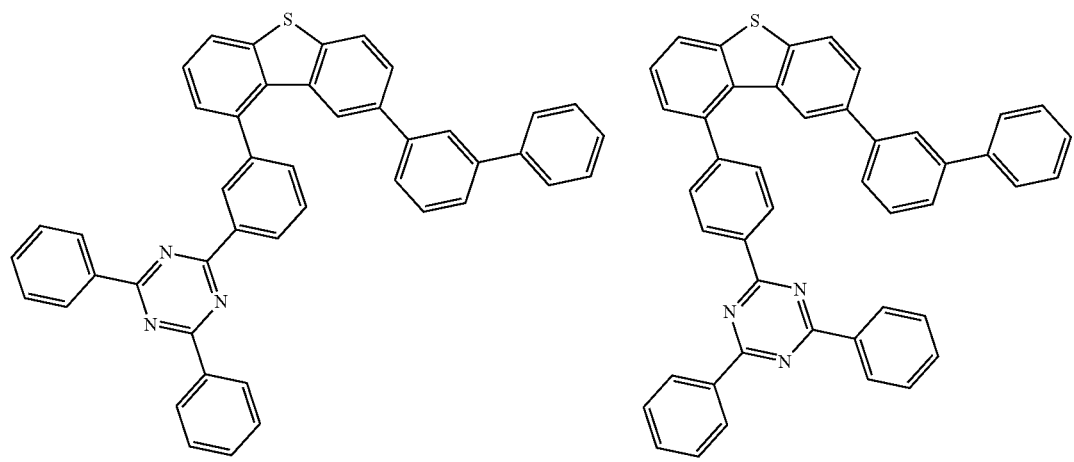

-continued
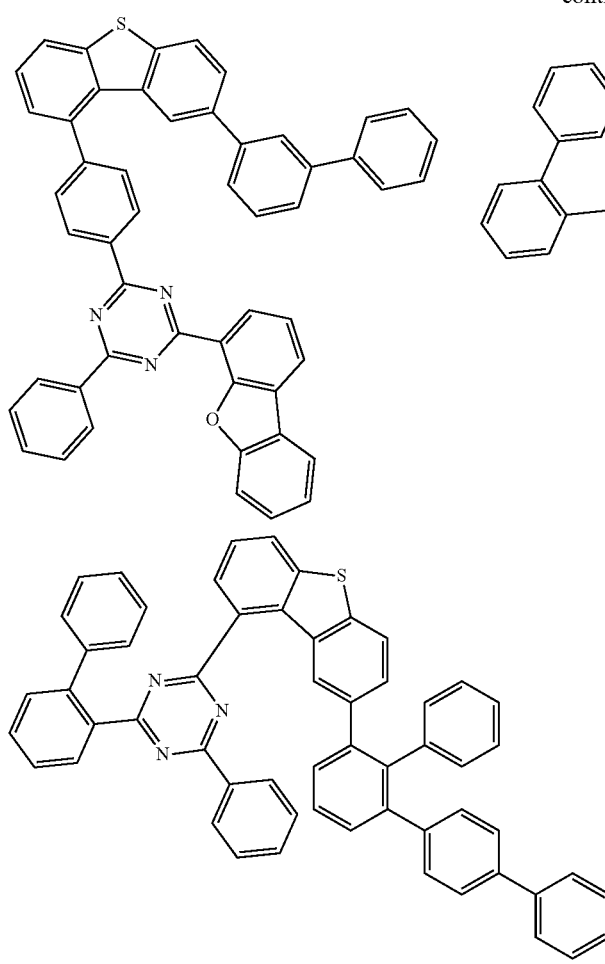
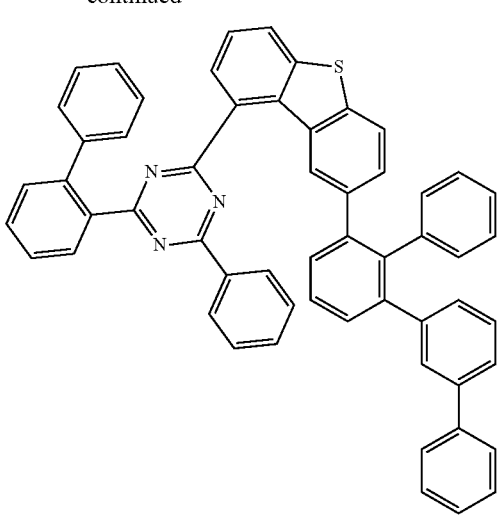
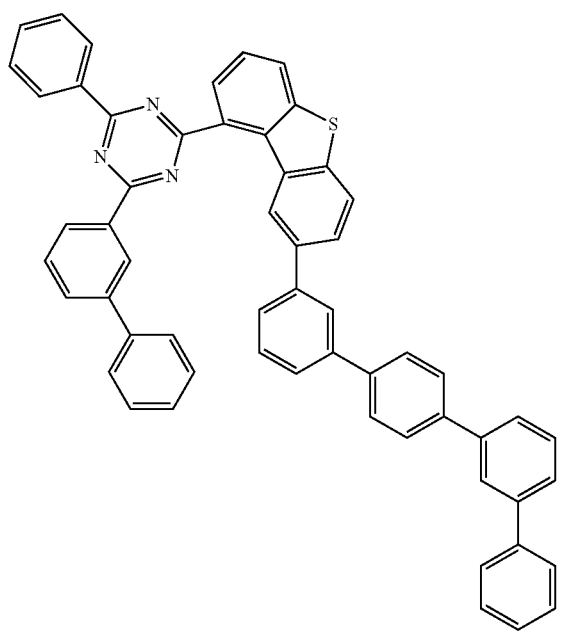

-continued
283 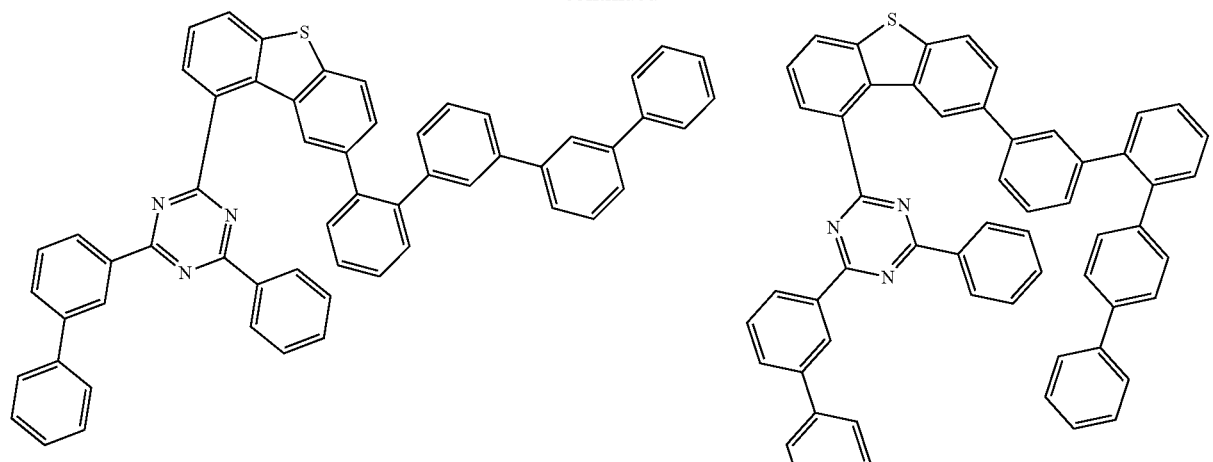
284
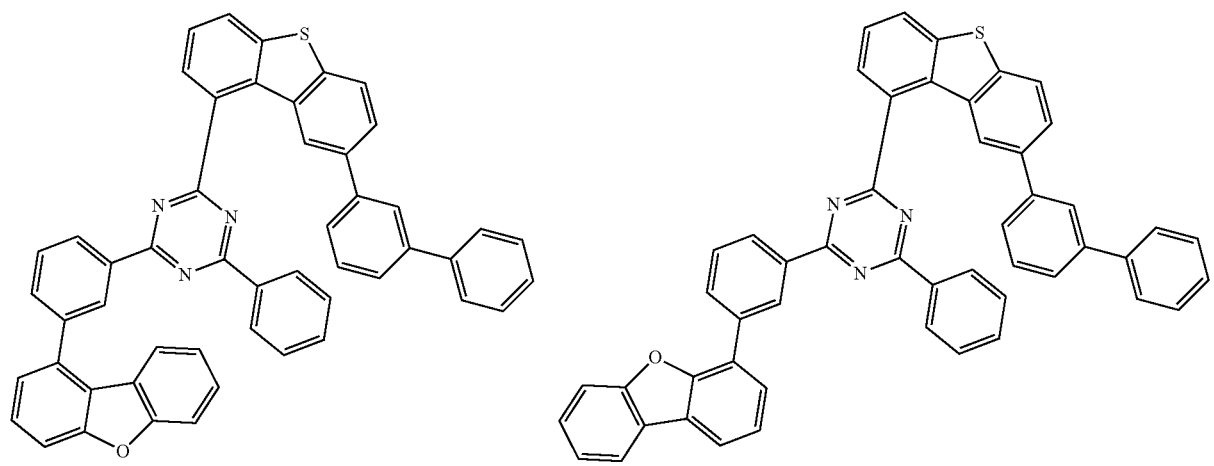
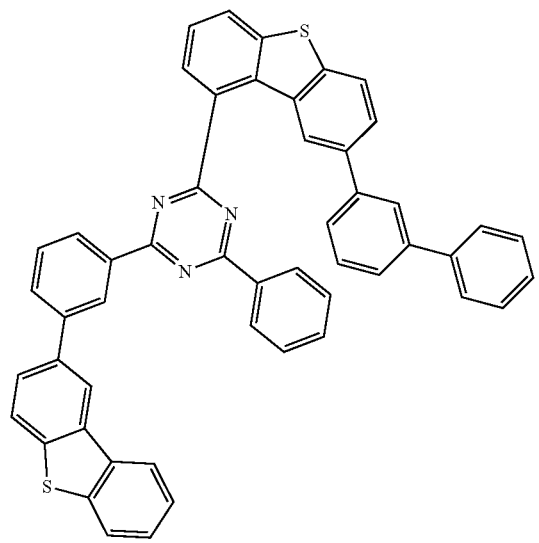

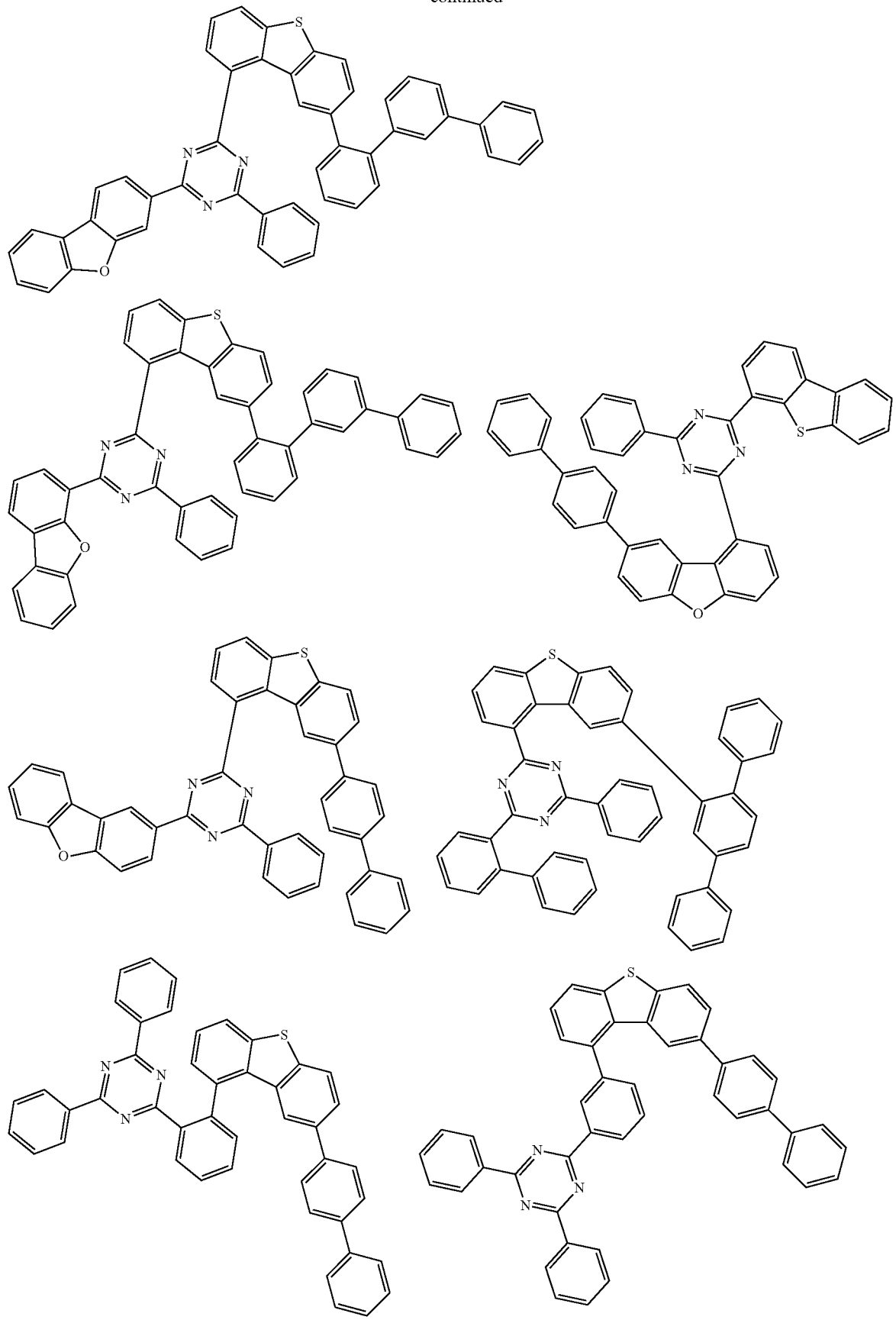

-continued
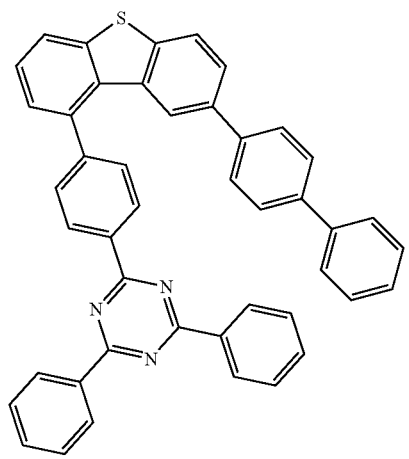
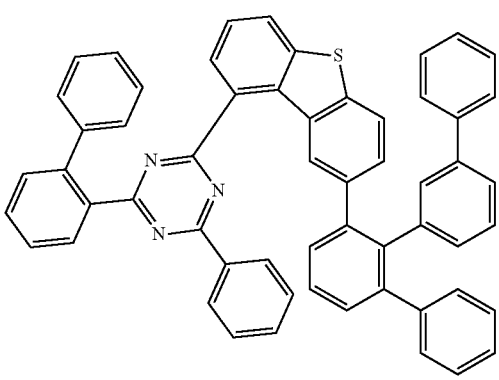
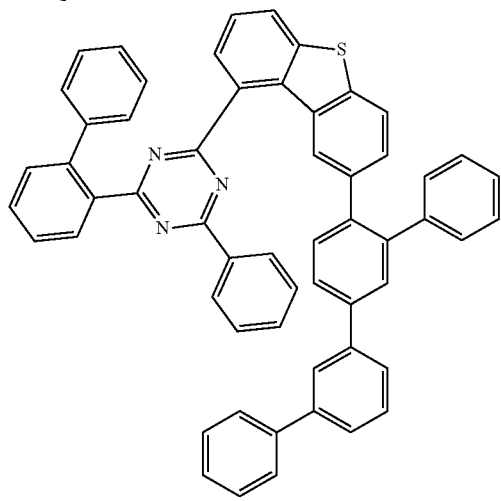
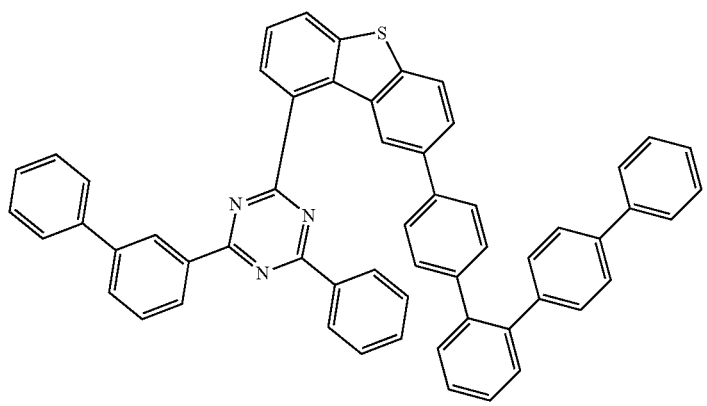
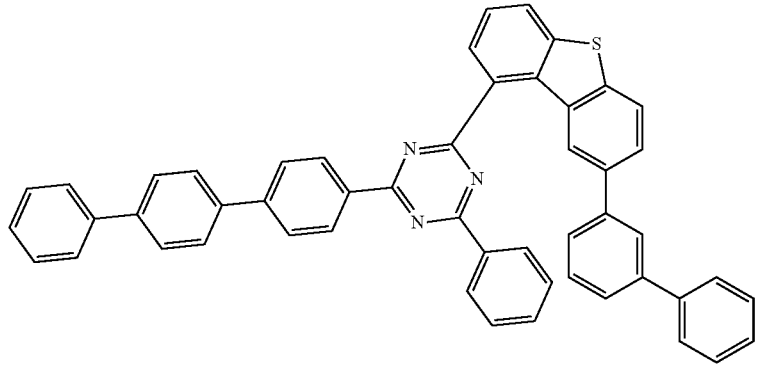

289 290
-continued
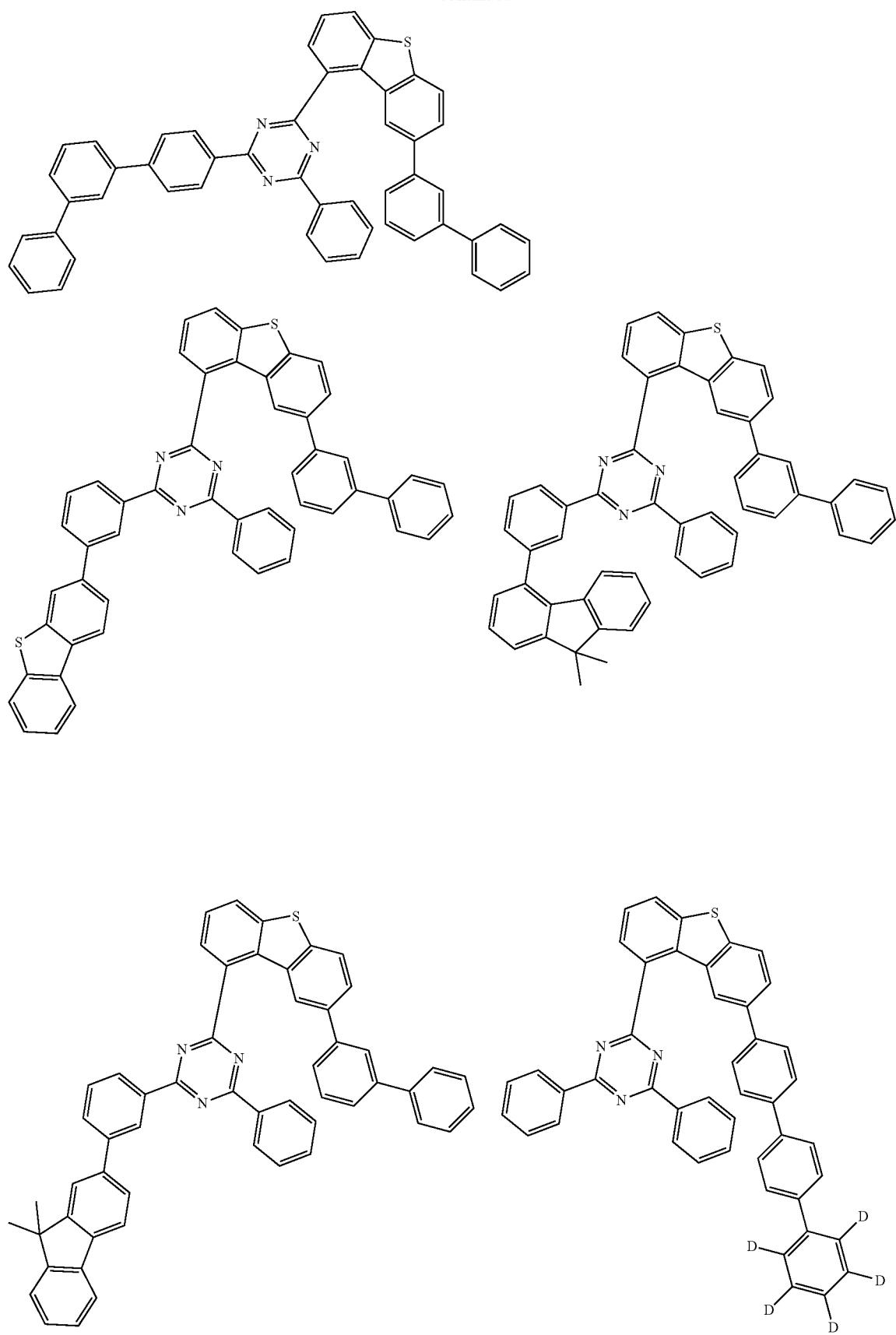

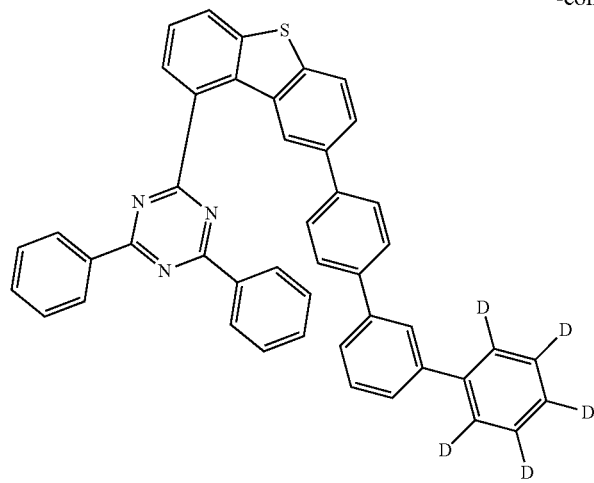
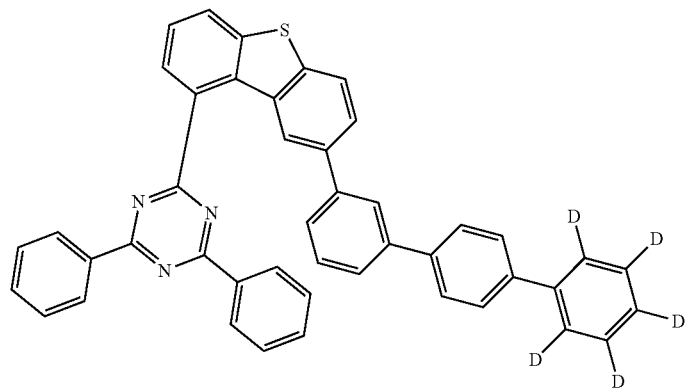
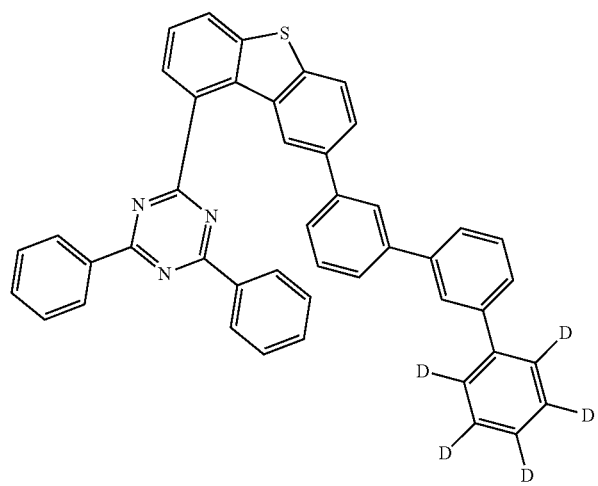
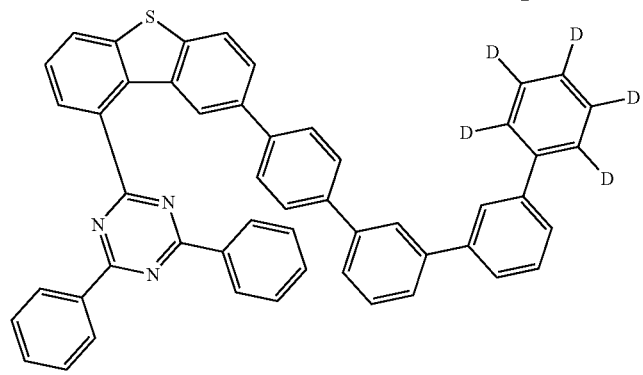

293 294
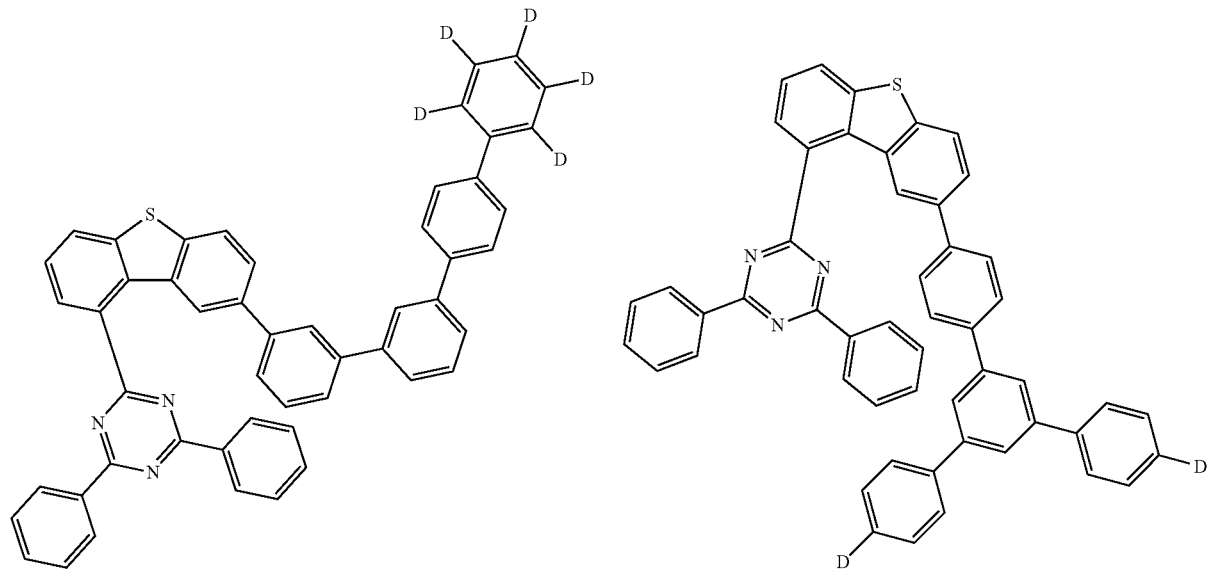
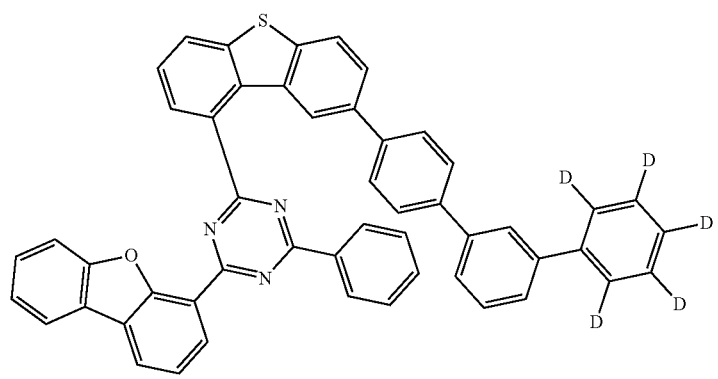
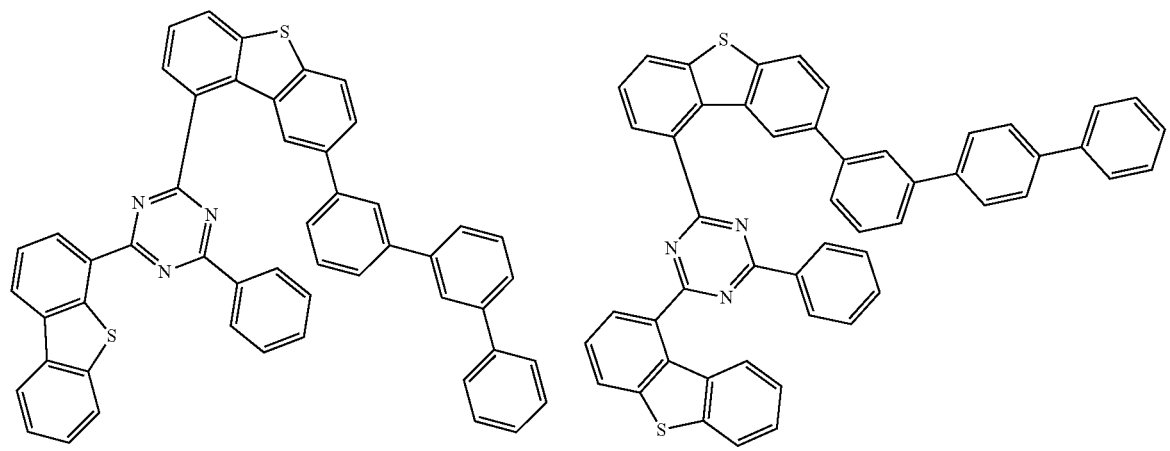

295
296
-continued
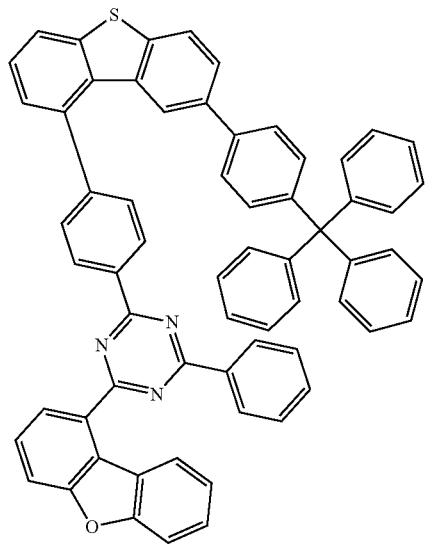
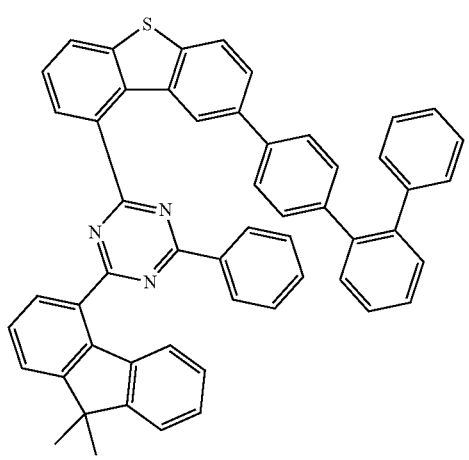
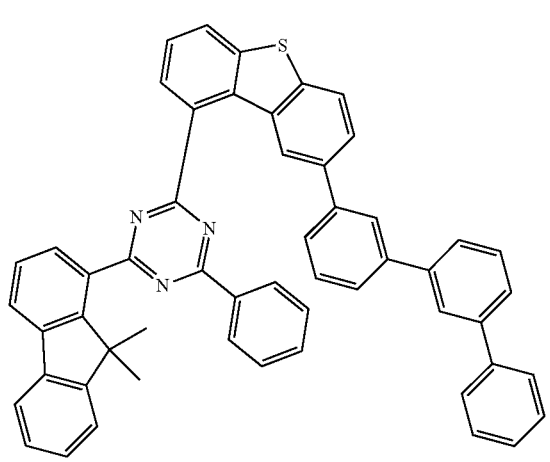
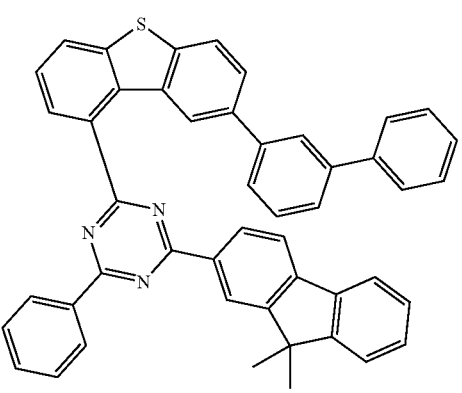
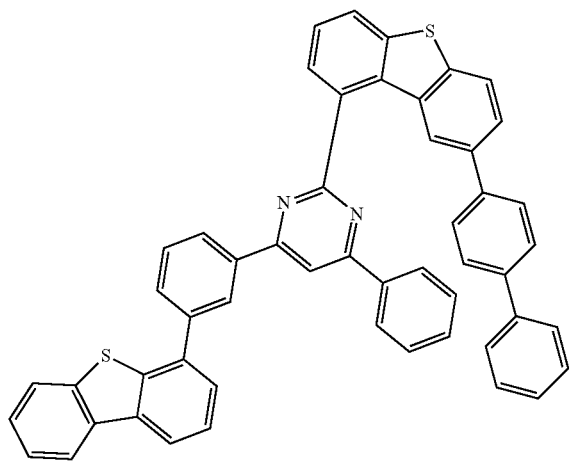
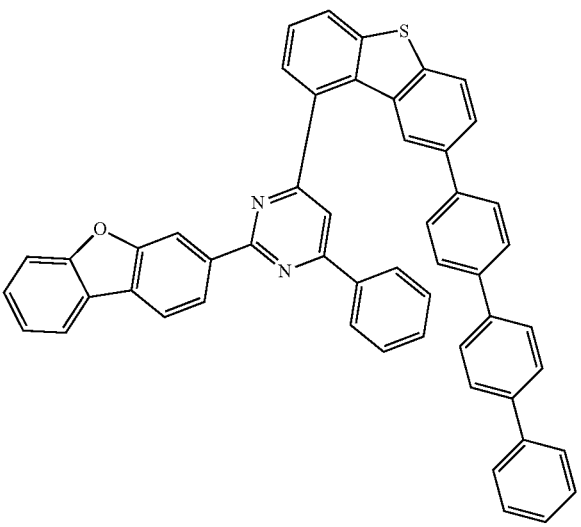

-continued
297
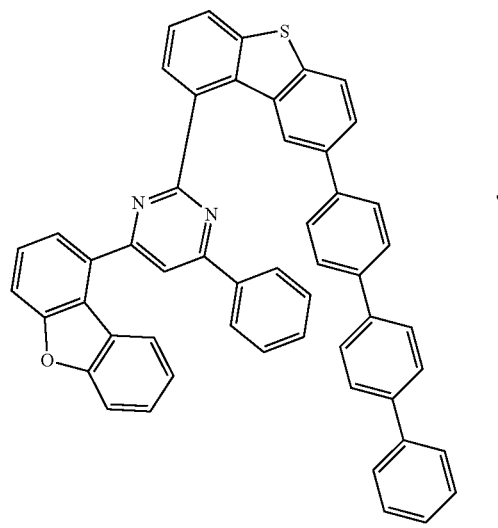
298
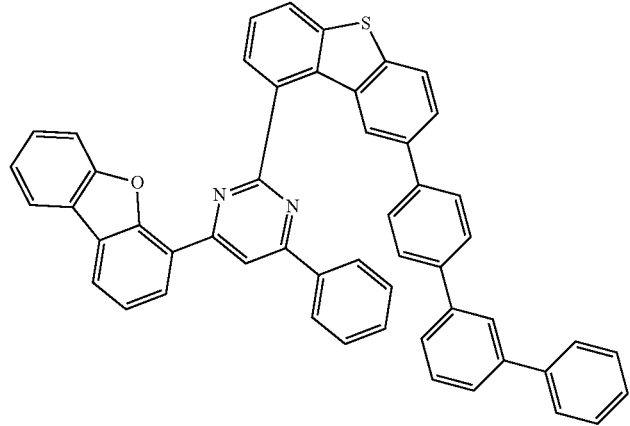
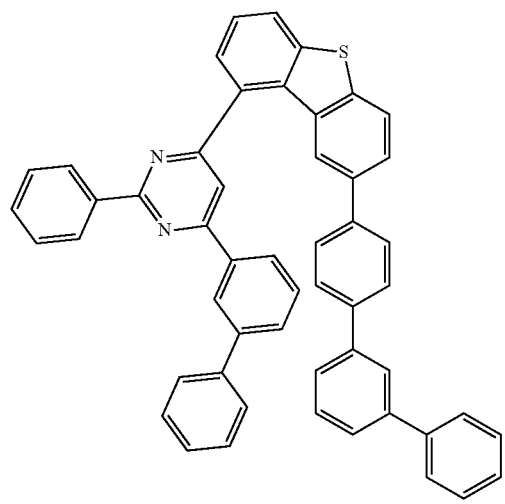
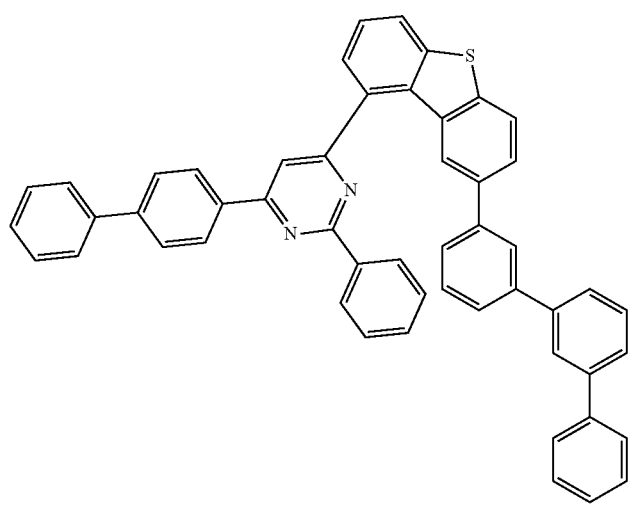
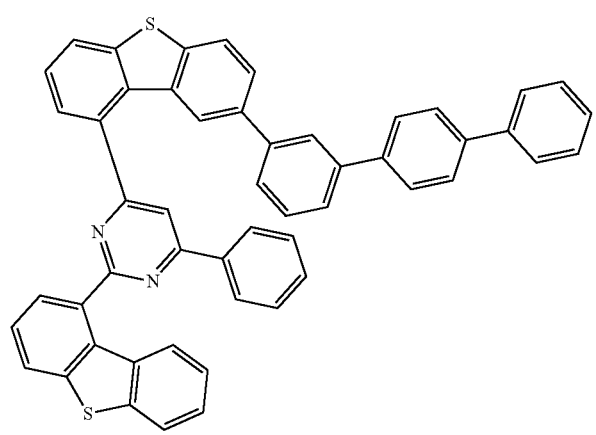
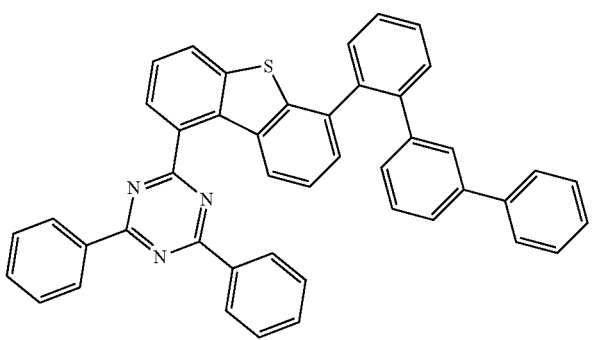

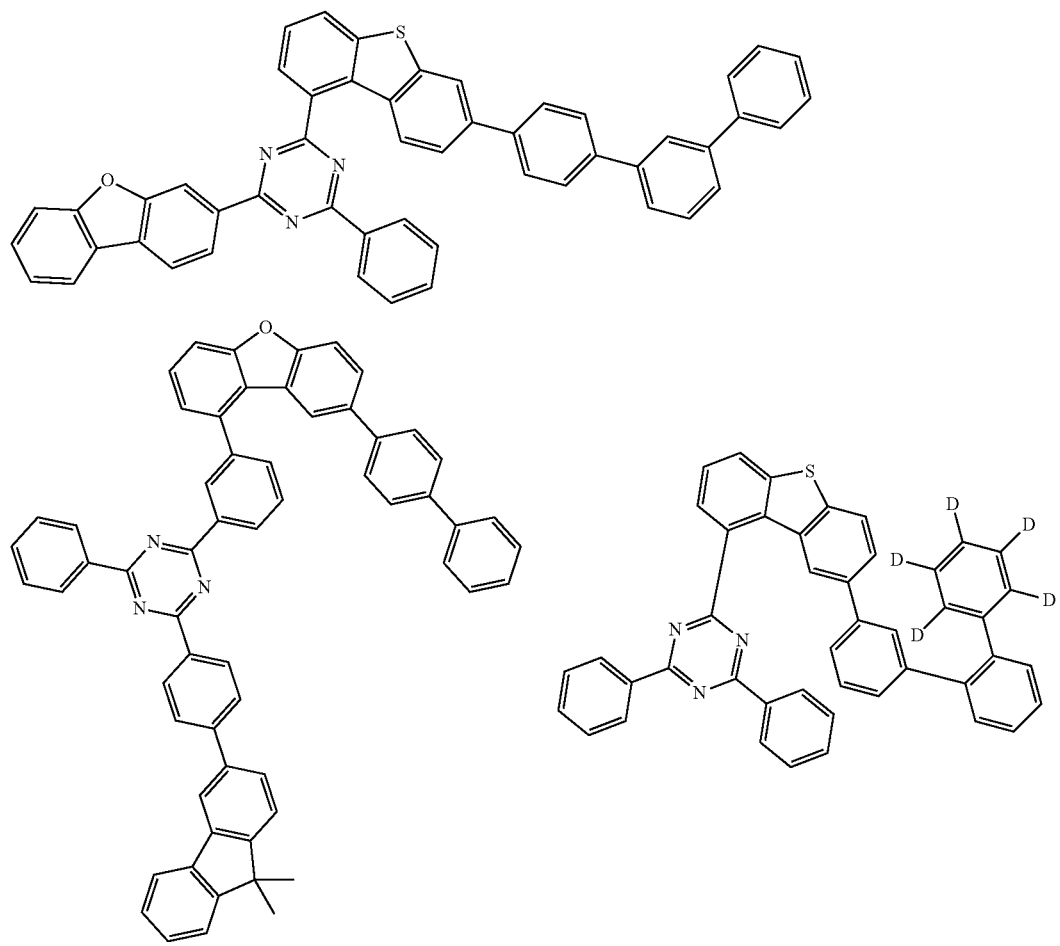
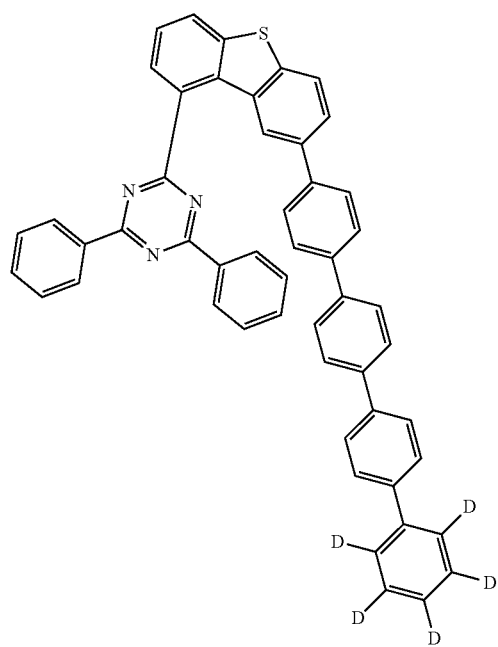

-continued
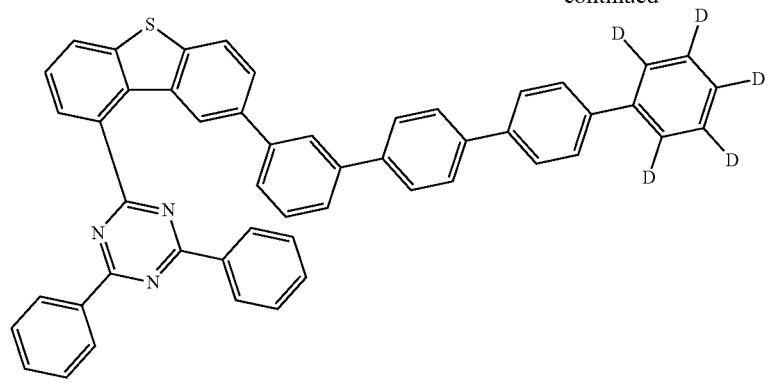
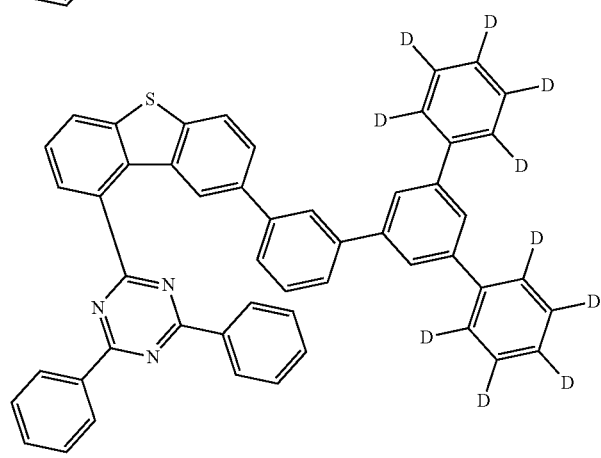
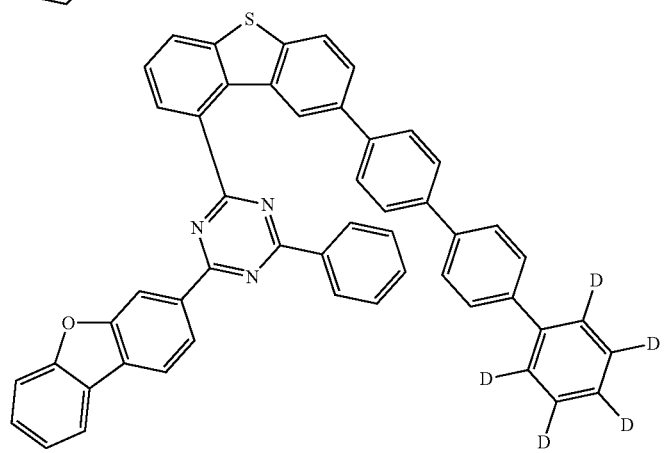
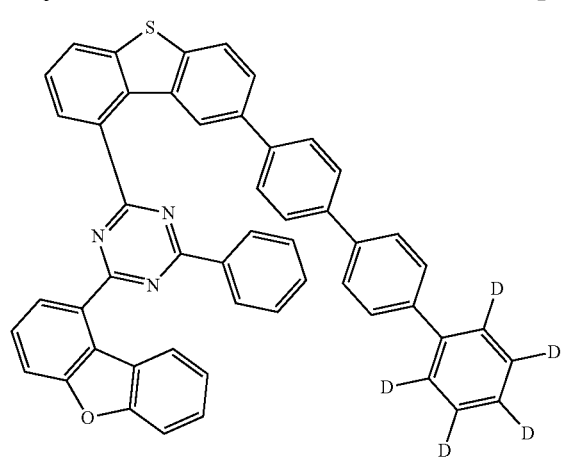
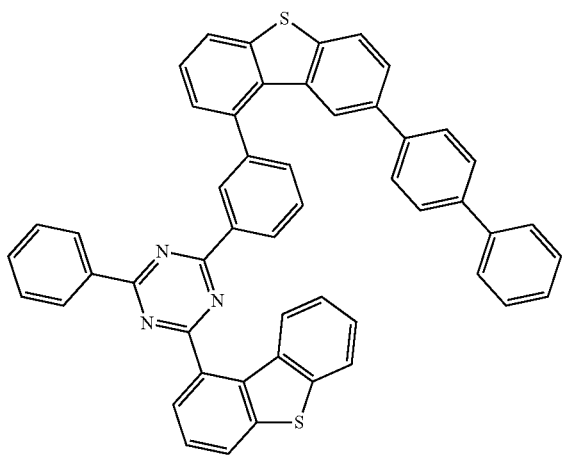

303
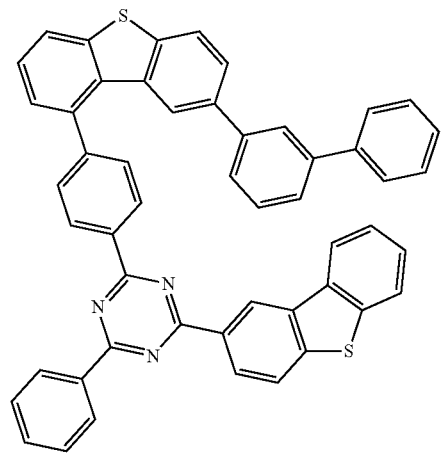
304
-continued
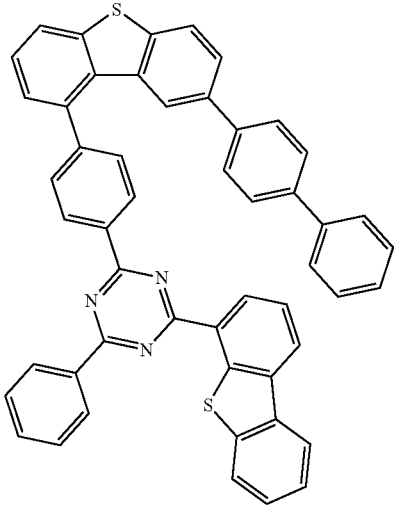
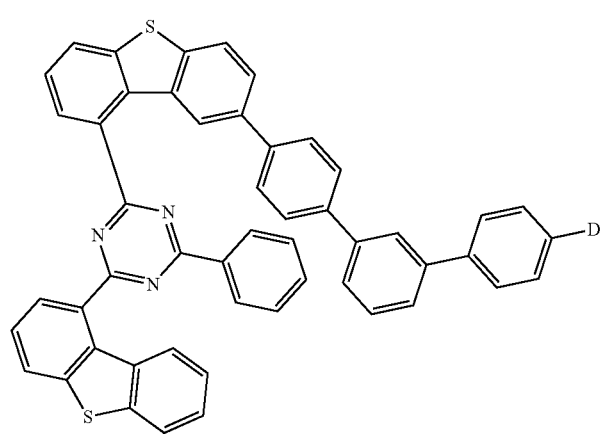
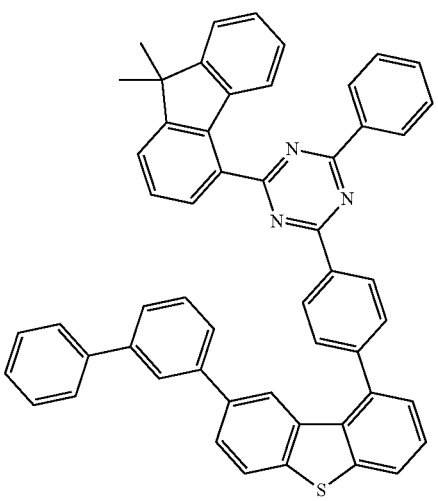
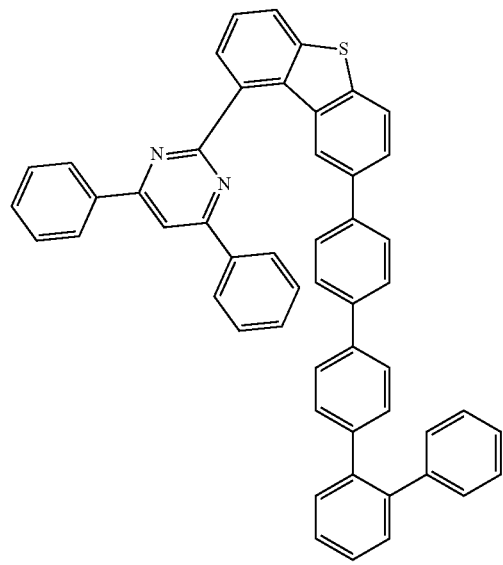
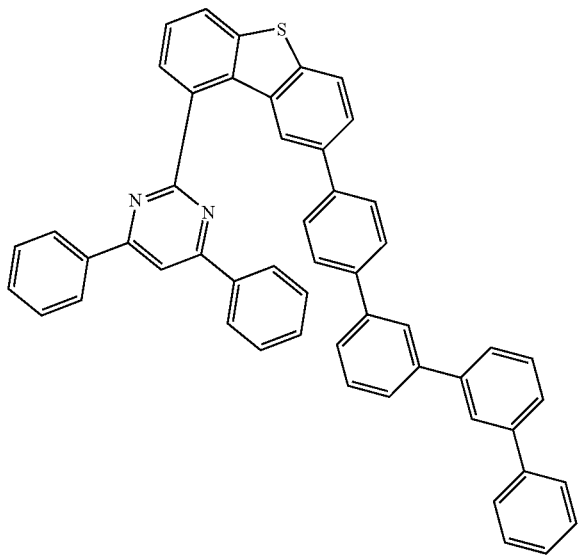

-continued
305 306
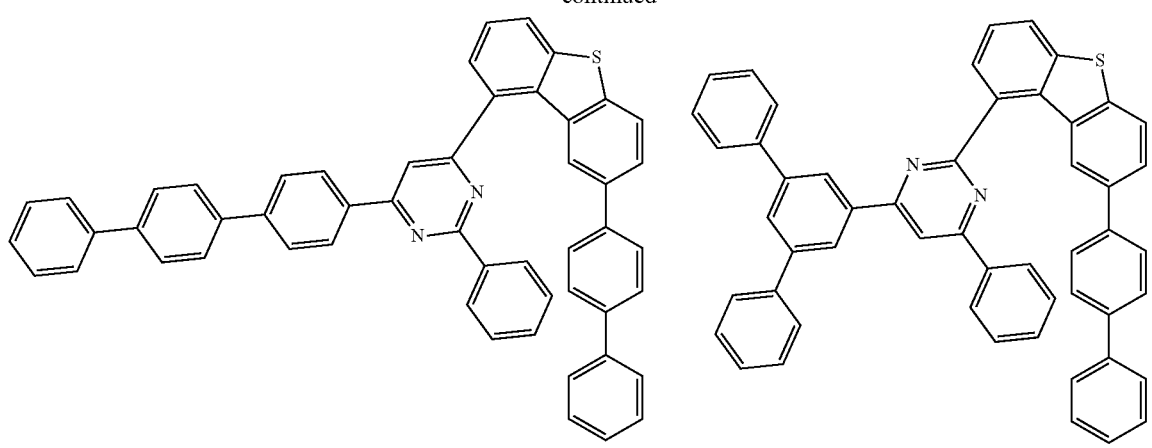
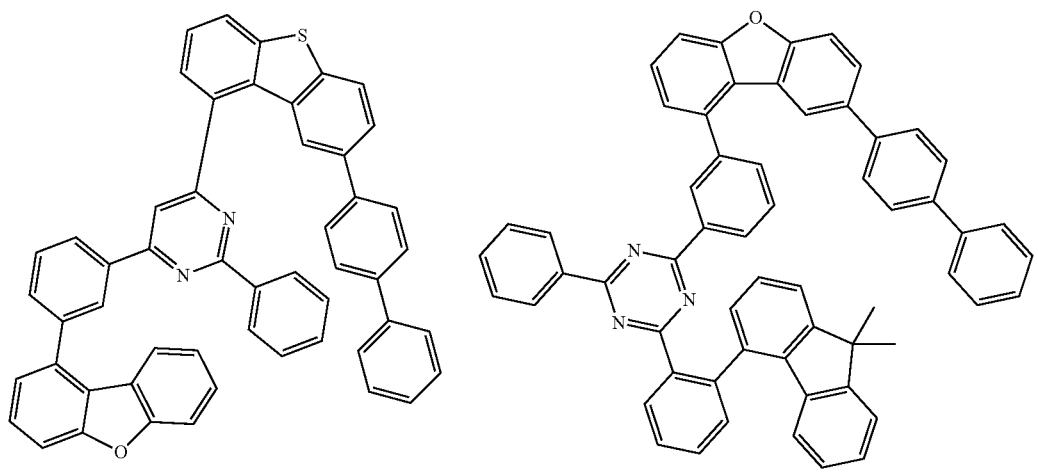
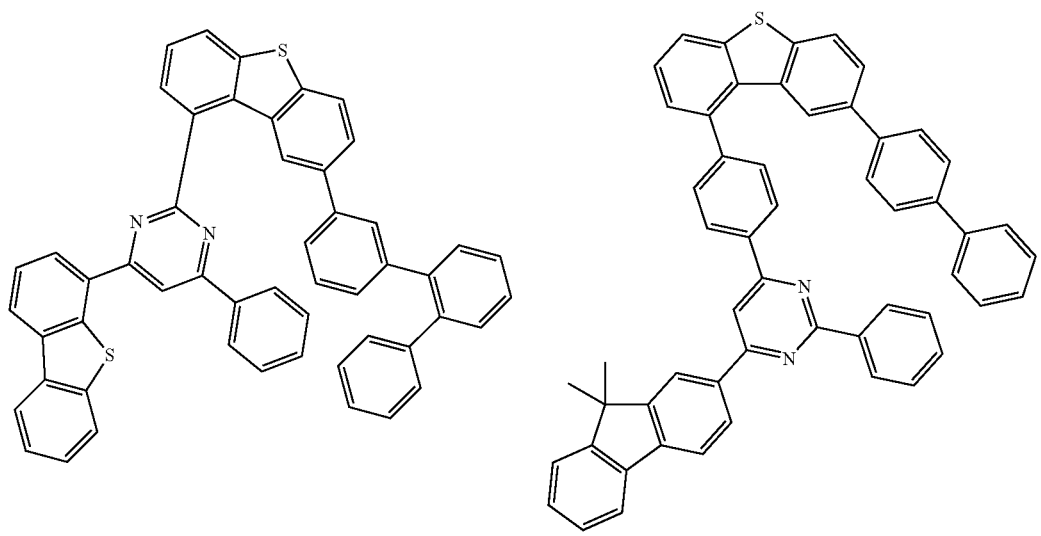

-continued
307
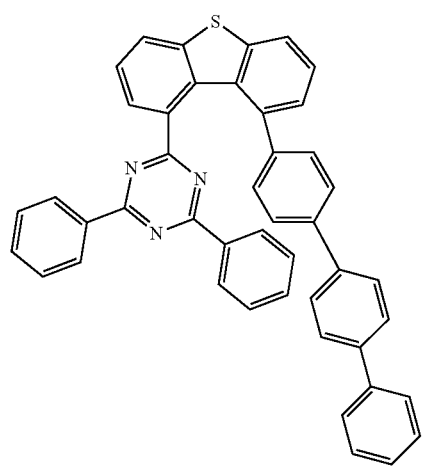
308
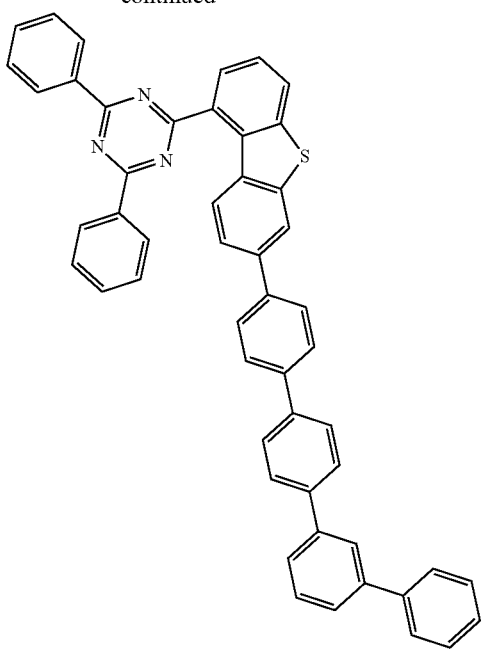
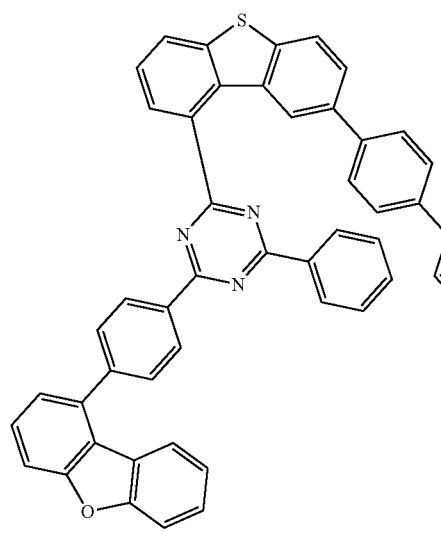
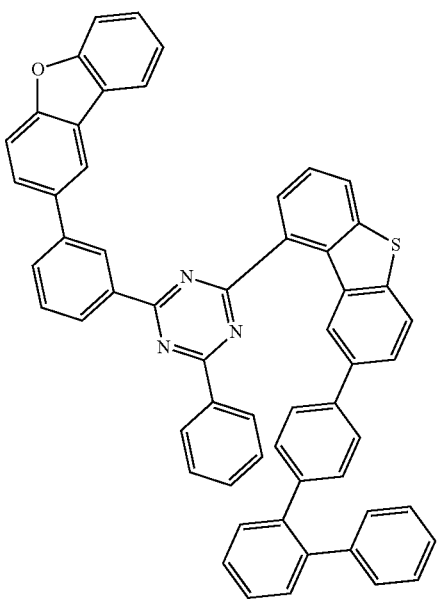

309 310
-continued
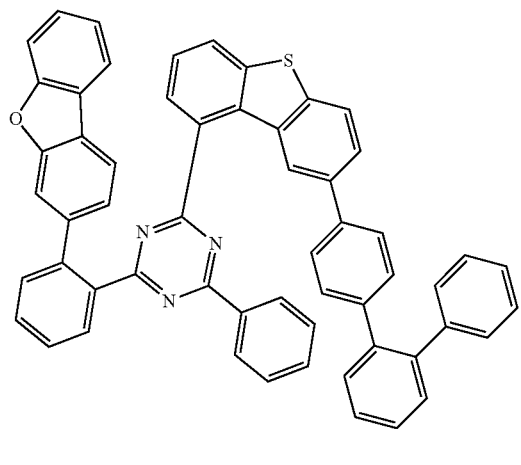
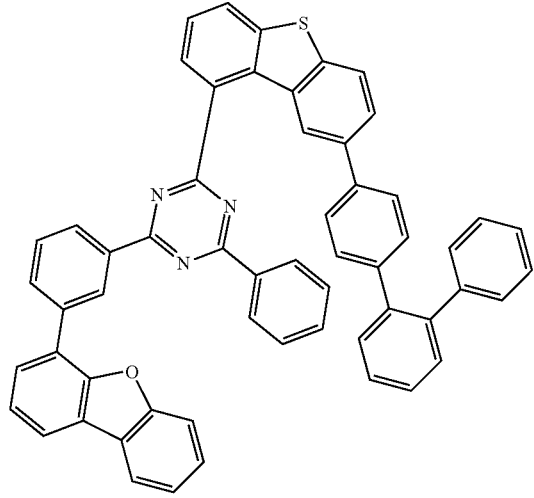
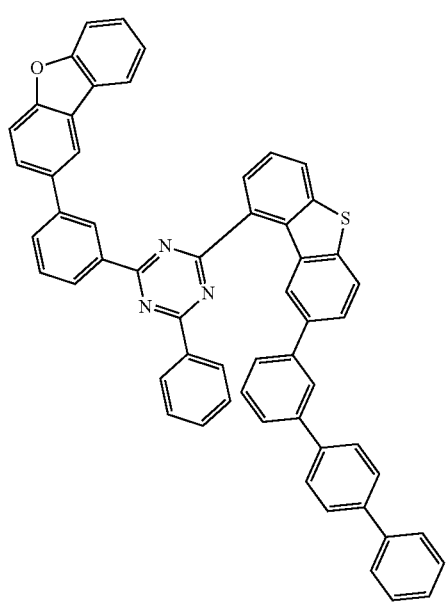
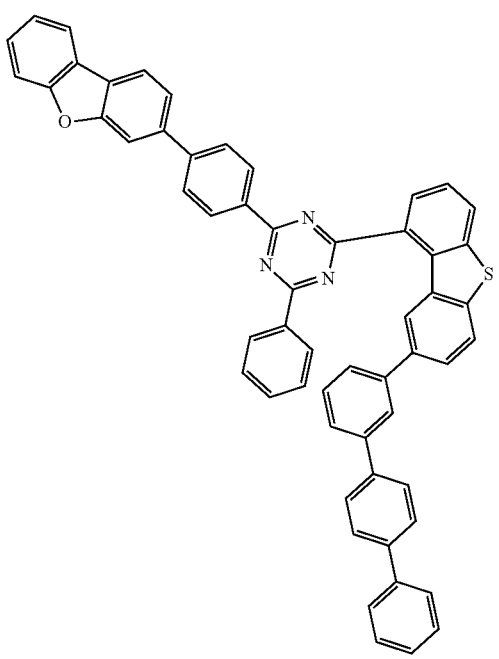
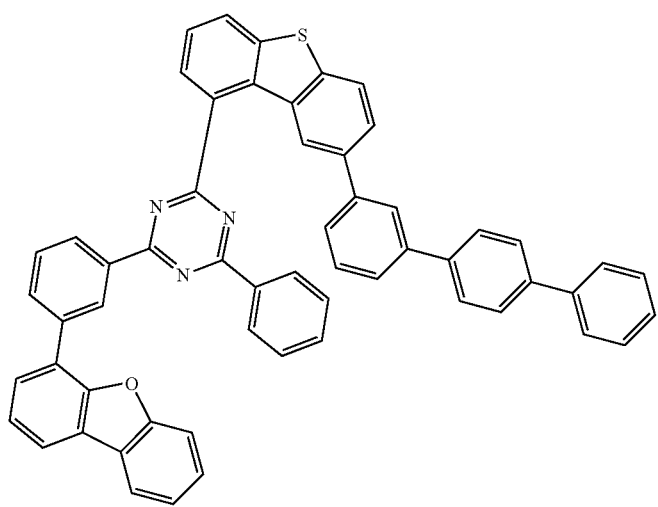

311 312
-continued
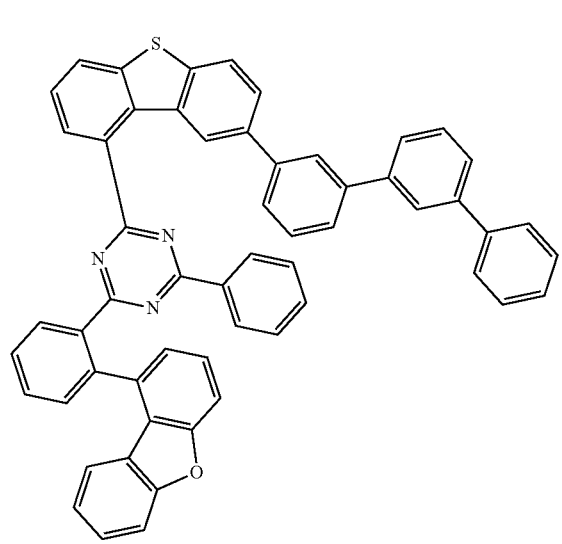
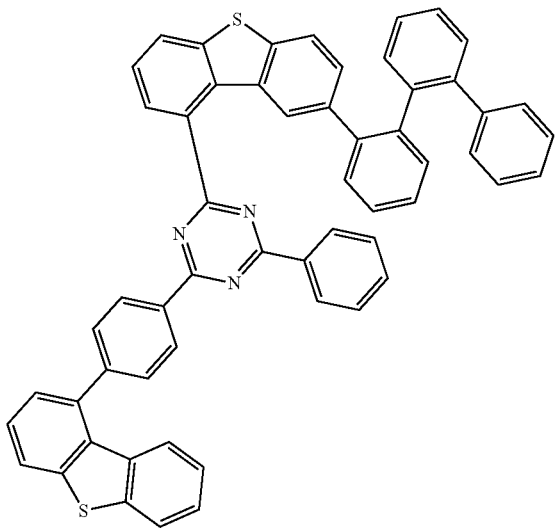
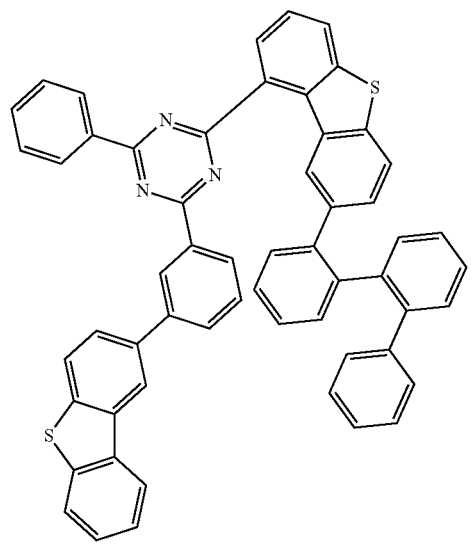
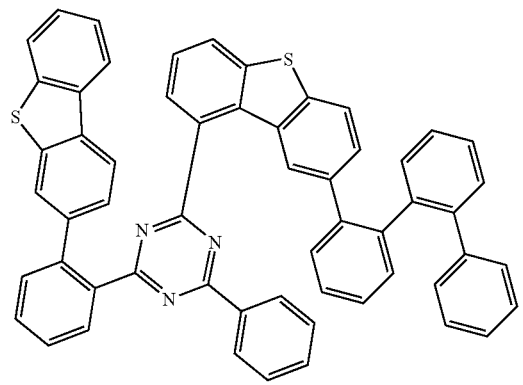
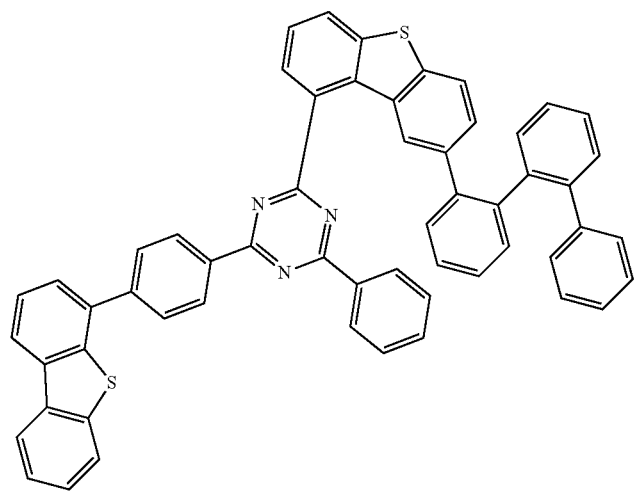

313
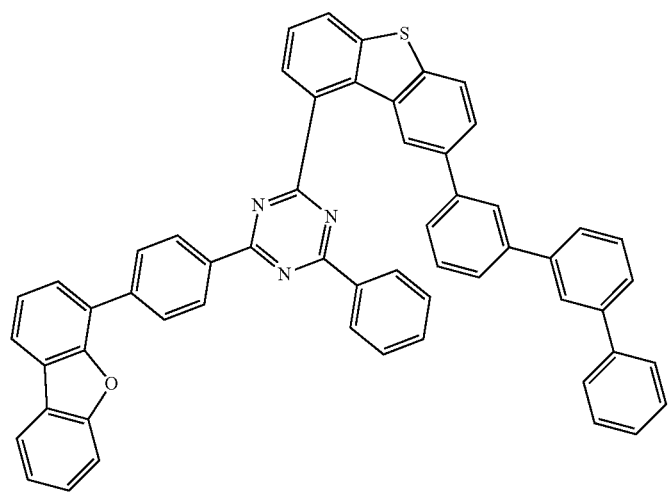
314
-continued
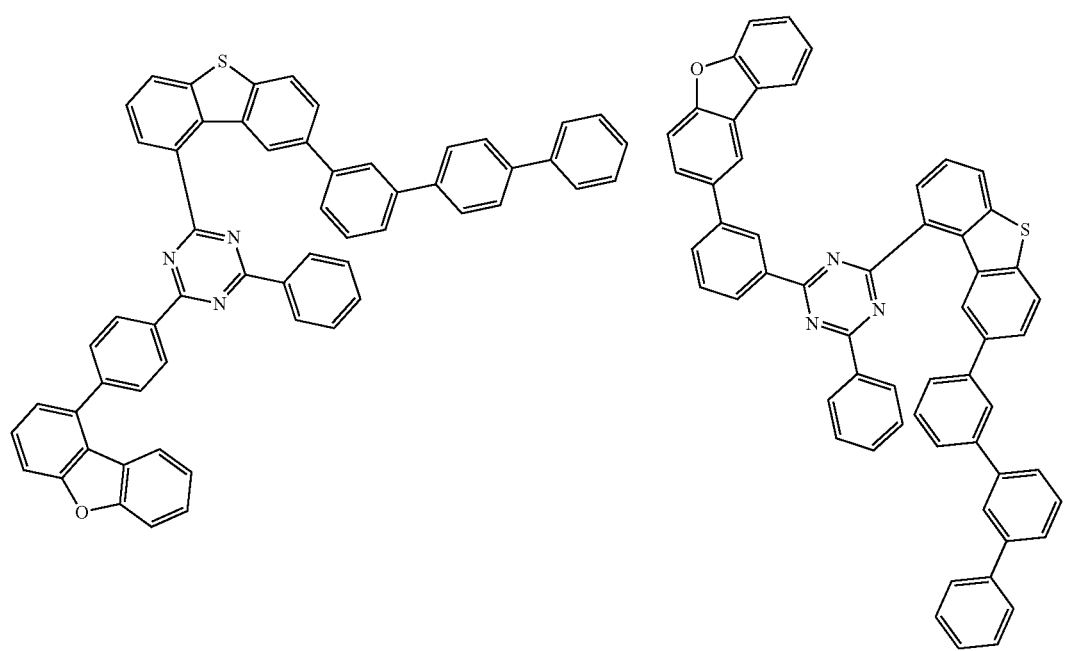

-continued
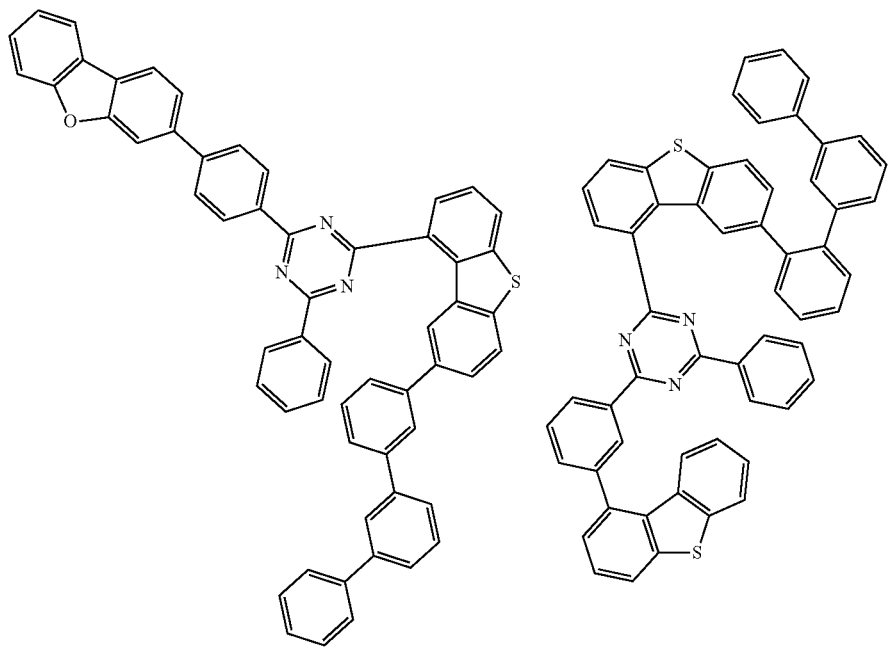
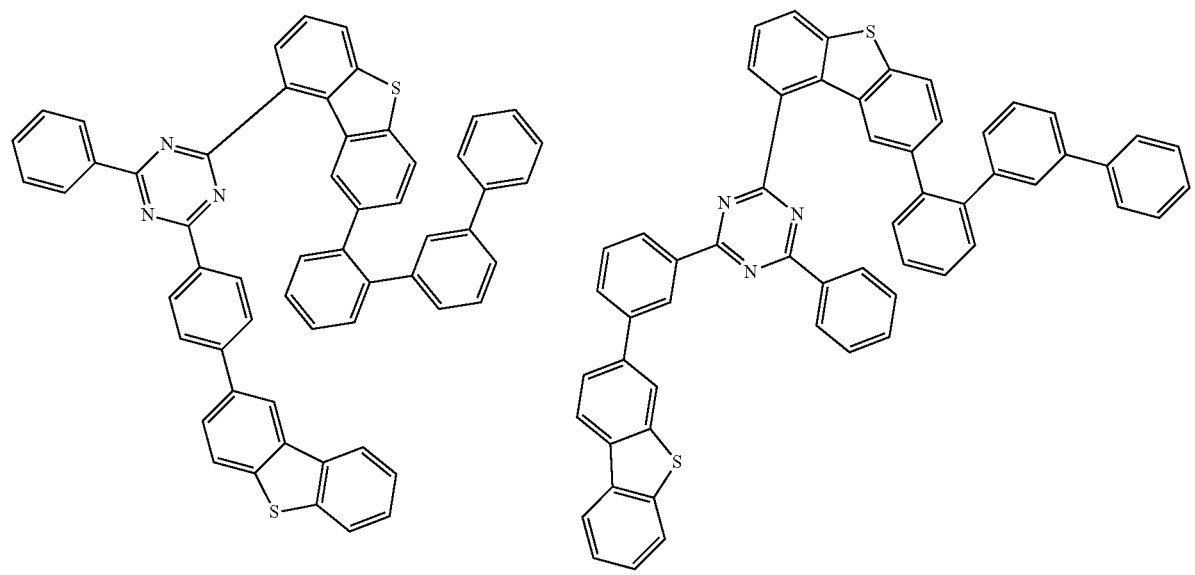

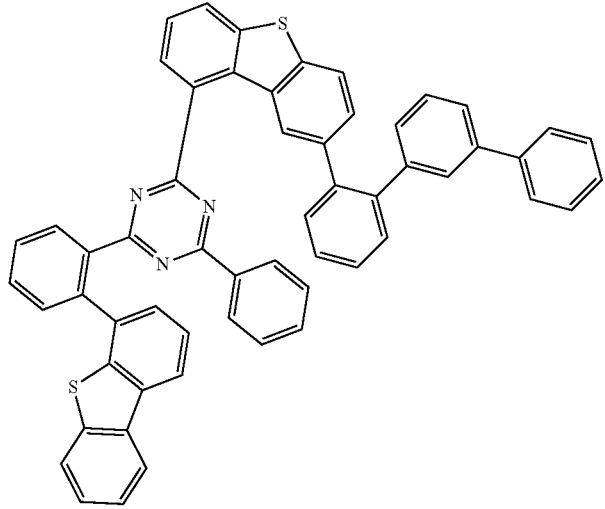
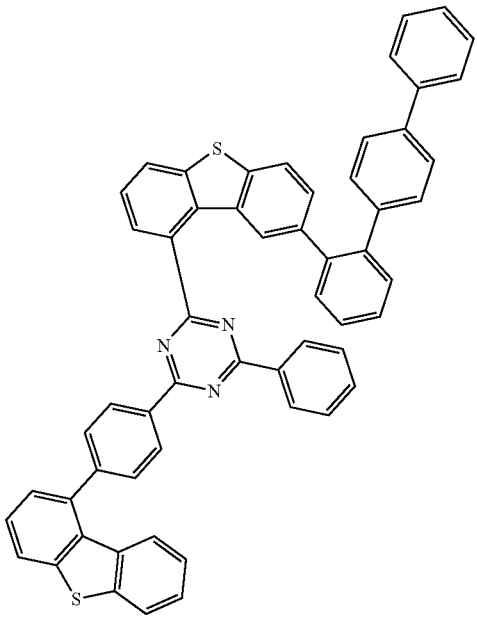
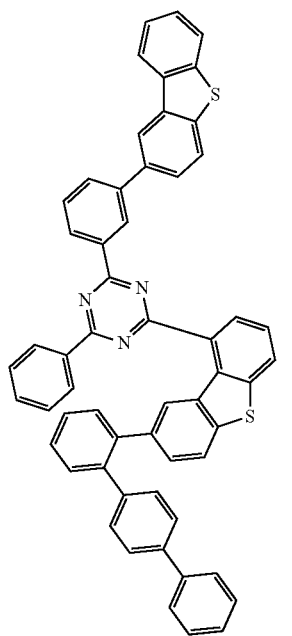
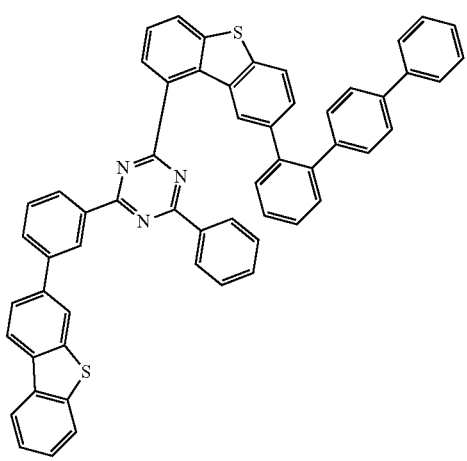
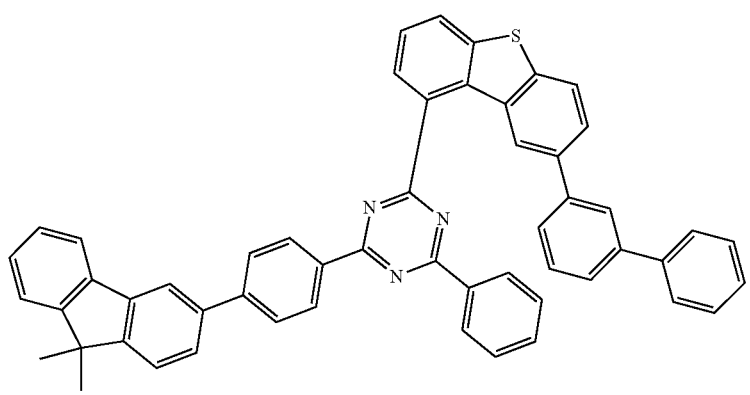

-continued
319
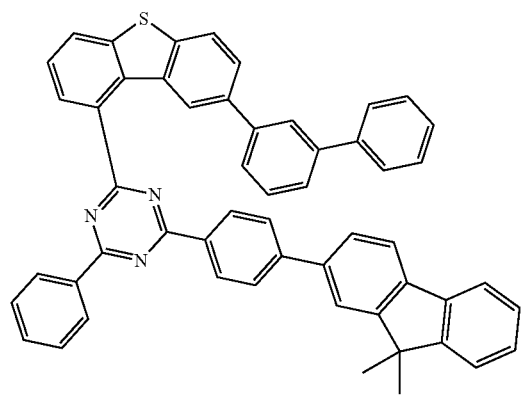
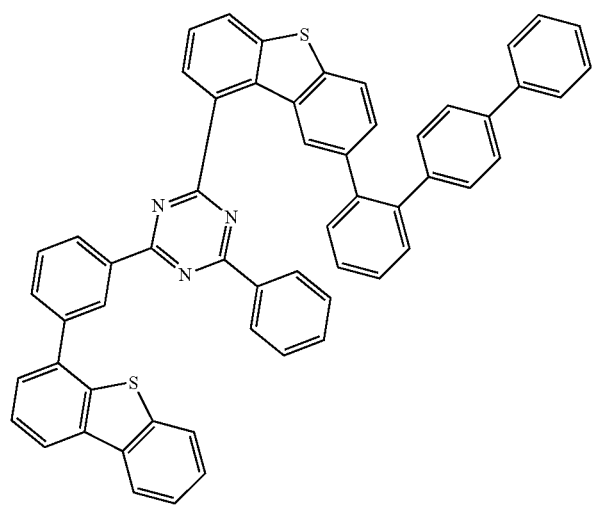
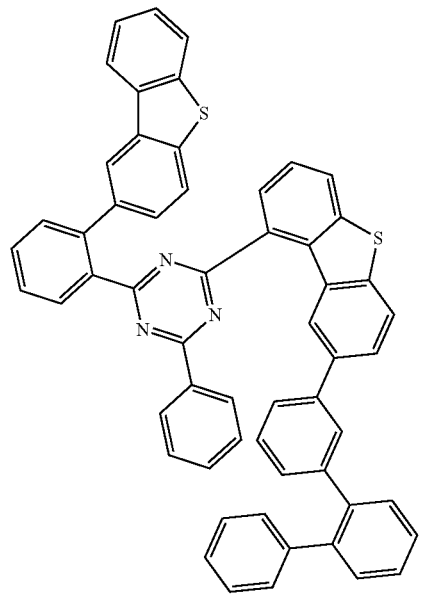
320
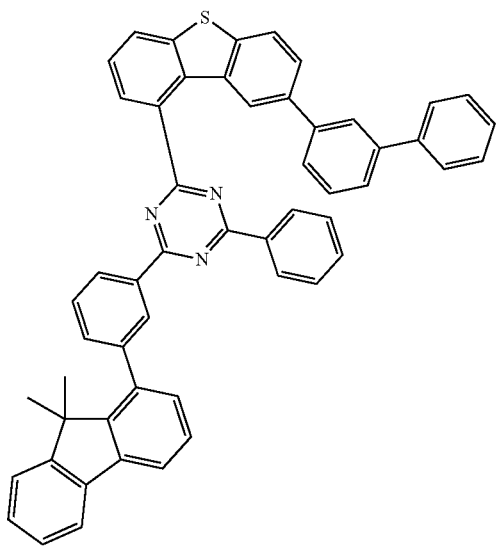
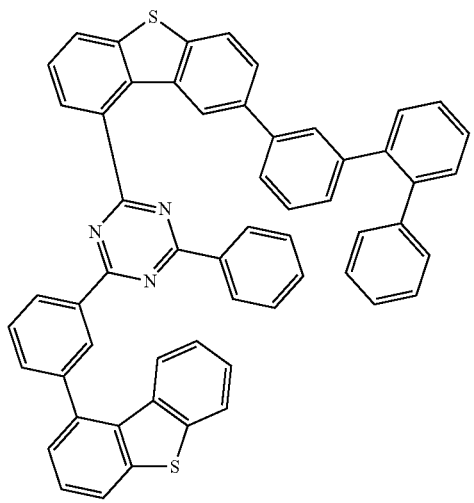
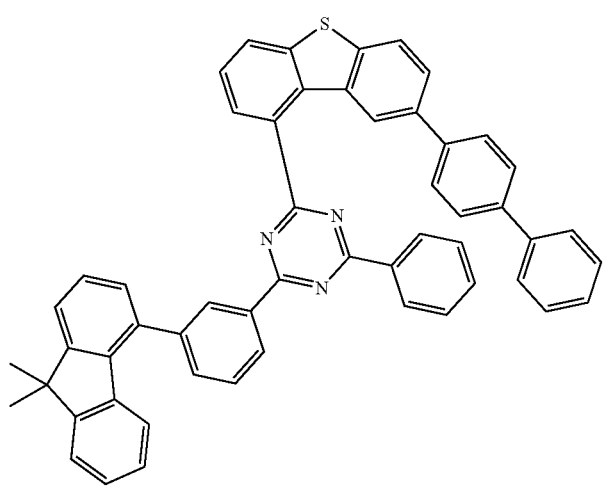

-continued
321 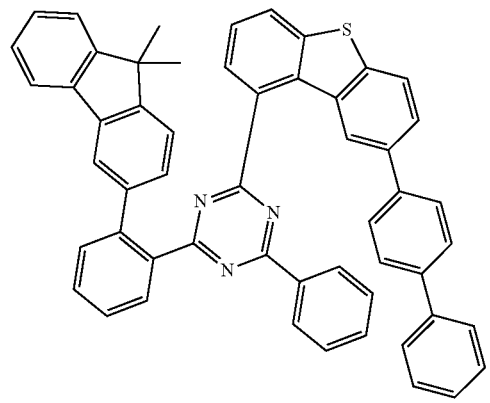
322 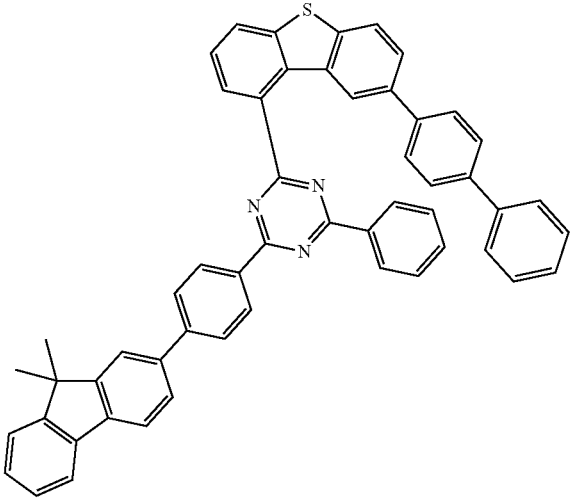
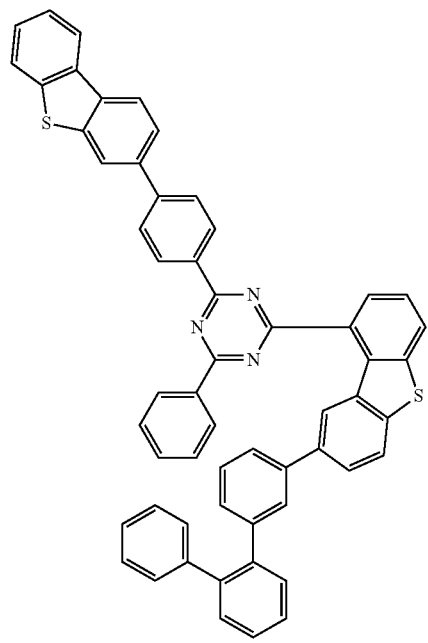
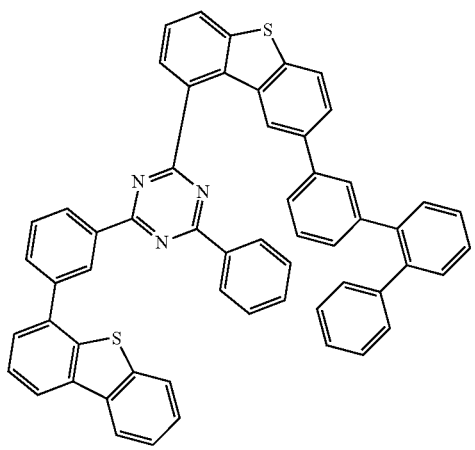

323
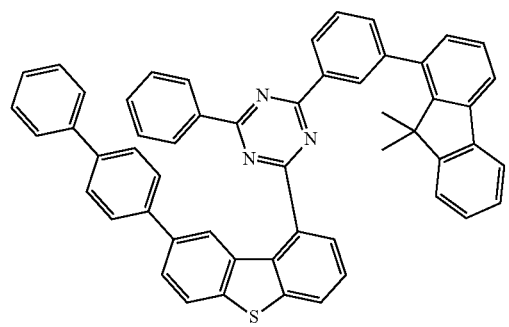
-continued
324
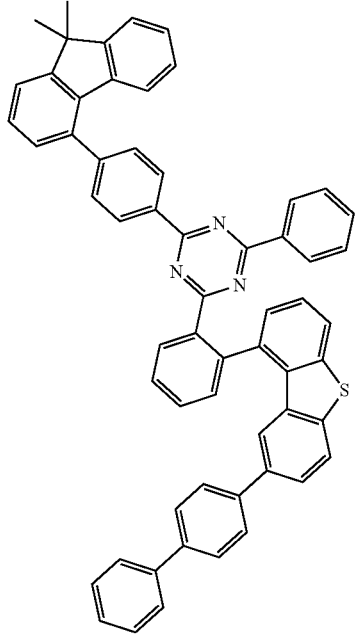
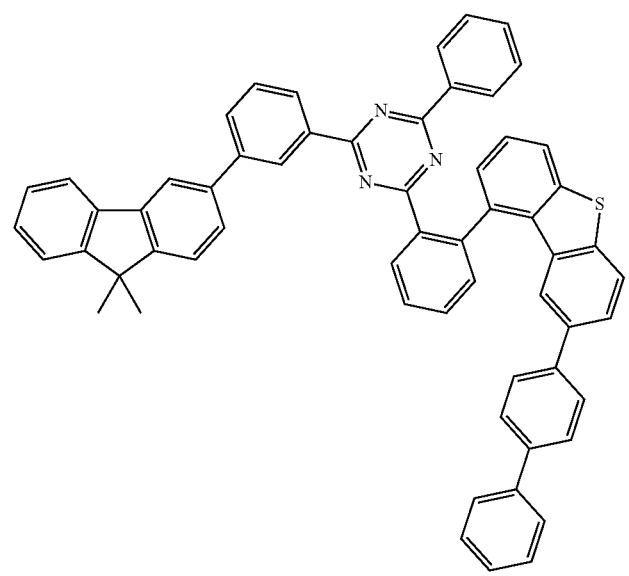

-continued
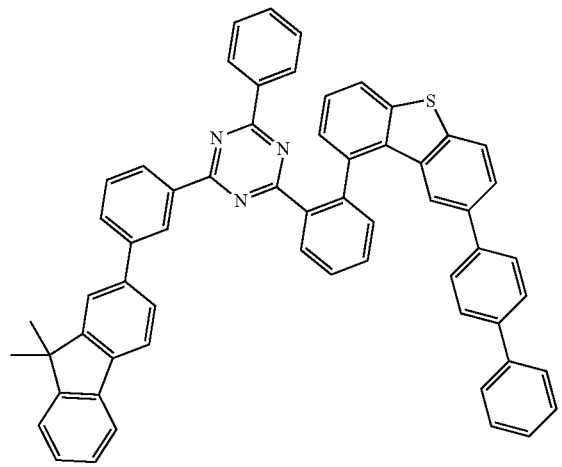
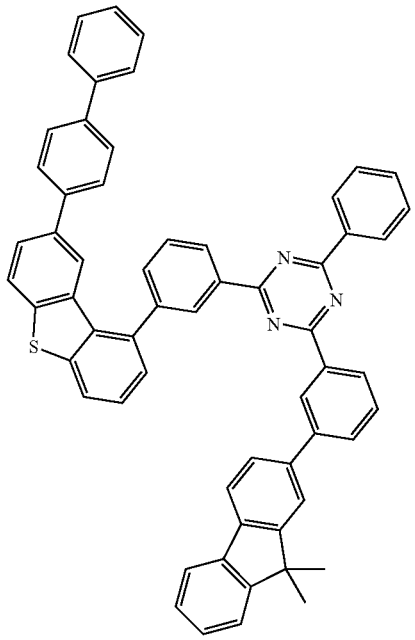
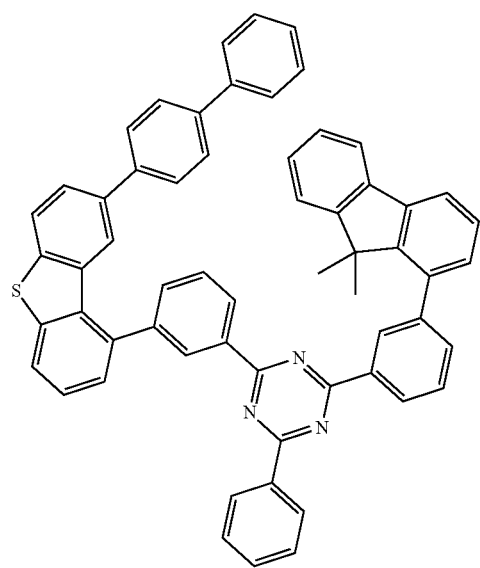
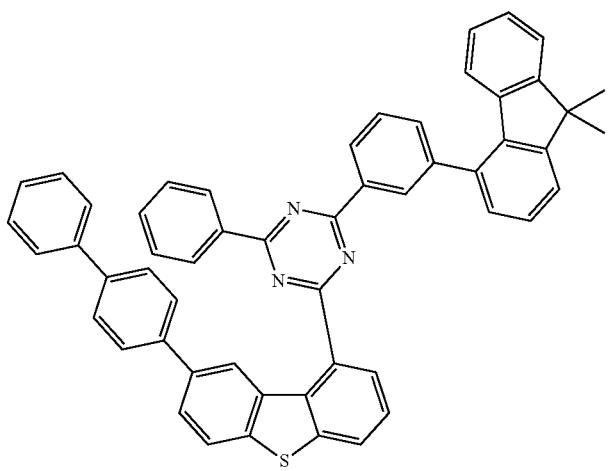
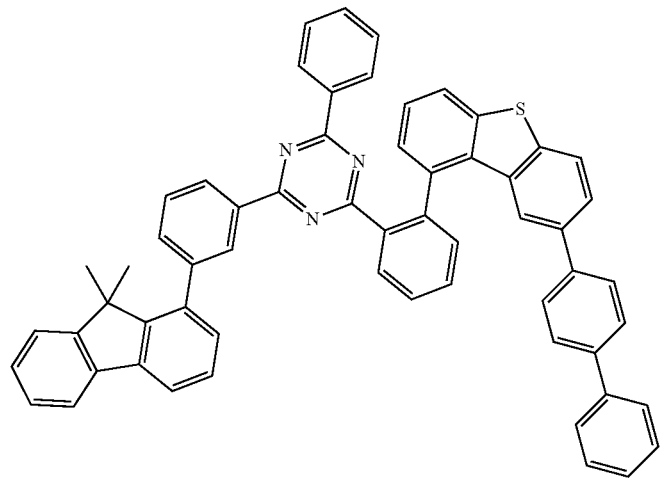

-continued
327
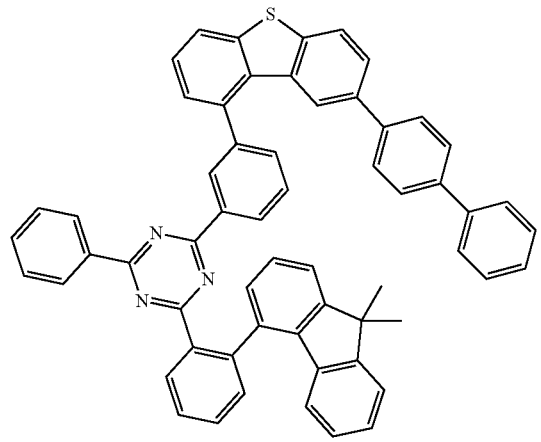
328
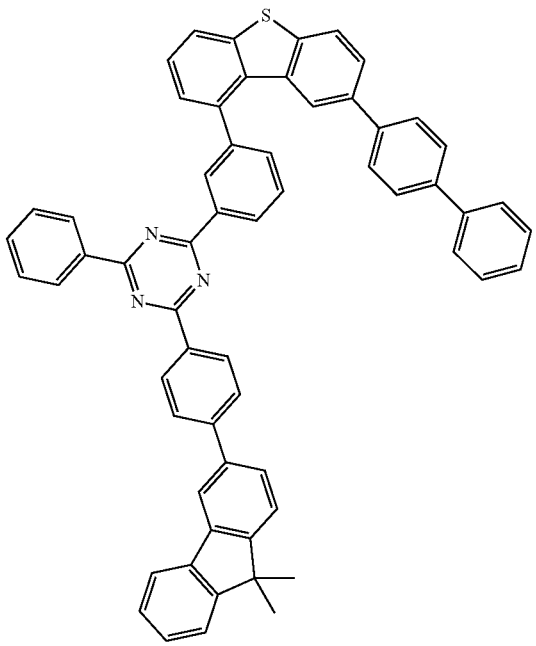
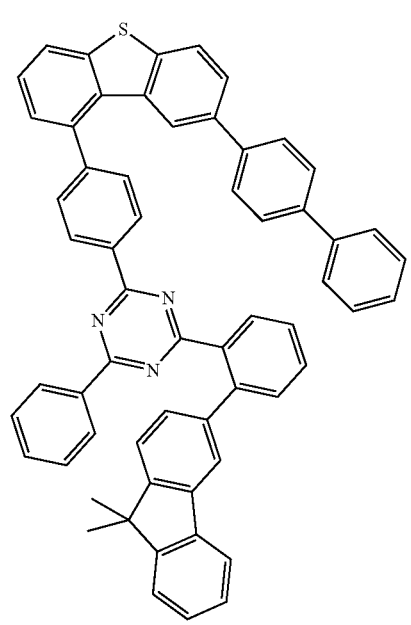
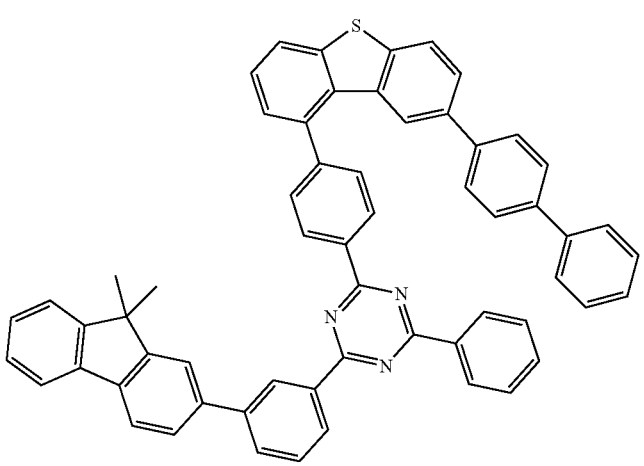

-continued
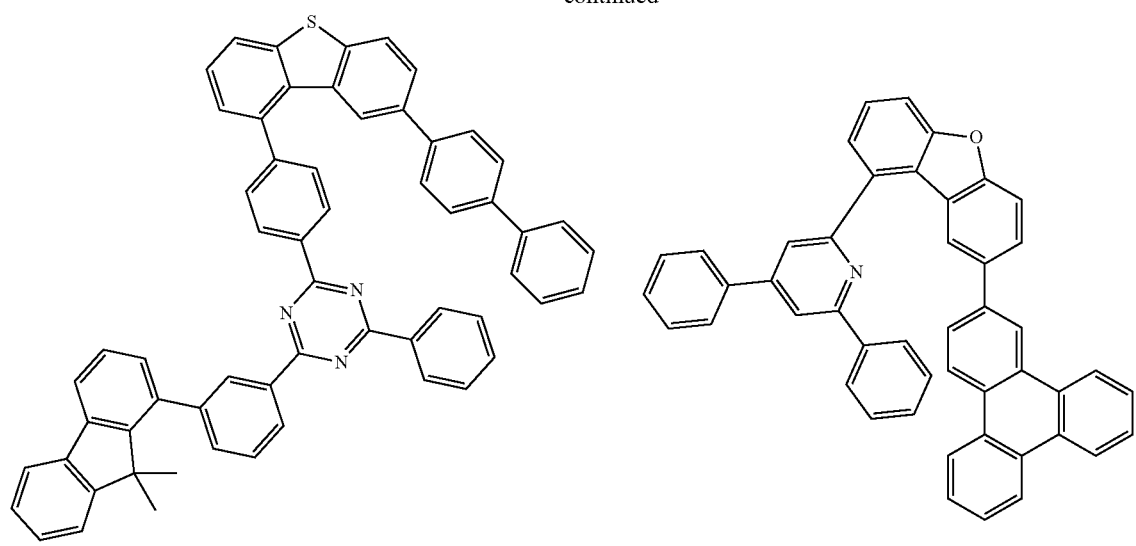
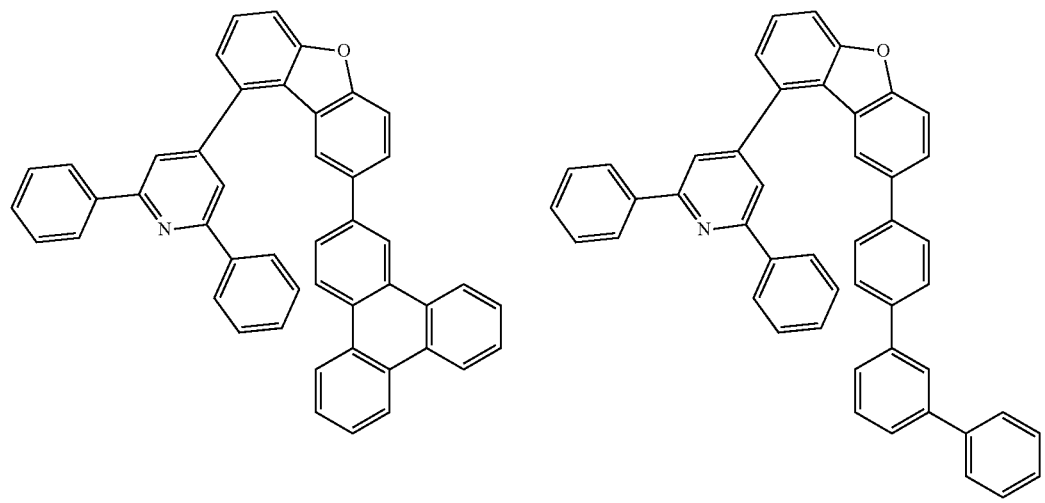
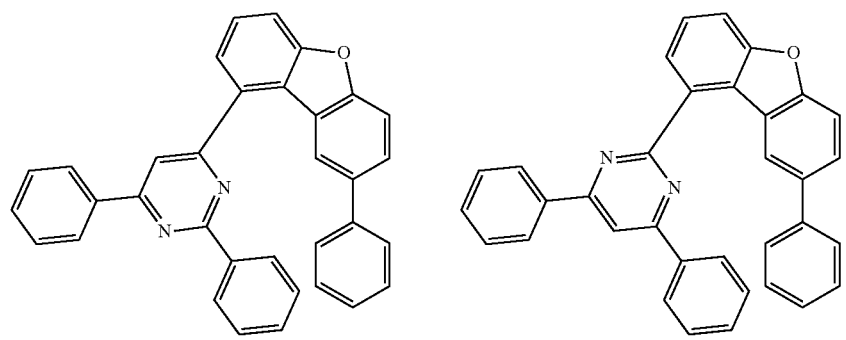

-continued

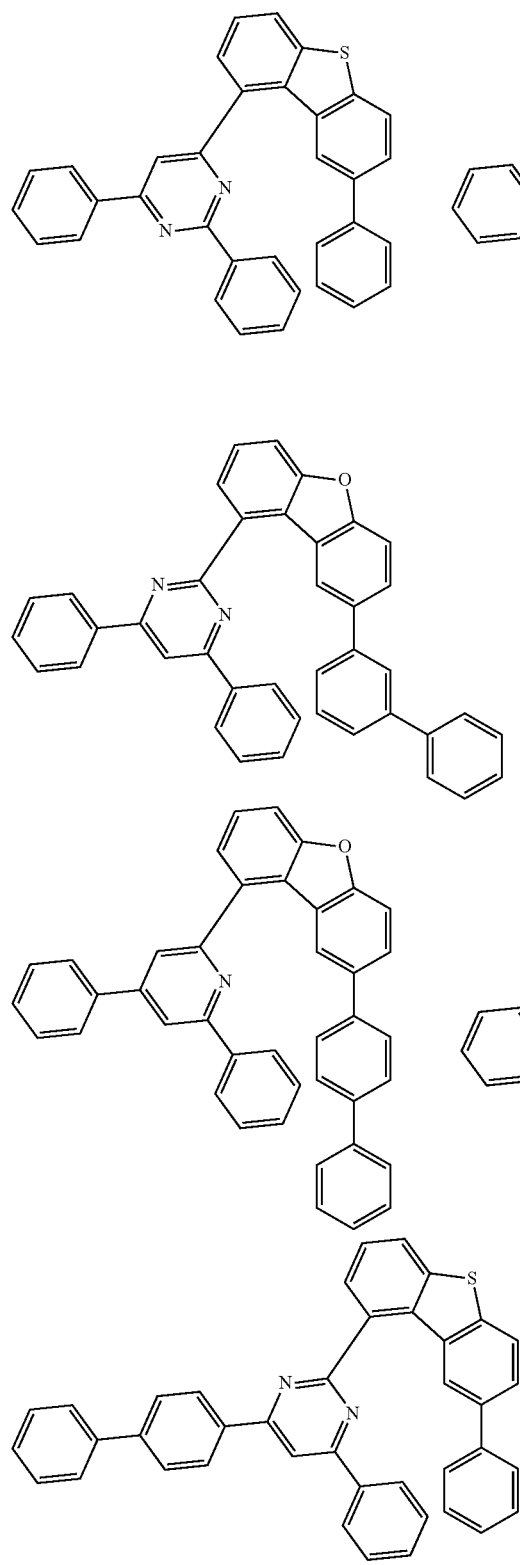

The compound represented by Chemical Formula 1 has a structure in which an N-atom-containing heteroaryl substituent group such as a pyridinyl group, a pyrimidinyl group, or a triazinyl group is connected to a specific position of dibenzofuran or dibenzothiophene core, and an aryl substituent group which is an aromatic group is connected to a specific position of the dibenzofuran or dibenzothiophene core, and thereby an organic light emitting device using the same has a higher efficiency, a lower driving voltage and a longer life time than an organic light emitting device using a compound in which a non-aromatic condensed ring group such as a fluorenyl group is connected.

Meanwhile, the compound represented by Chemical Formula 1 can be prepared in the same manner as shown in the following Reaction Scheme 1:

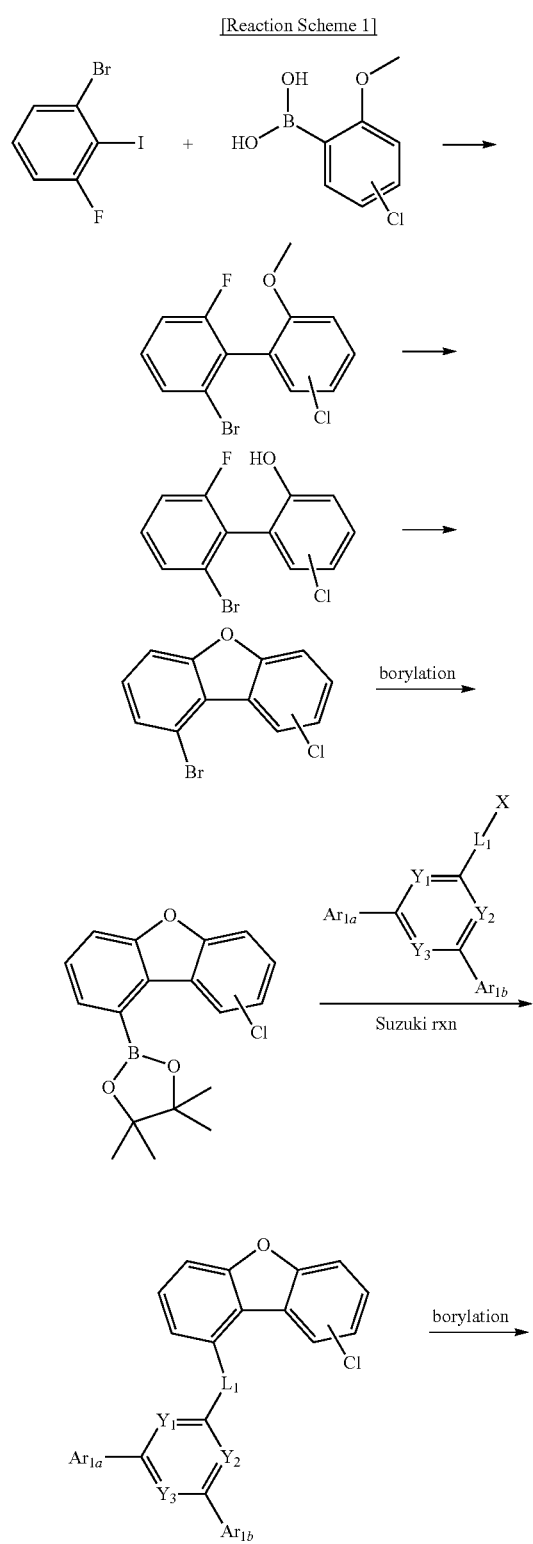

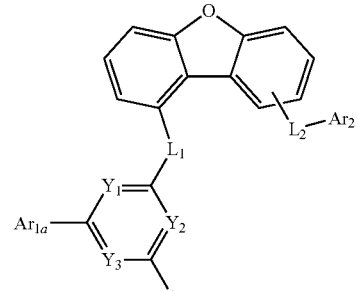

In Reaction Scheme 1, $L_1$, $L_2$, $Y_1$ to $Y_3$, $Ar_{1a}$, $Ar_{1b}$ and $Ar_2$ are as defined in Chemical Formula 1.

The compound represented by Chemical Formula 1 can be prepared by appropriately substituting the starting material in accordance with the structure of the compound to be prepared with reference to Reaction Scheme 1.

In addition, the present invention provides an organic light emitting device comprising the compound represented by Chemical Formula 1. In one example, the present invention provides an organic light emitting device comprising: a first electrode; a second electrode provided to face the first electrode; and one or more organic material layers provided between the first electrode and the second electrode, wherein one or more of the organic material layers comprise the compound of Chemical Formula 1.

The organic material layer of the organic light emitting device of the present invention may have a single layer structure, or a multilayered structure in which two or more organic material layers are laminated. For example, the organic light emitting device of the present invention may have a structure including a hole injection layer, a hole transport layer, a light emitting layer, an electron transport layer, an electron injection layer, and the like as the organic material layer. However, the structure of the organic light emitting device is not limited thereto, but may include a smaller number of organic layers.

Specifically, the organic material layer may include a light emitting layer, and the light emitting layer includes the compound represented by Chemical Formula 1.

In this case, the compound represented by Chemical Formula 1 can be used as a host material in the light emitting layer.

Further, the organic light emitting device according to the present invention may be an organic light emitting device having a structure (normal type) where an anode, one or more organic material layers, and a cathode are sequentially laminated on a substrate. Further, the organic light emitting device according to the present invention may be an organic light emitting device having an inverted direction structure (inverted type) where the cathode, one or more organic material layers, and the anode are sequentially laminated on the substrate. For example, the structure of the organic light emitting device according to one embodiment of the present invention is illustrated in FIGS. 1 and 2.

FIG. 1 illustrates an example of an organic light emitting device including a substrate 1, an anode 2, a light emitting layer 3, and a cathode 4. In such a structure, the compound represented by Chemical Formula 1 may be included in the light emitting layer.

Figure 2:
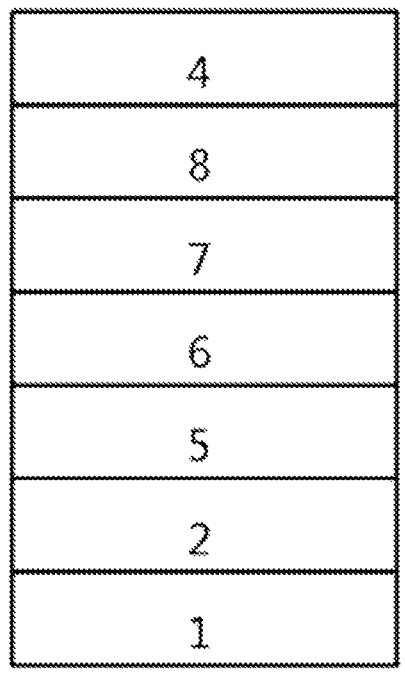
FIG. 2 shows an example of an organic light emitting element comprising a substrate 1, an anode 2, a hole injection layer 5, a hole transport layer 6, a light emitting layer 7, an electron transport layer 8 and a cathode 4.

FIG. 2 illustrates an example of an organic light emitting device including a substrate 1, an anode 2, a hole injection layer 5, a hole transport layer 6, a light emitting layer 7, an electron transport layer 8, and a cathode 4. In such a structure, the compound represented by Chemical Formula 1 may be included in one or more layers of the hole injection layer, the hole transport layer, the light emitting layer, and the electron transport layer.

The organic light emitting device according to the present invention may be manufactured by using materials and methods known in the art, except that one or more of organic material layers include the compound represented by Chemical Formula 1. Further, in the case where the organic light emitting device includes a plurality of organic material layers, the organic material layers may be formed of the same materials or different materials.

For example, the organic light emitting device according to the present invention may be manufactured by sequentially laminating the first electrode, the organic material layer, and the second electrode on the substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, the organic material layer, and an anode material on the substrate.

Further, the compound represented by Chemical Formula 1 may be formed as the organic material layer by a vacuum deposition method as well as a solution coating method during the production of the organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

In one example, the first electrode is the anode, and the second electrode is the cathode, and alternatively, the first electrode is the cathode, and the second electrode is the anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material layer is a layer injecting the holes from the electrode, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer receiving the holes from the hole injection layer and transporting the holes to the light emitting layer, and the hole transport material is a material that can receive the holes from the anode or the hole injection layer and transport the holes to the light emitting layer, and a material having large mobility to the holes is suitable. Specific examples thereof include an arylamine-based organic material, a conductive polymer, a block copolymer in which a conjugate portion and a non-conjugate portion are present together, and the like, but are not limited thereto.

The light emitting material layer is a material that can receive the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex ($Alq_3$); a carbazole-based compound; a dimerized styryl compound; BAlq; a 10-hydroxybenzoquinoline-metal compound; benzoxazole, benzothiazole, and benzimidazole-based compounds; a poly(p-phenylenevinylene) (PPV)-based polymer; a spiro compound; polyfluorene, rubrene, and the like, but are not limited thereto.

The light emitting layer may include a host material and a dopant material. Examples of the host material include a condensation aromatic cycle derivative, a heterocycle-containing compound, or the like. Specific examples of the condensation aromatic cycle derivative include an anthracene derivative, a pyrene derivative, a naphthalene derivative, a pentacene derivative, a phenanthrene compound, a fluoranthene compound, and the like, and specific examples of the heterocycle-containing compound include a carbazole derivative, a dibenzofuran derivative, a ladder-type furan compound, a pyrimidine derivative, and the like, but are not limited thereto.

Examples of the dopant material include an aromatic amine derivative, a styrylamine compound, a boron complex, a fluoranthene compound, a metal complex, and the like. Specifically, the aromatic amine derivative is a condensation aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport material is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. Particularly, it is preferable to use the compound represented by the above-mentioned chemical formula 1 as an electron transport material. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)-gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the used material.

Further, the compound represented by Chemical Formula 1 may be included in an organic solar cell or an organic transistor in addition to the organic light emitting device.

The preparation of the compound represented by Chemical Formula 1 and the organic light emitting device including the same will be described in detail in the following examples. However, these examples are presented for illustrative purposes only, and the scope of the present invention is not limited thereto.

Synthesis Example 1: Preparation of Intermediate Compound P-6

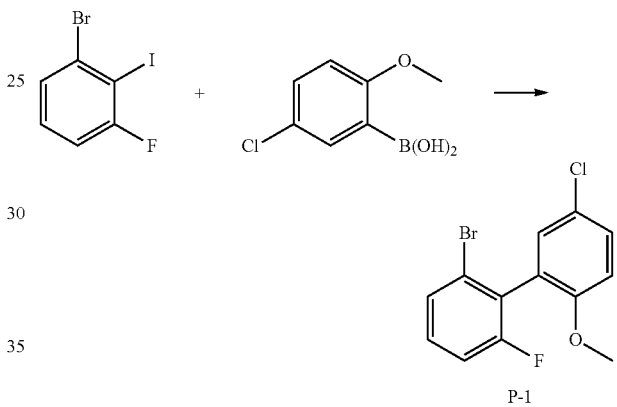

1-Bromo-3-fluoro-2-iodobenzene (100 g, 333.5 mmol) and (5-chloro-2-methoxyphenyl)boronic acid (62.2 g, 333.5 mmol) were dissolved in 800 ml of tetrahydrofuran (THF). Then, 2M sodium carbonate ($Na_2CO_3$) solution (500 mL) and tetrakis(triphenylphosphine)palladium(0) [$Pd(PPh_3)_4$] (7.7 g, 6.7 mmol) were added thereto, and the mixture was refluxed for 12 hours. After completion of the reaction, the mixture was cooled to room temperature, and then was extracted three times with water and toluene. The toluene layer was separated and dried with magnesium sulfate, and the filtrate was distilled under reduced pressure. The resulting mixture was recrystallized three times using chloroform and ethanol to obtain Compound P-1 (53.7 g, yield 51%; MS: $[M+H]^+=314$),

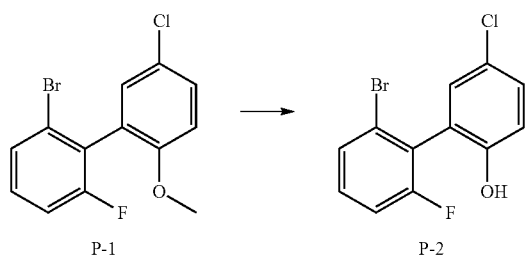

Compound P-1 (50.0 g, 158.5 mmol) was dissolved in dichloromethane (600 ml) and then cooled to 0° C. Boron tribromide (15.8 ml, 166.4 mmol) was slowly added dropwise thereto and then stirred for 12 hours. After completion of the reaction, the mixture was washed three times with water, dried with magnesium sulfate, and filtered. The filtrate was distilled under reduced pressure and purified by column chromatography to obtain Compound P-2 (47.4 g, yield 99%; MS: [M+H]$^+$=300).

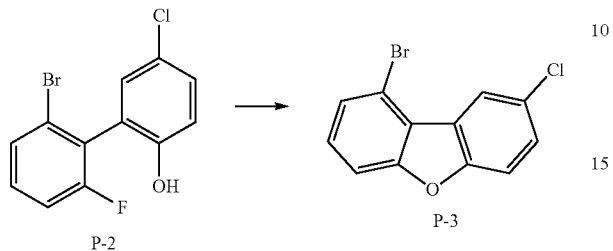

Compound P-2 (40.0 g, 132.7 mmol) was dissolved in distilled dimethylformamide (DMF) (400 ml). This solution was cooled to 0° C. and sodium hydride (3.5 g, 145.9 mmol) was slowly added dropwise thereto. After stirring for 20 minutes, the mixture was stirred at 100° C. for 1 hour. After completion of the reaction, the reaction mixture was cooled to room temperature and 100 ml of ethanol was slowly added. The mixture was distilled under reduced pressure, and the resulting mixture was recrystallized from chloroform and ethyl acetate to obtain Compound P-3 (30.3 g, yield 81%; MS: [M+H]$^+$=280).

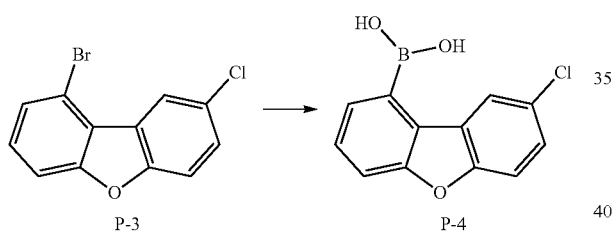

After Compound P-3 (30.0 g, 106.6 mmol) was dissolved in tetrahydrofuran (300 ml), the temperature was lowered to −78° C. and 1.7M tert-butyllithium (t-BuLi) (62.7 ml, 106.6 mmol) was slowly added. After stirring at the same temperature for one hour, triisopropyl borate (B(OiPr)$_3$) (28.3 ml, 213.1 mmol) was added and stirred for 3 hours while gradually increasing the temperature to room temperature. To the reaction mixture was added 2N aqueous hydrochloric acid solution (200 mil) and then stirred at room temperature for 1.5 hours. The resulting precipitate was filtered, washed sequentially with water and ethyl ether, and dried under vacuum. After drying, the mixture was dispersed in ethyl ether, stirred for 2 hours, filtered and dried to obtain Compound P-4 (24.4 g, yield 93%; MS: [M+H]$^+$=247).

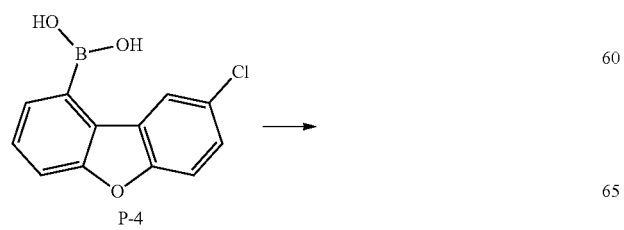

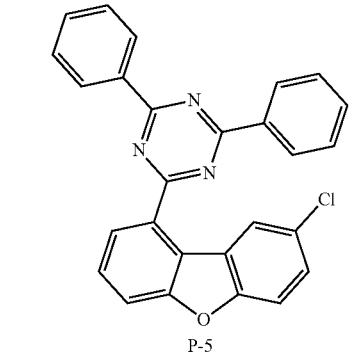

After Compound P-4 (20.0 g, 81.2 mmol) and 2-chloro-4,6-diphenyl-1,3,5-triazine (21.8 g, 81.2 mmol) were dispersed in tetrahydrofuran (250 ml), 2M aqueous potassium carbonate solution (aq. K$_2$CO$_3$) (33.6 ml, 243.5 mmol) was added, tetrakis(triphenylphosphine)palladium [Pd(PPh$_3$)$_4$] (1.9 g, 2 mol %) was added, and then the mixture was stirred and refluxed for 4 hours. The temperature was lowered to room temperature and the resulting solid was filtered. The filtrated solid was recrystallized from tetrahydrofuran and ethyl acetate, filtered and then dried to obtain Compound P-5 (32.4 g, yield 92%; MS: [M+H]$^+$=434).

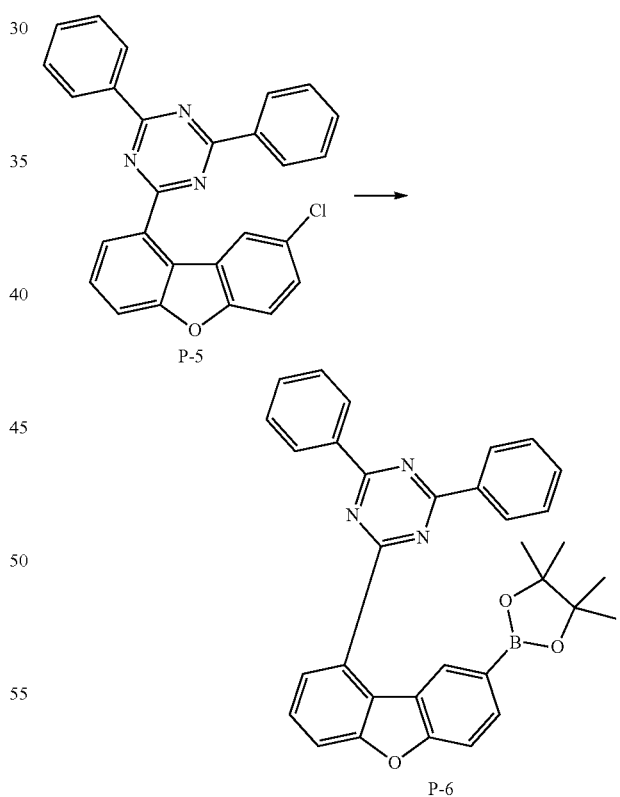

Compound P-5 (30 g, 69.2 mmol), bis(pinacolato)diboron (19.3 g, 76.1 mmol), potassium acetate (20.4 g, 207.5 mmol), and tetrakis (triphenylphosphine)palladium(0) [Pd(PPh$_3$)$_4$] (1.6 g, 2 mol %) was added to tetrahydrofuran (300 ml) and refluxed for 12 hours. After completion of the reaction, the mixture was cooled to room temperature and distilled under reduced pressure to remove the solvent. This was dissolved in chloroform, washed three times with water, and then the organic layer was separated, dried with magnesium sulfate and then distilled under reduced pressure to obtain Compound P-6 (34.5 g, yield 95%; MS: [M+H]$^+$=526).

Synthesis Example 1-1: Preparation of Compound 1

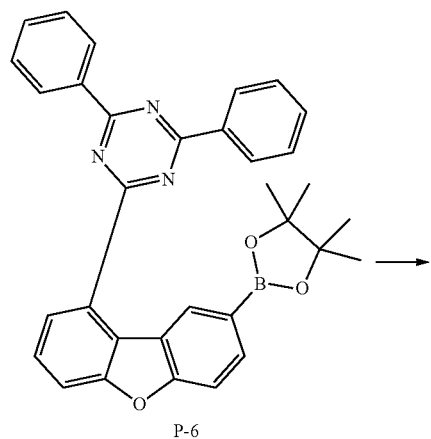

P-6

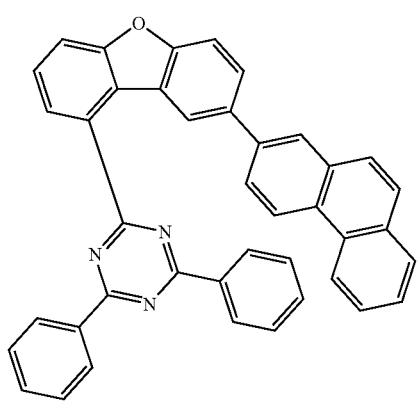

Compound 1

After Compound P-6 (20.0 g, 38.1 mmol) and 2-bromophenanthrene (9.8 g, 38.1 mmol) were dispersed in tetrahydrofuran (250 ml), 2M aqueous potassium carbonate solution (aq. K$_2$CO$_3$) (57.2 ml, 114.3 mmol) was added and tetrakis(triphenylphosphine)palladium [Pd(PPh$_3$)$_4$] (1.4 g, 2 mol %) was added, and then the mixture was stirred and refluxed for 5 hours. The temperature was lowered to room temperature and the resulting solid was filtered. The filtered solid was recrystallized from chloroform and ethyl acetate, filtered and then dried to obtain Compound 1 (17.8 g, yield 81%; MS: [M+H]$^+$=576).

Synthesis Example 1-2: Preparation of Compound 2

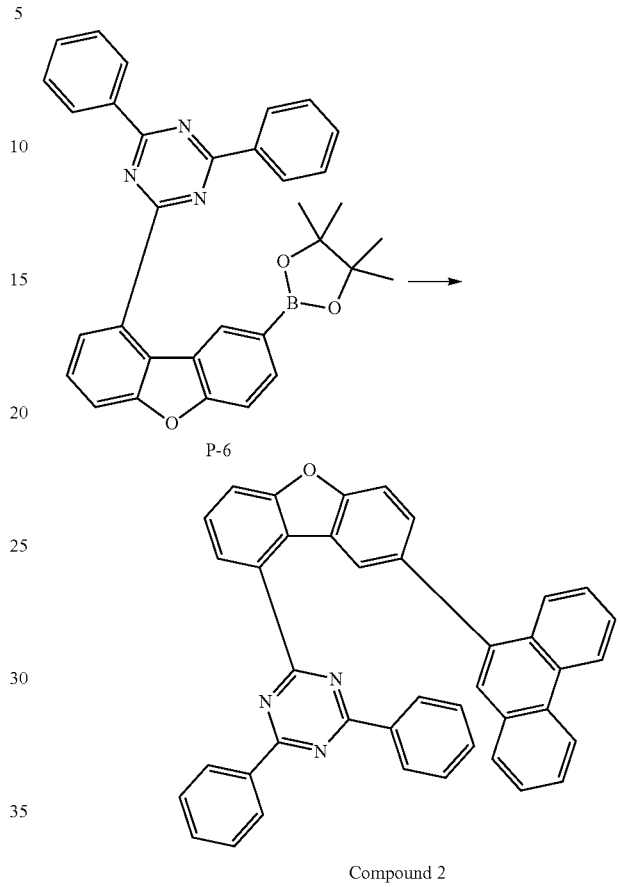

Compound 2

Compound 2 (18.4 g, yield 84%; MS: [M+H]$^+$=576) was prepared in the same manner as in Synthesis Example 1-1, except that 9-bromophenanthrene (9.8 g, 38.1 mmol) was used instead of 2-bromophenanthrene.

Synthesis Example 1-3: Preparation of Compound 3

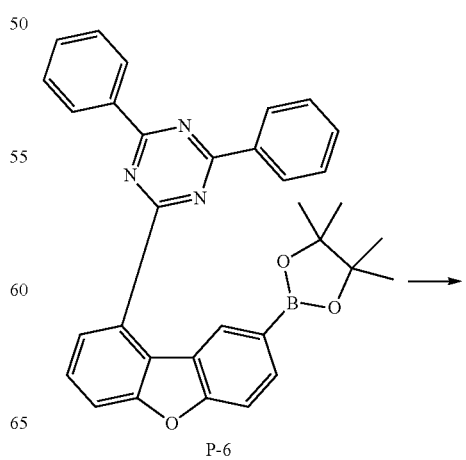

P-6

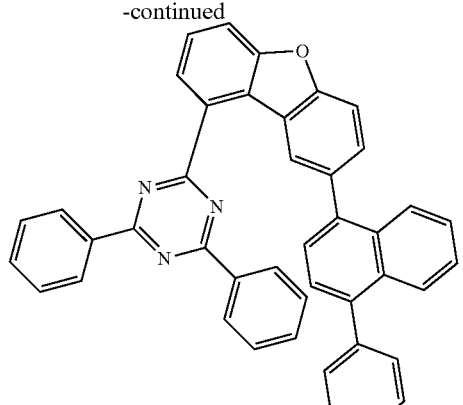

Compound 3

Compound 3 (18.8 g, yield 82%; MS: [M+H]$^+$=602) was prepared in the same manner as in Synthesis Example 1-1, except that 1-bromo-4-phenylnaphthalene (10.8 g, 38.1 mmol) was used instead of 2-bromophenanithrene.

Synthesis Example 1-4: Preparation of Compound 4

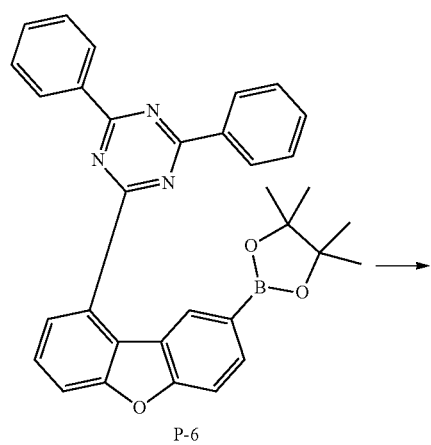

P-6

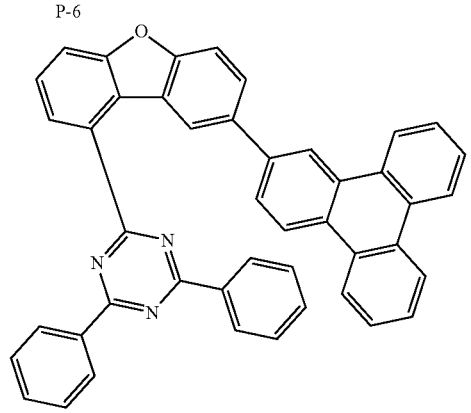

Compound 4

Compound 4 (21.0 g, yield 88%; MS: [M+H]$^+$=626) was prepared in the same manner as in Synthesis Example 1-1, except that 2-bromotriphenylene (11.7 g, 38.1 mmol) was used instead of 2-bromophenanthrene.

Synthesis Example 1-5: Preparation of Compound 11

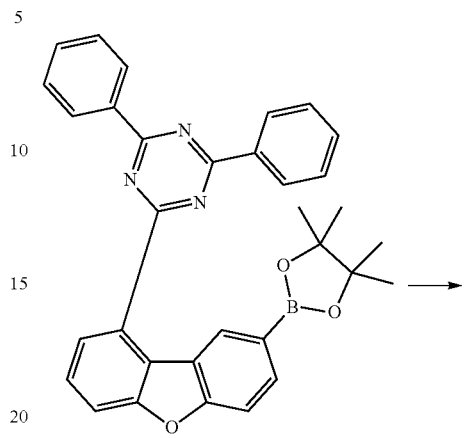

P-6

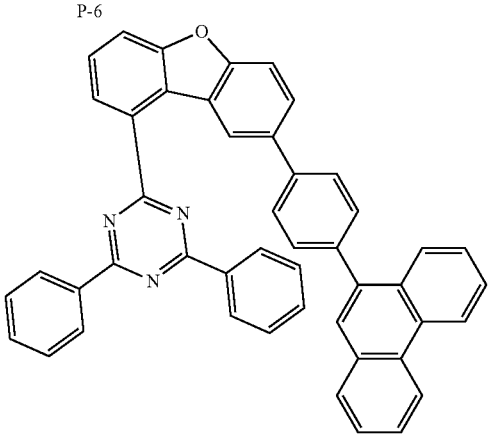

Compound 11

Compound 11 (19.9 g, yield 80%; MS: [M+H]$^+$=652) was prepared in the same manner as in Synthesis Example 1-1, except that 9-(4-bromophenyl)phenanthrene (12.7 g, 38.1 mmol) was used instead of 2-bromophenanthrene.

Synthesis Example 1-6: Preparation of Compound 12

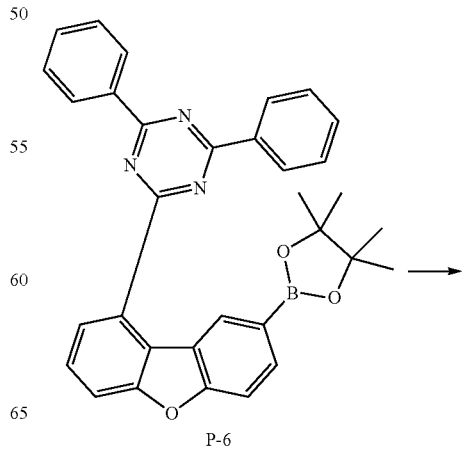

P-6

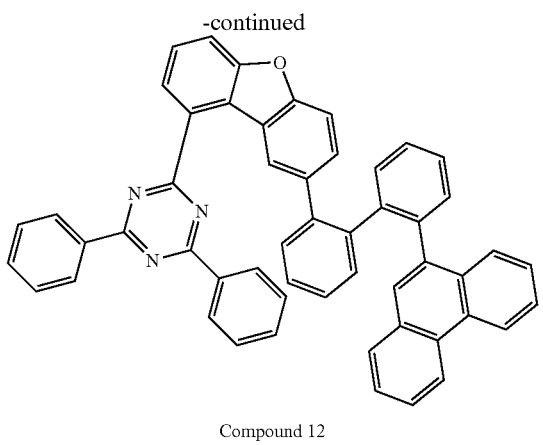

Compound 12

Compound 12 (22.5 g, yield 81%; MS: [M+H]$^+$=728) was prepared in the same manner as in Synthesis Example 1-1, except that 9-(2'-bromo-[1,1'-biphenyl]-2-yl)phenanthrene (15.6 g, 38.1 mmol) was used instead of 2-bromophenanthrene.

Synthesis Example 1-7: Preparation of Compound 13

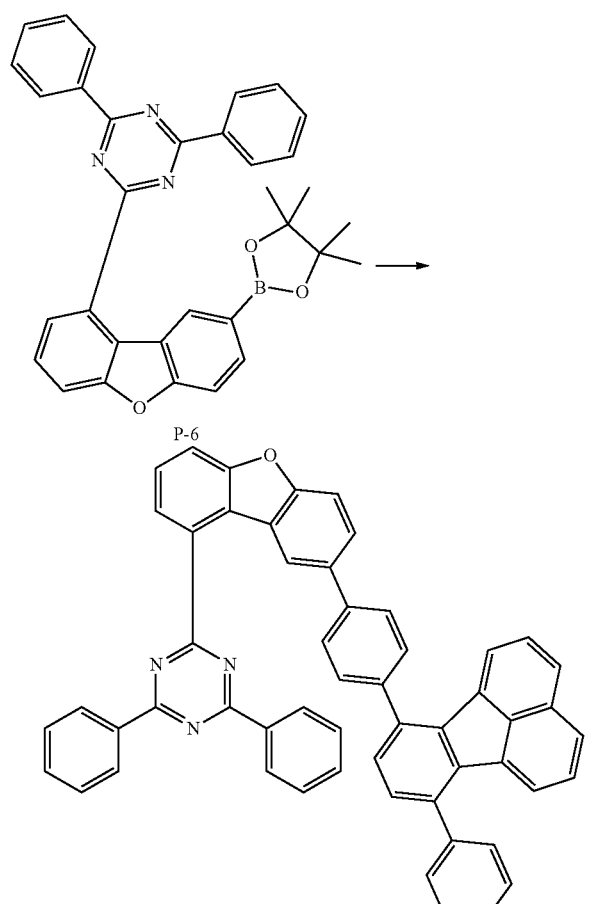

Compound 13

Compound 13 (21.8 g, yield 76%; MS: [M+H]$^+$=752) was prepared in the same manner as in Synthesis Example 1-1, except that 7-(4-bromophenyl)-10-phenylfluoranthene (16.5 g, 38.1 mmol) was used instead of 2-bromophenanthrene.

Synthesis Example 1-8: Preparation of Compound 25

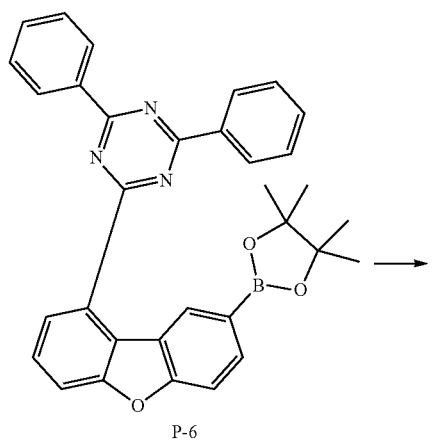

P-6

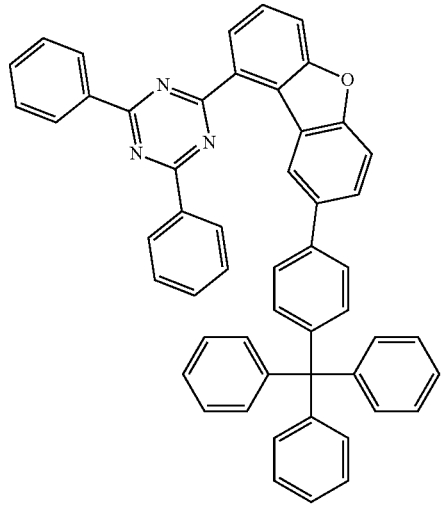

Compound 25

Compound 25 (24.3 g, yield 89%; MS: [M+H]$^+$=718) was prepared in the same manner as in Synthesis Example 1-1, except that ((4-bromophenyl)methanetriyl)tribenzene (15.2 g, 38.1 mmol) was used instead of 2-bromophenanthrene.

Synthesis Example 1-9: Preparation of Compound 26

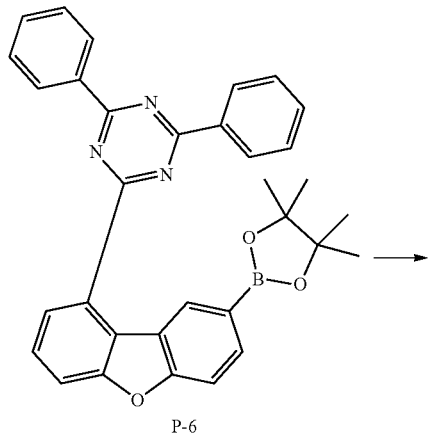

P-6

Synthesis Example 1-10: Preparation of Compound 28

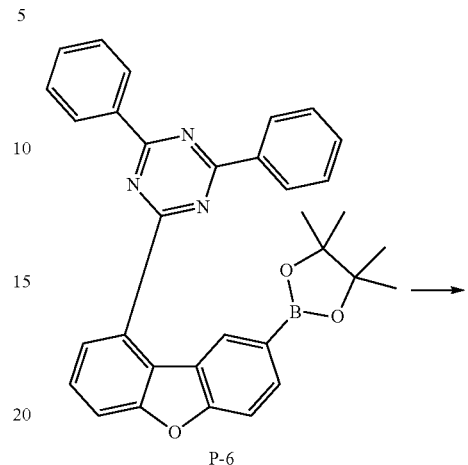

P-6

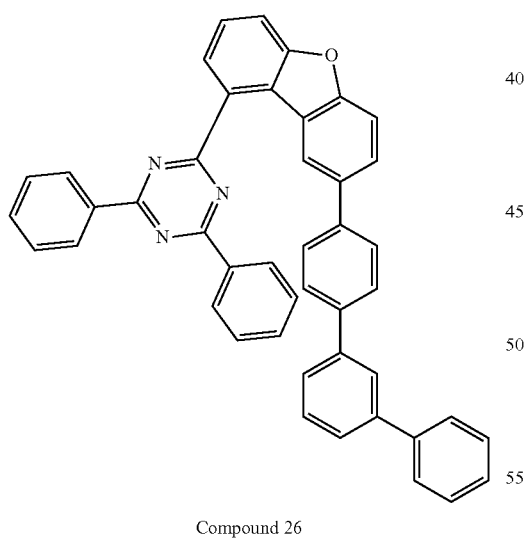

Compound 26

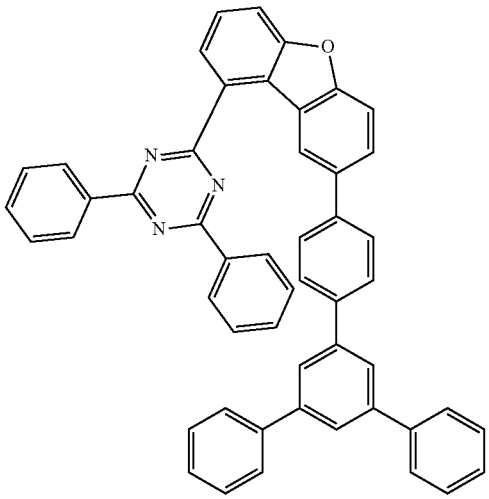

Compound 28

Compound 26 (19.9 g, yield 83%; MS: [M+H]$^+$=628) was prepared in the same manner as in Synthesis Example 1-1, except that 4-bromo-1,1':3',1''-terphenyl (11.8 g, 38.1 mmol) was used instead of 2-bromophenanthrene.

Compound 28 (21.7 g, yield 81%; MS: [M+H]$^+$=704) was prepared in the same manner as in Synthesis Example 1-1, except that 4-bromo-5'-phenyl-1,1':3',1''-terphenyl (14.7 g, 38.1 mmol) was used instead of 2-bromophenanthrene.

Synthesis Example 1-11: Preparation of Compound 46

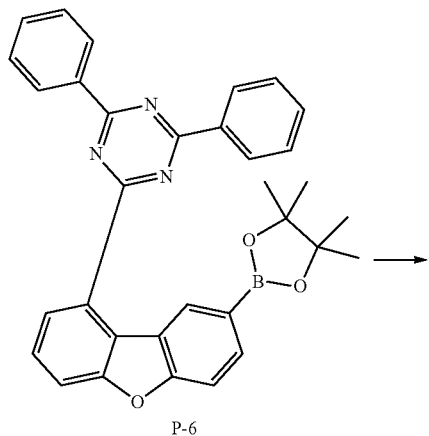
P-6

Synthesis Example 1-12: Preparation of Compound 55

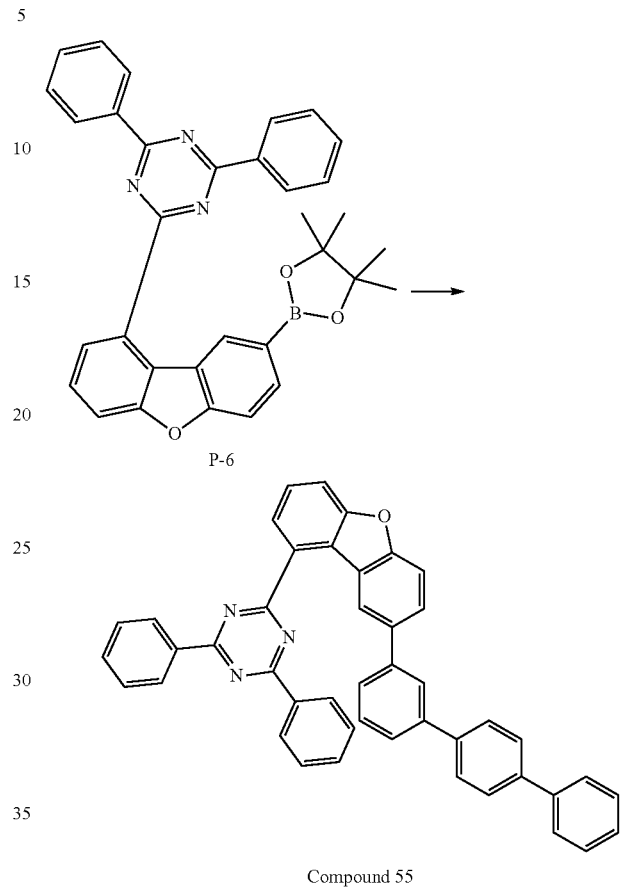
P-6

Compound 55

Compound 55 (20.6 g, yield 86%; MS: [M+H]$^+$=628) was prepared in the same manner as in Synthesis Example 1-1, except that 3-bromo-1,1':4',1''-terphenyl (11.8 g, 38.1 mmol) was used instead of 2-bromophenanthrene.

Synthesis Example 1-13: Preparation of Compound 57

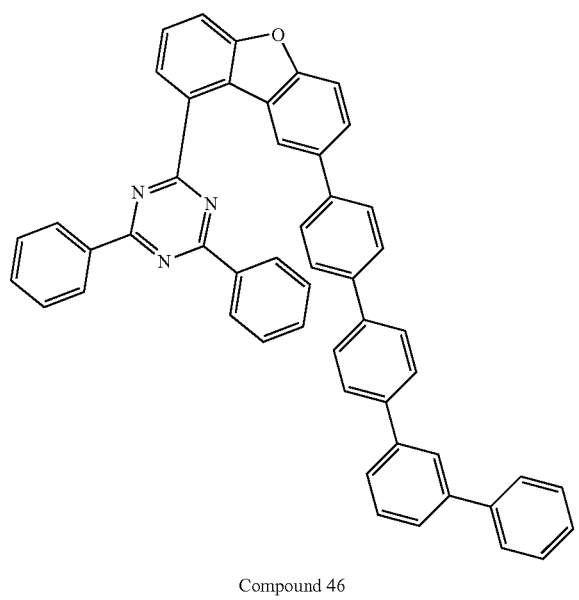
Compound 46

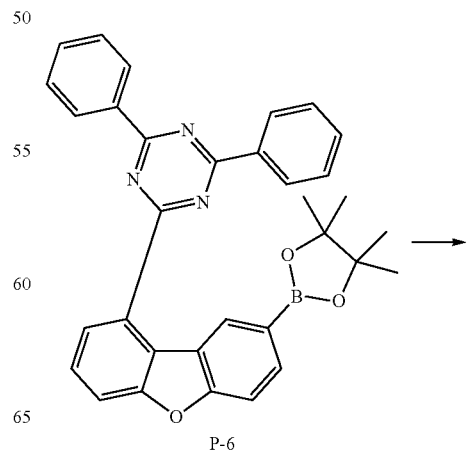
P-6

Compound 46 (22.3 g, yield 83%; MS: [M+H]$^+$=704) was prepared in the same manner as in Synthesis Example 1-1, except that 4'''-bromo-1, 1:3',1:4,1'''-quaterphenyl (14.7 g, 38.1 mmol) was used instead of 2-bromophenanthrene.

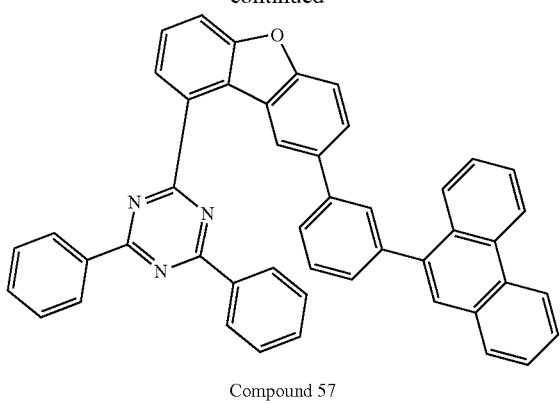

Compound 57

Compound 57 (20.4 g, yield 82%; MS: [M+H]⁺=652) was prepared in the same manner as in Synthesis Example 1-1, except that 9-(3-bromophenyl)phenanthrene (12.7 g, 38.1 mmol) was used instead of 2-bromophenanthrene.

Synthesis Example 1-14: Preparation of Compound 62

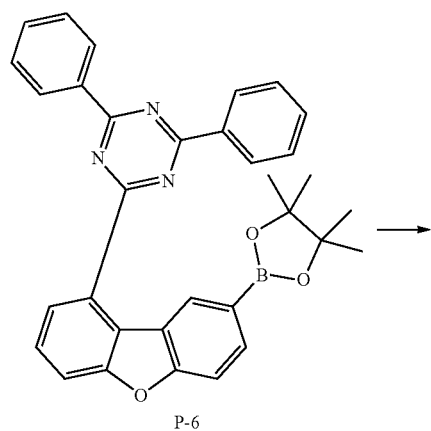

P-6

Compound 62

Compound 62 (22.3 g, yield 83%; MS: [M+H]⁺=704) was prepared in the same manner as in Synthesis Example 1-1, except that 3-bromo-5'-phenyl-1,1:3',1"-terphenyl (14.7 g, 38.1 mmol) was used instead of 2-bromophenanthrene.

Synthesis Example 1-15: Preparation of Compound 65

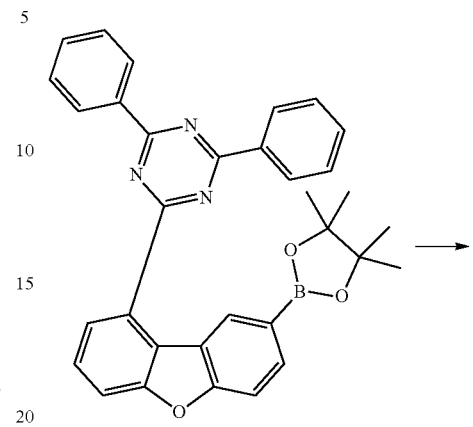

P-6

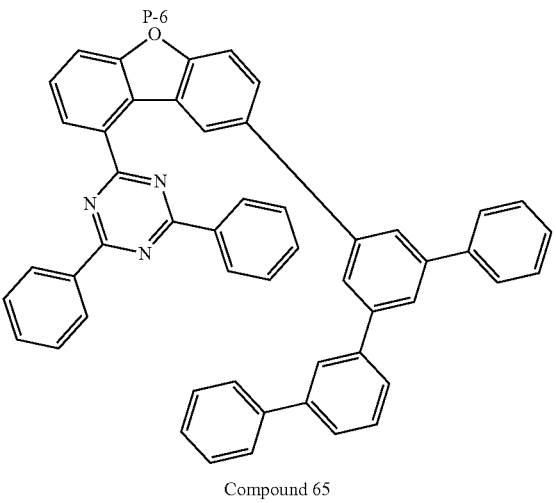

Compound 65

Compound 65 (21.7 g, yield 81%; MS: [M+H]⁺=704) was prepared in the same manner as in Synthesis Example 1-1, except that 5'-bromo-1,1':3,1":3",1"'-quaterphenyl (14.7 g, 38.1 mmol) was used instead of 2-bromophenanthrene.

Synthesis Example 1-16: Preparation of Compound 66

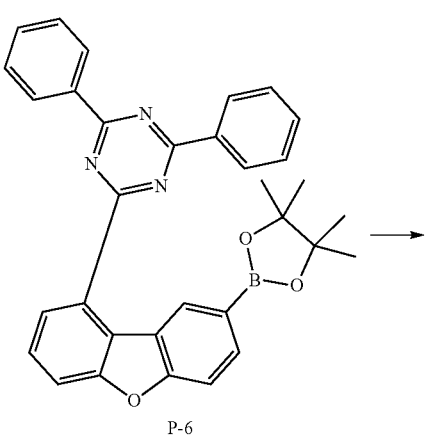

P-6

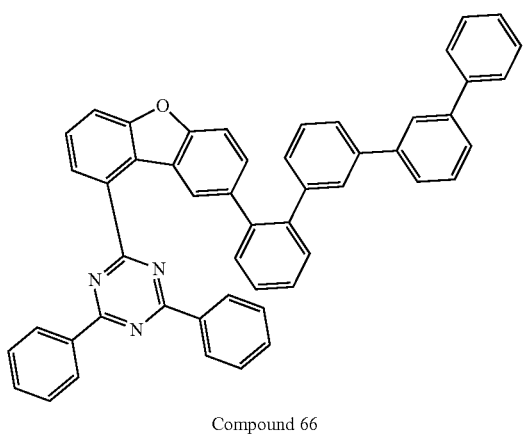

Compound 66

Compound 66 (20.6 g, yield 77%; MS: [M+H]$^+$=704) was prepared in the same manner as in Synthesis Example 1-1, except that 2-bromo-1,1':3',1":3",1'''quaterphenyl (14.7 g, 38.1 mmol) was used instead of 2-bromophenanthrene.

Synthesis Example 1-17: Preparation of Compound 68

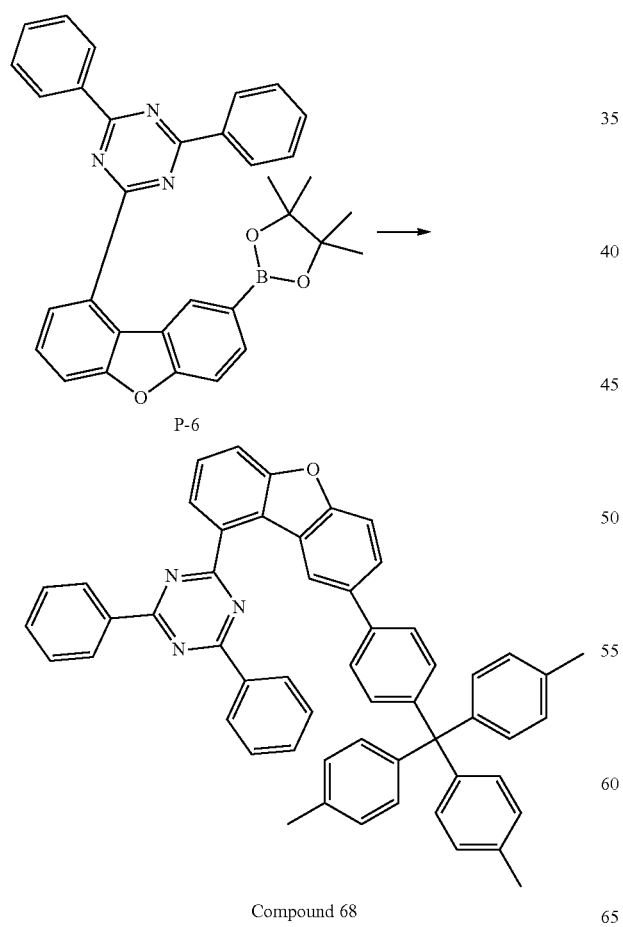

Compound 68

Compound 68 (22.9 g, yield 79%; MS: [M+H]$^+$=760) was prepared in the same manner as in Synthesis Example 1-1, except that 4,4',4"-((4-bromophenyl)methanetriyl)tris(methylbenzene) (16.9 g, 38.1 mmol) was used instead of 2-bromophenanthrene.

Synthesis Example 1-18: Preparation of Compound 72

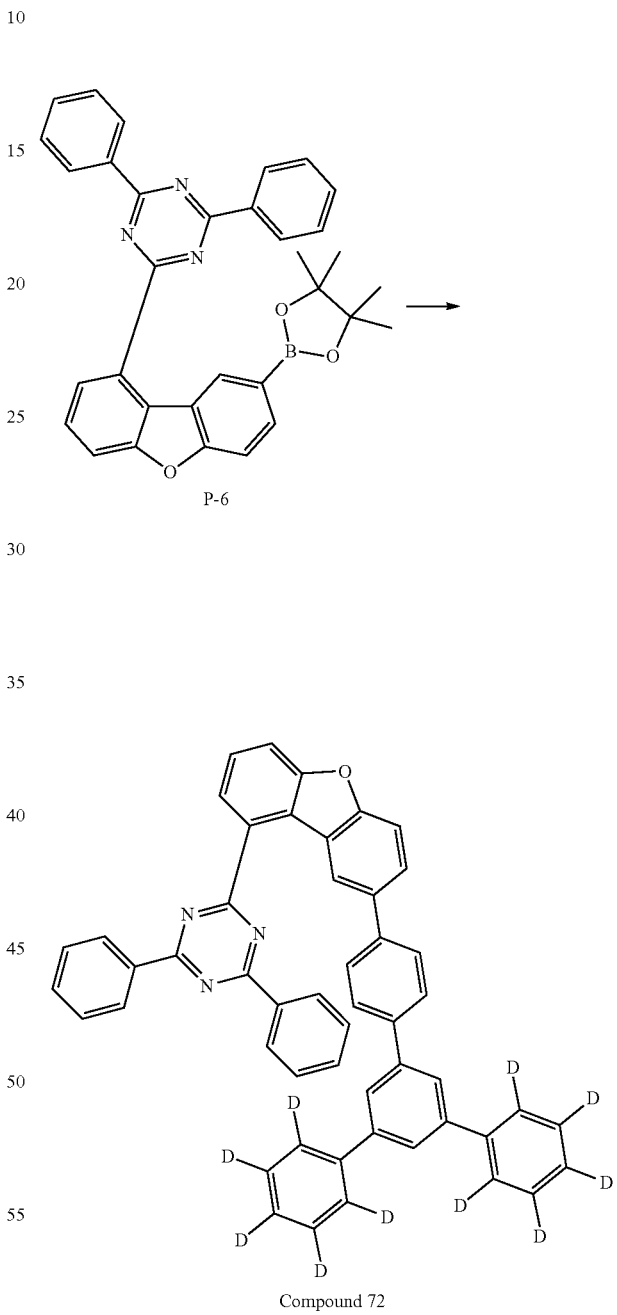

Compound 72

Compound 72 (20.7 g, yield 76%; MS: [M+H]$^+$=714) was prepared in the same manner as in Synthesis Example 1-1, except that 5'-(4-bromophenyl)-1,1':3',1"-terphenyl-2,2",3,3",4,4",5,5",6,6"-d10 (15.1 g, 38.1 mmol) was used instead of 2-bromophenanthrene.

Synthesis Example 1-19: Preparation of Compound 81

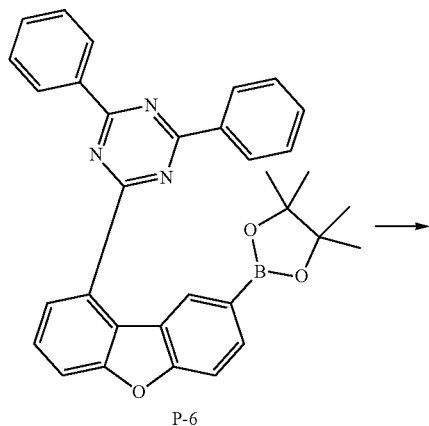

P-6

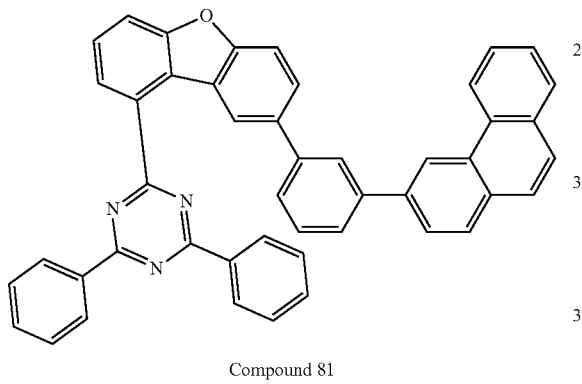

Compound 81

Compound 81 (18.9 g, yield 76%; MS: [M+H]$^+$=652) was prepared in the same manner as in Synthesis Example 1-1, except that 3-(3-bromophenyl)phenanthrene (12.7 g, 38.1 mmol) was used instead of 2-bromophenanthrene.

Synthesis Example 1-20: Preparation of Compound 59

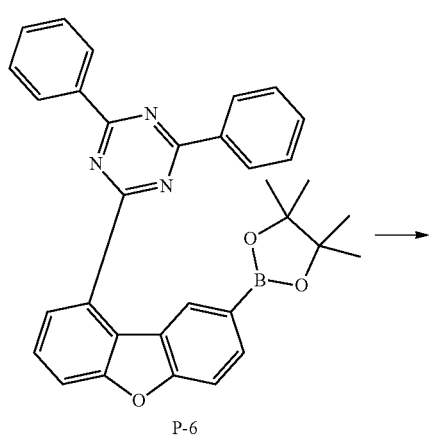

P-6

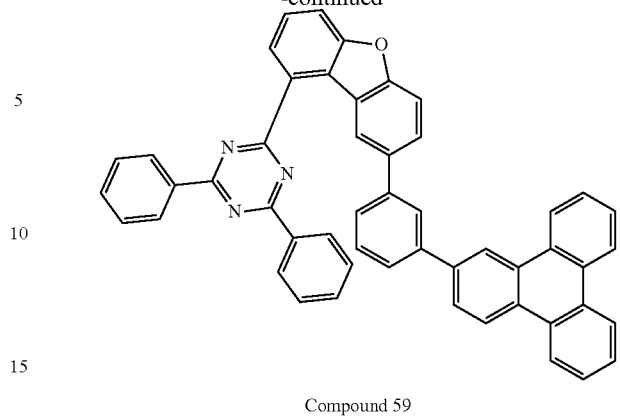

Compound 59

Compound 59 (19.5 g, yield 73%; MS: [M+H]$^+$=702) was prepared in the same manner as in Synthesis Example 1-1, except that 2-(3-bromophenyl)triphenylene (14.6 g, 38.1 mmol) was used instead of 2-bromophenanthrene.

Synthesis Example 1-21: Preparation of Compound 45

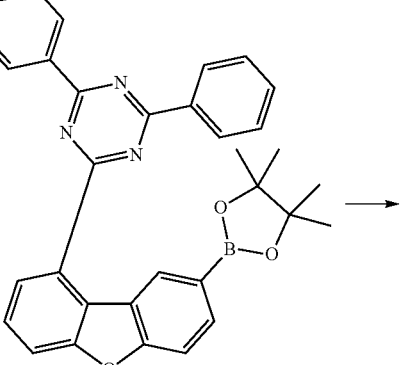

P-6

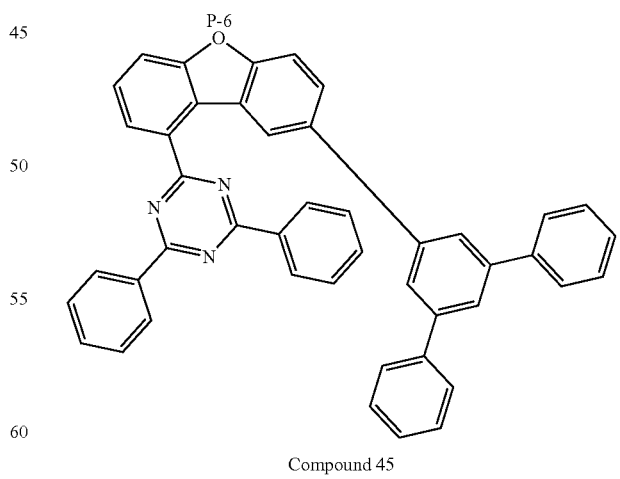

Compound 45

Compound 45 (19.4 g, yield 81%; MS: [M+H]$^+$=628) was prepared in the same manner as in Synthesis Example 1-1, except that 5'-bromo-1,1':3',1''-terphenyl (11.8 g, 38.1 mmol) was used instead of 2-bromophenanthrene.

Synthesis Example 1-22: Preparation of Compound 54

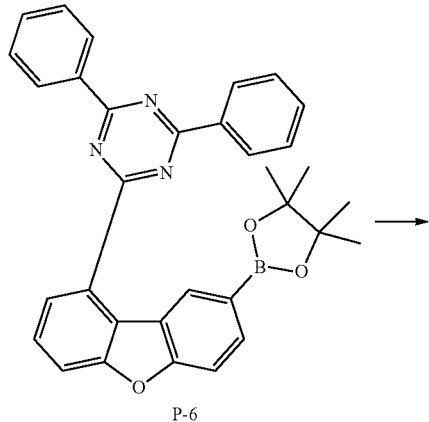
P-6

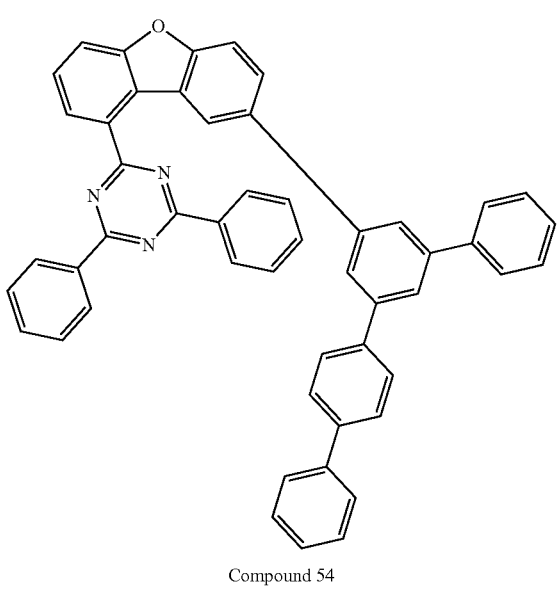
Compound 54

Compound 54 (21.2 g, yield 79%; MS: [M+H]⁺=704) was prepared in the same manner as in Synthesis Example 1-1, except that 5'-bromo-1,1':3,1":4",1‴-quaterphenyl (14.7 g, 38.1 mmol) was used instead of 2-bromophenanthrene.

Synthesis Example 1-23: Preparation of Compound 29

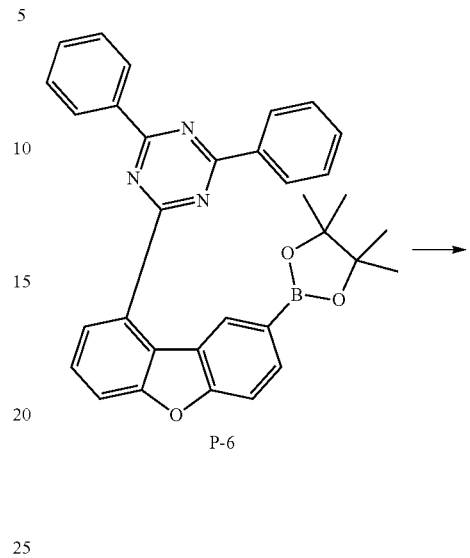
P-6

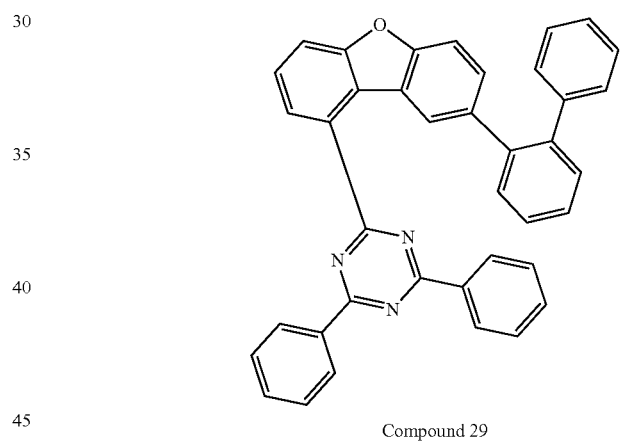
Compound 29

Compound 29 (15.6 g, yield 74%; MS: [M+H]⁺=552) was prepared in the same manner as in Synthesis Example 1-1, except that 2-bromo-1,1'-biphenyl (8.9 g, 38.1 mmol) was used instead of 2-bromophenanthrene.

Synthesis Example 2: Preparation of Intermediate Compound P-8

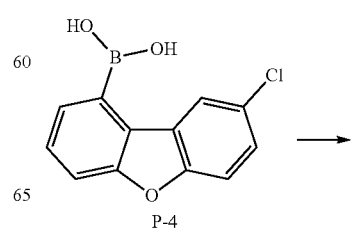
P-4

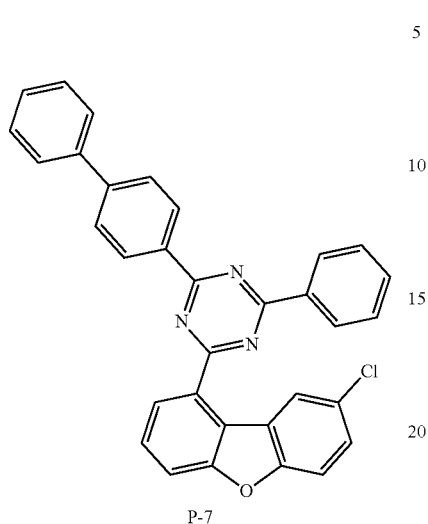

P-7

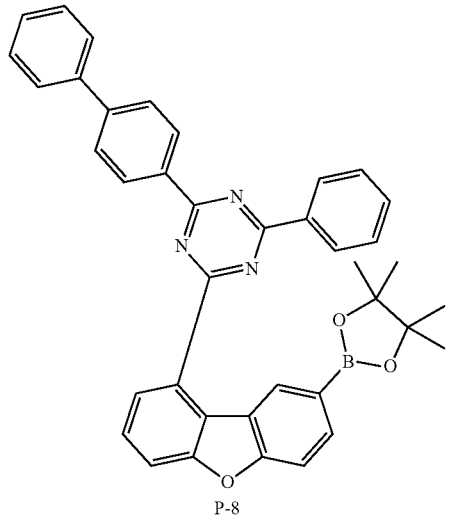

P-8

After Compound P-4 (40.0 g, 162.3 mmol) and 2-([1,1'-biphenyl]-4-yl)-4-chloro-6-phenyl-1,3,5-triazine (55.8 g, 162.3 mmol) were dispersed in tetrahydrofuran (500 ml), 2M potassium carbonate aqueous solution (aq. $K_2CO_3$) (67.2 ml, 486.9 mmol) was added and then tetrakis(triphenylphosphine) palladium [$Pd(PPh_3)_4$] (3.8 g, 2 mol %) was added, and the mixture was stirred and refluxed for 4 hours. The temperature was lowered to room temperature and the resulting solid was filtered. The filtered solid was recrystallized from tetrahydrofuran and ethyl acetate, filtered and then dried to obtain Compound P-7 (73.7 g, yield 89%; MS: $[M+H]^+$=510).

Compound P-7 (70.5 g, 138.3 mmol), bis(pinacolato)diboron (38.6 g, 152.13 mmol), potassium acetate (40.7 g, 414.9 mmol), and tetrakis(triphenylphosphine)palladium(0) [$Pd(PPha)_4$] (3.2 g, 2 mol %) were added to tetrahydrofuran (600 ml) and refluxed for 12 hours. After completion of the reaction, the reaction mixture was cooled to room temperature and distilled under reduced pressure to remove the solvent. This was dissolved in chloroform and washed three times with water. The organic layer was separated, dried with magnesium sulfate, and then distilled under reduced pressure to obtain Compound P-8 (75.7 g, yield 91%; MS: $[M+H]^+$=602).

Synthesis Example 2-1: Preparation of Compound 9

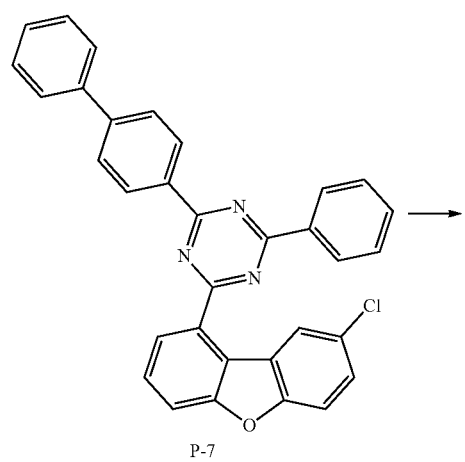

P-7 →

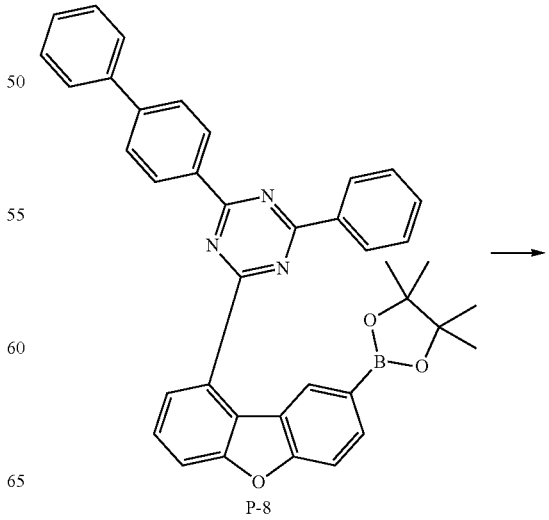

P-8 →

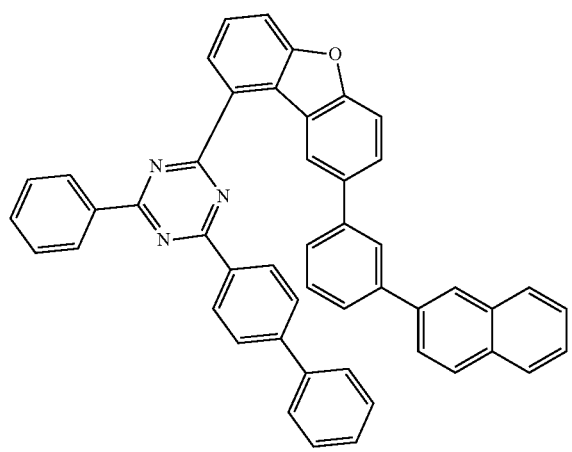

Compound 9

Compound 9 (19.9 g, yield 77%; MS: [M+H]$^+$=678) was prepared in the same manner as in Synthesis Example 1-1, except for using Compound P-8 (22.9 g, 38.1 mmol) instead of Compound P-6, and 2-(3-bromophenyl)naphthalene (10.8 g, 38.1 mmol) instead of 2-bromophenanthrene.

Synthesis Example 2-2: Preparation of Compound 27

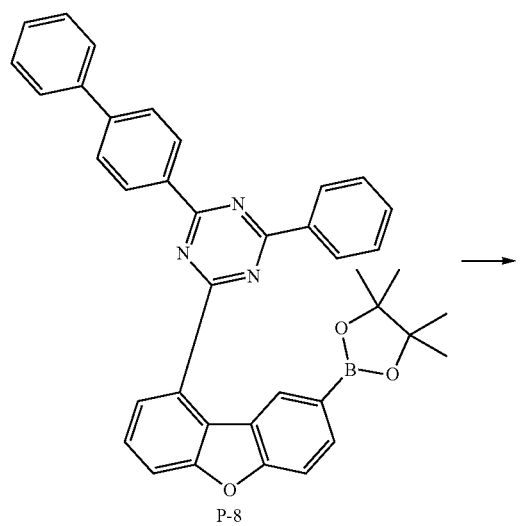

P-8

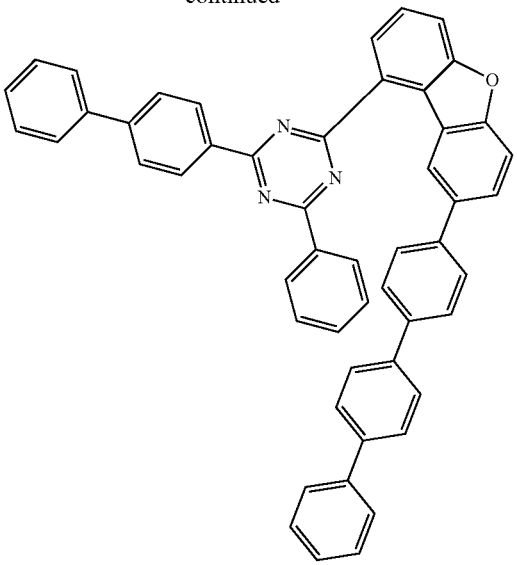

Compound 27

Compound 27 (21.2 g, yield 79%; MS: [M+H]$^+$=704) was prepared in the same manner as in Synthesis Example 1-1, except for using Compound P-8 (22.9 g, 38.1 mmol) instead of Compound P-6, and 4-bromo-1,1':4',1''-terphenyl (11.8 g, 38.1 mmol) instead of 2-bromophenanthrene.

Synthesis Example 3: Preparation of Intermediate Compound P-10

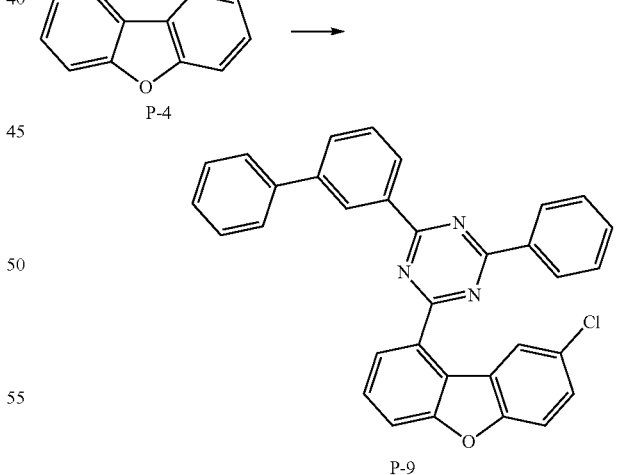

P-4

P-9

After Compound P-4 (40.0 g, 162.3 mmol) and 2-([1,1'-biphenyl]-3-yl)-4-chloro-6-phenyl-1,3,5-triazine (55.8 g, 162.3 mmol) were dispersed in tetrahydrofuran (500 ml), 2M potassium carbonate aqueous solution (aq. K$_2$CO$_3$) (67.2 ml, 486.9 mmol) was added and tetrakis(triphenylphosphine)palladium [Pd(PPh$_3$)$_4$](3.8 g, 2 mol %) was added, and then the mixture was stirred and refluxed for 4 hours. The temperature was lowered to room temperature and the resulting solid was filtered. The filtrated solid was recrystallized from tetrahydrofuran and ethyl acetate, filtered and then dried to obtain Compound P-9 (69.5 g, yield 84%; MS: [M+H]$^+$=510).

Synthesis Example 3-1: Preparation of Compound 6

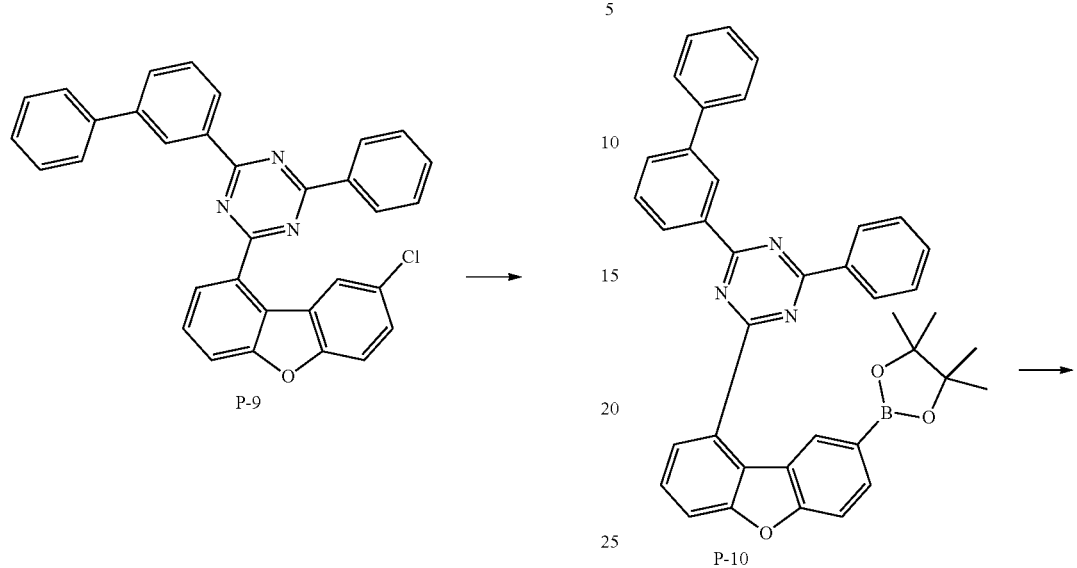

Compound P-9 (70.5 g, 138.3 mmol) bis(pinacolato) diboron (38.6 g, 152.13 mmol), potassium acetate (40.7 g, 414.9 mmol) and tetrakis (triphenylphosphine)palladium(0) [Pd(PPh$_3$)$_4$](3.2 g, 2 mol %) were added to tetrahydrofuran (600 ml) and refluxed for 12 hours. After completion of the reaction, the reaction mixture was cooled to room temperature and distilled under reduced pressure to remove the solvent. This was dissolved in chloroform and washed three times with water. The organic layer was separated, dried with magnesium sulfate, and distilled under reduced pressure to obtain Compound P-10 (73.5 g, yield 88%/o; MS: [M+H]$^+$=602).

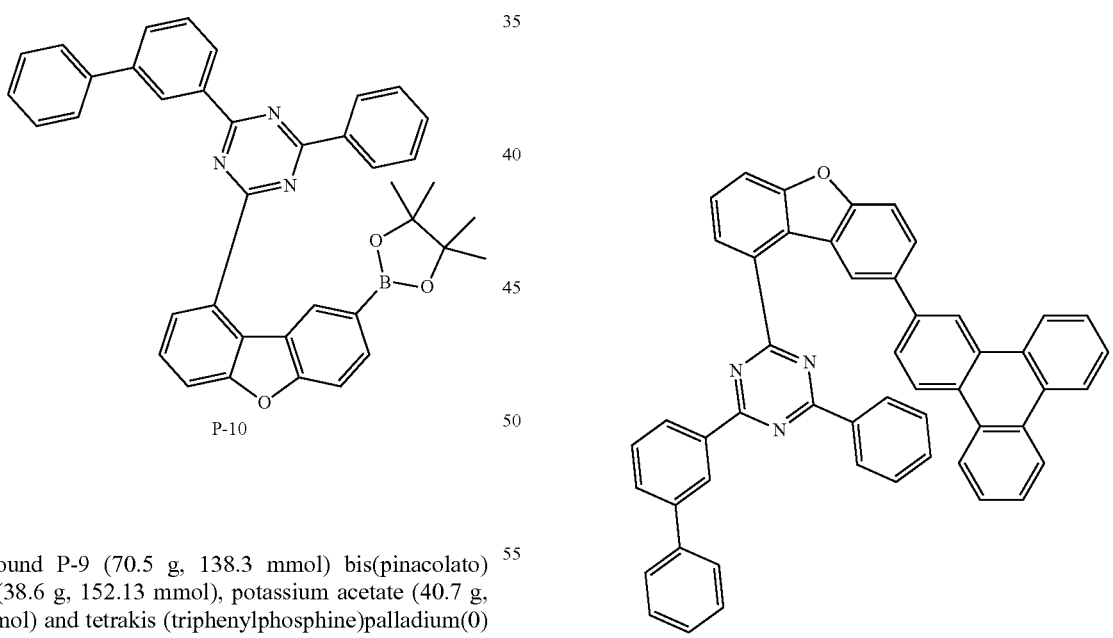

Compound 6

Compound 6 (20.3 g, yield 76%; MS: [M+H]$^+$=702) was prepared in the same manner as in Synthesis Example 1-1, except for using Compound P-10 (22.9 g, 38.1 mmol) instead of Compound P-6, and 2-bromotriphenylene (11.7 g, 38.1 mmol) instead of 2-bromophenanthrene.

Synthesis Example 3-2: Preparation of Compound 36

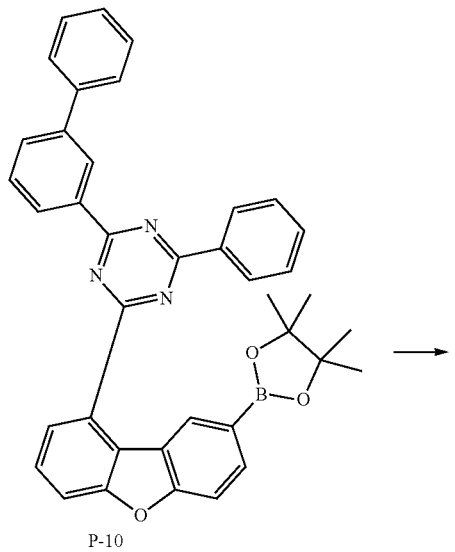

P-10

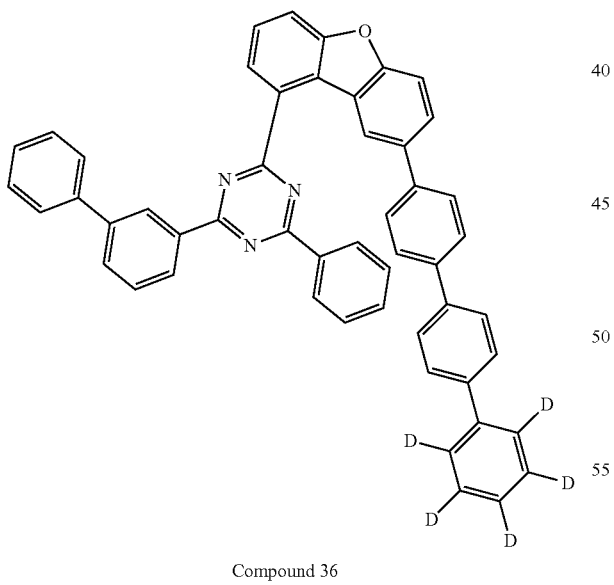

Compound 36

Compound 36 (21.1 g, yield 78%; MS: [M+H]⁺=709) was prepared in the same manner as in Synthesis Example 1-1, except for using Compound P-10 (22.9 g, 38.1 mmol) instead of Compound P-6, and 4-bromo-1,1':4',1''-terphenyl-2'',3'',4'',5'',6''-d5 (12.0 g, 38.1 mmol) instead of 2-bromophenanthrene.

Synthesis Example 3-3: Preparation of Compound 49

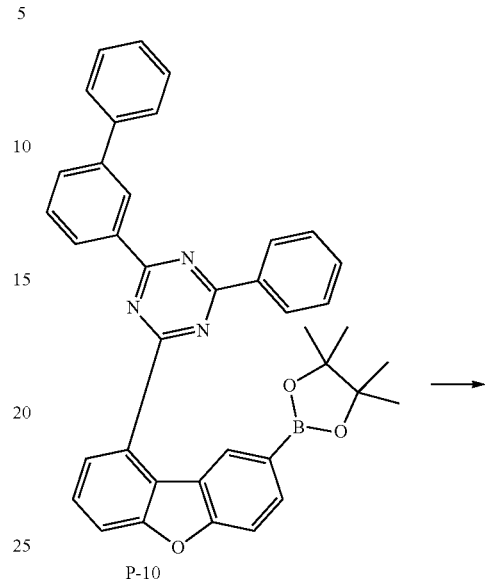

P-10

Compound 49

Compound 49 (20.4 g, yield 71%; MS: [M+H]⁺=754) was prepared in the same manner as in Synthesis Example 1-1, except for using Compound P-10 (22.9 g, 38.1 mmol) instead of Compound P-6, and 1-([1,1'-biphenyl]-2-yl)-4-bromonaphthalene (13.7 g, 38.1 mmol) instead of 2-bromophenanthrene.

Synthesis Example 3-4: Preparation of Compound 61

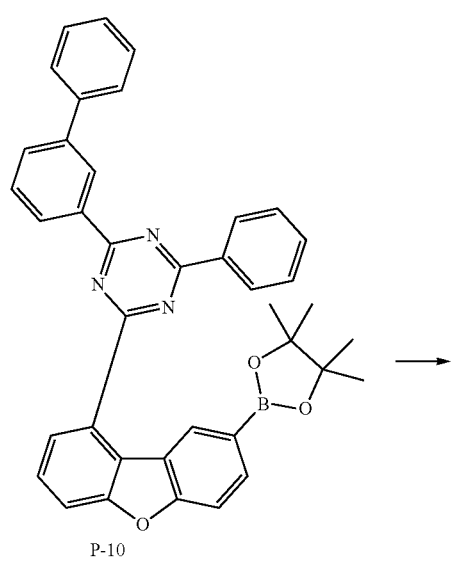

P-10

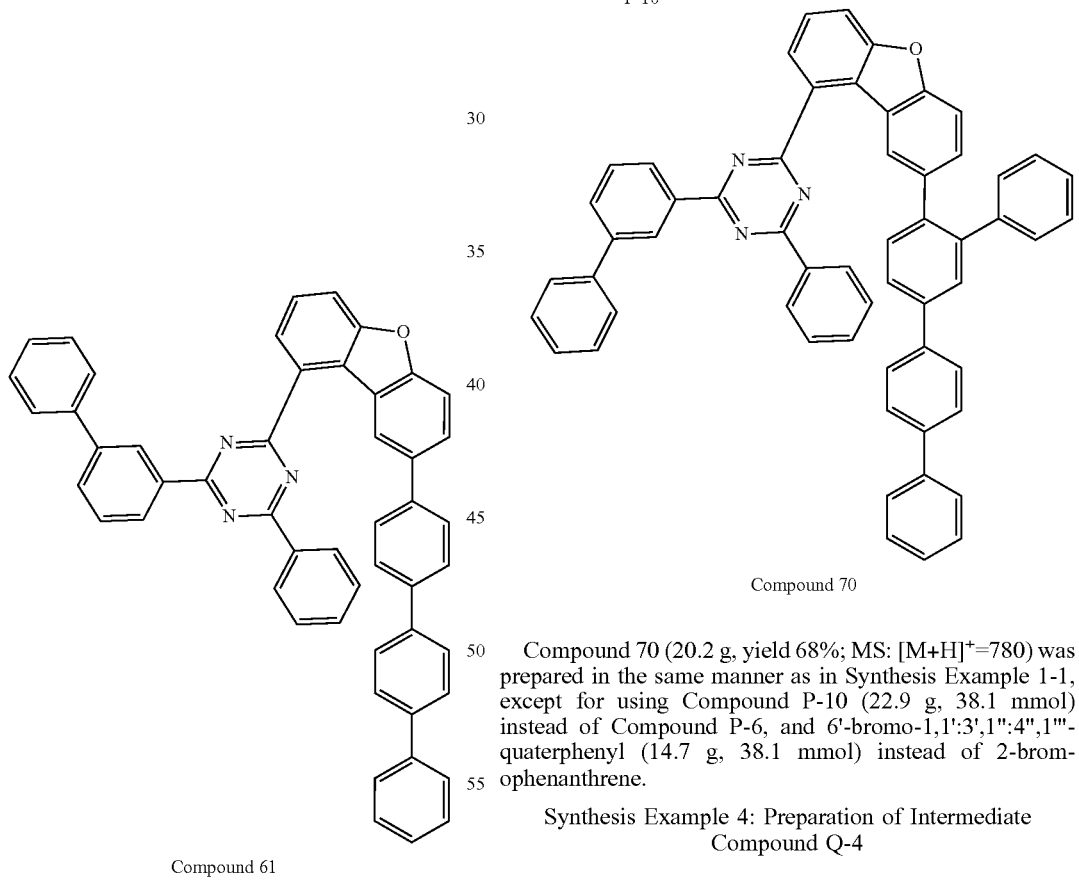

Compound 61

Compound 61 (19.8 g, yield 74%; MS: [M+H]$^+$=704) was prepared in the same manner as in Synthesis Example 1-1, except for using Compound P-10 (22.9 g, 38.1 mmol) instead of Compound P-6, and 4-bromo-1,1':4',1''-terphenyl (11.8 g, 38.1 mmol) instead of 2-bromophenanthrene.

Synthesis Example 3-5: Preparation of Compound 70

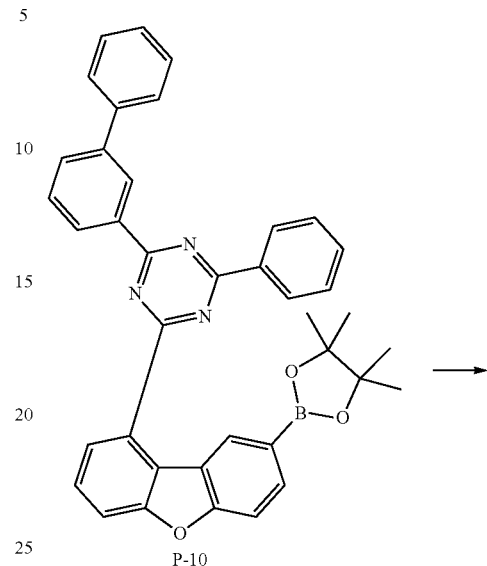

P-10

Compound 70

Compound 70 (20.2 g, yield 68%; MS: [M+H]$^+$=780) was prepared in the same manner as in Synthesis Example 1-1, except for using Compound P-10 (22.9 g, 38.1 mmol) instead of Compound P-6, and 6'-bromo-1,1':3',1'':4'',1'''-quaterphenyl (14.7 g, 38.1 mmol) instead of 2-bromophenanthrene.

Synthesis Example 4: Preparation of Intermediate Compound Q-4

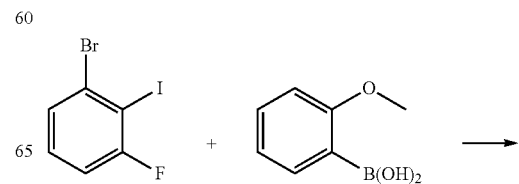

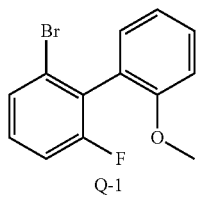

Q-1

Compound Q-1 (81.6 g, yield 87%; MS: [M+H]⁺=280) was prepared in the same manner as in Synthesis Example 1-1, except that (2-methoxyphenyl)boronic acid (50.7 g, 333.5 mmol) was used instead of (5-chloro-2-methoxyphenyl)boronic acid (62.2 g, 333.5 mmol).

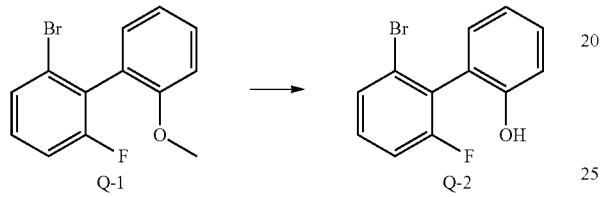

Compound Q-2 (71.2 g, yield 99%; MS: [M+H]⁺=266) was prepared in the same manner as in Synthesis Example 1-1, except that Compound Q-1 (75.7 g, 269.4 mmol) was used instead of Compound P-1 (85.0 g, 269.4 mmol).

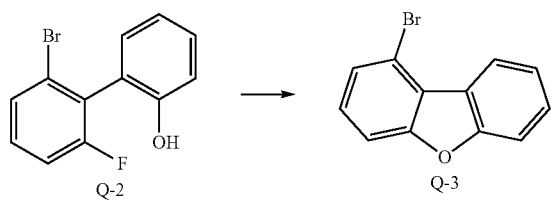

Compound Q-3 (62.3 g, yield 95%; MS: [M+H]⁺=246) was prepared in the same manner as in Synthesis Example 1-1, except that Compound Q-2 (70.9 g, 265.3 mmol) was used instead of Compound P-2 (80.0 g, 265.3 mmol).

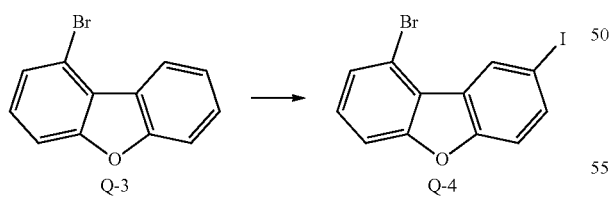

Compound Q-3 (40 g, 161.9 mmol) was dissolved in 200 ml of acetic acid, to which iodine (4.16 g, 81.0 mmol), iodic acid (6.3 g, 36.0 mmol) and sulfuric acid (10 mi) were added and stirred at 65° C. for 3 hours. After completion of the reaction, the mixture was cooled to room temperature and water was added. The resulting solid was filtered, washed with water and then recrystallized from toluene and ethyl acetate to obtain Compound Q-4 (50.1 g, yield 83%; MS: [M+H]⁺=372).

Synthesis Example 4-1: Preparation of Intermediate Compound Q-5

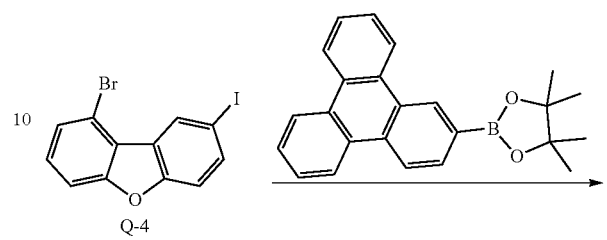

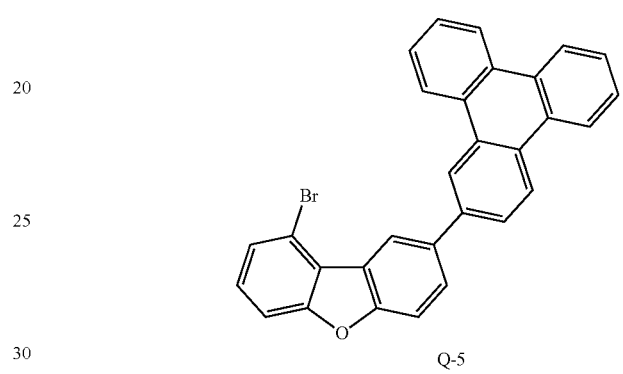

Compound Q-4 (30 g, 80.4 mmol) and 4,4,5,5-tetramethyl-2-(triphenylen-2-yl)-1,3,2-dioxaborolane (28.5 g, 80.4 mmol) were dissolved in 300 ml of tetrahydrofuran (THF), to which 2M sodium carbonate (Na₂CO₃) solution (120 mL) and tetrakis (triphenylphosphine)palladium(0) [Pd(PPh₃)₄] (1.9 g, 2 mol %) and refluxed for 6 hours. After completion of the reaction, the mixture was cooled to room temperature, and the resulting mixture was extracted three times with water and toluene. The toluene layer was separated and dried over magnesium sulfate. The filtrate was distilled under reduced pressure, and the obtained mixture was recrystallized from chloroform and ethyl acetate to obtain Compound Q-5 (28.9 g, yield 76%; MS: [M+H]⁺=473).

Synthesis Example 4-2: Preparation of Intermediate Compound Q-6

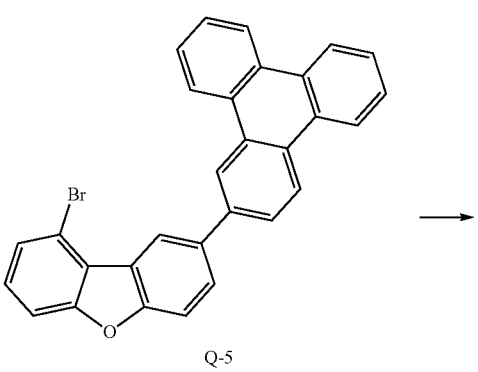

-continued

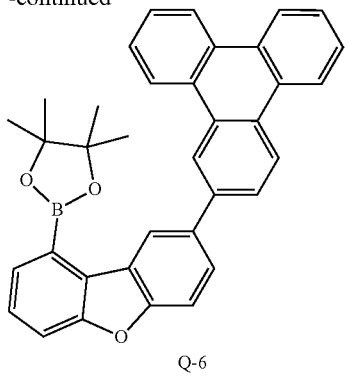
Q-6

Compound Q-5 (25 g, 52.8 mmol), bis(pinacolato)diboron (14.9 g, 58.1 mmol), potassium acetate (15.5 g, 158.4 mmol) and tetrakis(triphenylphosphine) palladium(0) [Pd(PPh$_3$)$_4$] (1.2 g, 2 mol %) was added to tetrahydrofuran (300 ml) and refluxed for 12 hours. After completion of the reaction, the mixture was cooled to room temperature and distilled under reduced pressure to remove the solvent. This was dissolved in chloroform and washed three times with water. The organic layer was separated, dried with magnesium sulfate, and then distilled under reduced pressure to obtain Compound Q-6 (25.0 g, yield 91%; MS: [M+H]$^+$=521).

Synthesis Example 4-3: Preparation of Compound 7

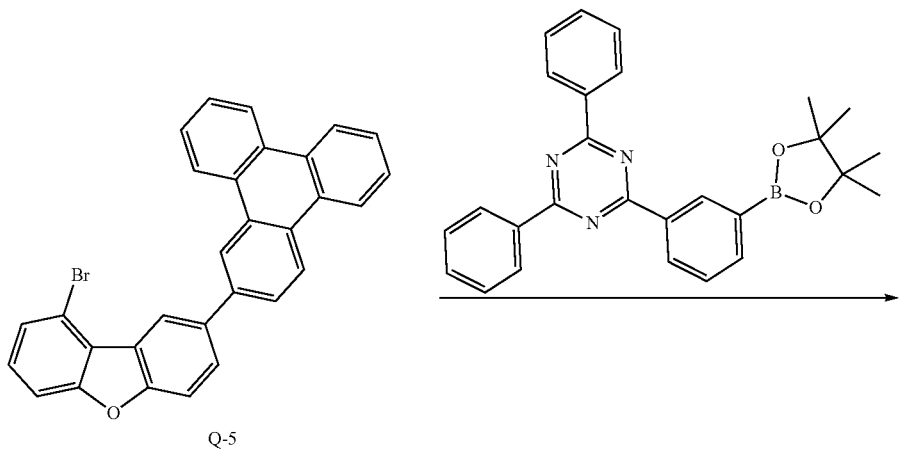
Q-5

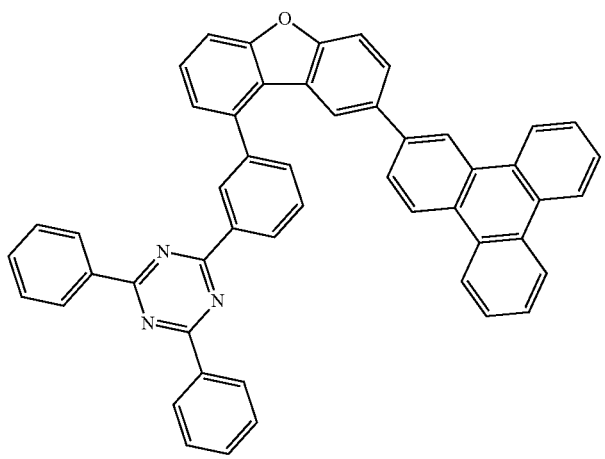
Compound 7

Compound 7 (19.0 g, yield 71%; MS: [M+H]⁺=702) was prepared in the same manner as in Synthesis Example 1-1, except for using 2,4-diphenyl-6-(3-(4,4,5,5-tetramethyl-1,3,2-dioxaborolan-2-yl)phenyl)-1,3,5-triazine (16.6 g, 38.1 mmol) instead of Compound P-6, and Compound Q-5 (18.0 g, 38.1 mmol) instead of 2-bromophenanthrene.

Synthesis Example 4-4: Preparation of Compound 8

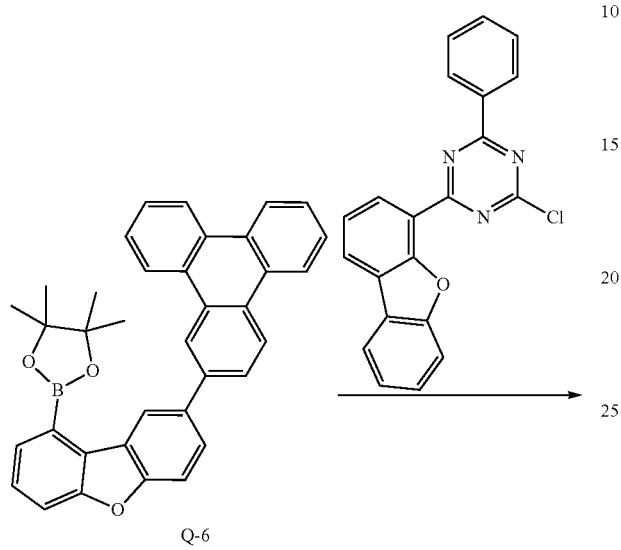

Q-6

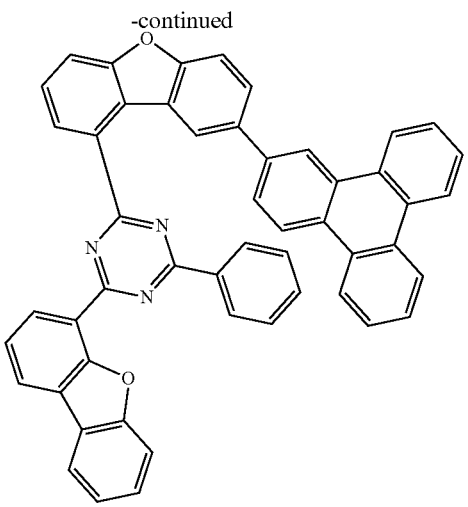

Compound 8

Compound 8 (19.9 g, yield 73%; MS: [M+H]⁺=716) was prepared in the same manner as in Synthesis Example 1-1, except for using Compound Q-6 (19.8 g, 38.1 mmol) instead of Compound P-6, and 2-chloro-4-(dibenzo[b,d]furan-4-yl)-6-phenyl-1,3,5-triazine (13.6 g, 38.1 mmol) instead of 2-bromophenanthrene.

Synthesis Example 4-5: Preparation of Compound 19

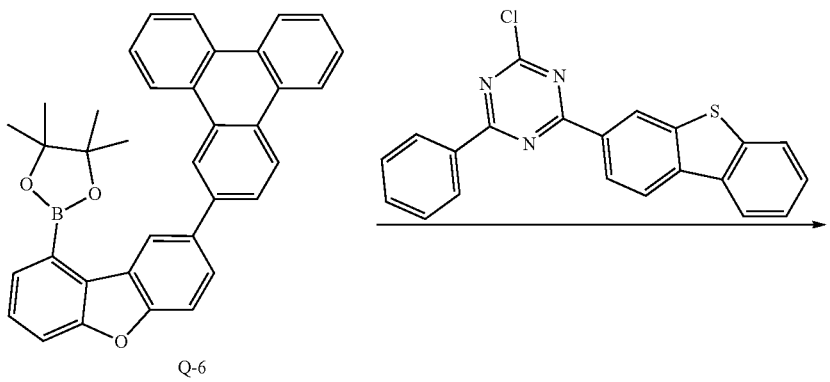

Q-6

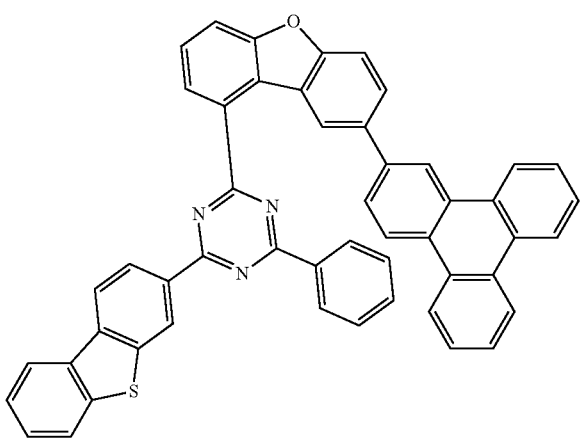

Compound 19

Compound 19 (19.5 g, yield 70%; MS: [M+H]⁺=732) was prepared in the same manner as in Synthesis Example 1-1, except for using Compound Q-6 (19.8 g, 38.1 mmol) instead of Compound P-6, and 2-chloro-4-(dibenzo[b,d]thiophen-3-yl)-6-phenyl-1,3,5-triazine (14.2 g, 38.1 mmol) instead of 2-bromophenanthrene.

Synthesis Example 4-6: Preparation of Compound 48

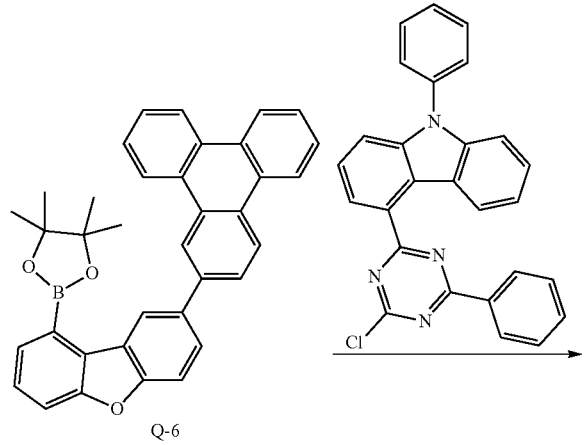

Compound 48

Compound 48 (22.3 g, yield 74%; MS: [M+H]⁺=791) was prepared in the same manner as in Synthesis Example 1-1, except for using Compound Q-6 (19.8 g, 38.1 mmol) instead of Compound P-6, and 4-(4-chloro-6-phenyl-1,3,5-triazin-2-yl)-9-phenyl-9H-carbazole (16.5 g, 38.1 mmol) instead of 2-bromophenanthrene.

Synthesis Example 4-7: Preparation of Compound 58

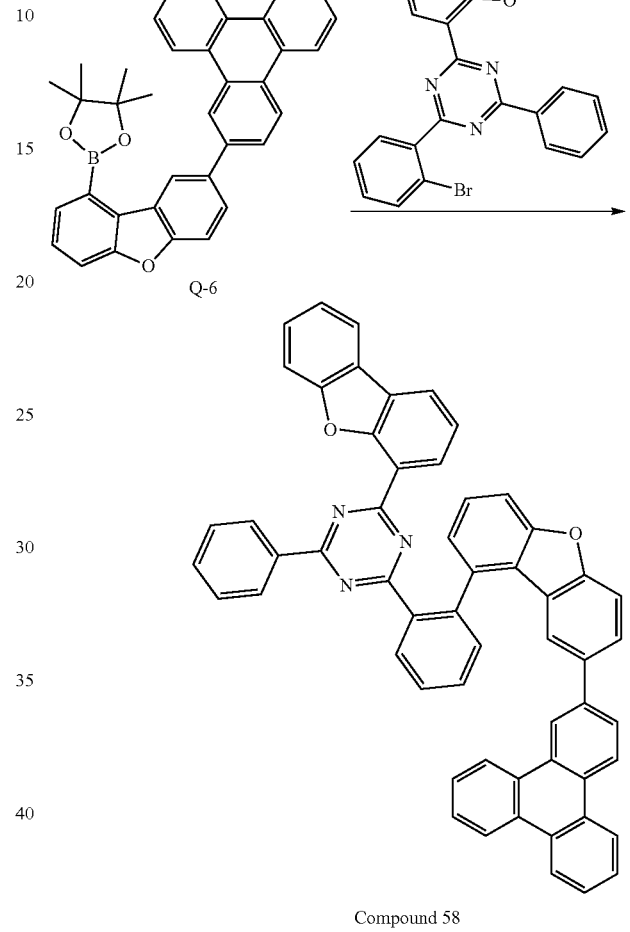

Compound 58

Compound 58 (18.7 g, yield 62%; MS: [M+H]⁺=792) was prepared in the same manner as in Synthesis Example 1-1, except for using Compound Q-6 (19.8 g, 38.1 mmol) instead of Compound P-6, and 2-(2-bromophenyl)-4-(dibenzo[b,d]furan-4-yl)-6-phenyl-1,3,5-triazine (18.2 g, 38.1 mmol) instead of 2-bromophenanthrene.

Synthesis Example 5-1: Preparation of Intermediate Compound Q-7

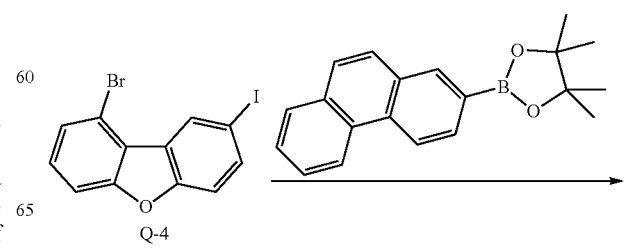

Q-4

-continued

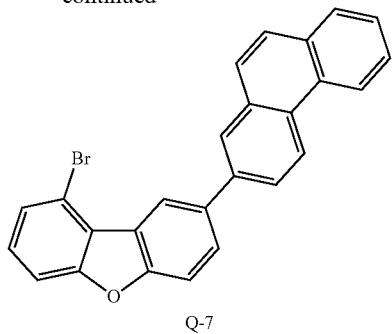

Q-7

Compound Q-7 (20.0 g, yield 59%; MS: [M+H]$^+$=423) was prepared in the same manner as in Synthesis Example 4-1, except that 4,4,5,5-tetramethyl-2-(phenanthren-2-yl)-1,3,2-dioxaborolane (24.5 g, 80.4 mmol) was used instead of 4,4,5,5-tetramethyl-2-(triphenylen-2-yl)-1,3,2-dioxaborolane (28.5 g, 80.4 mmol).

Synthesis Example 5-2: Preparation of Intermediate Compound Q-8

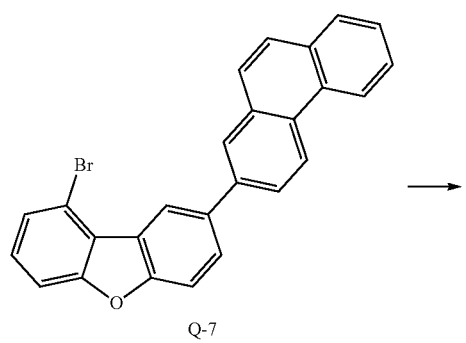

Q-7

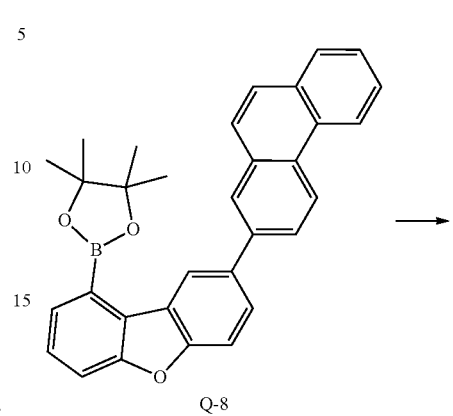

Q-8

Compound Q-8 (21.6 g, yield 87%; MS: [M+H]$^+$=471) was prepared in the same manner as in Synthesis Example 4-2, except that Compound Q-7 (22.4 g, 52.8 mmol) was used instead of Compound Q-5 (25 g, 52.8 mmol).

Synthesis Example 5-3: Preparation of Compound 10

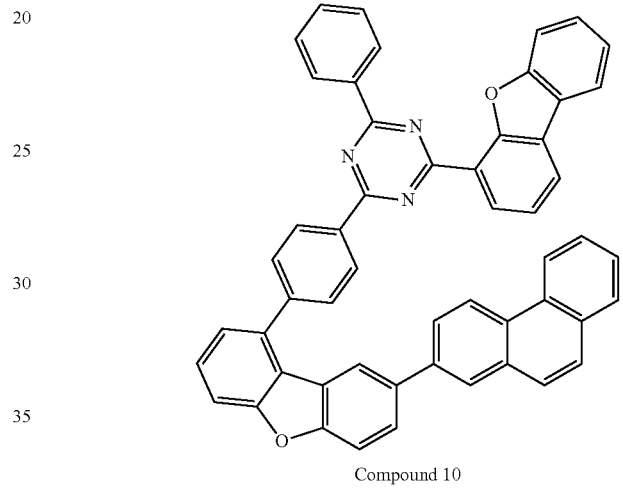

Compound 10

Compound 10 (18.4 g, yield 65%; MS: [M+H]$^+$=742) was prepared in the same manner as in Synthesis Example 1-1, except for using Compound Q-8 (17.9 g, 38.1 mmol) instead of Compound P-6, and 2-(4-chlorophenyl)-4-(dibenzo[b,d]furan-4-yl)-6-phenyl-1,3,5-triazine (16.5 g, 38.1 mmol) instead of 2-bromophenanthrene.

Synthesis Example 5-4: Preparation of Compound 15

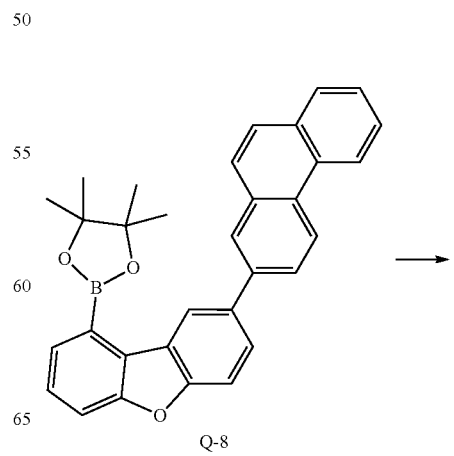

Q-8

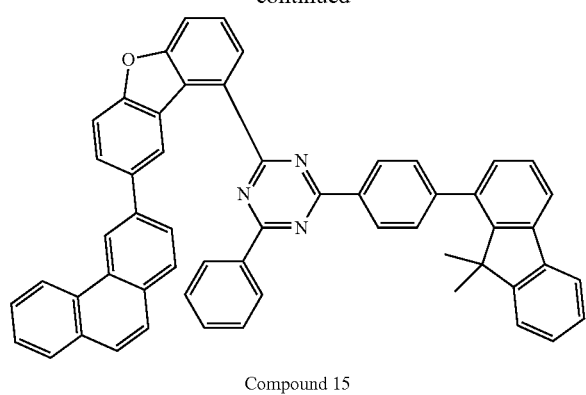

Compound 15

Compound 15 (15.8 g, yield 54%; MS: [M+H]$^+$=768) was prepared in the same manner as in Synthesis Example 1-1, except for using Compound Q-8 (17.9 g, 38.1 mmol) instead of Compound P-6, and 2-chloro-4-(4-(9,9-dimethyl-9H-fluoren-1-yl)phenyl)-6-phenyl-1,3,5-triazine (17.5 g, 38.1 mmol) instead of 2-bromophenanthrene.

Synthesis Example 6-1: Preparation of Intermediate Compound Q-9

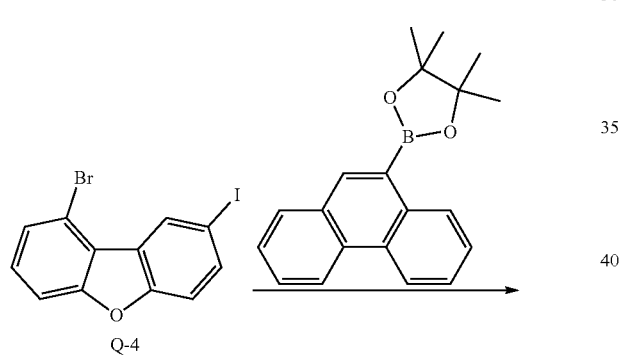

Q-4

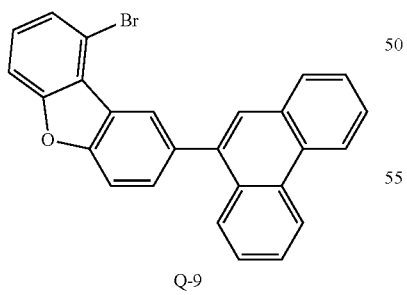

Q-9

Compound Q-9 (20.8 g, yield 61%; MS: [M+H]$^+$=423) was prepared in the same manner as in Synthesis Example 4-1, except that 4,4,5,5-tetramethyl-2-(phenanthren-9-yl)-1,3,2-dioxaborolane (24.5 g, 80.4 mmol) was used instead of 4,4,5,5-tetramethyl-2-(triphenylen-2-yl)-1,3,2-dioxaborolane (28.5 g, 80.4 mmol).

Synthesis Example 6-2: Preparation of Intermediate Compound Q-10

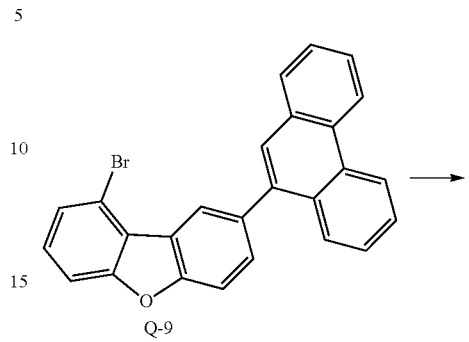

Q-9

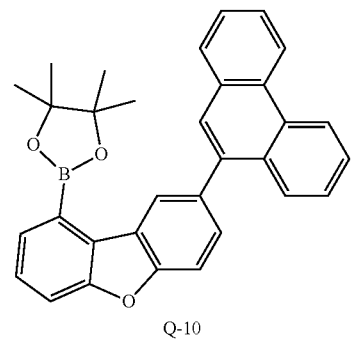

Q-10

Compound Q-10 (21.1 g, yield 85%; MS: [M+H]$^+$=471) was prepared in the same manner as in Synthesis Example 4-2, except that Compound Q-7 (22.4 g, 52.8 mmol) was used instead of Compound Q-5 (25 g, 52.8 mmol)

Synthesis Example 6-3: Preparation of Compound 50

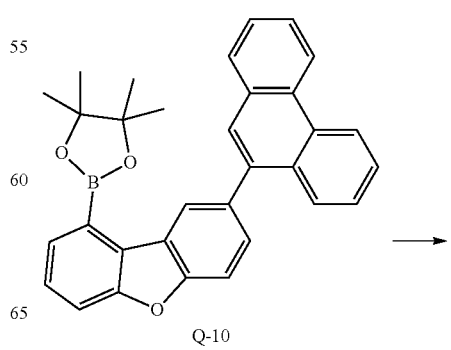

Q-10

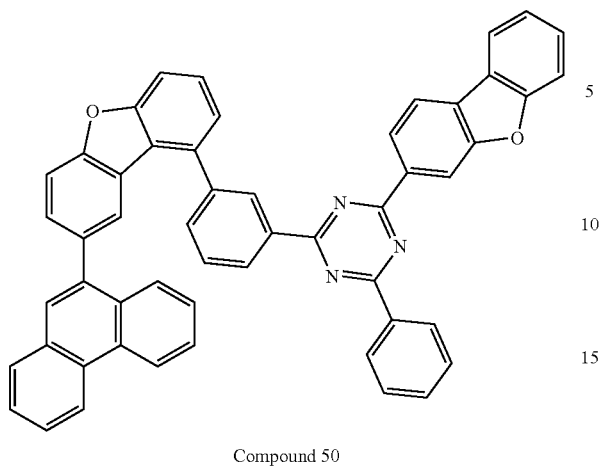

Compound 50

Compound 50 (14.4 g, yield 51%; MS: [M+H]$^+$=742) was prepared in the same manner as in Synthesis Example 1-1, except for using Compound Q-8 (17.9 g, 38.1 mmol) instead of Compound P-6, and 2-(3-chlorophenyl)-4-(dibenzo[b,d]furan-3-yl)-6-phenyl-1,3,5-triazine (16.6 g, 38.1 mmol) instead of 2-bromophenanthrene.

Synthesis Example 7-1: Preparation of Intermediate Compound Q-11

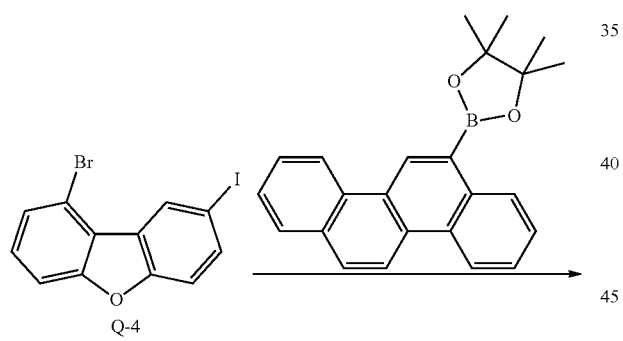

Compound Q-11 (23.6 g, yield 62%; MS: [M+H]$^+$=473) was prepared in the same manner as in Synthesis Example 4-1, except that 2-(chrysen-6-yl)-4,4,5,5-tetramethyl-1,3,2-dioxaborolane (28.4 g, 80.4 mmol) was used instead of 4,4,5,5-tetramethyl-2-(triphenylen-2-yl)-1,3,2-dioxaborolane (28.5 g, 80.4 mmol).

Synthesis Example 7-2: Preparation of Intermediate Compound Q-12

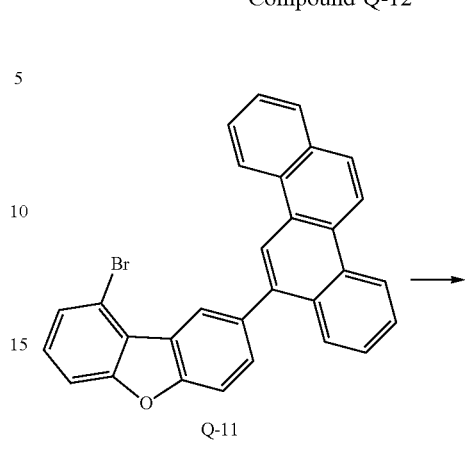

Compound Q-12 (22.5 g, yield 82%; MS: [M+H]$^+$=521) was prepared in the same manner as in Synthesis Example 4-2, except that Compound Q-11 (25.0 g, 52.8 mmol) was used instead of Compound Q-5 (25.0 g, 52.8 mmol).

Synthesis Example 7-3: Preparation of Compound 14

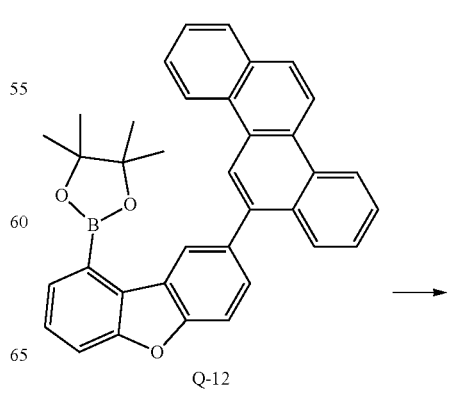

383

-continued

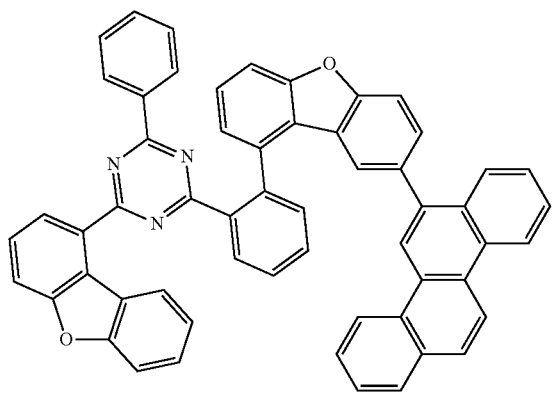

Compound 14

Compound 14 (14.5 g, yield 48%; MS: [M+H]⁺=792) was prepared in the same manner as in Synthesis Example 1-1, except for using Compound Q-12 (17.9 g, 38.1 mmol) instead of Compound P-6, and 2-(2-chlorophenyl)-4-(dibenzo[b,d]furan-1-yl)-6-phenyl-1,3,5-triazine (16.5 g, 38.1 mmol) instead of 2-bromophenanthrene.

Synthesis Example 8-1: Preparation of Intermediate Compound Q-13

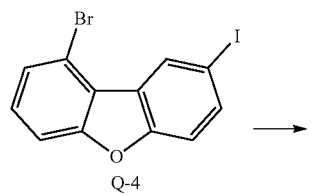

Q-4

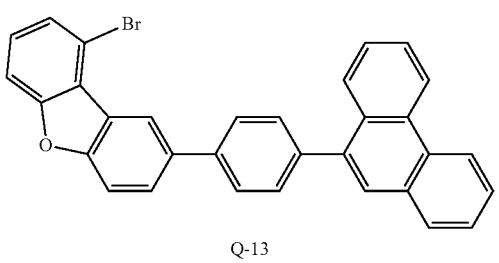

Q-13

Compound Q-13 (29.3 g, yield 73%; MS: [M+H]⁺=499) was prepared in the same manner as in Synthesis Example 4-1, except that 4,4,5,5-tetramethyl-2-(4-(phenanthren-9-yl)phenyl)-1,3,2-dioxaborolane (30.6 g, 80.4 mmol) was used instead of 4,4,5,5-tetramethyl-2-(triphenylen-2-yl)-1,3,2-dioxaborolane (28.5 g, 80.4 mmol).

384

Synthesis Example 8-2: Preparation of Intermediate Compound Q-14

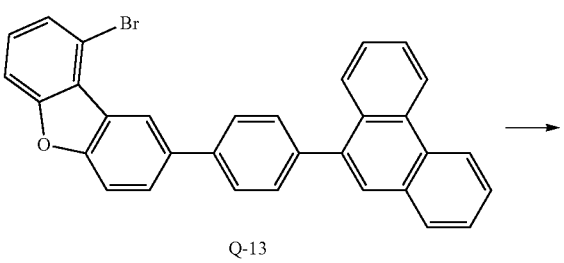

Q-13

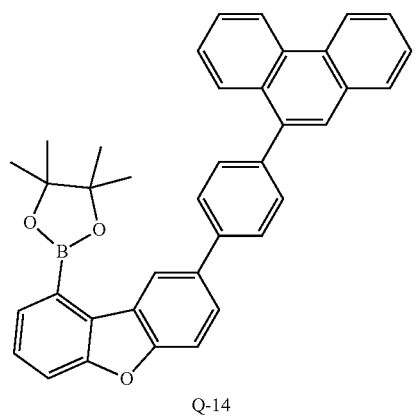

Q-14

Compound Q-14 (24.5 g, yield 85%; MS: [M+H]⁺=547) was prepared in the same manner as in Synthesis Example 4-2, except that Compound Q-13 (26.4 g, 52.8 mmol) was used instead of Compound Q-5 (25.0 g, 52.8 mmol).

Synthesis Example 8-3: Preparation of Compound 17

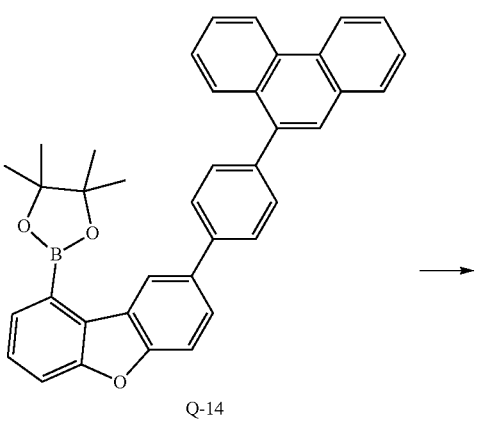

Q-14

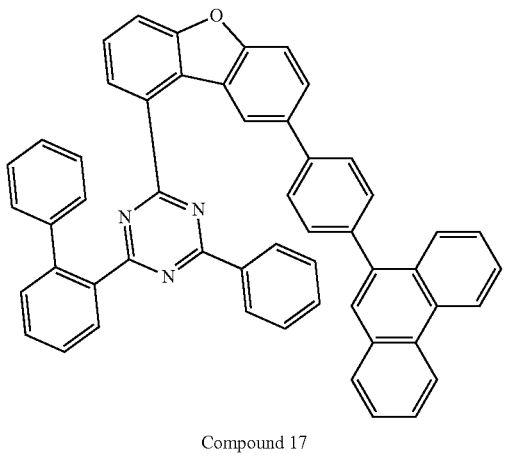

Compound 17

Compound 17 (18.9 g, yield 68%; MS: [M+H]$^+$=728) was prepared in the same manner as in Synthesis Example 1-1, except for using Compound Q-14 (20.8 g, 38.1 mmol) instead of Compound P-6, and 2-([1,1'-biphenyl]-2-yl)-4-chloro-6-phenyl-1,3,5-triazine (13.1 g, 38.1 mmol) instead of 2-bromophenanthrene.

Synthesis Example 9-1: Preparation of Intermediate Compound Q-15

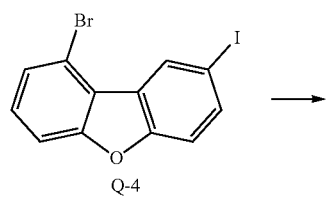

Q-4

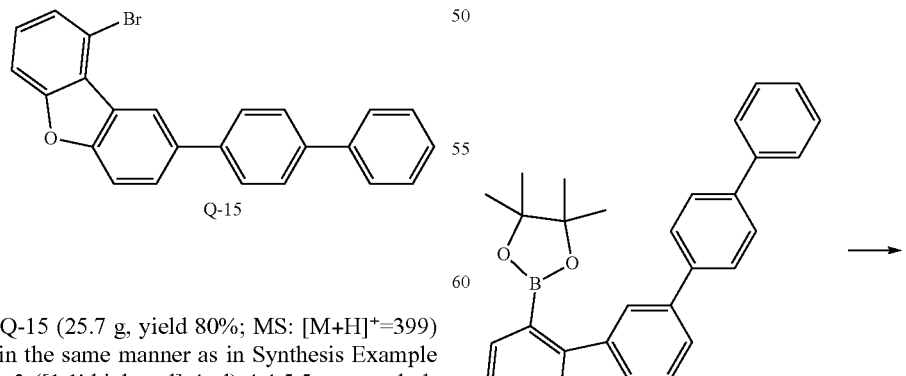

Q-15

Compound Q-15 (25.7 g, yield 80%; MS: [M+H]$^+$=399) was prepared in the same manner as in Synthesis Example 4-1, except that 2-([1,1'-biphenyl]-4-yl)-4,4,5,5-tetramethyl-1,3,2-dioxaborolane (22.5 g, 80.4 mmol) was used instead of 4,4,5,5-tetramethyl-2-(triphenylen-2-yl)-1,3,2-dioxaborolane (28.5 g, 80.4 mmol).

Synthesis Example 9-2: Preparation of Intermediate Compound Q-16

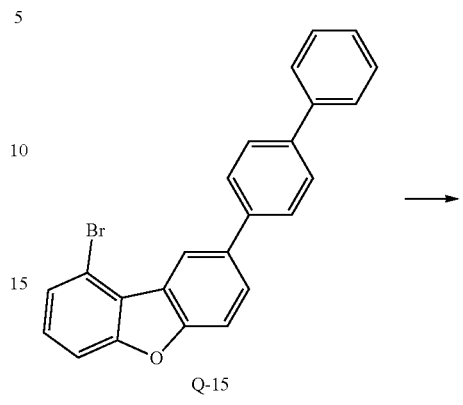

Q-15

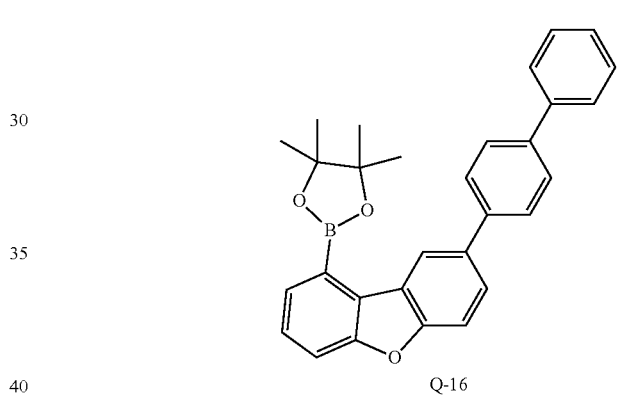

Q-16

Compound Q-16 (20.3 g, yield 86%; MS: [M+H]$^+$=447) was prepared in the same manner as in Synthesis Example 4-2, except that Compound Q-13 (21.1 g, 52.8 mmol) was used instead of Compound Q-5 (25.0 g, 52.8 mmol).

Synthesis Example 9-3: Preparation of Compound 30

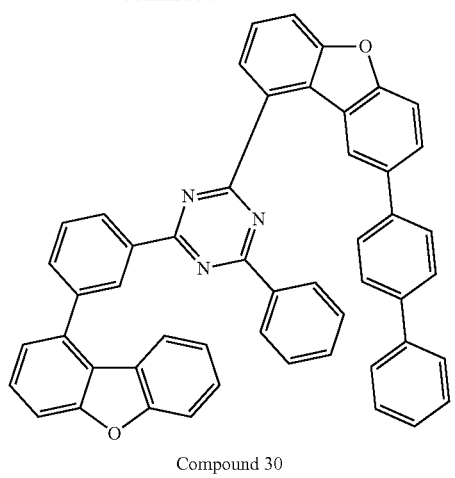

Compound 30

Compound 30 (18.9 g, yield 69%; MS: [M+H]$^+$=718) was prepared in the same manner as in Synthesis Example 1-1, except for using Compound Q-16 (17.0 g, 38.1 mmol) instead of Compound P-6, and 2-chloro-4-(3-(dibenzo[b,d]furan-1-yl)phenyl)-6-phenyl-1,3,5-triazine (16.5 g, 38.1 mmol) instead of 2-bromophenanthrene.

Synthesis Example 9-4: Preparation of Compound 39

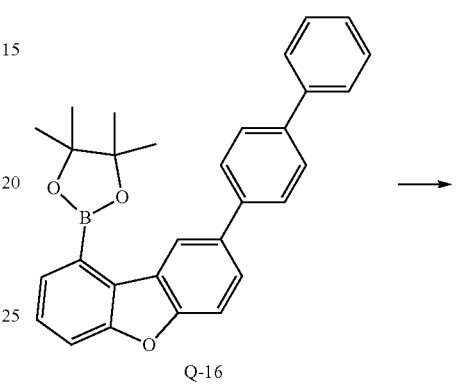

Q-16

Compound 39

Compound 39 (17.4 g, yield 65%; MS: [M+H]$^+$=704) was prepared in the same manner as in Synthesis Example 1-1, except for using Compound Q-16 (17.0 g, 38.1 mmol) instead of Compound P-6, and 2-([1,1':3',1''-terphenyl]-5'-yl)-4-chloro-6-phenyl-1,3,5-triazine (16.0 g, 38.1 mmol) instead of 2-bromophenanthrene.

Synthesis Example 9-5: Preparation of Compound 44

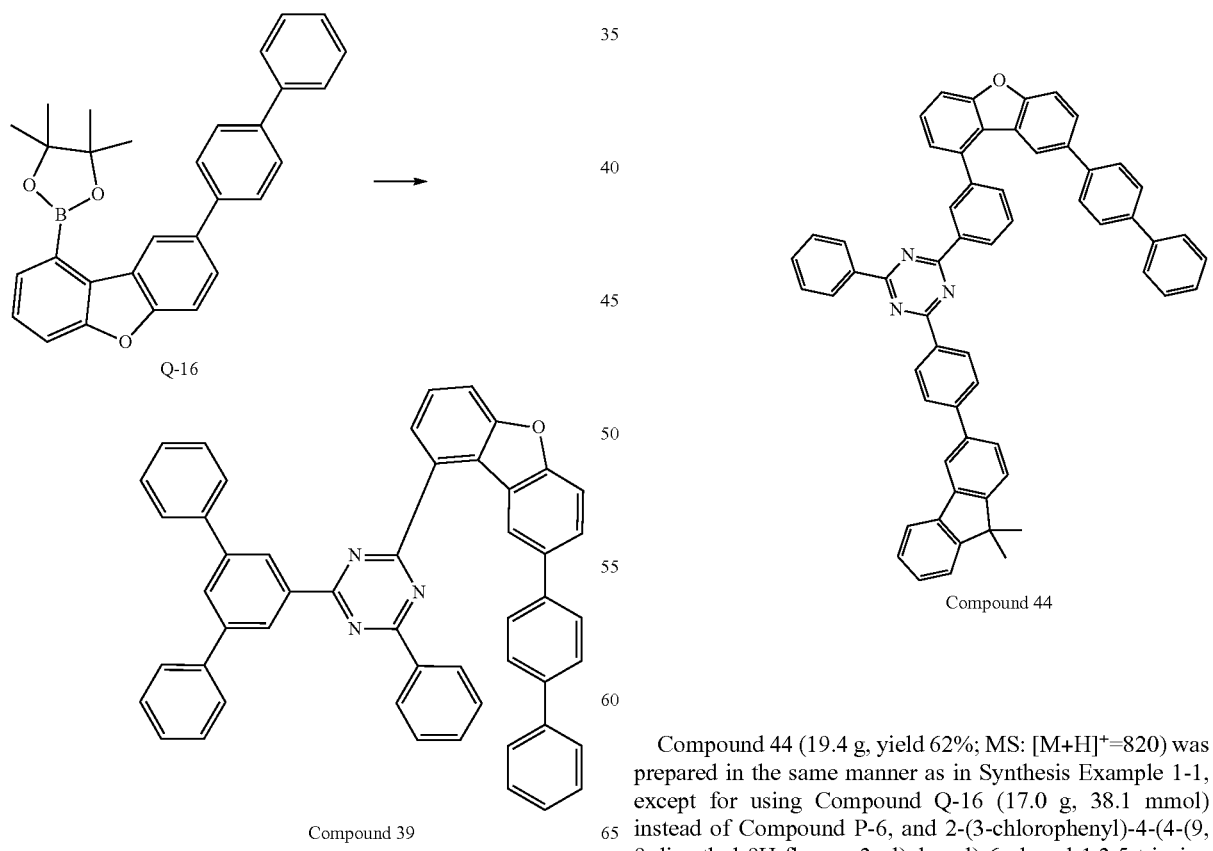

Compound 44

Compound 44 (19.4 g, yield 62%; MS: [M+H]$^+$=820) was prepared in the same manner as in Synthesis Example 1-1, except for using Compound Q-16 (17.0 g, 38.1 mmol) instead of Compound P-6, and 2-(3-chlorophenyl)-4-(4-(9,9-dimethyl-9H-fluoren-3-yl)phenyl)-6-phenyl-1,3,5-triazine (20.4 g, 38.1 mmol) instead of 2-bromophenanthrene.

Synthesis Example 9-6: Preparation of Compound 63

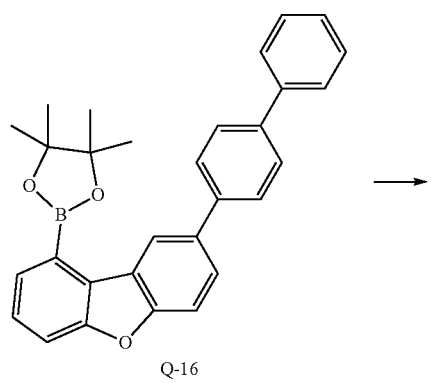
Q-16

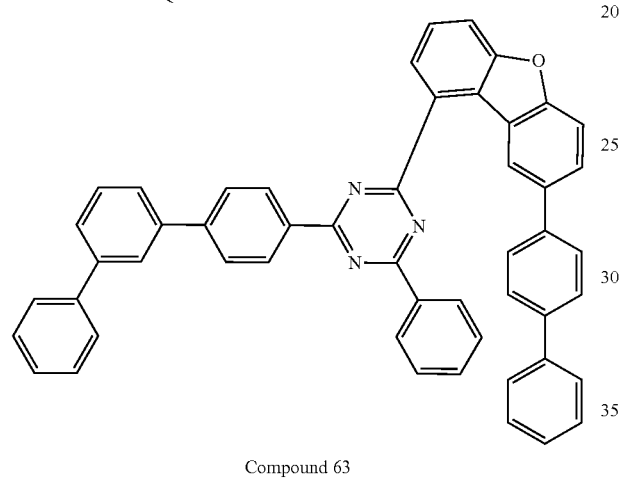
Compound 63

Compound 63 (17.4 g, yield 65%; MS: [M+H]⁺=704) was prepared in the same manner as in Synthesis Example 1-1, except for using Compound Q-16 (17.0 g, 38.1 mmol) instead of Compound P-6, and 2-([1,1':3',1''-terphenyl]-4-yl)-4-chloro-6-phenyl-1,3,5-triazine (16.0 g, 38.1 mmol) instead of 2-bromophenanthrene.

Synthesis Example 9-7: Preparation of Compound 64

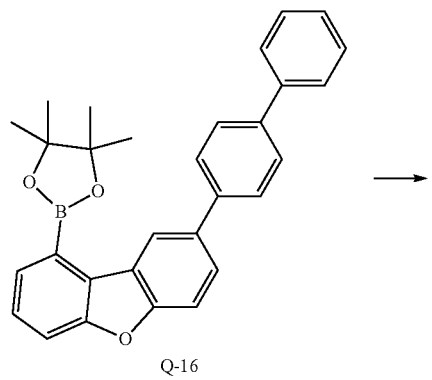
Q-16

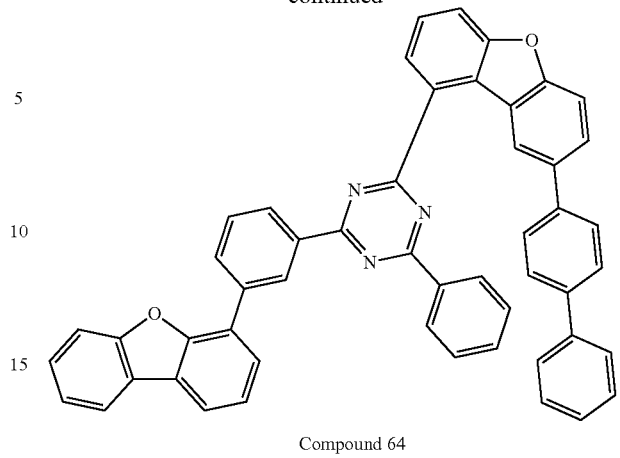
Compound 64

Compound 64 (17.5 g, yield 64%; MS: [M+H]⁺=718) was prepared in the same manner as in Synthesis Example 1-1, except for using Compound Q-16 (17.0 g, 38.1 mmol) instead of Compound P-6, and 2-chloro-4-(3-(dibenzo[b,d]furan-4-yl)phenyl)-6-phenyl-1,3,5-triazine (16.5 g, 38.1 mmol) instead of 2-bromophenanthrene.

Synthesis Example 9-8: Preparation of Compound 74

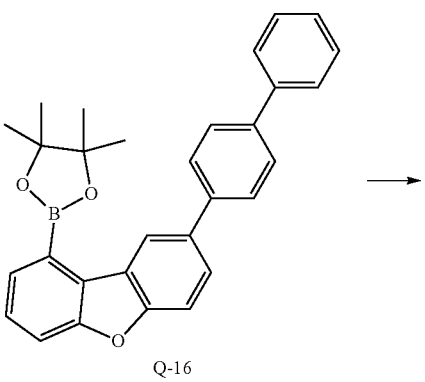
Q-16

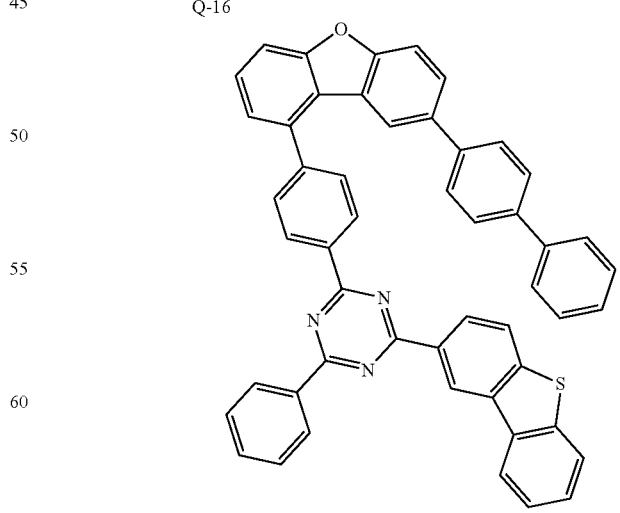
Compound 74

Compound 74 (17.3 g, yield 62%; MS: [M+H]$^+$=734) was prepared in the same manner as in Synthesis Example 1-1, except for using Compound Q-16 (17.0 g, 38.1 mmol) instead of Compound P-6, and 2-(4-chlorophenyl)-4-(dibenzo[b,d]thiophen-2-yl)-6-phenyl-1,3,5-triazine (17.1 g, 38.1 mmol) instead of 2-bromophenanthrene.

Synthesis Example 10-1: Preparation of Intermediate Compound Q-17

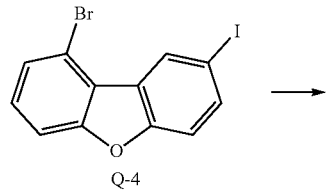

Q-4

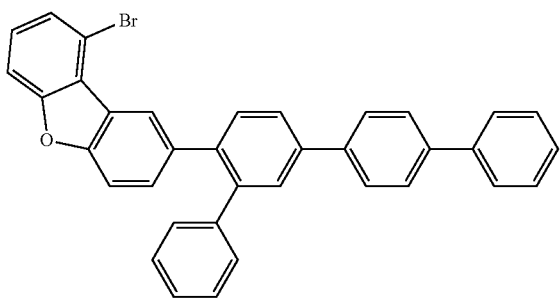

Q-17

Compound Q-17 (28.0 g, yield 63%; MS: [M+H]$^+$=551) was prepared in the same manner as in Synthesis Example 4-1, except that 6'-chloro-1,1':3',1":4",1'''-quaterphenyl (27.4 g, 80.4 mmol) was used instead of 4,4,5,5-tetramethyl-2-(triphenylen-2-yl)-1,3,2-dioxaborolane (28.5 g, 80.4 mmol).

Synthesis Example 10-2: Preparation of Intermediate Compound Q-18

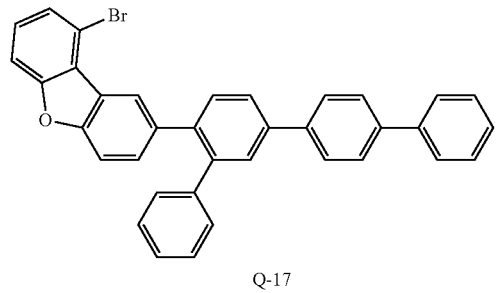

Q-17

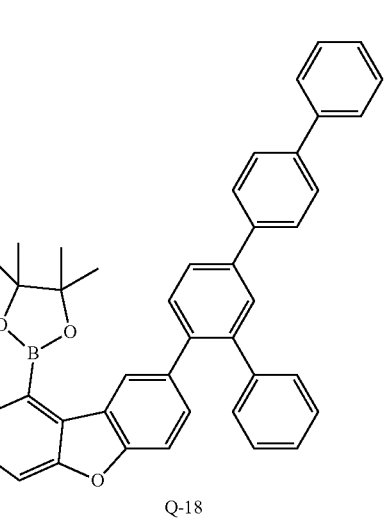

Q-18

Compound Q-18 (25.9 g, yield 82%; MS: [M+H]$^+$=599) was prepared in the same manner as in Synthesis Example 4-2, except that Compound Q-17 (29.1 g, 52.8 mmol) was used instead of Compound Q-5 (25.0 g, 52.8 mmol).

Synthesis Example 10-3: Preparation of Compound 31

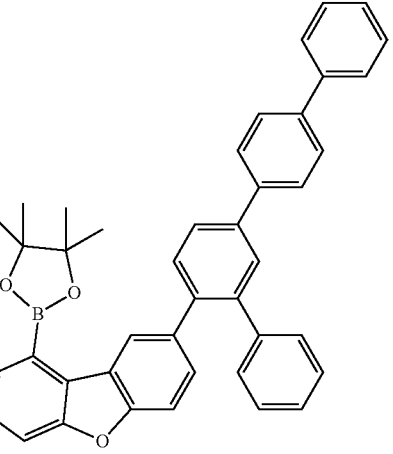

Q-18

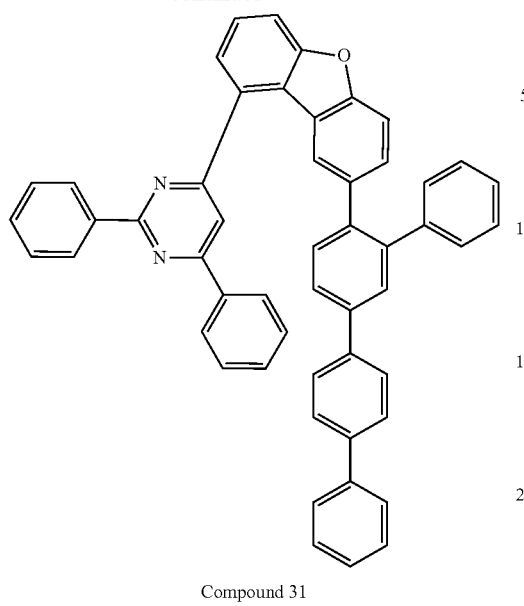

Compound 31

Compound 31 (18.2 g, yield 68%; MS: [M+H]⁺=703) was prepared in the same manner as in Synthesis Example 1-1, except for using Compound Q-18 (22.8 g, 38.1 mmol) instead of Compound P-6, and 4-chloro-2,6-diphenylpyrimidine (10.2 g, 38.1 mmol) instead of 2-bromophenanthrene.

Synthesis Example 11-1: Preparation of Intermediate Compound Q-19

Compound Q-19 (25.2 g, yield 66%; MS: [M+H]⁺=475) was prepared in the same manner as in Synthesis Example 4-1, except that 2-([1,1':2',1"-terphenyl]-2-yl)-4,4,5,5-tetramethyl-1,3,2-dioxaborolane (28.6 g, 80.4 mmol) was used instead of 4,4,5,5-tetramethyl-2-(triphenylen-2-yl)-1,3,2-dioxaborolane (28.5 g, 80.4 mmol).

Synthesis Example 11-2: Preparation of Intermediate Compound Q-20

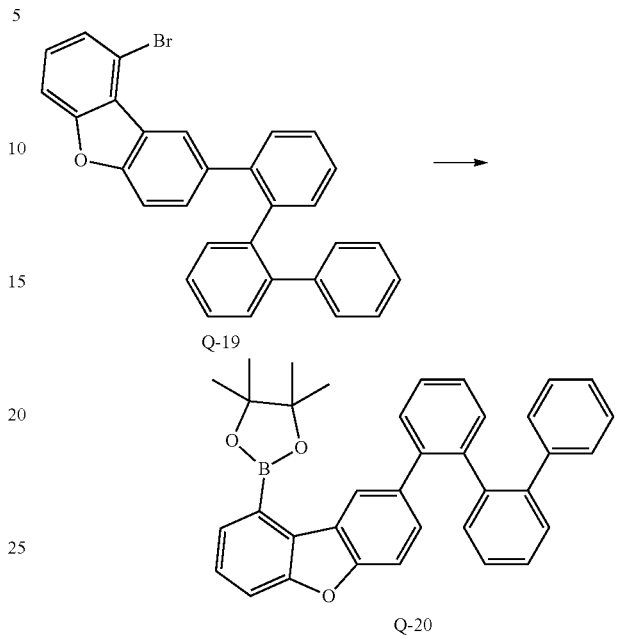

Compound Q-20 (22.1 g, yield 80%; MS: [M+H]⁺=523) was prepared in the same manner as in Synthesis Example 4-2, except that Compound Q-19 (25.1 g, 52.8 mmol) was used instead of Compound Q-5 (25.0 g, 52.8 mmol).

Synthesis Example 11-3: Preparation of Compound 32

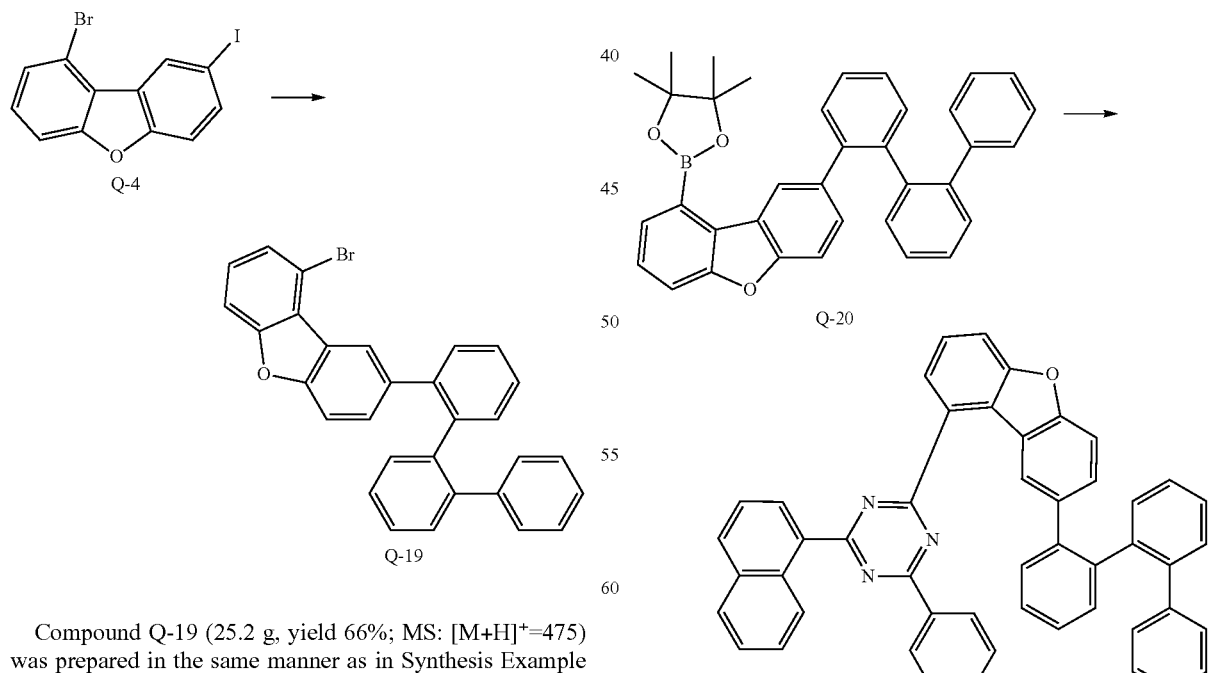

Compound 32

Compound 32 (15.8 g, yield 61%; MS: [M+H]$^+$=678) was prepared in the same manner as in Synthesis Example 1-1, except for using Q-20 (19.9 g, 38.1 mmol) instead of Compound P-6, and 2-chloro-4-(naphthalen-1-yl)-6-phenyl-1,3,5-triazine (12.1 g, 38.1 mmol) instead of 2-bromophenanthrene.

Synthesis Example 12-1: Preparation of Compound Q-21

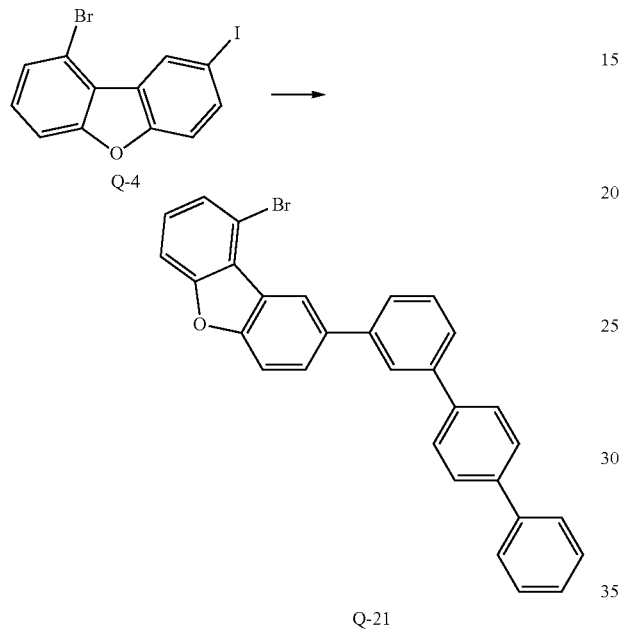

Q-21

Compound Q-21 (27.1 g, yield 71%; MS: [M+H]$^+$=475) was prepared in the same manner as in Synthesis Example 4-1, except that [1,1':4',1''-terphenyl]-3-ylboronic acid (22.0 g, 80.4 mmol) was used instead of 4,4,5,5-tetramethyl-2-(triphenylen-2-yl)-1,3,2-dioxaborolane (28.5 g, 80.4 mmol).

Synthesis Example 12-2: Preparation of Compound Q-22

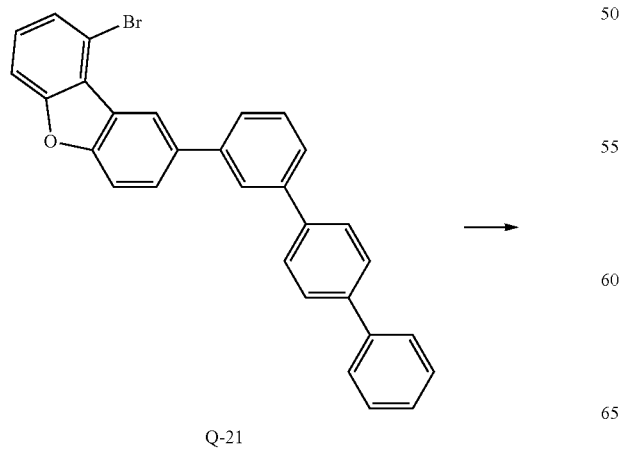

Q-21

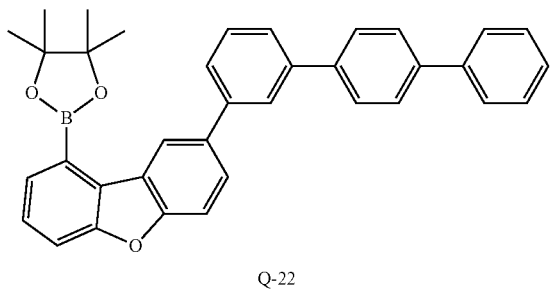

Q-22

Compound Q-22 (21.5 g, yield 78%; MS: [M+H]$^+$=523) was prepared in the same manner as in Synthesis Example 4-2, except that Compound Q-21 (25.1 g, 52.8 mmol) was used instead of Compound Q-5 (25.0 g, 52.8 mmol).

Synthesis Example 12-3: Preparation of Compound 33

Q-22

Compound 33

Compound 33 (18.8 g, yield 69%; MS: [M+H]$^+$=718) was prepared in the same manner as in Synthesis Example 1-1, except for using Compound Q-22 (19.9 g, 38.1 mmol) instead of Compound P-6, and 2-chloro-4-(dibenzo[b,d]furan-1-yl)-6-phenyl-1,3,5-triazine (13.6 g, 38.1 mmol) instead of 2-bromophenanthrene.

Synthesis Example 12-4: Preparation of Compound 67

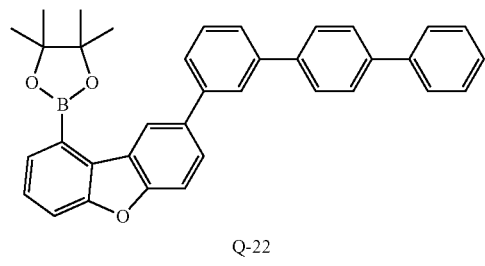

Q-22

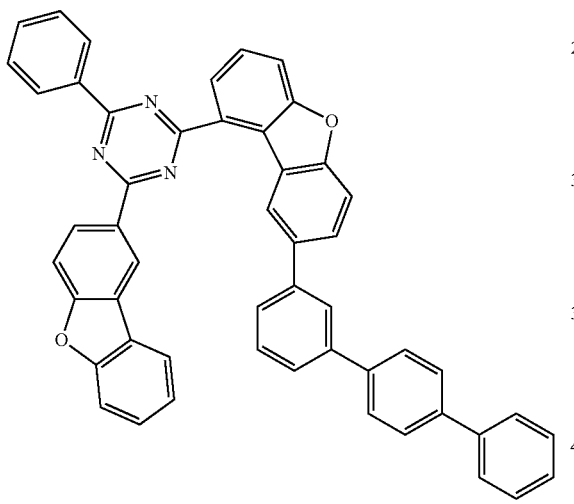

Compound 67

Compound 67 (17.2 g, yield 63%; MS: [M+H]⁺=718) was prepared in the same manner as in Synthesis Example 1-1, except for using Compound Q-22 (19.9 g, 38.1 mmol) instead of Compound P-6, and 2-chloro-4-(dibenzo[b,d]furan-2-yl)-6-phenyl-1,3,5-triazine (13.6 g, 38.1 mmol) instead of 2-bromophenanthrene.

Synthesis Example 13-1: Preparation of Intermediate Compound Q-23

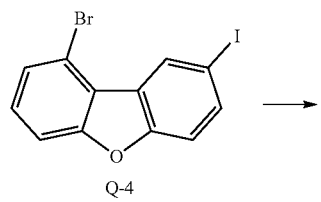

Q-4

-continued

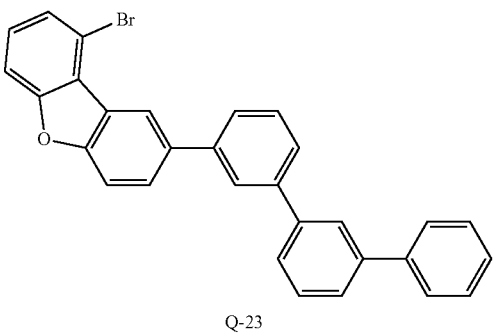

Q-23

Compound Q-23 (24.5 g, yield 64%; MS: [M+H]⁺=475) was prepared in the same manner as in Synthesis Example 4-1, except that [1,1':3',1''-terphenyl]-3-ylboronic acid (22.0 g, 80.4 mmol) was used instead of 4,4,5,5-tetramethyl-2-(triphenylen-2-yl)-1,3,2-dioxaborolane (28.5 g, 80.4 mmol).

Synthesis Example 13-2: Preparation of Intermediate Compound Q-24

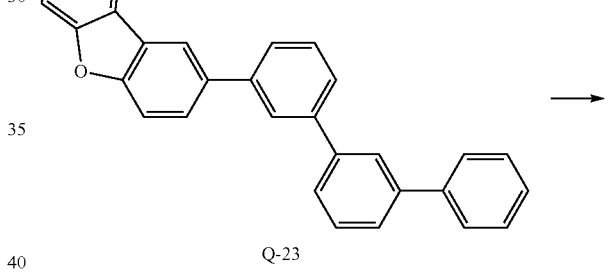

Q-23

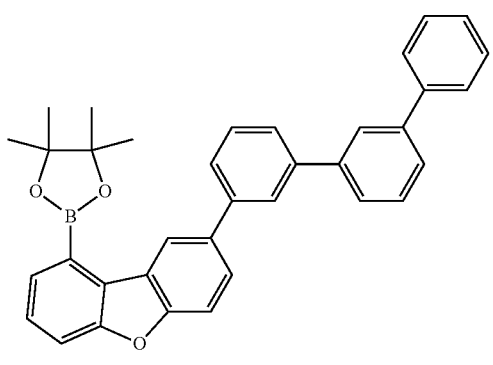

Q-24

Compound Q-24 (20.7 g, yield 75%; MS: [M+H]⁺=523) was prepared in the same manner as in Synthesis Example 4-2, except that Compound Q-23 (25.1 g, 52.8 mmol) was used instead of Compound Q-5 (25.0 g, 52.8 mmol).

Synthesis Example 13-3: Preparation of Compound 34

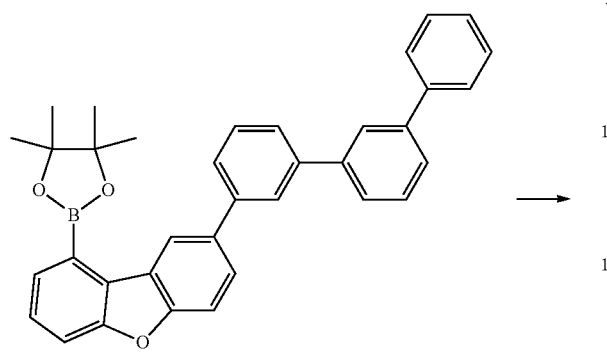

Q-24

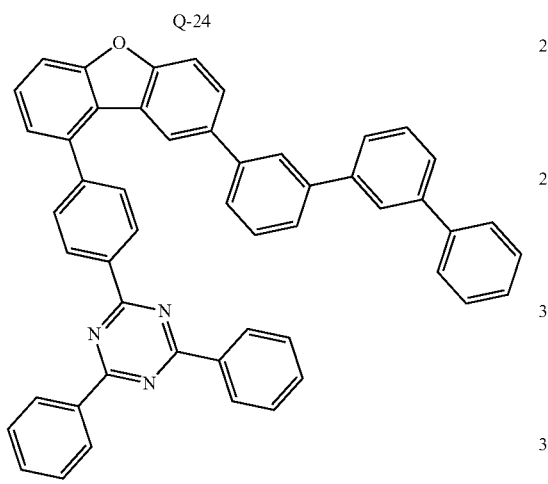

Compound 34

Compound 34 (19.6 g, yield 73%; MS: [M+H]⁺=704) was prepared in the same manner as in Synthesis Example 4-1, except for using Q-24 (19.9 g, 38.1 mmol) instead of Compound P-6, and 2-(4-chlorophenyl)-4,6-diphenyl-1,3,5-triazine (13.1 g, 38.1 mmol) instead of 2-bromophenanthrene.

Synthesis Example 13-4: Preparation of Compound 69

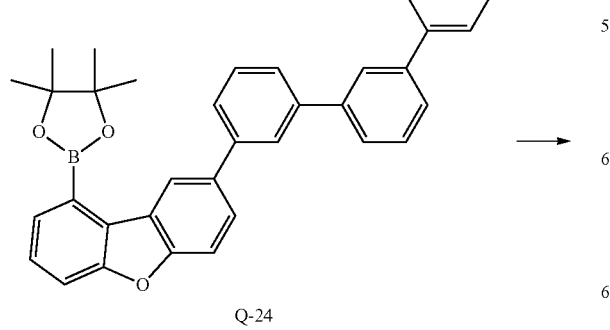

Q-24

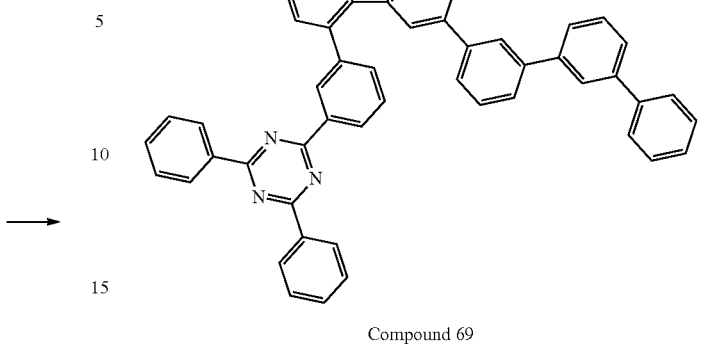

Compound 69

Compound 69 (18.8 g, yield 70%; MS: [M+H]⁺=704) was prepared in the same manner as in Synthesis Example 1-1, except for using Q-24 (19.9 g, 38.1 mmol) instead of Compound P-6, and 2-(3-chlorophenyl)-4,6-diphenyl-1,3,5-triazine (13.1 g, 38.1 mmol) instead of 2-bromophenanthrene.

Synthesis Example 14-1: Preparation of Intermediate Compound Q-25

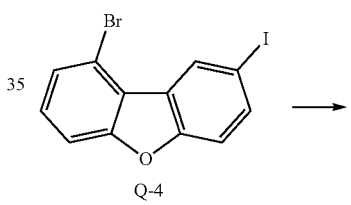

Q-4

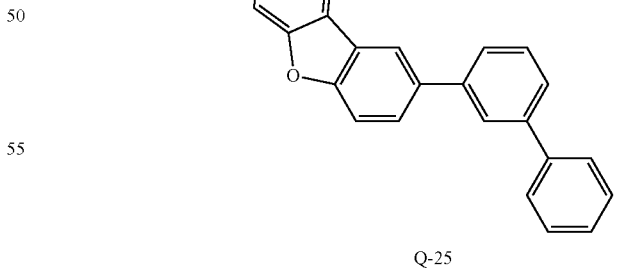

Q-25

Compound Q-25 (21.8 g, yield 68%; MS: [M+H]⁺=399) was prepared in the same manner as in Synthesis Example 4-1, except that [1,1'-biphenyl]-3-ylboronic acid (15.9 g, 80.4 mmol) was used instead of 4,4,5,5-tetramethyl-2-(triphenylen-2-yl)-1,3,2-dioxaborolane (28.5 g, 80.4 mmol).

Synthesis Example 14-2: Preparation of Intermediate Compound Q-26

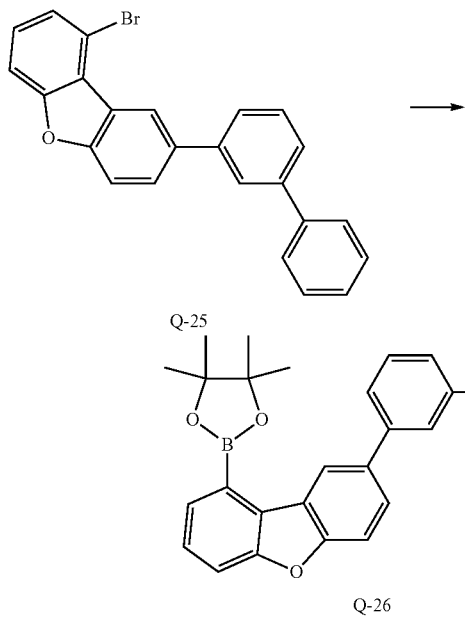

Compound Q-26 (16.5 g, yield 70%; MS: $[M+H]^+=447$) was prepared in the same manner as in Synthesis Example 4-2, except that Compound Q-25 (21.1 g, 52.8 mmol) was used instead of Compound Q-5 (25.0 g, 52.8 mmol).

Synthesis Example 14-3: Preparation of Compound 35

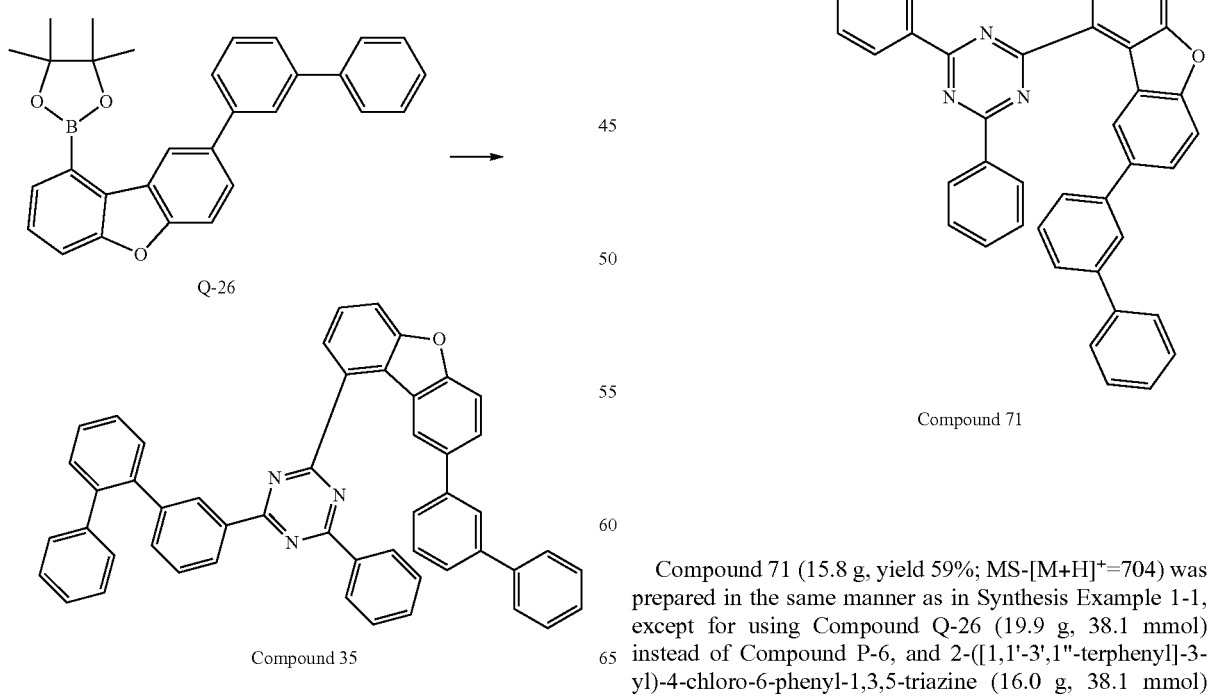

Compound 35 (17.4 g, yield 65%; MS: $[M+H]^+=704$) was prepared in the same manner as in Synthesis Example 1-1, except for using Compound Q-26 (19.9 g, 38.1 mmol) instead of Compound P-6, and 2-([1,1':2',1''-terphenyl]-3-yl)-4-chloro-6-phenyl-1,3,5-triazine (16.0 g, 38.1 mmol) instead of 2-bromophenanthrene.

Synthesis Example 14-4: Preparation of Compound 71

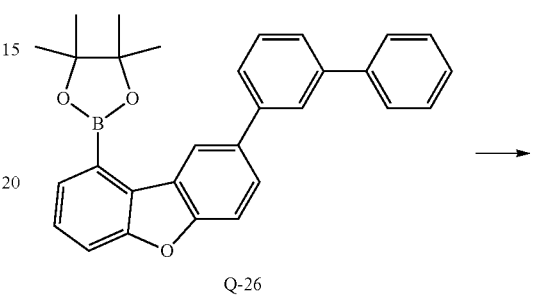

Compound 71 (15.8 g, yield 59%; MS-$[M+H]^+=704$) was prepared in the same manner as in Synthesis Example 1-1, except for using Compound Q-26 (19.9 g, 38.1 mmol) instead of Compound P-6, and 2-([1,1'-3',1''-terphenyl]-3-yl)-4-chloro-6-phenyl-1,3,5-triazine (16.0 g, 38.1 mmol) instead of 2-bromophenanthrene.

Synthesis Example 15-1: Preparation of Intermediate Compound Q-27

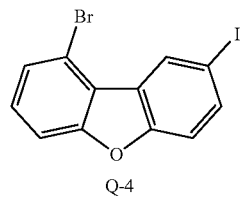 

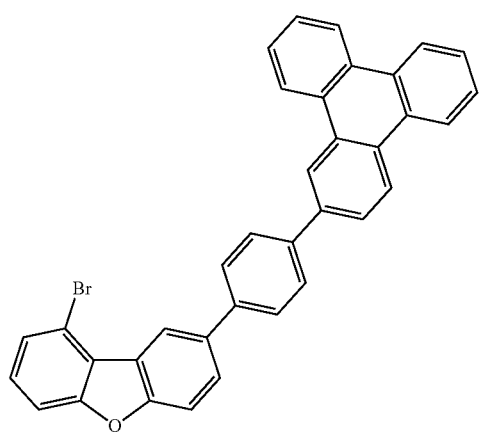

Q-27

Compound Q-27 (27.4 g, yield 62%; MS: [M+H]⁺=549) was prepared in the same manner as in Synthesis Example 4-1, except that (4-(triphenylen-2-yl)phenyl)boronic acid (28.0 g, 80.4 mmol) was used instead of 4,4,5,5-tetramethyl-2-(triphenylen-2-yl)-1,3,2-dioxaborolane (28.5 g, 80.4 mmol).

Synthesis Example 15-2: Preparation of Intermediate Compound Q-28

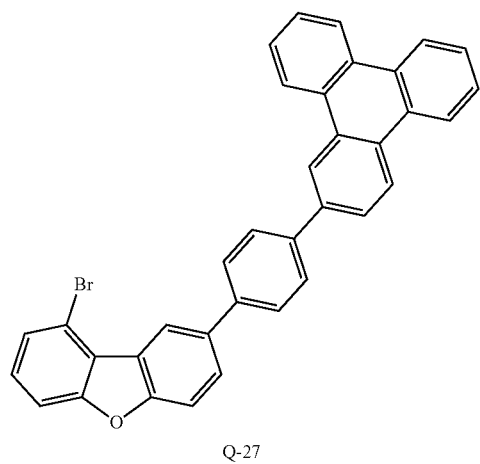 

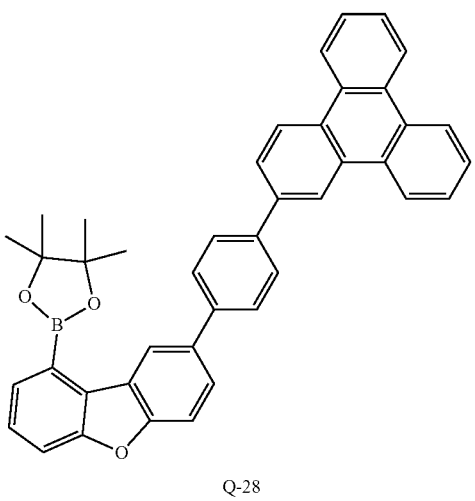

Q-28

Compound Q-28 (26.1 g, yield 83%; MS: [M+H]⁺=597) was prepared in the same manner as in Synthesis Example 4-2, except that Compound Q-27 (29.0 g, 52.8 mmol) was used instead of Compound Q-5 (25.0 g, 52.8 mmol).

Synthesis Example 15-3: Preparation of Compound 47

405

-continued

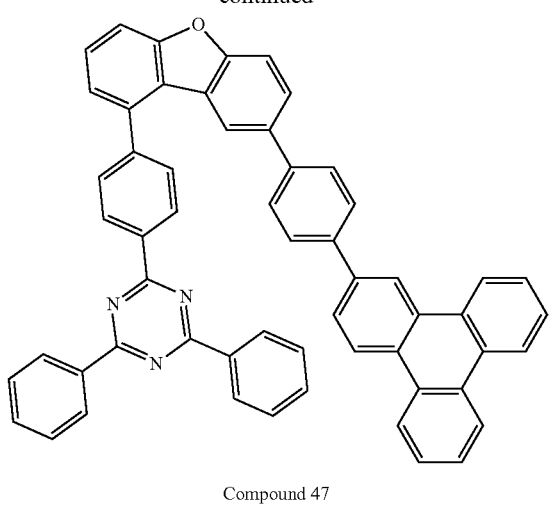

Compound 47

Compound 47 (20.2 g, yield 68%; MS: [M+H]⁺=778) was prepared in the same manner as in Synthesis Example 1-1, except for using Compound Q-28 (19.9 g, 38.1 mmol) instead of Compound P-6, and 2-(4-chlorophenyl)-4,6-diphenyl-1,3,5-triazine (13.1 g, 38.1 mmol) instead of 2-bromophenanthrene.

Synthesis Example 16-1: Preparation of Intermediate Compound Q-29

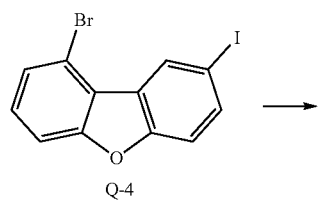

Q-4

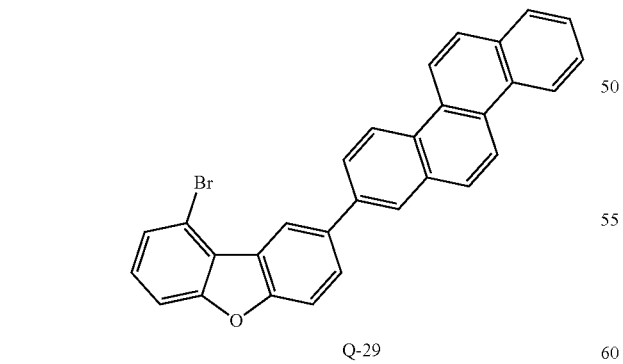

Q-29

Compound 29 (22.5 g, yield 59%; MS: [M+H]⁺=473) was prepared in the same manner as in Synthesis Example 4-1, except that chrysen-2-ylboronic acid (21.9 g, 80.4 mmol) was used instead of 4,4,5,5-tetramethyl-2-(triphenylen-2-yl)-1,3,2-dioxaborolane (28.5 g, 80.4 mmol).

406

Synthesis Example 16-2: Preparation of Intermediate Compound Q-30

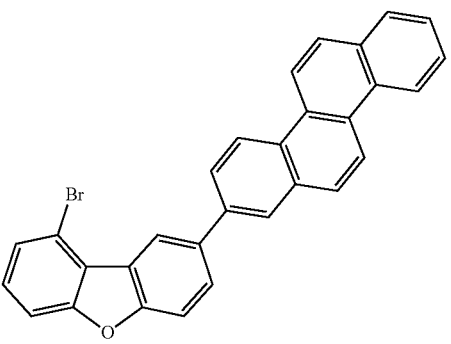

Q-29

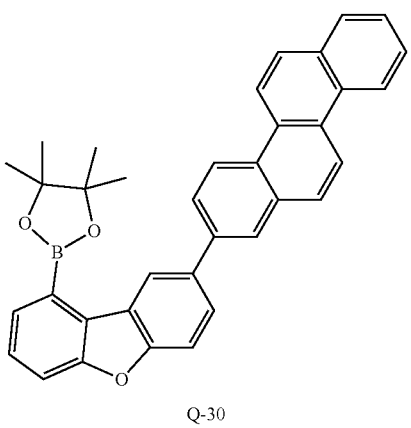

Q-30

Compound Q-30 (23.9 g, yield 87%; MS: [M+H]⁺=521) was prepared in the same manner as in Synthesis Example 4-2, except that Compound Q-29 (25.0 g, 52.8 mmol) was used instead of Compound Q-5 (25.0 g, 52.8 mmol).

Synthesis Example 16-3: Preparation of Compound 51

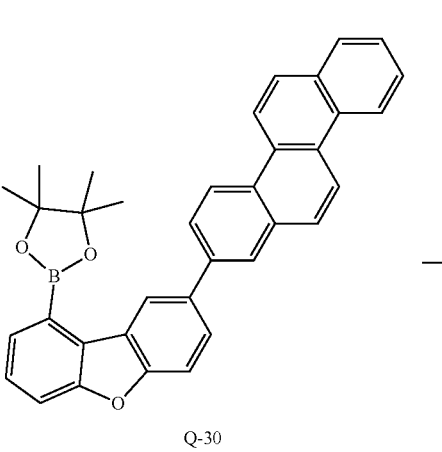

Q-30

407

-continued

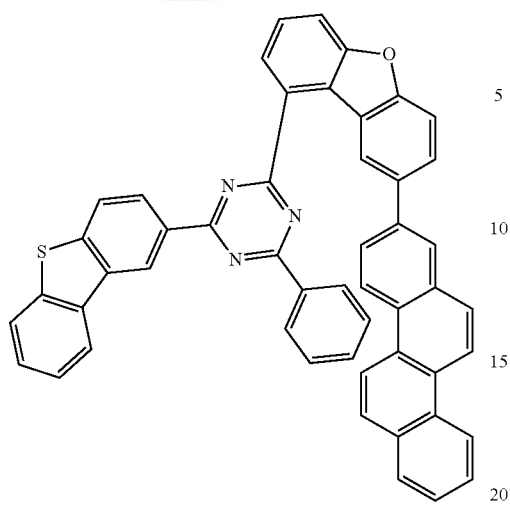

Compound 51

Compound 51 (17.0 g, yield 61%; MS: [M+H]⁺=732) was prepared in the same manner as in Synthesis Example 1-1, except for using Compound Q-30 (19.8 g, 38.1 mmol) instead of Compound P-6, and 2-chloro-4-(dibenzo[b,d]thiophen-2-yl)-6-phenyl-1,3,5-triazine (14.2 g, 38.1 mmol) instead of 2-bromophenanthrene.

Synthesis Example 17-1: Preparation of Intermediate Compound Q-31

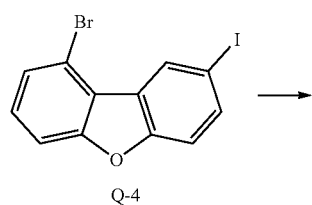

Q-4

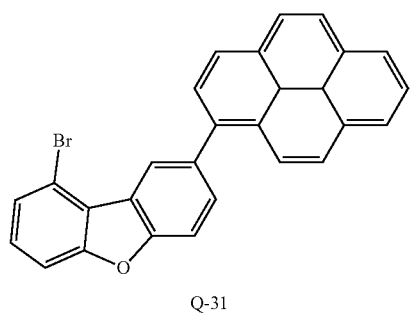

Q-31

Compound Q-31 (22.8 g, yield 63%; MS: [M+H]⁺=449) was prepared in the same manner as in Synthesis Example 4-1, except that (3a1,5a1-dihydropyren-1-yl)boronic acid (19.9 g, 80.4 mmol) was used instead of 4,4,5,5-tetramethyl-2-(triphenylen-2-yl)-1,3,2-dioxaborolane (28.5 g, 80.4 mmol).

408

Synthesis Example 17-2: Preparation of Intermediate Compound Q-32

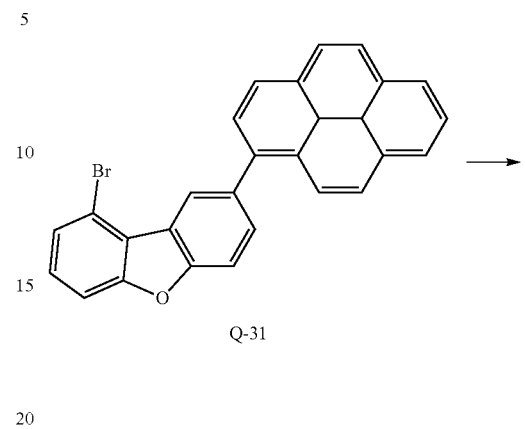

Q-31

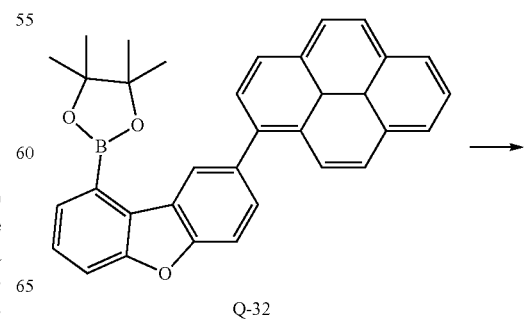

Q-32

Compound Q-32 (22.3 g, yield 85%; MS: [M+H]⁺=497) was prepared in the same manner as in Synthesis Example 4-2, except that Compound Q-31 (23.7 g, 52.8 mmol) was used instead of Compound Q-5 (25.0 g, 52.8 mmol).

Synthesis Example 17-3: Preparation of Compound 52

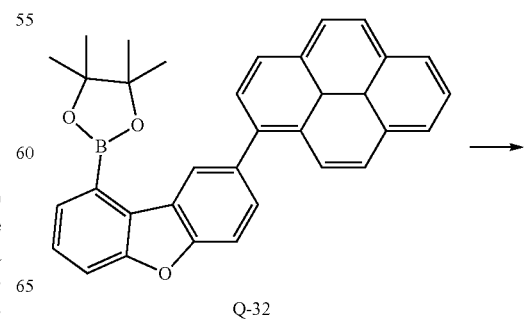

Q-32

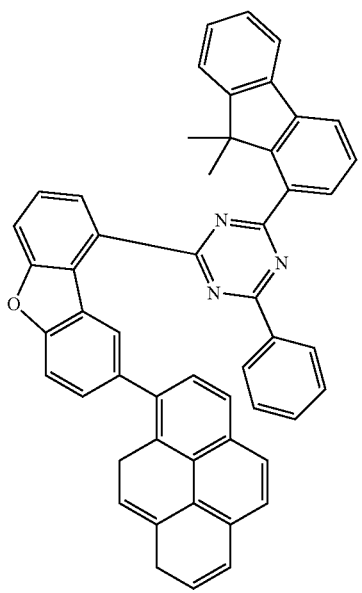

Compound 52

Compound 52 (17.0 g, yield 62%; MS: [M+H]$^+$=718) was prepared in the same manner as in Synthesis Example 1-1, except for using Compound Q-32 (18.9 g, 38.1 mmol) instead of Compound P-6, and 2-chloro-4-(9,9-dimethyl-9H-fluoren-1-yl)-6-phenyl-1,3,5-triazine (14.6 g, 38.1 mmol) instead of 2-bromophenanthrene.

Synthesis Example 18-1: Preparation of Intermediate Compound Q-33

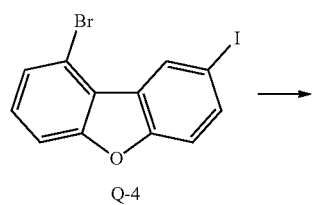

Q-4

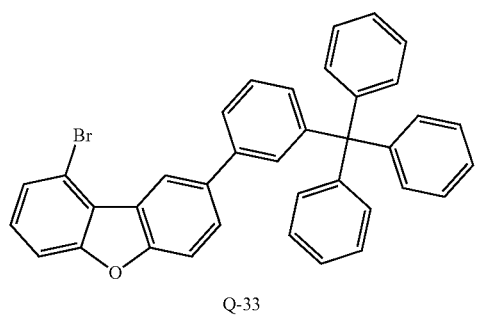

Q-33

Compound Q-33 (27.3 g, yield 60%; MS: [M+H]$^+$=565) was prepared in the same manner as in Synthesis Example 4-1, except that (3-tritylphenyl)boronic acid (29.3 g, 80.4 mmol) was used instead of 4,4,5,5-tetramethyl-2-(triphenylen-2-yl)-1,3,2-dioxaborolane (28.5 g, 80.4 mmol).

Synthesis Example 18-2: Preparation of Intermediate Compound Q-34

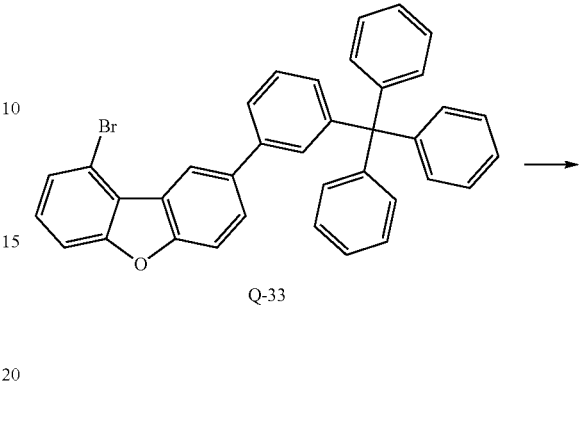

Q-33

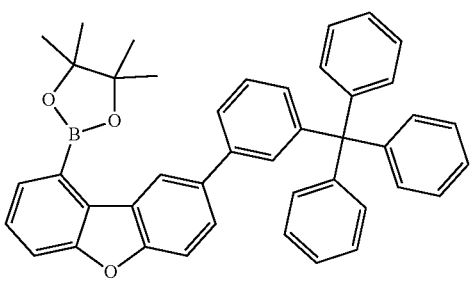

Q-34

Compound Q-34 (28.1 g, yield 87%; MS: [M+H]$^+$=613) was prepared in the same manner as in Synthesis Example 4-2, except that Compound Q-33 (13.4 g, 52.8 mmol) was used instead of Compound Q-5 (25.0 g, 52.8 mmol).

Synthesis Example 18-3: Preparation of Compound 56

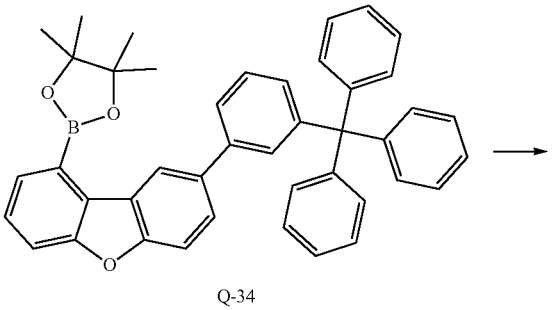

Q-34

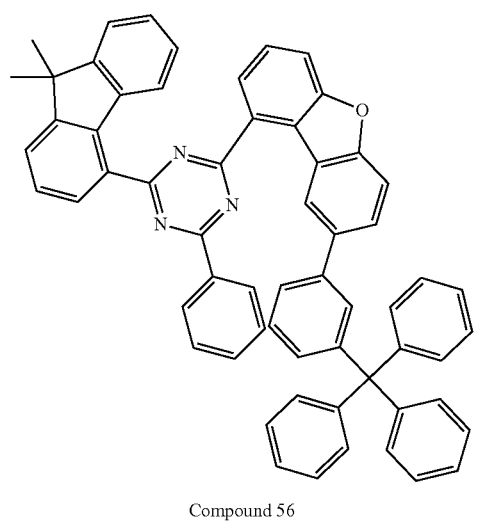

Compound 56

Compound 56 (20.3 g, yield 64%; MS: [M+H]⁺=834) was prepared in the same manner as in Synthesis Example 1-1, except for using Compound Q-34 (23.3 g, 38.1 mmol) instead of Compound P-6, and 2-chloro-4-(9,9-dimethyl-9H-fluoren-4-yl)-6-phenyl-1,3,5-triazine (14.6 g, 38.1 mmol) instead of 2-bromophenanthrene.

Synthesis Example 19-1: Preparation of Intermediate Compound Q-35

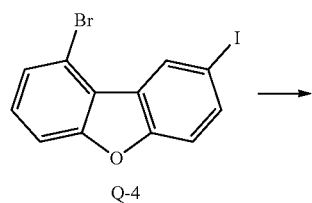

Q-4

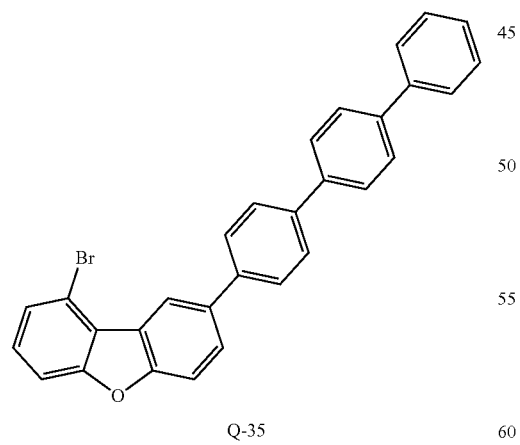

Q-35

Compound Q-35 (21.0 g, yield 55%; MS: [M+H]⁺=475) was prepared in the same manner as in Synthesis Example 4-1, except that [1,1':4',1''-terphenyl]-4-ylboronic acid (22.0 g, 80.4 mmol) was used instead of 4,4,5,5-tetramethyl-2-(triphenylen-2-yl)-1,3,2-dioxaborolane (28.5 g, 80.4 mmol).

Synthesis Example 19-2: Preparation of Intermediate Compound Q-36

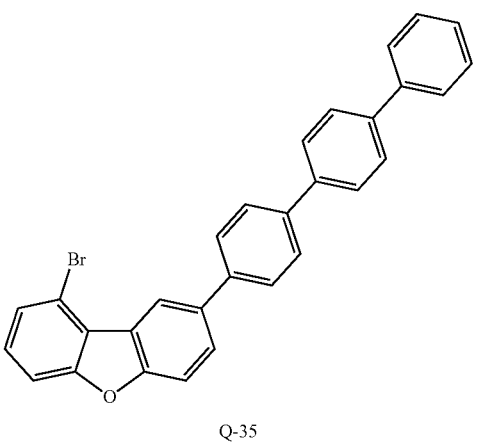

Q-35

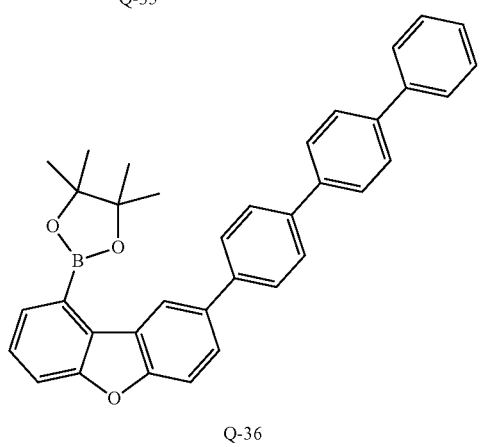

Q-36

Compound Q-36 (24.6 g, yield 89%; MS: [M+H]⁺=523) was prepared in the same manner as in Synthesis Example 4-2, except that Compound Q-35 (25.1 g, 52.8 mmol) was used instead of Compound Q-5 (25.0 g, 52.8 mmol).

Synthesis Example 19-3: Preparation of Compound 75

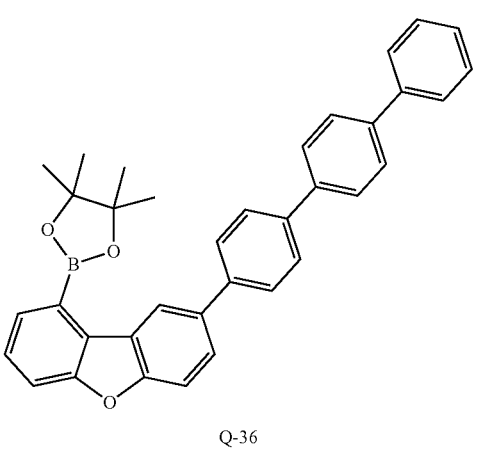

Q-36

-continued

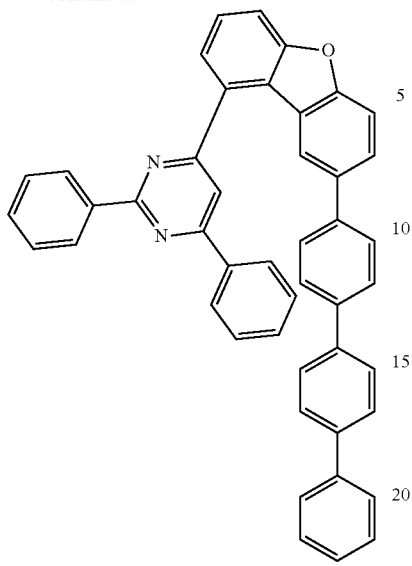

Compound 75

Compound 75 (16.0 g, yield 67%; MS: [M+H]⁺=627) was prepared in the same manner as in Synthesis Example 1-1, except for using Compound Q-36 (19.9 g, 38.1 mmol) instead of Compound P-6, and 4-chloro-2,6-diphenylpyrimidine (10.2 g, 38.1 mmol) instead of 2-bromophenanthrene.

Synthesis Example 20: Preparation of Intermediate Compound R-6

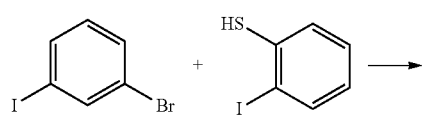

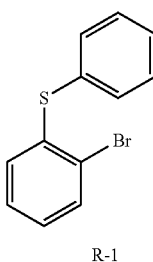

R-1

1-Bromo-3-iodobenzene (50 g, 176.7 mmol) and 2-bromothiophenol (40.1 g, 212.0 mmol) were dispersed in ethanol (EtOH, 500 ml) to which NaOH (9.2 g, 229.7 mmol) was added and then refluxed for 6 hours. After completion of the reaction, the reaction solution was cooled to room temperature, and water was added thereto. The obtained organic layer was distilled under reduced pressure. The mixture was filtered through silica gel to obtain Compound R-1 (48.6 g, yield 80%; MS: [M+H]⁺=342).

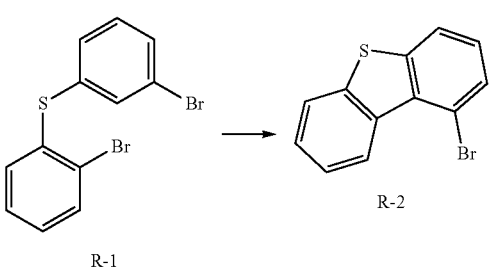

After Compound R-1 (40.0 g, 116.3 mmol) was dissolved in 500 ml of dichloromethane (DCM), 2,3-dichloro-5,6-dicyano-1,4-benzoquinone (DDQ) (31.6 g, 140.0 mmol) was added thereto and stirred at room temperature for 24 hours. After completion of the reaction, the mixture was extracted three times with an excess amount of water. The organic layer was dried over magnesium sulfate and then distilled under reduced pressure to obtain Compound R-2 (21.7 g, yield 71%; MS: [M+H]⁺=262).

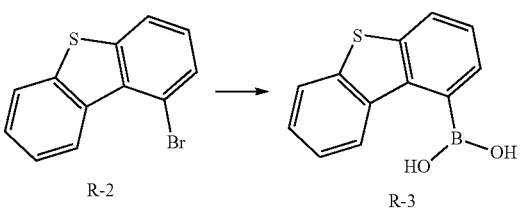

After Compound R-2 (20 g, 76.0 mmol) was dissolved in tetrahydrofuran (250 ml), the temperature was lowered to −78° C. and 1.7M tert-butyllithium (t-BuLi) (44.7 ml, 76.0 mmol) was slowly added. After stirring at the same temperature for one hour, triisopropylborate (B(OiPr)₃) (20.1 ml, 152.0 mmol) was added and stirred for 3 hours while gradually raising the temperature to room temperature. To the reaction mixture was added 2N aqueous hydrochloric acid solution (100 ml) and the mixture was stirred at room temperature for 1.5 hours. The resulting precipitate was filtered, washed sequentially with water and ethyl ether, and dried under vacuum. After drying, the reaction mixture was dispersed in ethyl ether, stirred for two hours, filtered and dried to obtain Compound R-3 (151 g, yield 87%; MS: [M+H]⁺=229).

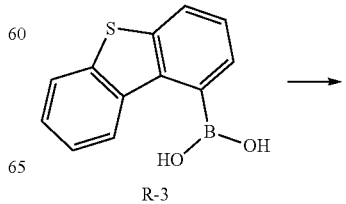

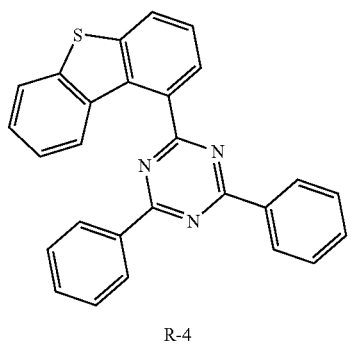

R-4

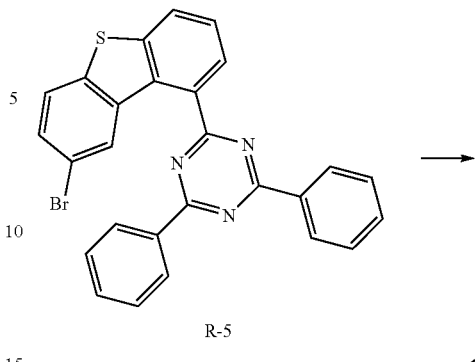

R-5

After Compound R-3 (15.0 g, 65.8 mmol) and 2-chloro-4,6-diphenyl-1,3,5-triazine (17.6 g, 162.3 mmol) were dispersed in tetrahydrofuran (200 ml), 2M potassium aqueous solution (aq.K$_2$CO$_3$) (98.7 ml, 197.4 mmol) was added and tetrakis(triphenylphosphine)palladium [Pd(PPh$_3$)$_4$] (1.5 g, 2 mol %) was added. The mixture was stirred and refluxed for 5 hours. The temperature was lowered to room temperature and the resulting solid was filtered. The filtered solid was recrystallized from tetrahydrofuran and ethyl acetate, filtered and then dried to obtain compound R-4 (24.1 g, yield 88%; MS: [M+H]$^+$=416).

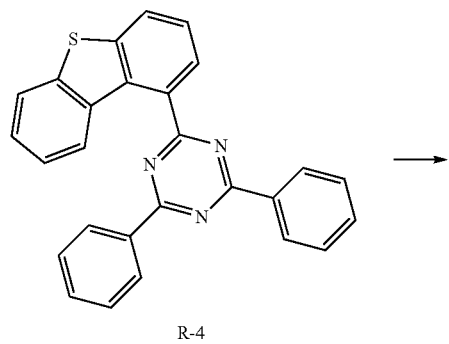

R-4

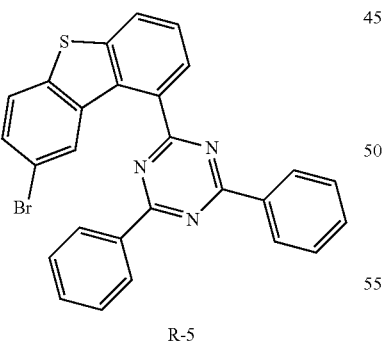

R-5

Compound R-4 (40 g, 96.3 mmol) was dissolved in chloroform (350 mL) to which acetic acid (350 mL) was added and Br$_2$ (5.2 mL, 101.1 mmol) was added dropwise at 0° C. The obtained mixture was warmed to room temperature and stirred for 5 hours. After completion of the reaction, the reaction solution was concentrated and recrystallized from ethanol to obtain Compound R-5 (34.3 g, yield 72%; MS: [M+H]$^+$=494).

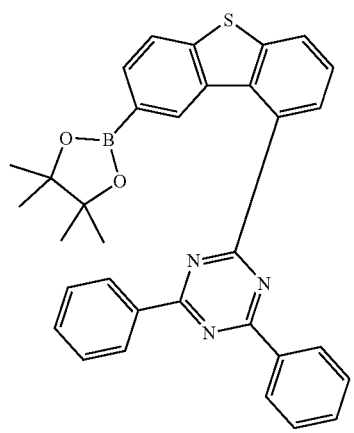

R-6

Compound R-5 (40 g, 80.9 mmol), bis(pinacolato)diboron (24.7 g, 97.1 mmol), potassium acetate (33.5 g, 242.7 mmol) and tetrakis(triphenylphosphine)palladium(0) [Pd(PPh$_3$)$_4$] (1.9 g, 2 mol %) were added to tetrahydrofuran (500 ml) and refluxed for 12 hours. After completion of the reaction, the mixture was cooled to room temperature, and distilled under reduced pressure to remove the solvent. This was dissolved in chloroform and washed three times with water. The organic layer was separated, dried with magnesium sulfate and distilled under reduced pressure to obtain Compound R-6 (39.9 g, yield 91%; MS: [M+H]$^+$=542).

Synthesis Example 20-1: Preparation of Compound 5

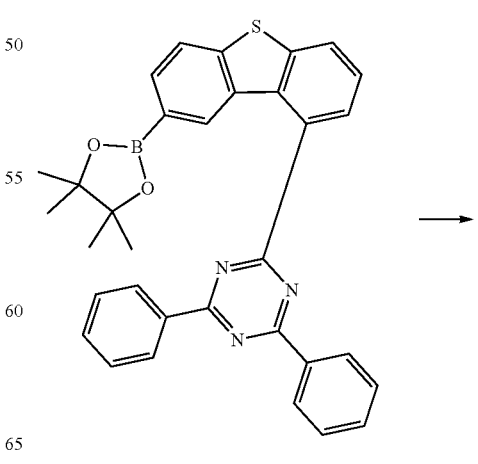

R-6

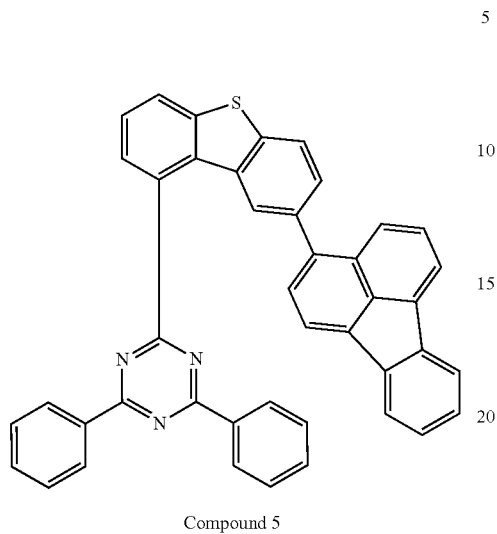

Compound 5

Compound 5 (17.9 g, yield 76%; MS: [M+H]⁺=616) was prepared in the same manner as in Synthesis Example 1-1, except for using Compound R-6 (20.6 g, 38.1 mmol) instead of Compound P-6, and 3-bromofluoranthene (10.7 g, 38.1 mmol) instead of 2-bromophenanthrene.

Synthesis Example 20-2: Preparation of Compound 53

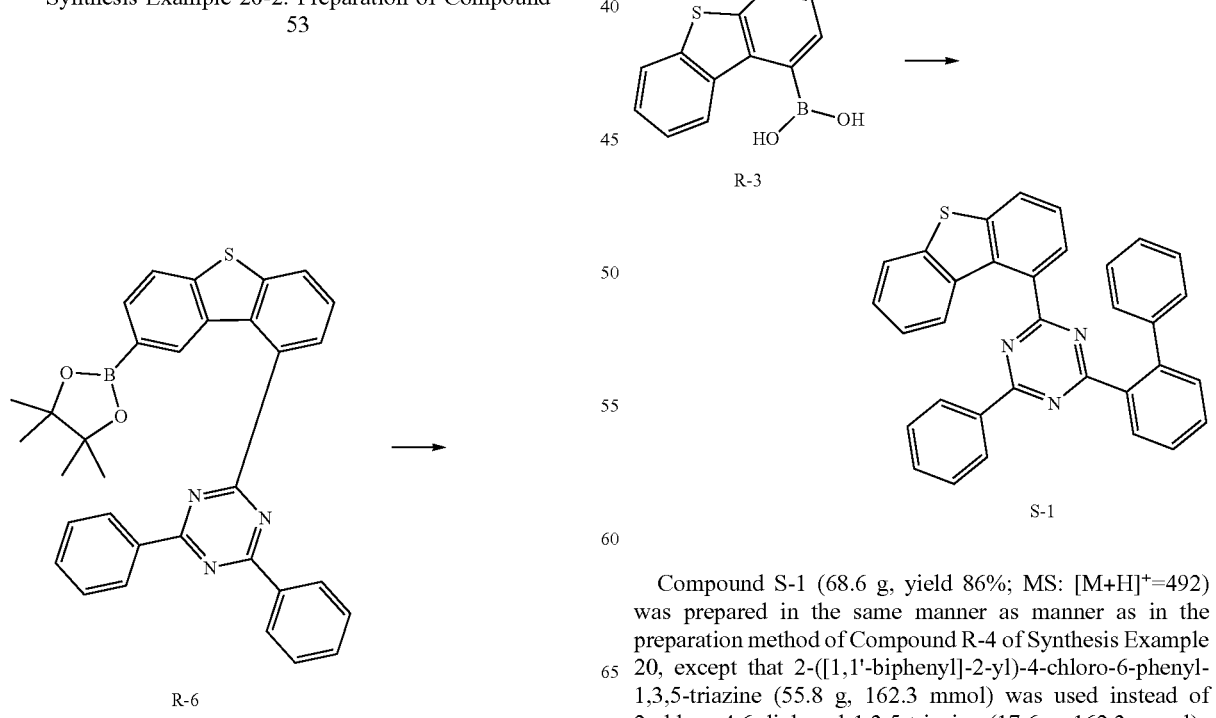

R-6

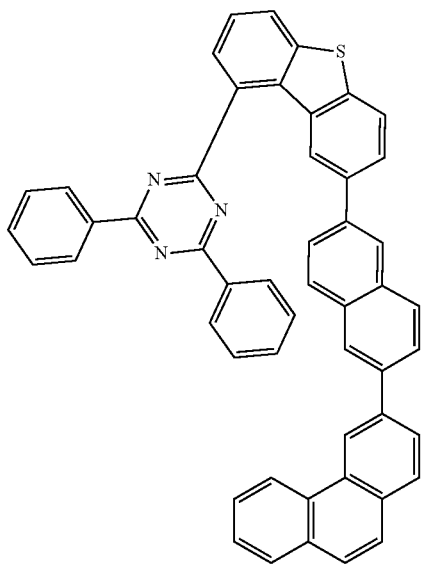

Compound 53

Compound 53 (18.9 g, yield 69%; MS: [M+H]⁺=718) was prepared in the same manner as in Synthesis Example 1-1, except for using Compound R-6 (20.6 g, 38.1 mmol) instead of Compound P-6, and 3-(6-bromonaphthalen-2-yl)phenanthrene (14.6 g, 38.1 mmol) instead of 2-bromophenanthrene.

Synthesis Example 21: Preparation of Intermediate Compound S-2

R-3

S-1

Compound S-1 (68.6 g, yield 86%; MS: [M+H]⁺=492) was prepared in the same manner as manner as in the preparation method of Compound R-4 of Synthesis Example 20, except that 2-([1,1'-biphenyl]-2-yl)-4-chloro-6-phenyl-1,3,5-triazine (55.8 g, 162.3 mmol) was used instead of 2-chloro-4,6-diphenyl-1,3,5-triazine (17.6 g, 162.3 mmol).

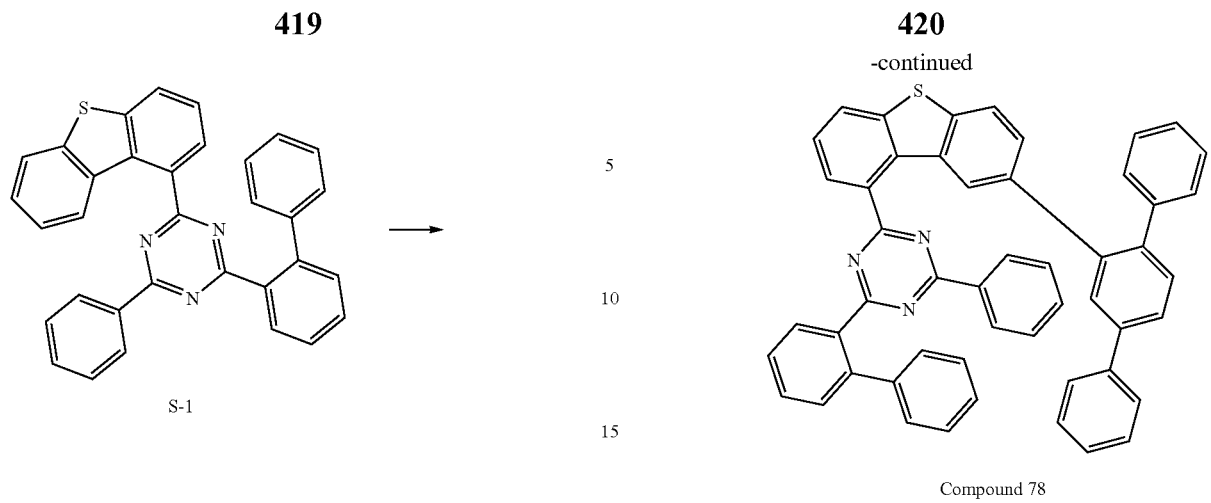

S-1

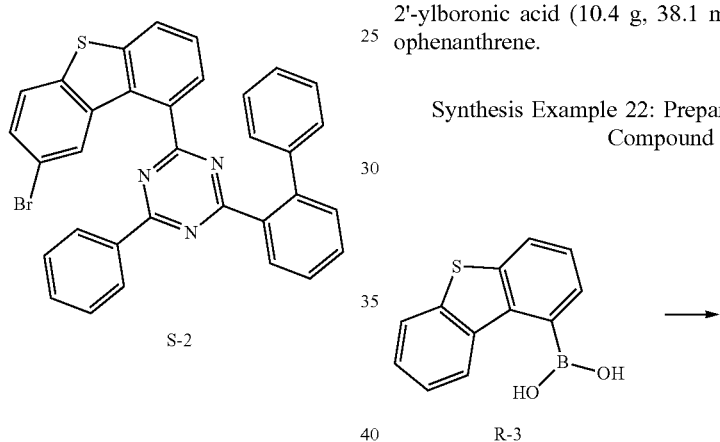

S-2

Compound S-2 (50.5 g, yield 92%; MS: [M+H]$^+$=492) was prepared in the same manner as manner as in the preparation method of Compound R-5 of Synthesis Example 20, except that Compound S-1 (47.3 g, 96.3 mmol) was used instead of Compound R-4 (40 g, 96.3 mmol).

Synthesis Example 21-1: Preparation of Compound 78

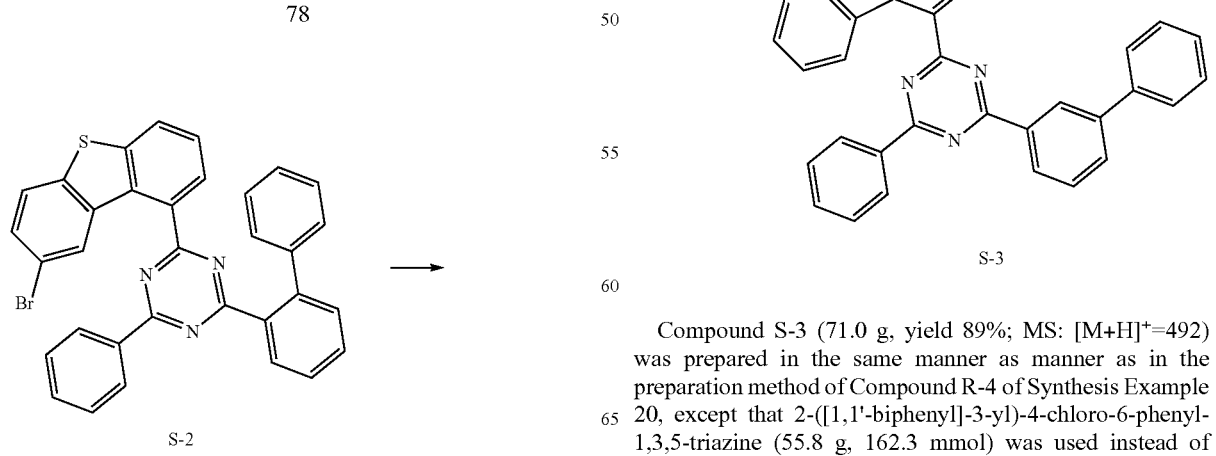

Compound 78

Compound 78 (14.8 g, yield 54%; MS: [M+H]$^+$=720) was prepared in the same manner as manner as in Synthesis Example 1-1, except for using Compound S-2 (20.6 g, 38.1 mmol) instead of Compound P-6, and [1,1':4',1''-terphenyl]-2'-ylboronic acid (10.4 g, 38.1 mmol) instead of 2-bromophenanthrene.

Synthesis Example 22: Preparation of Intermediate Compound S-3

R-3

S-3

Compound S-3 (71.0 g, yield 89%; MS: [M+H]$^+$=492) was prepared in the same manner as manner as in the preparation method of Compound R-4 of Synthesis Example 20, except that 2-([1,1'-biphenyl]-3-yl)-4-chloro-6-phenyl-1,3,5-triazine (55.8 g, 162.3 mmol) was used instead of 2-chloro-4,6-diphenyl-1,3,5-triazine (17.6 g, 162.3 mmol).

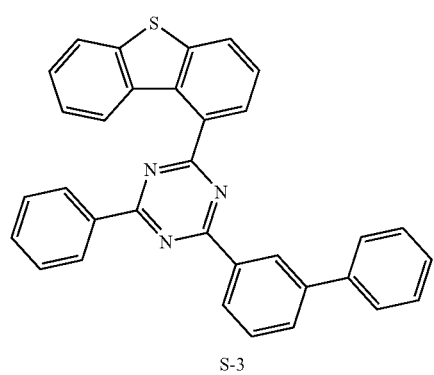

S-3

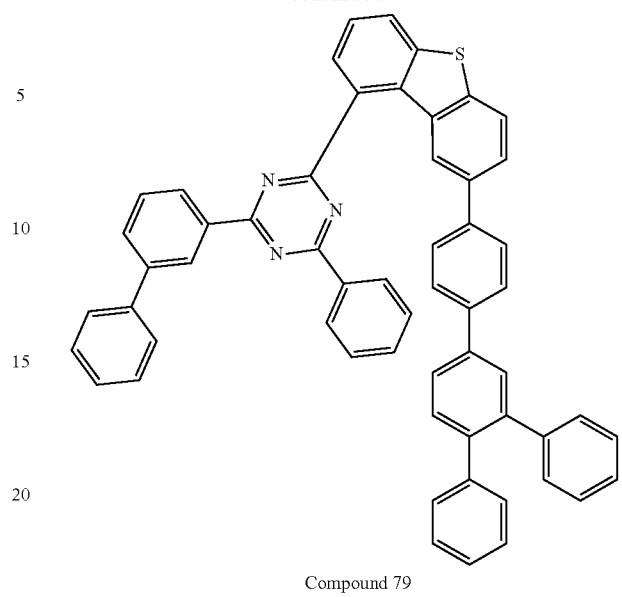

Compound 79

Compound 79 (20.6 g, yield 68%; MS: [M+H]$^+$=796) was prepared in the same manner as manner as in Synthesis Example 1-1, except for using S-4 (21.7 g, 38.1 mmol) instead of Compound P-6, and (4'-phenyl-[1,1':3',1"-terphenyl]-4-yl)boronic acid (13.3 g, 38.1 mmol) instead of 2-bromophenanthrene.

Synthesis Example 23: Preparation of Intermediate Compound S-6

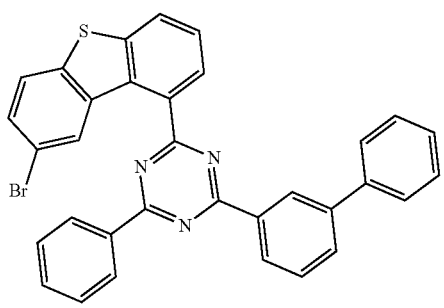

S-4

Compound S-4 (49.4 g, yield 90%; MS: [M+H]$^+$=570) was prepared in the same manner as manner as in the preparation method of Compound R-5 of Synthesis Example 20, except that Compound S-3 (47.3 g, 96.3 mmol) was used instead of Compound R-4 (40 g, 96.3 mmol).

Synthesis Example 22-1: Preparation of Compound 79

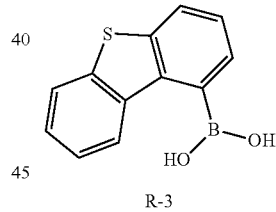

R-3

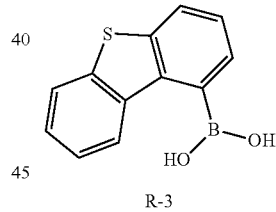

S-5

Compound S-5 (57.9 g, yield 86%; MS: [M+H]$^+$=415) was prepared in the same manner as manner as in the preparation method of Compound R-4 of Synthesis Example 20, except that 2-chloro-4,6-diphenylpyrimidine (43.3 g, 162.3 mmol) was used instead of 2-chloro-4,6-diphenyl-1,3,5-triazine (17.6 g, 162.3 mmol).

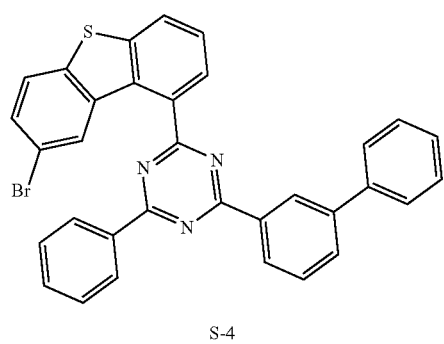

S-4

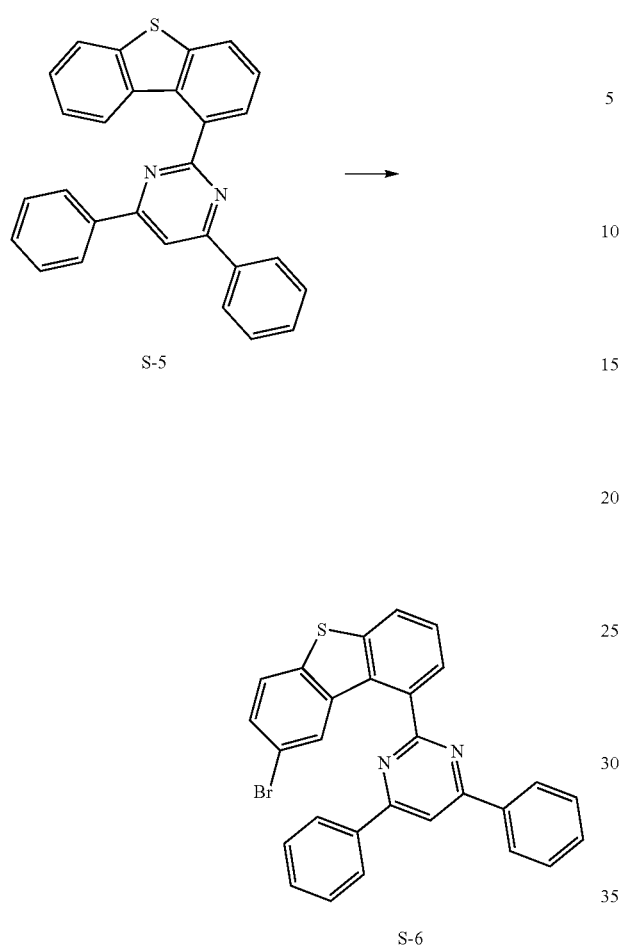

S-5

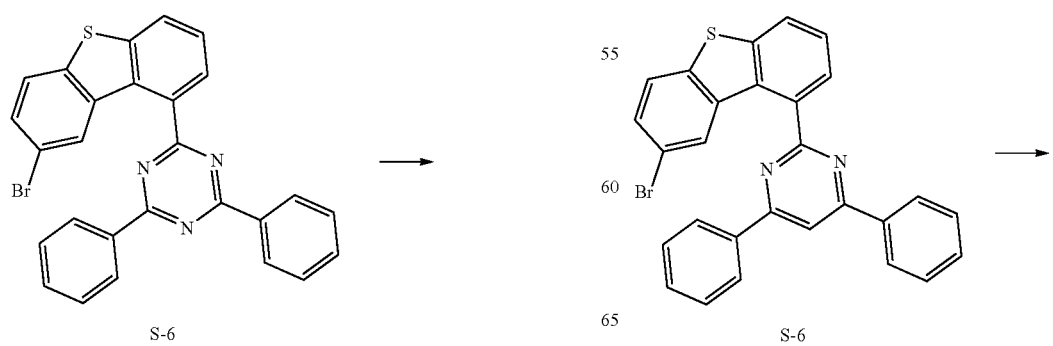

Compound 43

Compound S-6 (41.3 g, yield 87%; MS: [M+H]⁺=493) was prepared in the same manner as manner as in the preparation method of Compound R-5 of Synthesis Example 20, except that Compound S-3 (39.9 g, 96.3 mmol) was used instead of Compound R-4 (40 g, 96.3 mmol).

Synthesis Example 23-1: Preparation of Compound 43

Compound 43 (18.4 g, yield 67%; MS: [M+H]⁺=719) was prepared in the same manner as manner as in Synthesis Example 1-1, except for using S-6 (18.8 g, 38.1 mmol) instead of Compound P-6, and [1,1':3',1'':3'',1'''-quaterphenyl]-4-ylboronic acid (13.3 g, 38.1 mmol) instead of 2-bromophenanthrene.

Synthesis Example 23-2: Preparation of Compound 80

-continued

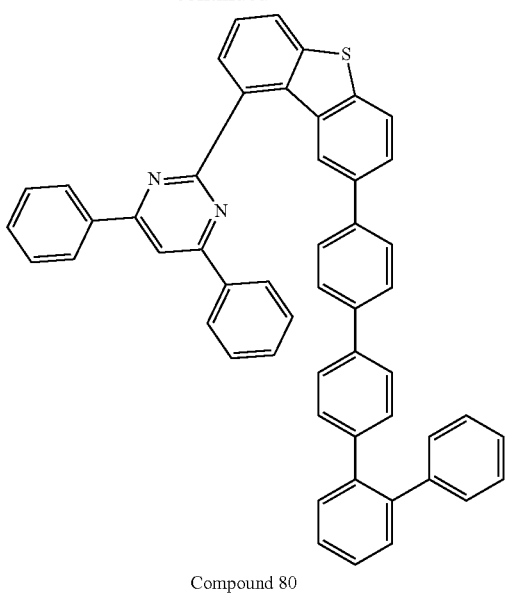

Compound 80

Compound 80 (17.8 g, yield 65%; MS: [M+H]$^+$=719) was prepared in the same manner as manner as in Synthesis Example 1-1, except for using S-6 (18.8 g, 38.1 mmol) instead of Compound P-6, and [1,1':2',1":4",1'''-quaterphenyl]-4'''-ylboronic acid (13.3 g, 38.1 mmol) instead of 2-bromophenanthrene.

Synthesis Example 24: Preparation of Intermediate Compound S-8

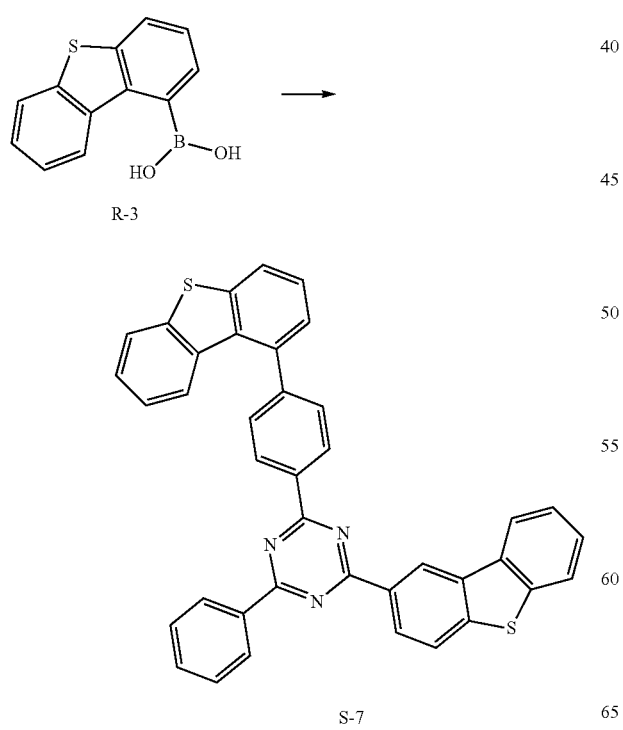

R-3

S-7

Compound S-7 (80.5 g, yield 83%; MS: [M+H]$^+$=598) was prepared in the same manner as manner as in the preparation method of Compound R-4 of Synthesis Example 20, except that 2-(4-chlorophenyl)-4-(dibenzo[b,d]thiophen-2-yl)-6-phenyl-1,3,5-triazine (73.0 g, 162.3 mmol) was used instead of 2-chloro-4,6-diphenyl-1,3,5-triazine (17.6 g, 162.3 mmol).

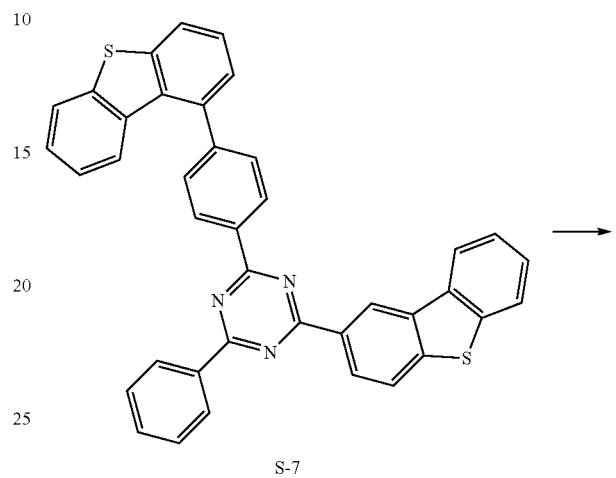

S-7

S-8

Compound S-8 (52.8 g, yield 81%; MS: [M+H]$^+$=676) was prepared in the same manner as manner as in the preparation method of Compound R-5 of Synthesis Example 20, except that Compound S-7 (57.6 g, 96.3 mmol) was used instead of Compound R-4 (40 g, 96.3 mmol).

Synthesis Example 24-1: Preparation of Compound 18

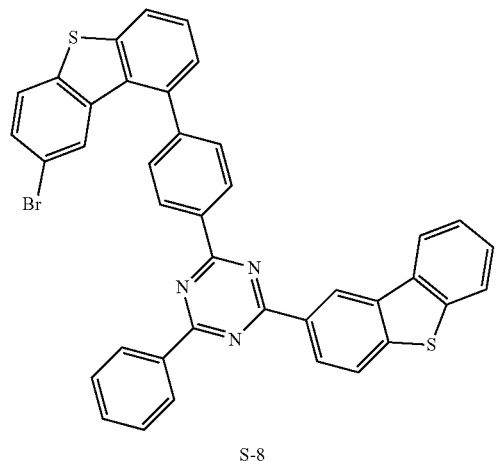

S-8

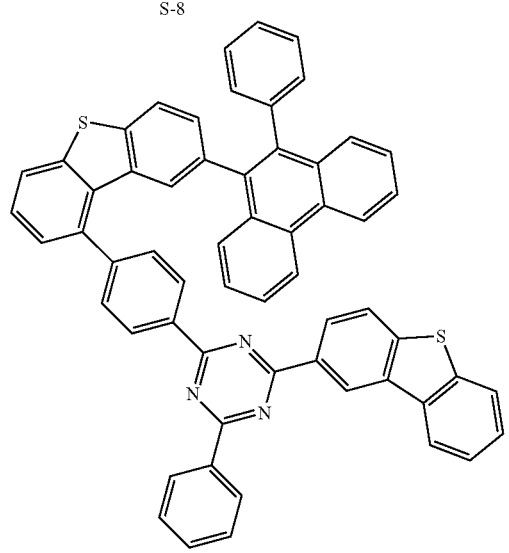

Compound 18

Compound 18 (17.5 g, yield 54%; MS: [M+H]$^+$=850) was prepared in the same manner as manner as in Synthesis Example 1-1, except for using Compound S-8 (18.8 g, 38.1 mmol) instead of Compound P-6, and 4,4,5,5-tetramethyl-2-(10-phenylphenanthren-9-yl)-1,3,2-dioxaborolane (14.5 g, 38.1 mmol) instead of 2-bromophenanthrene.

Synthesis Example 25: Preparation of Intermediate Compound S-10

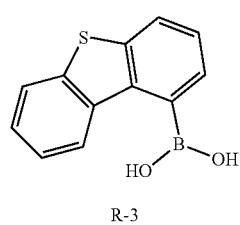

R-3

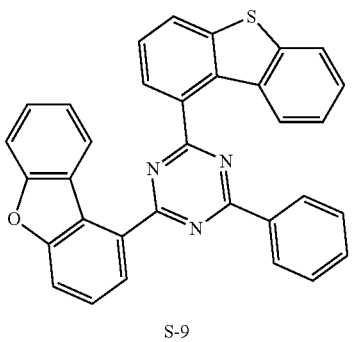

S-9

Compound S-9 (71.4 g, yield 87%; MS: [M+H]$^+$=506) was prepared in the same manner as manner as in the preparation method of Compound R-4 of Synthesis Example 20, except that 2-chloro-4-(dibenzo[b,d]furan-1-yl)-6-phenyl-1,3,5-triazine (58.1 g, 162.3 mmol) was used instead of 2-chloro-4,6-diphenyl-1,3,5-triazine (17.6 g, 162.3 mmol).

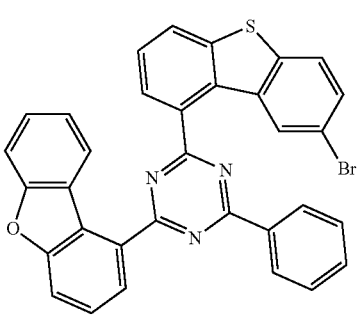

S-10

Compound S-10 (46.2 g, yield 82%; MS: [M+H]$^+$=584) was prepared in the same manner as manner as in the preparation method of Compound R-5 of Synthesis Example 20, except that Compound S-9 (48.7 g, 96.3 mmol) was used instead of Compound R-4 (40 g, 96.3 mmol).

Synthesis Example 25-1: Preparation of Compound 20

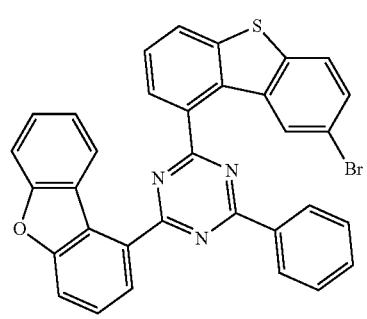 

S-10

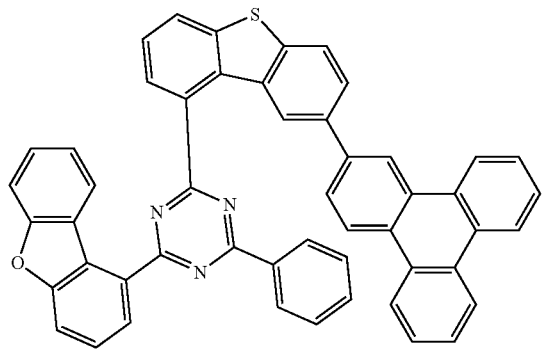

Compound 20

Compound 20 (18.7 g, yield 67%; MS: [M+H]⁺=732) was prepared in the same manner as manner as in Synthesis Example 1-1, except for using Compound S-10 (34.5 g, 38.1 mmol) instead of Compound P-6, and triphenylen-2-ylboronic acid (10.4 g, 38.1 mmol) instead of 2-bromophenanthrene.

Synthesis Example 26: Preparation of Intermediate Compound S-12

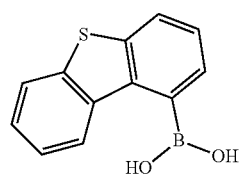 

R-3

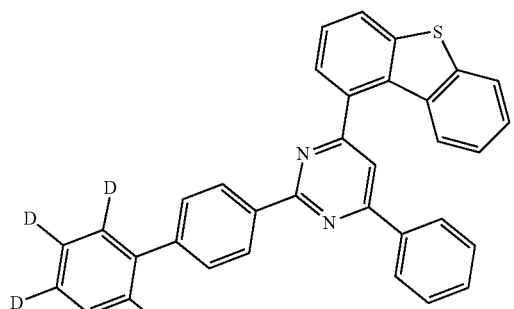

S-11

Compound S-11 (71.6 g, yield 89%; MS: [M+H]⁺=496) was prepared in the same manner as manner as in the preparation method of Compound R-4 of Synthesis Example 20, except that 2-([1,1'-biphenyl]-4-yl-2',3',4',5',6'-d5)-4-chloro-6-phenylpyrimidine (56.5 g, 162.3 mmol) was used instead of 2-chloro-4,6-diphenyl-1,3,5-triazine (17.6 g, 162.3 mmol).

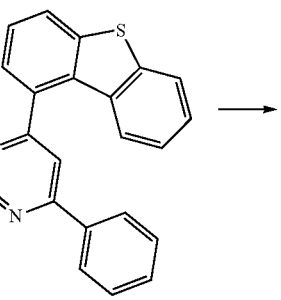

S-11

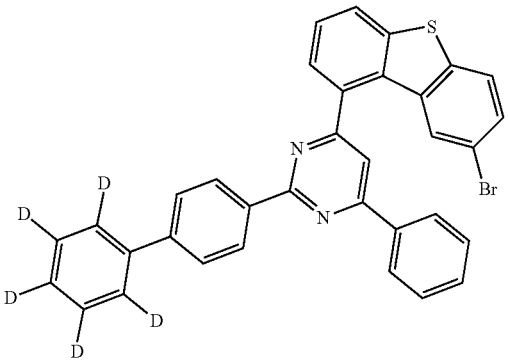

S-12

Compound S-12 (47.0 g, yield 85%; MS: [M+H]⁺=574) was prepared in the same manner as manner as in the preparation method of Compound R-5 of Synthesis Example 20, except that Compound S-11 (47.7 g, 96.3 mmol) was used instead of Compound R-4 (40 g, 96.3 mmol).

Synthesis Example 26-1: Preparation of Compound 24

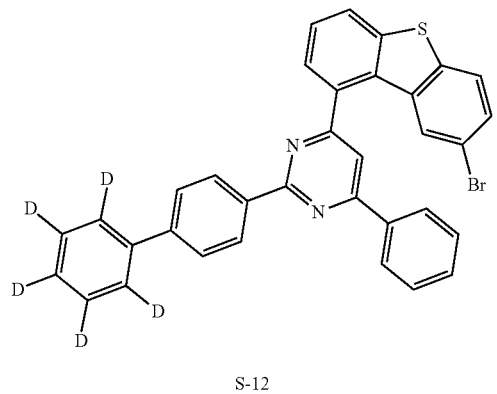

S-12

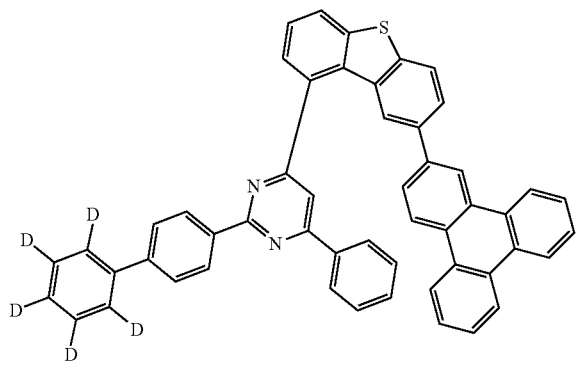

Compound 24

Compound 24 (19.5 g, yield 71%; MS: [M+H]⁺=722) was prepared in the same manner as manner as in Synthesis Example 1-1, except for using Compound S-12 (21.9 g, 38.1 mmol) instead of Compound P-6, and triphenylen-2-ylboronic acid (10.4 g, 38.1 mmol) instead of 2-bromophenanthrene.

Synthesis Example 27-1: Preparation of Intermediate Compound Q-37

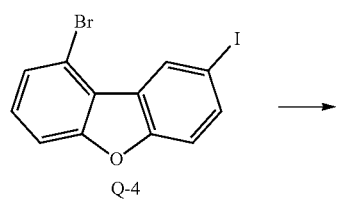

Q-4

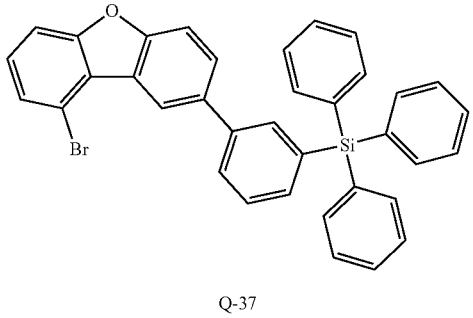

Q-37

Compound Q-37 (30.6 g, yield 60%; MS: [M+H]⁺=581) was prepared in the same manner as manner as in Synthesis Example 4-1, except that (3-(triphenylsilyl)phenyl)boronic acid (30.6 g, 80.4 mmol) was used instead of 4,4,5,5-tetramethyl-2-(triphenylen-2-yl)-1,3,2-dioxaborolane (28.5 g, 80.4 mmol).

Synthesis Example 27-2: Preparation of Intermediate Compound Q-38

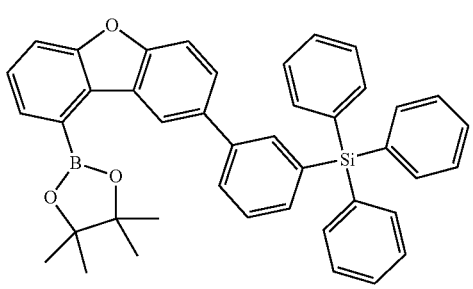

Q-37

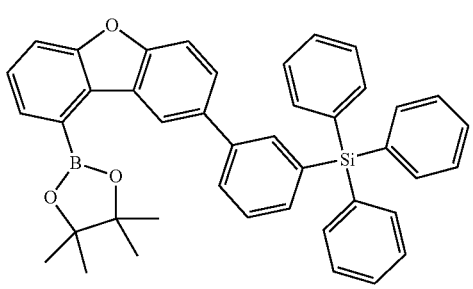

Q-38

Compound Q-38 (28.5 g, yield 86%; MS: [M+H]⁺=629) was prepared in the same manner as in Synthesis Example 4-2, except that Compound Q-37 (30.7 g, 52.8 mmol) was used instead of Compound Q-5 (25.0 g, 52.8 mmol).

Synthesis Example 27-3: Preparation of Compound 38

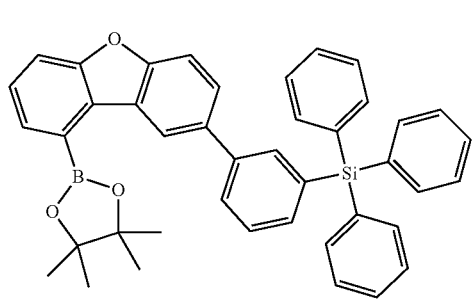

Q-38

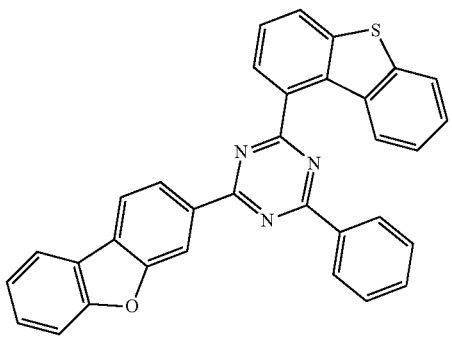

S-13

Compound S-13 (71.4 g, yield 87%; MS: [M+H]$^+$=506) was prepared in the same manner as manner as in the preparation method of Compound R-4 of Synthesis Example 20, except that 2-chloro-4-(dibenzo[b,d]furan-3-yl)-6-phenyl-1,3,5-triazine (58.1 g, 162.3 mmol) was used instead of 2-chloro-4,6-diphenyl-1,3,5-triazine (17.6 g, 162.3 mmol).

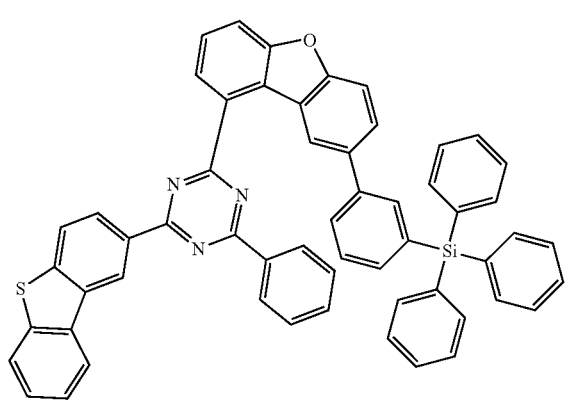

Compound 38

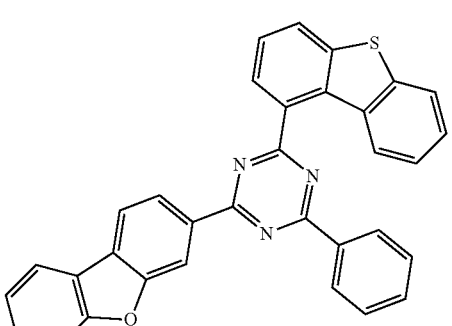

S-13

Compound 38 (19.2 g, yield 60%; MS: [M+H]$^+$=840) was prepared in the same manner as manner as in Synthesis Example 1-1, except for using Q-38 (24.0 g, 38.1 mmol) instead of Compound P-6, and 2-chloro-4-(dibenzo[b,d]thiophen-2-yl)-6-phenyl-1,3,5-triazine (14.2 g, 38.1 mmol) instead of 2-bromophenanthrene.

Synthesis Example 28: Preparation of Intermediate Compound S-14

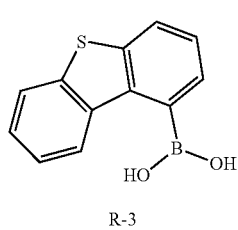

R-3

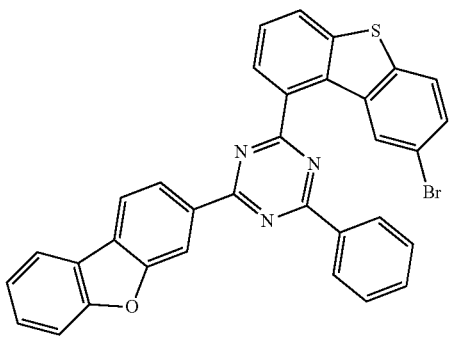

S-14

Compound S-14 (50.1 g, yield 89%; MS: [M+H]$^+$=584) was prepared in the same manner as manner as in the preparation method of Compound R-5 of Synthesis Example 20, except that Compound S-13 (48.7 g, 96.3 mmol) was used instead of Compound R-4 (40 g, 96.3 mmol).

Synthesis Example 28-1: Preparation of Compound 41

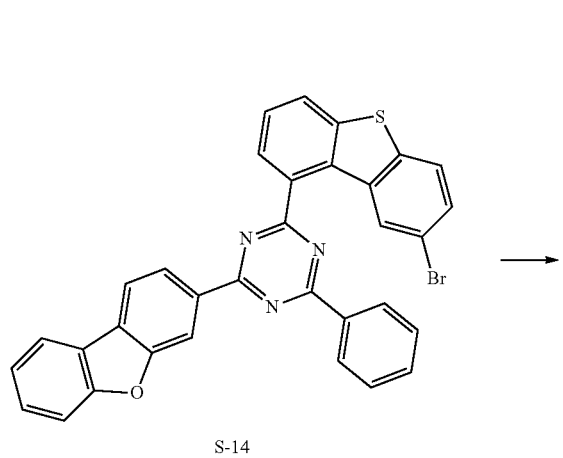

S-14

↓

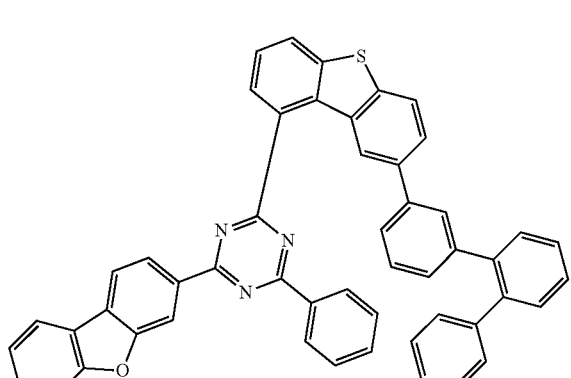

Compound 41

Compound 41 (19.3 g, yield 69%; MS: [M+H]⁺=734) was prepared in the same manner as manner as in Synthesis Example 1-1, except for using Compound S-14 (21.9 g, 38.1 mmol) instead of Compound P-6, and [1,1':2',1''-terphenyl]-3-ylboronic acid (10.4 g, 38.1 mmol) instead of 2-bromophenanthrene.

Synthesis Example 29: Preparation of Intermediate Compound S-16

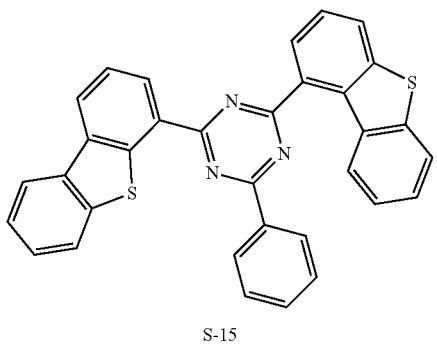

R-3

→

S-15

Compound S-15 (78.7 g, yield 93%; MS: [M+H]⁺=522) was prepared in the same manner as manner as in the preparation method of Compound R-4 of Synthesis Example 20, except that 2-chloro-4-(dibenzo[b,d]thiophen-4-yl)-6-phenyl-1,3,5-triazine (60.7 g, 162.3 mmol) was used instead of 2-chloro-4,6-diphenyl-1,3,5-triazine (17.6 g, 162.3 mmol).

S-15

→

S-16

Compound S-16 (50.3 g, yield 87%; MS: [M+H]⁺=600) was prepared in the same manner as manner as in the preparation method of Compound R-5 of Synthesis Example 20, except that Compound S-15 (50.2 g, 96.3 mmol) was used instead of Compound R-4 (40 g, 96.3 mmol).

Synthesis Example 29-1: Preparation of Compound 42

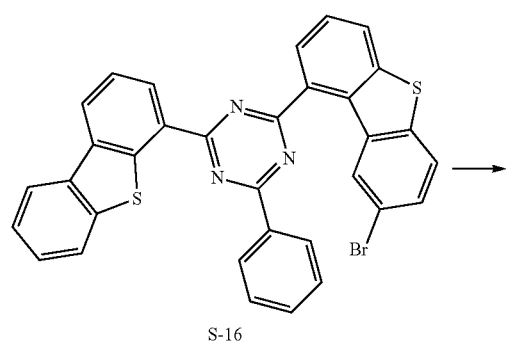

S-16

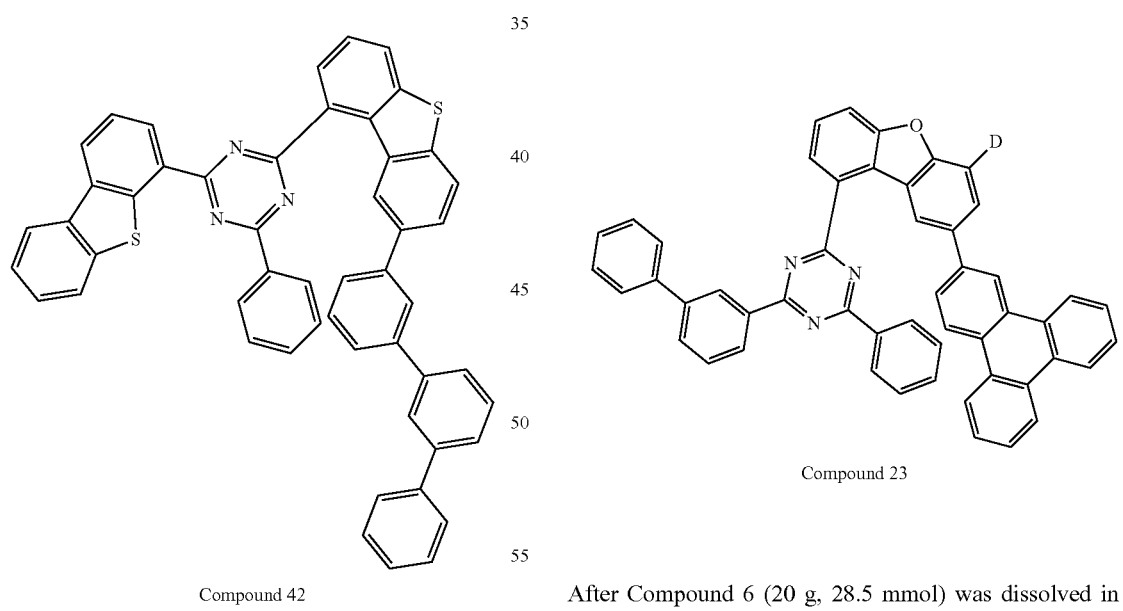

Compound 42

Compound 42 (20.6 g, yield 72%; MS: [M+H]⁺=750) was prepared in the same manner as manner as in Synthesis Example 1-1, except for using Compound S-16 (22.9 g, 38.1 mmol) instead of Compound P-6, and [1,1':3',1''-terphenyl]-3-ylboronic acid (10.4 g, 38.1 mmol) instead of 2-bromophenanthrene.

Synthesis Example 30: Preparation of Compound 23

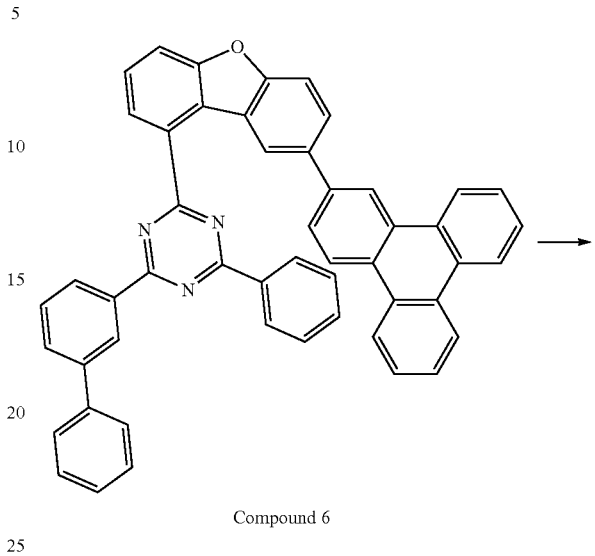

Compound 6

Compound 23

After Compound 6 (20 g, 28.5 mmol) was dissolved in tetrahydrofuran (500 ml), the temperature was lowered to −78° C. and 1.7 M tert-butyllithium (t-BuLi) (16.8 ml, 28.5 mmol) was slowly added thereto. After stirring at the same temperature for one hour, excess D₂O was added dropwise to terminate the reaction. The temperature is gradually increased to room temperature, the organic layer was separated, dried with magnesium sulfate and distilled under reduced pressure. The obtained mixture was purified by column chromatography with hexane/ethyl acetate (10:1) to obtain Compound 23 (9.6 g, yield 48%; MS: [M+H]⁺=703).

Synthesis Example 31: Preparation of Compound 60

Synthesis Example 32-1: Preparation of Intermediate Compound Q-39

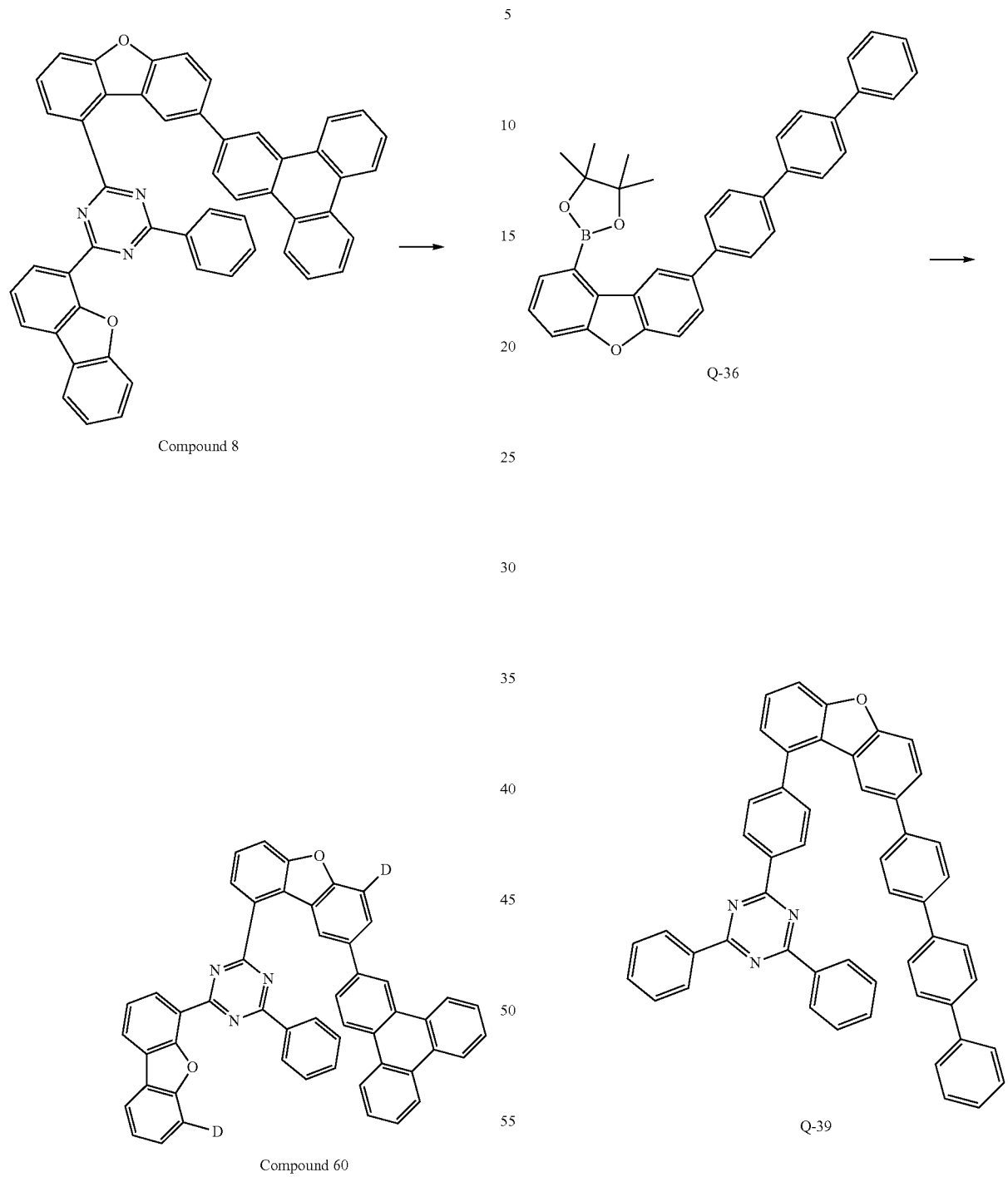

Compound 60 (8.6 g, yield 42%; MS: [M+H]$^+$=718) was prepared in the same manner as manner as in Synthesis Example 30, except that Compound 8 (20.4 g, 28.5 mmol) and 1.7M tert-butyllithium (t-BuLi) (33.5 ml, 57.0 mmol) were used instead of Compound P-6.

Compound Q-39 (22.0 g, yield 82%; MS: [M+H]$^+$=704) was prepared in the same manner as manner as in Synthesis Example 1-1, except for using Compound Q-36 (19.9 g, 38.1 mmol) instead of Compound P-6, and 2-(4-chlorophenyl)-4,6-diphenyl-1,3,5-triazine (13.1 g, 38.1 mmol) instead of 2-bromophenanthrene.

Synthesis Example 32-2: Preparation of Compound 73

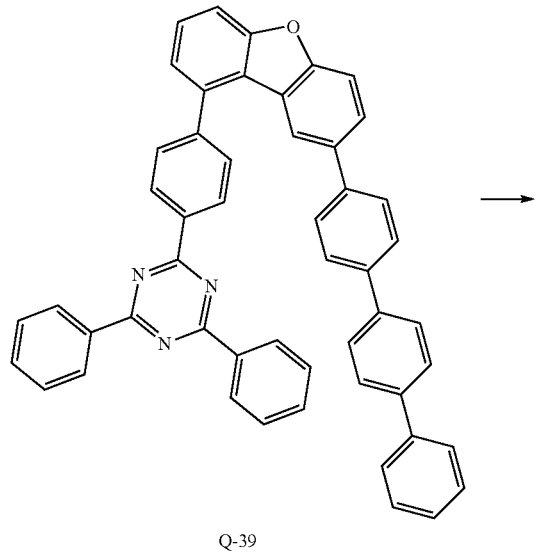

Compound 73 (9.9 g yield 49%; MS: [M+H]⁺=705) was prepared in the same manner as manner as in Synthesis Example 30, except that Compound Q-39 (20.1 g, 28.5 mmol) was used instead of Compound 6.

Synthesis Example 33: Preparation of Intermediate Compound T-7

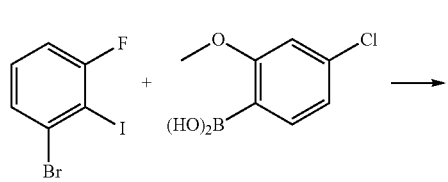

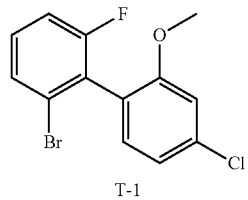

Compound T-1 (65.3 g, yield 62%; MS: [M+H]⁺=314) was prepared in the same manner as manner as in the preparation method of Compound P-1 of Synthesis Example 1, except that (4-chloro-2-methoxyphenyl)boronic acid) (62.2 g, 333.5 mmol) was used instead of (5-chloro-2-methoxyphenyl)boronic acid) (62.2 g, 333.5 mmol).

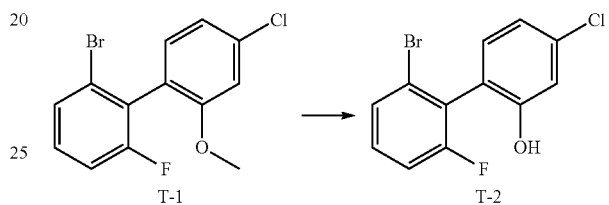

Compound T-2 (43.0 g, yield 90%; MS: [M+H]⁺=300) was prepared in the same manner as manner as in the preparation method of Compound P-2 of Synthesis Example 1, except that Compound T-1 (50.0 g, 158.5 mmol) was used instead of Compound P-1 (50.0 g, 158.5 mmol).

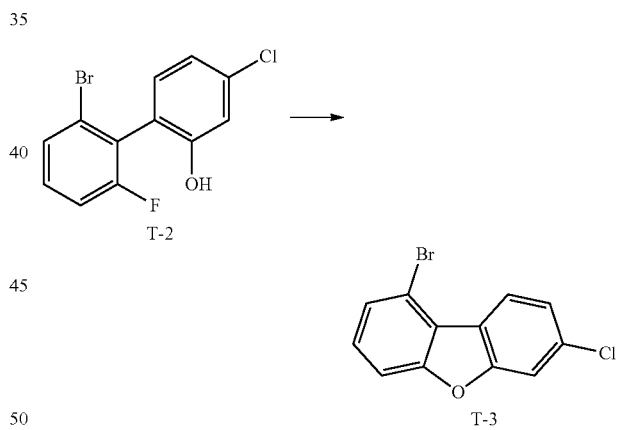

Compound T-3 (30.6 g, yield 82%; MS: [M+H]⁺=280) was prepared in the same manner as manner as in the preparation method of Compound P-3 of Synthesis Example 1, except that Compound T-2 (40.0 g, 132.7 mmol) was used instead of Compound P-2 (40.0 g, 132.7 mmol).

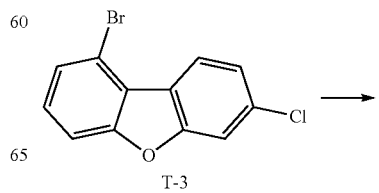

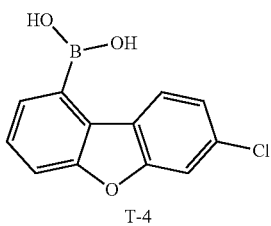
T-4

Compound T-4 (25.0 g, yield 95%; MS: [M+H]⁺=247) was prepared in the same manner as manner as in the preparation method of Compound P-4 of Synthesis Example 1, except that Compound T-3 (30.0 g, 106.6 mmol) was used instead of Compound P-3 (30.0 g, 106.6 mmol).

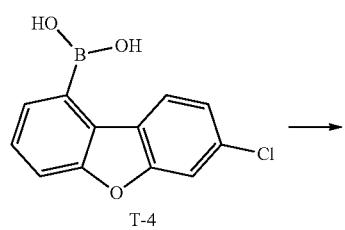
T-4

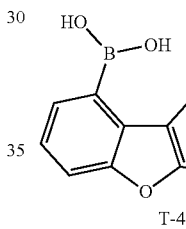
T-5

Compound T-5 (31.7 g, yield 90%; MS: [M+H]⁺=434) was prepared in the same manner as manner as in the preparation method of Compound P-5 of Synthesis Example 1, except that Compound T-4 (20.0 g, 81.2 mmol) was used instead of Compound P-4 (20.0 g, 81.2 mmol).

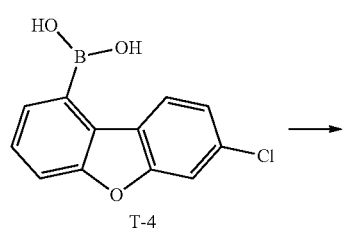
T-4

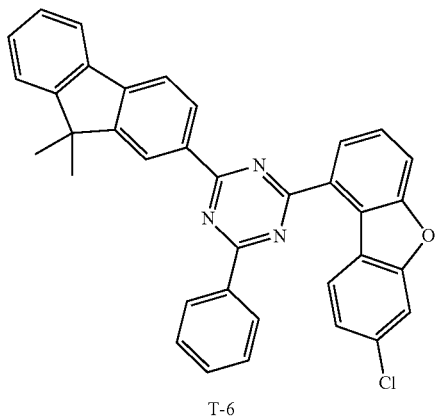
T-6

Compound T-6 (37.1 g, yield 83%; MS: [M+H]⁺=550) was prepared in the same manner as manner as in the preparation method of Compound P-5 of Synthesis Example 1, except for using Compound T-4 (20.0 g, 81.2 mmol) instead of Compound P-4 (20.0 g, 81.2 mmol), and 2-chloro-4-(9,9-dimethyl-9H-fluoren-2-yl)-6-phenyl-1,3,5-triazine (31.1 g, 81.2 mmol) instead of 2-chloro-4,6-diphenyl-1,3,5-triazine.

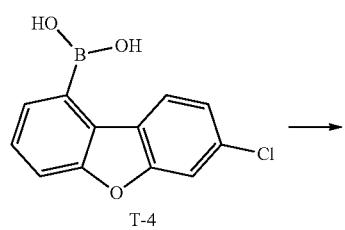
T-4

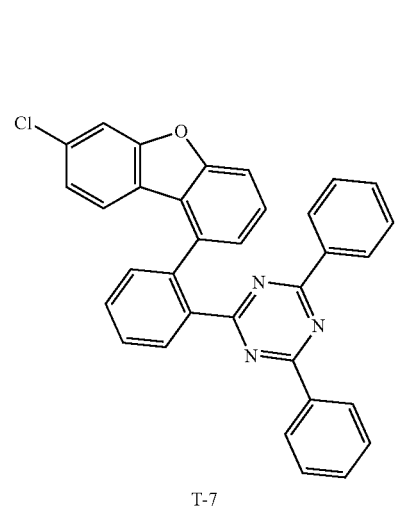
T-7

Compound T-7 (29.4 g, yield 71%; MS: [M+H]⁺=510) was prepared in the same manner as manner as in the preparation method of Compound P-5 of Synthesis Example 1, except for using Compound T-4 (20.0 g, 81.2 mmol) instead of Compound P-4 (20.0 g, 81.2 mmol), and 2-(2-chlorophenyl)-4,6-diphenyl-1,3,5-triazine (27.9 g, 81.2 mmol) instead of 2-chloro-4,6-diphenyl-1,3,5-triazine.

Synthesis Example 33-1: Preparation of Compound 76

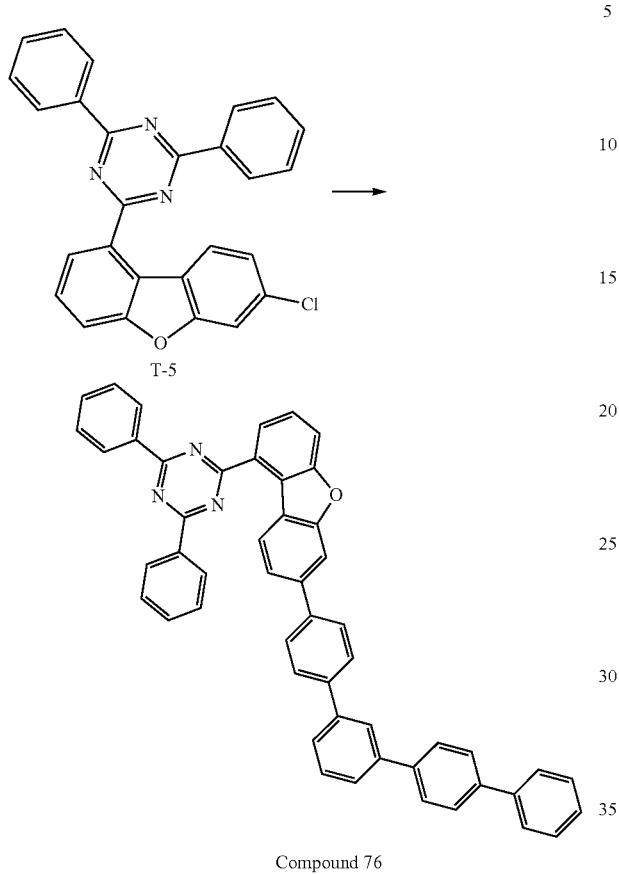

T-5

Compound 76

Compound 76 (23.9 g, yield 89%; MS: [M+H]⁺=704) was prepared in the same manner as manner as in Synthesis Example 1-1, except for using Compound T-5 (16.5 g, 38.1 mmol) instead of Compound P-6, and [1,1':3',1'':4'',1'''-quaterphenyl]-4-ylboronic acid (13.3 g, 38.1 mmol) instead of 2-bromophenanthrene.

Synthesis Example 33-2: Preparation of Compound 40

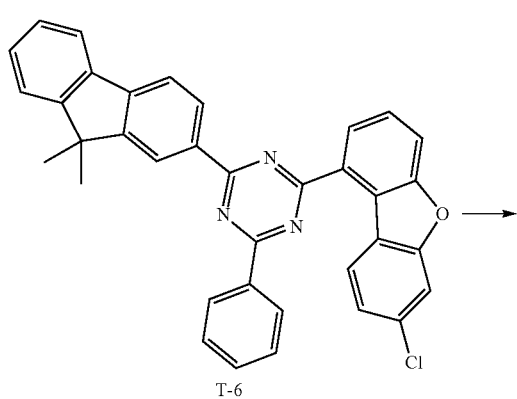

T-6

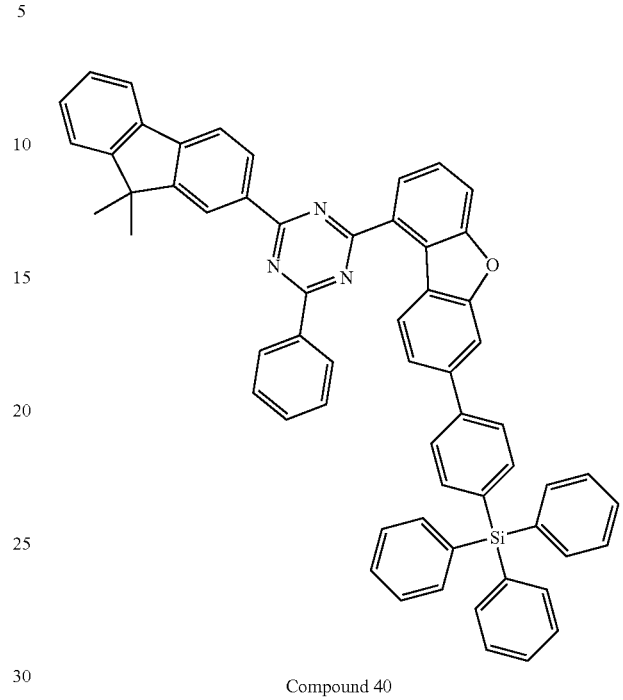

Compound 40

Compound 40 (26.6 g, yield 82%; MS: [M+H]⁺=850) was prepared in the same manner as manner as in Synthesis Example 1-1, except for using Compound T-6 (21.0 g, 38.1 mmol) instead of Compound P-6, and 4-(triphenylsilyl)phenyl)boronic acid (14.5 g, 38.1 mmol) instead of 2-bromophenanthrene.

Synthesis Example 33-3: Preparation of Compound 21

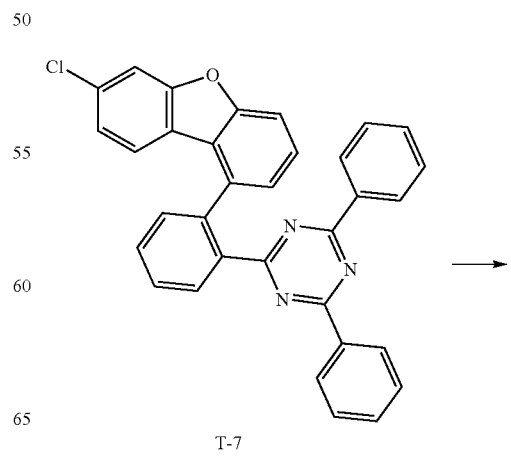

T-7

-continued

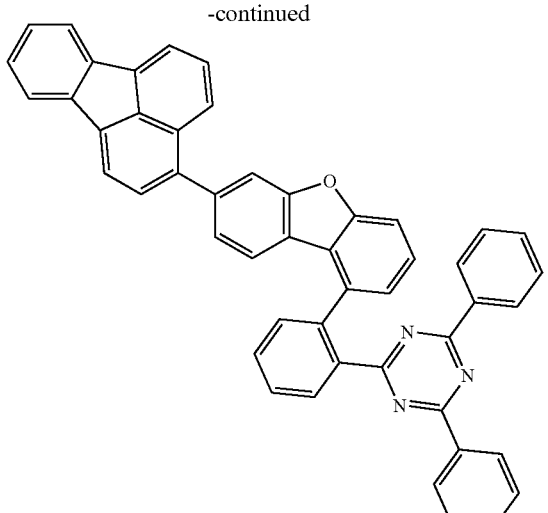

Compound 21

Compound 21 (22.1 g, yield 86%; MS: [M+H]$^+$=676) was prepared in the same manner as manner as in Synthesis Example 1-1, except for using Compound T-7 (19.4 g, 38.1 mmol) instead of Compound P-6, and fluoranthen-3-ylboronic acid (9.4 g, 38.1 mmol) instead of 2-bromophenanthrene.

Synthesis Example 34: Preparation of Intermediate Compound U-8

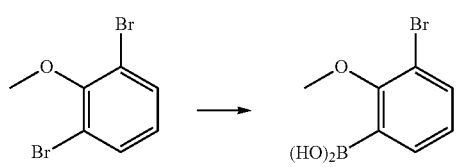

After 1,3-dibromo-2-methoxybenzene (113.2 g, 426.4 mmol) was dissolved in tetrahydrofuran (1000 ml), the temperature was lowered to −78° C. and 17M tert-butyl lithium (t-BuLi) (251.7 ml, 426.4 mmol) was slowly added. After stirring at the same temperature for one hour, triisopropyl borate (B(OiPr)$_3$) (113.2 ml, 852.4 mmol) was added and stirred for 3 hours while gradually raising the temperature to room temperature. To the reaction mixture was added 2N aqueous hydrochloric acid solution (800 ml) and the mixture was stirred at room temperature for 1.5 hours. The resulting precipitate was filtered, washed sequentially with water and ethyl ether, and dried under vacuum. After drying, the residue was recrystallized from chloroform and ethyl acetate and dried to obtain (3-bromo-2-methoxyphenyl)boronic acid (89.6 g, yield 91%; MS: [M+H]=230).

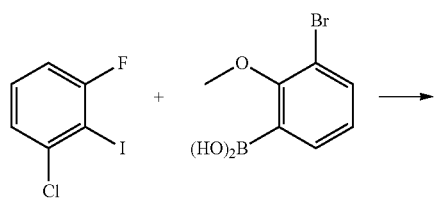

-continued

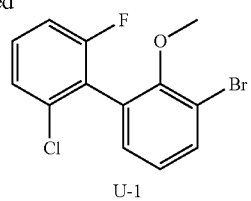
U-1

Compound U-1 (55.8 g, yield 53%; MS: [M+H]$^+$=314) was prepared in the same manner as manner as in the preparation method of Compound P-1 of Synthesis Example 1, except for using 1-chloro-3-fluoro-2-iodobenzene (85.5 g, 333.5 mmol) instead of 1-bromo-3-fluoro-2-iodobenzene, and (3-bromo-2-methoxyphenyl)boronic acid (77.0 g, 333.5 mmol) instead of (5-chloro-2-methoxyphenyl)boronic acid.

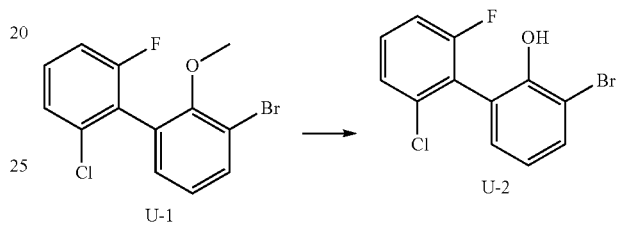

Compound U-2 (39.7 g, yield 83%; MS: [M+H]$^+$=300) was prepared in the same manner as manner as in the preparation method of Compound P-2 of Synthesis Example 1, except that Compound U-1 (50.0 g, 158.5 mmol) was used instead of Compound P-1 (50.0 g, 158.5 mmol).

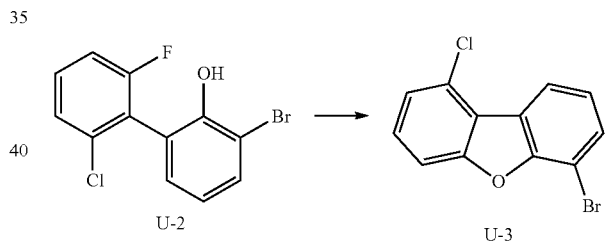

Compound U-3 (31.4 g, yield 84%; MS: [M+H]$^+$=280) was prepared in the same manner as manner as in the preparation method of Compound P-3 of Synthesis Example 1, except that Compound U-2 (40.0 g, 132.7 mmol) was used instead of Compound P-2 (40.0 g, 132.7 mmol).

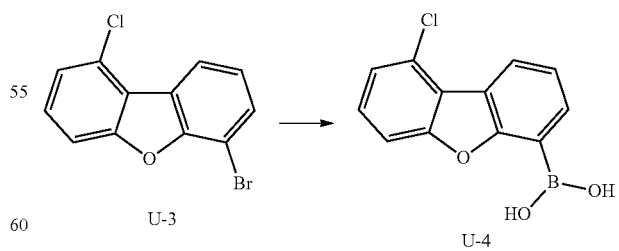

Compound U-4 (25.5 g, yield 97%; MS: [M+H]$^+$=247) was prepared in the same manner as manner as in the preparation method of Compound P-4 of Synthesis Example 1, except that Compound U-3 (30.0 g, 106.6 mmol) was used instead of Compound P-3 (30.0 g, 106.6 mmol).

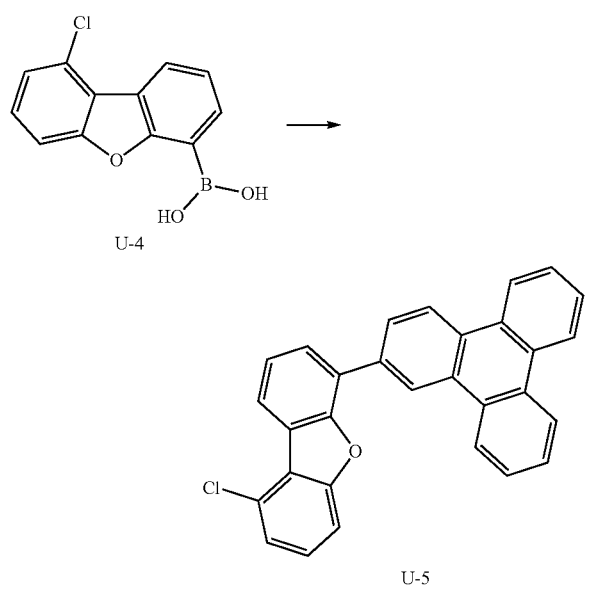

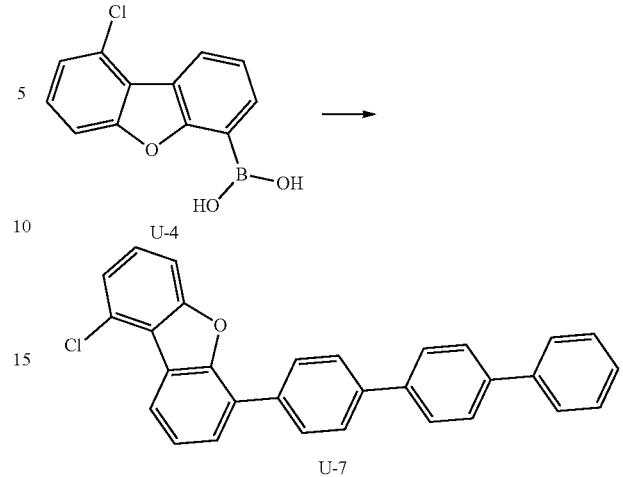

Compound U-7 (30.8 g, yield 88%; MS: [M+H]⁺=431) was prepared in the same manner as manner as in the preparation method of Compound P-5 of Synthesis Example 1, except for using Compound U-4 (20.0 g, 81.2 mmol) instead of Compound P-4, and [1,1':4',1''-terphenyl]-4-ylboronic acid (22.3 g, 81.2 mmol) instead of 2-chloro-4,6-diphenyl-1,3,5-triazine.

Compound U-5 (31.1 g, yield 86%; MS: [M+H]⁺=445) was prepared in the same manner as manner as in the preparation method of Compound P-5 of Synthesis Example 1, except for using Compound U-4 (20.0 g, 81.2 mmol) instead of Compound P-4 (20.0 g, 81.2 mmol), and triphenylen-2-ylboronic acid (22.1 g, 81.2 mmol) instead of 2-chloro-4,6-diphenyl-1,3,5-triazine.

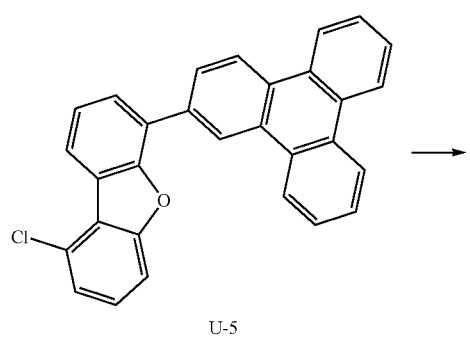

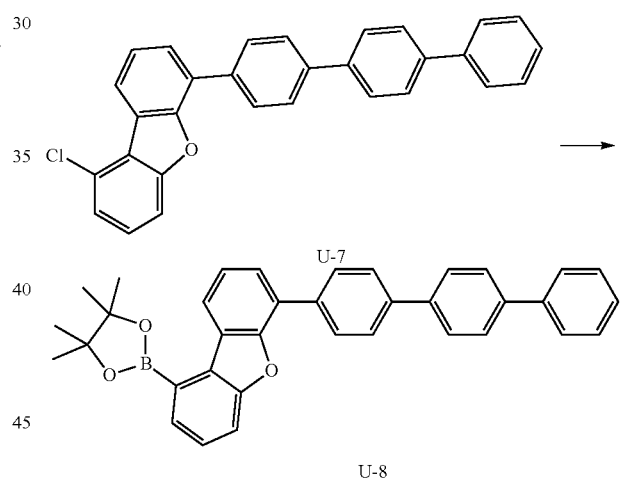

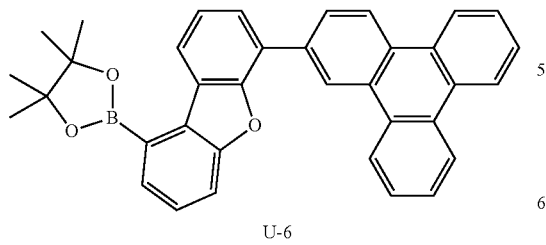

Compound U-6 (24.7 g, yield 90%; MS: [M+H]⁺=521) was prepared in the same manner as in Synthesis Example 4-2, except that Compound U-5 (22.6 g, 52.8 mmol) was used instead of Compound Q-5 (25.0 g, 52.8 mmol).

Compound U-8 (24.3 g, yield 88%; MS: [M+H]⁺=523) was prepared in the same manner as in Synthesis Example 4-2, except that Compound U-7 (22.8 g, 52.8 mmol) was used instead of Compound Q-5.

Synthesis Example 34-1: Preparation of Compound 22

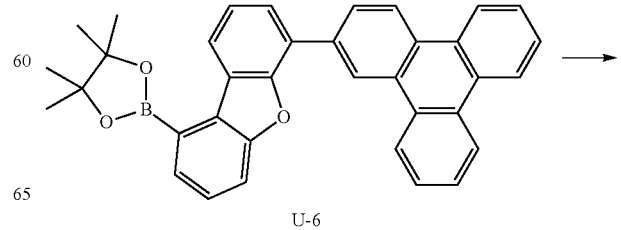

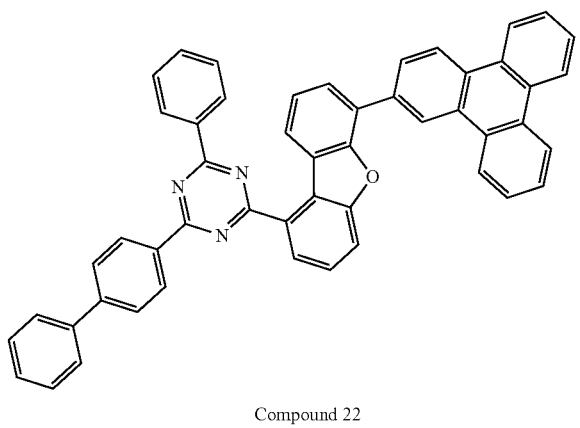

Compound 22

Compound 22 Compound 22 (35.4 g, yield 93%; MS: [M+H]⁺=702) was prepared in the same manner as manner as in Synthesis Example 1-1, except for using Compound U-6 (19.8 g, 38.1 mmol) instead of Compound P-6, and 2-([1,1'-biphenyl]-4-yl)-4-chloro-6-phenyl-1,3,5-triazine (13.1 g, 38.1 mmol) instead of 2-bromophenanthrene.

Synthesis Example 34-2: Preparation of Compound 77

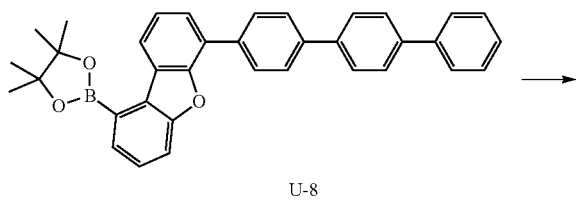

U-8

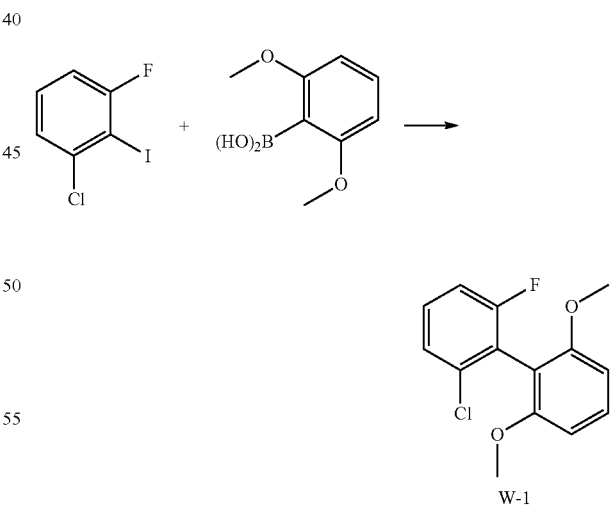

Compound 77

Compound 77 (24.9 g, yield 91%; MS: [M+H]⁺=718) was prepared in Synthesis Example 1-1, except for using Compound U-8 (19.9 g, 38.1 mmol) instead of Compound P-6, and 2-chloro-4-(dibenzo[b,d]furan-2-yl)-6-phenyl-1,3,5-triazine (13.6 g, 38.1 mmol) instead of 2-bromophenanthrene.

Synthesis Example 35: Preparation of Intermediate Compound W-8

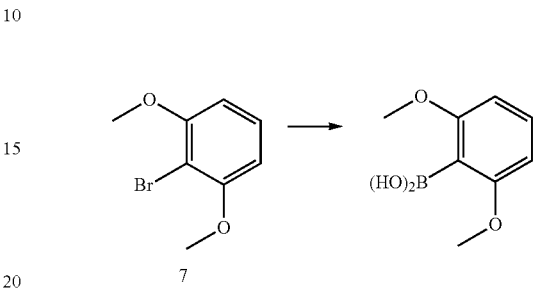

7

After 2-bromo-1,3-dimethoxybenzene (92.6 g, 426.4 mmol) was dissolved in tetrahydrofuran (1000 ml), the temperature was lowered to −78° C. and 1.7M tert-butyl lithium (t-BuLi) (251.7 ml, 426.4 mmol) was slowly added. After stirring at the same temperature for 1 hour, triisopropylborate (B(OiPr)₃) (113.2 ml, 852.4 mmol) was added and the mixture was stirred for 3 hours while gradually raising the temperature to room temperature. To the reaction mixture was added 2N aqueous hydrochloric acid solution (800 ml) and the mixture was stirred at room temperature for 1.5 hours. The resulting precipitate was filtered, washed sequentially with water and ethyl ether, and dried under vacuum. After drying, the reaction product was recrystallized from chloroform and ethyl acetate and dried to obtain (2,6-dimethoxyphenyl)boronic acid (63.6 g, yield 82%; MS: [M+H]⁺=183).

W-1

Compound W-1 (35.6 g, yield 40%; MS: [M+H]⁺=267) was prepared in the same manner as manner as in the preparation method of Compound P-1 of Synthesis Example 1, except for using 1-chloro-3-fluoro-2-iodobenzene (85.5 g, 333.5 mmol) instead of 1-bromo-3-fluoro-2-iodobenzene, and (2,6-dimethoxyphenyl)boronic acid (60.7 g, 333.5 mmol) instead of (5-chloro-2-methoxyphenyl)boronic acid.

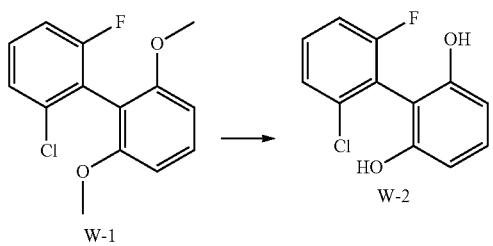

Compound W-2 (33.3 g, yield 88%; MS: [M+H]$^+$=239) was prepared in the same manner as manner as in the preparation method of Compound P-2 of Synthesis Example 1, except that Compound W-1 (42.3 g, 158.5 mmol) was used instead of Compound P-1 (50.0 g, 158.5 mmol), and boron tribromide (31.6 ml, 332.9 mmol) was used.

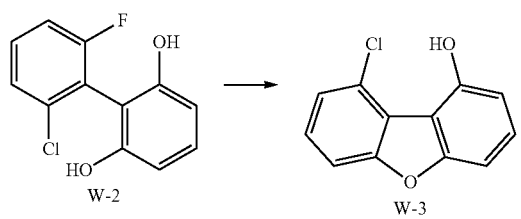

Compound W-3 (23.5 g, yield 81%; MS: [M+H]$^+$=219) was prepared in the same manner as manner as in the preparation method of Compound P-3 of Synthesis Example 1, except that Compound W-2 (31.7 g, 132.7 mmol) was used instead of Compound P-2 (40.0 g, 132.7 mmol).

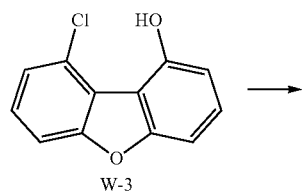

After Compound W-3 (20.0 g, 91.5 mmol) was dispersed in acetonitrile (250 ml), calcium carbonate (51.2 g, 109.8 mmol) and nonafluorobutanesulfonyl fluoride (41.6 g, 137.3 mmol) were added thereto. The mixture was stirred at 80° C. for 1 hour. The reaction mixture was cooled to room temperature, filtered, washed with ethanol and water, and then dried to obtain Compound W-4 (38.9 g, yield 85%; MS: [M+H]$^+$=500).

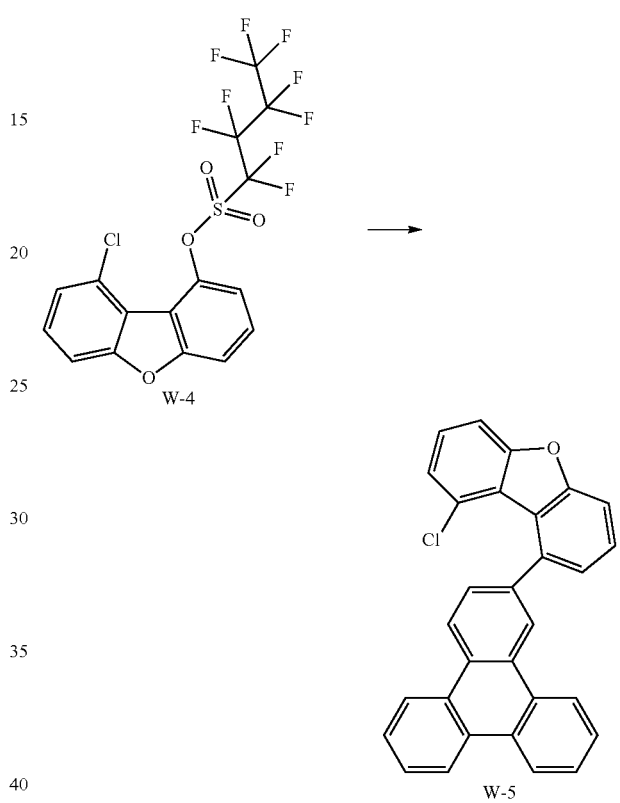

Compound W-5 (21.6 g, yield 62%; MS: [M+H]$^+$=429) was prepared in the same manner as manner as in the preparation method of Compound P-5 of Synthesis Example 1, except for using Compound W-4 (40.7 g, 81.2 mmol) instead of Compound P-4, and triphenylen-2-ylboronic acid (22.1 g, 81.2 mmol) instead of 2-chloro-4,6-diphenyl-1,3,5-triazine.

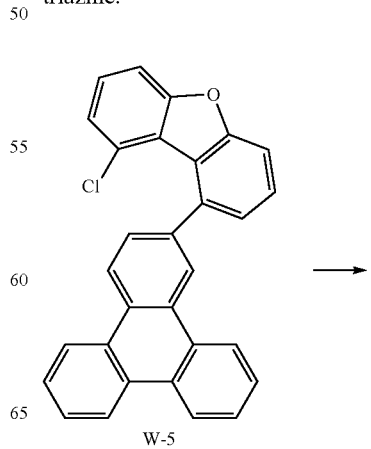

-continued

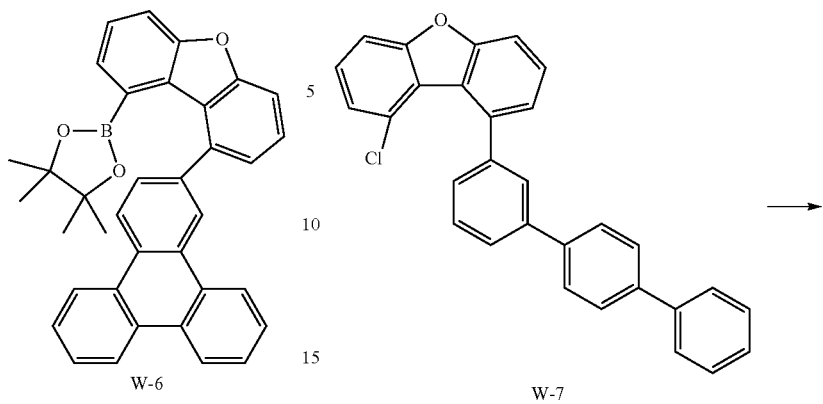

Compound W-6 (23.4 g, yield 85%; MS: [M+H]$^+$=521) was prepared in the same manner as in Synthesis Example 4-2, except that Compound W-5 (22.6 g, 52.8 mmol) was used instead of Compound Q-5.

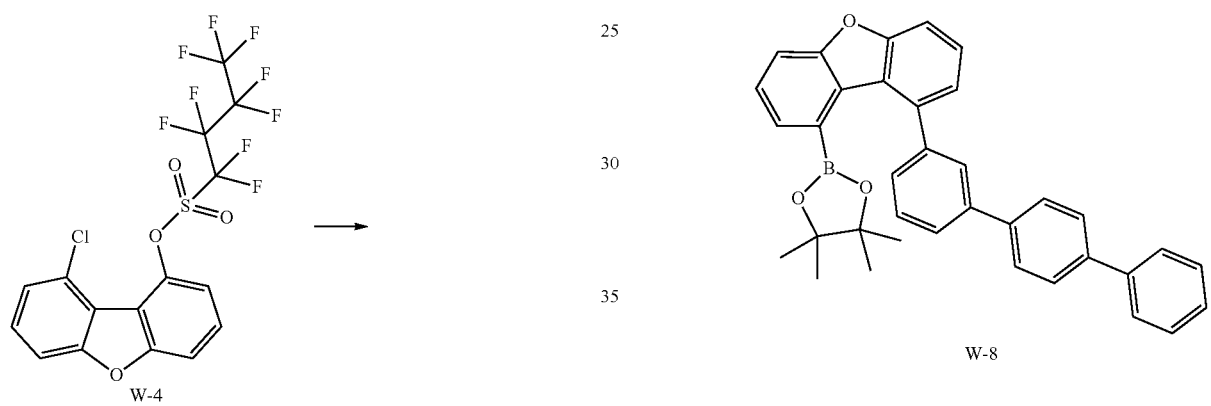

Compound W-7 (22.0 g, yield 63%; MS: [M+H]$^+$=431) was prepared in the same manner as manner as in the preparation method of Compound P-5 of Synthesis Example 1, except for using Compound W-4 (40.7 g, 81.2 mmol) instead of Compound P-4, and [1,1':4',1''-terphenyl]-3-ylboronic acid (22.3 g, 81.2 mmol) instead of 2-chloro-4,6-diphenyl-1,3,5-triazine.

Compound W-8 (22.1 g, yield 80%; MS: [M+H]$^+$=523) was prepared in the same manner as in Synthesis Example 4-2, except that Compound W-7 (22.8 g, 52.8 mmol) was used instead of Compound Q-5.

Synthesis Example 35-1: Preparation of Compound 16

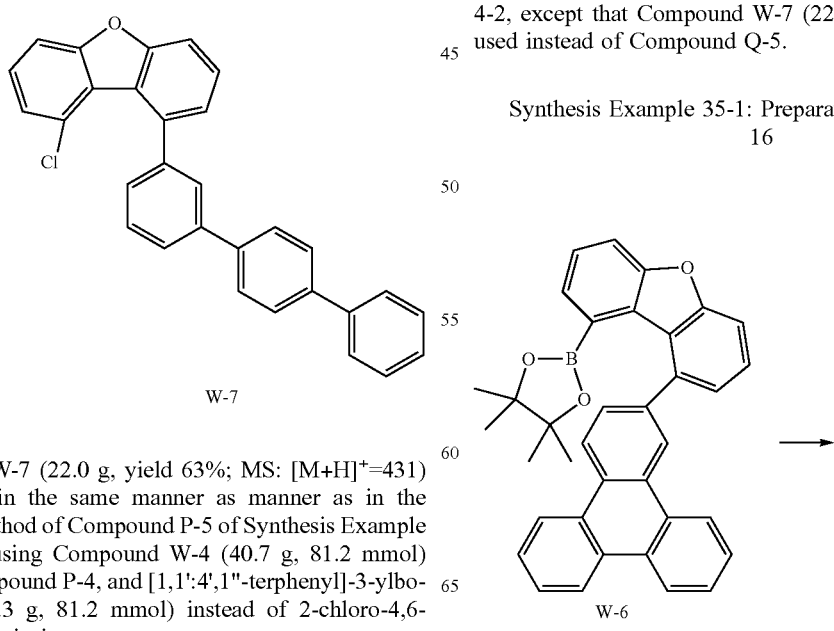

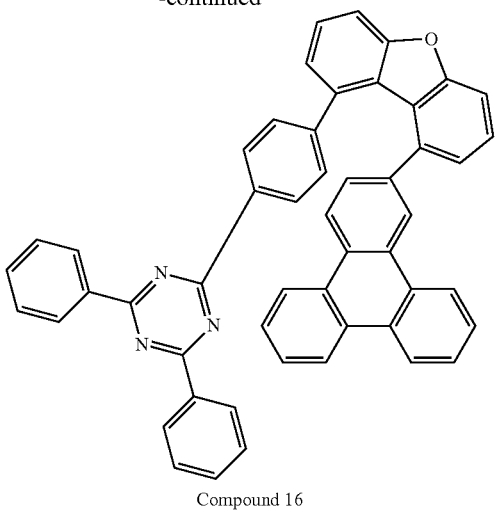

Compound 16

Compound 16 (19.5 g, yield 73%; MS: [M+H]$^+$=702) was prepared in the same manner as manner as in Synthesis Example 1-1, except for using Compound W-6 (19.8 g, 38.1 mmol) instead of Compound P-6, and 2-(4-chlorophenyl)-4,6-diphenyl-1,3,5-triazine (13.1 g, 38.1 mmol) instead of 2-bromophenanthrene.

Synthesis Example 35-2: Preparation of Compound 37

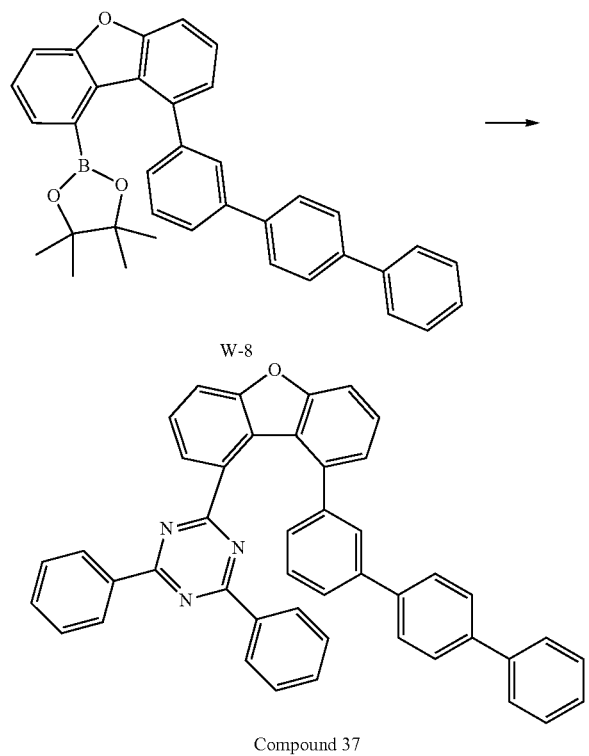

Compound 37 (15.5 g, yield 65%; MS: [M+H]$^+$=628) was prepared in the same manner as manner as in Synthesis Example 1-1, except for using Compound W-8 (19.9 g, 38.1 mmol) instead of Compound P-6, and 2-chloro-4,6-diphenyl-1,3,5-triazine (10.2 g, 38.1 mmol) instead of 2-bromophenanthrene.

Synthesis Example 36: Preparation of Compound A

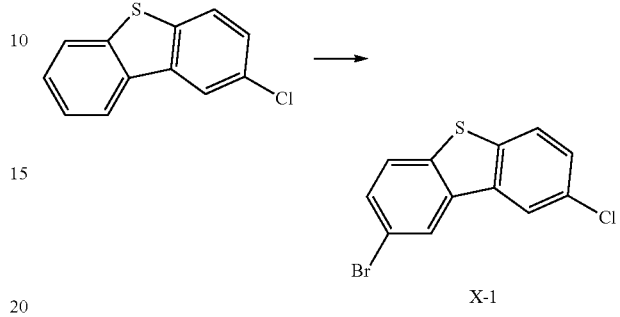

After 50 g (23.0 mmol) of 2-chlorodibenzothiophene was diluted with 300 mL of chloroform, 18 mL (0.34 mol) of bromine was slowly added and stirred at room temperature for 12 hours. After completion of the reaction, the precipitated solid was filtered, dissolved again in excess chloroform by heating, and then washed with 20% sodium thiosulfate aqueous solution, and the organic layer was separated. This was washed again with a saturated aqueous sodium hydrogen carbonate solution, the organic layer was separated, water was dried with anhydrous magnesium sulfate, and concentrated under reduced pressure. To the concentrated compound was added 300 mL of ethyl acetate, and the mixture was stirred under reflux. The resulting slurry was cooled at room temperature, filtered, and then dried under nitrogen to obtain a light brown compound X-1 (32 g, yield 47%; MS: [M+H]$^+$=296).

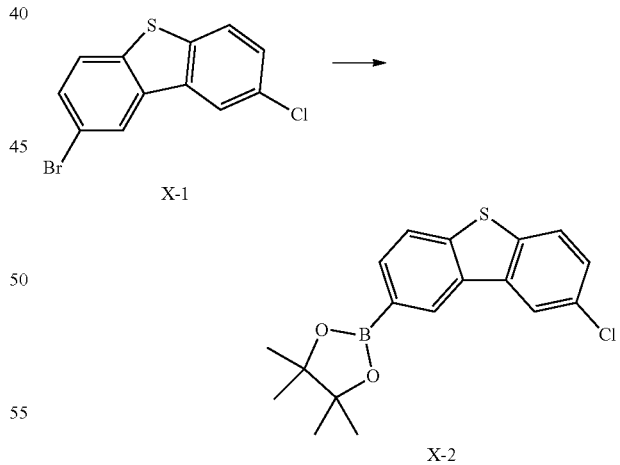

After 48 g (0.16 mol) of Compound X-1 was dissolved in 500 mL of 1,4-dioxane, 49 g (0.19 mol) of bis(pinacolato) diboron was added thereto. 31.4 g (0.32 mol) of potassium acetate was then added with stirring, and the mixture was heated to reflux. Under stirring and reflux, 2.7 g (0.005 mol) of dibenzylidene acetone palladium and 2.7 g (0.01 mol) of tricyclohexylphosphine were added, and the mixture was stirred under reflux for 12 hours. After completion of the reaction, the reactant was cooled to room temperature, washed with water, and extracted twice with chloroform. The collected organic layer was washed once with water, and water was removed with anhydrous magnesium sulfate, followed by filtration and concentration. The concentrate was heated under stirring with a small amount of ethyl acetate and an excess of hexane mixed solution and filtered to obtain a white compound X-2 (43 g, yield 78%; MS [M+H]$^+$=345).

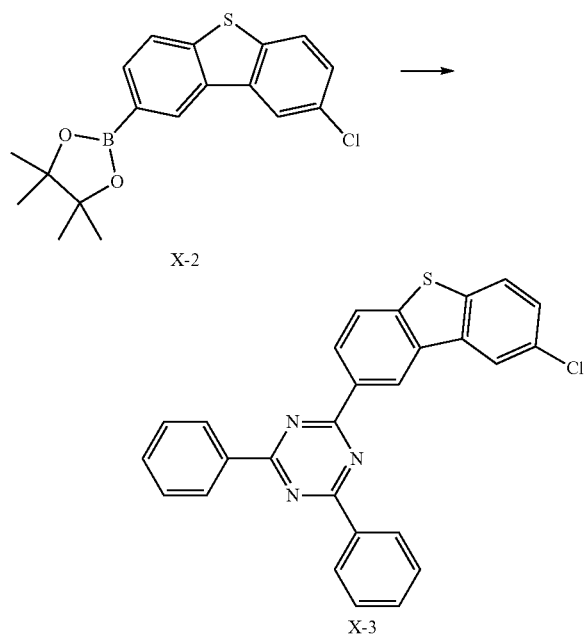

10 g (0.03 mol) of Compound X-2 and 8.4 g (0.03 mol) of 2-chloro-4,6-diphenyl-1,3,5-triazine were dissolved in 100 mL of 1,4-dioxane to which K$_3$PO$_4$ 19 g (0.09 mol) was added and the mixture was stirred under reflux. To this mixture were added 570 mg (0.001 mol) of dibenzylideneacetone palladium and 560 mg (0.002 mol) of tricyclohexylphosphine, and the mixture was stirred under reflux for 12 hours. After completion of the reaction, the reactant was cooled to room temperature, washed with water, extracted twice with ethyl acetate, water was removed with anhydrous magnesium sulfate, filtered, and concentrated under reduced pressure so that a small amount of ethyl acetate remained. An excess amount of acetone was added to the concentrated compound, slurried and then filtered to obtain a white compound X-3 (11 g, yield 83%; MS: [M+H]$^+$=150).

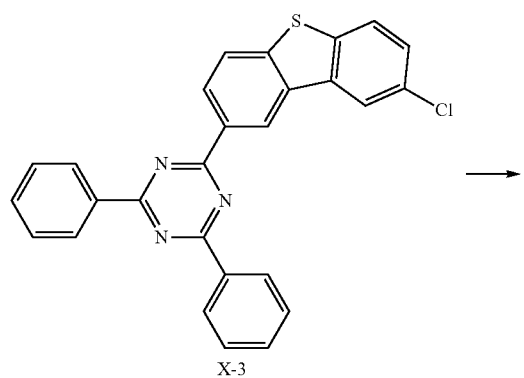

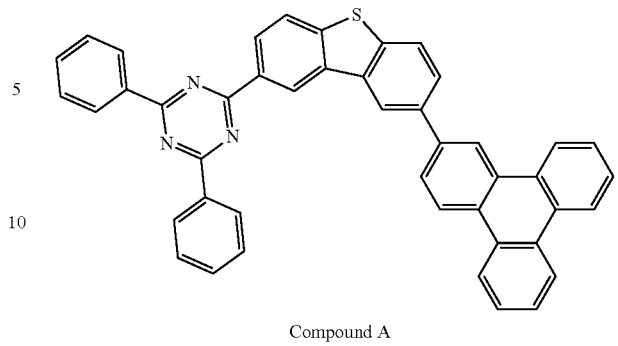

Compound A 10 g (0.022 mol) of Compound 1-3 and 6.0 g (0.022 mol) of triphenylen-2-ylboronic acid were diluted in 80 mL of 1,4-dioxane, and 13.9 g (0.066 mol) of K$_3$PO$_4$ was added to the mixed solution, followed by heating, and the mixture was stirred under reflux. To this mixture was added 380 mg (0.66 mmol) of dibenzylideneacetone palladium and 370 mg (1.3 mmol) of tricyclohexylphosphine and stirred under reflux for 12 hours. After completion of the reaction, the reactant was cooled to room temperature, and the precipitated solid was filtered, dissolved in chloroform, and washed twice with water. The collected organic layer was dried over anhydrous magnesium sulfate, filtered and purified by recrystallization using chloroform and ethyl acetate as a mixed solution to obtain a white Compound A (9.6 g, yield 68%; MS: [M+H]$^+$=642).

Synthesis Example 37: Preparation of Compound B

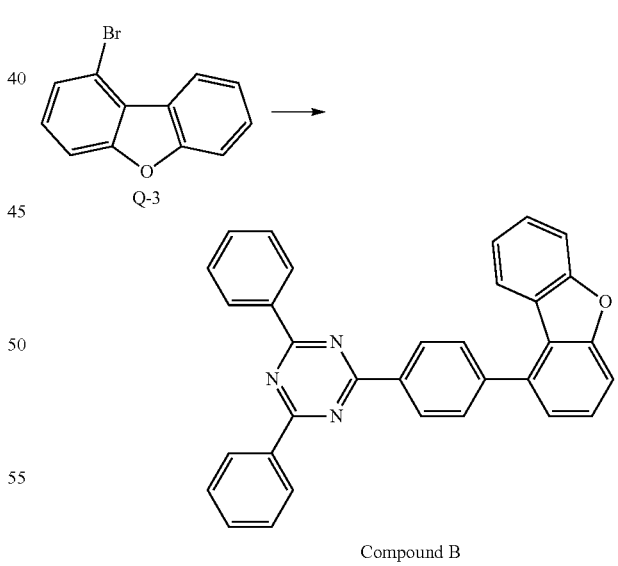

Compound B

Compound B (35.5 g, yield 92%; MS: [M+H]$^+$=476) was prepared in the same manner as manner as in the preparation method of Compound P-5 of Synthesis Example 1, except for using Compound Q-3 (20.1 g, 81.2 mmol) instead of Compound P-4, and (4-(4,6-diphenyl-1,3,5-triazin-2-yl)phenyl)boronic acid (28.7 g, 81.2 mmol) instead of 2-chloro-4,6-diphenyl-1,3,5-triazine.

Synthesis Example 38: Preparation of Compound C

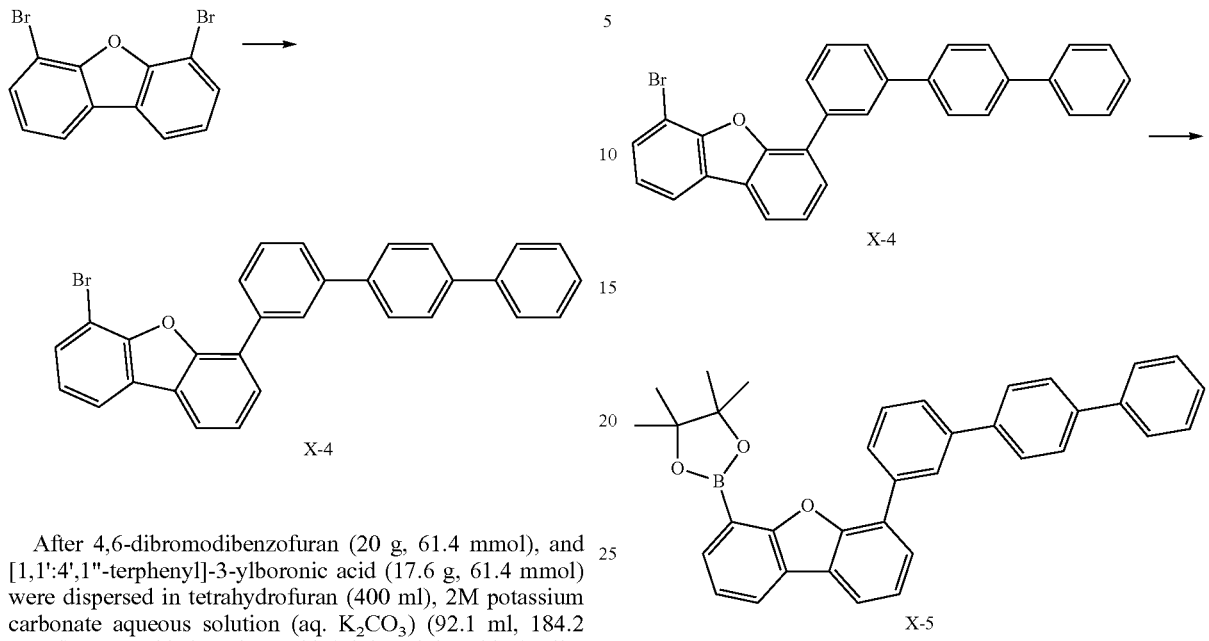

After 4,6-dibromodibenzofuran (20 g, 61.4 mmol), and [1,1':4',1''-terphenyl]-3-ylboronic acid (17.6 g, 61.4 mmol) were dispersed in tetrahydrofuran (400 ml), 2M potassium carbonate aqueous solution (aq. $K_2CO_3$) (92.1 ml, 184.2 mmol) was added and tetrakis(triphenylphosphine)palladium [Pd(PPh$_3$)$_4$] (1.4 g, 2 mol %) was added, and the mixture was stirred under reflux. After lowering the temperature to room temperature, the mixture was extracted with water and toluene, and the organic layer was dried with magnesium sulfate (MgSO$_4$) and then distilled under reduced pressure. The resulting mixture was purified by column chromatography on silica gel with hexane:ethyl acetate (15:1) to obtain Compound X-4 (54.3 g, yield 62%; MS: [M+H]$^+$=475).

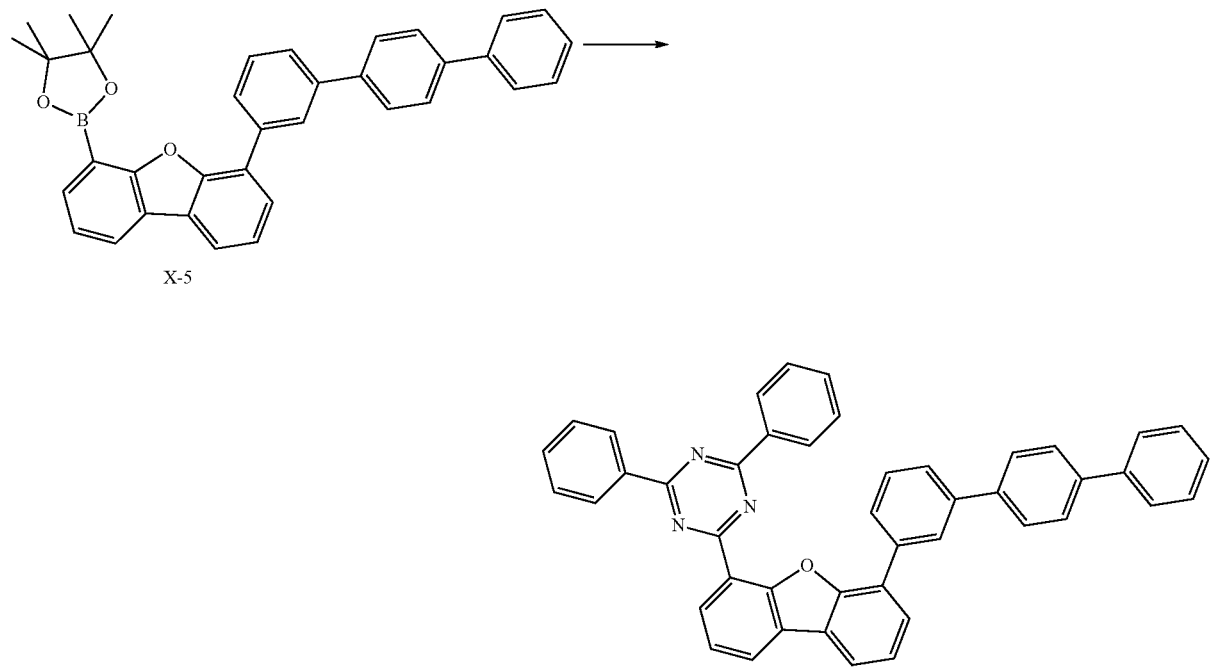

Compound X-5 (25.4 g, yield 92%; MS: [M+H]$^+$=523) was prepared in the same manner as in Synthesis Example 4-2, except that Compound X-4 (25.1 g, 52.8 mmol) was used instead of Compound Q-5 (25.0 g, 52.8 mmol).

Compound C (19.9 g, yield 83%; MS: [M+H]⁺=628) was prepared in the same manner as manner as in Synthesis Example 1-1, except for using Compound X-5 (19.9 g, 38.1 mmol) instead of Compound P-6, and 2-chloro-4,6-diphenyl-1,3,5-triazine (10.2 g, 38.1 mmol) instead of 2-bromophenanthrene.

Synthesis Example 39: Preparation of Compound D

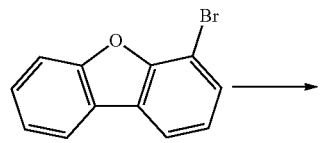

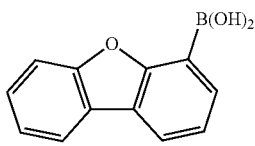

Dibenzo[b,d]furan-4-ylboronic acid (21.2 g, yield 94%; MS: [M+H]⁺=213) was prepared in the same manner as manner as in the preparation method of Compound P-4 of Synthesis Example 1, except that 4-bromodibenzo[b,d]furan (26.3 g, 106.6 mmol) was used instead of Compound P-3.

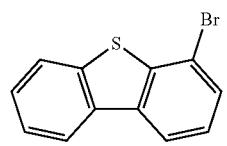

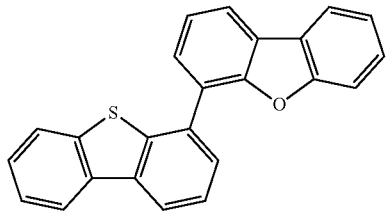

X-6

Compound X-6 (25.3 g, yield 89%; MS: [M+H]⁺=351) was prepared in the same manner as manner as in the preparation method of Compound P-5 of Synthesis Example 1, except for using 4-bromodibenzo[b,d]thiophene (21.4 g, 81.2 mmol) instead of Compound P-4, and dibenzo[b,d]furan-4-ylboronic acid (17.2 g, 81.2 mmol) instead of 2-chloro-4,6-diphenyl-1,3,5-triazine.

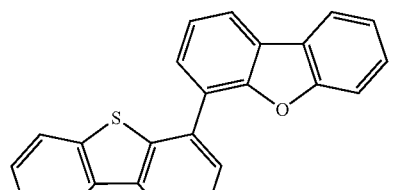

X-6

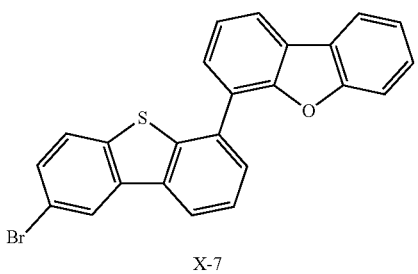

X-7

A mixture was prepared in the same manner as manner as in the preparation method of Compound P-5 of Synthesis Example 20, except for using Compound X-6 (25.0 g, 71.3 mmol), chloroform (200 ml), acetic acid (200 ml) and Br₂ (3.8 mL, 74.9 mmol) instead of Compound R-4, and then purified by column chromatography on silica gel with hexane:ethyl acetate (10:1) to obtain Compound X-7 (14.4 g, yield 47%; MS: [M+H]⁺=428).

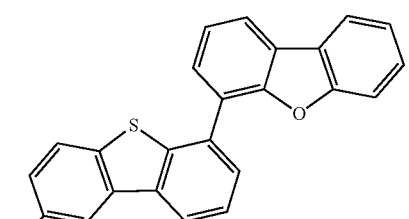

X-7

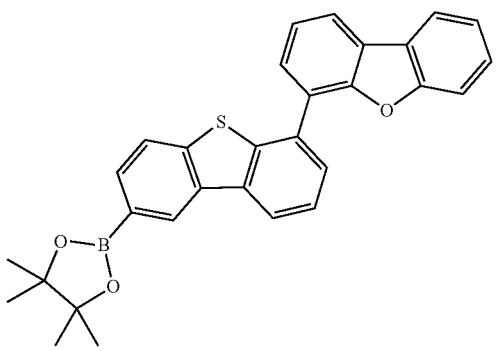

X-8

Compound X-8 (23.9 g, yield 95%; MS: [M+H]⁺=477) was prepared in the same manner as in Synthesis Example 4-2, except that Compound X-7 (22.7 g, 52.8 mmol) was used instead of Compound Q-5.

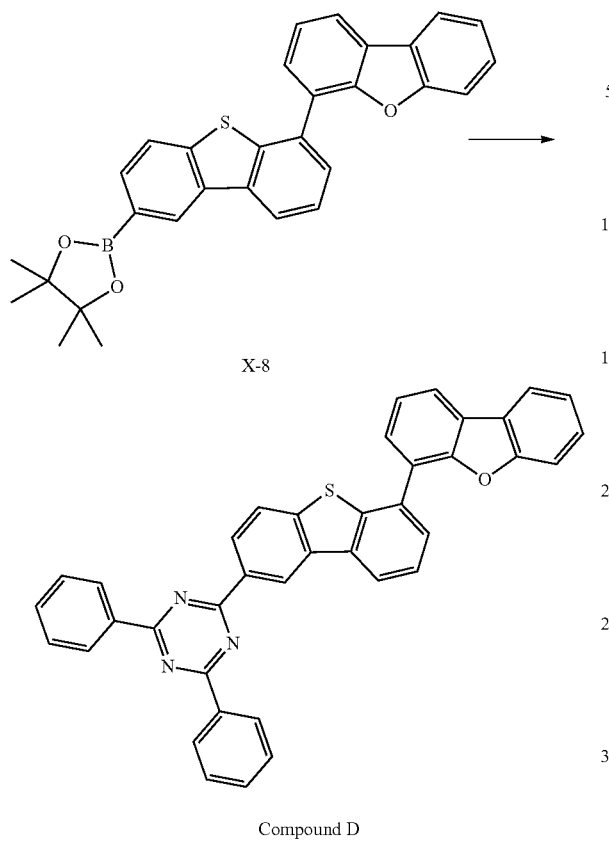

Compound D

Compound D (19.7 g, yield 89%; MS: [M+H]⁺=582) was prepared in the same manner as manner as in Synthesis Example 1-1, except for using Compound X-8 (18.2 g, 38.1 mmol) instead of Compound Q-5, and 2-chloro-4,6-diphenyl-1,3,5-triazine (10.2 g, 38.1 mmol) instead of 2-bromophenanthrene.

Synthesis Example 40: Preparation of Compound E

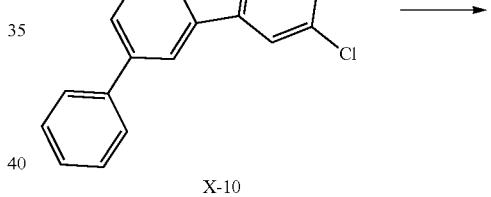

Compound X-9 (56.3 g, yield 87%; MS: [M+H]⁺=280) was prepared in the same manner as manner as in the preparation method of Compound X-1 of Synthesis Example 36, except that 2-chlorodibenzofuran (46.6 g, 230.0 mmol) was used instead of 2-chlorodibenzothiophene.

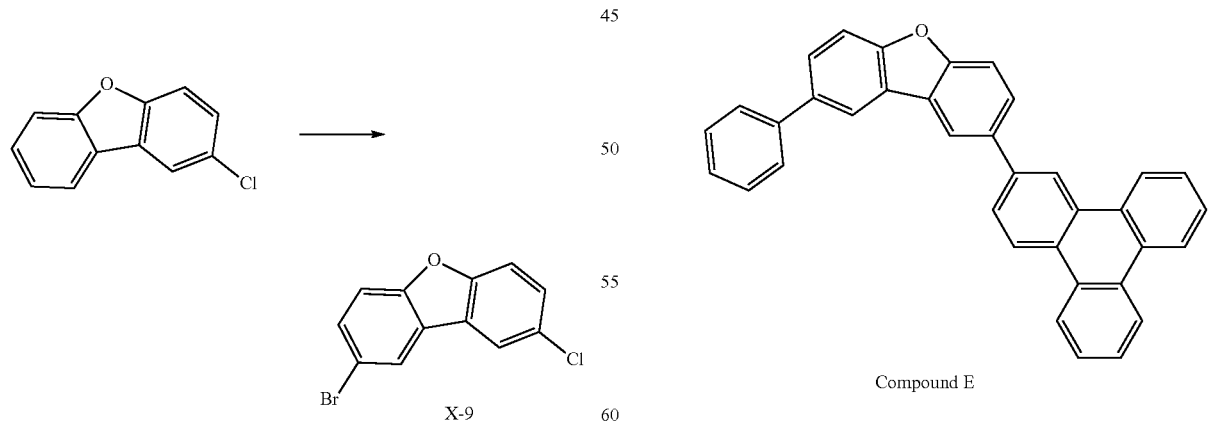

Compound X-10 (21.7 g, yield 96%; MS: [M+H]⁺=279) was prepared in the same manner as manner as in the preparation method of Compound P-5 of Synthesis Example 1, except for using Compound X-9 (22.9 g, 81.2 mmol) instead of Compound P-4, and phenylboronic acid (17.3 g, 81.2 mmol) instead of 2-chloro-4,6-diphenyl-1,3,5-triazine.

Compound E

Compound E (15.6 g, yield 87%; MS: [M+H]⁺=471) was prepared in the same manner as manner as in Synthesis Example 1-1, except for using Compound X-10 (10.6 g, 38.1 mmol) instead of Compound P-6, and triphenylen-2-ylboronic acid (10.4 g, 38.1 mmol) instead of 2-bromophenanthrene.

Synthesis Example 41: Preparation of Compound F

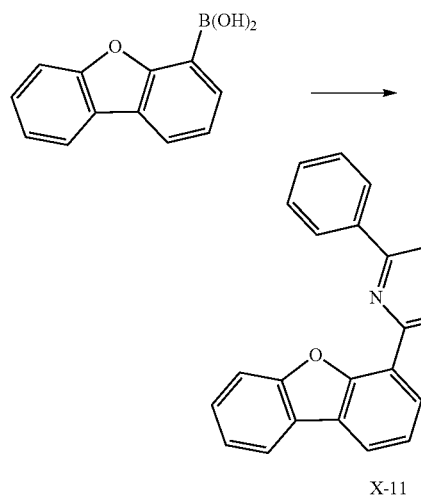

X-11

Compound X-11 (29.0 g, yield 89%; MS: [M+H]$^+$=400) was prepared in the same manner as manner as in the preparation method of Compound P-5 of Synthesis Example 1, except for using dibenzo[b,d]furan-4-ylboronic acid (17.2 g, 81.2 mmol) instead of Compound P-4, and 2-chloro-4,6-diphenyl-1,3,5-triazine (21.7 g, 81.2 mmol) instead of 2-chloro-4,6-diphenyl-1,3,5-triazine.

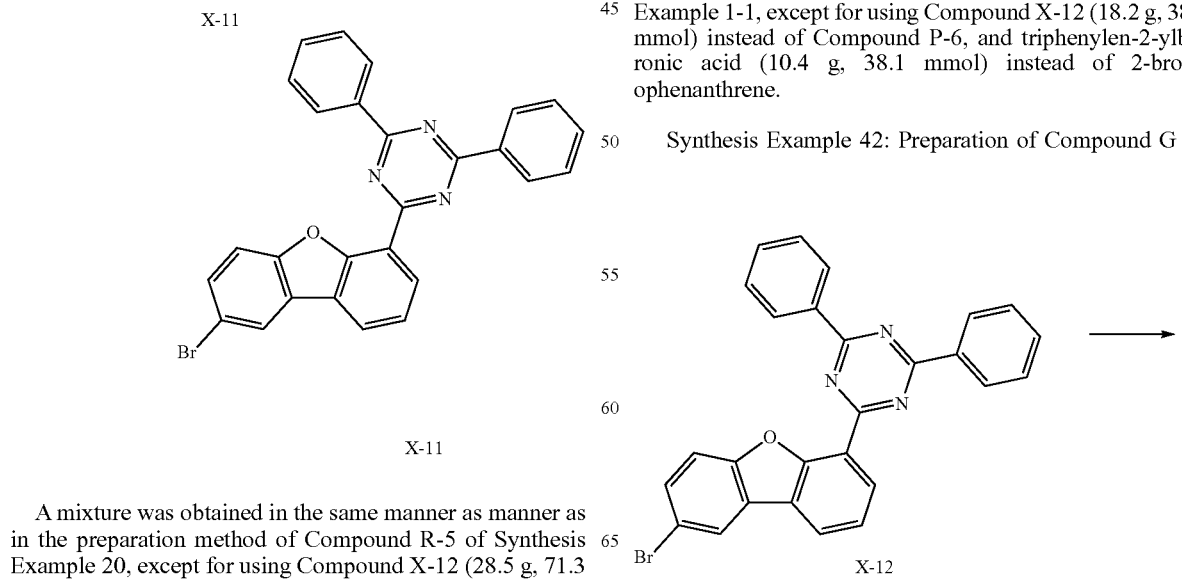

A mixture was obtained in the same manner as manner as in the preparation method of Compound R-5 of Synthesis Example 20, except for using Compound X-12 (28.5 g, 71.3 mmol), chloroform (200 ml), acetic acid (200 ml) and Br$_2$ (3.8 mL, 74.9 mmol) instead of Compound R-4, and then purified by column chromatography on silica gel with hexane:ethyl acetate (10:1) to obtain Compound X-12 (23.5 g, yield 69%; MS: [M+H]$^+$=478).

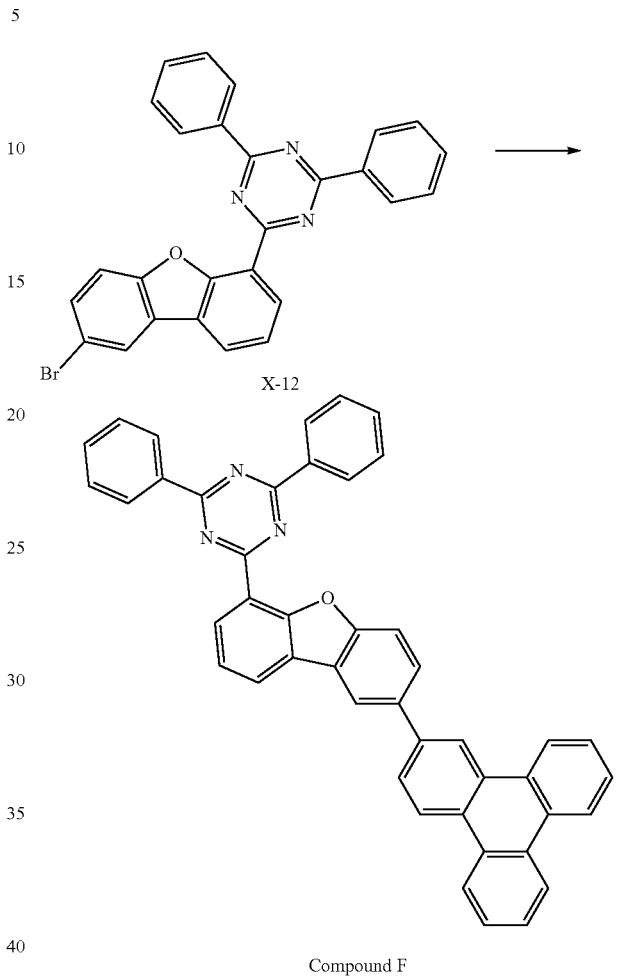

Compound F

Compound F (21.7 g, yield 91%; MS: [M+H]$^+$=626) was prepared in the same manner as manner as in Synthesis Example 1-1, except for using Compound X-12 (18.2 g, 38.1 mmol) instead of Compound P-6, and triphenylen-2-ylboronic acid (10.4 g, 38.1 mmol) instead of 2-bromophenanthrene.

Synthesis Example 42: Preparation of Compound G

-continued

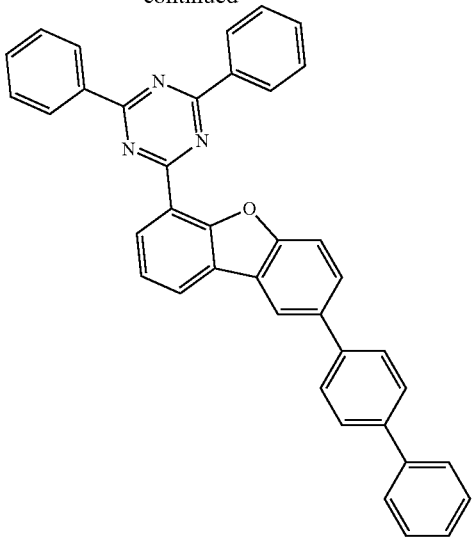

Compound G

Compound G (19.8 g, yield 94%; MS: [M+H]$^+$=552) was prepared in the same manner as manner as in Synthesis Example 1-1, except for using Compound X-12 (18.2 g, 38.1 mmol) instead of Compound P-6, and [1,1'-biphenyl]-4-ylboronic acid (7.5 g, 38.1 mmol) instead of 2-bromophenanthrene.

Synthesis Example 43: Preparation of Compound H

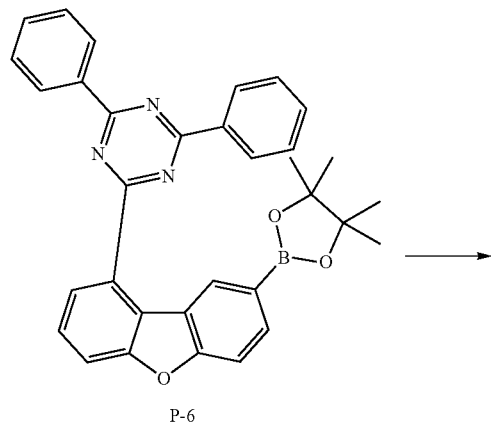

P-6

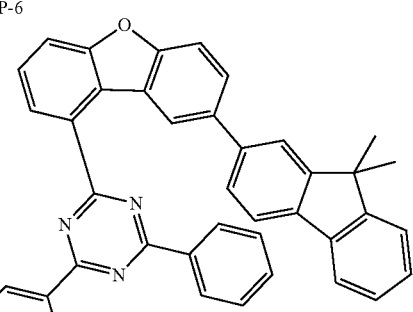

Compound H

Compound H (16.2 g, yield 72%; MS: [M+H]$^+$=560) was prepared in the same manner as manner as in Synthesis Example 1-1, except that 2-bromo-9,9-dimethyl-9H-fluorene (10.4 g, 38.1 mmol) was used instead of 2-bromophenanthrene.

Example 1

A glass substrate on which a thin film of ITO (indium tin oxide) was coated in a thickness of 1,300 Å was put into distilled water containing the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of HI-1 as described below was thermally deposited under vacuum to a thicknesses of 50 Å to form the hole injection layer.

On the hole injection layer, the compound of HT-1 was thermally deposited under vacuum to a thicknesses of 250 Å to form a hole transport layer, and a compound of HT-2 was deposited under vacuum to a thickness of 50 Å on the HT-1 deposition layer to form an electron blocking layer.

Next, on the HT-2 vapor deposition layer, the compound 1 prepared in Synthesis Example 1-1 was co-deposited with 12% by weight of a phosphorescent dopant YGD-1 to form a light emitting layer having a thickness of 400 Å.

On the light emitting layer, a material of ET-1 was deposited under vacuum to a thickness of 250 Å, and additionally a material of ET-2 was co-deposited with 2% by weight of L$_1$ to a thickness of 100 Å to form an electron transport layer and an electron injection layer. Aluminum was deposited on the electron injection layer to a thickness of 1000 Å to form a cathode.

In the above process, the vapor deposition rate of the organic material was maintained at 0.4 to 0.7 Å/sec, the deposition rate of aluminum was maintained at 2 Å/sec, and the degree of vacuum during vapor deposition was maintained at 2×10$^{-7}$~5×10$^{-6}$ torr.

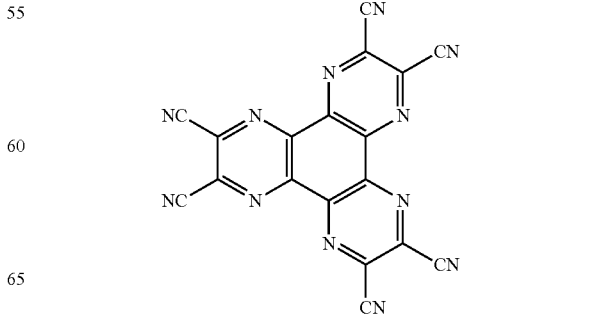

HI-1

HT-1
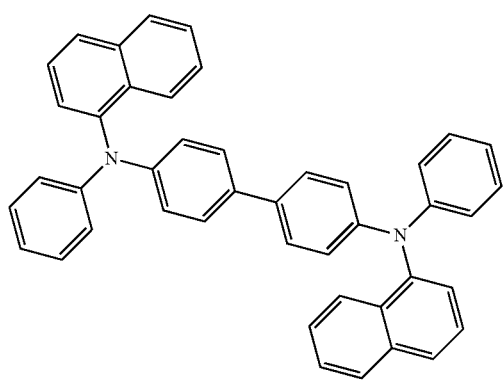
PH-1
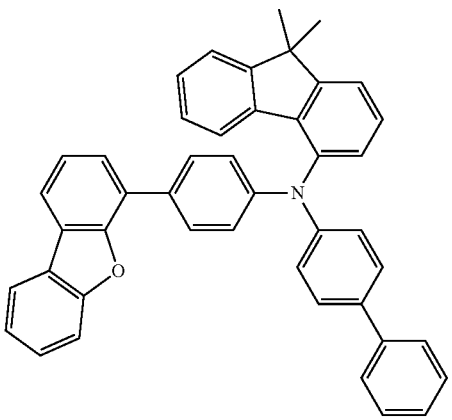
HT-2
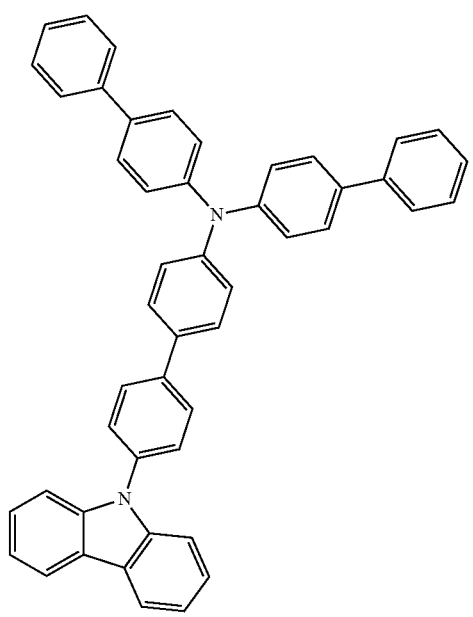
PH-2
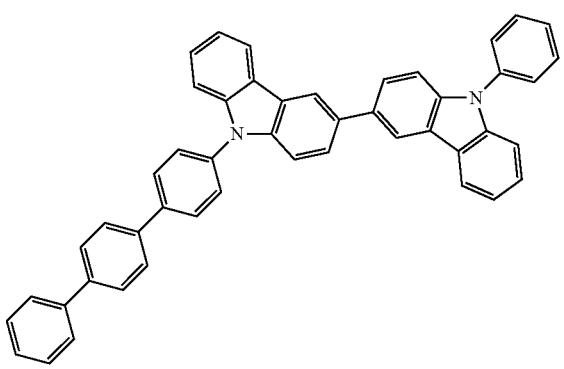
YGD-1
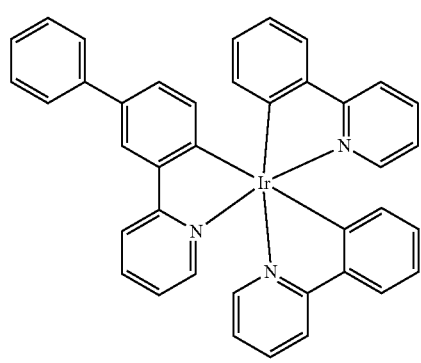
PH-3
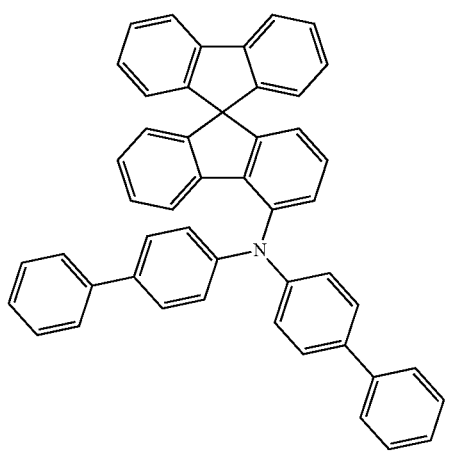

-continued

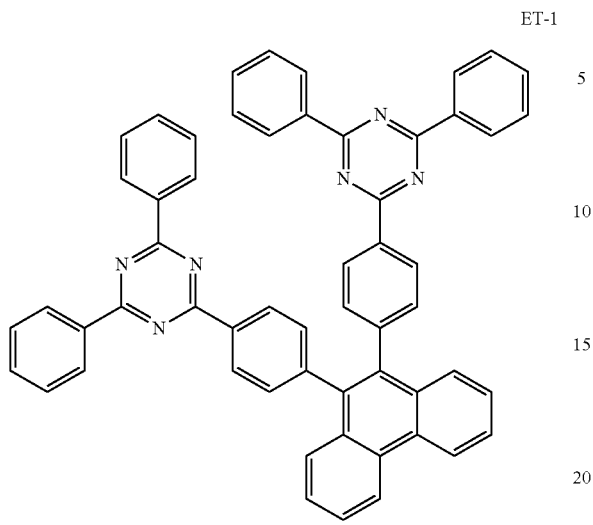

ET-1

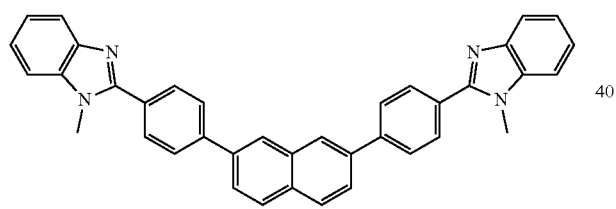

ET-2

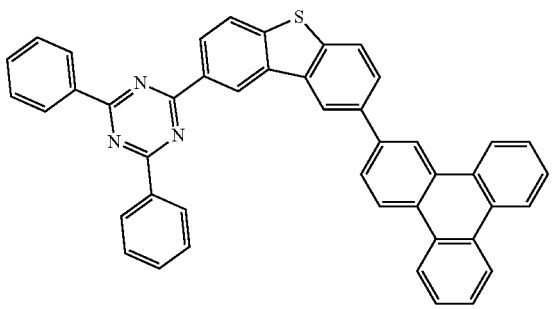

Compound A

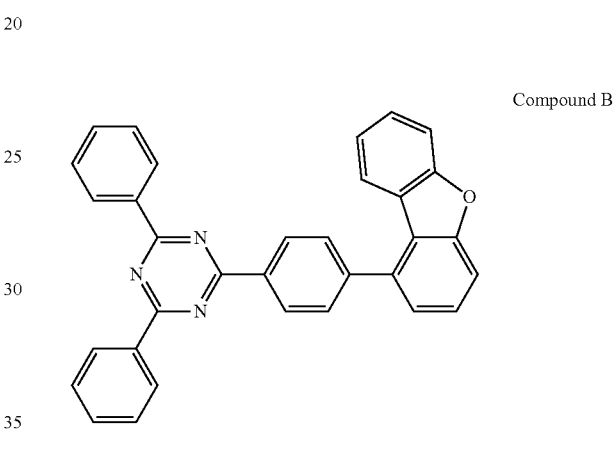

Compound B

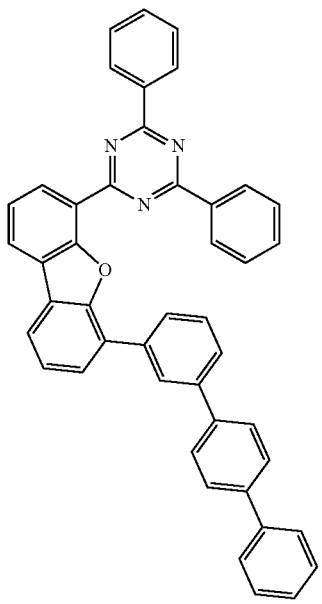

Compound C

Examples 2 to 49

The organic light emitting devices of Examples 2 to 49 were each fabricated in the same manner as in Example 1, except that the phosphorescent host material and the dopant content at the time of forming the light emitting layer were changed as shown in Tables 1 to 3 below.

Comparative Examples 1 to 10

The organic light emitting devices of Comparative Examples 1 to 10 were each fabricated in the same manner as in Example 1, except that the phosphorescent host material and the dopant content at the time of forming the light emitting layer were changed as shown in Table 3 below. Here, the host materials represented by compound A to compound I used in Comparative Examples are as follows.

-continued

Compound D

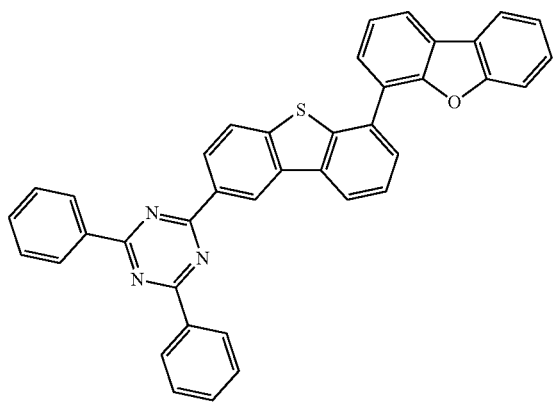

Compound E

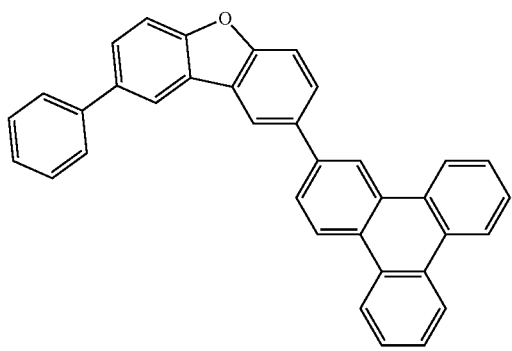

Compound F

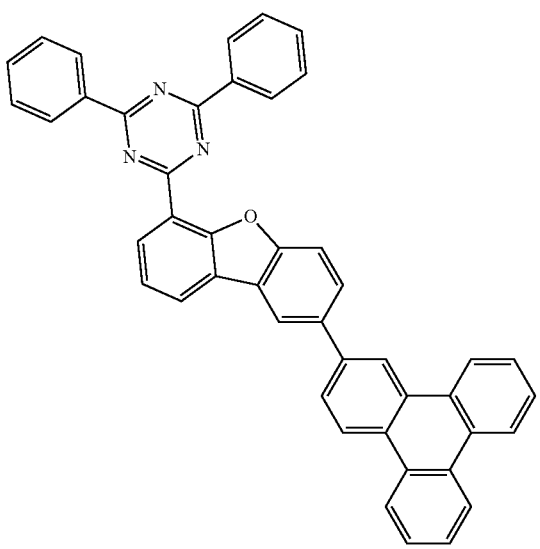

-continued

Compound G

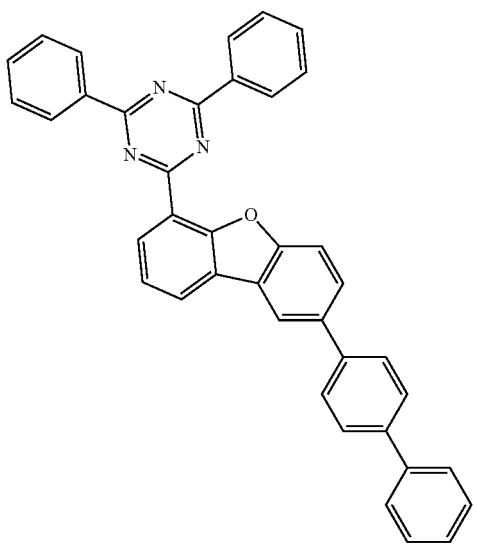

Compound H

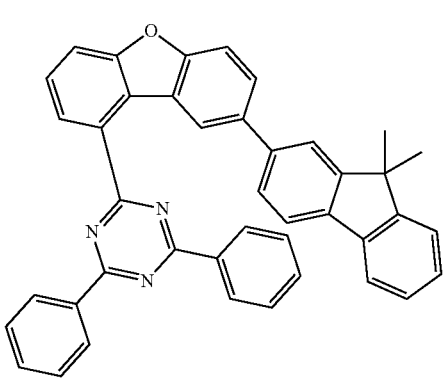

Compound I

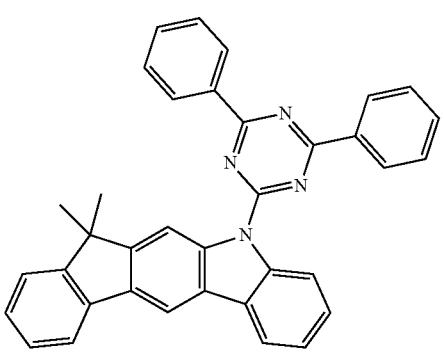

Experimental Example 1

After an electric current was applied to each of the organic light emitting devices fabricated in Examples 1 to 49 and Comparative Examples 1 to 10, the voltage, efficiency, luminance, color coordinate and life time were measured, and the results are shown in Tables 1 to 3 below. In this case, T95 means the time required for the luminance to be reduced to 95% when the initial luminance at a light density of 50 mA/cm² was taken as 100%.

TABLE 1

| No. | Host: dopant (thickness, Å) dopant content | Voltage(V) (@ 10 mA/cm$^2$) | Efficiency (Cd/A) (@10 mA/cm$^2$) | Color coordinate (x, y) | Life time (T$_{95}$, h) (@50 mA/cm$^2$) |
|---|---|---|---|---|---|
| Example 1 | compound 1: YGD-1 (400)12% | 2.99 | 62.8 | (0.46, 0.54) | 47.5 |
| Example 2 | compound 2: YGD-1(400)12% | 2.99 | 64.1 | (0.46, 0.53) | 50.5 |
| Example 3 | compound 3: YGD-1(400)16% | 2.97 | 65.0 | (0.46, 0.52) | 47.0 |
| Example 4 | compound 4: YGD-1(400)12% | 3.15 | 62.8 | (0.46, 0.53) | 78.6 |
| Example 5 | compound 5: YGD-1(400)14% | 3.11 | 53.8 | (0.47, 0.52) | 46.4 |
| Example 6 | compound 6: YGD-1(400)12% | 3.23 | 62.7 | (0.47, 0.53) | 49.9 |
| Example 7 | compound 7: YGD-1(400)12% | 3.20 | 63.1 | (0.46, 0.53) | 50.3 |
| Example 8 | compound 8: YGD-1(400)16% | 3.30 | 55.7 | (0.47, 0.52) | 87.9 |
| Example 9 | compound 9: YGD-1(400)16% | 2.97 | 64.2 | (0.46, 0.54) | 70.5 |
| Example 10 | compound 10: YGD-1(400)16% | 3.12 | 60.3 | (0.47, 0.53) | 47.7 |
| Example 11 | compound 11: YGD-1(400)16% | 2.89 | 63.0 | (0.46, 0.53) | 69.8 |
| Example 12 | compound 14: YGD-1(400)16% | 3.08 | 56.1 | (0.45, 0.54) | 47.6 |
| Example 13 | compound 15: YGD-1(400)12% | 3.00 | 63.0 | (0.46, 0.53) | 47.1 |
| Example 14 | compound 16: YGD-1(400)12% | 3.28 | 63.2 | (0.46, 0.53) | 41.8 |
| Example 15 | compound 12: YGD-1(200:200)16% | 3.55 | 65.9 | (0.46, 0.52) | 126.2 |
| Example 16 | compound 13: PH-1:YGD-1(160:240)16% | 3.51 | 67.2 | (0.46, 0.53) | 116.0 |
| Example 17 | compound 4: PH-2:YGD-1(160:240)12% | 3.57 | 67.7 | (0.46, 0.53) | 191.9 |
| Example 18 | compound 17: PH-2:YGD-1(200:200)16% | 3.53 | 67.8 | (0.47, 0.53) | 125.1 |
| Example 19 | compound 18: PH-2:YGD-1(160:240)12% | 3.56 | 70.2 | (0.45, 0.53) | 132.8 |
| Example 20 | compound 19: PH-2:YGD-1(200:200)15% | 3.50 | 68.9 | (0.46, 0.53) | 352.0 |

TABLE 2

| No. | Host: dopant (thickness, Å) dopant content | Voltage(V) (@ 10 mA/cm$^2$) | Efficiency (Cd/A) (@ 10 mA/cm$^2$) | Color coordinate (x, y) | Life time (T$_{95}$, h) (@50 mA/cm$^2$) |
|---|---|---|---|---|---|
| Example 21 | compound 20: PH-3:YGD-1(160:240)12% | 3.64 | 65.4 | (0.45, 0.54) | 155.7 |
| Example 22 | compound 21: PH-2:YGD-1(200:200)14% | 3.58 | 64.1 | (0.46, 0.54) | 100.3 |
| Example 23 | compound 22: PH-3:YGD-1(200:200)16% | 3.60 | 66.5 | (0.46, 0.54) | 115.6 |
| Example 24 | compound 23: PH-2:YGD-1(160:240)12% | 3.71 | 66.8 | (0.46, 0.53) | 180.3 |
| Example 25 | compound 24: PH-2:YGD-1(160:240)12% | 3.48 | 67.1 | (0.46, 0.53) | 230.7 |
| Example 26 | compound 25: YGD-1 (400)16% | 3.12 | 60.3 | (0.46, 0.52) | 48.3 |
| Example 27 | compound 26: YGD-1 (400)12% | 3.01 | 61.7 | (0.48, 0.51) | 84.9 |
| Example 28 | compound 27: YGD-1 (400)16% | 2.98 | 58.5 | (0.48, 0.51) | 76.1 |
| Example 29 | compound 28: YGD-1 (400)16% | 3.00 | 67.1 | (0.47, 0.52) | 87.2 |
| Example 30 | compound 29: YGD-1(400)16% | 3.04 | 65.4 | (0.46, 0.53) | 68.1 |
| Example 31 | compound 30: YGD-1(400)16% | 3.01 | 66.1 | (0.46, 0.52) | 73.6 |
| Example 32 | compound 31: YGD-1(400)12% | 3.12 | 60.2 | (0.46, 0.53) | 77.2 |

TABLE 2-continued

| No. | Host: dopant (thickness, Å) dopant content | Voltage(V) (@ 10 mA/cm$^2$) | Efficiency (Cd/A) (@ 10 mA/cm$^2$) | Color coordinate (x, y) | Life time (T$_{95}$, h) (@50 mA/cm$^2$) |
|---|---|---|---|---|---|
| Example 33 | compound 32: YGD-1(400)12% | 3.08 | 64.2 | (0.45, 0.53) | 76.8 |
| Example 34 | compound 33: YGD-1(400)16% | 3.11 | 52.6 | (0.45, 0.53) | 46.2 |
| Example 35 | compound 34: YGD-1(400)16% | 2.97 | 59.9 | (0.46, 0.54) | 74.3 |
| Example 36 | compound 35: YGD-1(400)12% | 3.04 | 62.4 | (0.45, 0.53) | 79.8 |
| Example 37 | compound 36: YGD-1(400)16% | 3.10 | 59.15 | (0.45, 0.55) | 48.4 |
| Example 38 | compound 37: YGD-1(400)14% | 3.01 | 59.2 | (0.45, 0.53) | 44.1 |
| Example 39 | compound 38: PH-1:YGD-1(200:200)12% | 3.52 | 67.2 | (0.46, 0.53) | 160.3 |
| Example 40 | compound 39: PH-2:YGD-1(160:240)16% | 3.49 | 72.4 | (0.45, 0.54) | 265.8 |

TABLE 3

| No. | Host: dopant (thickness, Å) dopant content | Voltage(V) (@ 10 mA/cm$^2$) | Efficiency (Cd/A) (@ 10 mA/cm$^2$) | Color coordinate (x, y) | Life time (T$_{95}$, h) (@50 mA/cm$^2$) |
|---|---|---|---|---|---|
| Example 41 | compound 40: PH-3:YGD-1 (200:200)16% | 3.61 | 62.6 | (0.44, 0.54) | 102.8 |
| Example 42 | compound 41: PH-2:YGD-1(160:240)16% | 3.48 | 65.1 | (0.47, 0.53) | 272.1 |
| Example 43 | compound 42: PH-2:YGD-1(160:240)12% | 3.52 | 67.7 | (0.45, 0.54) | 326.1 |
| Example 44 | compound 43: PH-3:YGD-1(160:240)12% | 3.55 | 62.4 | (0.45, 0.53) | 239.8 |
| Example 45 | compound 44: PH-3:YGD-1(200:200)16% | 3.60 | 60.0 | (0.46, 0.52) | 154.2 |
| Example 46 | compound 46: PH-1:YGD-1(160:240)16% | 3.62 | 64.68 | (0.45, 0.53) | 175.3 |
| Example 47 | compound 28: PH-2:YGD-1(160:240)16% | 3.51 | 67.9 | (0.45, 0.54) | 330.2 |
| Example 48 | compound 81: PH-2:YGD-1(160:240)12% | 3.53 | 65.3 | (0.47, 0.54) | 289.6 |
| Example 49 | compound 45: PH-2:YGD-1(160:240)12% | 3.50 | 68.1 | (0.45, 0.52) | 349.8 |
| Comparative Example 1 | compound A: YGD-1(400)12% | 3.21 | 61.9 | (0.46, 0.53) | 25.9 |
| Comparative Example 2 | compound B: YGD-1(400)12% | 3.17 | 56.2 | (0.47, 0.52) | 27.3 |
| Comparative Example 3 | compound C: YGD-1(400)12% | 2.92 | 62.2 | (0.48, 0.50) | 20.3 |
| Comparative Example 4 | compound D: YGD-1(400)12% | 3.11 | 67.3 | (0.48, 0.53) | 26.2 |
| Comparative Example 5 | compound E: YGD-1(400)12% | 4.73 | 28.11 | (0.47, 0.51) | 22.2 |
| Comparative Example 6 | compound F: YGD-1(400)12% | 3.15 | 53.2 | (0.48, 0.50) | 27.5 |
| Comparative Example 7 | compound G: YGD-1(400)12% | 3.14 | 52.7 | (0.49, 0.50) | 26.9 |
| Comparative Example 8 | compound H: YGD-1(400)12% | 3.14 | 56.8 | (0.49, 0.50) | 28.9 |
| Comparative Example 9 | compound I: YGD-1(400)12% | 3.0 | 60 | (0.46, 0.53) | 31.5 |
| Comparative Example10 | compound A: PH-1:YGD-1(160:240)16% | 3.63 | 64.3 | (0.47, 0.53) | 63.2 |

Example 50

A compound of HI-1 described below was thermally deposited under vacuum to a thicknesses of 150 Å on the ITO transparent electrode prepared as in Example 1 to form the hole injection layer.

On the hole injection layer, the compound of HT-1 was thermally deposited under vacuum to a thicknesses of 1150 Å, and then a compound of HT-3 was deposited under vacuum to a thickness of 500 Å to form a hole transport layer.

Next, on the hole transport layer, the compound 47 prepared in Synthesis Example 15-3 was co-deposited with 5% by weight of a phosphorescent dopant GD-1 to form a light emitting layer having a thickness of 400 Å.

On the light emitting layer, a material of ET-3 was deposited under vacuum to a thickness of 50 Å to form a hole blocking layer, and a material of ET-4 and LIQ were deposited under vacuum at a weight ratio of 1:1 to form an electron transport layer. Lithium fluoride (LiF) was sequentially deposited on the electron transport layer in a thickness of 10 Å, and Mg was deposited with Ag of 10% by weight on the electron transport layer to form an electron injection layer having a thickness of 200 Å. Aluminum was deposited thereon in a thickness of 1000 Å to form a cathode.

In the above process, the vapor deposition rate of the organic material was maintained at 0.4 to 0.7 Å/sec, the lithium fluoride of the cathode was maintained at a deposition rate of 0.3 Å/sec, and the deposition rate of aluminum was maintained at 2 Å/sec. The degree of vacuum during vapor deposition was maintained at $1\times10^{-7}$~$5\times10^{-8}$ torr.

HT-3

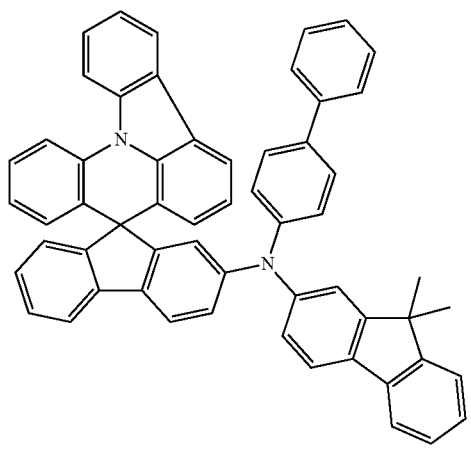

GD-1

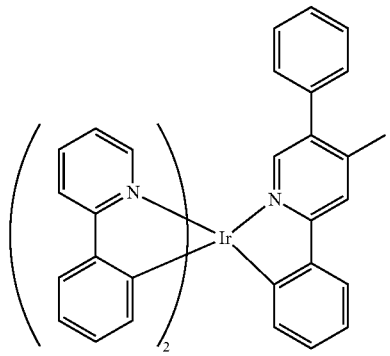

ET-3

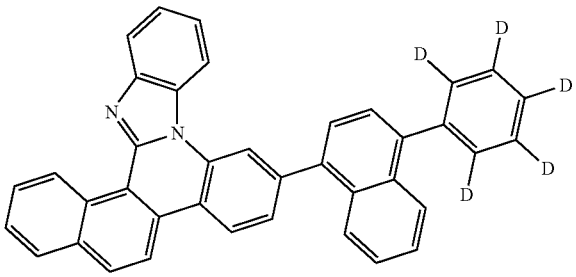

ET-4

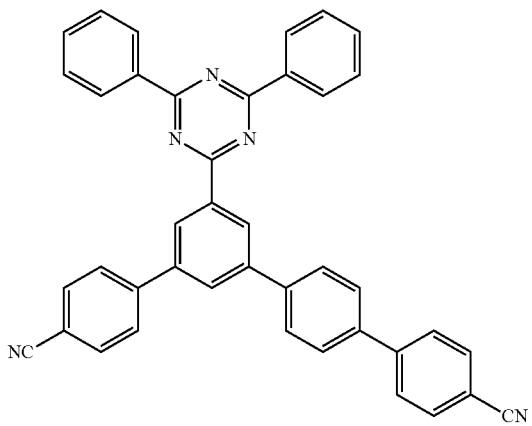

Examples 51 to 90

The organic light emitting devices of Examples 51 to 90 were each fabricated in the same manner as in Example 50, except that the phosphorescent host material and the dopant content at the time of forming the light emitting layer were changed as shown in Tables 4 and 5 below.

Comparative Examples 11 to 19

The organic light emitting devices of Comparative Examples 11 to 19 were each fabricated in the same manner as in Example 50, except that the phosphorescent host material and the dopant content at the time of forming the light emitting layer were changed as shown in Table 6 below. In this case, the host materials represented by compound A to compound I used in Comparative Examples are as described above.

Experimental Example 2

After an electric current was applied to each of the organic light emitting devices fabricated in Examples 50 to 90 and Comparative Examples 11 to 19, the voltage, efficiency, luminance, color coordinate and life time were measured, and the results are shown in Tables 4 to 6 below. In this case, T95 means the time required for the luminance to be reduced to 95% when the initial luminance at a light density of 20 mA/cm² was taken as 100%.

TABLE 4

| No. | Host: dopant (thickness, Å) dopant content | Voltage(V) (@ 10 mA/cm$^2$) | Efficiency (Cd/A) (@ 10 mA/cm$^2$) | Color coordinate (x, y) | Life time ($T_{95}$, h) (@50 mA/cm$^2$) |
|---|---|---|---|---|---|
| Example 50 | compound 47: GD-1(400)5% | 4 | 50.8 | (0.349, 0.612) | 52.9 |
| Example 51 | compound 48: GD-1(400)5% | 4.01 | 51.1 | (0.350, 0.610) | 66.4 |
| Example 52 | compound 49: GD-1(400)7% | 3.98 | 51.2 | (0.350, 0.611) | 59.65 |
| Example 53 | compound 50: GD-1(400)5% | 4.11 | 51.8 | (0.348, 0.612) | 51.8 |
| Example 54 | compound 51: GD-1(400)5% | 4.09 | 50.2 | (0.345, 0.612) | 51.4 |
| Example 55 | compound 52: GD-1(400)7% | 4.1 | 50.8 | (0.348, 0.610) | 51.5 |
| Example 56 | compound 16: GD-1(400)5% | 4.08 | 49.1 | (0.349, 0.610) | 46.7 |
| Example 57 | compound 53: GD-1(400)7% | 4.02 | 51.8 | (0.348, 0.612) | 55.5 |
| Example 58 | compound 20: GD-1(400)5% | 3.97 | 52.8 | (0.349, 0.611) | 67.7 |
| Example 59 | compound 54: GD-1(400)5% | 4.01 | 52.4 | (0.350, 0.613) | 66.2 |
| Example 60 | compound 46: GD-1(400)5% | 4.0 | 52.9 | (0.349, 0.612) | 65.6 |
| Example 61 | compound 55: GD-1(400)5% | 3.99 | 52.7 | (0.350, 0.611) | 65.8 |
| Example 62 | compound 56: GD-1(400)10% | 3.99 | 52.4 | (0.347, 0.612) | 51.3 |
| Example 63 | compound 4: PH-2:GD-1(200:200)5% | 3.71 | 55.1 | (0.351, 0.609) | 110.2 |
| Example 64 | compound 57: PH-3:GD-1(200:200)5% | 4.07 | 52.9 | (0.348, 0.612) | 79.9 |
| Example 65 | compound 58: PH-1:GD-1(200:200)5% | 4.2 | 51.7 | (0.347, 0.610) | 88.7 |
| Example 66 | compound 6: PH-2:GD-1(200:200)5% | 4.21 | 53.4 | (0.347, 0.613) | 100.1 |
| Example 67 | compound 50: PH-2:GD-1(160:240)7% | 4.17 | 58.1 | (0.348, 0.612) | 78.9 |
| Example 68 | compound 60: PH-2:GD-1(160:240)5% | 4.23 | 51.7 | (0.347, 0.611) | 89.2 |
| Example 69 | compound 61: PH-3:GD-1(200:200)5% | 4.11 | 54.2 | (0.351, 0.613) | 106.2 |
| Example 70 | compound 62: PH-2:GD-1(160:240)5% | 4.22 | 51.9 | (0.351, 0.613) | 170.7 |

TABLE 5

| No. | Host: dopant (thickness, Å) dopant content | Voltage(V) (@ 10 mA/cm$^2$) | Efficiency (Cd/A) (@ 10 mA/cm$^2$) | Color coordinate (x, y) | Life time ($T_{95}$, h) (@50 mA/cm$^2$) |
|---|---|---|---|---|---|
| Example 71 | compound 63: PH-3:GD-1(200:200)5% | 4.31 | 54.2 | (0.349, 0.613) | 134.9 |
| Example 72 | compound 64: PH-1:GD-1(160:240)7% | 4.30 | 54.3 | (0.347, 0.612) | 135.4 |
| Example 73 | compound 65: PH-2:GD-1(200:200)5% | 4.19 | 52.9 | (0.351, 0.613) | 170.9 |
| Example 74 | compound 66: PH-1:GD-1(160:240)10% | 3.92 | 52.3 | (0.351, 0.613) | 171.4 |
| Example 75 | compound 67: PH-2:GD-1(200:200)5% | 4.12 | 54.9 | (0.350, 0.611) | 128.2 |
| Example 76 | compound 68: PH-1:GD-1(160:240)5% | 3.76 | 56.8 | (0.352, 0.609) | 104 |
| Example 77 | compound 69: PH-2:GD-1(160:240)7% | 4.10 | 55.1 | (0.351, 0.613) | 103.2 |
| Example 78 | compound 70: PH-1:GD-1(160:240)5% | 4.17 | 56.53 | (0.351, 0.613) | 104.5 |
| Example 79 | compound 71: PH-3:GD-1(200:200)7% | 4.24 | 54.6 | (0.346, 0.612) | 137.9 |
| Example 80 | compound 72: PH-2:GD-1(200:200)5% | 4.32 | 56.1 | (0.350, 0.612) | 158.8 |
| Example 81 | compound 73: PH-2:GD-1(160:240)5% | 4.42 | 51.24 | (0.346, 0.611) | 102.5 |

TABLE 5-continued

| No. | Host: dopant (thickness, Å) dopant content | Voltage(V) (@ 10 mA/cm²) | Efficiency (Cd/A) (@ 10 mA/cm²) | Color coordinate (x, y) | Life time ($T_{95}$, h) (@50 mA/cm²) |
|---|---|---|---|---|---|
| Example 82 | compound 74: PH-2:GD-1(160:240)10% | 4.13 | 54.7 | (0.350, 0.611) | 119.9 |
| Example 83 | compound 75: PH-3:GD-1(200:200)7% | 4.43 | 50.35 | (0.346, 0.613) | 95.2 |
| Example 84 | compound 76: PH-3:GD-1(160:240)10% | 4.14 | 52.8 | (0.346, 0.612) | 105.7 |
| Example 85 | compound 77: PH-1:GD-1(200:200)5% | 4.35 | 56.4 | (0.347, 0.611) | 62.9 |
| Example 86 | compound 78: PH-1:GD-1(200:200)5% | 3.92 | 54 | (0.352, 0.609) | 81.2 |
| Example 87 | compound 79: PH-3:GD-1(160:240)5% | 4.16 | 56.13 | (0.351, 0.613) | 104.3 |
| Example 88 | compound 80: PH-1:GD-1(160:240)5% | 4.32 | 50.89 | (0.346, 0.611) | 100.4 |
| Example 89 | compound 59: PH-1:GD-1(160:240)6% | 4.29 | 53.7 | (0.347, 0.614) | 92.6 |
| Example 90 | compound 45: PH-1:GD-1(160:240)7% | 4.31 | 57.3 | (0.350, 0.611) | 168.1 |

TABLE 6

| No. | Host: dopant (thickness, Å) dopant content | Voltage(V) (@ 10 mA/cm²) | Efficiency (Cd/A) (@ 10 mA/cm²) | Color coordinate (x, y) | Life time ($T_{95}$, h) (@50 mA/cm²) |
|---|---|---|---|---|---|
| Comparative Example 11 | compound A: GD-1(400)5% | 4.18 | 51.2 | (0.351, 0.609) | 18.3 |
| Comparative Example 12 | compound B: GD-1(400)5% | 4.16 | 46.1 | (0.352, 0.611) | 23.1 |
| Comparative Example 13 | compound C: GD-1(400)5% | 4.10 | 61.8 | (0.351, 0.610) | 16.3 |
| Comparative Example 14 | compound D: GD-1(400)5% | 4.21 | 62.4 | (0.351, 0.609) | 19.8 |
| Comparative Example 15 | compound E: GD-1(400)5% | 5.80 | 37.1 | (0.350, 0.611) | 14.7 |
| Comparative Example16 | compound F: GD-1(400)5% | 4.08 | 44.0 | (0.352, 0.609) | 22.8 |
| Comparative Example 17 | compound G: GD-1(400)5% | 4.09 | 43.2 | (0.352, 0.609) | 22.0 |
| Comparative Example 18 | compound H: GD-1(400)5% | 4.19 | 51.0 | (0.352, 0.610) | 27.1 |
| Comparative Example 19 | compound I: GD-1(400)5% | 4.1 | 47 | (0.349, 0.611) | 32.2 |

As shown in Tables 1 to 6 above, the organic light emitting devices fabricated using the compound according to the present invention as a phosphorescent host material exhibited excellent performance in terms of driving voltage, current efficiency, and lifetime as compared with the organic light emitting devices of Comparative Examples.

Particularly, the organic light emitting devices according to Examples showed an increase in lifetime of at least 150% as compared with the organic light emitting devices according to Comparative Examples 9 and 19 using Compound I, which is a phosphorescent host material commonly used in the art. Further, the organic light emitting devices according to Examples 4, 8 and 50 showed an increase in lifetime of about 250% as compared with the organic light emitting devices according to Comparative Examples 1, 6, 11 and 16 using Compounds A and F in which the substitution position of triazinyl group is different from that of the compound according to the present invention. Further, the organic light emitting device according to Example 28 also showed an increase in lifetime of about 370% or more as compared with the organic light emitting device according to Comparative Example 3 using Compound C, and the organic light emitting device according to Examples 30 and 31 also showed an increase in lifetime of about 250% or more as compared with the organic light emitting device according to Comparative Example 7 using Compound G.

In addition, it could be seen that the driving voltage, current efficiency and lifetime of the organic light emitting device according to Comparative Example 5 using the compound E containing no triazinyl group were significantly lower than those of the organic light emitting device according to Examples. Further, the organic light emitting device according to Comparative Examples 8 and 18 using the compound H substituted with a dimethylfluorenyl group showed a remarkably low life time as compared with the organic light emitting device according to Examples, which is believed to be due to the generation of impurities resulting from the formation of radicals by dimethylfluorenyl in the polymer.

| Explanation of Signs | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A compound of Chemical Formulae 1-2 to 1-4:

[Chemical Formula 1-2]

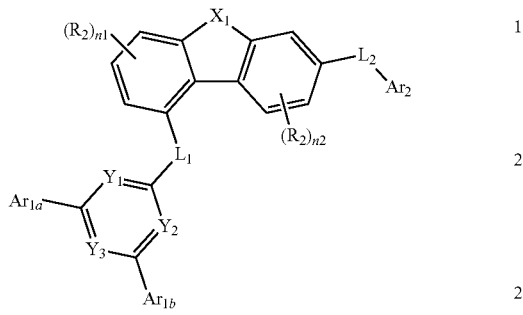

[Chemical Formula 1-3]

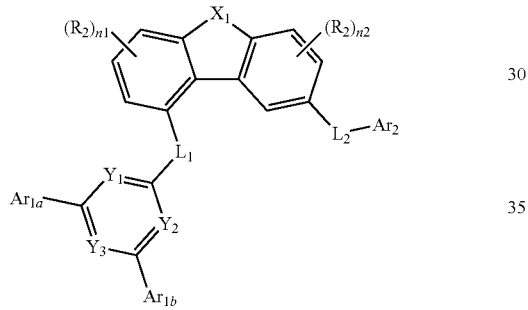

[Chemical Formula 1-4]

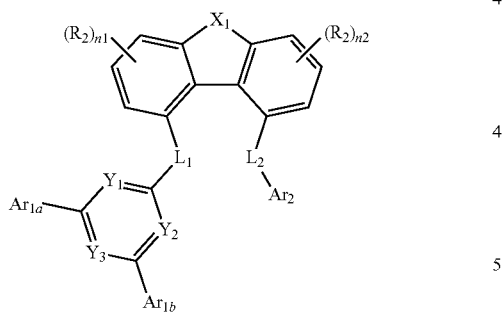

wherein in Chemical Formulae 1-2 to 1-4:
$X_1$ is O or S;
$L_1$ is a single bond;
$L_2$ is a single bond, a substituted or unsubstituted phenylene, a substituted or unsubstituted naphthylene, or a substituted or unsubstituted biphenylenyl;
$Y_1$ to $Y_3$ are each independently N or $CR_3$, provided that at least one of $Y_1$ to $Y_3$ is N;
$Ar_{1a}$ and $Ar_{1b}$ are each independently a substituted or unsubstituted $C_{6-60}$ aryl or a substituted or unsubstituted $C_{1-60}$ heteroaryl containing 1 to 3 heteroatoms selected from the group consisting of O and S;
$R_1$ and $R_2$ are each independently hydrogen, deuterium, cyano, or a substituted or unsubstituted $C_{1-10}$ alkyl;

each $R_3$ is independently hydrogen, deuterium, halogen, cyano, nitro, amino, a substituted or unsubstituted $C_{1-60}$ alkyl, a substituted or unsubstituted $C_{1-60}$ haloalkyl, a substituted or unsubstituted $C_{1-60}$ alkoxy, a substituted or unsubstituted $C_{1-60}$ haloalkoxy, a substituted or unsubstituted $C_{3-60}$ cycloalkyl, a substituted or unsubstituted $C_{2-60}$ alkenyl, a substituted or unsubstituted $C_{6-60}$ aryl, a substituted or unsubstituted $C_{6-60}$ aryloxy, or a substituted or unsubstituted $C_{1-60}$ heteroaryl containing at least one heteroatom selected from the group consisting of N, O and S;

$n_1$ and $n_2$ are each independently an integer of 0 to 3; and $Ar_2$ is any one selected from the group consisting of:

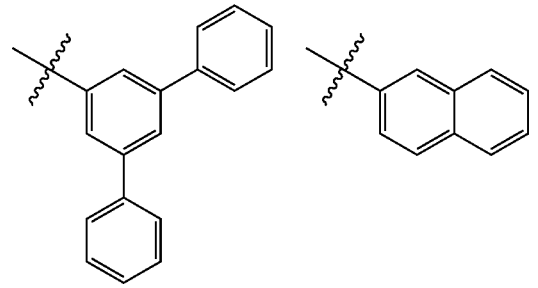

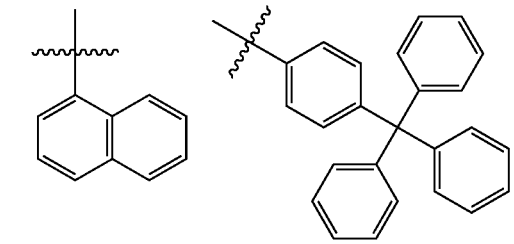

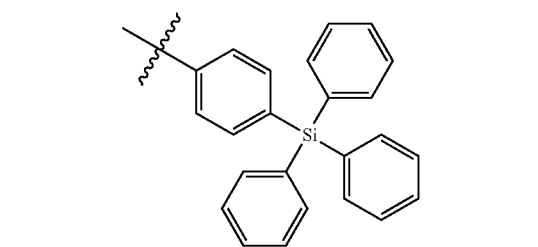

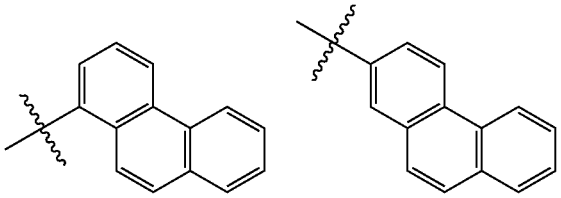

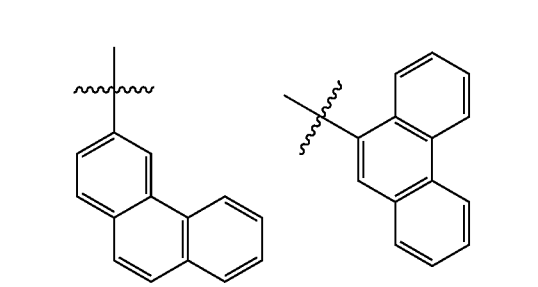

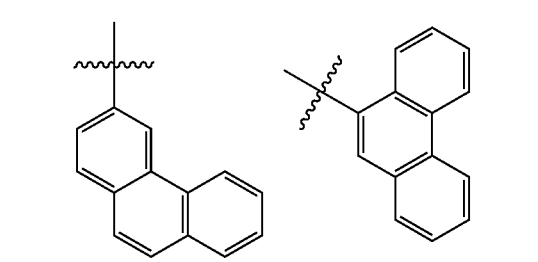

489
-continued
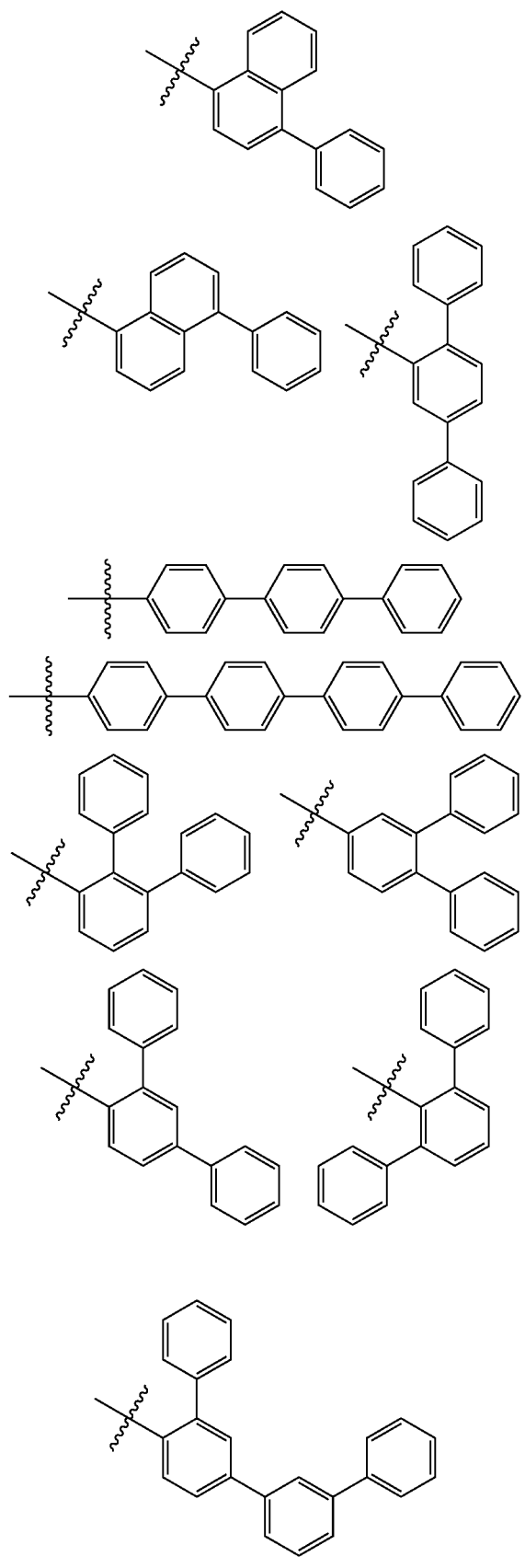
490
-continued
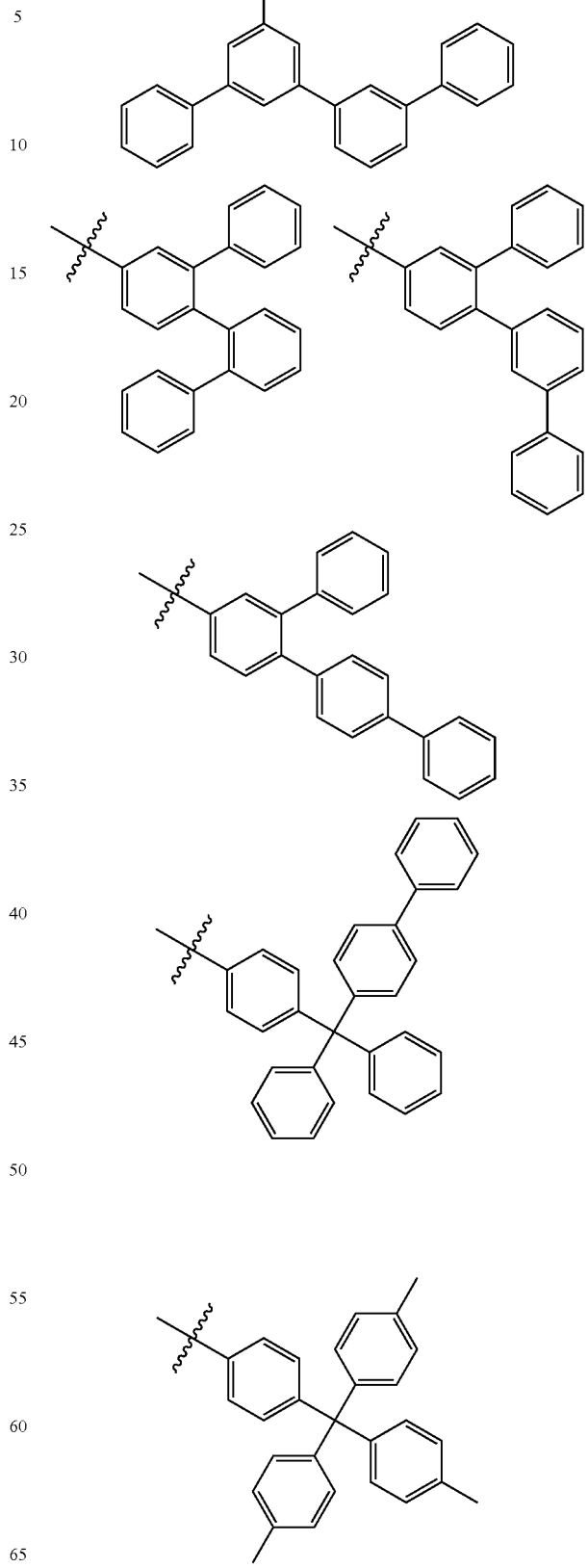

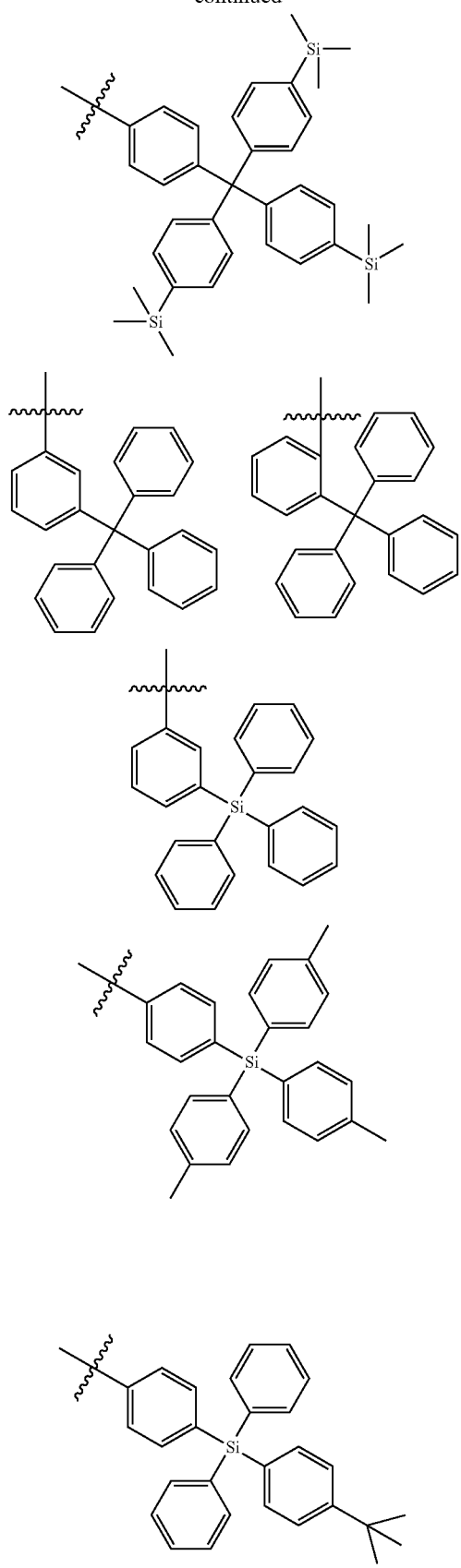

493
-continued
494
-continued
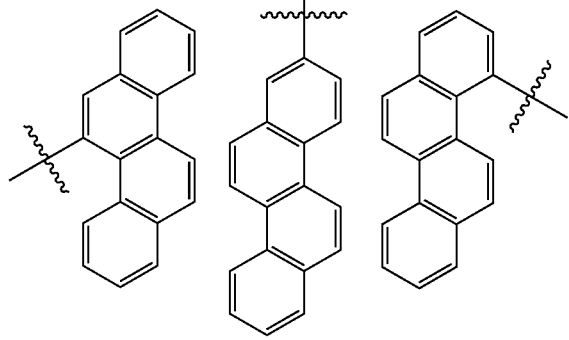
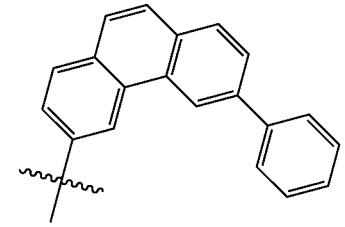
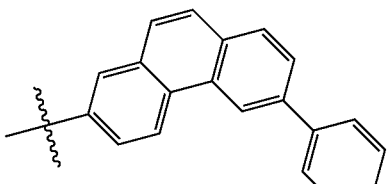
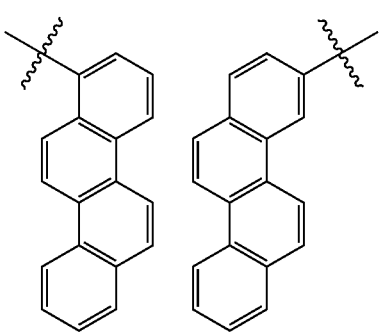
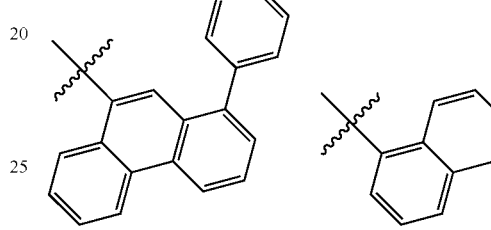
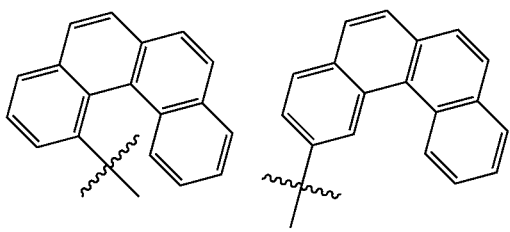
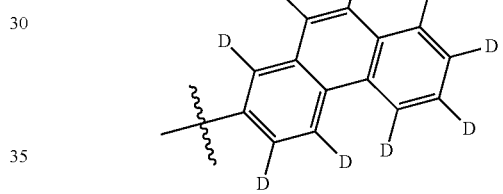
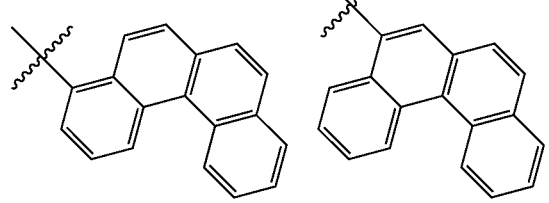
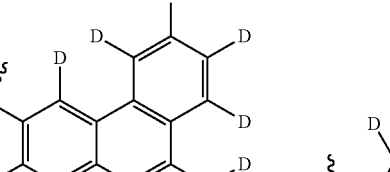
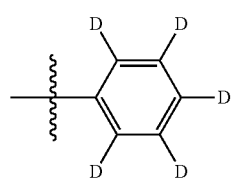
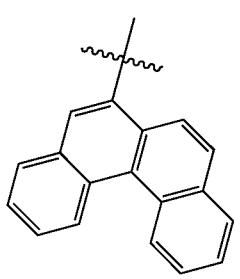
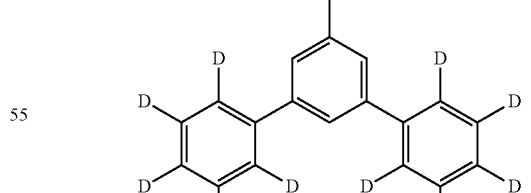
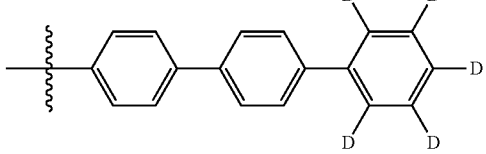

495
-continued
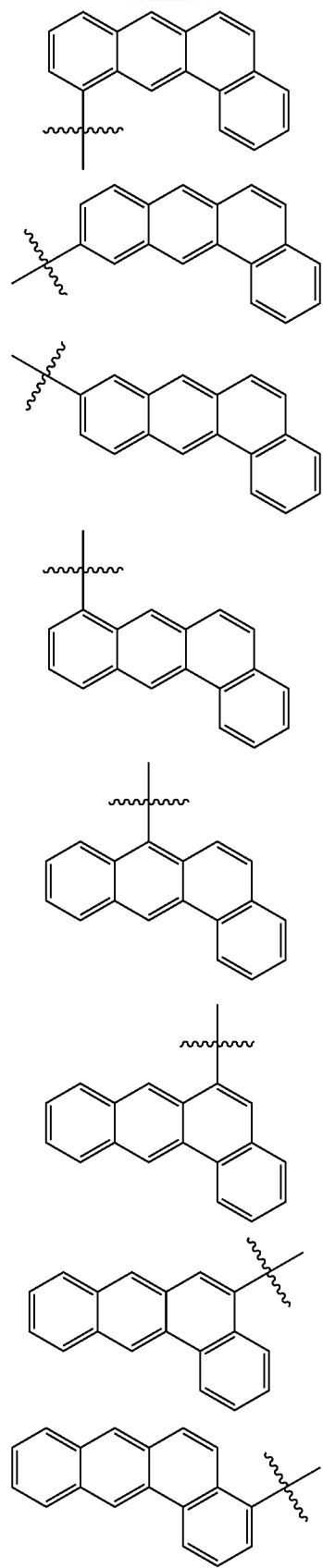
496
-continued
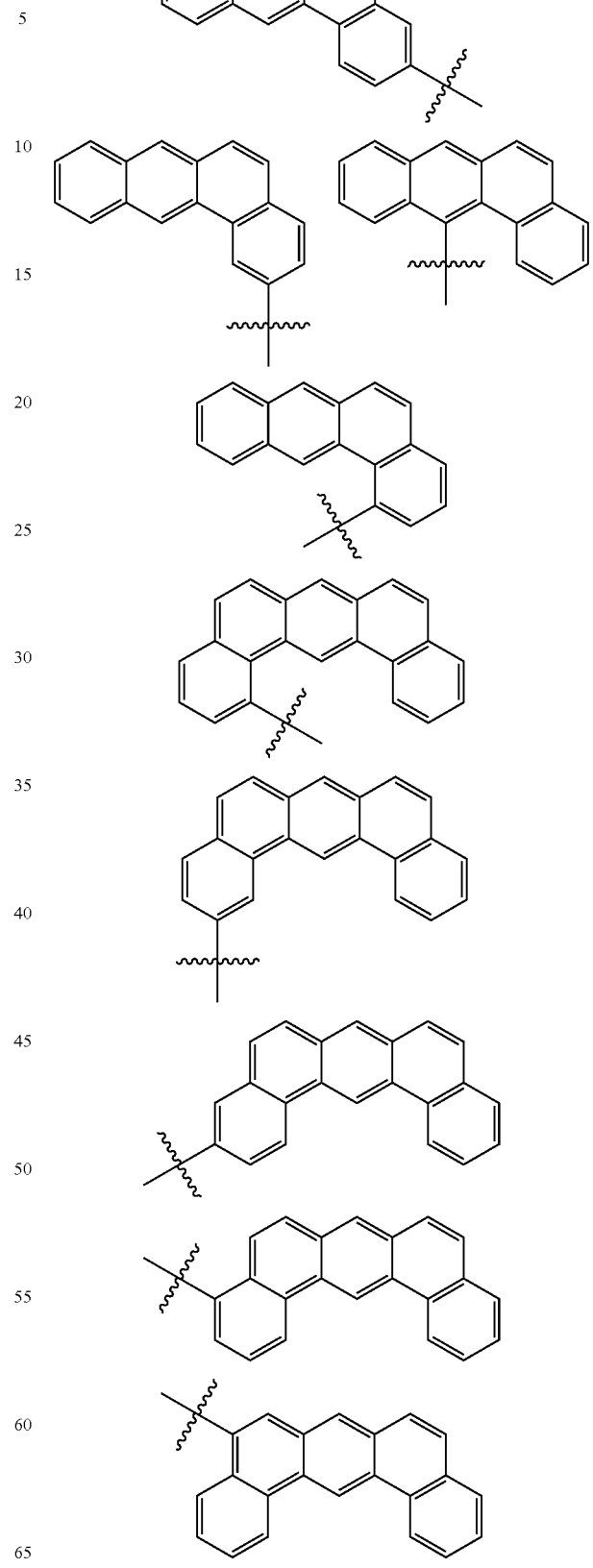

497
-continued
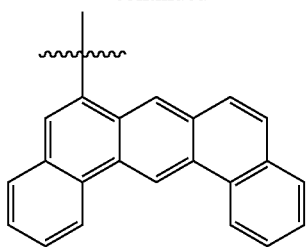
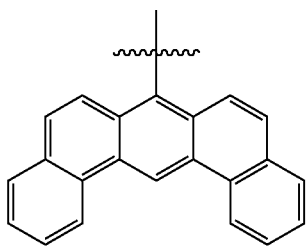
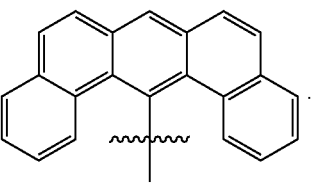
2. The compound of claim 1, wherein L2 is a single bond, or any one selected from the group consisting of:
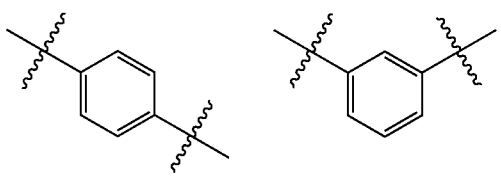
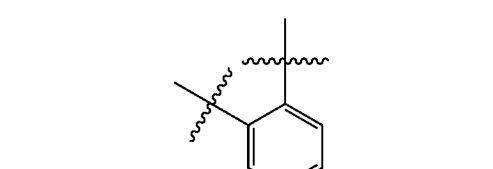
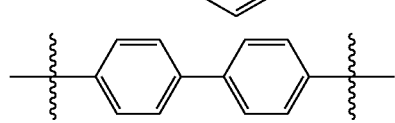
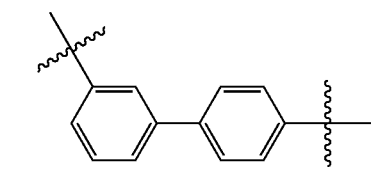
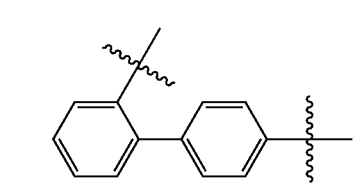
498
-continued
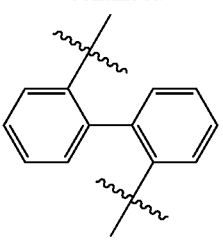
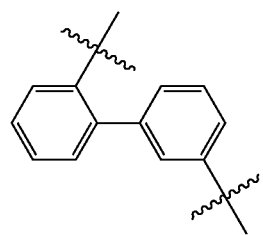
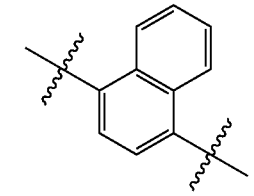
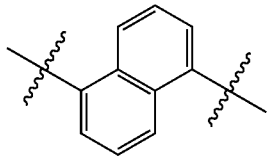
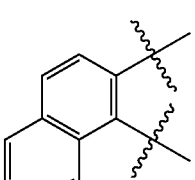
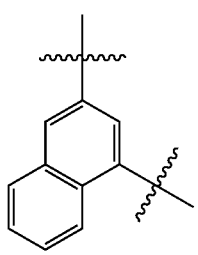
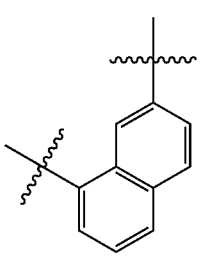

-continued

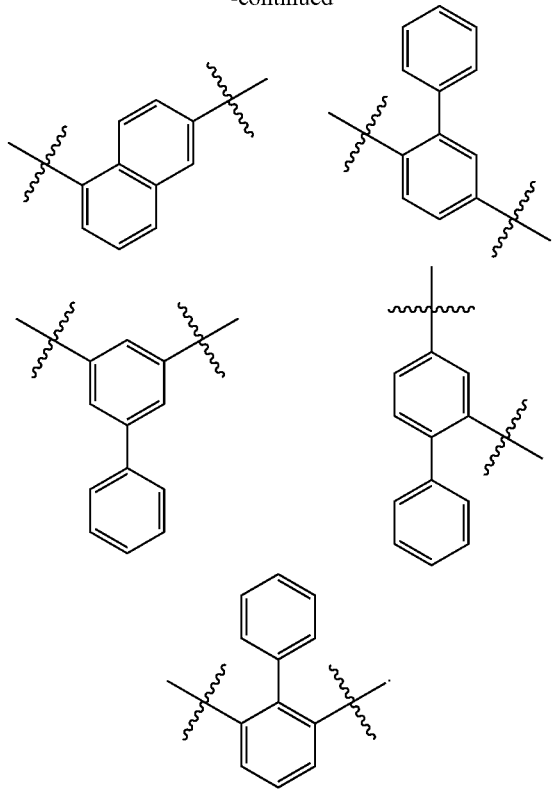

3. The compound of claim 1, wherein
$Y_1$ is N, $Y_2$ is N, and $Y_3$ is N; or
$Y_1$ is N, $Y_2$ is N, and $Y_3$ is CH; or
$Y_1$ is N, $Y_2$ is CH, and $Y_3$ is N; or
$Y_1$ is N, $Y_2$ is CH, and $Y_3$ is CH; or
$Y_1$ is CH, $Y_2$ is CH, and $Y_3$ is N.

4. The compound of claim 1, wherein $Ar_{1a}$ and $Ar_{1b}$ are each independently any one selected from the group consisting of:

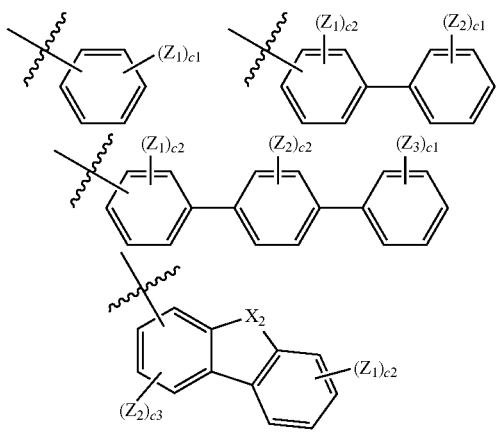

wherein:
$X_2$ is O, S, or $CZ_5Z_6$;
$Z_1$ to $Z_3$, $Z_5$, and $Z_6$ are each independently hydrogen, deuterium, halogen, cyano, nitro, amino, a substituted or unsubstituted $C_{1-20}$ alkyl, a substituted or unsubstituted $C_{1-20}$ haloalkyl, a substituted or unsubstituted $C_{6-20}$ aryl, or a substituted or unsubstituted $C_{1-20}$ heteroaryl containing one or more heteroatoms selected from the group consisting of N, O and S;
c1 is an integer of 0 to 5;
c2 is an integer of 0 to 4; and
c3 is an integer of 0 to 3.

5. The compound of claim 4, wherein
$Ar_{1a}$ and $Ar_{1b}$ are each independently any one selected from the group consisting of:

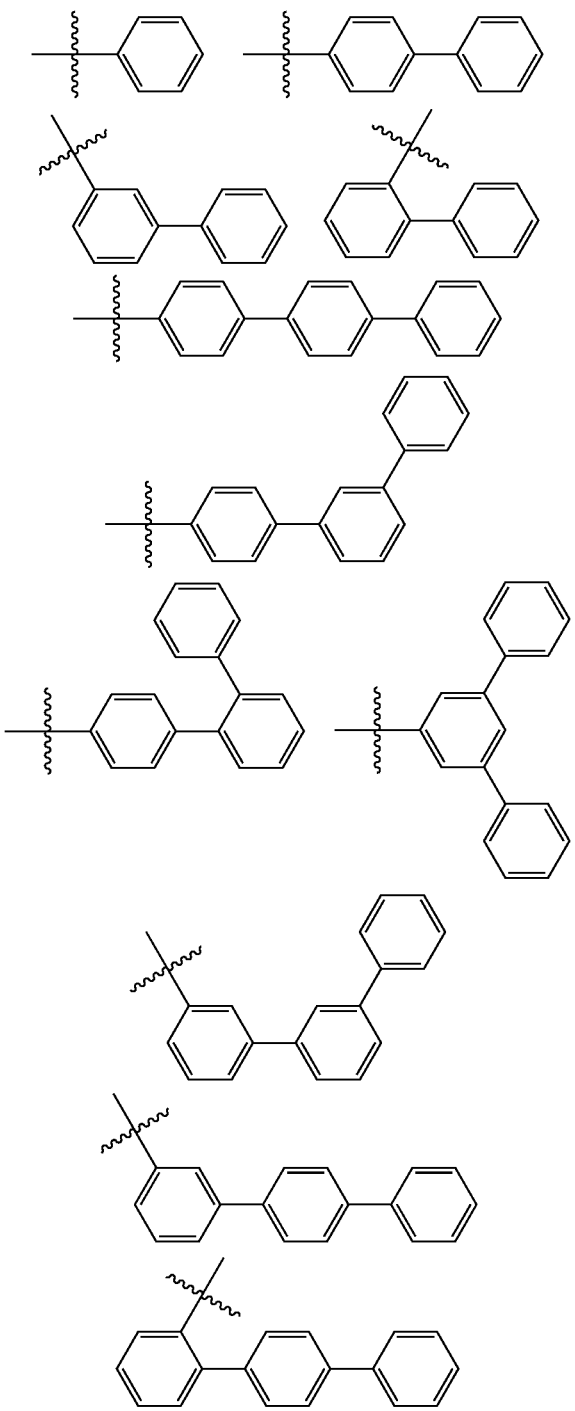

501
-continued
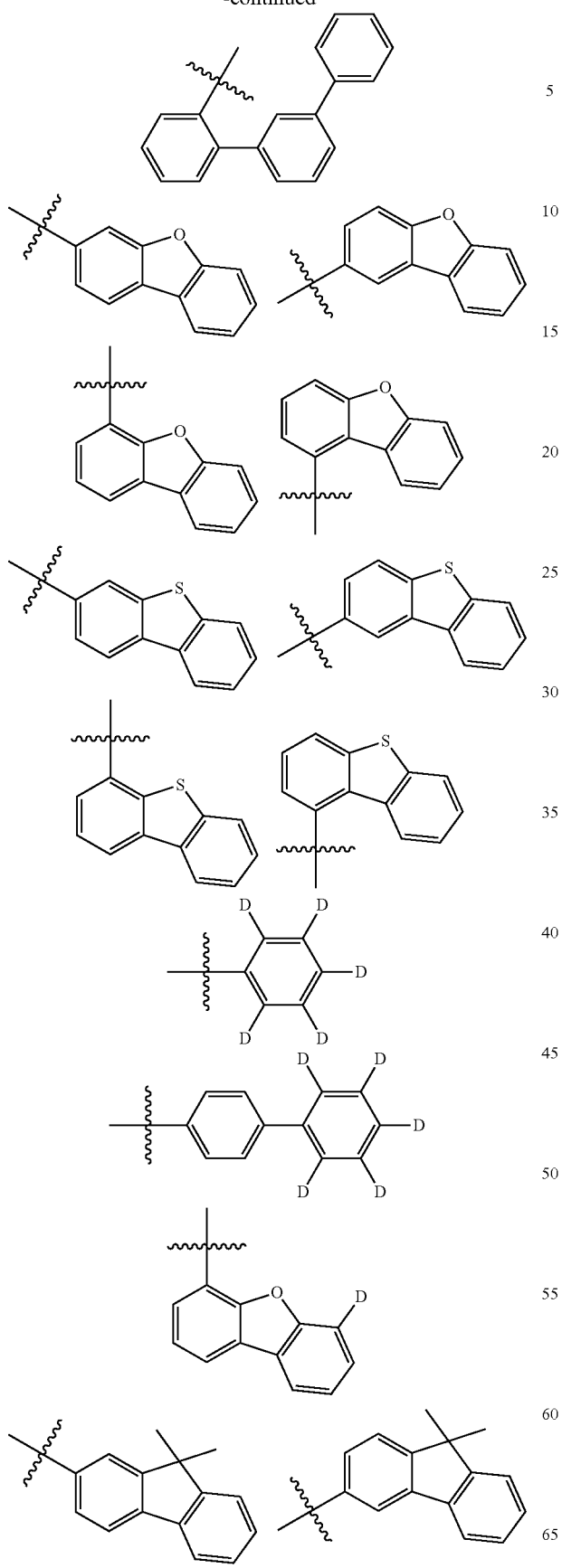
502
-continued
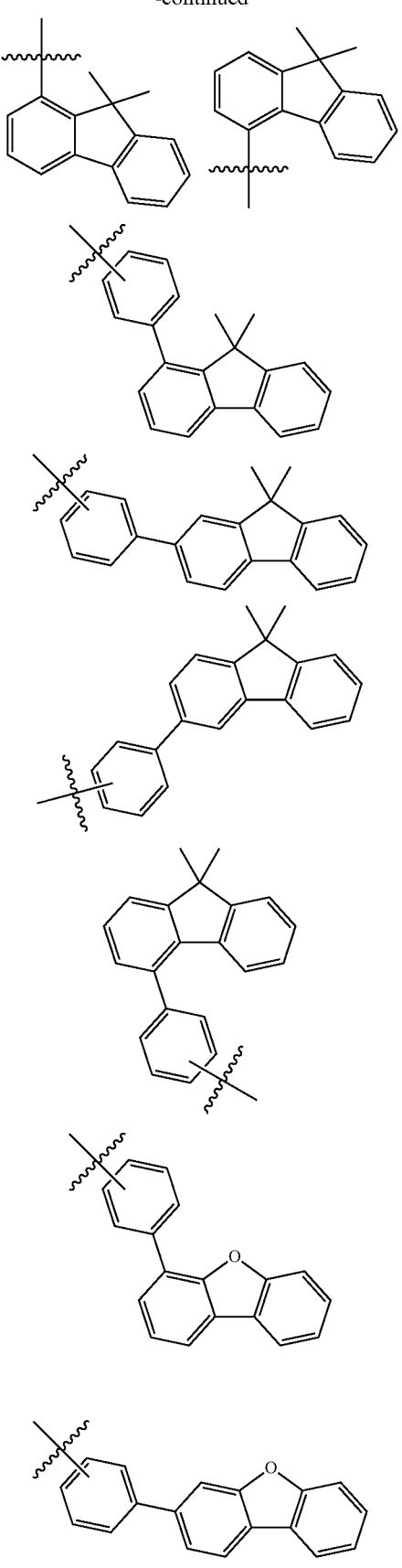

-continued
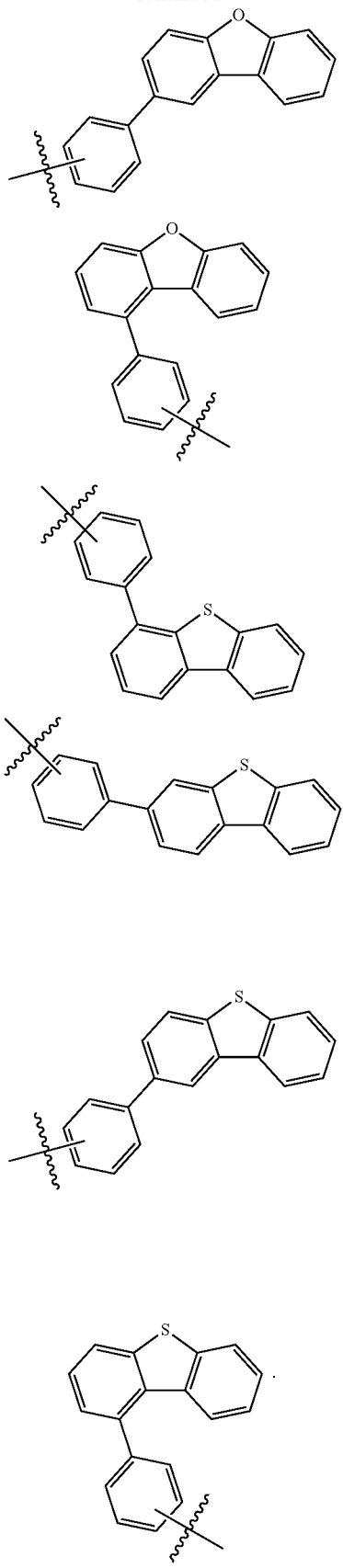
6. The compound of claim 1, wherein the compound is any one compound selected from the group consisting of:
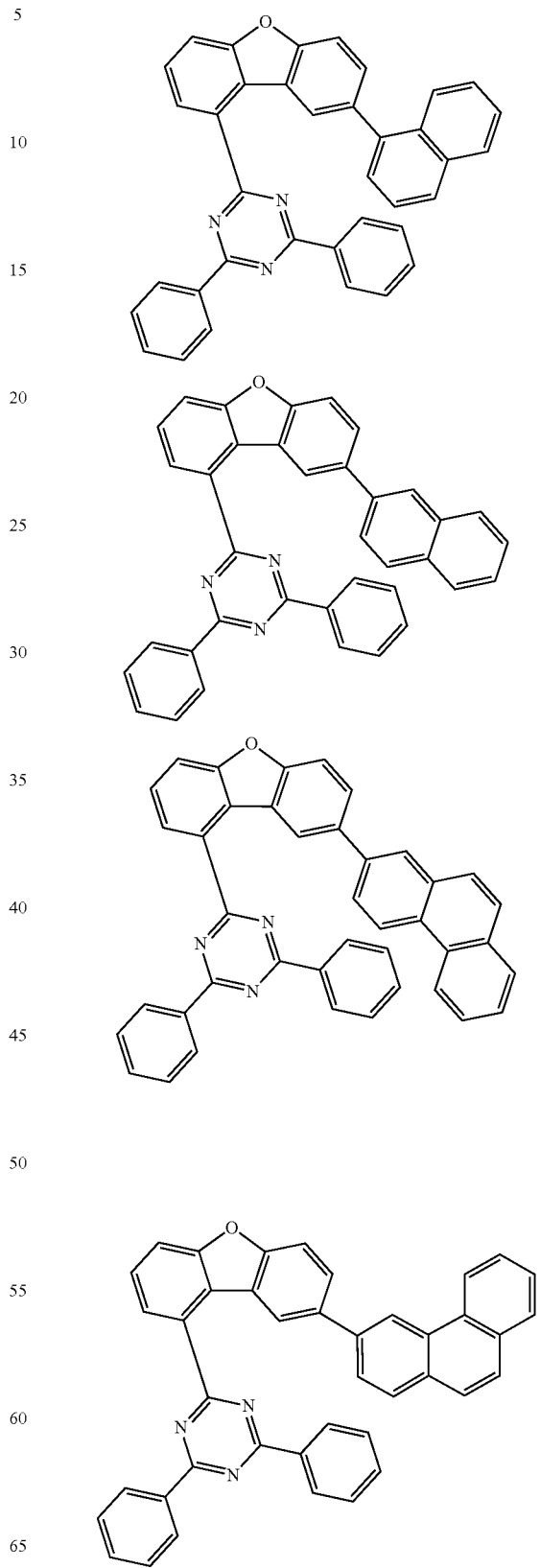

505
-continued
506
-continued
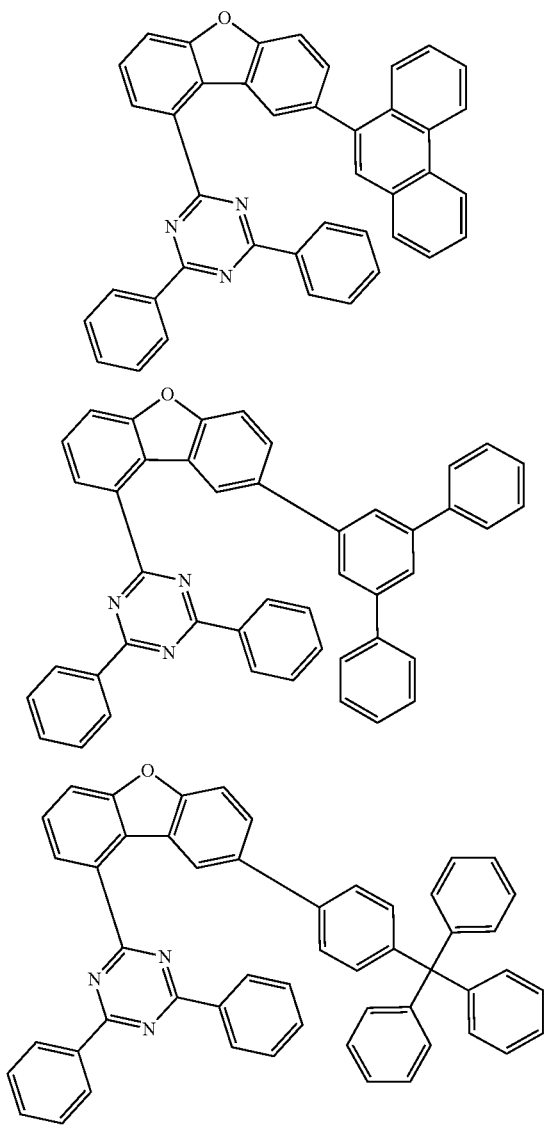
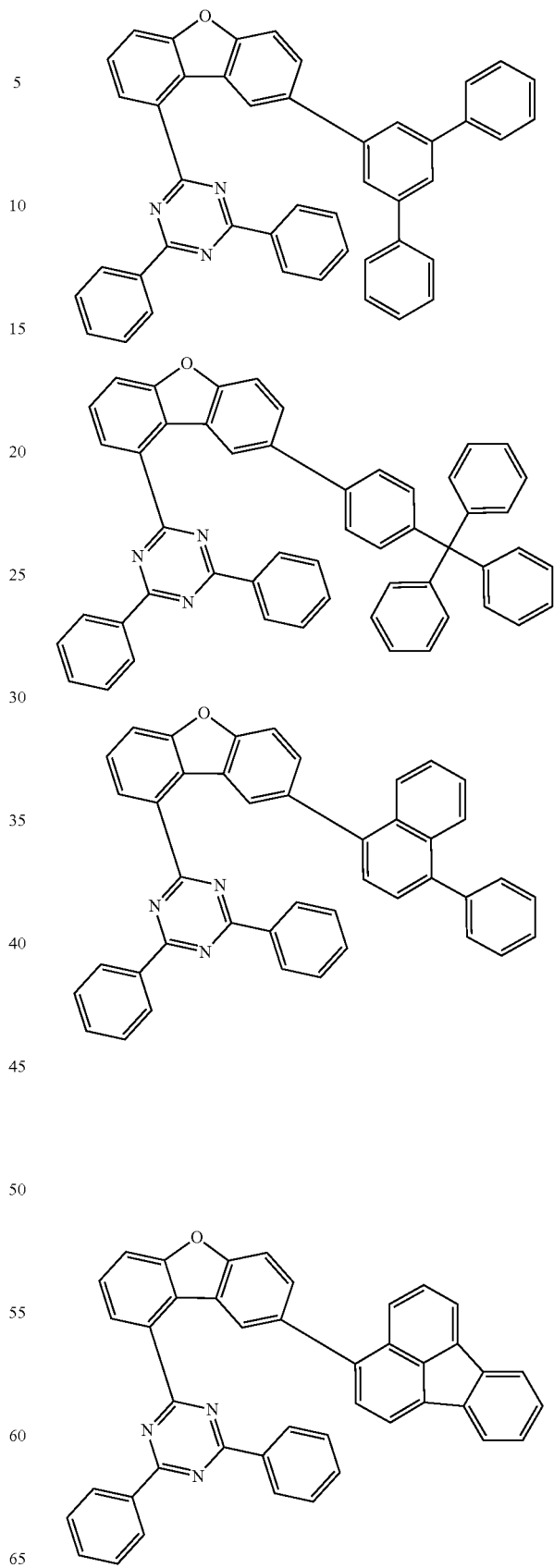

507
-continued
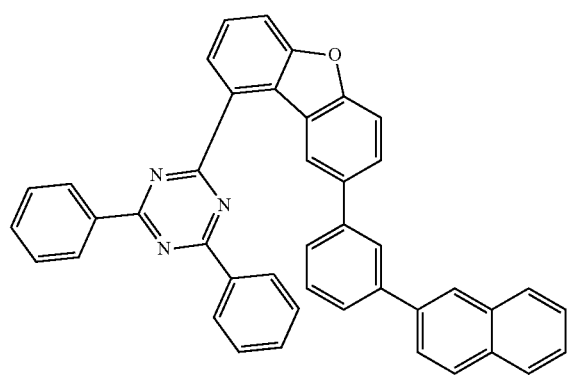
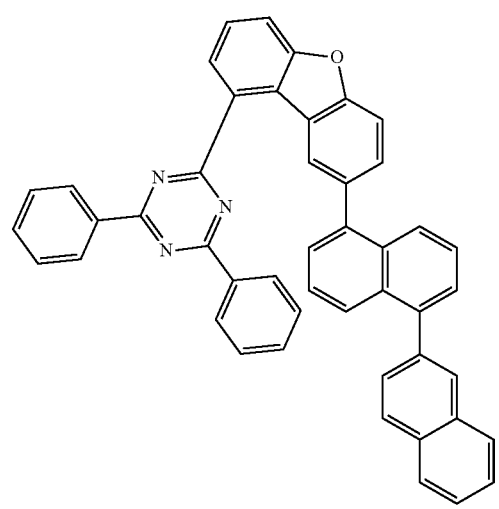
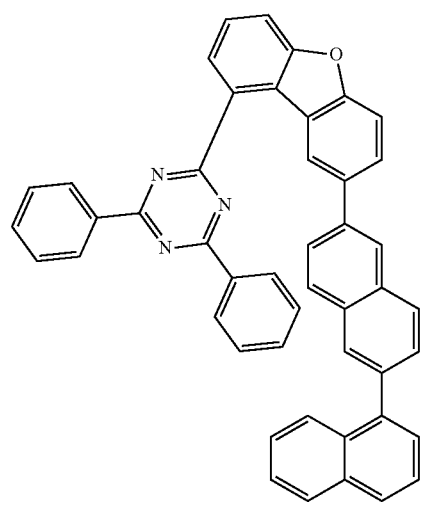
508
-continued
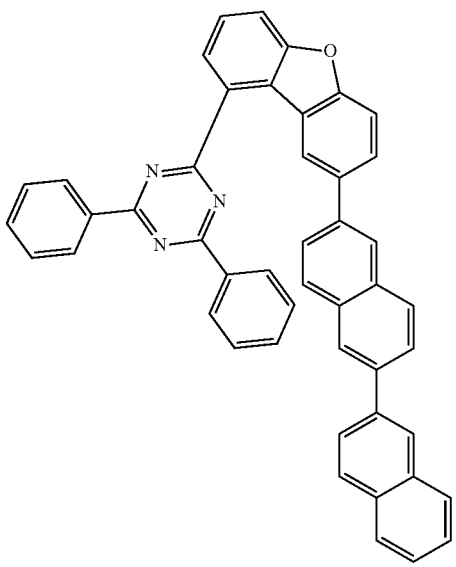
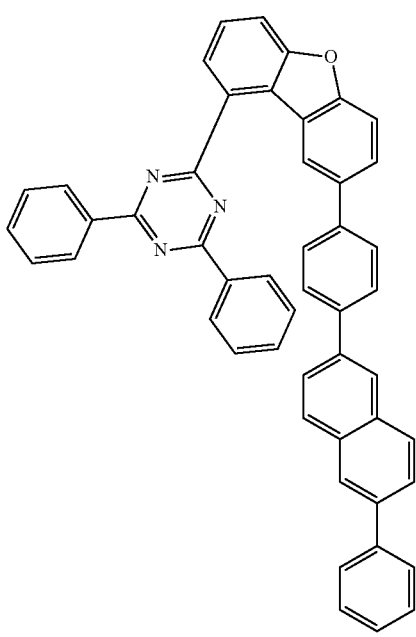

509
-continued
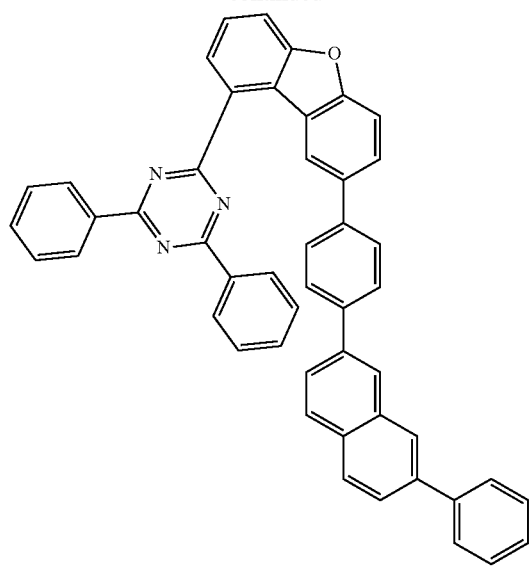
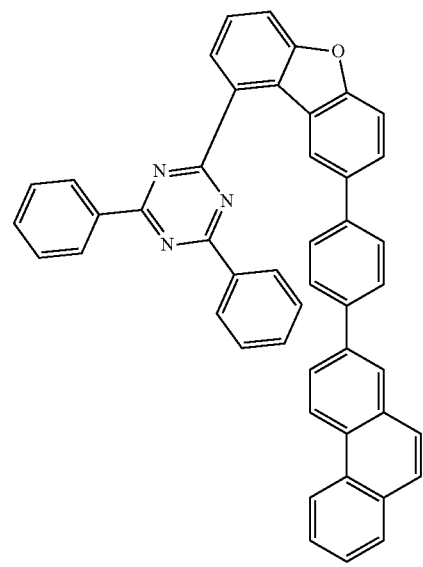
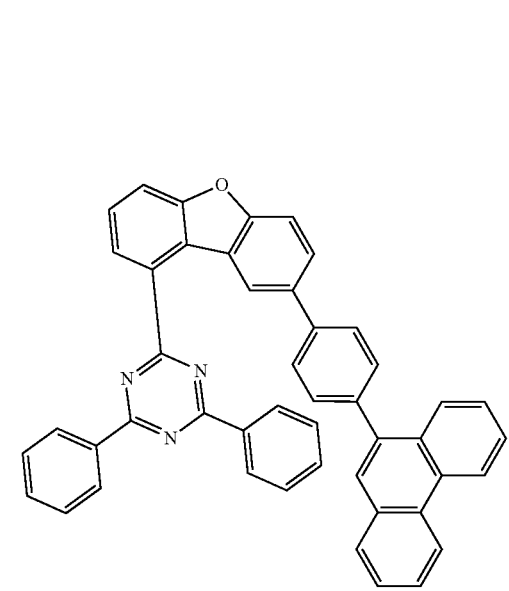
510
-continued
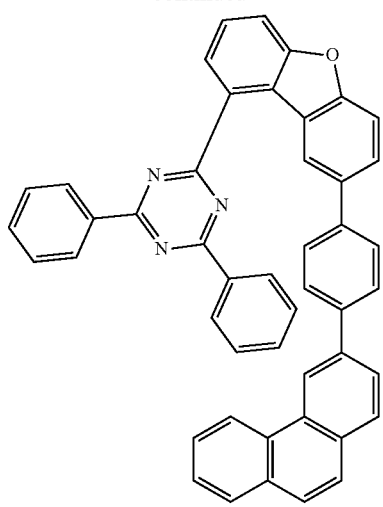
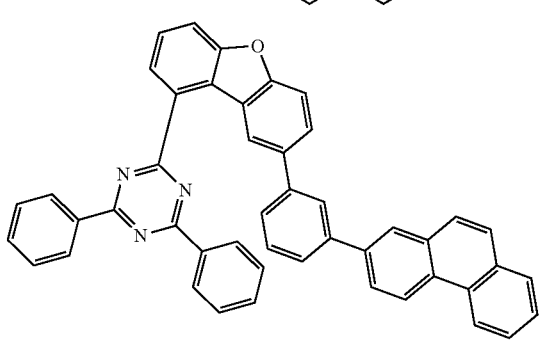
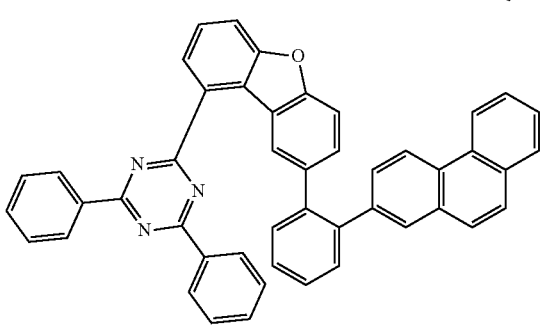
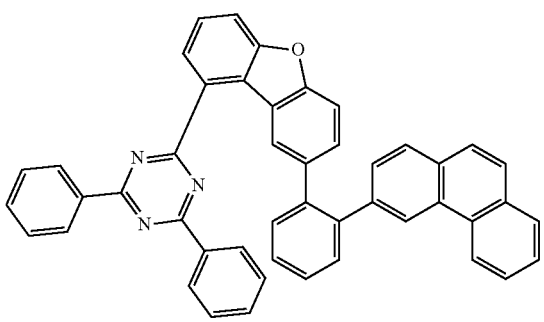

511
-continued
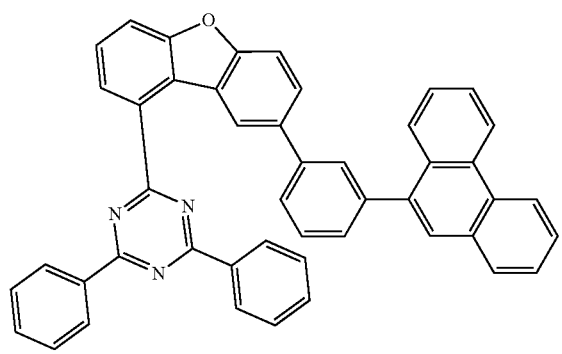
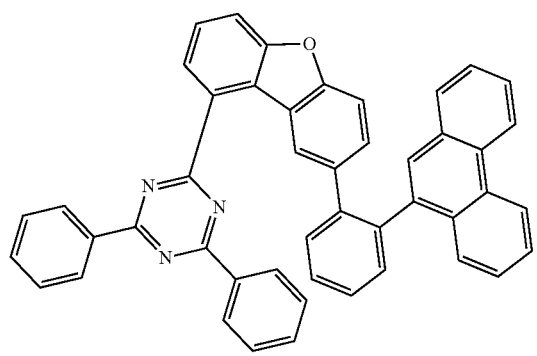
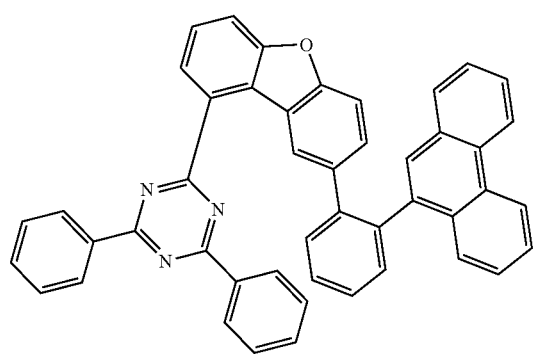
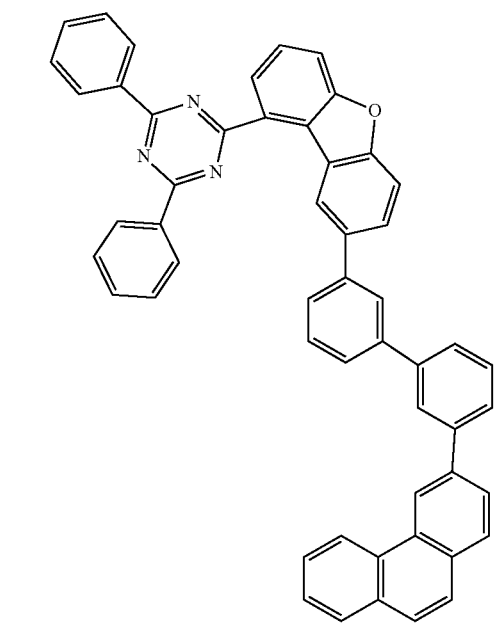
512
-continued
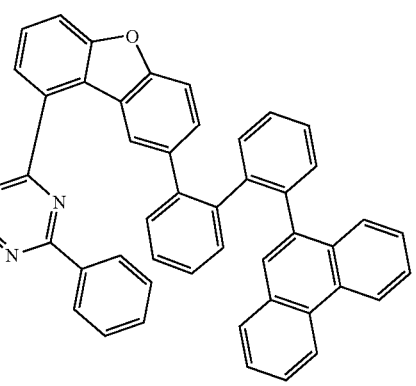
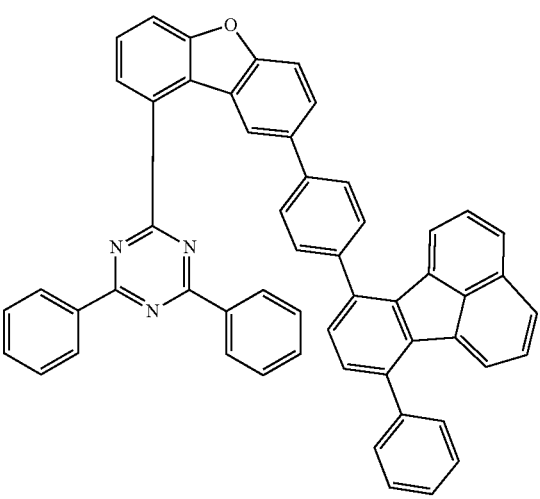
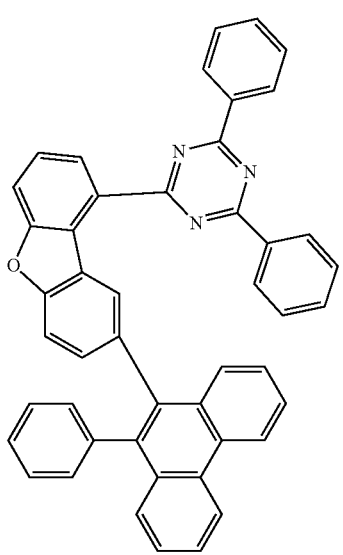

513
-continued
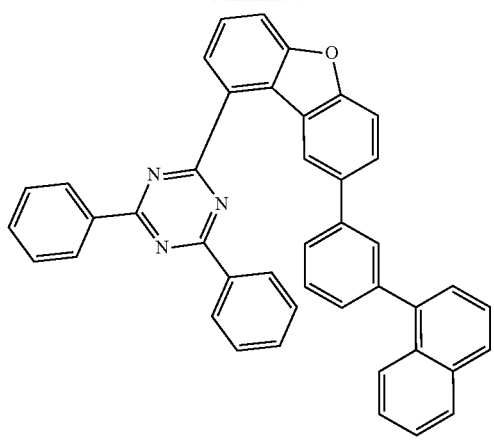
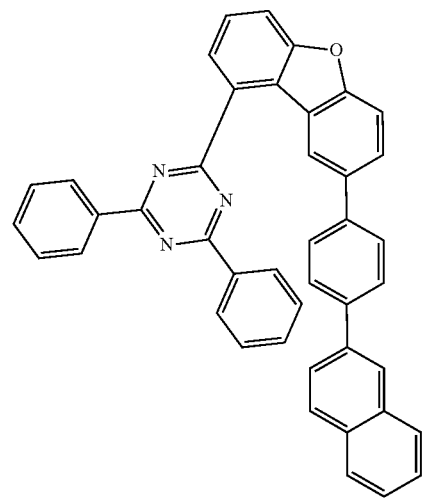
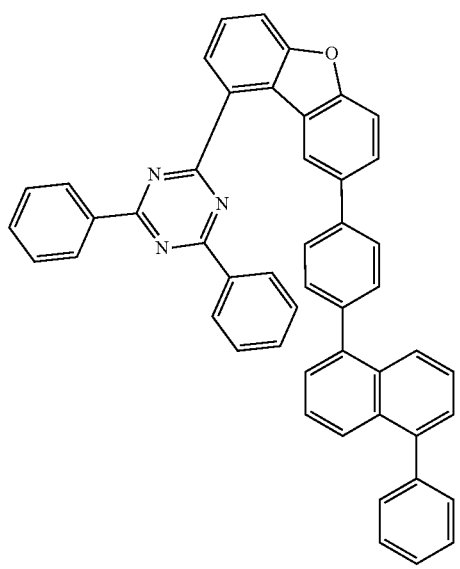
514
-continued
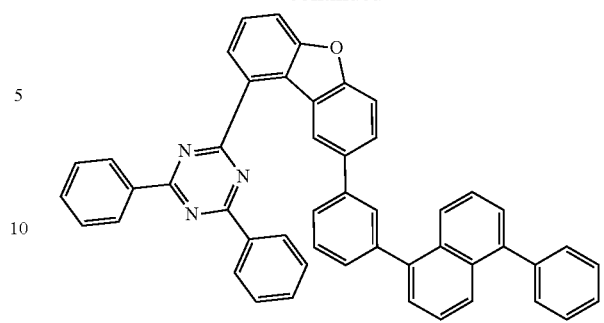
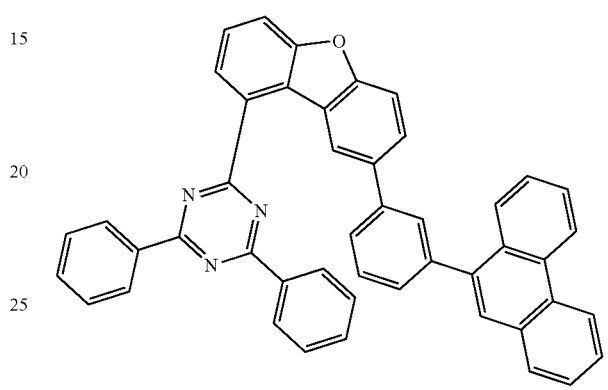
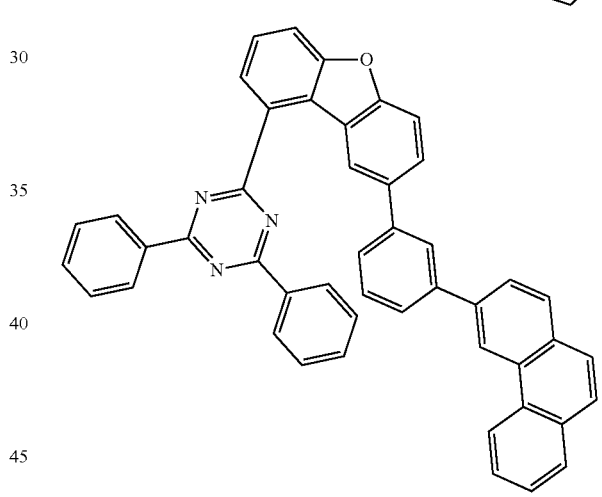
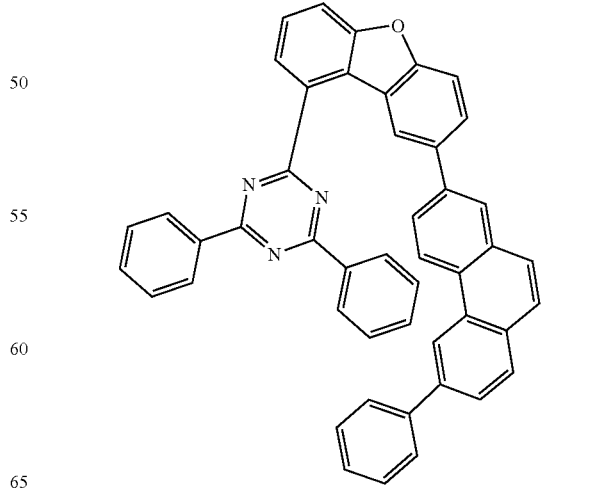

515
-continued
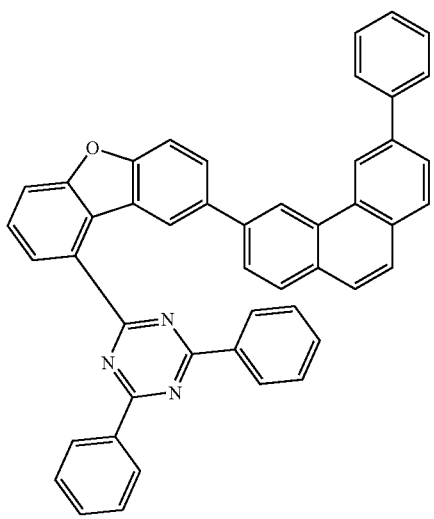
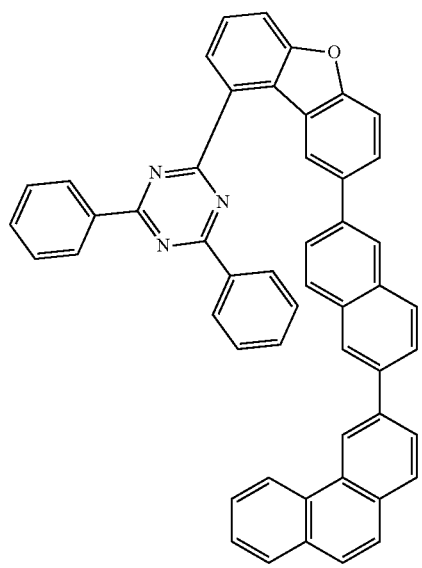
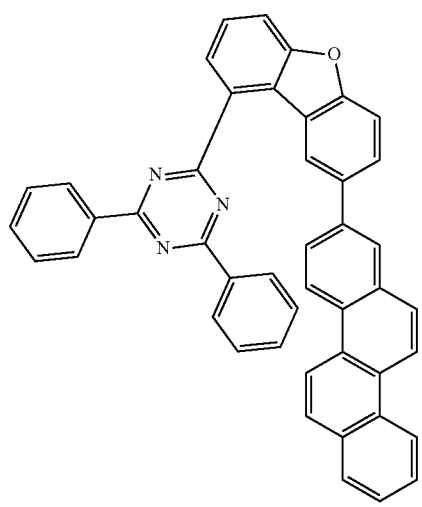
516
-continued
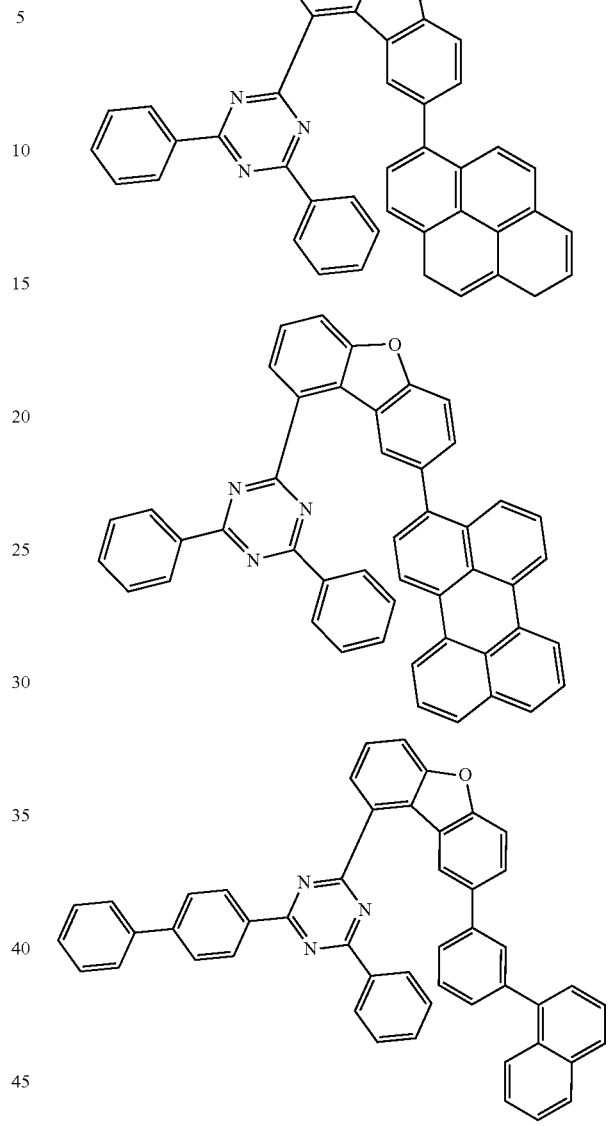
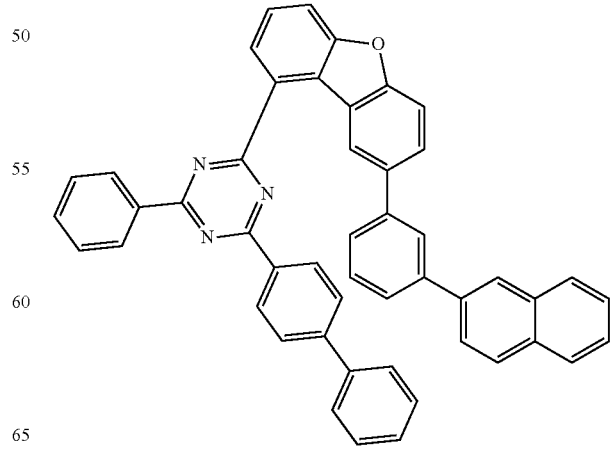

517
-continued
518
-continued
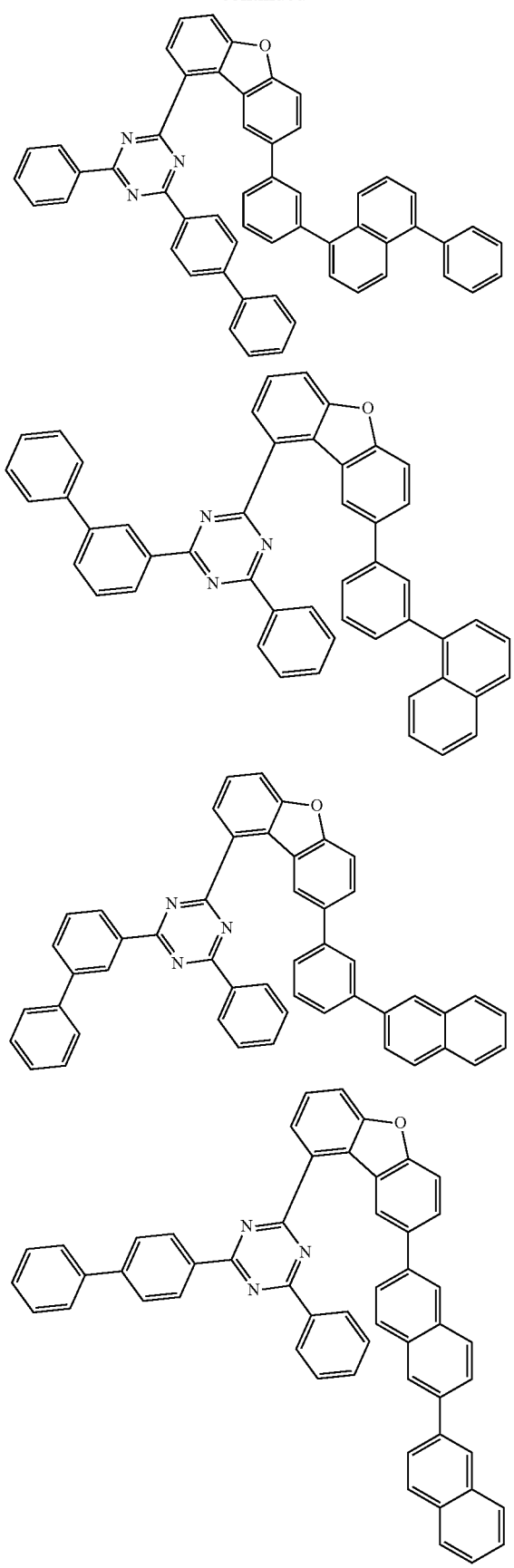
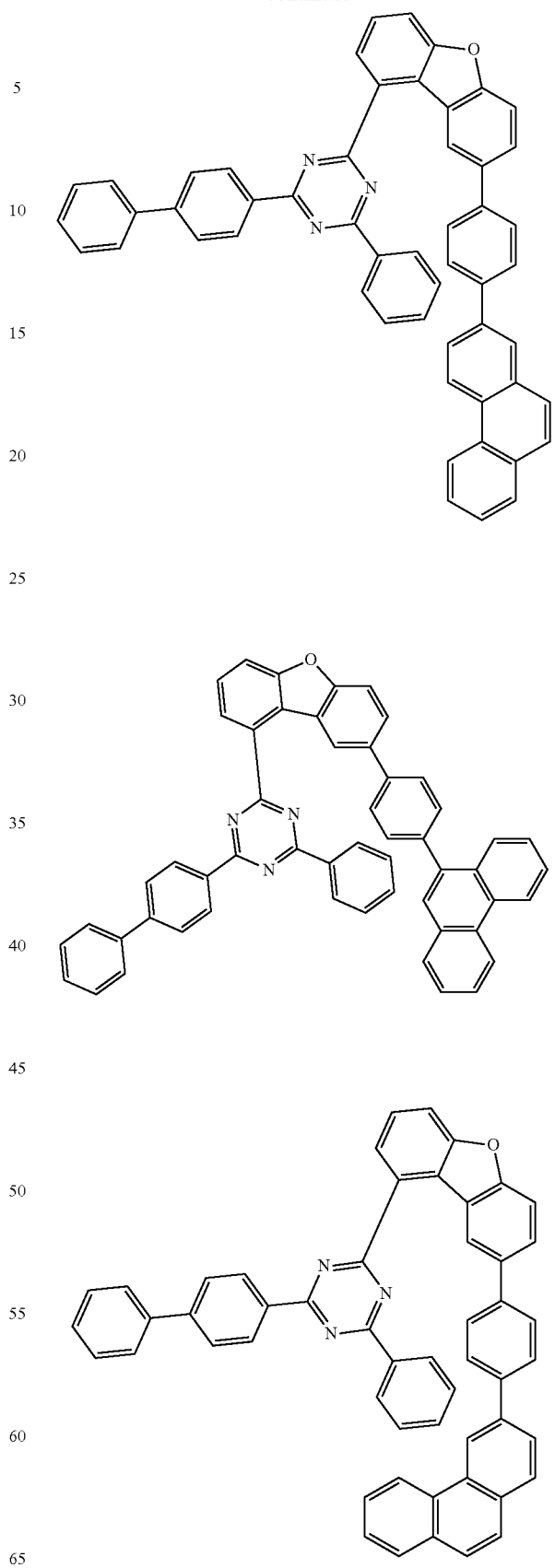

519
-continued
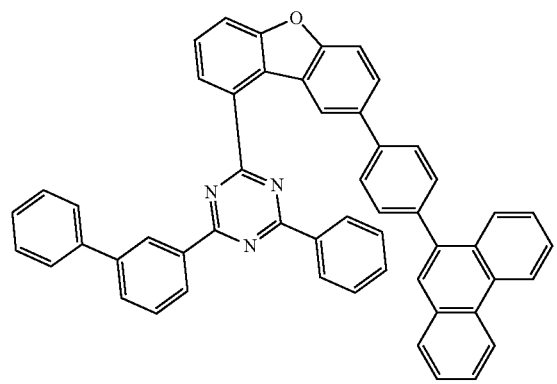
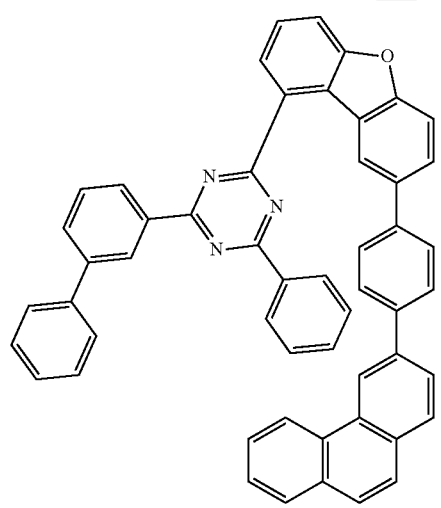
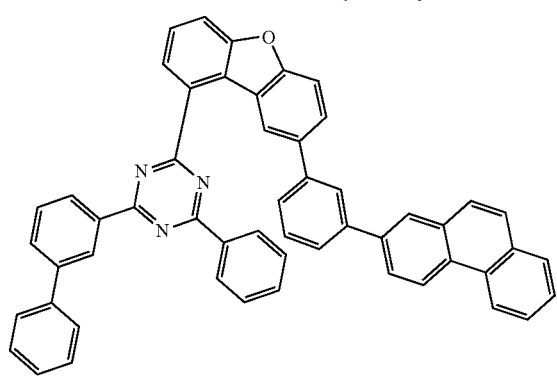
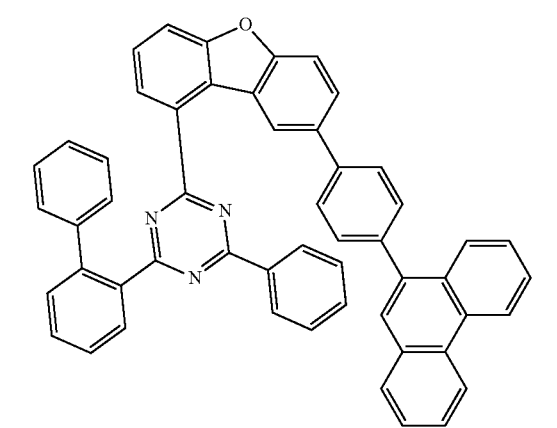
520
-continued
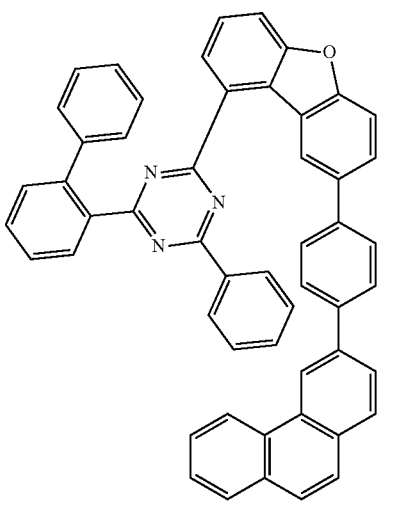
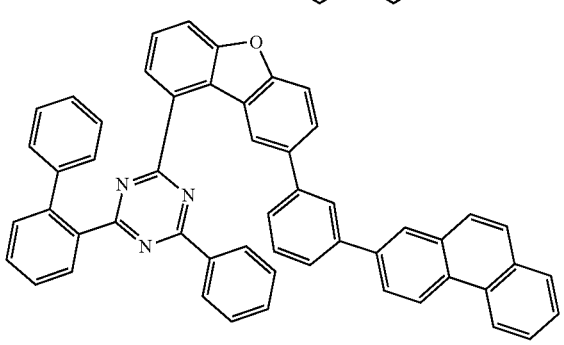
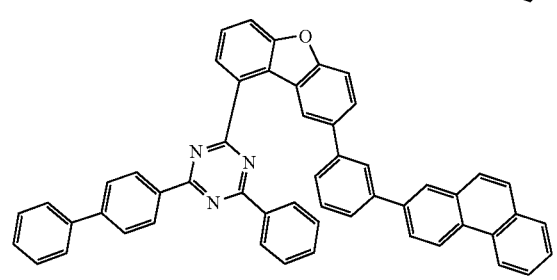
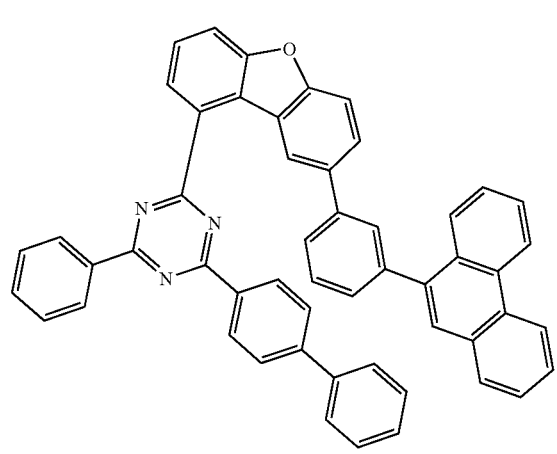

521
-continued
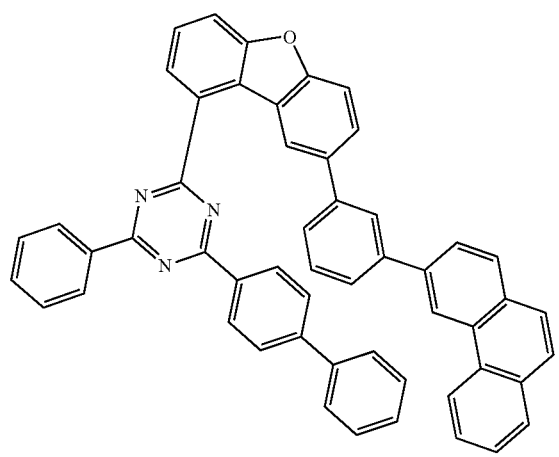
522
-continued
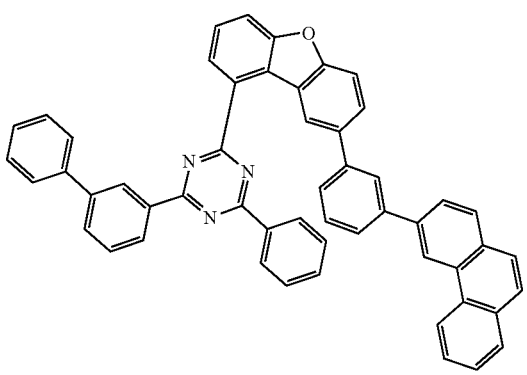
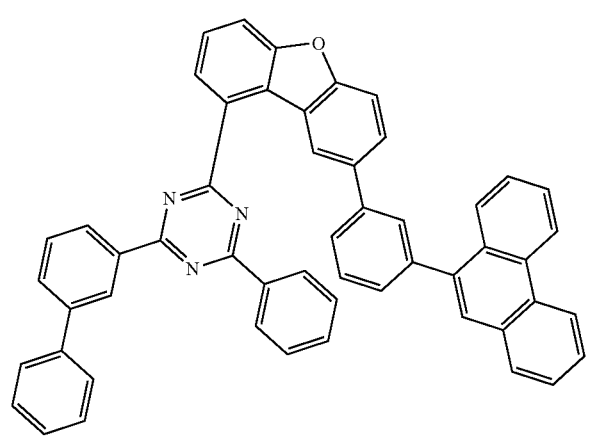
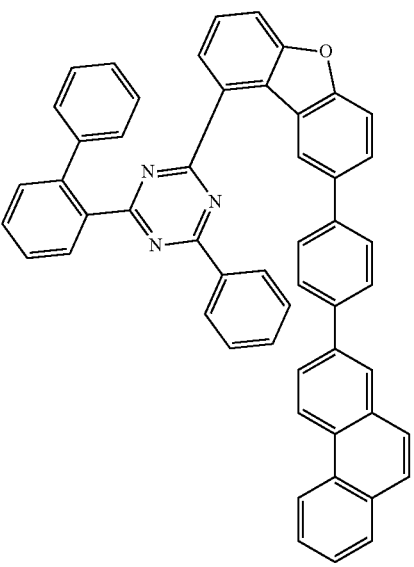
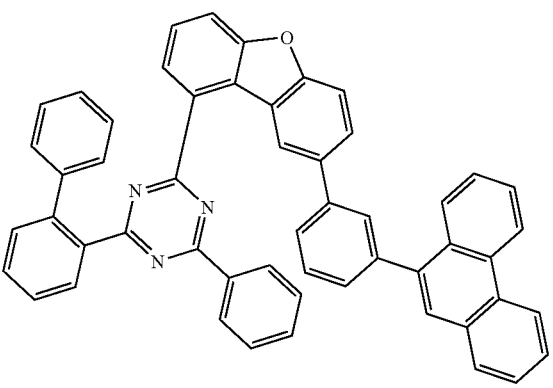

523
-continued
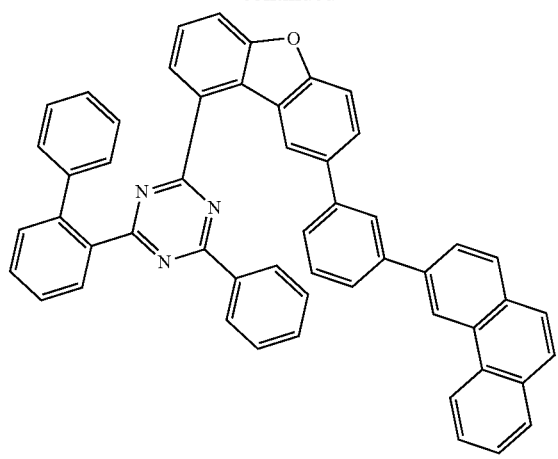
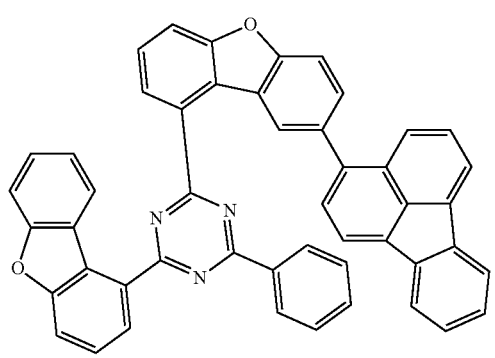
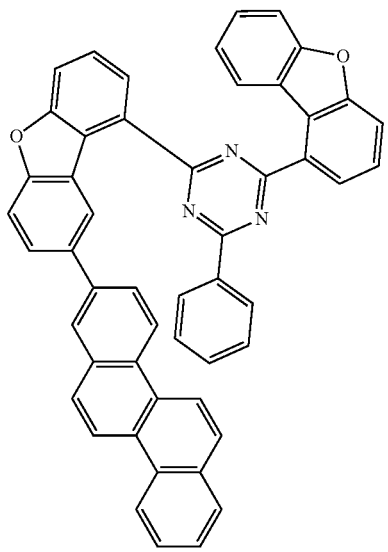
524
-continued
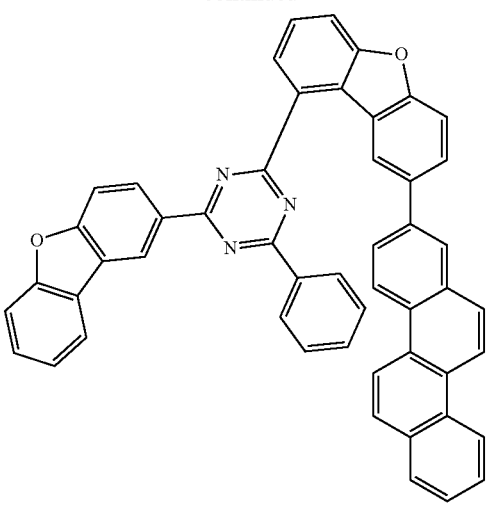
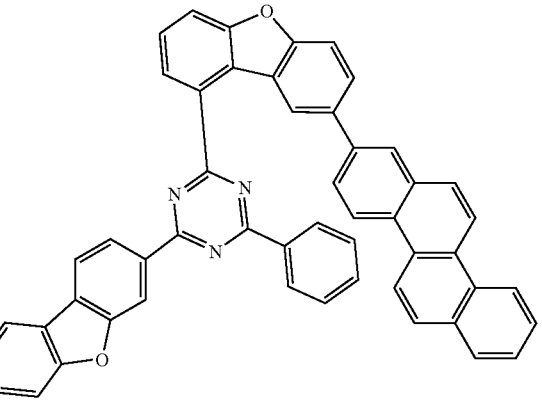
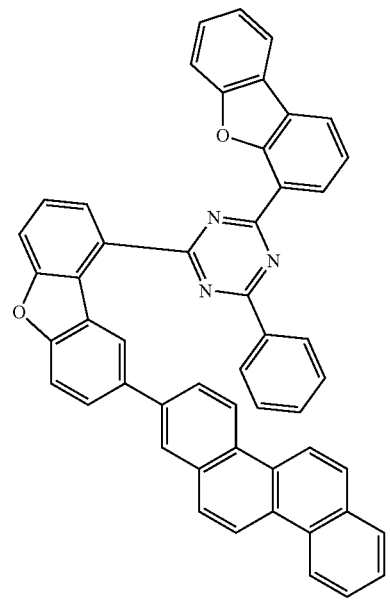

525
-continued
526
-continued
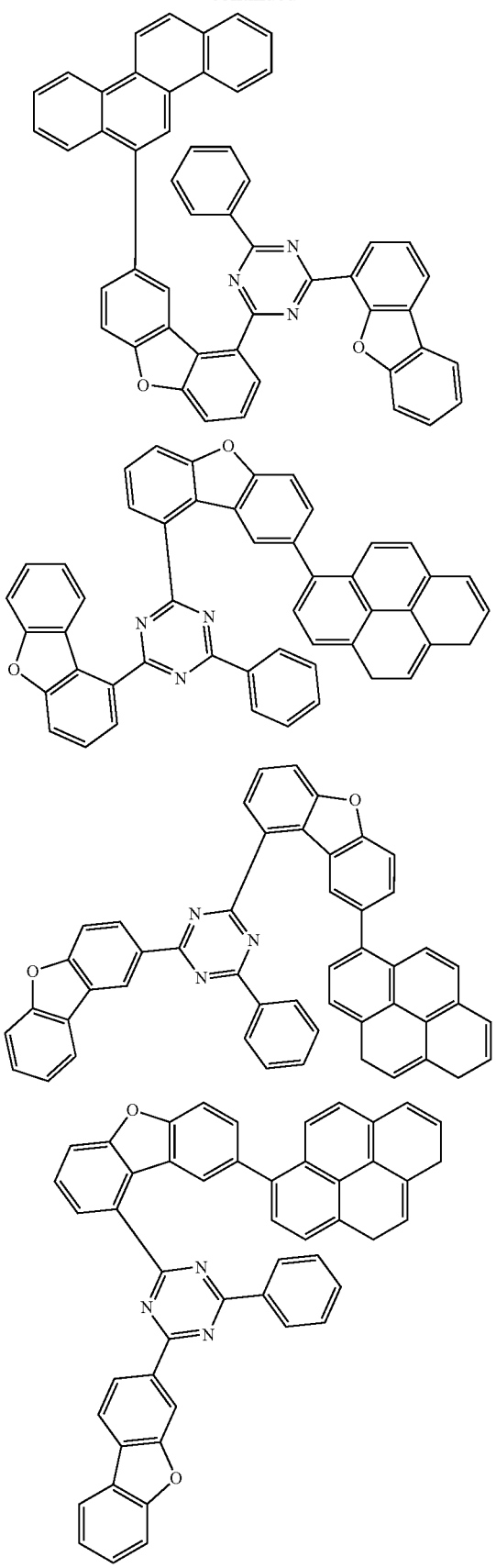
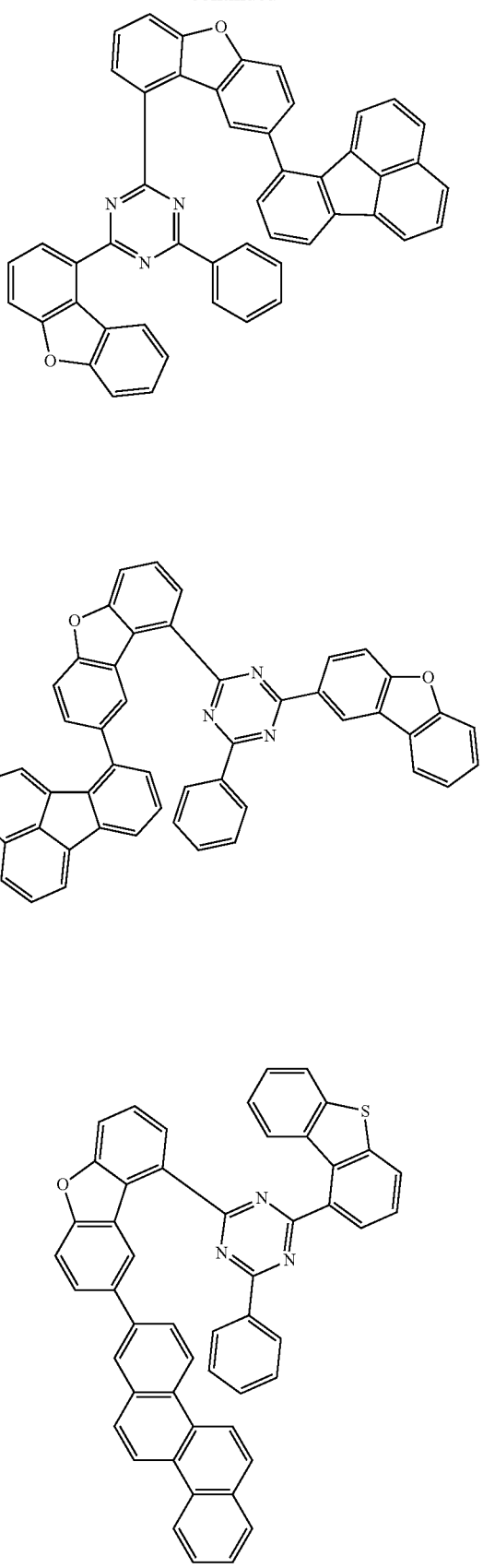

527
-continued
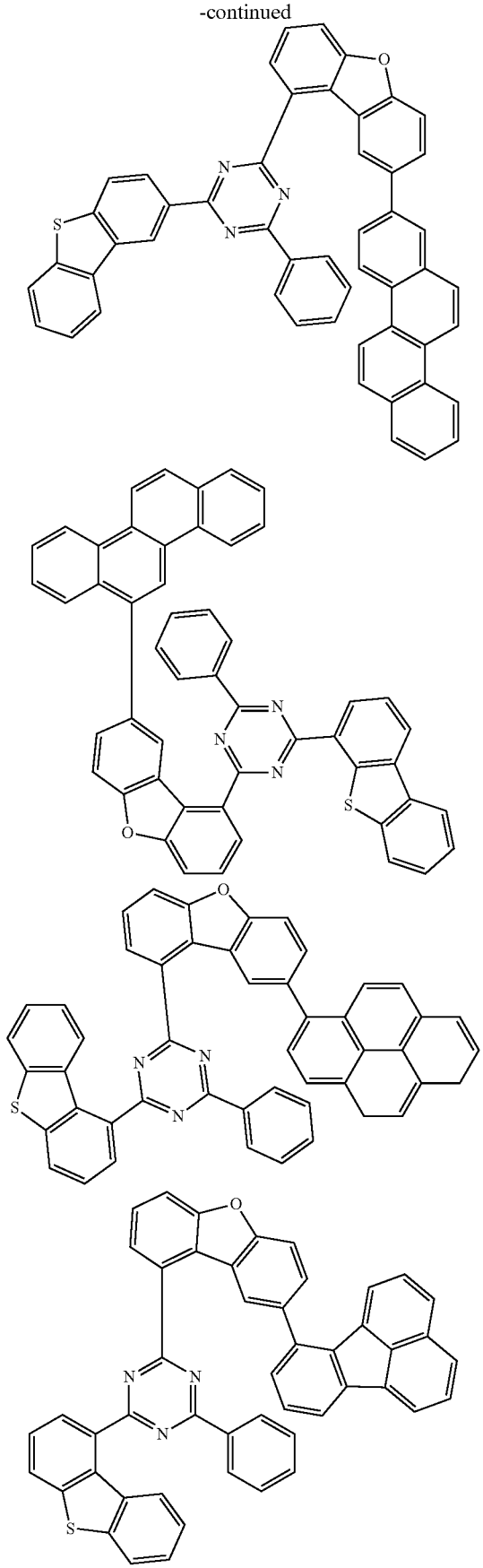
528
-continued
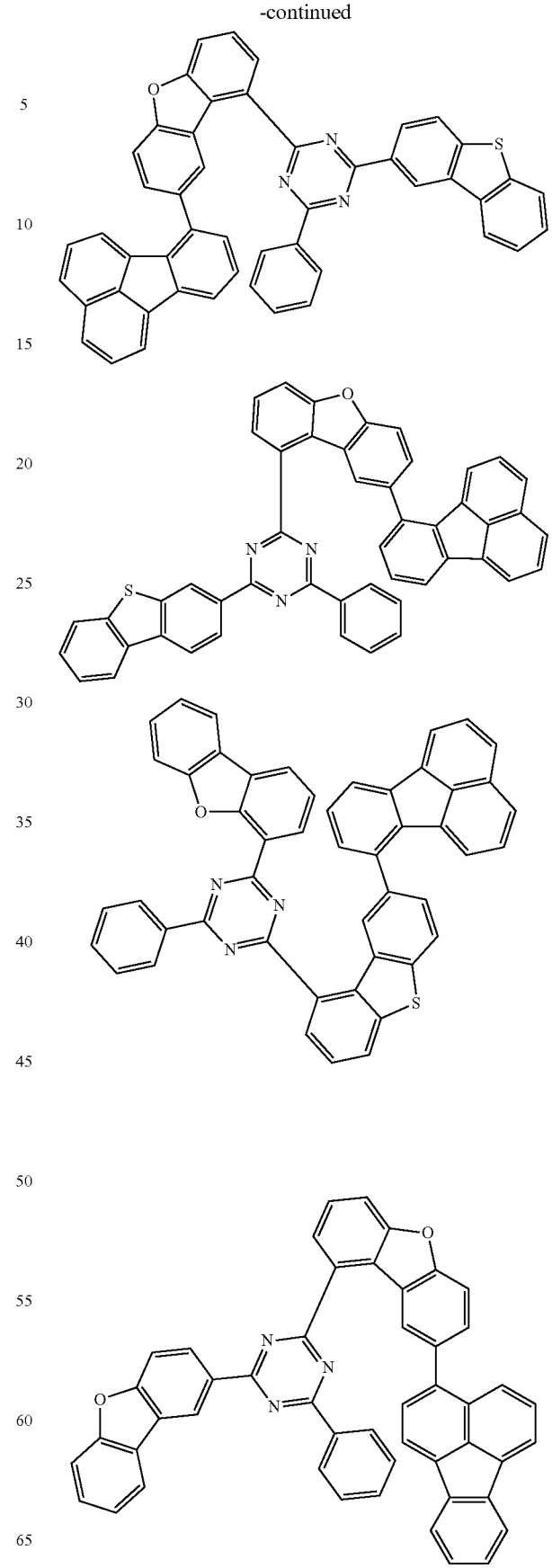

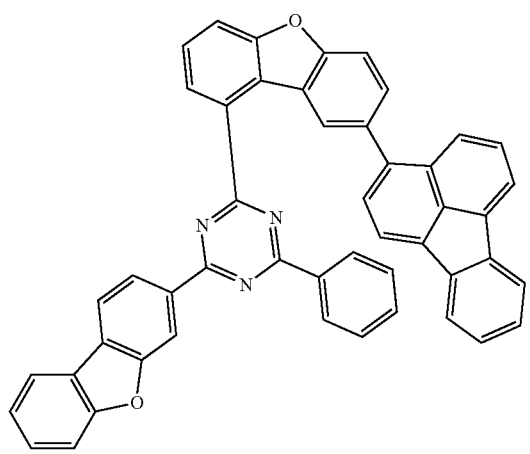
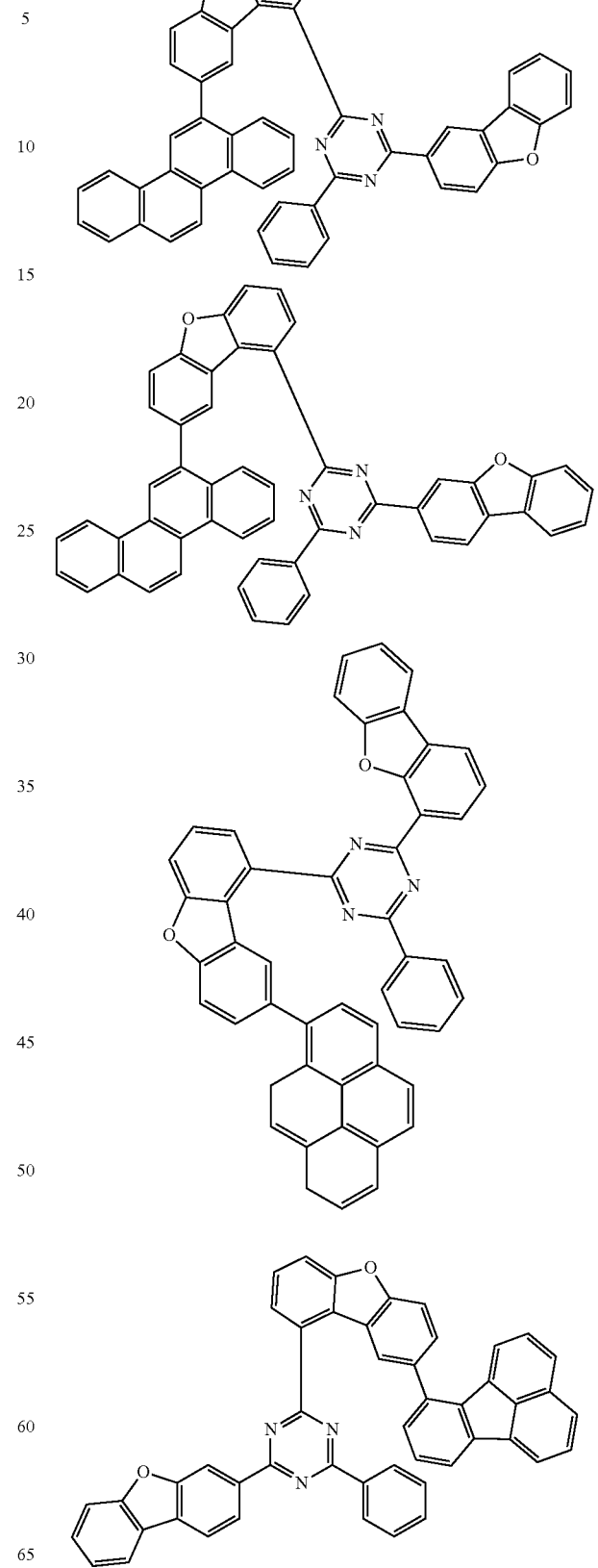

531
-continued
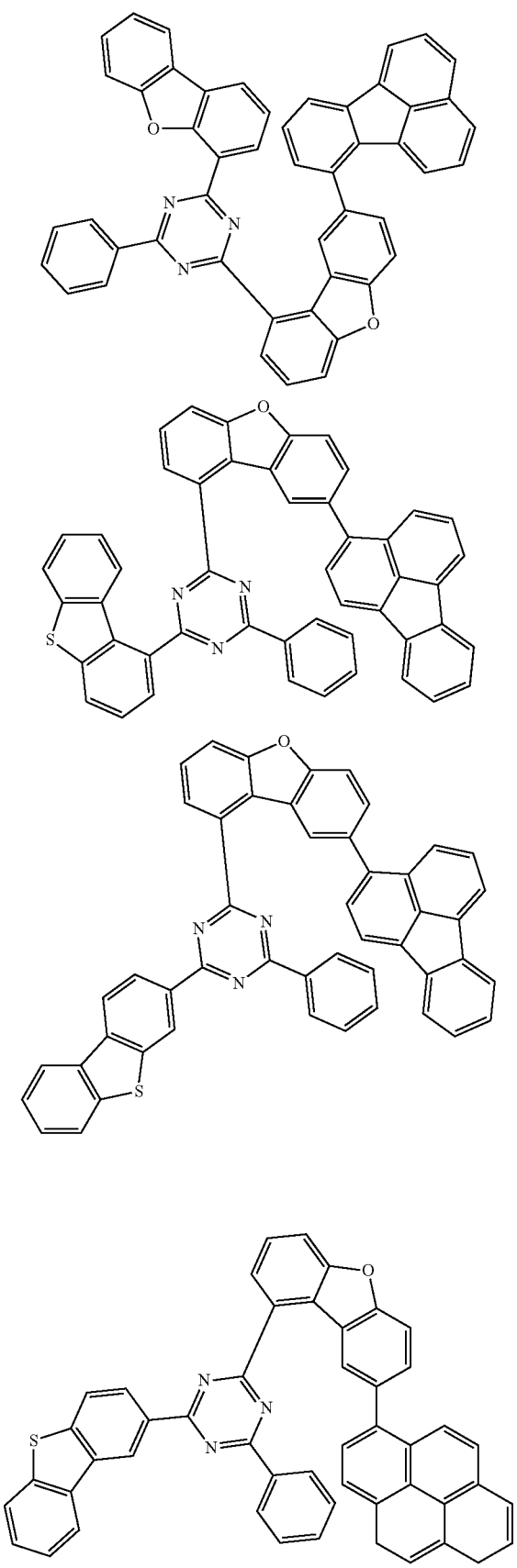
532
-continued
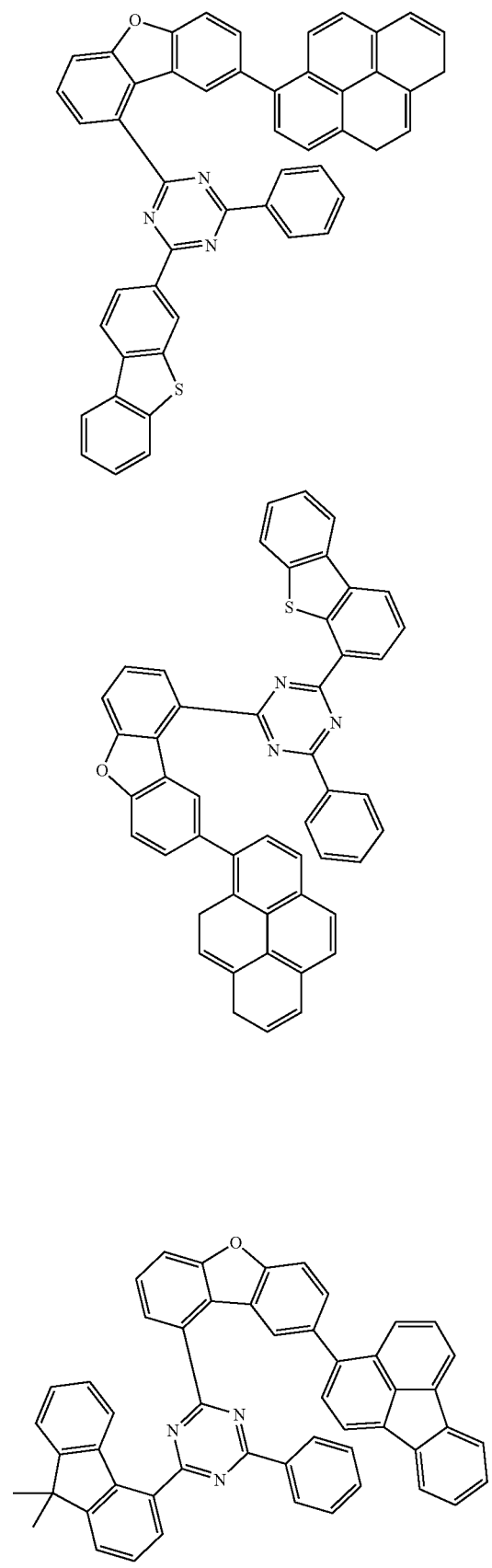

533
-continued
534
-continued
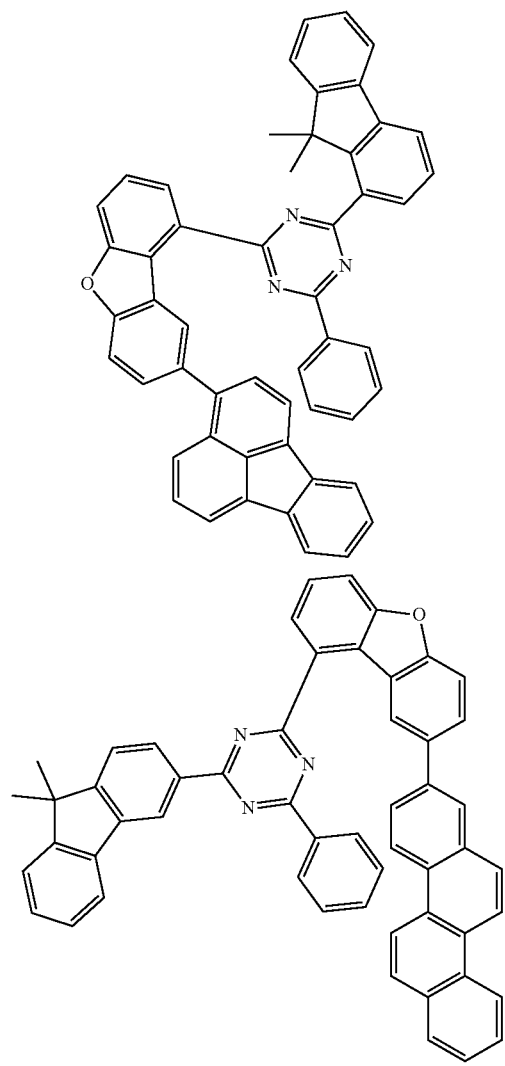
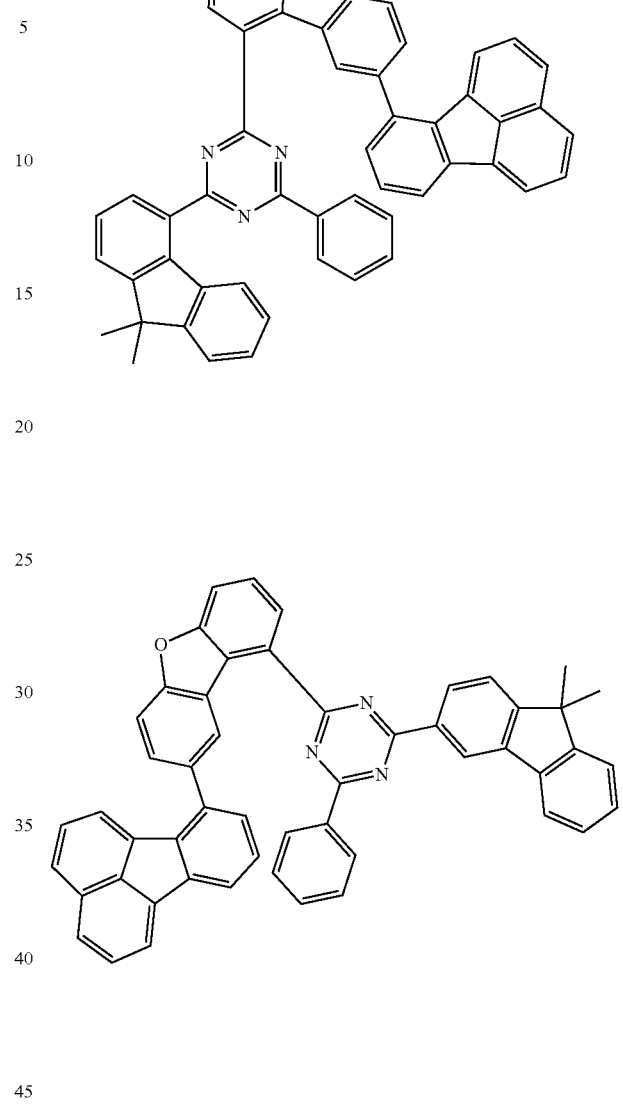
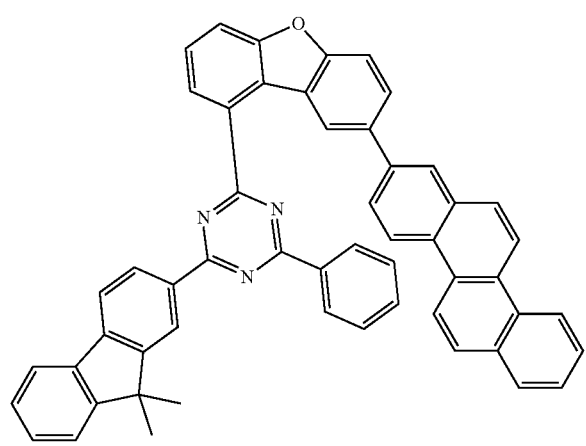
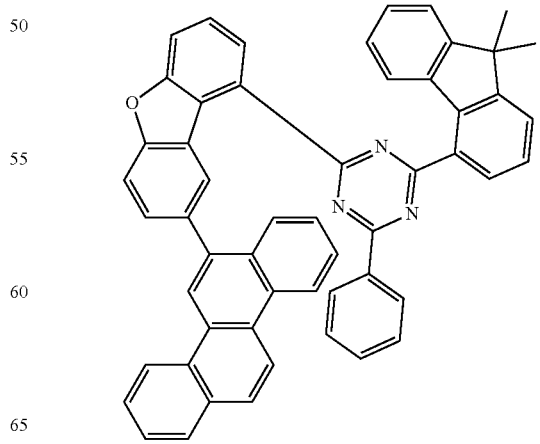

535
-continued
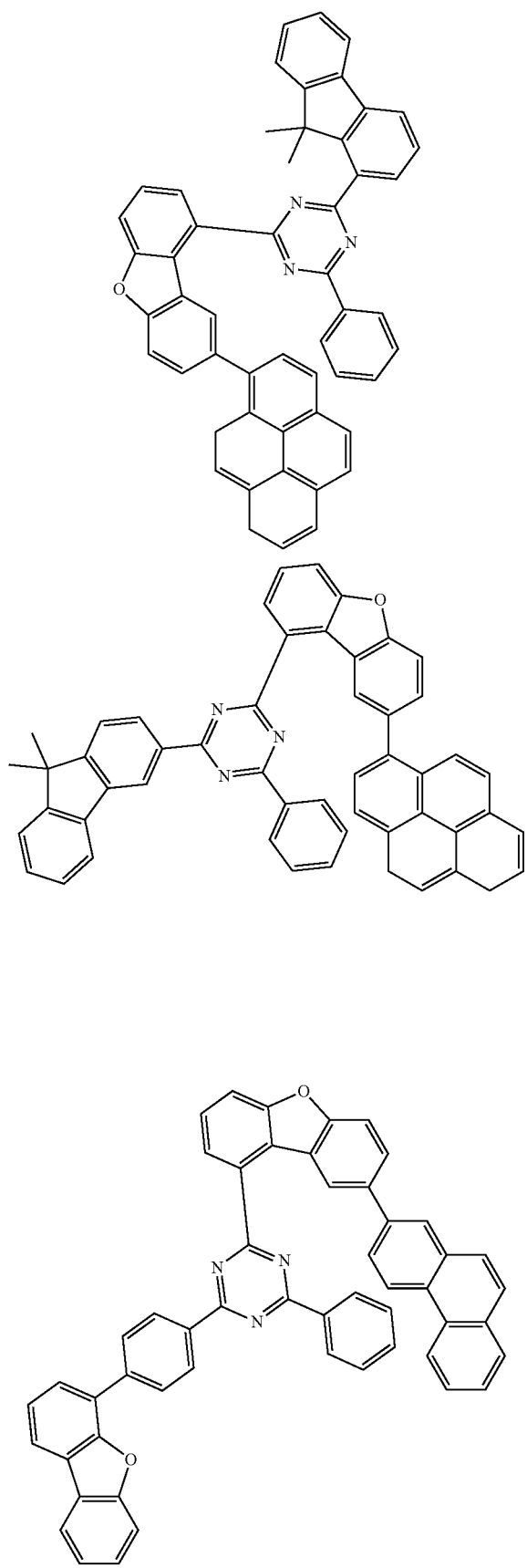
536
-continued
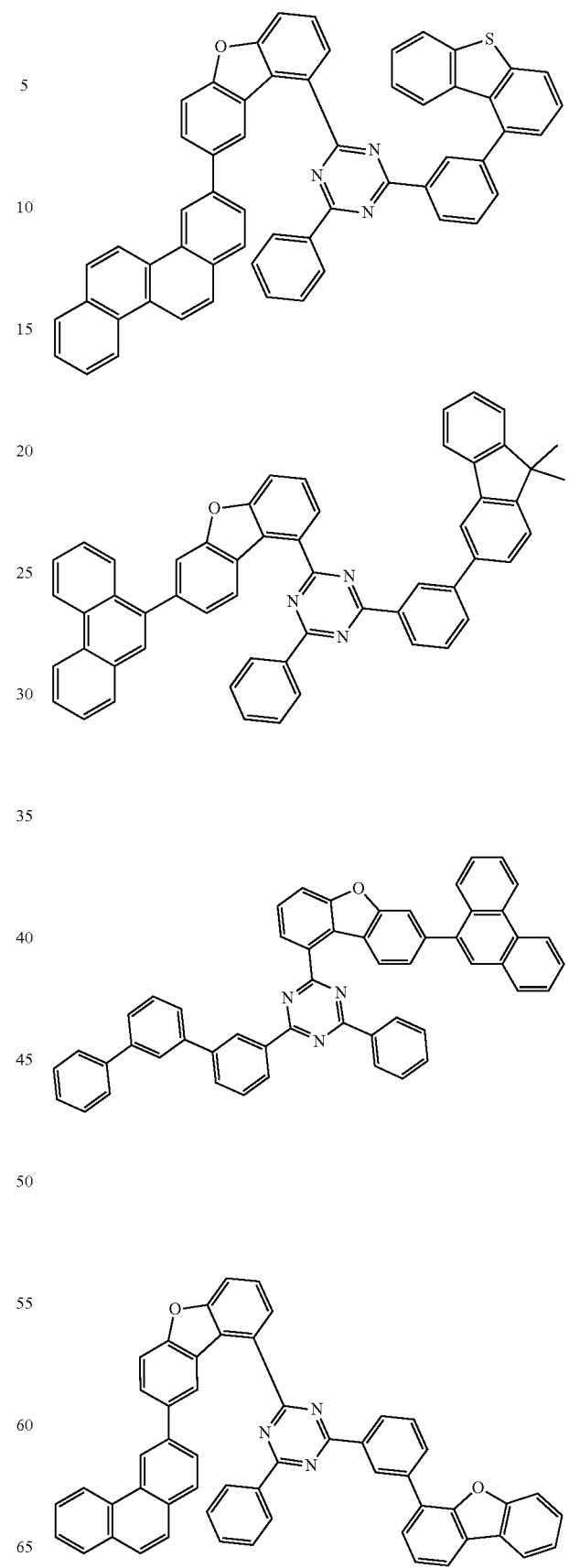

537
-continued
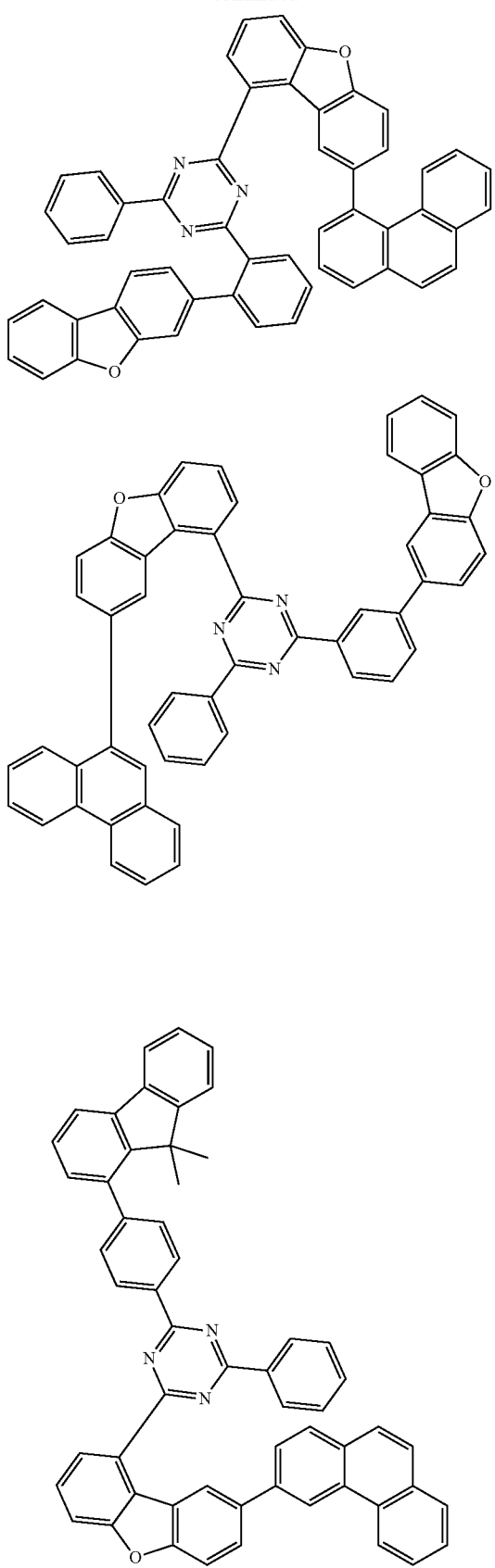
538
-continued
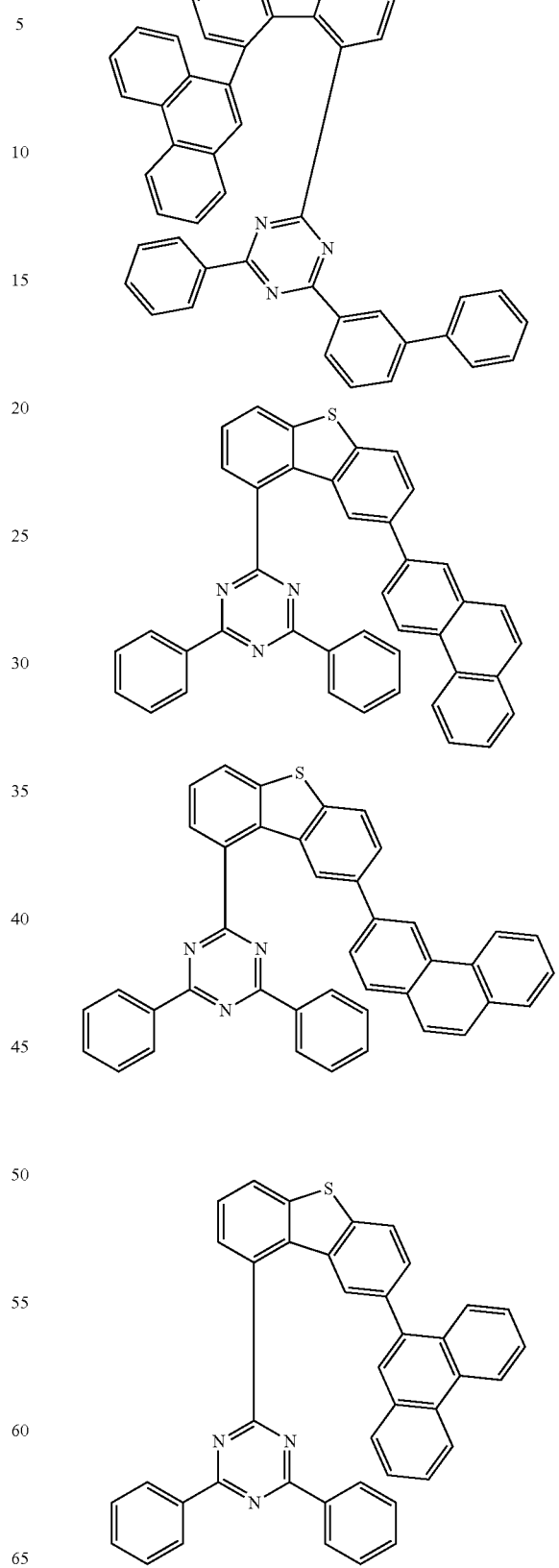

539
-continued
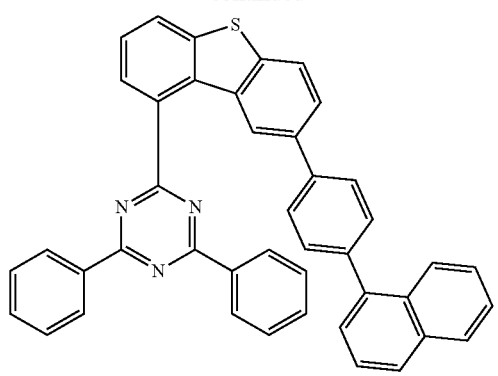
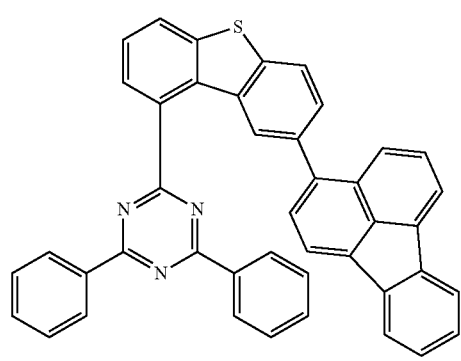
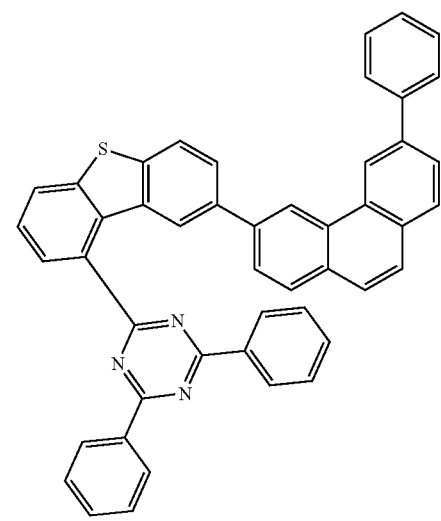
540
-continued
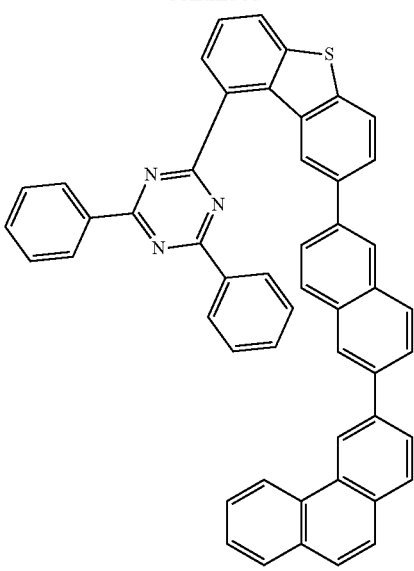
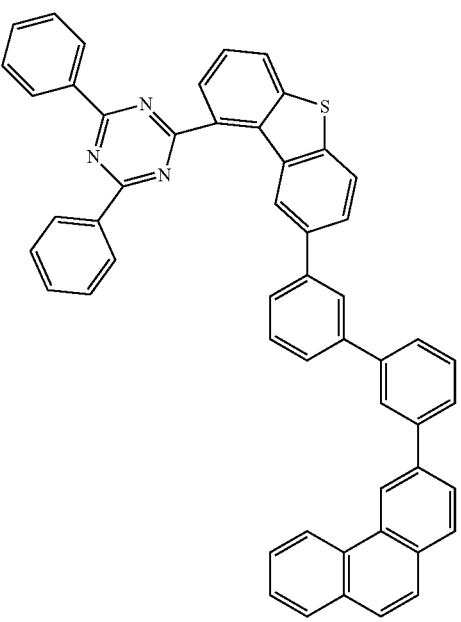
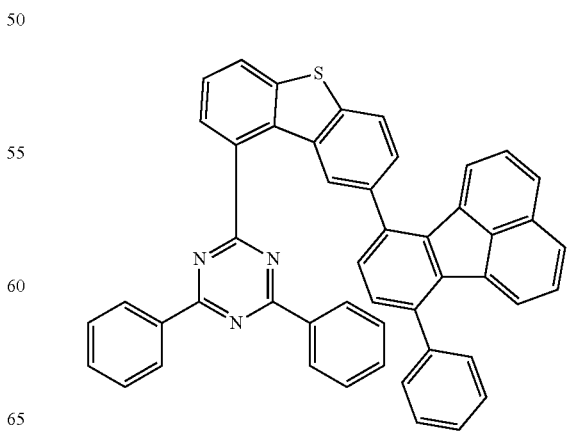

541
-continued
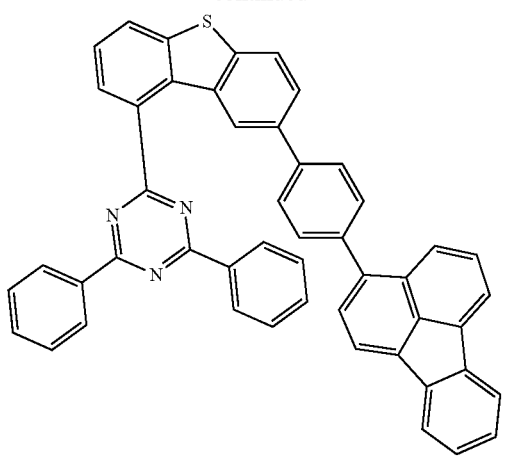
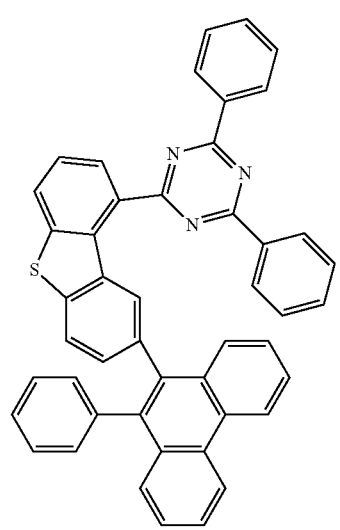
542
-continued
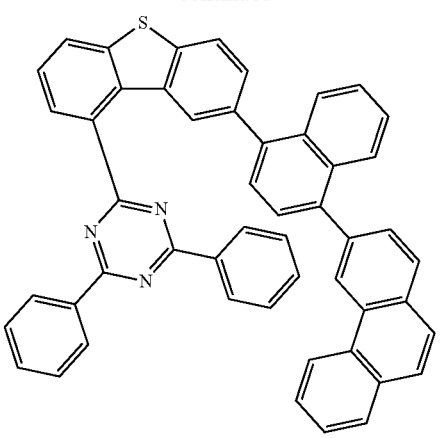
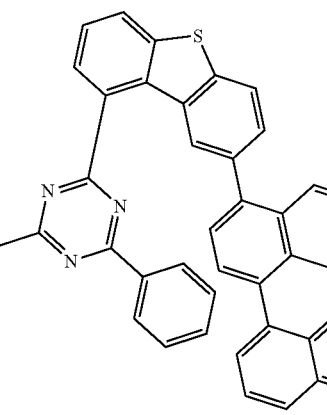
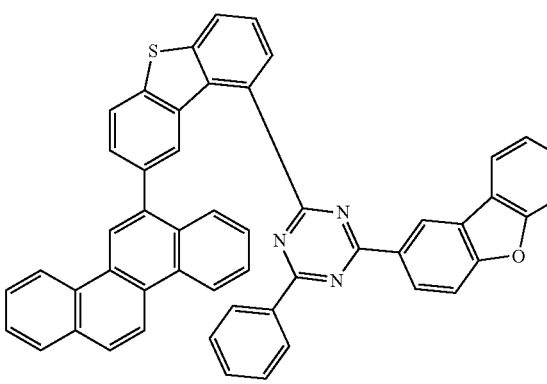
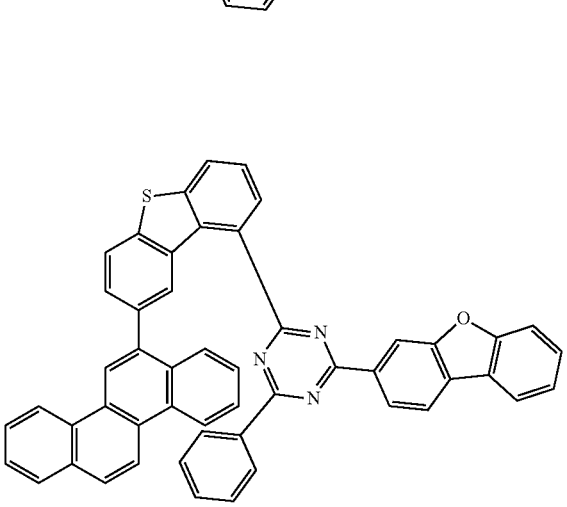

543
-continued
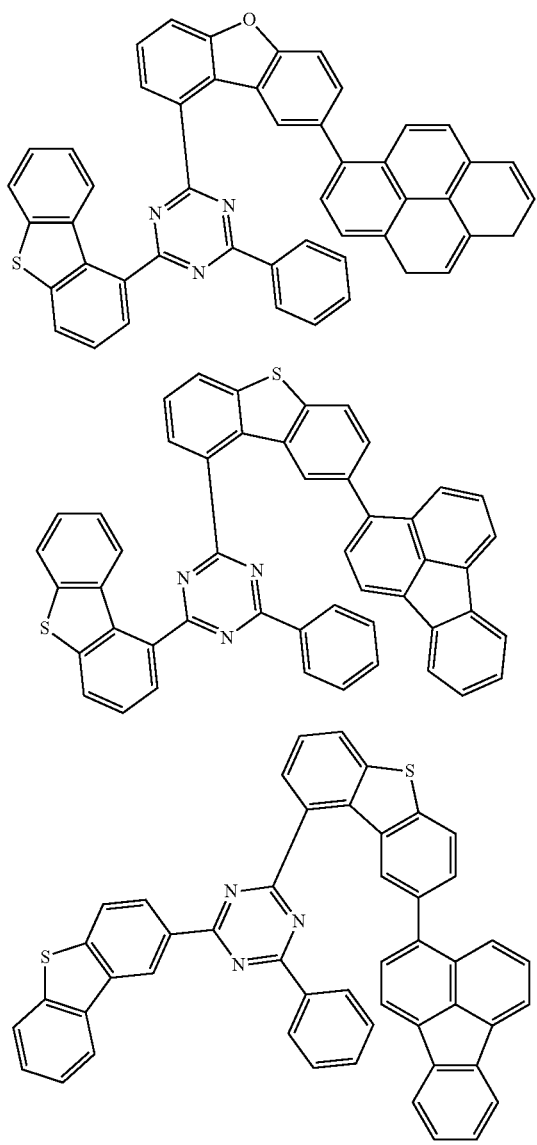
544
-continued
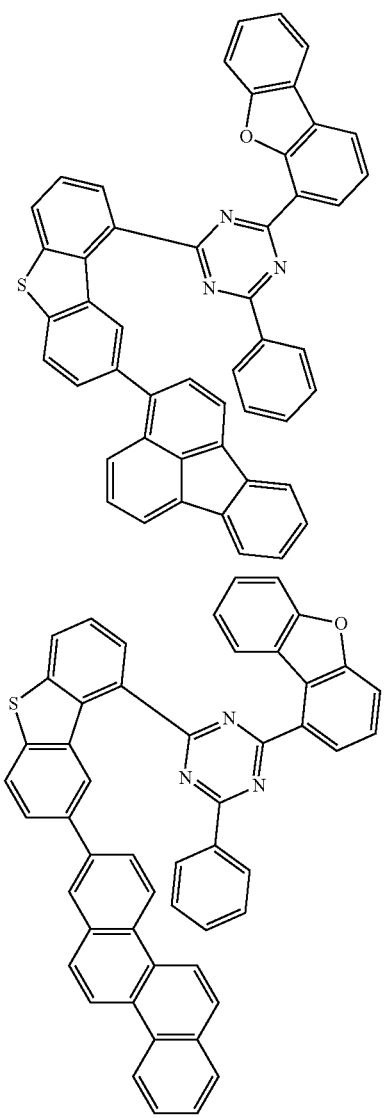
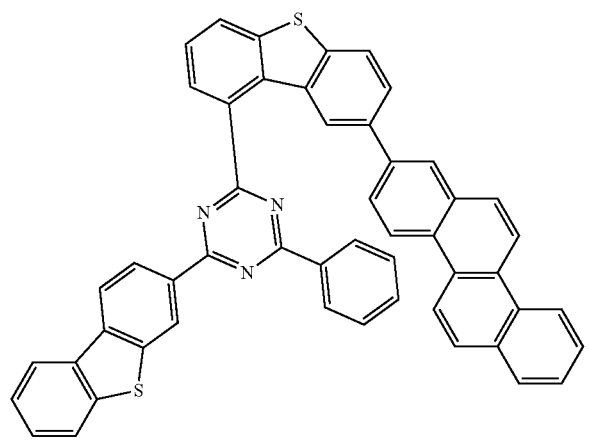
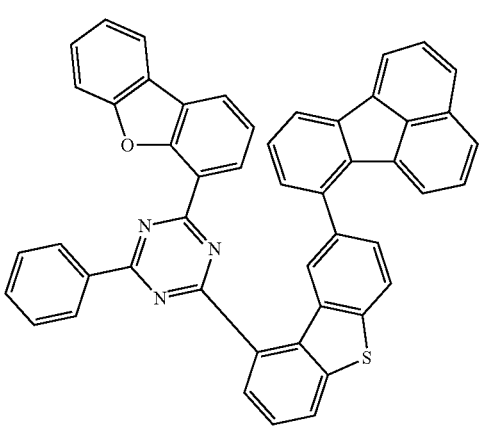

545
-continued
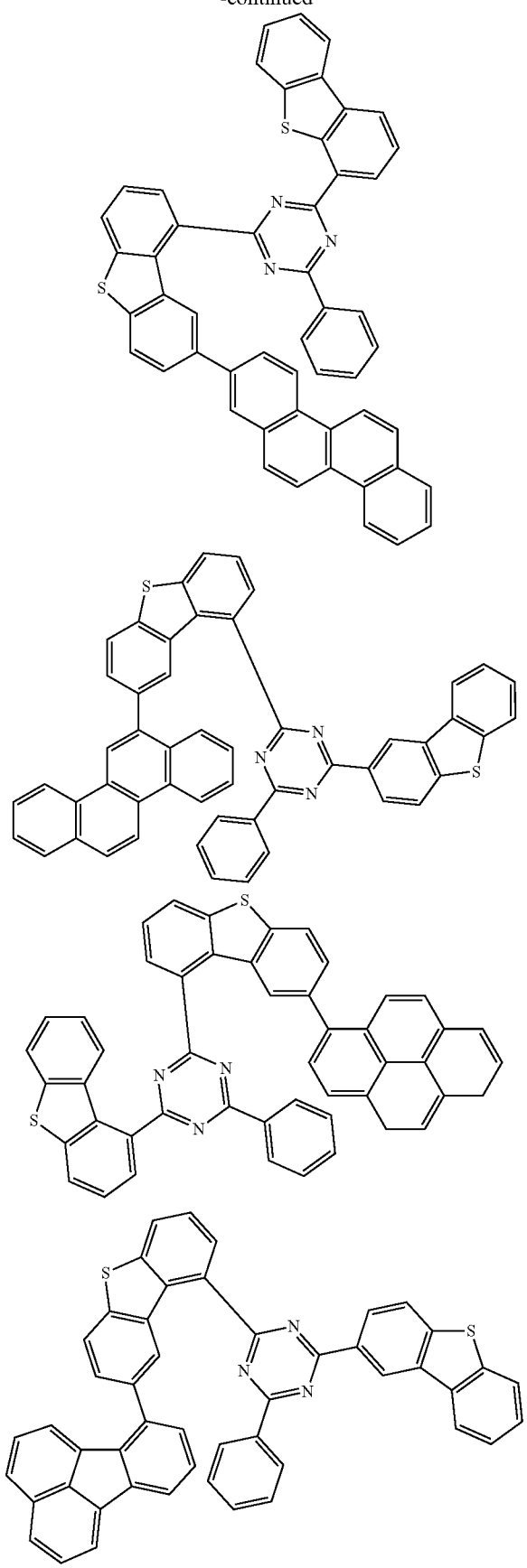
546
-continued
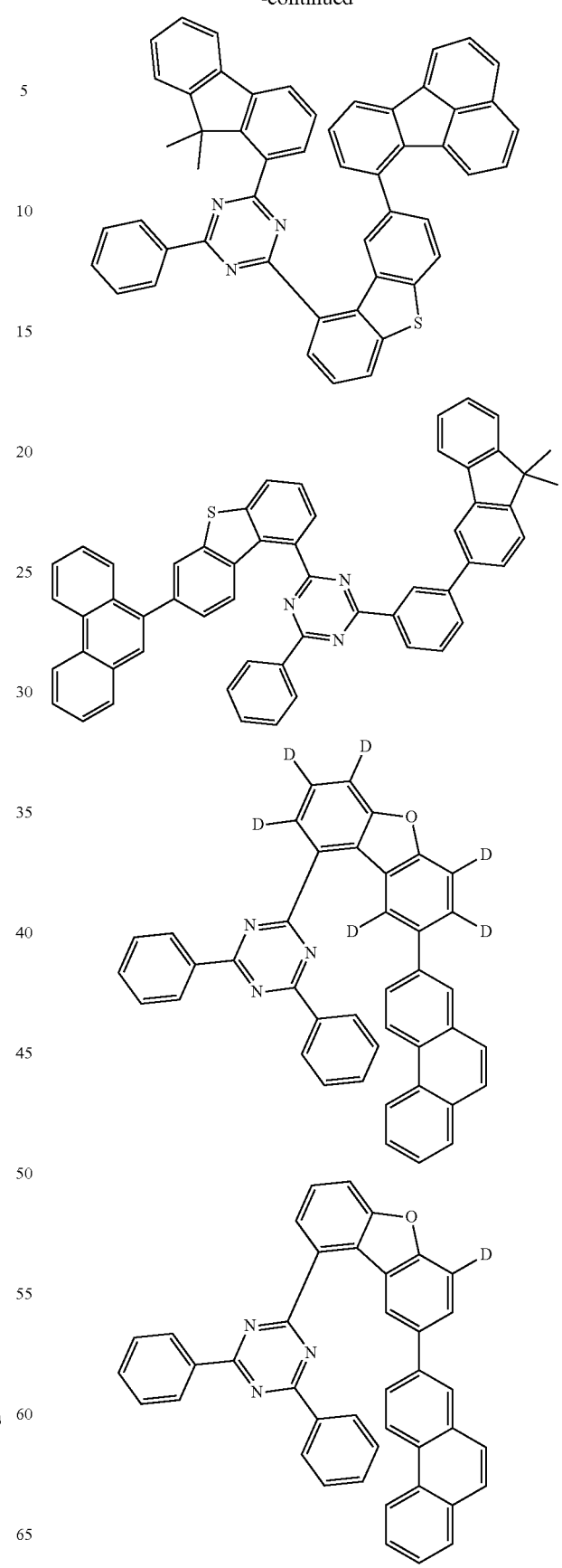

547
-continued
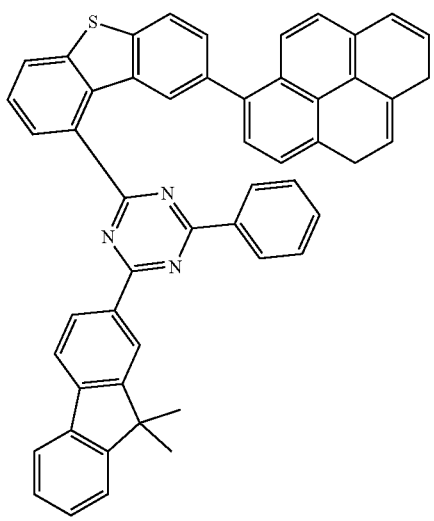
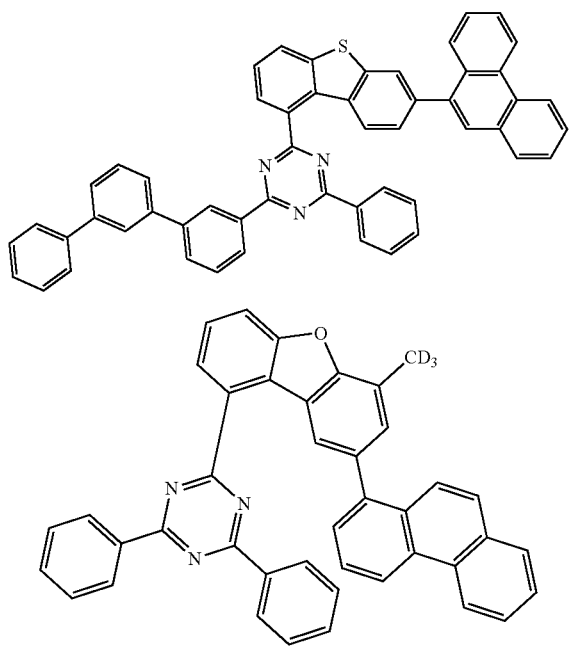
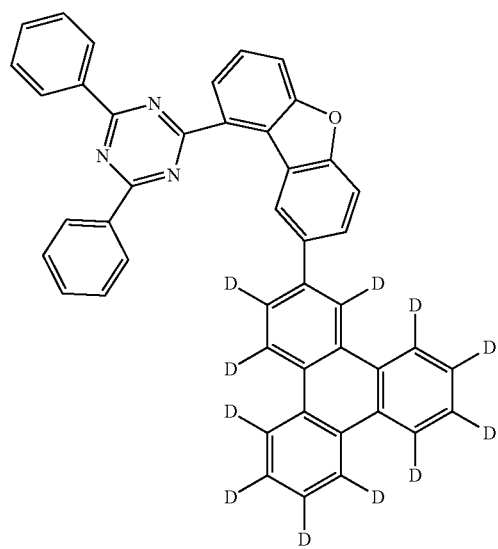
548
-continued
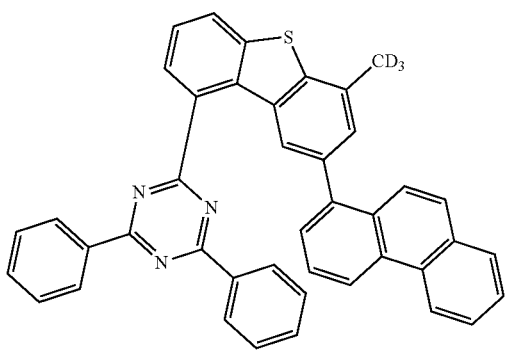
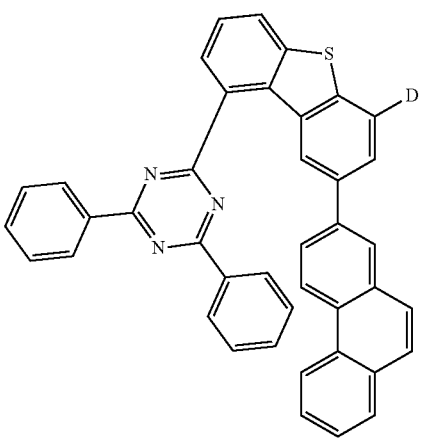
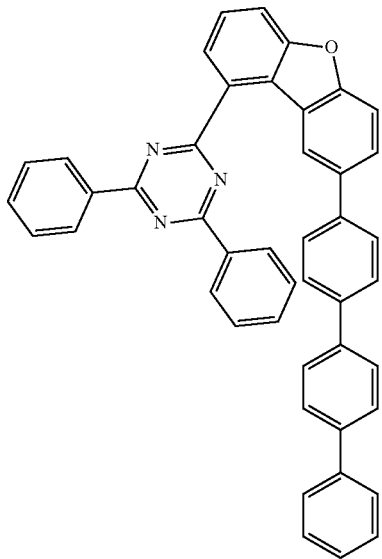

549
-continued
550
-continued
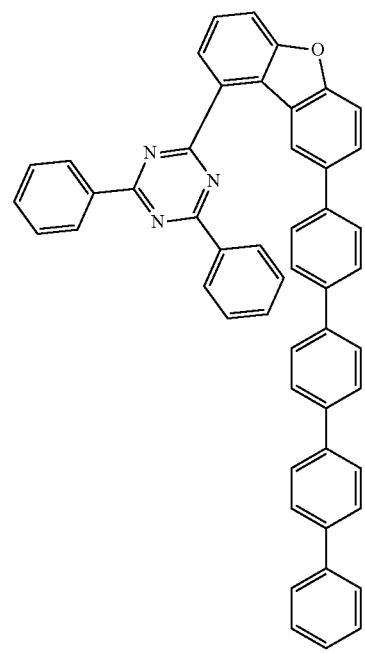
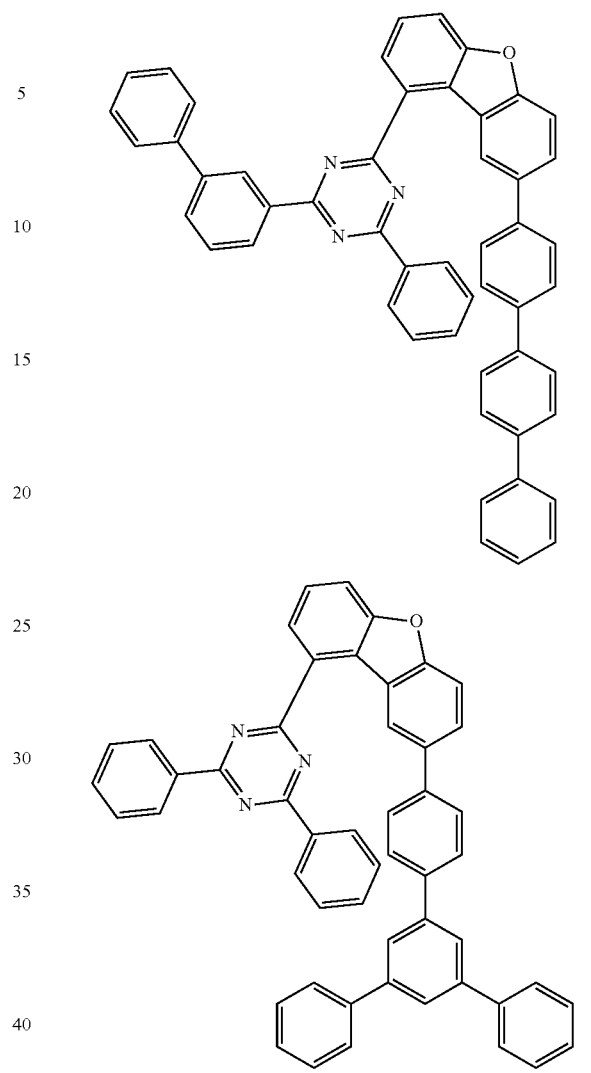
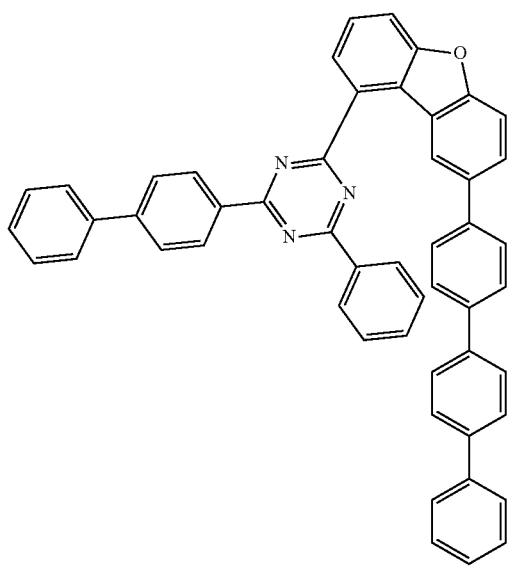

551
-continued
552
-continued
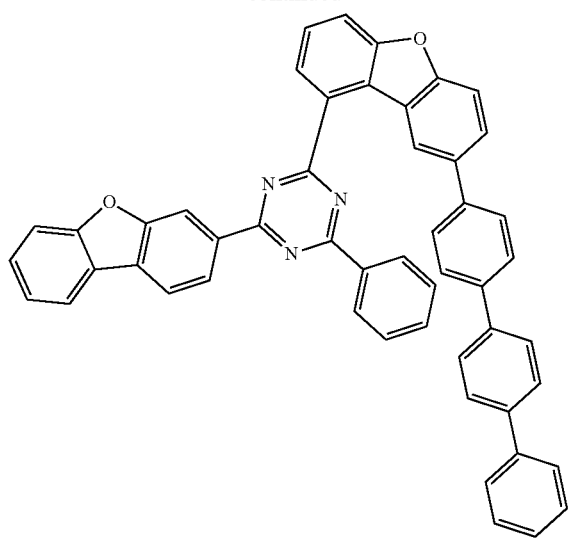
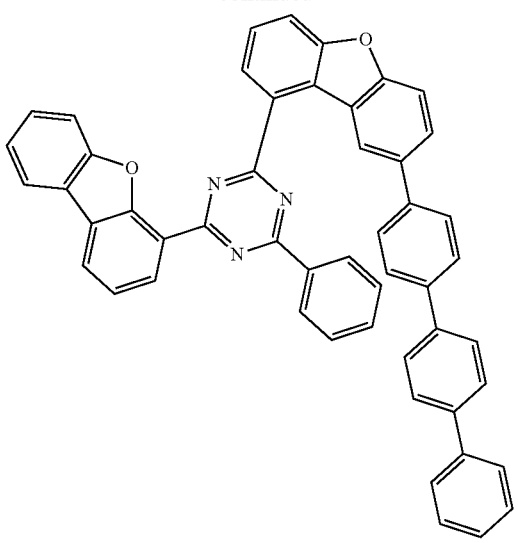
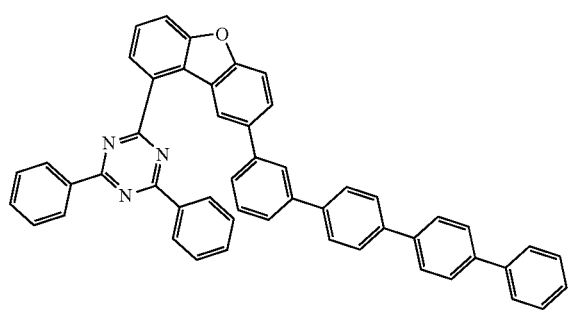
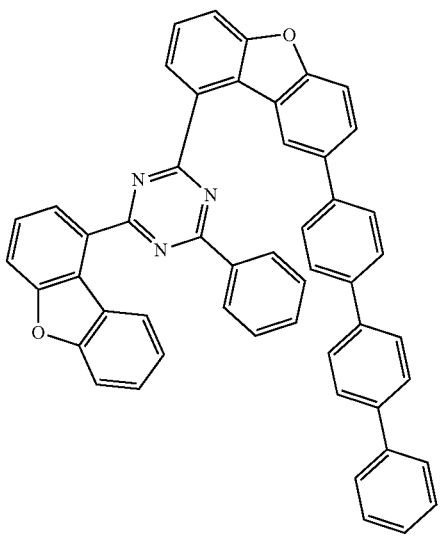
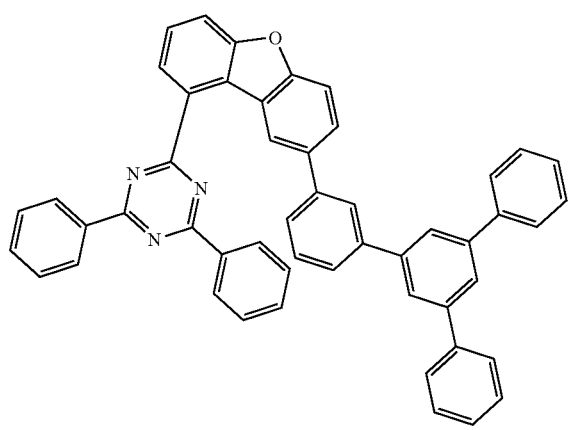
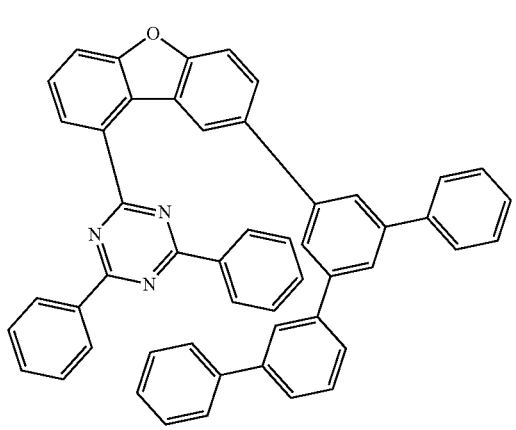

553
-continued
554
-continued
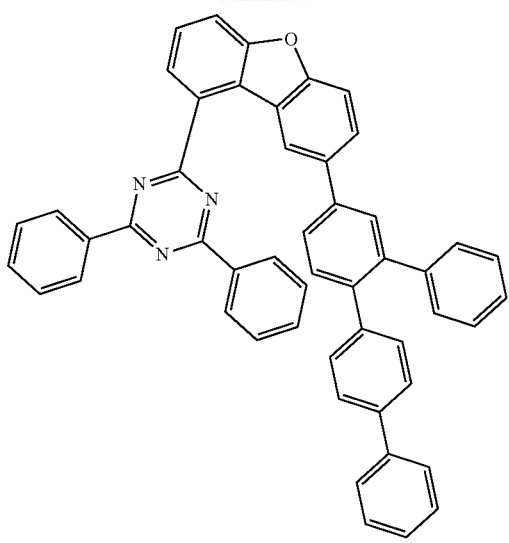
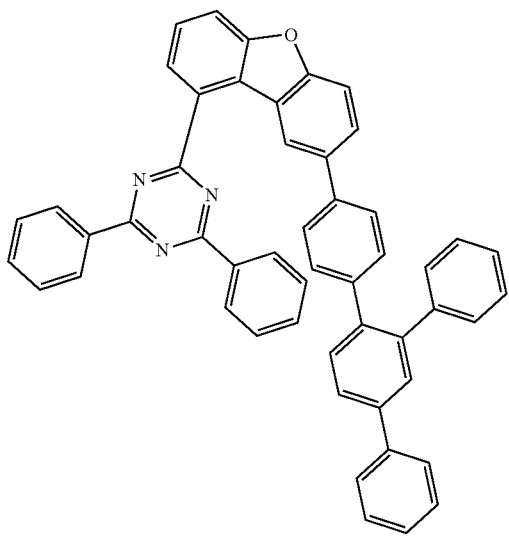
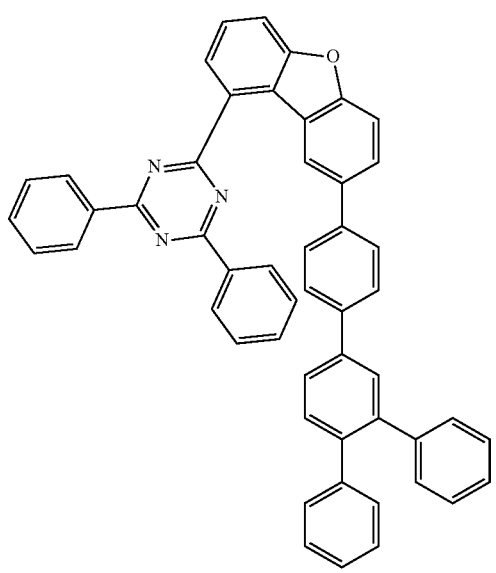
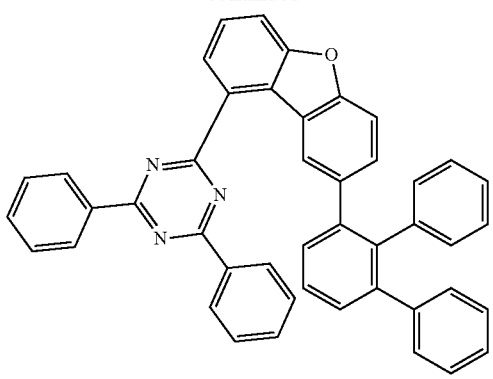
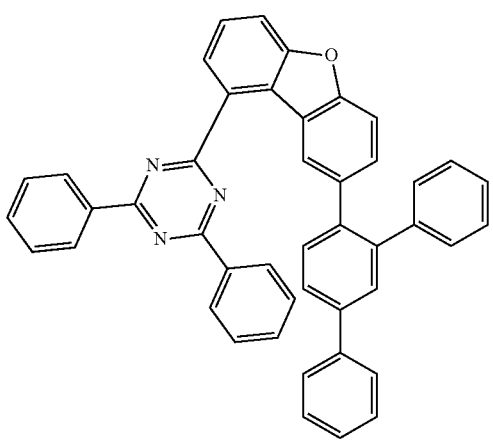
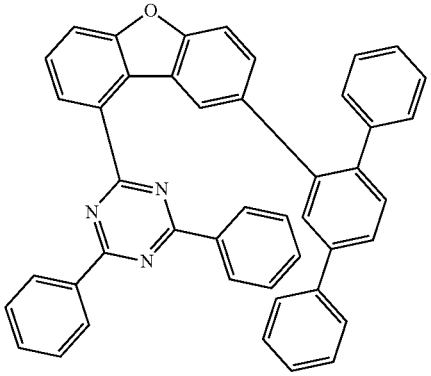
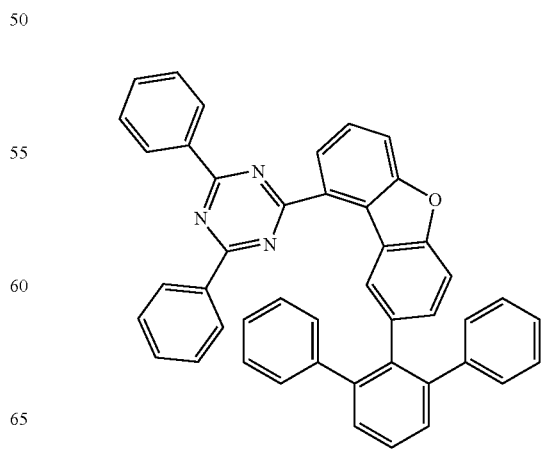

555
-continued
556
-continued
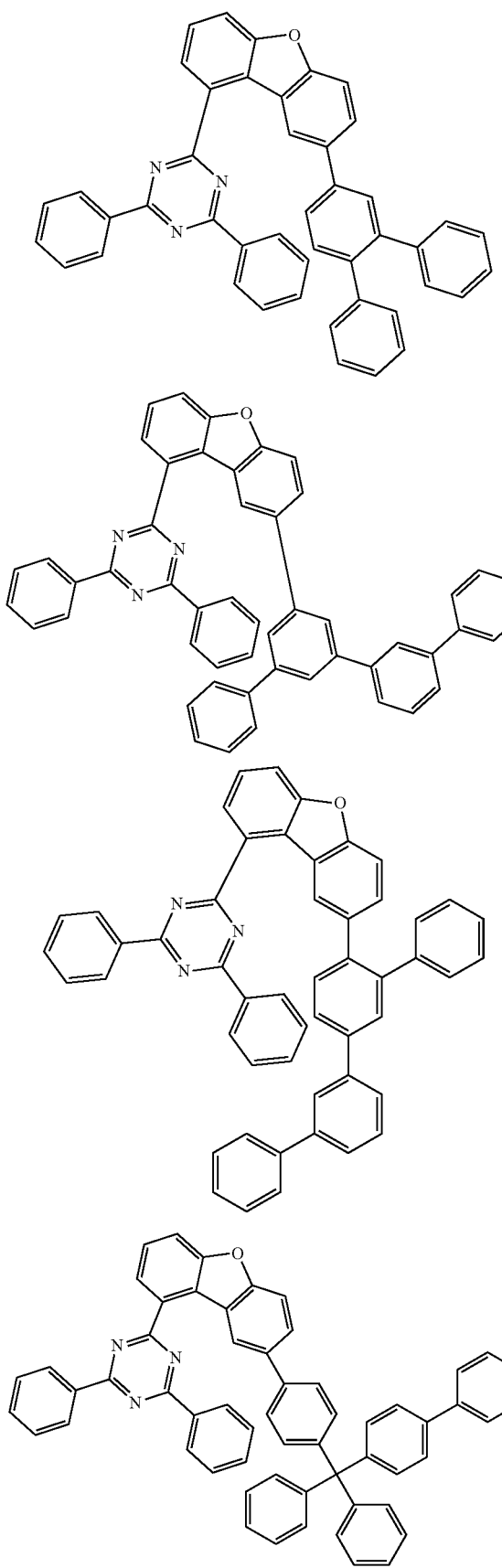
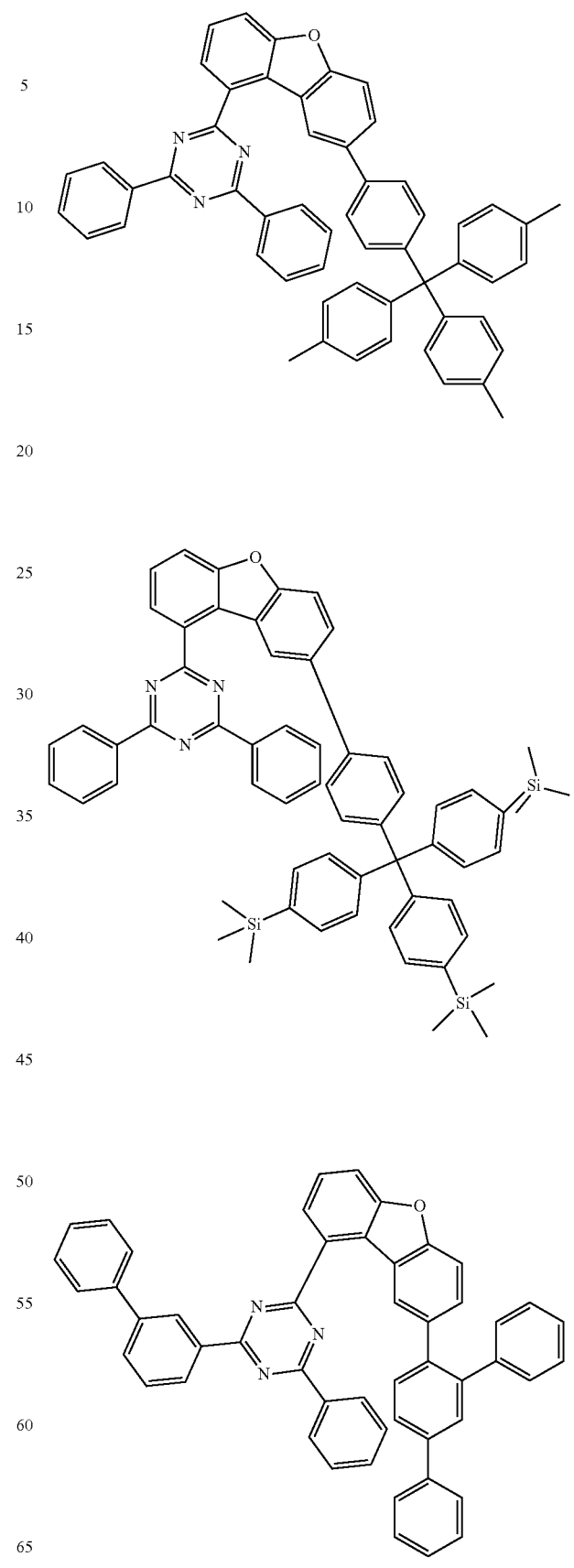

557
-continued
558
-continued
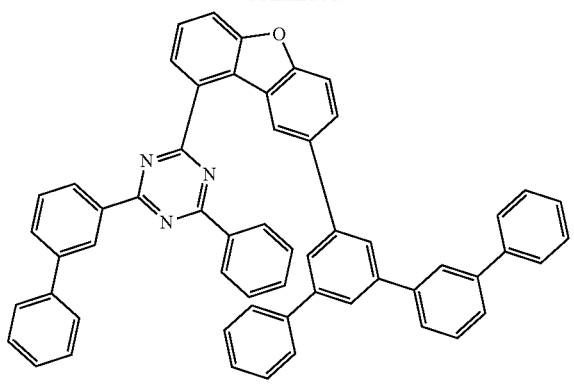
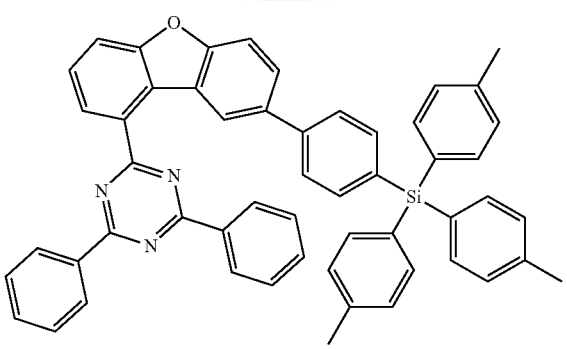 [SMILES: Cc1ccc([Si](c2ccc(C)cc2)(c2ccc(C)cc2)c2ccc(-c3ccc4oc5cccc(-c6nc(-c7ccccc7)nc(-c7ccccc7)n6)c5c4c3)cc2)cc1]
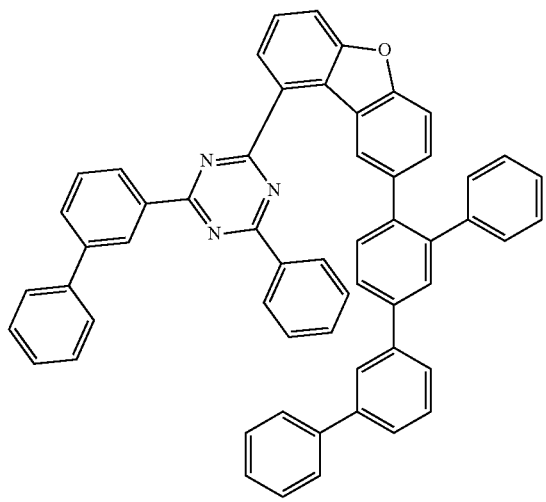
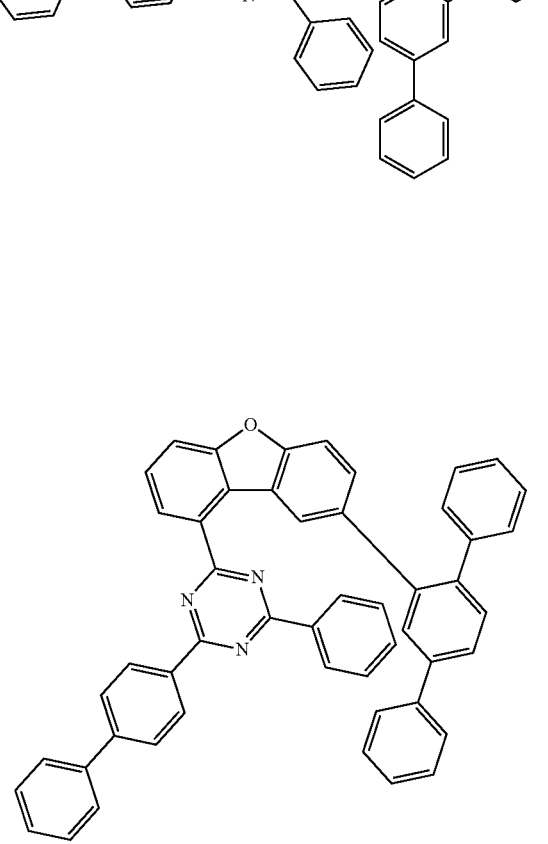

559
-continued
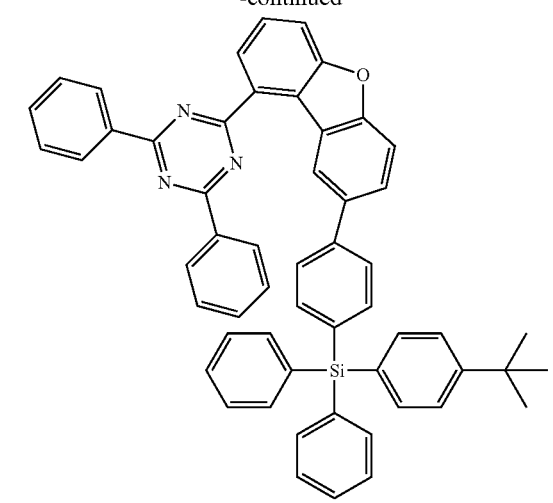
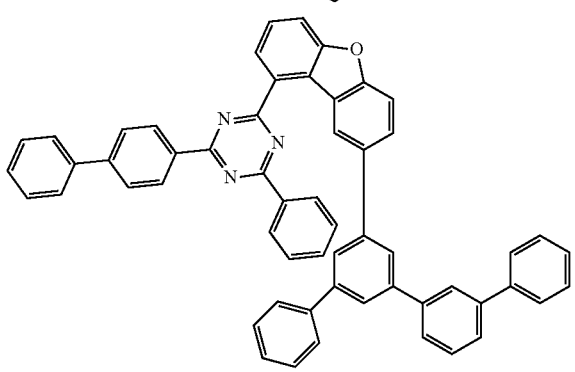
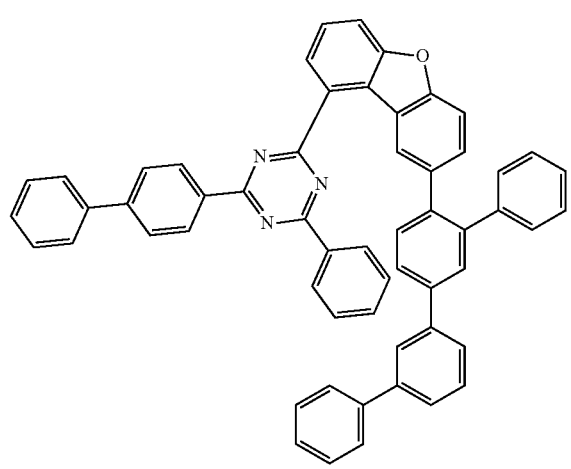
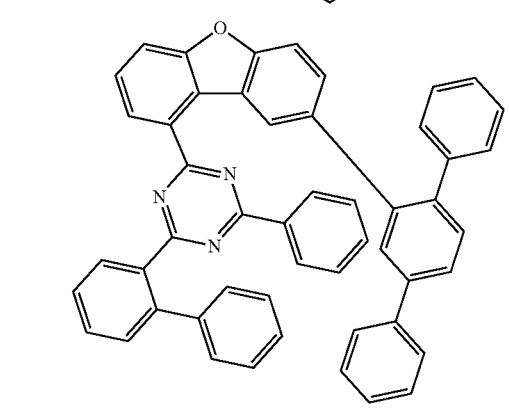
560
-continued
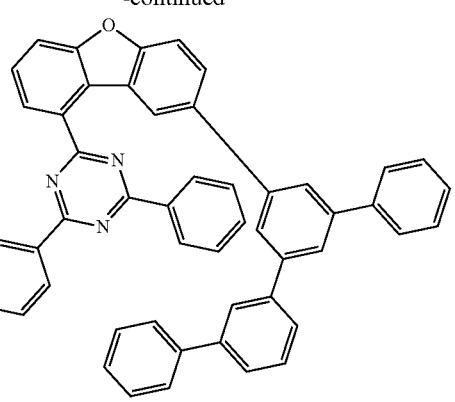
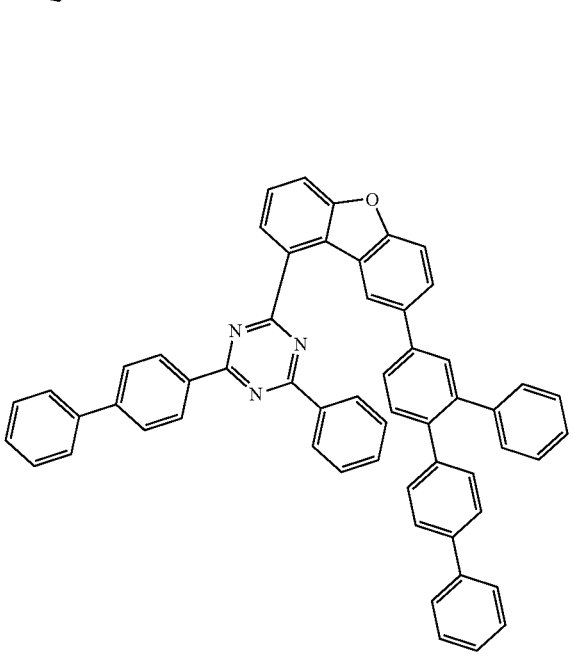
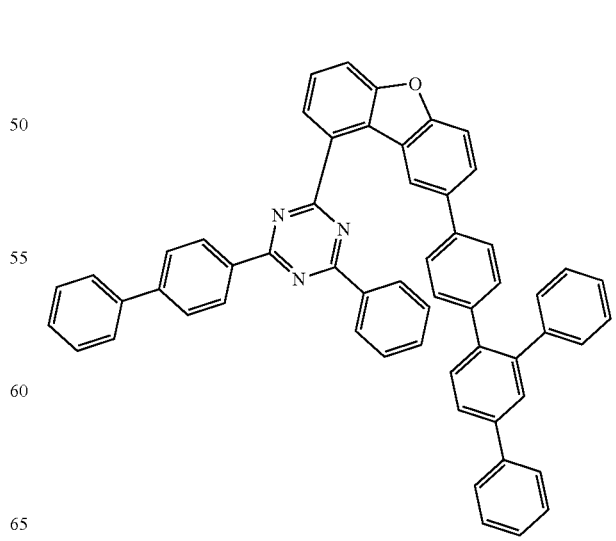

561
-continued
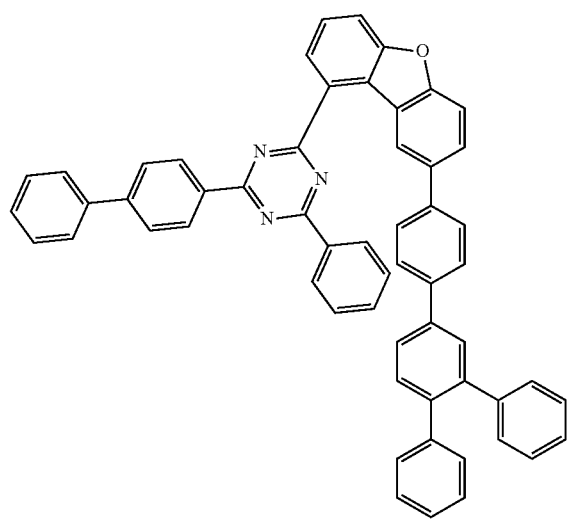
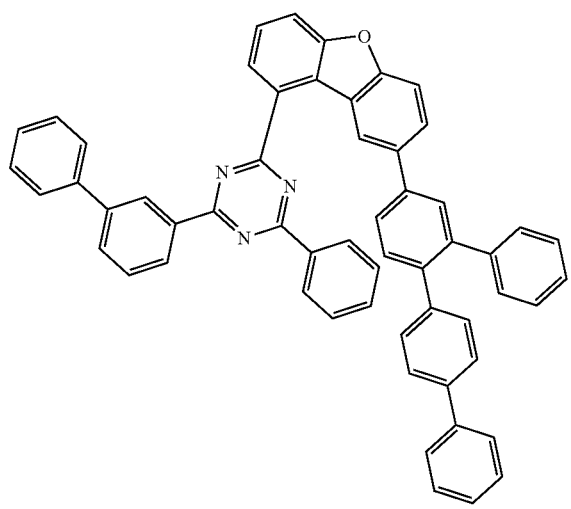
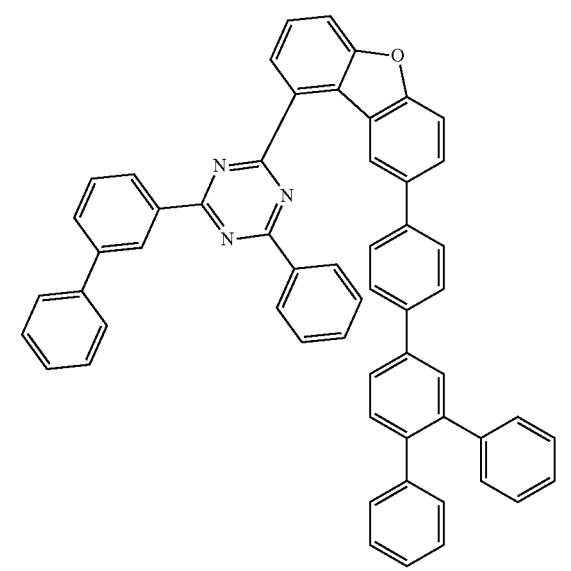
562
-continued
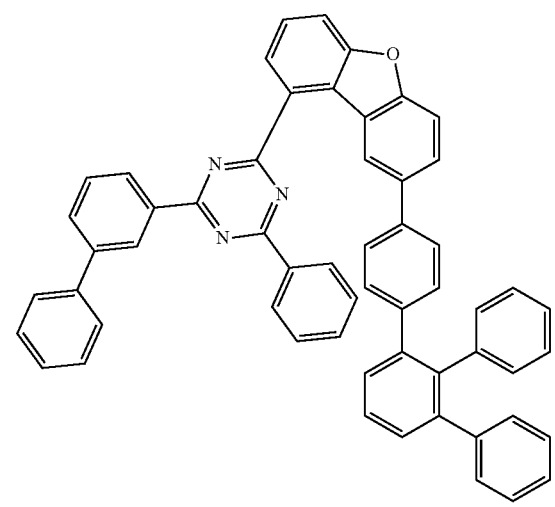
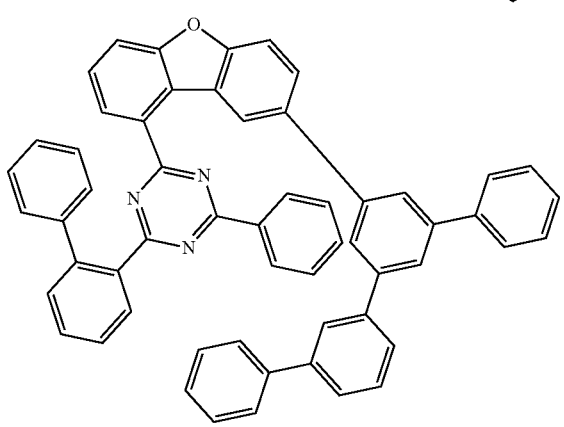
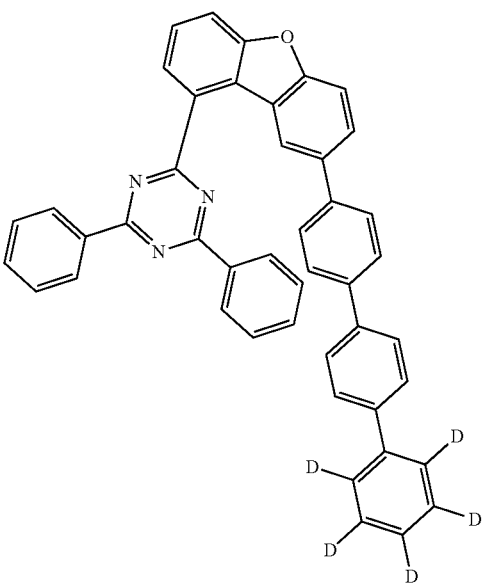

563
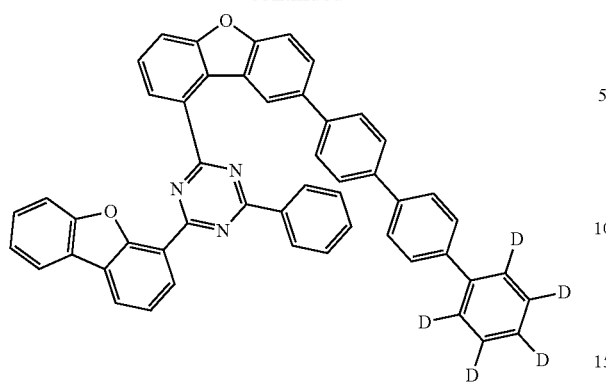
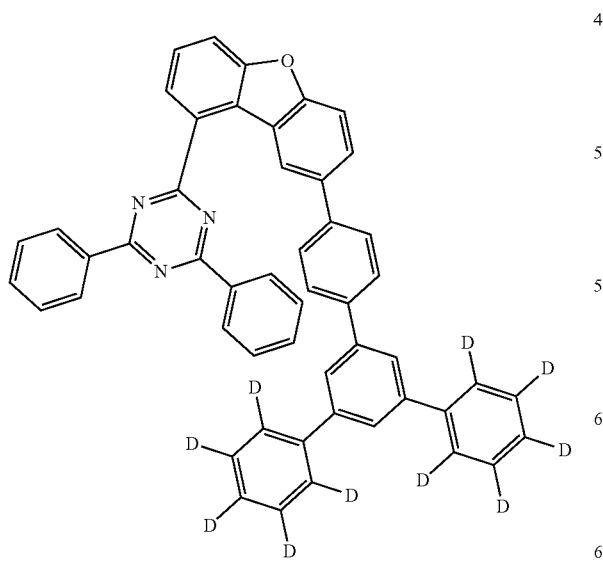
564
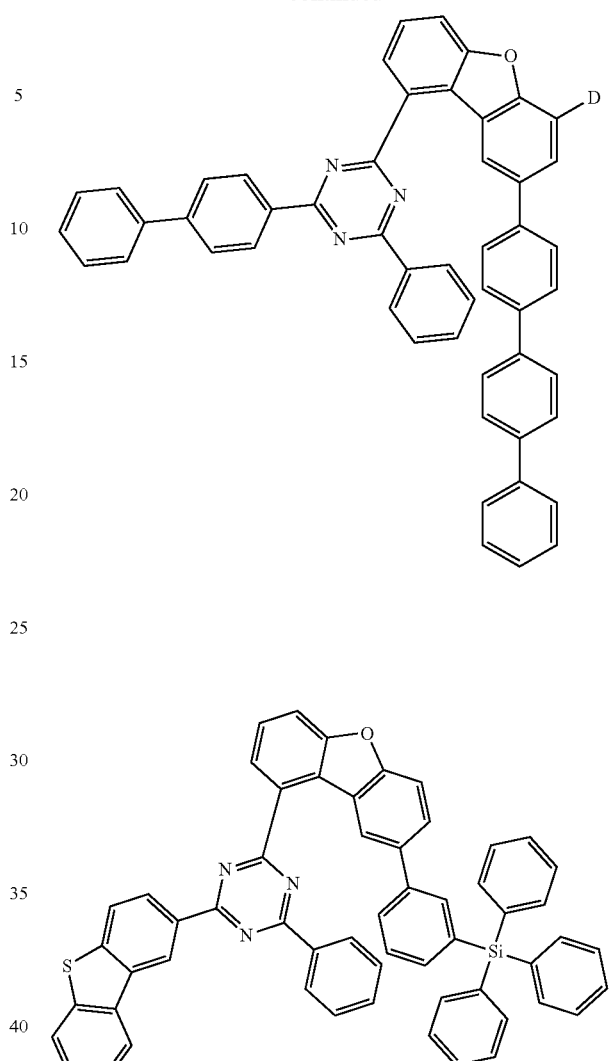

565
-continued
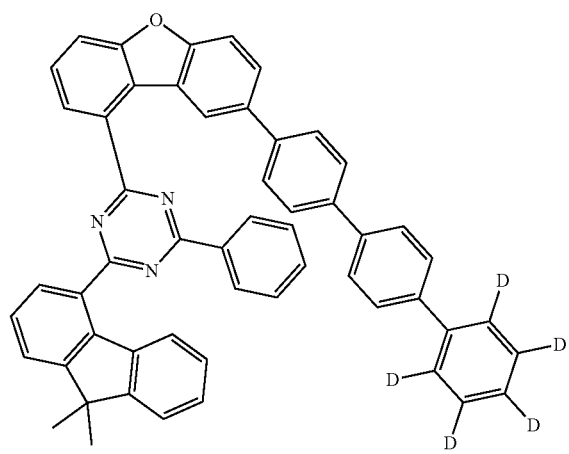
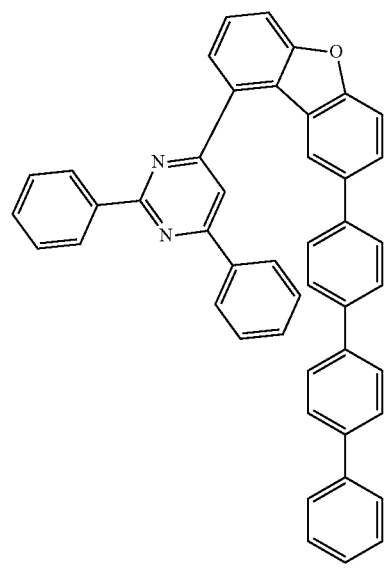
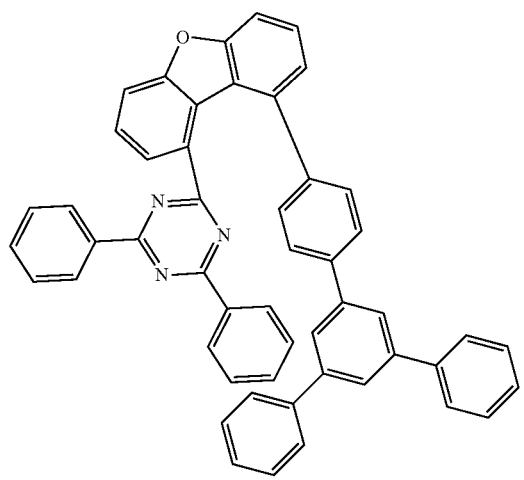
566
-continued
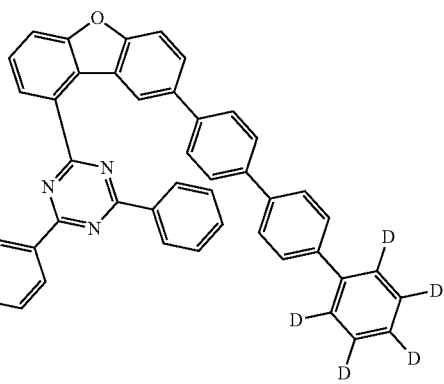
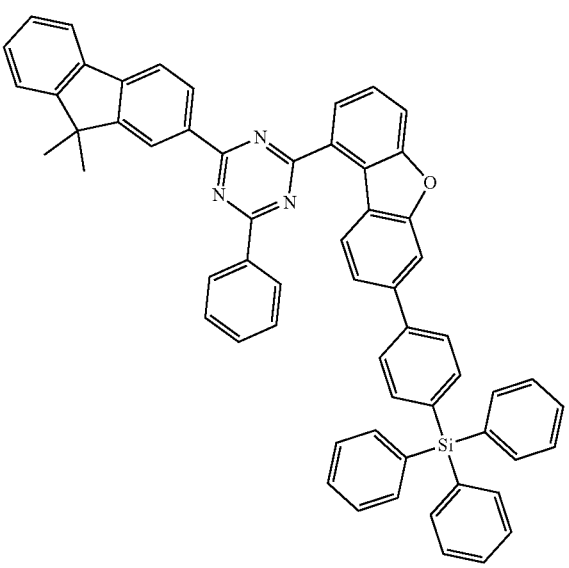
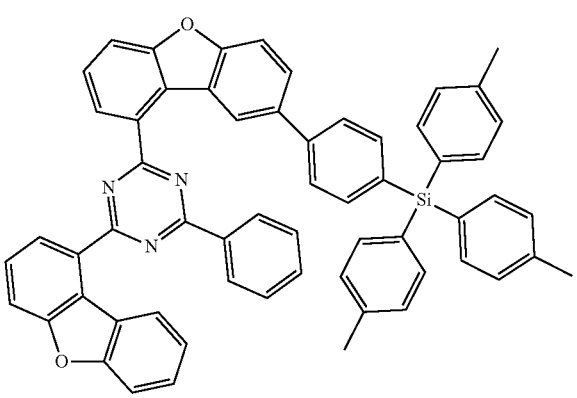

567
-continued
568
-continued
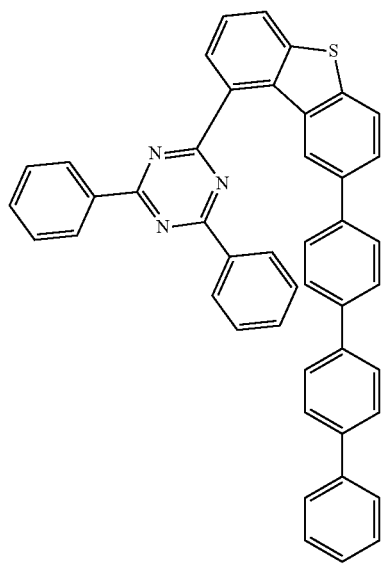
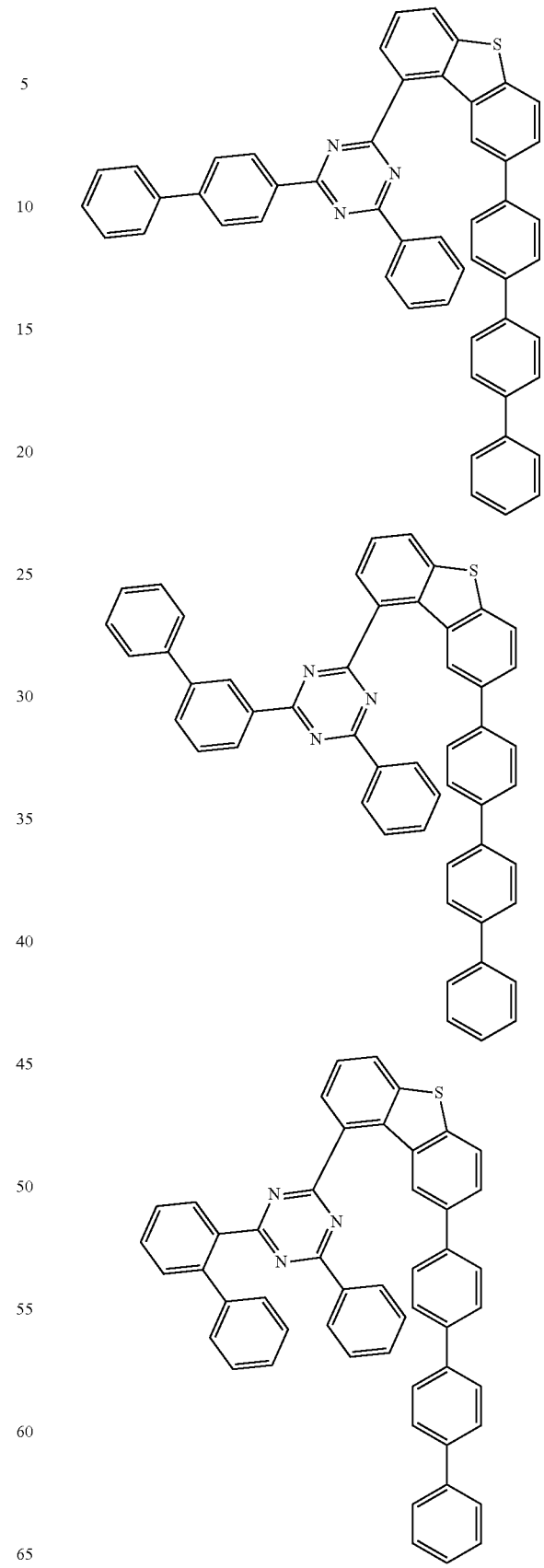

569
-continued
570
-continued
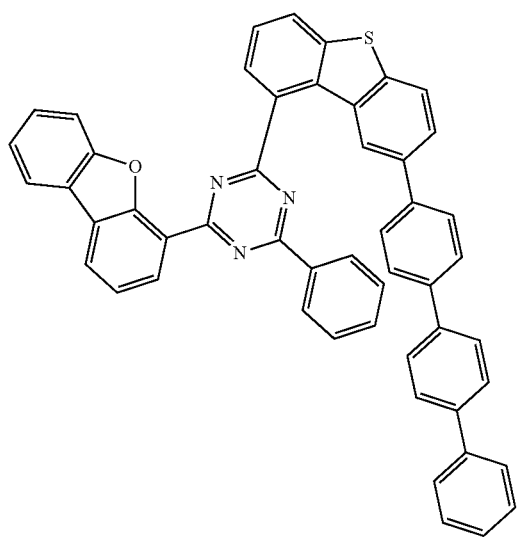
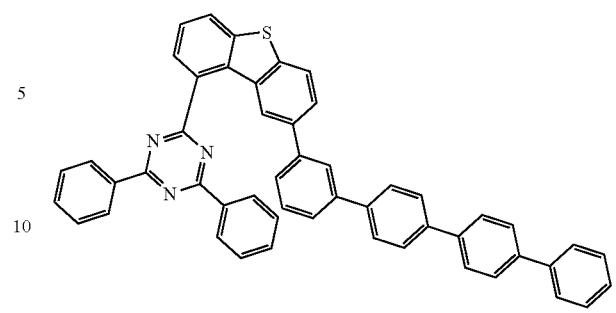
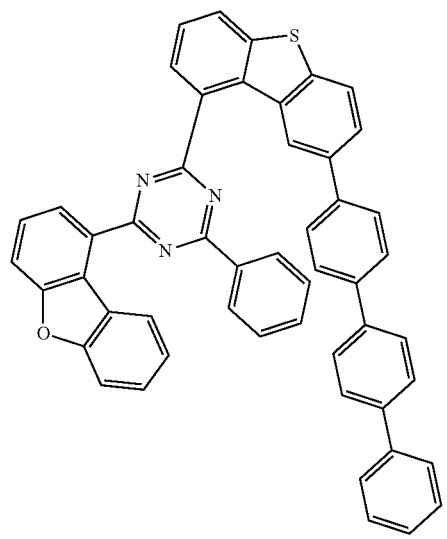
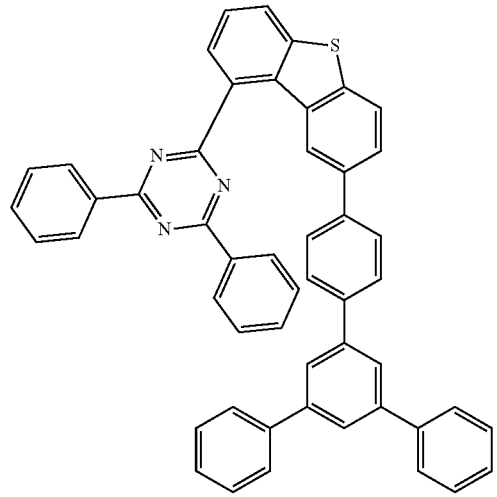
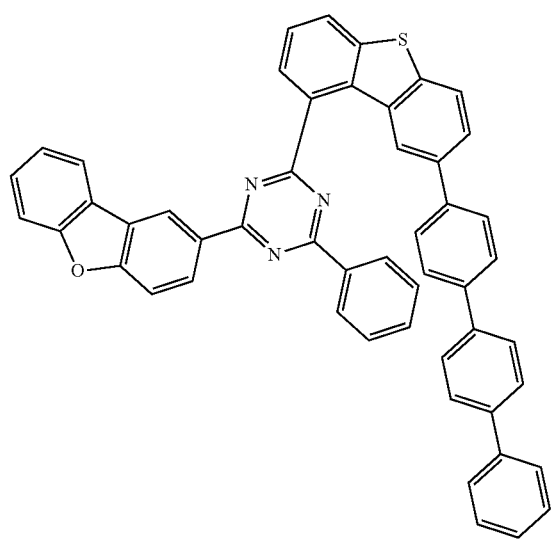
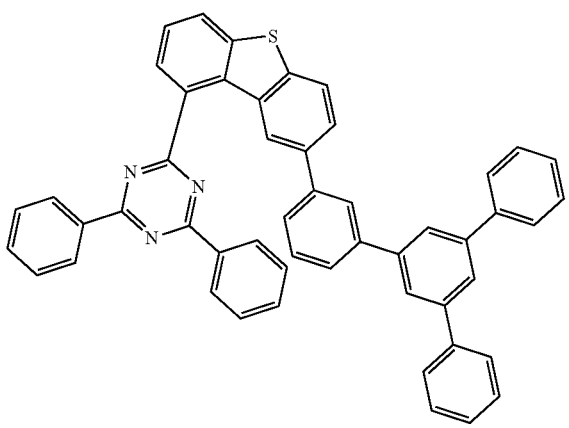

571
-continued
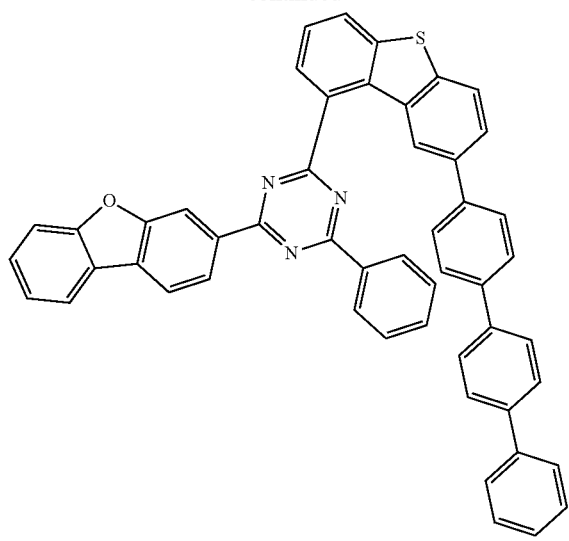
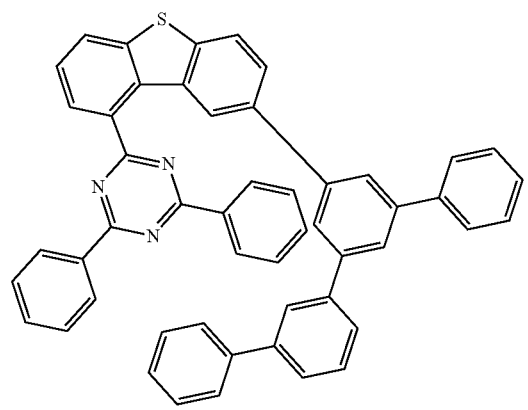
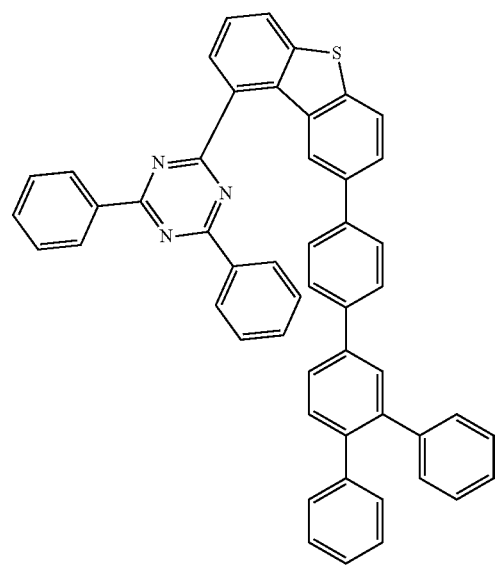
572
-continued
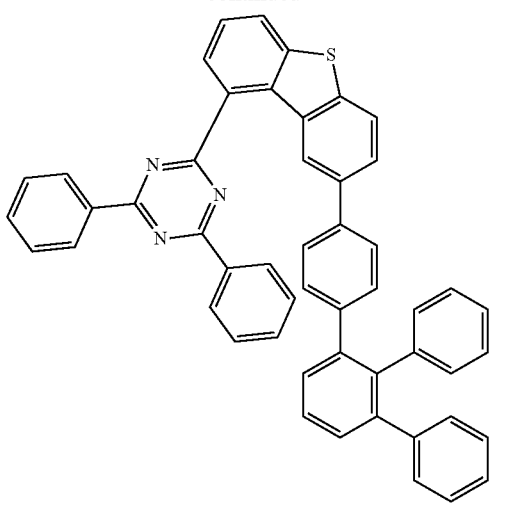
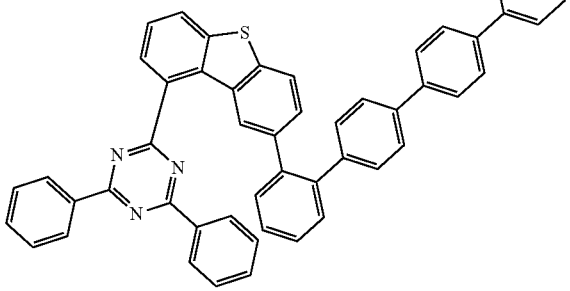
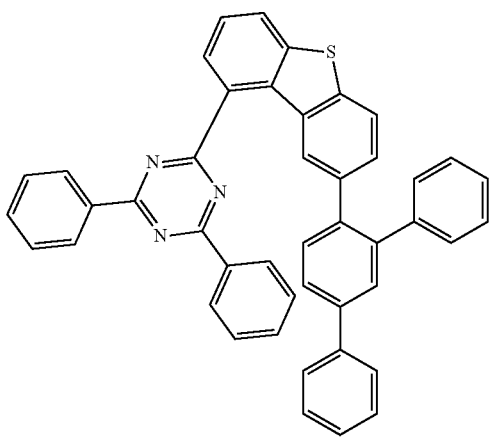
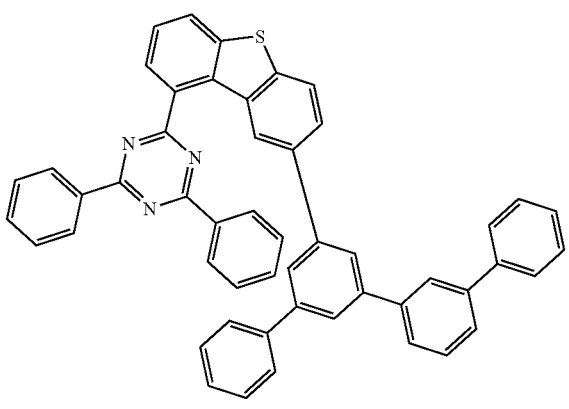

573
-continued
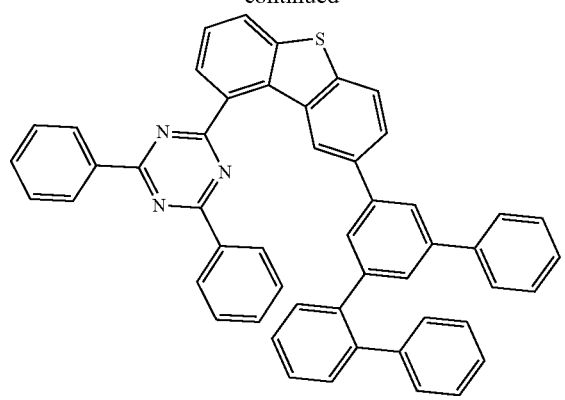
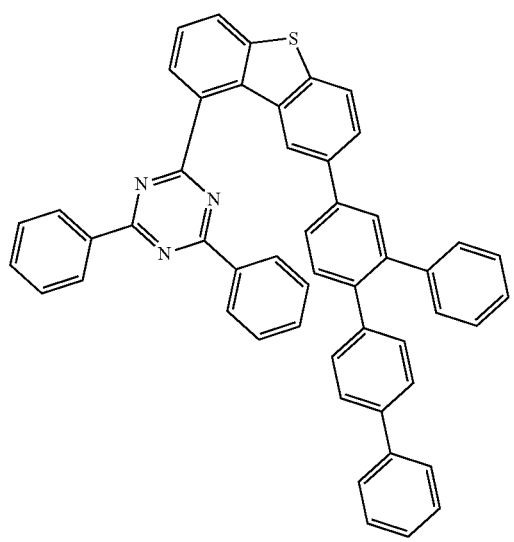
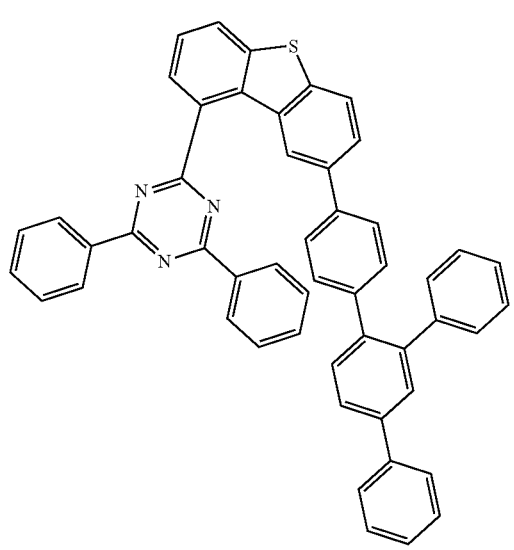
574
-continued
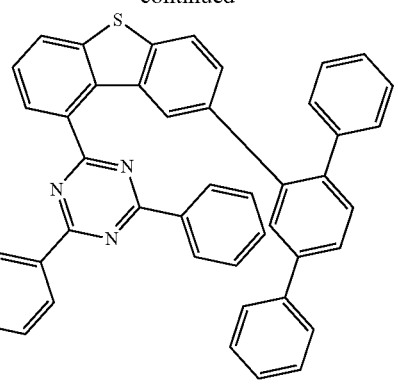
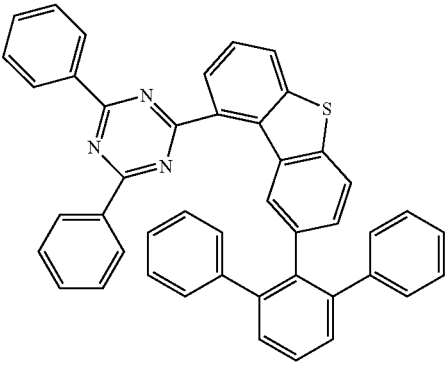
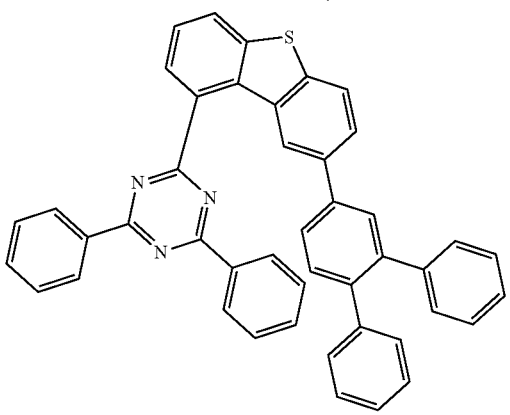
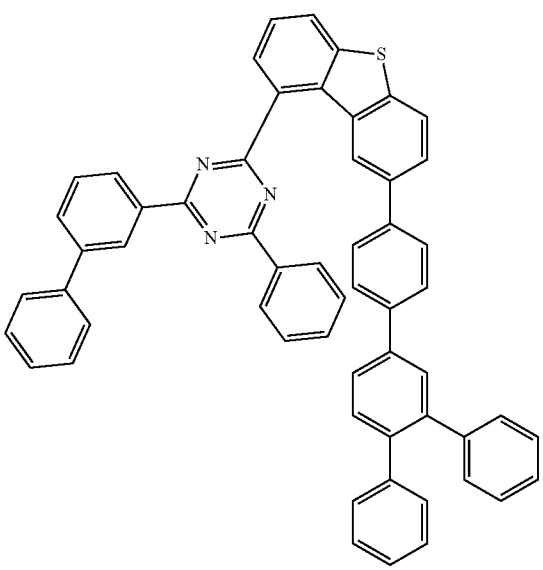

575
-continued
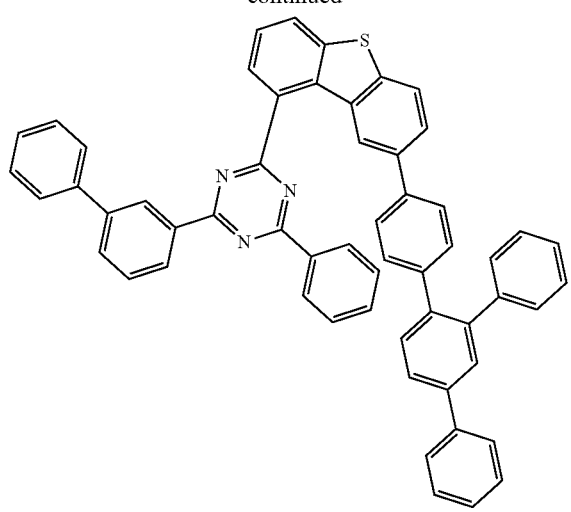
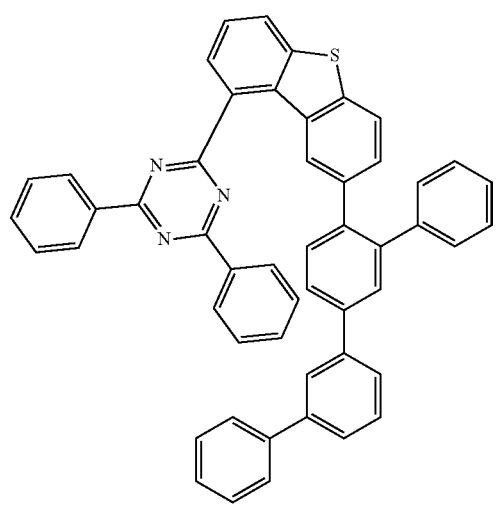
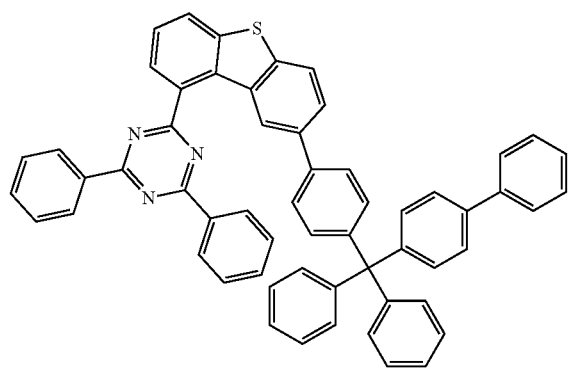
576
-continued
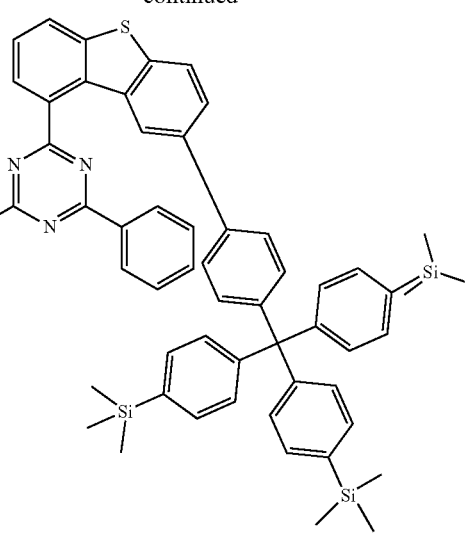
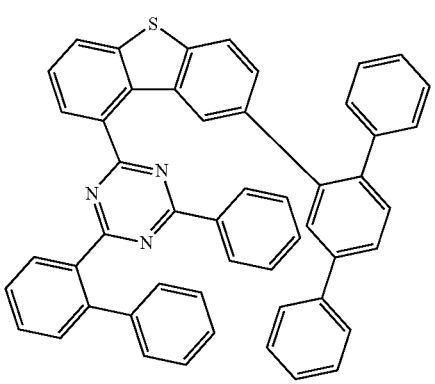
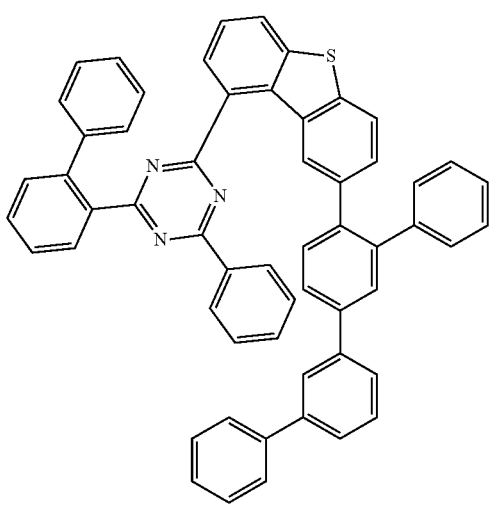

577
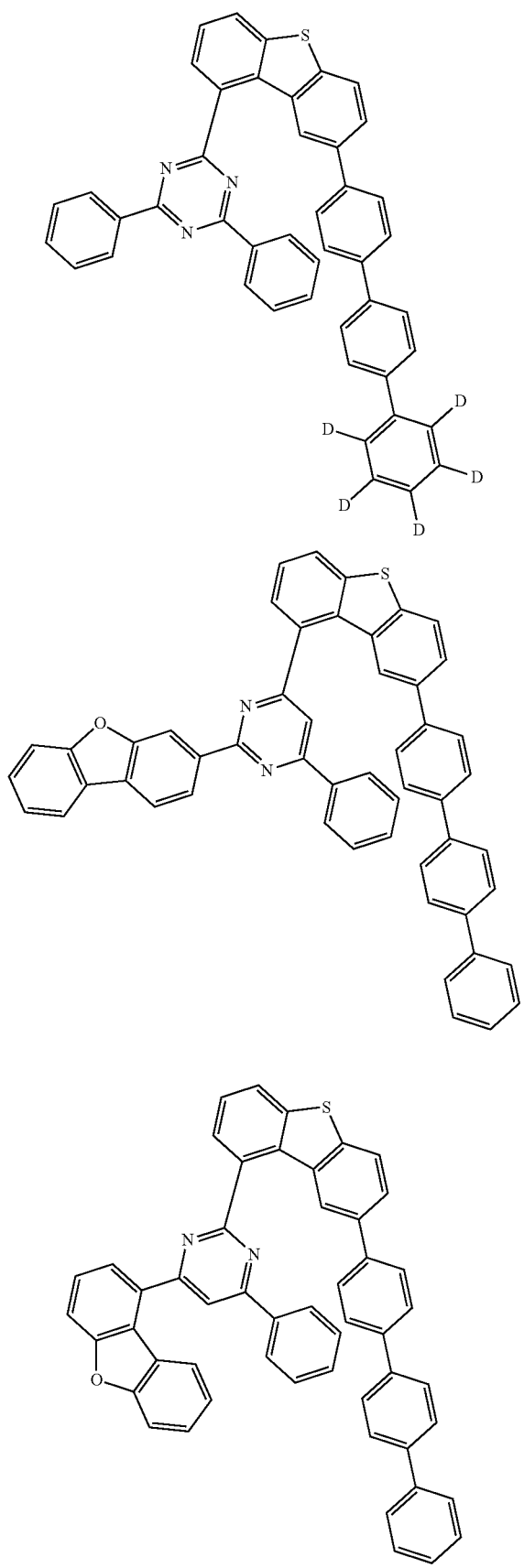 [SMILES: [2H]c1c([2H])c([2H])c(-c2ccc(-c3ccc(-c4ccc5sc6cccc(-c7nc(-c8ccccc8)nc(-c8ccccc8)n7)c6c5c4)cc3)cc2)c([2H])c1[2H] ; c1ccc(-c2ccc(-c3ccc(-c4ccc5sc6cccc(-c7cc(-c8ccccc8)nc(-c8ccc9c(c8)oc8ccccc89)n7)c6c5c4)cc3)cc2)cc1 ; c1ccc(-c2ccc(-c3ccc(-c4ccc5sc6cccc(-c7nc(-c8ccccc8)cc(-c8cccc9oc%10ccccc%10c89)n7)c6c5c4)cc3)cc2)cc1]
578
-continued
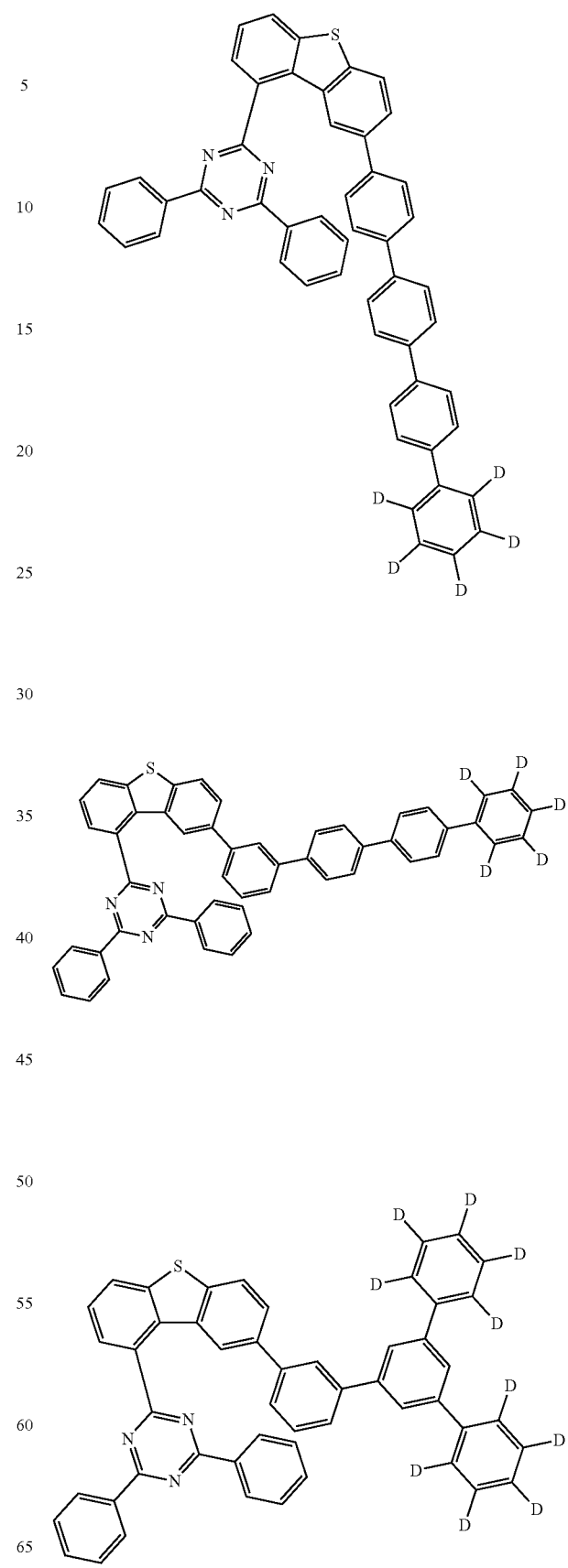

-continued

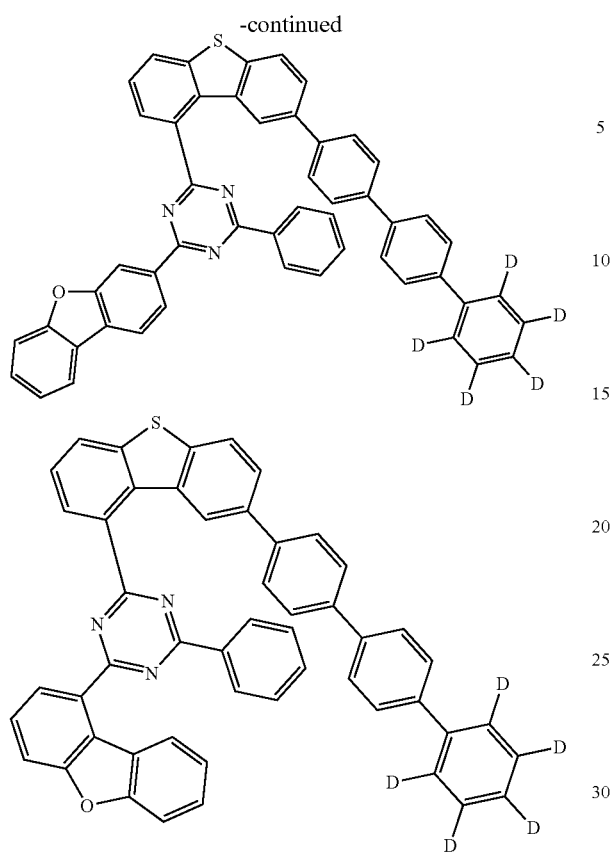

-continued

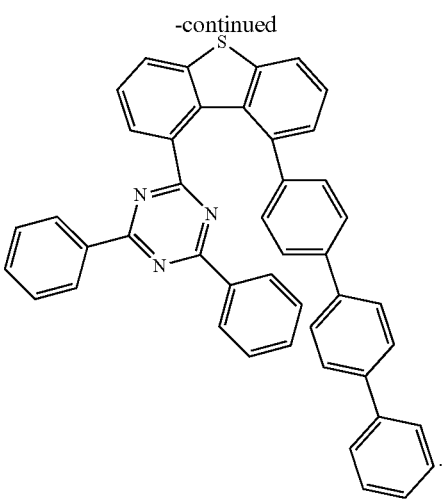

7. An organic light emitting device comprising: a first electrode; a second electrode provided to face the first electrode; and one or more organic material layers provided between the first electrode and the second electrode, wherein one or more of the organic material layers include the compound of claim 1.

8. The organic light emitting device of claim 7, wherein the organic material layer containing the compound is a light emitting layer.

9. The organic light emitting device of claim 8, wherein the compound is used as a host material.

\* \* \* \* \*

UNITED STATES PATENT AND TRADEMARK OFFICE
CERTIFICATE OF CORRECTION

PATENT NO. : 12,167,689 B2
APPLICATION NO. : 17/842520
DATED : December 10, 2024
INVENTOR(S) : Jung et al.

Page 1 of 1

It is certified that error appears in the above-identified patent and that said Letters Patent is hereby corrected as shown below:

In the Claims

In Claim 6, at Column 511, the structure at Lines 29-42 should be deleted.

Signed and Sealed this
Eleventh Day of February, 2025

Coke Morgan Stewart
*Acting Director of the United States Patent and Trademark Office*